United States Patent
Stanton et al.

(10) Patent No.: US 7,125,660 B2
(45) Date of Patent: Oct. 24, 2006

(54) NUCLEIC ACID SENSOR MOLECULES AND METHODS OF USING SAME

(75) Inventors: Martin Stanton, Stow, MA (US); David Epstein, Belmont, MA (US); Nobuko Hamaguchi, Framingham, MA (US); Markus Kurz, Newton, MA (US); Tony Keefe, Cambridge, MA (US); Charles Wilson, Concord, MA (US); Dilara Grate, Waltham, MA (US); Kristin A. Marshall, Arlington, MA (US); Thomas G. McCauley, Somerville, MA (US); Jeffrey C. Kurz, Somerville, MA (US)

(73) Assignee: Archemix Corp., Cambridge, MA (US)

( * ) Notice: Subject to any disclaimer, the term of this patent is extended or adjusted under 35 U.S.C. 154(b) by 482 days.

(21) Appl. No.: 10/215,982

(22) Filed: Aug. 9, 2002

(65) Prior Publication Data

US 2004/0219523 A1 Nov. 4, 2004

Related U.S. Application Data

(63) Continuation-in-part of application No. 09/952,680, filed on Sep. 13, 2001, now abandoned.

(60) Provisional application No. 60/391,719, filed on Jun. 26, 2002, provisional application No. 60/385,097, filed on May 31, 2002, provisional application No. 60/376,744, filed on May 1, 2002, provisional application No. 60/369,887, filed on Apr. 4, 2002, provisional application No. 60/367,991, filed on Mar. 25, 2002, provisional application No. 60/364,486, filed on Mar. 13, 2002, provisional application No. 60/349,959, filed on Jan. 18, 2002, provisional application No. 60/338,186, filed on Nov. 13, 2001, provisional application No. 60/313,932, filed on Aug. 21, 2001, provisional application No. 60/311,378, filed on Aug. 9, 2001, provisional application No. 60/232,454, filed on Sep. 13, 2000.

(51) Int. Cl.
*C12Q 1/00* (2006.01)
*C12Q 1/68* (2006.01)
*C07H 19/00* (2006.01)

(52) U.S. Cl. ............... 435/4; 435/6; 536/22.1
(58) Field of Classification Search ............ 435/4, 435/6; 536/22.1
See application file for complete search history.

(56) References Cited

U.S. PATENT DOCUMENTS

| | | | |
|---|---|---|---|
| 4,577,109 A | 3/1986 | Hirschfeld | 250/461.1 |
| 4,594,319 A | 6/1986 | Sharma | 435/7 |
| 4,762,799 A | 8/1988 | Seitz et al. | 436/79 |
| 4,822,746 A | 4/1989 | Walt | 436/528 |
| 4,929,561 A | 5/1990 | Hirschfeld | 436/116 |
| 5,037,615 A | 8/1991 | Kane | 422/82.08 |
| 5,437,840 A | 8/1995 | King et al. | 422/82.08 |
| 5,491,063 A | 2/1996 | Fisher et al. | 435/6 |
| 5,496,698 A | 3/1996 | Draper et al. | |
| 5,525,468 A | 6/1996 | McSwiggen | |
| 5,583,020 A | 12/1996 | Sullivan | |
| 5,585,245 A | 12/1996 | Johnsson et al. | 435/7.1 |
| 5,587,293 A | 12/1996 | Kauvar et al. | 435/7.21 |
| 5,589,332 A | 12/1996 | Shih et al. | |
| 5,610,052 A | 3/1997 | Thompson et al. | |
| 5,616,488 A | 4/1997 | Sullivan et al. | |
| 5,616,490 A | 4/1997 | Sullivan et al. | |
| 5,627,053 A | 5/1997 | Usman et al. | |
| 5,631,359 A | 5/1997 | Chowrira et al. | |
| 5,631,360 A | 5/1997 | Usman et al. | |
| 5,639,647 A | 6/1997 | Usman et al. | |
| 5,646,020 A | 7/1997 | Swiggen et al. | |
| 5,648,269 A | 7/1997 | Lakowicz et al. | 436/68 |
| 5,672,501 A | 9/1997 | Matulic-Adamic et al. | |
| 5,672,511 A | 9/1997 | Beigelman et al. | |
| 5,686,599 A | 11/1997 | Tracz | |
| 5,700,923 A | 12/1997 | Goodchild et al. | 536/23.1 |
| 5,716,824 A | 2/1998 | Beigelman et al. | |
| 5,741,462 A | 4/1998 | Nova et al. | 422/68.1 |
| 5,750,390 A | 5/1998 | Thompson et al. | |
| 5,756,291 A | 5/1998 | Griffin et al. | 435/6 |
| 5,763,175 A | 6/1998 | Brenner | 435/6 |
| 5,763,263 A | 6/1998 | Dehlinger | 435/287 |
| 5,767,263 A | 6/1998 | Usman et al. | |
| 5,776,782 A | 7/1998 | Tsuji | 436/171 |
| 5,780,272 A | 7/1998 | Jarrell | 435/91.31 |
| 5,783,425 A | 7/1998 | Dudycz et al. | |
| 5,801,158 A | 9/1998 | Thompson et al. | |
| 5,807,743 A | 9/1998 | Stinchcomb et al. | |

(Continued)

FOREIGN PATENT DOCUMENTS

WO    WO 95/06731    3/1994

(Continued)

OTHER PUBLICATIONS

Basararsky, et al., in Microarray Biochip Technology, ed. by M. Schena, Eaton Publishing Co., 2000, Natick, MA, pp. 265-284.

(Continued)

*Primary Examiner*—Ethan Whisenant
(74) *Attorney, Agent, or Firm*—Mintz, Levin, Cohn, Ferris, Glovsky and Popeo, P.C.; Ivor R. Elrifi

(57) ABSTRACT

Methods for engineering a nucleic acid sensor molecule are provided. Biosensors comprise a plurality of nucleic acid sensor molecules labeled with a first signaling moiety and a second signaling moiety. The nucleic acid sensor molecules recognizes target molecules which do not naturally bind to DNA. Binding of a target molecule to the sensor molecules triggers a change in the proximity of the signaling moieties which leads to a change in the optical properties of the nucleic acid sensor molecules on the biosensor. Reagents and systems for performing the method are also provided. The method is useful in diagnostic applications and drug optimization.

54 Claims, 90 Drawing Sheets

U.S. PATENT DOCUMENTS

| | | | |
|---|---|---|---|
| 5,811,300 A | 9/1998 | Sullivan et al. | |
| 5,831,071 A | 11/1998 | Usman et al. | |
| 5,834,186 A | 11/1998 | George et al. | |
| 5,840,876 A | 11/1998 | Beigelman et al. | |
| 5,843,658 A | 12/1998 | Uchiyama et al. | 435/6 |
| 5,861,288 A | 1/1999 | Usman et al. | |
| 5,866,348 A | 2/1999 | Scheirer | 435/8 |
| 5,877,022 A | 3/1999 | Stinchcomb et al. | |
| 5,879,938 A | 3/1999 | Usman et al. | |
| 5,891,683 A | 4/1999 | Usman et al. | |
| 5,891,684 A | 4/1999 | Usman et al. | |
| 5,902,880 A | 5/1999 | Thompson | |
| 5,962,675 A | 10/1999 | Beigelman et al. | |
| 5,977,343 A | 11/1999 | Tracz | |
| 5,985,621 A | 11/1999 | Usman et al. | |
| 5,998,203 A | 12/1999 | Matulic-Adamic et al. | |
| 6,016,195 A | 1/2000 | Peters | 356/342 |
| 6,046,165 A | 4/2000 | Laughon et al. | 514/12 |
| 6,048,709 A | 4/2000 | Falb | 435/69.1 |
| 6,051,380 A | 4/2000 | Sosnowski et al. | 435/6 |
| 6,054,558 A | 4/2000 | Falb et al. | 530/350 |
| 6,060,252 A | 5/2000 | Hellyer et al. | 435/6 |
| 6,063,566 A | 5/2000 | Joyce | 435/6 |
| 6,087,477 A | 7/2000 | Falb et al. | 530/350 |
| 6,093,555 A | 7/2000 | Dudycz et al. | |
| 6,103,890 A | 8/2000 | Jarvis et al. | |
| 6,117,657 A | 9/2000 | Usman et al. | |
| 6,127,173 A | 10/2000 | Eckstein et al. | |
| 6,127,535 A | 10/2000 | Beigelman et al. | |
| 6,140,491 A | 10/2000 | Usman et al. | |
| 6,146,886 A | 11/2000 | Thompson | |
| 6,159,951 A | 12/2000 | Karpeisky et al. | |
| 6,183,959 B1 | 2/2001 | Thompson | |
| 6,194,150 B1 | 2/2001 | Stinchcomb et al. | |
| 6,201,113 B1 | 3/2001 | Todd et al. | |
| 6,248,878 B1 | 6/2001 | Matulic-Adamic et al. | |
| 6,251,666 B1 | 6/2001 | Beigelman | |
| 6,300,483 B1 | 10/2001 | Ludwig et al. | |
| 6,316,612 B1 | 11/2001 | Matulic-Adamic et al. | |
| 6,346,398 B1 | 2/2002 | Pavco et al. | |
| 6,353,098 B1 | 3/2002 | Usman et al. | |
| 6,362,323 B1 | 3/2002 | Usman et al. | |
| 6,365,374 B1 | 4/2002 | Usman et al. | |
| 6,379,954 B1 | 4/2002 | Dudycz et al. | |
| 6,395,713 B1 | 5/2002 | Beigelman et al. | |

FOREIGN PATENT DOCUMENTS

| | | |
|---|---|---|
| WO | WO 94/29452 | 12/1994 |
| WO | WO 95/11304 | 4/1995 |
| WO | WO 95/13378 | 5/1995 |
| WO | WO 95/13379 | 5/1995 |
| WO | WO 95/13380 | 5/1995 |
| WO | WO 95/23225 | 8/1995 |
| WO | WO 96/09392 | 3/1996 |
| WO | WO 96/18736 | 6/1996 |
| WO | WO 96/27026 | 6/1996 |
| WO | WO 97/10328 | 3/1997 |
| WO | WO 97/15662 | 5/1997 |
| WO | WO 97/26270 | 7/1997 |
| WO | WO 98/08974 | 3/1998 |
| WO | WO 98/24913 | 6/1998 |
| WO | WO 98/27104 | 6/1998 |
| WO | WO 98/33893 | 8/1998 |
| WO | WO 98/35058 | 8/1998 |
| WO | WO 98/43993 | 10/1998 |
| WO | WO 98/50530 | 11/1998 |
| WO | WO 99/31276 | 6/1999 |
| WO | WO 99/47704 | 9/1999 |
| WO | WO 99/50277 | 10/1999 |
| WO | WO 00/04141 | 1/2000 |
| WO | WO 00/17346 | 3/2000 |
| WO | WO 00/61729 | 10/2000 |
| WO | WO 00/70329 | 11/2000 |
| WO | WO 01/16312 | 3/2001 |
| WO | WO 01/57206 | 8/2001 |
| WO | WO 01/66721 | 9/2001 |
| WO | WO 02/22882 | 3/2002 |

OTHER PUBLICATIONS

Beaudet et al., Genome Res. 11: 600-608 (2001).
Bell, et al., J Biol Chem 273: 14309-14314 (1998).
Berzal-Herranz, et al., Genes and Development, 6(1):129-134 (1992).
Bianchini, et al., J Immunol Methods 252: 191-197 (2001).
Bloom, and Beavo, Proc. Natl. Acad. Sci. U S A 93: 14188-14192 (1996).
Bock, et al., Nature 355: 564-566 (1992).
Bolger, et al., Biochem J. 328: 539-548 (1997).
Chan, et al., J. Colloid and Interface Sci. 203:197-207 (1998).
Coleman, et al., Biochemistry 37(41): 14376-14385 (1998).
Soukup, and Breaker, Proc. Natl. Acad. Sci. USA 96: 3584-3589 (1999).
Cooper, et al., Biochemistry 29: 9261-9268 (1990).
Cox, et al. Biotechnology Progress, Nov.-Dec., 1998 14: 845-850.
DeRisi, et al., Science 278: 680-686 (1997).
Ellington, and Szostak, Nature 346: 818-822 (1990).
Fehrentz, et al., Biochem. Biophys. Res. Commun. 188: 865-872 (1992).
Gold, et al., Annual Review of Biochemistry 64: 763-797 (1995).
Gold, et al., Proc. Natl. Acad. Sci. 94: 59-64 (1997).
Griffiths, et al., EMBO. J 13: 3245-3260 (1994).
Goueli, et al., Methods Enzymol 333: 16-27(2001).
Green, and Szostak, Science, Dec. 18, 1992 258(5090):1910-1915.
Hamaguchi, N. et al., Anal. Biochem. 294: 126-131 (2001).
Heath, et al., in Cell Signalling: Experimental Strategies, ed. Reid, E., Cook, G.M.W., and Luzio, J.R.,: 193-194 (1999).
Heller and Morrison, in Rapid Detection and Identflcation of Infections Agents, Academic ress, Inc., San Diego, Calif.,: 245-256 (1985).
Heller, et al., in DNA Microarrays: A Practical Approach, ed. by M. Schena, Oxford University Press, Oxford : 187-202 (1999).
Jellinek, et al., Biochemistry 34: 11363-11372 (1995).
Jenne, et al., Nature Biotechnology, 19(1): 56-61 (2001).
Jenison, et al., Science, 263: 1425-1429 (1994).
Joyce, in Molecular Biology of RNA: UCLA Symposia on Molecular and Cellular Biology, ed. T. R.Cech , Liss, N.Y.:361-371 (1989).
Koizumi, et al., Nat Struct Biol 6(11): 1-10 (1999).
Koizumi, et al., Nucleic Acids Symp Ser 42: 275-276 (1999).
Kraus, et al., Journal of Immunology 160: 5209-5212 (1998).
Burns, et al., Science 282: 484-487 (1998).
Kubik, et al., Nucleic Acids Res. 22(13): 2619-2626 (1994).
Lin, et al. Nucleic Acids Res. 22: 5229-5234 (1994).
Liu, and Tan, Anal. Chem. 71: 5054-5059 (1999).
Chee, et al., Science, 274: 610-614 (1996).
Tang, and Breaker, Chemistry & Biology 4(6): 453-459 (1997).
Morrison, in Nonisotopic DNA Probe Techniques, Kricka, ed., Academic Press, Inc., San Diego, CA, chapter 13 (1992).
Obata, et al., J Biol Chem 275(46): 36108-36115 (2000).
Pagratis, et al., Nat. Biotechnol. 15: 68-73 (1997).
Pieken, et al., Science 253: 314-317 (1991).
Pillai, et al., Proc Natl Acad Sci USA 90: 11970-11974 (1993).
Potyrailo, et al., Anal Chem, 70(16): 3419-3425 (1998).
Robertson, and Joyce, Nature 344(6265):467-468 (1990).
Robertson, and Ellington, Nucleic Acids Res. 28(8):1751-1759 (2000).
Schena, and Davis, in Microarray Biochip Technology, ed. by M. Schena, Eaton Publishing Co., Natick, MA: 1-18: (2000).
Schermer, in DNA Microarrays: A Practical Approach, ed. by M. Schena, Oxford University Press, Oxford, 17-42: (1999).
Schluep, and Cooney, Bioseparation 7: 317-326 (1999).
Seelig , and Jaschke, Chemistry and Biology, 6(3): 167-76 (1999).
Seetherman, et al., Nature Biotech. 19:336-341 (2001).

Service, Science 282: 399-401 (1998).
Seiwert, et al., Chem Biol 7(11): 833-843 (2000).
Simone, et al., Trends Genet 14(7): 272-276 (1998).
Singh, et al., RNA 5: 1348-1356 (1999).
Singh, et al., BioTechniques 29: 344-351 (2000).
Sirinarumitr, et al., Mol Cell Probes 11: 273-280 (1997).
Sokol, et al., Proc. Natl. Acad. Sci. 95: 11538-11543 (1998).
Soukup, et al., Journal of Molecular Biology 298: 623-632 (2000).
Sproat, et al., Nuci. Acid Res. 19: 733-.738 (1991).
Soukup, et al., RNA 7: 524-536 (2001).
Weeks, et al., Current Opinion in Structural Biology 7(3): 336-342 (1997).
Tasset, et al., J Mol Biol, 272: 688-698 (1997).
Tuerk, and Gold, Science 249: 505-510 (1990).
Taylor, et al., Methods Enzymol. 333: 333-342 (2001).
Tyagi, et al., Nature Biotechnology 14: 303-308 (1996).
Walter, and Burke, RNA 3: 392-402 (1997).
Walter, et al., The EMBO Journal 17: 2378-2391 (1998).
Williams, et al., Nucleic Acids Research, 22(11): 2003-2009 (1994).
Wilson, and Szostak, Nature 374: 777-782 (1995).
Zammatteo, et al., Anal. Biochem. 280:143-150 (2000).
Zhang, et al., Nature 390: 96-100 (1997).
Fitzwater and Polisky., Methods in Enzymology. 267: 275-301 (1996).
Golden, et al., Journal of Biotechnology. 81(2-3): 167-178 (2000).
Ringquist, et al., Cytometry. 33(4): 394-405 (1998).
Wallace, et al., European Biophysics Journal. 29(4-5): 254 (2000).
Yamamoto, et al., Genes to Cells. 5(5): 389-396 (2000).
International Search Report for PCT/US01/28835. Mailed on Jan. 13, 2003.
Tuschl, et al. (1994). Science 266: 785-789.
Haseloff and Gerlach (1988). Nature 334: 585-591.
International Search Report for PCT/US 02/25319, mailed Jul. 17, 2003.
Andersson et al. *J. Urol.*, 161(5):1707-1712 (1999).
Arora et al. *J. Cell. Physiol.*, 167(3):434-442 (1996).
Ballard et al. *J. Urol.*, 159(6):2164-2171 (1998).
Barlocco et al. *J. Med. Chem.*, 44(15):2403-2410 (2001).
Berzas-Nevado et al. *Electrophoresis*, 22(10):2004-2009 (2001).
Breaker R.R. *Curr. Opin. Biotech.*, 7:442-448 (1996).
Breaker R.R. *Chem. Rev.*, 97:371-390 (1997).
Breaker R.R. *Curr. Opin. Chem. Biol.*, 1:26-31 (1997).
Breaker R.R. *Nat. Biotech.*, 15:427-131 (1997).
Breaker R.R. Intracellular Ribozyme Applications in Principles and Protocols, pp. 1-19; Horizon Scientific Press, Wymondham UK, Rossi and Couture, eds., (1999).
Breaker R.R. *Curr. Opin. Biotech.*, 13:31-39 (2002).
Bruchez et al. *Science*, 281:2013-2016 (1998).
Burns et al. *Science*, 282:484-487 (1998).
Burt et al. *J. Biol. Chem.*, 273(17):10367-10375 (1998).
Caceci et al. *BYTE*, 9(5):340-362 (1984).
Carmi et al. *Chem. & Biol.*, 3:1039-1046 (1996).
Chan et al. *Science*, 281:2016-2018 (1998).
Chee et al. *Science*, 274:610-614 (1996).
Chen et al. *Proc. Natl. Acad. Sci. USA*, 90:4528-4532 (1993).
Ciesiolka et al. *Methods in Enzymology*, 267:315-335 (1996).
Conti M. *Mol. Endocrinol.*, 14(9):1317-1327 (2000).
Cotten et al. *Nucl. Acids Res.*, 19(10):2629-2635 (1991).
Drews J. *Science*, 287:1960-1964 (2000).
Emorine et al. *Proc. Natl. Acad. Sci. USA*, 84:6995-6999 (1987).
Fedor et al. *Proc. Natl. Acad. Sci. USA*, 87:1668-1672 (1990).
Franke et al. *EMBO J.*, 16(2):252-259 (1997).
Froehler B.C. *Tet. Lett.*, 27(46):5575-5578 (1986).
Froehler et al. *Nucl. Acids Res.*, 14(13):5399-5407 (1986).
Ghanouni et al. *Proc. Natl. Acad. Sci. USA*, 98(11):5997-6002 (2001).
Gold L. *Nat. Biotech.*, 20: 671-672 (2002).
Greene et al. *Science*, 231:1150-1154 (1986).
Guatelli et al. *Proc. Natl. Acad. Sci. USA*, 87:1874-1878 (1990).
Hampe et al. *Biotechnol.*, 77(203):219-234 (2000).
Hampel et al. *Biochem.*, 28(12):4929-4933 (1989).
Han et al. *Nat. Biotechnol.*, 19(7):631-635 (2001).
Hartig et al. *Nat. Biotech.*, 20:717-722 (2002).
Hirose et al. *Tet. Lett.*, 28:2449-2452 (1978).
Hobbs et al. *Biochem.*, 12(25):5138-5145 (1973).
Horinouchi et al. *Pharmacol.*, 62(2):98-102 (2001).
Hu et al. *J. Med. Chem.*, 44(9):1456-1466 (2001).
Jameson et al. *Methods in Enzymology*, 246:283-300 (1995).
Jameson et al. *Methods*, 19(2):222-233 (1999).
Jeremy et al. *Br. J. Urol.*, 79(6):958-963 (1997).
Jhaveri et al. *J. Am. Chem. Soc.*, 122(11):2469-2473 (2000).
Koizumi et al. *FEBS Lett.*, 239(2):285-288 (1988).
Kozasa et al. *J. Biol. Chem.*, 270(4):1734-1741 (1995).
Kwoh et al. *Proc. Natl. Acad. Sci. USA*, 86:1173-1177 (1989).
Lakowicz et al. *Rev. Sci. Instrum.*, 62(7):1727-1734 (1991).
Large et al. *J. Clin. Invest.*, 100(12):3005-3013 (1997).
Lee et al. *Methods in Enzymology*, 237:146-164 (1994).
Li et al. *J. Biol. Chem.*, 273(26):16265-16272 (1998).
Li et al. *Curr. Opin. Struct. Biol.*, 9:315-323 (1999).
Li et al. *Proc. Natl. Acad. Sci. USA*, 96:2746-2751 (1999).
Mace et al. *Microarray Biochip Technology*, ed. by M. Schena, Eaton Publishing Co., Natick, MA, pp. 39-64 (2000).
Mansour et al. *Biochem.*, 35(48):15529-15536 (1996).
Marshall et al. *Nat. Struct. Biol.*, 6(11):992-994 (1999).
Min et al. *J. Biol. Chem.*, 268(13):9400-9404 (1993).
Min et al. *Int. J. Impot. Res.*, 12(Suppl. 3):S32-S39 (2000).
Monroe et al. *Immunity*, 11(2):201-212 (1999).
Moreland et al. *Life Sci.*, 62(20):309-318 (1998).
Morrison et al. *Anal. Biochem.*, 183(2):231-244 (1989).
Müller et al. *Trends Pharmacol. Sci.*, 17(8):294-298 (1996).
Nagaoka et al. *Diabetes*, 47(7):1135-1144 (1998).
Nagatomo et al. *Cardiovasc. Drug Rev.*, 19(1):9-24 (2001).
Nasir et al. *Comb. Chem. High Throughput Screen.*, 2(4):177-190 (1999).
Obemolte et al. *Biochim. Biophys. Acta*, 1353(3):287-297 (1997).
O'Shannessy D.J. *J. Chromatography*, 510:13-21 (1990).
Pei et al. *Proc. Natl. Acad. Sci. USA*, 91:2699-2702 (1994).
Proudnikov et al. *Nucl. Acids Res.*, 24(22):4535-4532 (1996).
Ramsay et al. *Br. J. Pharmacol.*, 133(2):315-323 (2001).
Richter et al. *Protein Expr. Purif.*, 19(3):375-383 (2000).
Robberson et al. *Biochem.*, 11(4):533-537 (1972).
Robertson et al. *Nat. Biotech.*, 17:62-66 (1999).
Robertson et al. *Nat. Biotech.* 19:650-655 (2001).
Robinson et al. *Lancet*, 357:2007-2011 (2001).
Ruhn et al. *J. Chromatography A*, 669(1-2):9-19 (1994).
Saiki et al. *Science*, 230:1350-1354 (1985).
Saiki et al. *Science*, 239:487-491 (1988).
Sako et al. *Nat. Cell Biol.*, 2(3):168-172 (2000).
Sassanfar et al. *Nature*, 364:550-553 (1993).
Sheppard et al. *Proc. Natl. Acad. Sci. USA*, 80:233-236 (1983).
Shiau et al. *Cell*, 95(7):927-937 (1998).
Sood et al. *Nucl. Acids Res.*, 4(8):2757-2765 (1977).
Soukup et al. *RNA*, 5:1308-1325 (1999).
Soukup et al. *Structure*, 7(7):783-791 (1999).
Soukup et al. *Tren. Biotech.*, 17:469-476 (1999).
Soukup et al. in *Ribozyme Biochem. Biotech.*, Eaton Publishing, Chapter 8, pp. 149-170, Krupp & Gaur, eds. (2000).
Stanton et al. *Eur. J. Pharmacol.*, 320(2-3):267-275 (1997).
Stanton et al. Poster Presentation at the National Cancer Institute Innovative Molecular Analysis Technologies Program Meeting, Jul. 6-8, Chantilly, Virginia (2000).
Tang et al. *Nucl. Acids Res.*, 26(18):4214-4221 (1998).
Tang et al. *RNA*, 3:914-925 (1997).
Truskey et al. *J. Cell Sci.*, 103:491-499 (1992).
Tyagi et al. *Nature Biotech.*, 16:49-53 (1998).
Uhlenbeck O.C. *Nature*, 328:596-600 (1987).
Usman et al. *J. Clin. Invest.*, 106(10):1197-1202 (2000).
Wang et al. *Biochem. Biophys. Res. Commun.*, 234(2):320-324 (1997).
Wenzel-Seifert et al. *Mol. Pharmacol.*, 58(5):954-966 (2000).
Wu et al. *Anal. Biochem.*, 218(1):1-13 (1994).
Wu et al. *Nucl. Acids Res.*, 24(17):3472-3473 (1996).
International Search Report for PCT/US02/25319, mailed Jul. 13, 2004.
Vaish et al. *Nature Biotechnology*, published online Jul. 15, 2002, pp. 1-6.

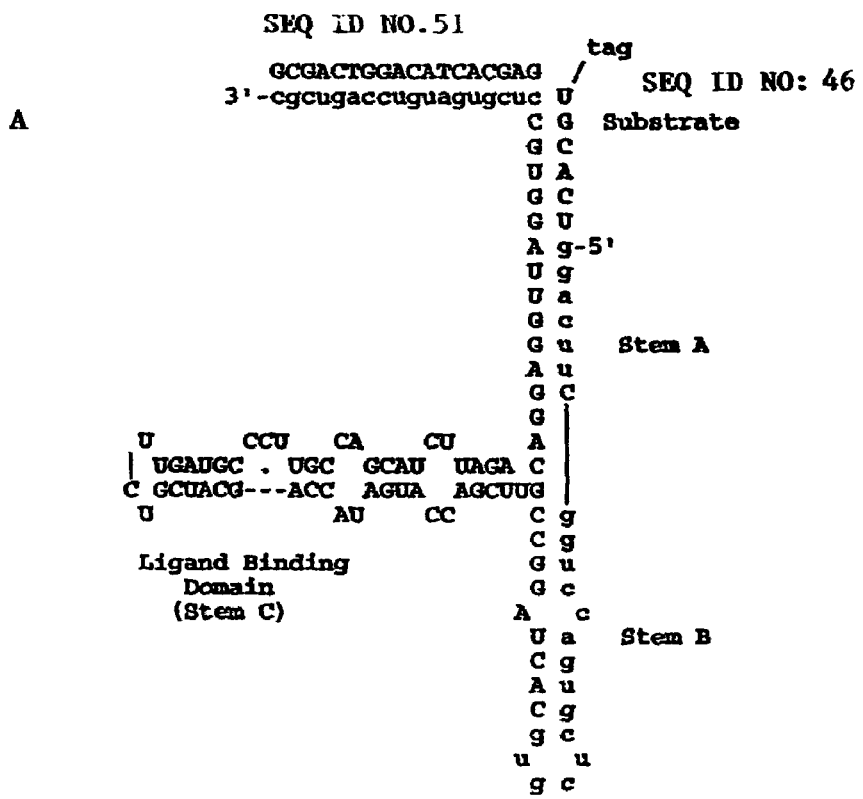
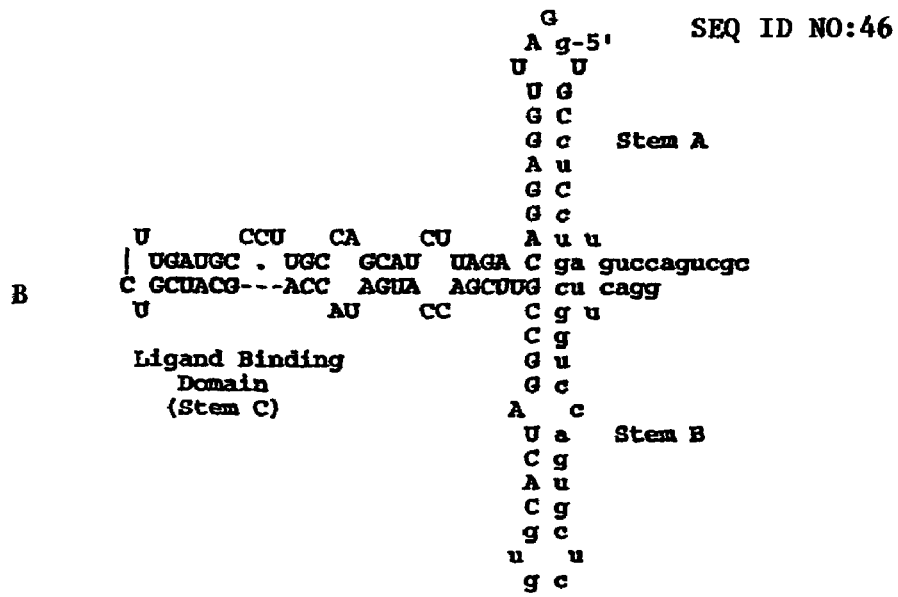
FIGURE 2

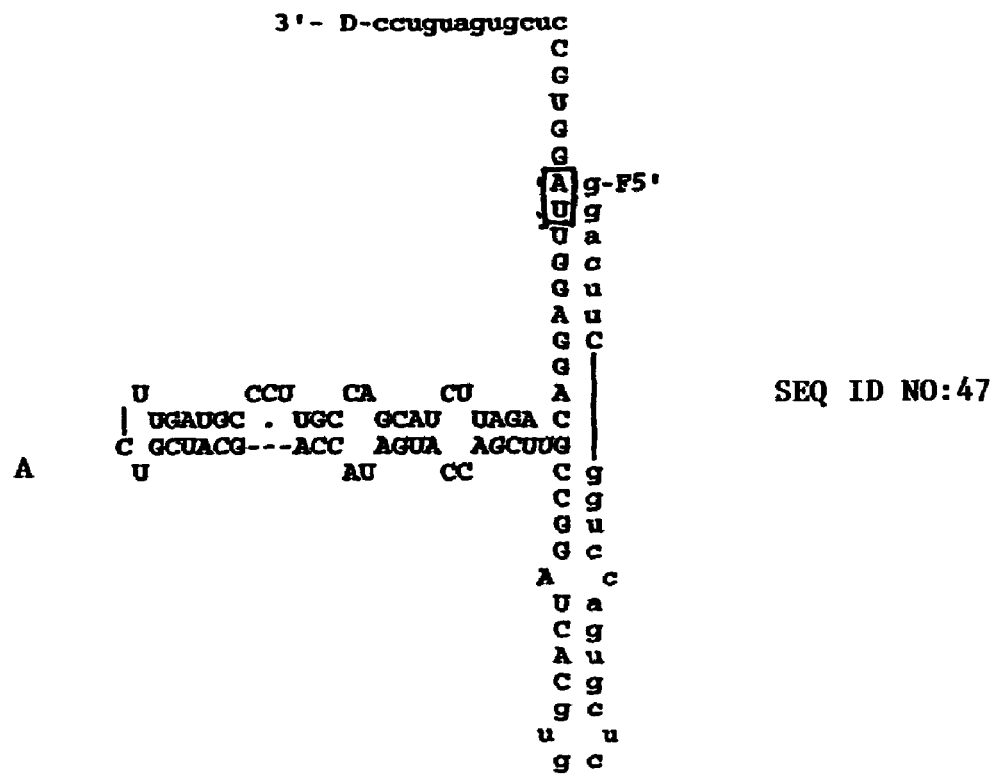
UNQUENCHED LIGAND-BOUND FORM
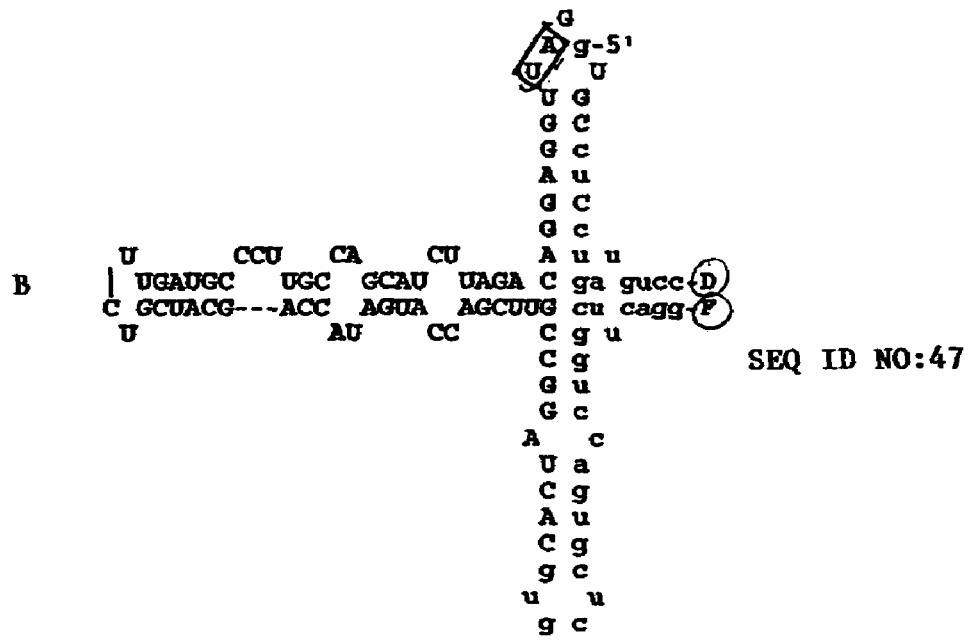
QUENCHED NO-LIGAND FORM
FIGURE 3

A
```
      A    CC      CA
    A GGC UUGG  GUGGUAU -D
    A CCG AACC  A-F
      G    --      AU
```
SEQ ID NO:49

UNQUENCHED LIGAND-BOUND FORM

B
```
       CC      GA
     G UUGGC UGGUAU-D
     G AGCCG ACCAUA-F
     AA      -A
```
SEQ ID NO:49

QUENCHED NO-LIGAND FORM

FIGURE 6

Figure 13
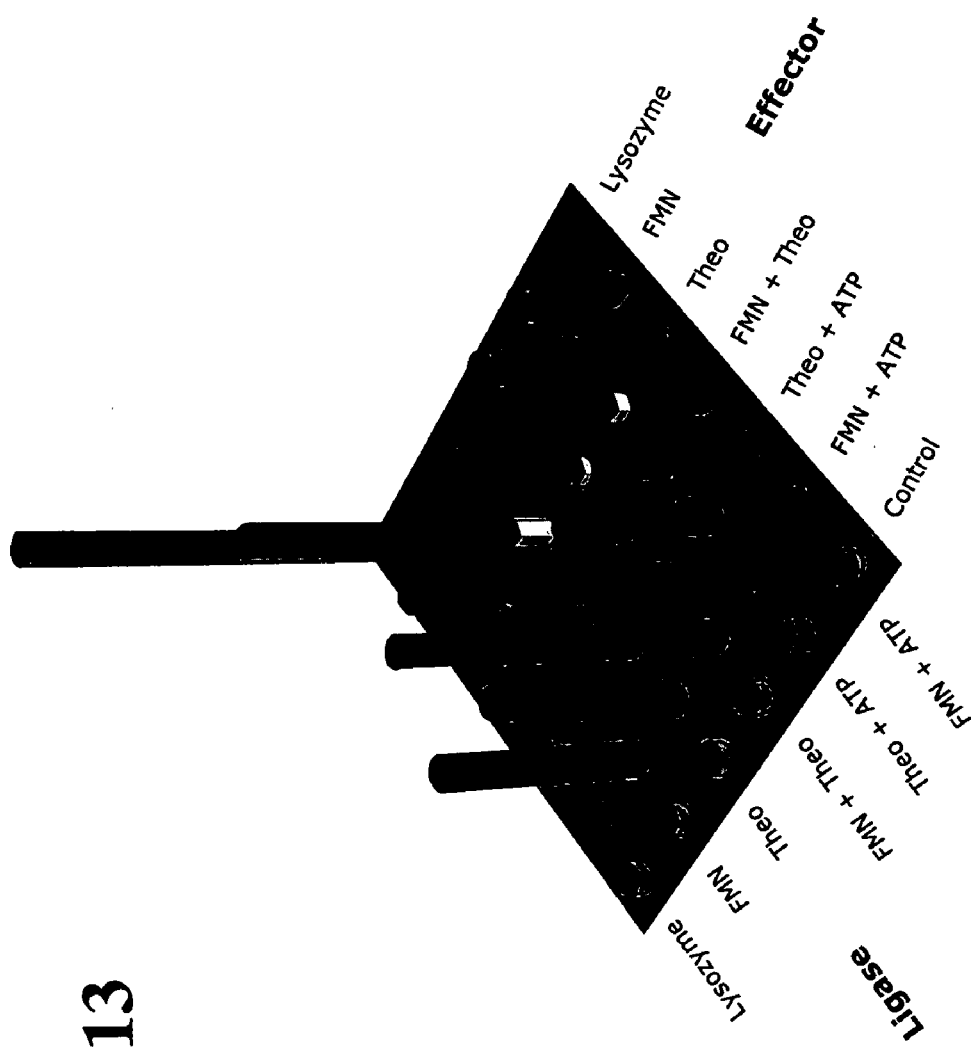
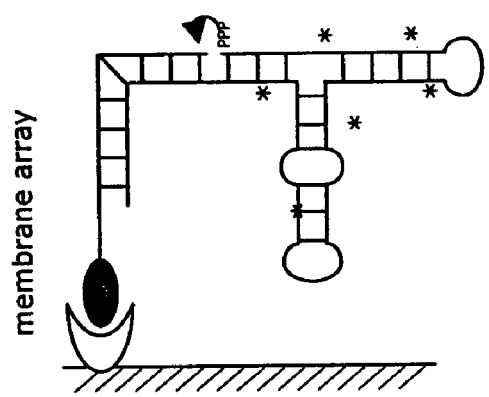

SEQ ID NO:80

| | top -5' NNNN 3'<br>bottom-3' NNNN 5' | Activity |
|---|---|---|
| 1-14 | ACGU<br>GCUGG | +++ |
| 1-13 | UACGU<br>UUCU | +++ |
| 1-2 | ACGU<br>UUCC | ++ |
| 1-6 | ACGU<br>UAUC | + |
| 2-7 | CAGU<br>UUCC | +++ |
| 2-2 | CUAG<br>AUCC | + |
| 2-3 | UUAA<br>UCAA | + |
| 2-13 | CUGG<br>AAAU | + |
| 2-14 | GAUC<br>UUUU | + |
| 2-20 | UUAA<br>AGCG | + |

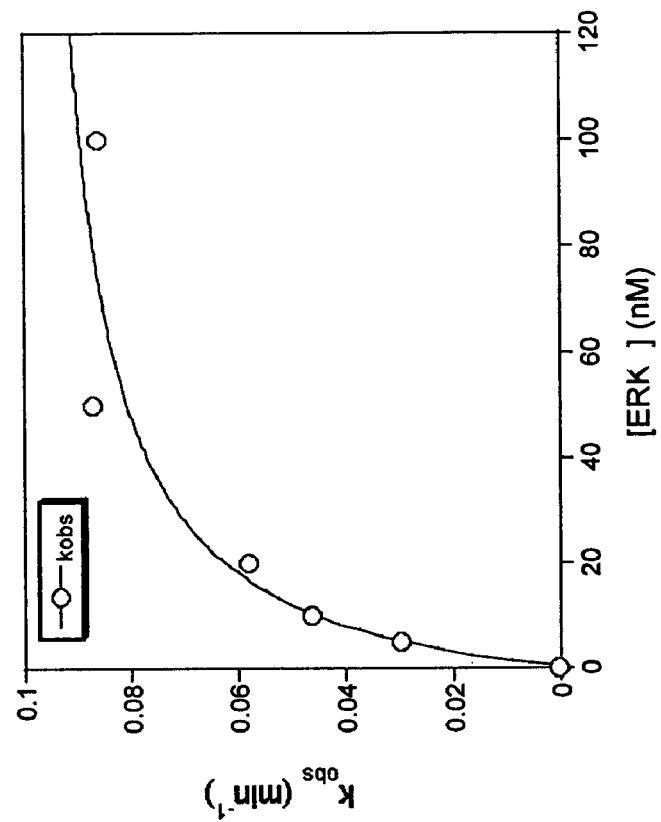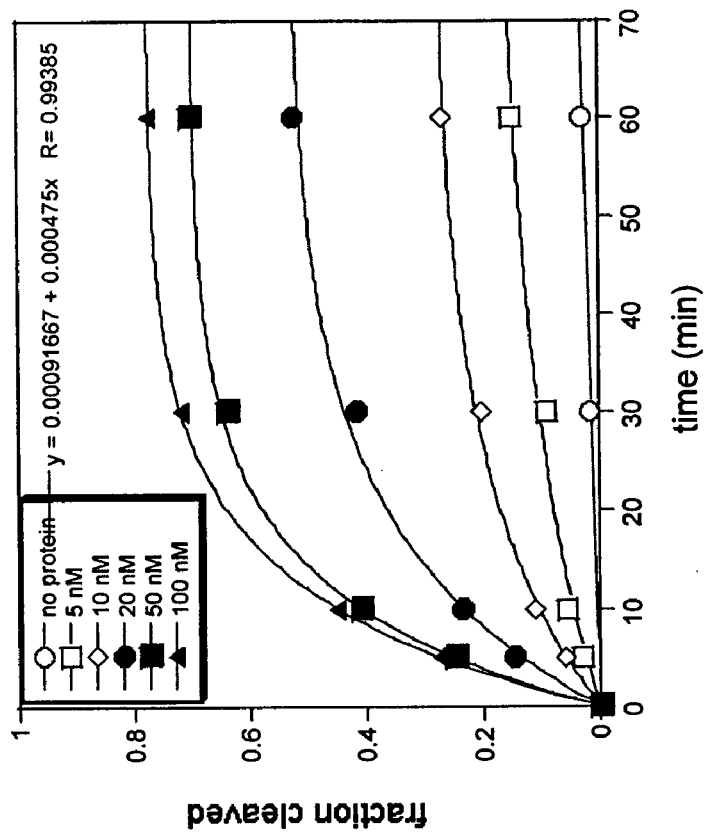
Figure 21

Construct 6 SEQ ID NO: 81
GGGCGACCCUGAUGAGUCAGAGACGCAGACGCUAGCGAAUUGGUUCCUCGAAAGGGGAAAGCGUUAUUAAGAAACCAAAAUGUUACGAAACGGUGAAAGGCCGUAGGUUGCC
Construct 7 SEQ ID NO: 82
GGGCGACCCUGAUGAGUCACGAGACGCAGACGCUAGCGAAUUGGUUCCUCGAAAGGGGAAAGCGUUAUUAAGAAACCAAAAUUGUUACGAAACGGUGAAAGGCCGUAGGUUGCC
Construct 8 SEQ ID NO: 83
GGGCGACCCUGAUGAGUCACGCAGACGCAGACGCUAGCGAAUUGGUUCCUCGAAAGGGGAAAGCGUUAUUAAGAAACCAAAAUGUUCGAAACGGUGAAAGGCCGUAGGUUGCC
Construct 9 SEQ ID NO: 84
GGGCGACCCUGAUGAGUCAGCGAGACGCUAGCGAAUUGGUUCCUCGAAAGGGGAAAGCGUUAUUAAGAAACCAAAAUGUUUACGAAACGGUGAAAGGCCGUAGGUUGCC
Construct 10 SEQ ID NO: 85
GGGCGACCCUGAUGAGUCACGCAGACGCUAGCGAAUUGGUUCCUCGAAAGGGGAAAGCGUUAUUAAGAAACCAAAAUGUUGCGAAACGGUGAAAGGCCGUAGGUUGCC
Construct 11 SEQ ID NO: 86
GGGCGACCCUGAUGAGUCACGCAGACGCUAGCGAAUUGGUUCCUCGAAAGGGGAAAGCGUUAUUAAGAAACCAAAAUGUCGAAACGGUGAAAGGCCGUAGGUUGCC
Construct 12 SEQ ID NO: 87
GGGCGACCCUGAUGAGCCUUGCAGACGCUAGCGAAUUGGUUCCUCGAAAGGGGAAAGCGUUAUUAAGAAACCAAAAUGUACGAAACGGUGAAAGGCCGUAGGUUGCC
Construct 13 SEQ ID NO: 88
GGGCGACCCUGAUGAGUGGGCAGACGCUAGCGAAUUGGUUCCUCGAAAGGGGAAAGCGUUAUUAAGAAACCAAAAUGUCAUACGAAACGGUGAAAGGCCGUAGGUUGCC
Construct 14 SEQ ID NO: 89
GGGCGACCCUGAUGAGUCUGGCAGACGCUAGCGAAUUGGUUCCUCGAAAGGGGAAAGCGUUAUUAAGAAACCAAAAUGUCUACGAAACGGUGAAAGGCCGUAGGUUGCC

| | sequences | activity | stability |
|---|---|---|---|
| Construct 6 | GUGUUA CGCACU | ++ | -32.41Kcal |
| Construct 7 | UGUUA GCACU | Constitutively active | -29.11Kcal |
| Construct 8 | GUGUU CGCAC | Constitutively active | No predicted duplex formation |
| Construct 9 | GUUUA CGACU | Constitutively active | -29.41Kcal |
| Construct 10 | GUGUUG CGCACU | ++ | -32.7Kcal |
| Construct 11 | GUG CGU | Constitutively active | -30.71Kcal |
| Construct 12 | GUACGU CGUUCC | +++ | No predicted duplex formation |
| Construct 13 | GUCAUA CGGUCU | Constitutively active | -32.41Kcal |
| Construct 14 | GUCUUA CGGUCU | Constitutively active | No predicted duplex formation |

Sequences of ERK-modulated ligase nucleic acid sensor molecules

DG.20.58A   SEQ ID NO: 109   construct 17
GGACUUCGGCGAAAGCCGUUCGACCACGCUAAGGAGGAUUUCCGAAAGCGGCUACGGUCCGCCAGUGUCUUAGACAG
GAGGUUAGGUGCCGUCCGACUGAUCUCGGAGUUAAACG DG.20.58B   SEQ ID NO: 110   construct 18
GGACUUCGGCGAAAGCCGUUCGACCAGCGUAAGGAGGAUUUCCGAAAGCGGCUACGGUCCGCCAGUUCUUAGACAGGA
GGUUAGGUGCCGUCCGACUGAUCUCGGAGUUAAACG DG.20.58C   SEQ ID NO: 112   construct 20
GGACUUCGGCGAAAGCCGUUCGACCACGGUAAGGAGGAUUUCCGAAAGCGGCUACGGUCCGCCAUUGUCUUAGACAG
GAGGUUAGGUGCCGUCCGACUGAUCUCGGAGUUAAACG DG.20.58D   SEQ ID NO: 113   construct 21
GGACUUCGGCGAAAGCCGUUCGACCACCUUAAGGAGGAUUUCCGAAAGCGGCUACGGUCCGCCACGUUCUUAGACAG
GAGGUUAGGUGCCGUCCGACUGAUCUCGGAGUUAAACG DG.20.58E   SEQ ID NO: 111   construct 19
GGACUUCGGCGAAAGCCGUUCGACCAGCGUAAGGAGGAUUUCCGAAAGCGGCUACGGUCCGCCAGCUCUUAGACAGGA
GGUUAGGUGCCGUCCGACUGAUCUCGGAGUUAAACG DG.20.58F   SEQ ID NO: 114   construct 22
GGACUUCGGCGAAAGCCGUUCGACCCGGUAAGGAGGAUUUCCGAAAGCGGCUACGGUCCGCCAGUGCUUAGACAGGA
GGUUAGGUGCCGUCCGACUGAUCUCGGAGUUAAACG DG.20.58G   SEQ ID NO: 115   construct 23
GGACUUCGGCGAAAGCCGUUCGACCGCUAAGGAGGAUUUCCGAAAGCGGCUACGGUCCGCCAGUCUUAGACAGGAGG
UUAGGUGCCGUCCGACUGAUCUCGGAGUUAAACG DG.20.58H   SEQ ID NO: 117   construct 25
GGACUUCGGCGAAAGCCGUUCGACCGUUCGACCGGUAAGGAGGAUUUCCGAAAGCGGCUACGGUCCGCCAUUGCUUAGACAGGA
GGUUAGGUGCCGUCCGACUGAUCUCGGAGUUAAACG DG.20.58I   SEQ ID NO: 118   construct 26
GGACUUCGGCGAAAGCCGUUCGACCCUUAAGGAGGAUUUCCGAAAGCGGCUACGGUCCGCCACGUCUUAGACAGGA
GGUUAGGUGCCGUCCGACUGAUCUCGGAGUUAAACG DG.20.58J   SEQ ID NO: 116   construct 24
GGACUUCGGCGAAAGCCGUUCGACCGCUAAGGAGGAUUUCCGAAAGCGGCUACGGUCCGCCAGCCUUAGACAGGAGG
UUAGGUGCCGUCCGACUGAUCUCGGAGUUAAACG

A     3-piece ligase platform         1-piece ligase platform

Construct 27
SEQ ID NO:108

Construct 28
SEQ ID NO:119

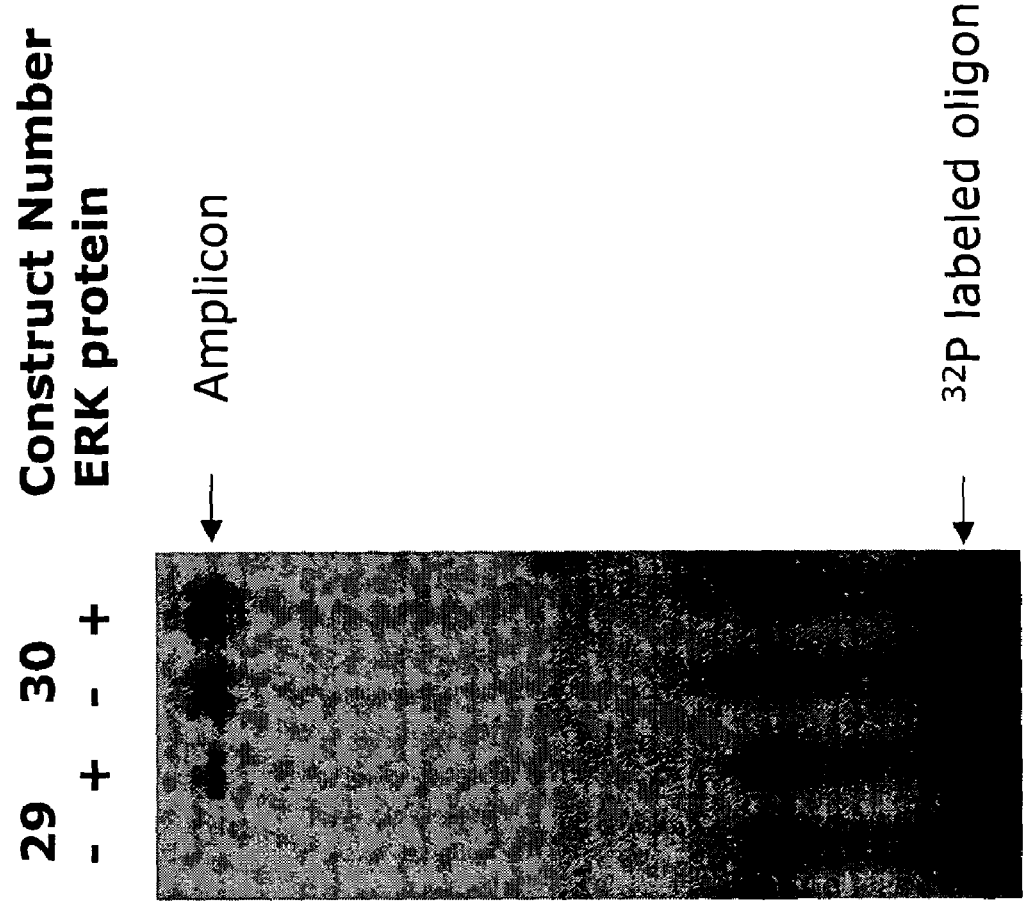

Effector-oligonucleotide-binding region

SEQ ID NO: 352

```
                                                              oligonucleotide substrate
                                    Sequence tag               SEQ ID NO: 350
GCAAAUUGAGGCUCUAGUCAGCCUGC  U                              
                          C-G                                
                          G-C                                
                          U-A    oligonucleotide
                          G-C                                
                          G U                                
                          A G — 5'
                          U-A                                
                          U-A                                
                          G-C                                
                          G-U                                
                          A-U                                
                          G-C                                
                          G  A                               
                          A  C —                             
                             CU  UAGA                        
                  UG NNN(N)U      AGCUU — G    C-G           
                  AC NNN(N)A  CC              C-G            
                                              G-C            
                                              A  G           
                                               AA            
      A   A                                                  
   A G A  C                                                  
   A A    A                                                  
   U A    A                                                  
     A A  GGGGAA  AGCGUU                                           
 A  CUCCUU  UCGCAG                                           
  G    G  A   C                                              
   G A    G C                                                
     U  AAG                                                  
```

3'

Target-modulation domain

Figure 41

Construct sequence Data

Constructs (these are RNA transcript sequences given as DNA sequences)

Construct 31 (TK.16.118.K) + SEQ ID NO: 121
GGACTTCGGCGAAAGCCGTTCGACCACGTCAGACGCTAGCGAATTGGTTCCTCGAAAGGGGAAAGCGTTATTAAGAAACCAAAATG
AGTGTCTTAGACAGGAGGTTAGGTGCGGCTTTGGTCCAAGGACATCTCGAAT Construct 32 (TK.16.118.L) + SEQ ID NO: 122
GGACTTCGGCGAAAGCCGTTCGACCAGTCAGACGCTAGCGAATTGGTTCCTCGAAAGGGGAAAGCGTTATTAAGAAACCAAAATGA
GTTCTTAGACAGGAGGTTAGGTGCGGCTTTGGTCCAAGGACATCTCGAAT Construct 33 (TK.16.118.M) ++ SEQ ID NO: 123
GGACTTCGGCGAAAGCCGTTCGACACGGTCAGACGCTAGCGAATTGGTTCCTCGAAAGGGGAAAGCGTTATTAAGAAACCAAAATG
ATTGTCTTAGACAGGAGGTTAGGTGCGGCTTTGGTCCAAGGACATCTCGAAT Construct 34 (TK.16.118.N) I SEQ ID NO: 124
GGACTTCGGCGAAAGCCGTTCGACCACCTTCAGACGCTAGCGAATTGGTTCCTCGAAAGGGGAAAGCGTTATTAAGAAACCAAAATG
ACGTTCTTAGACAGGAGGTTAGGTGCGGCTTTGGTCCAAGGACATCTCGAAT Construct 35 (TK.16.118.O) C SEQ ID NO: 125
GGACTTCGGCGAAAGCCGTTCGACCAGCTCAGACGCTAGCGAATTGGTTCCTCGAAAGGGGAAAGCGTTATTAAGAAACCAAAATGA
GCTCTTAGACAGGAGGTTAGGTGCGGCTTTGGTCCAAGGACATCTCGAAT Construct 36 (TK.16.118.P) I SEQ ID NO: 126
GGACTTCGGCGAAAGCCGTTCGACCCGTCAGACGCTAGCGAATTGGTTCCTCGAAAGGGGAAAGCGTTATTAAGAAACCAAAATGA
GTGCTTAGACAGGAGGTTAGGTGCGGCTTTGGTCCAAGGACATCTCGAAT Construct 37 (TK.16.118.Q) ++ SEQ ID NO: 127
GGACTTCGGCGAAAGCCGTTCGACCGTTCAGACGCTAGCGAATTGGTTCCTCGAAAGGGGAAAGCGTTATTAAGAAACCAAAATGA
TCTTAGACAGGAGGTTAGGTGCGGCTTTGGTCCAAGGACATCTCGAAT Construct 38 (TK.16.118.R) ++ SEQ ID NO: 128
GGACTTCGGCGAAAGCCGTTCGACCGGTCAGACGCTAGCGAATTGGTTCCTCGAAAGGGGAAAGCGTTATTAAGAAACCAAAATGA
TTGCTTAGACAGGAGGTTAGGTGCGGCTTTGGTCCAAGGACATCTCGAAT Construct 39 (TK.16.118.S) I SEQ ID NO: 129
GGACTTCGGCGAAAGCCGTTCGACCCCTTCAGACGCTAGCGAATTGGTTCCTCGAAAGGGGAAAGCGTTATTAAGAAACCAAAATGA
CGTCTTAGACAGGAGGTTAGGTGCGGCTTTGGTCCAAGGACATCTCGAAT Construct 40 (TK.16.118.T) + SEQ ID NO: 130
GGACTTCGGCGAAAGCCGTTCGACCGCTCAGACGCTAGCGAATTGGTTCCTCGAAAGGGGAAAGCGTTATTAAGAAACCAAAATGAG
CCTTAGACAGGAGGTTAGGTGCGGCTTTGGTCCAAGGACATCTCGAAT

- I    Inactive
- C    Constitutively Active
- +    Effector-dependent
- ++   Greater Effector-Dependence than +

• ppERK library

5'GGACTTCGGGCGAAAGCCCGTTCGACCNNNN(N)(N)CAGACGCTA
GCGAATTGGTTCCTCGAAAGGGAAGGAAAGCGTTATTAAGAAACCAAAA
TGNNNN(N)(N)CTTAGACACAGGAGGTTAGGTGCGTCAATGCTGCAA
GTTACTG 3'  SEQ ID NO: 354

• ERK library

GGACTTCGGGCGAAAGCCCGTTCGACCNNNN(N)(N)AAGGAGGATTTC
CGAAAGCGGCTACGGTCCGCNNNN(N)(N)CTTAGACAGGAGGTTA
GGTGCGTAGGTAACCGATAGTCCG  SEQ ID NO:355

Figure 44A

SEQ ID NO:356

```
        G    G
AGAGGCU UAGA— C
UCUC    CC   C–G
        AGCUU–G U G
```

CW45-33-A08 (3.18, 2/18)

AGGGG3'
UCUCC 5'

CW45-33-C08 (11.3, 1/18)
SEQ ID NO:131

AACAG
UAGU

CW45-33-C09 (18.6, 1/18)
SEQ ID NO:132

AGUAG
UCAU

CW45-33-F08 (9.5, 1/18)
SEQ ID NO:90

ACAAG
UGUCC

CW45-33-H08 (36, 1/18)
SEQ ID NO:91

AGCGA
UCGCU

CW45-33-H09 (33, 1/18)
SEQ ID NO:92

GGUUG
UCAA

CW45-33-A10 (11.4, 1/18)
SEQ ID NO:93

AACAG
UUGU

CW45-33-F09 (14.2, 2/18)
SEQ ID NO:94

AGAAG
UCUUC

CW45-33-G08 (11.4, 1/18)
SEQ ID NO:95

AAAAG
UUUU

CW45-33-D09 (17.3, 5/18)
SEQ ID NO:133

---

Designed Library:
3–5 nt stem
25% of each A, C, U, G
37.5% complementary

Result of selection:
4–5 nt stem
27.8% A
27.8% U
25.6% G
18.9% C
1st pair 90% A-U
2nd pair 60% GC
95.5% complementary

Figure 44B

```
          A
GAACCGCU UAGA─C
         AGCUU─G
GUUGG cc      C─G
              T G
```

CW45-33-A02 (4.46, 1/31)
One C->U mutation in 5' ligase
SEQ ID NO:44

UGAUCG3'       AGUAAG   SEQ ID
GUUGG5'        UCUU     NO:38
CW45-33-B04(5.05, 5/31)   CW45-33-D05(2, 1/31)
SEQ ID NO:45
               CGGUGG   SEQ ID
CGUGU          GACGC    NO:39
GUACG
CW45-33-C04(6.2, 1/31)    CW45-33-E01(2, 1/31)
SEQ ID NO:5
               GCAGAU   SEQ ID
UUAUCG         UGUUUA   NO:96
GAUGG
CW45-33-D04(9.0, 1/31)    CW45-33-G02(3, 1/31)
One deletion, one A to G
mutation in aptamer structure   AUUAGA   SEQ ID
SEQ ID NO:6                     UGAUUU   NO:97

CGCAGG         CW45-33-G03(3, 1/31)
GGUGUC
CW45-33-F03(4, 1/31)      AUCGG    SEQ ID
SEQ ID NO:7               UCGC     NO:98

CW45-33-H03(2, 1/31)
```

```
Designed Library:
4-6 nt stem
25% of each A, C, U, G
37.5% complementary

Result of selection:
4-6 nt stem
4-6 pairing
18.0% A
28.9% U
36.7% G
16.4% C 89.8% complementary
```

```
GUGUGG    SEQ ID
AACGC     NO:8
CW45-33-D01(2, 1/31)

CAAU      SEQ ID
GUUG      NO:99
CW45-33-H1(1, 3/31)

CUAA      SEQ ID
GAUU      NO:100
CW45-33-B05(1, 1/31)
```

CW45-33-D01(2, 1/31)
AGGG
UCAUC
SEQ ID NO:37

- CW45.33.A02 sequence SEQ ID NO:44

5'GGACUUCGGGCGAAAGUCGUUCGACCGGUUGCAGAGACGCUAGCGA
AUUGGUUCCUCGAAAGGGGAAAGCGUUAUUAAGAAACCAAAUGGAA
CCGCUUAGAGACAGGAGGUUAGGGUGC3'

- CW45.33.D04 SEQ ID NO:6

5'GGACUUCGGGCGAAAGCCGUUCGACCGGUAGCAGAGACGCUAGCGA
AUUGGU_CCUCGAAG GGGGAAAGCGUUAUUAAGAAACCAAAUGUUA
UCGCUUAGAGACAGGAGGUUAGGGUGC3'

- Intracellular target drives circularization of transfected nucleic acid sensor molecule
- RT-PCR amplifies circular form to generate signal

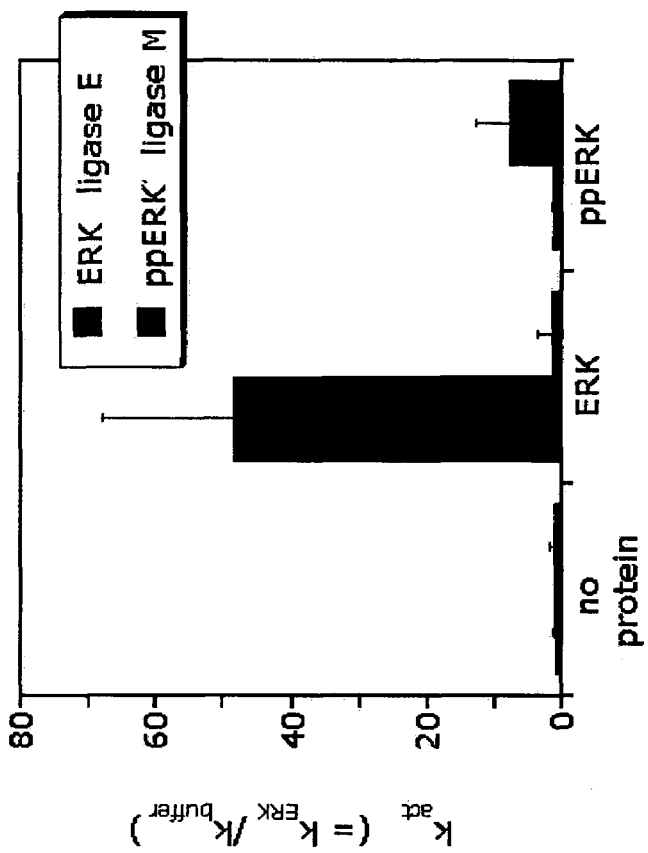
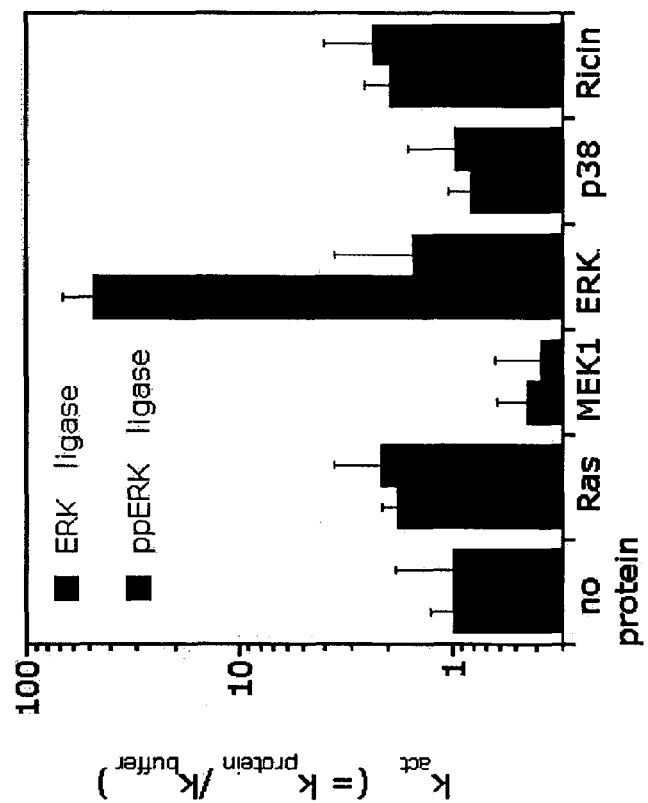
Figure 57

Figure 59

| ERK sensor | Switch factor | $K_{D,act}$ μM | $K_{D,ERK}$ μM | $k_{unact}$ nM/min | Det. limit |
|---|---|---|---|---|---|
| ERK aptamer | N/A | N/A | 0.0043 ± 0.0005 | N/A | N/A |
| Ligase 1 | ≥800 | ≥5 | ≥5 | ~0.004 | 40 nM |
| Ligase 2 | 76 ±20 | 0.75 ±0.08 | — | 0.04 ±0.01 | 10 nM |
| Ligase 3 | 65 ±16 | 0.28 ±0.08 | 1.2 ±0.1 | ~0.02 | 10 nM |
| Ligase 4 | 5 ±1 | 0.04 ±0.02 | 0.17 ±0.07 | ~0.3 | 40 nM |

A.
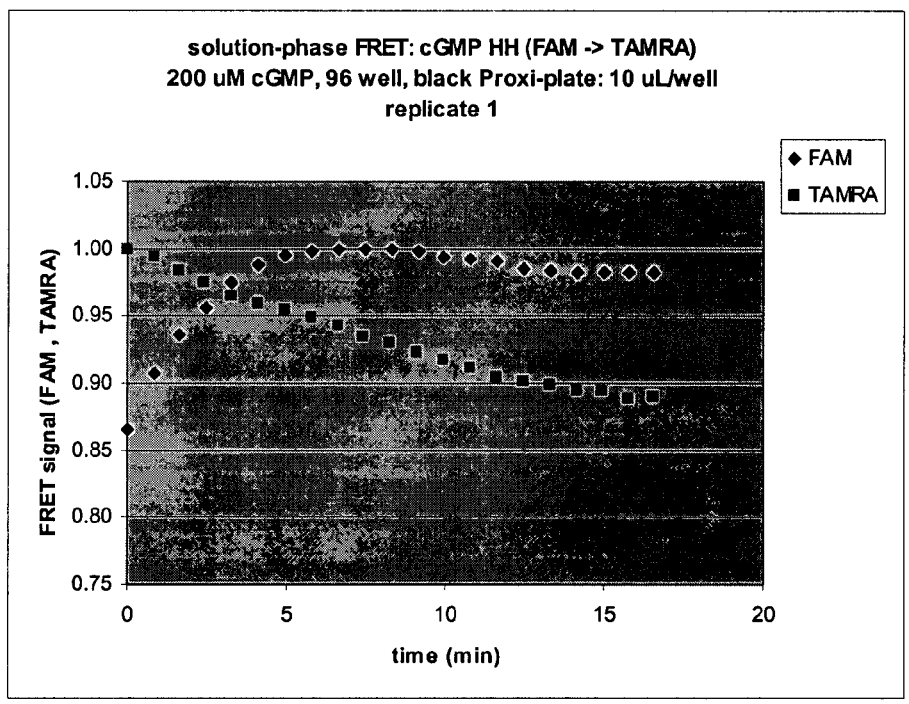
B.
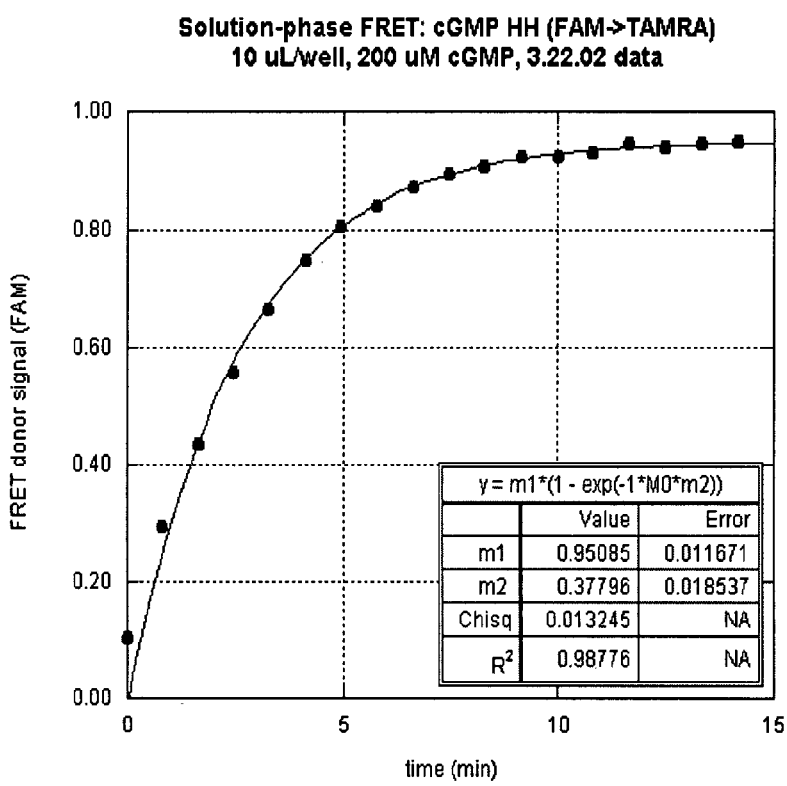
FIGURE 64.

C.

D.

E.

A. SPReeta SPR sensor
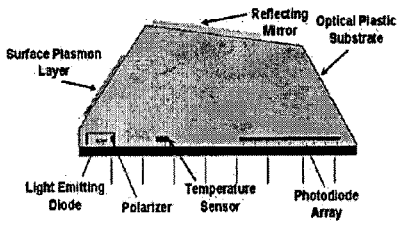
C. NASM loading
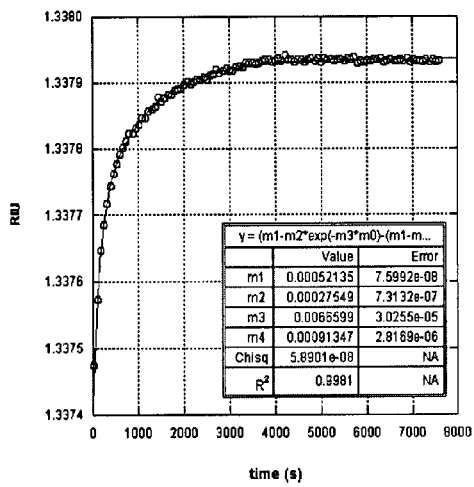
B. HH NASM
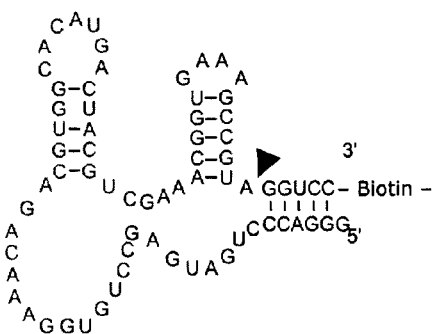
SEQ ID NO: 103 (same as cAMP)
D. Analyte-induced cleavage
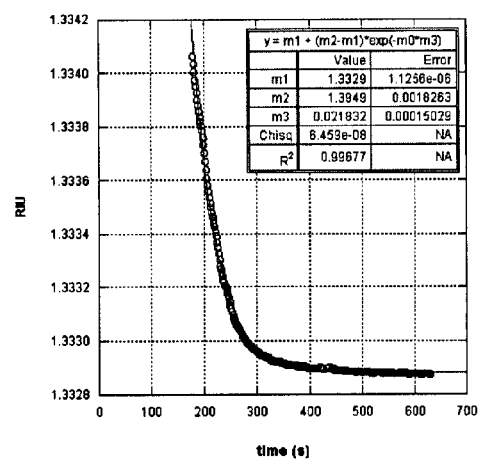
FIGURE 67 cGMP (90 nt)    SEQ ID NO: 135

5' thiol-GGAUAAUAGCCGUAGGUUGCGAAAGCGACCCUGAUGA
GCCCUGCGAUGCAGAAAGGUGCUGACGACACAUCGAAACGGUAGCGAGAG
CUC 3' cCMP (88 nt):    SEQ ID NO: 136

5' thiol-GGAUAAUAGCCGUAGGUUGCGAAAGCGACCCUGAUGA
CCUGUGGAAACAGACGUGGCACAUGACUACGU
GAAACGGUAGCGAGAGCUC 3' cAMP (88 nt):    SEQ ID NO: 137

5' thiol- GGAUAAUAGCCGUAGGUUGCGAAAGCGACCCUGAUGA
CCUUGCGAUGCAAAAAGGUGCUGACGACACAU
GAAACGGUAGCGAGAGCUC 3'

SEQ ID NO: 137

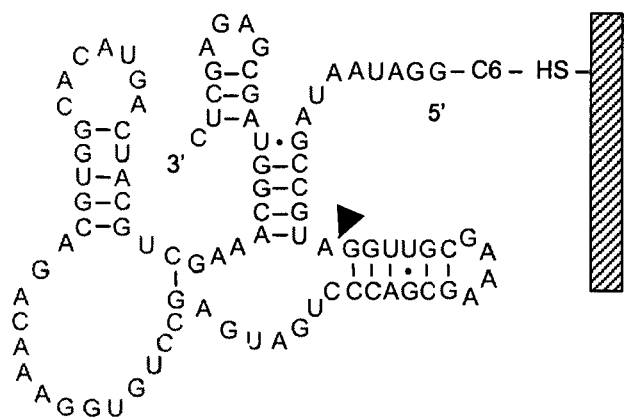

FIGURE 68 cCMP ((71 nt)):    SEQ ID NO: 138

5' GGGACCCUGAUGAG CCUUUAGGGCCAAGUGUGGUGAAAGACACACGU CGAAACGGUGAAAGCCGUAGGUCC-Biotin 3' cAMP ((70 nt):    SEQ ID NO: 103

5' GGGACCCUGAUGAG CCUGUGGAAACAGACGUGGCACAUGACUACGU CGAAACGGUGAAAGCCGUAGGUCC-Biotin 3' cGMP (70 nt):    SEQ ID NO: 139

5' GGGACCCUGAUGAG CCUUGCGAUGCAAAAAGGUGCUGACGACACAU CGAAACGGUGAAAGCCGUAGGUCC-Biotin 3' cCMP:     SEQ ID NO: 40

5' GGACCCUGAUGAG CCUUUAGGGCCAAGUGUGGUGAAAGACACACGU
CGAAACGGUGAAAGCCGUAGGUCCUUGCGUGGUUCUGUUCCCUUCUUCG 3' cAMP:     SEQ ID NO: 41

5' GGACCCUGAUGAG CCUGUGGAAACAGACGUGGCACAUGACUACGU
CGAAACGGUGAAAGCCGUAGGUCCUUGCGUGGUUCUGUUCCCUUCUUCG 3' cGMP:     SEQ ID NO: 42

5' GGACCCUGAUGAG CCUUGCGAUGCAAAAAGGUGCUGACGACACAU
CGAAACGGUGAAAGCCGUAGGUCCUUGCGUGGUUCUGUUCCCUUCUUCG 3'

Capture Oligo:     SEQ ID NO: 43

3'-ACGCACCAAGACAAGGGAAGAAGC-Biotin-5'

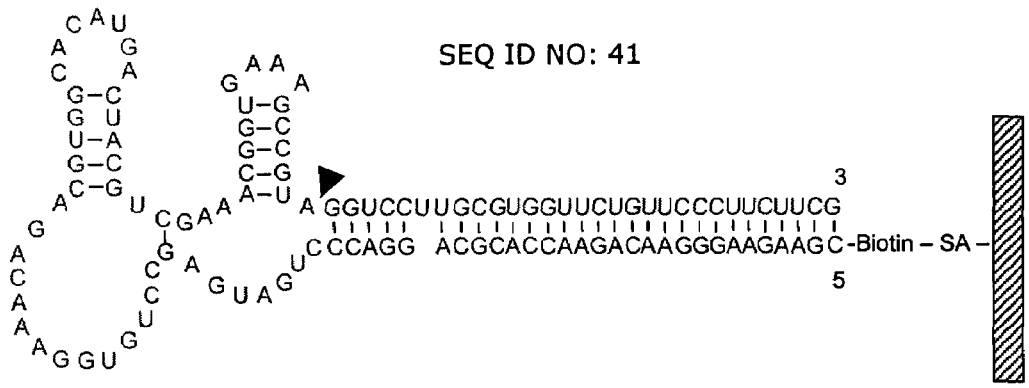

FIGURE 70

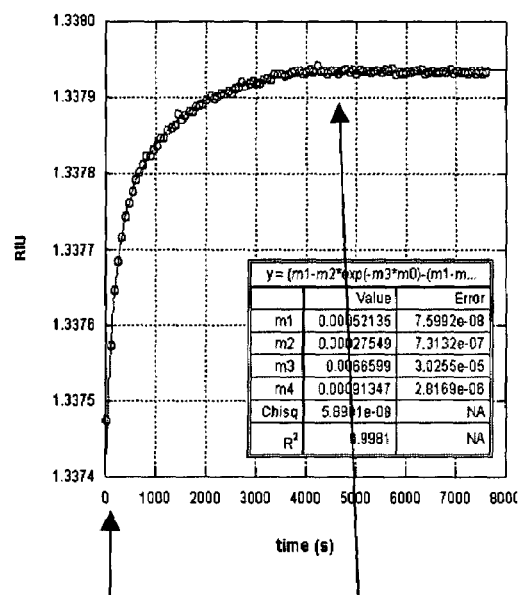
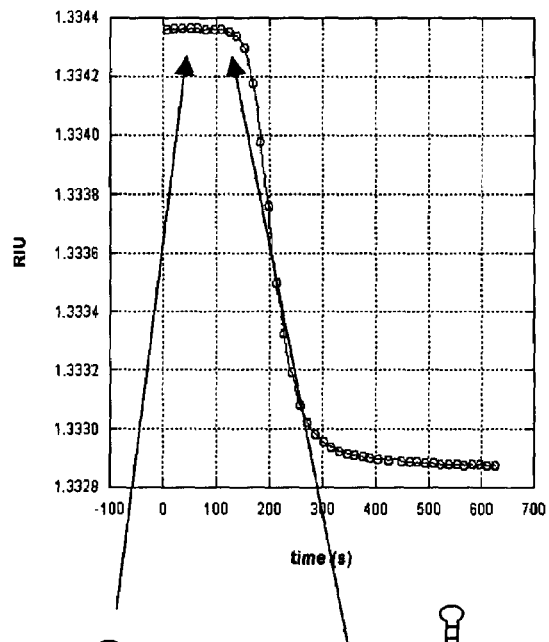
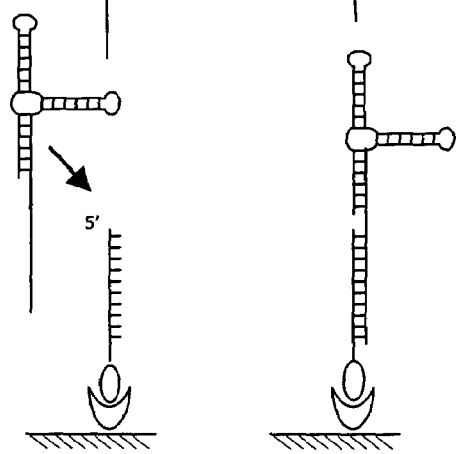
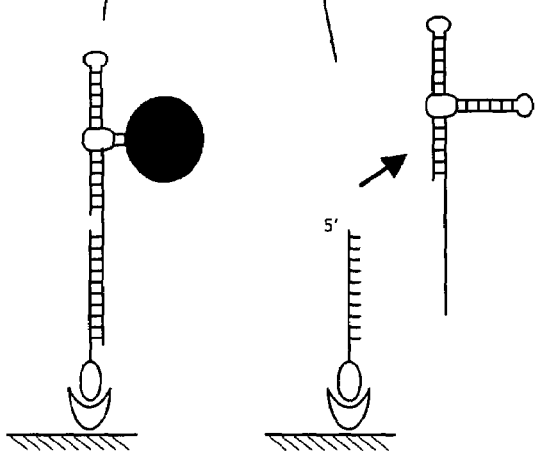
$K_{ads} \sim 0.41$ min$^{-1}$    $K_{clv} \sim 1.31$ min$^{-1}$
FIGURE 71

Figure 75
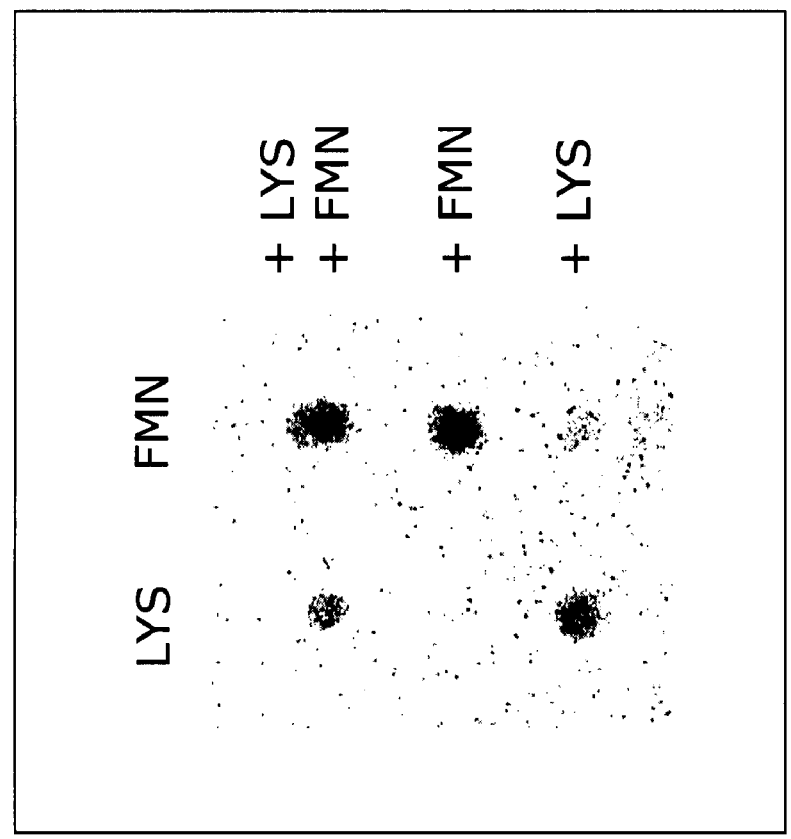
B
Ligated & Denatured
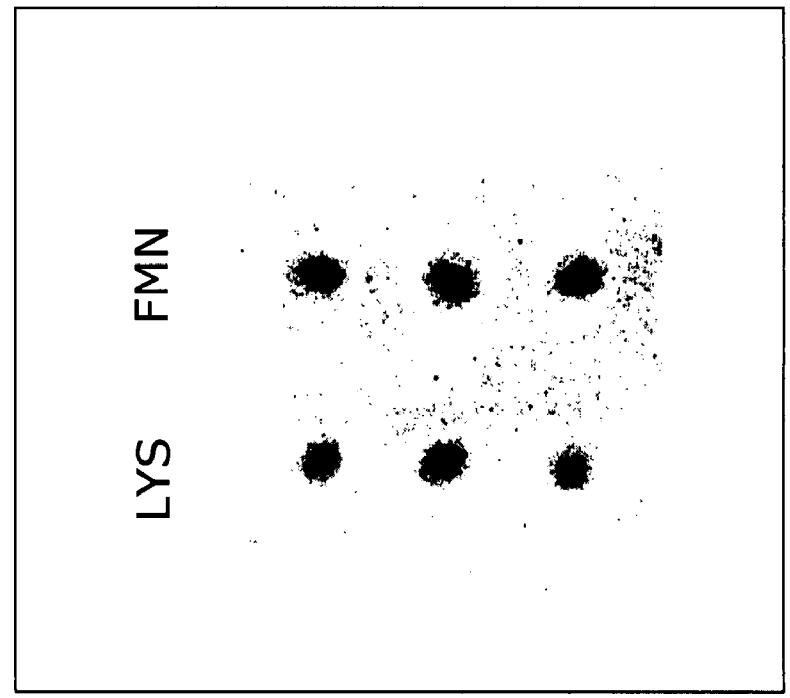
A
Hybridized & Washed

NUCLEIC ACID SENSOR MOLECULES AND METHODS OF USING SAME

RELATED APPLICATIONS

This application claims priority to U.S. Ser. No. 60/311,378, filed Aug. 9, 2001; U.S. Ser. No. 60/313,932, filed Aug. 21, 2001; U.S. Ser. No. 60/338,186, filed Nov. 13, 2001; U.S. Ser. No. 60/349,959, filed Jan. 18, 2002; U.S. Ser. No. 60/364,486, filed Mar. 13, 2002; U.S. Ser. No. 60/367,991, filed Mar. 25, 2002; U.S. Ser. No. 60/369,887, filed Apr. 4, 2002; U.S. Ser. No. 60/376,744, filed May 1, 2002; U.S. Ser. No. 60/385,097, filed May 31, 2002; U.S. Ser. No. 60/391,719, filed Jun. 26, 2002; and continuation-in-part U.S. Ser. No. 09/952,680, filed Sep. 13, 2001 now abandoned, which claims priority to U.S. Ser. No. 60/232,454, filed Sep. 13, 2000. The contents of these applications are incorporated herein by reference in their entirety.

FIELD OF THE INVENTION

The invention relates generally to nucleic acids and more particularly to nucleic acid sensor molecules containing a catalytically active domain that is modulated upon recognition of a target by a target modulation domain of the nucleic acid sensor molecule.

BACKGROUND OF THE INVENTION

In addition to carrying genetic information, nucleic acids can adopt complex three-dimensional structures. These three-dimensional structures are capable of specific recognition of target molecules and, furthermore, of catalyzing chemical reactions. Nucleic acids will thus provide candidate detection molecules for diverse target molecules, including those which that do not naturally recognize or bind to DNA or RNA.

A nucleic acid which binds to a non-nucleic acid target molecule through non-Watson-Crick base pairing is termed an aptamer. In aptamer selection, combinatorial libraries of oligonucleotides are screened in vitro to identify oligonucleotides, or aptamers, which bind with high affinity to preselected targets. Both small biomolecules (e.g., amino acids, nucleotides, NAD, S-adenosyl methionine, chloramphenicol), and large biomolecules (thrombin, Ku, DNA polymerases) are effective targets for aptamers. Aptamer biosensors have been used to detect specific analyte molecules. For example, fluorescently labeled anti-thrombin aptamers attached to a glass surface have been used to directly detect the presence of thrombin proteins in a sample by detecting changes in the optical properties of the aptamers (Potyrailo, et al., 1998). In this method continuous binding of thrombin to the labeled aptamer is requisite for detection to occur, since the concentration of thrombin in a test sample is monitored by directly detecting fluorescent emission of the aptamer-ligand complex. Another method of detecting binding of a ligand to an aptamer has also been described which relies on the use of fluorescence-quenching pairs whose fluorescence is sensitive to changes in secondary structure of the aptamer upon ligand binding (Stanton, et al. 2000) to form a fluorescent aptamer-ligand complex, and again, continuous binding of the ligand to the aptamer is required for signal generation and, hence, for detection to occur. A limitation with this type of aptamer-derived biosensor is that ligand-mediated changes in secondary structure were engineered into the aptamer molecule via a laborious engineering process in which four to six nucleotides were added to the 5' end of the aptamer that was complementary to the bases at the 3' end of the thrombin binding region. In the absence of thrombin, this structure forms a stem loop structure, while it forms a G-quartet structure in the presence of thrombin. Fluorescent and quenching groups attached to the 5' and 3' end signal this change. In aptamer-based detection without the use of amplification steps, assay sensitivity and hence the limit of detection is set empirically by the affinity of the aptamer-ligand complex, the KD value. Using aptamer-based sensor molecules one can detect analyte binding in both solution (homogeneous) and on solid supports (heterogeneous).

Other ligand detection methods known in the art are based upon antibody binding. Similar to the aptamer-based methods, antibody-based detection requires continuous ligand binding and ligand-antibody complex formation for the generation of a detectable signal. In addition, antibody methods such as ELISA or competitive RIA, while robust, are restricted in utility because these methods require that heterogeneous assay conditions be employed: 1] detection is done on a solid surface; 2] in most applications both a capture antibody and detection antibody are required; 3] for ELISA-based protein detection methods, the antibodies must recognize the folded, native structure of the protein that is present in cell or tissue isolates and; 4] antibody and protein based detection methods have not been described for intracellular or in vivo based analyte detection. That antibodies have not been employed for intracellular and in vivo based detection of proteins, drugs or metabolites is due to several technological factors. First monoclonal antibody fragments are unstable and do not fold properly when expressed as intracellular protein molecules. Second, intracellular detection requires homogeneous assay formats and these solution-based detection methods require the sensor to have a ligand sensing or modulation domain coupled directly to a catalytic or signal generating region of an enzyme or catalytic biomolecule. A fundamental and important consequence of the limitations of antibody-based detection methods is that they can not function as a universal reagent for all assays and tests that can be employed in drug discovery and development. These assays include 1] the initial discovery of a drug target through protein or metabolite profiling, 2] the subsequent use of that same drug target in the discovery of drug leads through high throughput screening and, 3] the optimization of drug leads against that same drug target through an evaluation of lead efficacy in mechanistic cellular and in vivo animal assays.

To streamline the drug discovery and development process and improve the efficiency of evaluating drug targets and drug leads, detection reagents are needed that can function in a context-independent manner. Needed then is a molecular sensor that can function in multiple assay environments and in multiple assay formats. The present invention is generally drawn to nucleic acid molecular sensors that can function in environments and formats that includes but are not limited to solution-based detection (homogeneous in vitro biochemical assays or in vivo cellular and animal assays), chip-based (heterogeneous in vitro assays on solid surfaces), and assays in complex biological isolates from blood plasma, cell lysates or tissue extracts.

Nucleic acid-based detection schemes have exploited the ligand-sensitive catalytic properties of some nucleic acids, e.g., such as ribozymes. Ribozyme-based prototype nucleic acid sensor molecules have been designed both by engineering and by in vitro selection methods. Engineering methods exploit the apparently modular nature of RNA structures; these sensors couple molecular recognition to signaling by simply joining individual target-modulation and catalytic RNA domains through a double-stranded or partially double-stranded RNA linker. ATP sensors, for example, were created by appending the previously-selected, ATP-binding aptamer-derived sequences (Sassanfar and Szostak, 1993) to either the self-cleaving hammerhead ribozyme (Tang and Breaker, 1997) or the L1 self-ligating ribozyme (Robertson and Ellington 2000). Robertson and Ellington (2000) have demonstrated that the enzymatic activity of a ligase ribozyme (derived from the L1 ligase described in Robertson and Ellington (1999)) can be modulated by a small molecule ligand, or small molecule target recognition. In this case, the ligase ribozyme can be employed as a nucleic acid sensor molecule and used to detect the presence and level of its cognate ligand by monitoring the ligation of a small, labeled second oligonucleotide substrate on to the ribozyme. A distinct feature of this detection method is that the actual detection event, e.g., monitoring oligonucleotide substrate ligation to the ribozyme, occurs after the ligand interacts with the nucleic sensor molecule. Hence, unlike antibody, or aptamer based detection methods, the ribozyme-based ligand detection method of Robertson and Ellington does not require continuous binding of the ligand to the sensor molecule in order to generate a detectable signal. In a complementary approach, radiolabeled hammerhead ribozymes which undergo cleavage upon binding to a ligand, have been used to detect ligand by monitoring the release of the label from the ribozyme (Soukup, et al., 2000, and Breaker, 1998). Limitations of the use of ligand modulated hammerhead ribozymes described by Soukup, et al., 2000, and Breaker, 1998 include: 1] the need for a two-step detection method for determining the enzymatic activity of the surface-immobilized hammerhead-derived sensors; 2] the need for radiometric determination of hammerhead activity in both solution and solid-surface based assay formats; 3] the need for significant chemical and structural modification of the hammerhead-based biosensor to render them suitable for optical based detection methods.

Another limitation of the engineering method to sensor generation is that it has been generally thought not to be applicable to the development of protein-dependent ribozymes. Robertson and Ellington (2001) describe their own efforts to extend this methodology to the identification of protein and peptide-dependent ribozymes, but state that simply appending aptamer-derived sequences to the catalytic domain of the L1 ligase at stem C, yields little or no target dependent modulation. Furthermore, the authors state that the "principles required for engineering protein-dependent ribozymes must be fundamentally different from those for identifying ribozymes dependent on small-molecules." Hence, in order to identify protein and peptide dependent ribozymes, Ellington and Robertson undertook a laborious in vitro selection process which involved randomization of the catalytic core of the L1 ligase coupled with multiple rounds of positive and negative selection. Ellington and Roberts (2000) describe several limitations of the ligase-derived sensors that they developed. First, the nucleoprotein enzymes developed by Ellington and Robertson (2000) required a laborious in vitro selection process to identify peptide and protein dependent ligases. Secondly, Ellington and Roberts (1999) describe a region of the L1 ligase that is required for allosteric ribozyme function, termed the effector oligonucleotide binding domain. It was postulated that the effector oligonucleotide binding domain of the ligase formed complementary base pairing interactions with the oligonucleotide substrate binding site, driving the ribozyme into an inactive conformation. The effector oligonucleotide, when added to the L1 ligase activates (kact) the enzyme by over 10,000 fold over the L1 ligase reaction measure in the absence of effector (kunact). Hence, the native L1-ligase has a switch factor ($kact/k_{unact}$) greater than 10,000, which determines the sensitivity of a ribozyme-based detection method. When the effector oligonucleotide binding domain of the L1 ligase is deleted, the ligase activity of the deletion mutant is only 3–5 fold lower than the ligase activity of L1 ligase with the effector oligonucleotide bound to the effector oligonucleotide binding domain (Ellington and Robertson (1999). This indicates that L1 ligases deleted of the effector oligonucleotide binding domain may not be not subject to further allosteric regulation. Hence, a hindrance to the development of L1 ligase-based biosensor technology is the lack of a general method for the generation of biosensors that can work in multiple assay and detection formats required of solution-based and chip-based biosensors and, those that can work in multiplexed formats and in complex biological extracts.

SUMMARY OF THE INVENTION

The nucleic acid sensor molecules of the present invention are used to monitor the presence or concentration of various target molecules (proteins, post-translationally modified forms of proteins, peptides, nucleic acids, oligosaccharides, nucleotides, metabolites, drugs, toxins, biohazards, and ions) and function in solution-based homogeneous assays using optical or other detection methods; in solution-based homogeneous assays using PCR-based or other nucleotide amplification-based detection methods; in homogeneous intracellular assays using PCR-based detection or other nucleotide amplification-based detection methods; in heterogeneous assays (surface-immobilized nucleic acid sensor molecules and surface-capture nucleic acid sensor molecules) using optical detection methods; and in heterogeneous assays (surface-immobilized nucleic acid sensor molecules and surface-capture nucleic acid sensor molecules) using PCR-based detection or other nucleotide amplification-based detection methods. And finally the nucleic acid sensor molecules of the present invention function in formats where the target analytes are present in complex biological mixtures, or the assays are themselves performed in multiplexed formats.

The nucleic acid sensor molecules of the present invention were developed through a combination of engineering and selection methods that are now shown to be useful for identifying nucleic acid sensor molecules against a wide variety of target molecules including proteins (including specific post-translationally modified forms of proteins) peptides, nucleic acids, oligosaccharides, nucleotides, metabolites, drugs, toxins, biohazards, ions, carbohydrates, glycoproteins, hormones, receptors, antibodies, viruses, transition state analogs, cofactors, dyes growth factory nutrients, etc.

In one embodiment of the invention the nucleic acid sensor molecules are based on cis-cleaving hammerhead ribozymes that have been designed to work as optical signaling molecules in a homogeneous assay format, and utilize fluorescence and FRET based methods of signal generation and detection.

In one embodiment of the invention nucleic acid sensor molecules are based on cis-cleaving hammerhead ribozymes that have been designed to work as optical signaling molecules affixed to a solid-support, and utilize fluorescence and FRET based methods of signal generation and detection.

In one embodiment of the invention the nucleic acid sensor molecules are based on cis-cleaving hammerhead ribozymes that have been designed to work as optical signaling molecules affixed to a solid-support and utilize surface plasmon resonance methods of signal generation and detection.

In one embodiment of the invention the nucleic acid sensor molecules are based on a 3-piece L1 ligase ribozyme that retains the effector oligonucleotide binding domain, and has been designed to detect target molecules, as a function of oligonucleotide substrate ligation to the nucleic acid sensor molecule, in solution using quantitative PCR-based methods.

In one embodiment of the invention the nucleic acid sensor molecules are based on a 2-piece L1 ligase ribozyme that couples the effector oligonucleotide substrate to the oligonucleotide substrate forming an oligonucleotide supersubstrate and, has been designed to detect target molecules, as a function of oligonucleotide supersubstrate ligation to the nucleic acid sensor molecule, in solution using quantitative PCR-based methods.

In one embodiment of the invention the nucleic acid sensor molecules are based on a 1-piece L1 ligase ribozyme that deletes the effector oligonucleotide binding domain. The 1-piece ligase is designed to self-ligate or circularize by joining the 3'-OH end and the PPP-5'-end of the ligase and detects target molecules, as a function of circularization of the nucleic acid sensor molecule, in solution using PCR-based methods.

In one embodiment of the invention the nucleic acid sensor molecules are based on a 3-piece L1 ligase ribozyme that retains the effector oligonucleotide binding domain, and has been designed to detect target molecules, as a function of oligonucleotide substrate ligation to the nucleic acid sensor molecule immobilized on a solid support and where the detection uses fluorescence-based methods.

In one embodiment of the invention the 3-piece L1 ligase nucleic acid sensor molecules detect target molecules, as a function of oligonucleotide substrate ligation to the nucleic acid sensor molecule in solution and then are subsequently captured on a solid support and detected using fluorescence-based methods.

In one embodiment of the invention the 3-piece L1 ligase nucleic acid sensor molecules detect target molecules, as a function of oligonucleotide substrate ligation to the nucleic acid sensor molecule in solution and then are subsequently captured on a solid support and detected using radiometric-based methods.

In one embodiment of the invention the nucleic acid sensor molecules are based on a 2-piece L1 ligase ribozyme and has been designed to detect target molecules, as a function of oligonucleotide substrate ligation to the nucleic acid sensor molecule immobilized on a solid support and where the detection uses optical methods such as fluorescence-based methods.

In one embodiment of the invention the 2-piece L1 ligase nucleic acid sensor molecules detect target molecules, as a function of oligonucleotide substrate ligation to the nucleic acid sensor molecule in solution and then are subsequently captured on a solid support and detected directly using fluoresence-based methods.

In one embodiment of the invention the 2-piece L1 ligase nucleic acid sensor molecules detect target molecules, as a function of oligonucleotide substrate ligation to the nucleic acid sensor molecule in solution and then are subsequently captured on a solid support and directly detected using radiometric-based methods.

In one embodiment of the invention the nucleic acid sensor molecules is based on a 1-piece L1 ligase ribozyme that is transfected into a mammalian cell. The 1-piece ligase is designed to self-ligate or circularize by joining the 3'-OH end and the PPP-5'-end of the ligase and detects intracellular target molecules, as a function of circularization of the nucleic acid sensor molecule. The circularized ligase molecules are then re-isolated from the cellular lysate and the amount of target present in the cell is quantified using solution based nucleotide amplification methods.

In one aspect, the invention includes a nucleic acid sensor molecule which includes a target modulation domain which recognizes a target molecule, a linker domain, a catalytic domain, and an optical signal generating unit.

In one embodiment, the nucleic acid sensor molecule of the invention has an optical signal generating unit that includes at least one signaling moiety. In another embodiment, the nucleic acid sensor molecule of the invention has an optical signal generating unit which includes at least a first signaling moiety and a second signaling moiety. In another embodiment, the first and second signaling moieties change proximity to each other upon recognition of a target by the target modulation domain. In another embodiment, the first and second signaling moieties include a fluorescent donor and a fluorescent quencher, and recognition of a target by the target modulation domain results in an increase in detectable fluorescence of said fluorescent donor. In another embodiment, the first signaling moiety and said second signaling moiety include fluorescent energy transfer (FRET) donor and acceptor groups, and recognition of a target by the target modulation domain results in a change in distance between said donor and acceptor groups, thereby changing optical properties of said molecule.

In another embodiment, the invention includes a nucleic acid sensor molecule where the optical signal generating unit consists essentially of a first signaling moiety which changes conformation upon recognition of a target by the target modulation domain, thereby resulting in a detectable optical signal.

In yet another embodiment, the nucleic acid sensor molecule includes at least one modified nucleic acid.

In still another embodiment, the catalytic domain of the nucleic acid sensor molecule includes an endonucleolytic ribozyme. The endonucleolytic ribozyme can be, for example, a cis-endonucleolytic ribozyme or a trans-endonucleolytic ribozyme. In one embodiment, the endonucleolytic ribozyme is a hammerhead ribozyme.

In another embodiment, the catalytic domain of the nucleic acid sensor includes a self-ligating ribozyme. The elf-ligating ribozyme can be, for example, a cis-ligase ribozyme or a trans-ligase ribozyme. The self-ligating ribozyme can be, e.g., a 1-piece ligase, 2-piece ligase or 3-piece ligase.

In another embodiment, the target modulation domain recognizes a target that is selected from proteins, post-translationally modified forms of proteins, peptides, nucleic acids, oligosaccharides, nucleotides, metabolites, drugs, toxins, biohazards, ions, carbohydrates, polysaccharides, hormones, receptors, antigens, antibodies, viruses, metabolites, co-factors, drugs, dyes, nutrients, or growth factors.

In one embodiment, the target modulation domain recognizes a protein or a post-translationally modified protein.

In another embodiment, the target modulation domain recognizes a post-translationally modified protein, wherein the post-translational modification can be a phosphorylation, prenylation, glycosylation, methionine removal, N-acetylation, acylation, acylation of cysteines, myristoylation, alkylation, ubiquitinylation, prolyl-4-hydroxylation, carboxylation of glutaminyl residues, advanced glycoslylation, deamination of glutamine and asparagine, addition of glycophosphatidylinositol, disulfide bond formation, hydroxylation, or lipidation.

In some embodiments, the target is a protein kinase. In other embodiments, the target is a phosphorylated protein kinase. The phosphorylated protein kinase can be a monophosphorylated protein kinase or a diphosphorylated protein kinase. In one embodiment, the target protein is ERK, such as ERK1 or ERK2. In other embodiments, the post-translationally modified protein is ppERK, such as such as ppERK1 or ppERK2.

In other embodiments, the nucleic acid sensor molecule includes a target modulation domain which recognizes a component of a MAP kinase pathway, a product of a MAP kinase pathway, a MAP kinase pathway associated protein, or an extracellular component of a MAP kinase pathway. In one embodiment, the target modulation domain recognizes a component of the ERK1/2 MAP kinase pathway, the JNK MAP kinase pathway, or the P38 MAP kinase pathway.

In some embodiments, the target modulation domain recognizes an endogenous form of a MAP Kinase (MEK), an endogenous form of a MAP Kinase Kinase (MEKK), or an endogenous form of MAP Kinase Kinase Kinase, (MEKKK). In other embodiments, the target modulation domain recognizes an endogenous form of RAF kinase. In still other embodiments, the target modulation domain recognizes a Ras protein, a phosphatase, s a GTP binding protein, a GPCR, a cytokine, a growth factor, a cellular metabolite, or a small molecule.

In some embodiments, the nucleic acid sensor molecule includes RNA, DNA, or both RNA and DNA.

The invention also relates to compositions containing a nucleic acid sensor molecule of the invention and a buffer. In some embodiments, the invention includes a composition containing a nucleic acid sensor molecule and a tissue extract, a cell extract or an in vitro cell culture. In other embodiments, a composition of the invention also includes an RNase inhibitor, such as, for example, Va-riboside, vanadyl, tRNA, polyU, RNaseIn or RNaseOut. In some embodiments, a composition of the invention is substantially RNase-free.

The invention also relates to a composition which includes at least one nucleic acid sensor molecule affixed to a substrate. In some embodiments, the substrate is glass, gold or other metal, silicon or other semiconductor material, nitrocellulose, nylon, or plastic. In particular embodiments, the nucleic acid sensor molecule is covalently attached to the substrate. In other embodiments, the nucleic acid sensor molecule is non-covalently attached to the substrate. In some embodiments, the nucleic acid sensor molecule is immobilized to the substrate via hybridization of a terminal portion of the nucleic acid sensor molecule to an oligonucleotide that is bound to the surface of the substrate.

In some embodiments, a composition includes a plurality of nucleic acid sensor molecules immobilized to the substrate via hybridization of a terminal portion of the nucleic acid sensor molecule to an array of oligonucleotides bound to the substrate at spatially discrete regions. In some embodiments, at least two members of this plurality each recognize different target molecules. The substrate can include, for example, at least 50 nucleic acid sensor molecules. In other embodiments, the substrate includes at least 250 nucleic acid sensor molecules, at least 500 nucleic acid sensor molecules, or at least 5000 nucleic acid sensor molecules.

In some aspects, the invention includes a system for detecting a target molecule which includes a composition according to the invention and a detector in optical communication with the composition, where the detector detects changes in the optical properties of the composition. In some embodiments, the system further includes a light source in optical communication with the composition. In some embodiments, the system also includes a processor for processing optical signals detected by the detector.

In one embodiment, the system for detecting a target molecule includes a plurality of nucleic acid sensor molecules where at least two of the biosensor molecules each recognize different target molecules.

In another aspect, the invention includes a method of identifying or detecting a target molecule in a sample by contacting a sample suspected of containing a target molecule with a nucleic acid sensor molecule of the invention, wherein a change in the signal generated by the optical signal generating unit indicates the presence of target in the sample. In some embodiments, the method further includes quantifying the change signal generated by the optical signal generating unit to quantify the amount of target molecule in the sample. In some embodiments, the sample is an environmental sample, biohazard materials, organic samples, drugs and toxins, flavors and fragrances, and biological samples. In particular embodiments, the sample is a biological sample such as cells, cell extracts or lysates, tissues or tissue extracts, bodily fluids, serum, blood and blood products.

In some embodiments, the method of identifying or detecting a target molecule in a sample detects of identifies proteins, post-translationally modified forms of proteins, peptides, nucleic acids, oligosaccharides, nucleotides, metabolites, drugs, toxins, biohazards, ions, carbohydrates, polysaccharides, hormones, receptors, antigens, antibodies, viruses, metabolites, co-factors, drugs, dyes, nutrients, or growth factors. In other embodiments, the method of the invention detects of identifies proteins or post-translationally modified forms of proteins. In some embodiments, the target is a post-translationally modified protein, where the post-translation modifications is phosphorylation, prenylation, glycosylation, methionine removal, N-acetylation, acylation, acylation of cysteines, myristoylation, alkylation, ubiquitinylation, prolyl-4-hydroxylation, carboxylation of glutaminyl residues, advanced glycoslylation, deamination of glutamine and asparagine, addition of glycophosphatidylinositol, disulfide bond formation, hydroxylation, or lipidation.

In some embodiments, the target is a protein kinase. In particular embodiments, the target is a phosphorylated protein kinase.

In another aspect, the invention includes a diagnostic system for identifying or detecting a target molecule, where the diagnostic system includes a nucleic acid sensor molecule of the invention and a detector in communication with the nucleic acid sensor molecule, wherein the detector detects changes in the signal generated by the optical signal generating unit of the nucleic acid sensor. In some embodiments, the diagnostic system further includes a processor for processing signals detected by the detector.

In another aspect, the invention includes a method of identifying or detecting a protein kinase in a sample by contacting a sample suspected of containing a protein kinase with a nucleic acid sensor molecule, wherein said nucleic acid sensor molecule has a target recognition domain that recognizes a protein kinase, and wherein a change in the signal generated by the optical signal generating unit indicates the presence of protein kinase in the sample. In some embodiments, the method further includes quantifying the amount of signal generated by the optical signal generating unit to quantify the amount of protein kinase in the sample.

In yet another aspect, the invention provides a method of identifying a modulator of protein kinase activity by contacting a test agent with a protein kinase and nucleic acid sensor molecule, wherein the nucleic acid sensor molecule has a target recognition domain that recognizes a protein kinase, recognition of the protein kinase by the target recognition domain of the nucleic acid sensor molecule results in a change in the signal generated by the optical signal generating unit and wherein changes in the signal generated by the optical signal generating unit in the presence and absence of the test agent indicates the test agent is a modulator, of the protein kinase activity.

In some embodiments, the catalytic domain of the nucleic acid sensor molecule includes a cis-ligase ribozyme or a trans-ligase ribozyme.

In another aspect, the invention provides a nucleic acid sensor molecule which includes a target modulation domain that recognizes ERK, a catalytic domain that includes a ligase or cis-hammerhead, and a linker domain that links the target modulation domain and the catalytic domain.

In another aspect, the invention includes a nucleic acid sensor molecule which includes a target modulation domain that recognizes phosphoERK, a catalytic domain that includes a ligase or a cis-hammerhead, and a linker domain that links the target modulation domain and the catalytic domain.

In yet another aspect, the invention provides a nucleic acid sensor molecule which includes a target modulation domain that recognizes lysozyme, a catalytic domain that includes a 1-piece cis-ligase and a linker domain that links the target modulation domain and the catalytic domain.

In still another aspect, the invention provides a nucleic acid sensor molecule which includes a target modulation domain that recognizes any one of cCMP, cAMP, or cGMP, a catalytic domain, and a linker domain that links the target modulation domain and the catalytic domain, wherein the nucleic acid sensor molecule includes an optical signal generating unit or a non-radioactive detectable label. In some embodiments, the nucleic acid sensor molecule includes an optical signal generating unit. In other embodiments, the nucleic acid sensor molecule includes a detectable label. In a particular embodiment, the label is a radioactive label, such as, for example, $^{32}P$, $^{33}P$, $^{14}C$, $^{35}S$, $^{3}H$, or $^{125}I$. In other embodiments, the nucleic acid sensor molecule comprises a fluorescent label, such as, for example, fluorescein, DABCYL, or a green fluorescent protein (GFP) moiety. In some embodiments, the optical signal generating unit includes a fluorescent moiety and a quenching moiety, wherein recognition by the target modulation domain causes causes a change in detectable fluorescence by the optical signal generating unit. In some embodiments, the nucleic acid sensor molecule includes an enzymatic label, or an affinity capture tag label.

In some embodiments, the nucleic acid sensor molecule includes a target modulation domain recognizes ERK1, ERK2 or both. In a particular embodiment, the nucleic acid sensor molecule includes a target modulation domain and catalytic domain are as shown by SEQ ID NO. 80, and the linker is randomized.

In some embodiments, the nucleic acid sensor molecule includes a target modulation domain and a catalytic domain as shown in any one of SEQ ID NOS. 47, 118 and 119, and the linker is randomized.

In another aspect, the invention provides a nucleic acid sensor molecule that recognizes ERK having the SEQ ID NO. 90–95, 108–116, 131–133, 140–295, 349, 351, or 356.

In another aspect, the invention provides a nucleic acid sensor molecule that recognizes phospoERK having the SEQ ID NO. 5–8, 37–39, 44–45, 81–89, 96–100, 121–130, 352, or 353.

In another aspect, the invention provides a nucleic acid sensor molecule that recognizes any one of cCMP, cAMP or cGMP, having the SEQ ID NO. 40–43, 103, or 135–139.

In another aspect, the invention provides a nucleic acid sensor molecule that recognizes lysozyme, having the SEQ ID NO. 46, 47, 76, or 105–107.

In another aspect, the invention provides a 1-piece ligase ribozyme including a target modulation domain that recognizes a target, a linker domain, and a catalytic domain wherein the 5' and 3' ends of the ligase ligate to each other upon recognition of the target by the modulation domain.

In another aspect, the invention provides a 2-piece ligase ribozyme including a target modulation domain that recognizes a target, a linker domain, and a catalytic domain including an oligonucleotide substrate ligation site and and oligonucleotide supersubstrate binding domain, wherein upon recognition of the target by the modulation domain, the 3' end of the an oligonucleotide supersubstrate is ligated to the 5' end of the oligonucleotide substrate ligation site.

In yet another aspect, the invention provides a 3-piece ligase ribozyme including a target modulation domain that recognizes a target, a linker domain, and a catalytic domain comprising comprising an oligonucleotide substrate binding domain capable of binding an oligonucleotide substrate and an effector-oligonucleotide binding site capable of binding an effector oligonucleotide, wherein upon recognition of the target by the modulation domain, and in the presence of binding of the effector oligonucleotide to the effector-oligonucleotide binding site, then the 3' end of the oligonucleotide substrate is ligated to the 5' end of the ligase.

The invention also provides a 1-piece ligase ribozyme comprising the nucleic acid sensor molecule shown in any one of SEQ ID NOS. 47, 105–107, 119.

The invention also provides a 2-piece ligase ribozyme comprising the nucleic acid sensor molecule shown in any one of SEQ ID NOS. 347, 349, and 351.

The invention further provides a 3-piece ligase ribozyme comprising the nucleic acid sensor molecule shown in any one of SEQ ID NOS. 46, 75, 76, 108–116, 118, 121–130, and 352.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1 depicts methodology for selecting nucleic acid sensor molecules of the invention.

FIGS. 2A and B show a nucleic acid sensor molecule (SEQ ID NO:46) according to one embodiment, in which the catalytic site includes a ligase site. FIG. 2A shows the conformation of the target molecule (SEQ ID NO:46) bound form of the nucleic acid sensor molecule with an effector oligo hybridized to its 3' end (SEQ ID NO:51). FIG. 2B shows the conformation of the non-target bound form of the nucleic acid (SEQ ID NO:46) sensor molecule.

FIGS. 3A and B show a nucleic acid sensor molecule (SEQ ID NO:47) derived from the nucleic acid sensor precursor molecule shown in FIGS. 2A and B in which first and second nucleotides are labeled with first and second signaling moieties (F and D, respectively).

FIG. 5A shows the conformation of the target molecule bound form of the nucleic acid sensor molecule (SEQ ID NO:48).

FIGS. 6A and B show a nucleic acid sensor molecule derived from the nucleic acid sensor molecule shown in FIGS. 3A and B in which first and second nucleotides are labeled with first and second signaling moieties (F and D, respectively) (SEQ ID NO:49).

FIG. 11A shows the beads prior to target binding and ligation (no emission from acceptor). FIG. 11B shows the beads after target binding and ligation (emission from acceptor detected).

FIG. 13. shows a schematic of fluorescence data generated by a biosensor array using the indicated nucleic acid sensors and target molecules.

FIG. 21 is a chart showing ERK2-dependence of cis-hammerhead cleavage.

FIG. 23B shows construct 6 (SEQ ID NO:81) 7 (SEQ ID NO:82), 8 (SEQ ID NO:83), 9 (SEQ ID NO:84), 10 (SEQ ID NO:85), 11 (SEQ ID NO:86) 12 (SEQ ID NO:87), 13 (SEQ ID NO:88), and 14 (SEQ ID NO:89).

FIG. 24 shows the linker region, activity, and stability of constructs 6 through 14.

FIG. 32 shows the sequences for constructs 17 (SEQ ID NO:109), 18 (SEQ ID NO:110), 19 (SEQ ID NO:111), 20 (SEQ ID NO:112), and 21 (SEQ ID NO:113), 22 (SEQ ID NO:114), 23 (SEQ ID NO:115), 24 (SEQ ID NO:116), 25 (SEQ ID NO:117), and 26 (SEQ ID NO:118).

FIG. 36 shows secondary structure representations of 3-piece construct 27 (SEQ ID NO:118) and 1-piece construct 28 (SEQ ID NO:119) ERK dependent ligases. 1-piece ERK dependent ligase is a slightly modified version of 3-piece system where the effector and substrate regions are replaced by a stable GNRA tetraloop.

FIG. 39B shows ligation assays run on constructs 29 (SEQ ID NO:349) and 30 (SEQ ID NO:351), in the absence or in the presence of 1 uM ERK.

FIG. 41 shows a schematic of the template for ppERK dependent ligase nucleic acid sensor molecules (SEQ ID NO:352) and its oligonucleotide substrate (SEQ ID NO:350).

FIG. 42 shows the nucleotide sequences for construct 31 (TK.16.118.K) (SEQ ID NO:121), construct 32 (TK.16.118.L) (SEQ ID NO:122), construct 33 (TK.16.118.M) (SEQ ID NO:123), construct 34 (TK.16.118.N) (SEQ ID NO:124), construct 35 (TK.16.118.O) (SEQ ID NO:125), construct 36 (TK.16.118.P) (SEQ ID NO:126), construct 37 (TK.16.118.Q) (SEQ ID NO:127), construct 38 (TK.16.118.R) (SEQ ID NO:128), construct 39 (TK.16.118.S) (SEQ ID NO:129), and construct 40 (TK.16.118.T) (SEQ ID NO:130).

FIG. 43 shows template sequences for the creation of a ppERK (SEQ ID NO:354) or ERK (SEQ ID NO:355) library of nucleic acid sensor molecules.

FIG. 44A shows the stem sequences of ERK dependent nucleic acid clones CW45-33-A08 (SEQ ID NO:356), CW45-33-C08 (SEQ ID NO:131), CW45-33-C09 (SEQ ID NO:132), CW45-33-D09 (SEQ ID NO:133), CW45-33-F08 (SEQ ID NO:90), CW45-33-H08 (SEQ ID NO:91), CW45-33-H09 (SEQ ID NO:92), CW45-33-A10 (SEQ ID NO:93), CW45-33-F09 (SEQ ID NO:94), and CW45-33-G08 (SEQ ID NO:95).

FIG. 44B shows the stem sequences of pp ERK dependent nucleic acid clones CW45-33-A02 (SEQ ID NO:44), CW45-33-B04 (SEQ ID NO:45), CW45-33-C04 (SEQ ID NO:5), CW45-33-D04 (SEQ ID NO:6), CW45-33-F03 (SEQ ID NO:7), CW45-33-D01 (SEQ ID NO:8), CW45-33-D02 (SEQ ID NO:37), CW45-33-D05 (SEQ ID NO:38), CW45-33-E01 (SEQ ID NO:39), CW45-33-G02 (SEQ ID NO:96), CW45-33-G03 (SEQ ID NO:97), CW45-33-H03 (SEQ ID NO:98), CW45-33-H1 (SEQ ID NO:99), and CW45-33-B05 (SEQ ID NO:100).

FIG. 45 nucleotide sequences of CW45-33-A02 (SEQ ID NO:44), and CW45-33-D04 (SEQ ID NO:6).

FIG. 57 shows bar graphs plotting the rate of activity of nucleic acid sensors when in the presence of different target molecules in vitro. Panel A shows the rate of activity in the presence of ERK and phosphorylated ERK for construct 19 (ligase E) on the left bar and construct 33 (ligase M) on the right bar. Panel B shows construct 19 and 33 rates of activity in the presence of Ras, MEK, ERK, p38, and ricin.

FIG. 59 lists the switch factor, dissociation constants, catalytic constant and detection limit for an ERK aptamer in comparison to four ERK dependent ligase nucleic acid sensor molecules.

FIG. 64 shows fitted kinetic time course signals observed from the solid-phase FRET sensor constructs in a solution-phase assay. FIG. 64A shows a graph that plots the signal observed from the donor fluorophore only in the presence of 200 uM cGMP. FIG. 64B shows a graph of the parametric fit to the experimental data shown in FIG. 64A, verifying that the rate constant for the solid-phase construct is in fact similar to that for the solution-phase construct under similar conditions.

FIG. 66A shows an endonuclease (hammerhead ribozyme)-based nucleic acid sensor immobilized linked to a gold surface via a thiol linker. FIG. 66B shows the fraction of this type of sensor cleaved and dissociated as a function of time in the presence of a fixed concentration of target. FIG. 66C shows the signal (image density) from a panel of immobilized sensors prior to their exposure to a target-mixture. FIG. 66D shows the signal from the uncleaved sensors after exposure to the mixture of all listed targets, while FIG. 66E represents the target-dependent cleavage signal. Specific target-dependent activity of each sensor is seen in each case for this multiplexed assay.

FIG. 67 shows a schematic diagram of the integrated SPReeta SPR sensor module (FIG. 67A), as well as the nucleic acid (hammerhead ribozyme) sensor molecule that is immobilized on the gold SPR layer (FIG. 67B). FIGS. 67C and 67D show typical real-time data generated by the SPR sensor system during sensor loading and target analyte-induced cleavage, respectively.

FIG. 68 gives the sequences for three cyclic nucleotide-dependent nucleic acid (hammerhead ribozyme) sensors dependent upon cGMP (SEQ ID NO:135), cCMP (SEQ ID NO:136), and cAMP (SEQ ID NO:137) in a conformation suitable for direct 5' surface attachment. The schematic shows the SPR sensor construct intended for direct 5' attachment to a native gold surface via a terminal thiol linker.

FIG. 70 gives the sequences for three cyclic nucleotide-dependent nucleic acid (hammerhead ribozyme) sensors dependent upon cCMP (SEQ ID NO:40), cAMP (SEQ ID NO:41), and cGMP (SEQ ID NO:42)in a conformation suitable for indirect surface attachment via a capture oligo. The schematic shows the SPR sensor construct intended for indirect surface attachment via a capture oligo to a neutravidin surface which has been passively adsorbed onto the gold SPR surface via cysteine residues.

FIG. 71 shows the surface loading (FIG. 71A) and target-dependent cleavage (FIG. 71B) of cGMP-dependent nucleic acid (hammerhead ribozyme) sensor molecules, as well as the physical configurations of the various nucleic acid sensor molecules (FIG. 71C) that give rise to the indicated portions of the kinetic data shown. The high signal to noise ratio (SNR) and dynamic range (DNR) of this SPR sensor array are clearly evident from the plots.

FIG. 75 shows a multiplex in situ ligase sensor chip, with pre-immobilized radiolabeled sensors activatable by lysozyme (LYS) and FMN.

DETAILED DESCRIPTION OF THE INVENTION

Figure 1A:
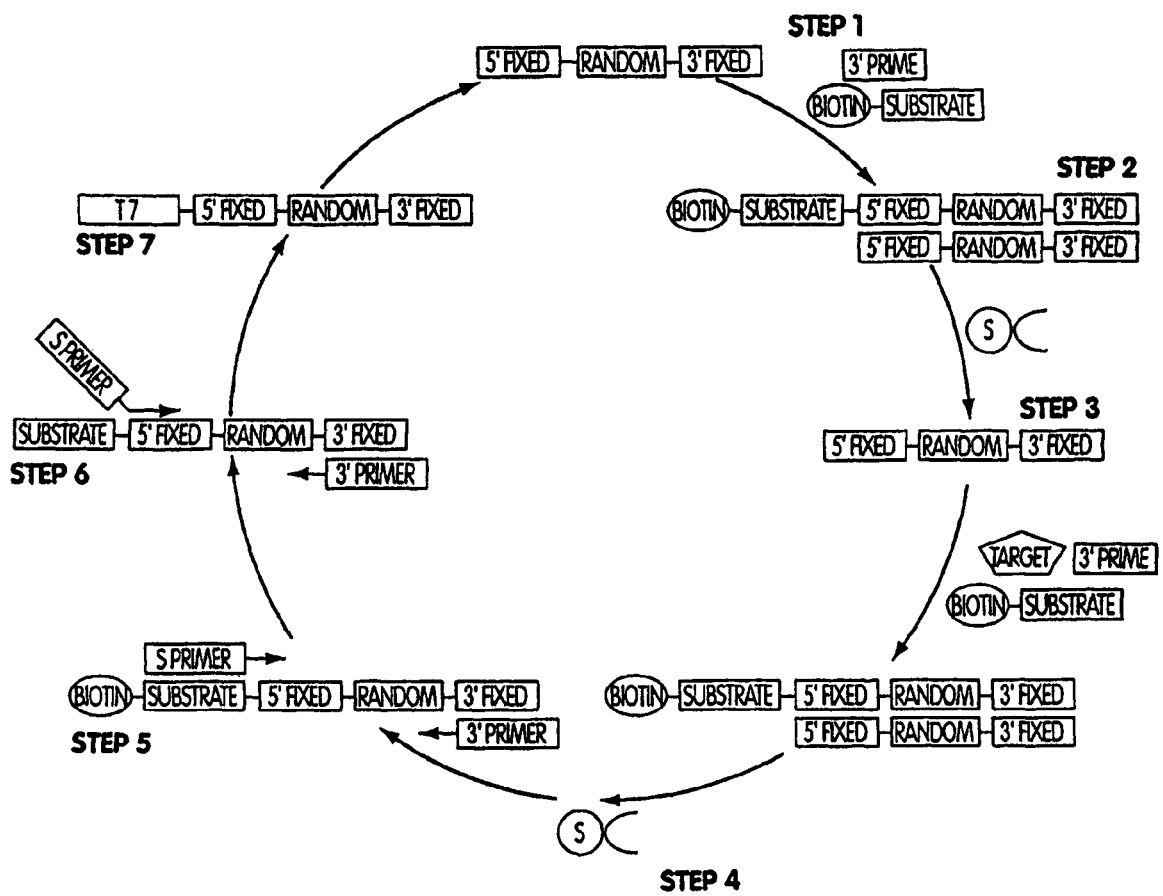
FIG. 1A is a flow diagram showing a method for selecting nucleic acid sensor precursor molecules having a target molecule activatable ligase activity according to one embodiment.

The invention is generally drawn to catalytic NASMs (also know as allosteric ribozymes, aptazymes and the like) and optical nucleic acid sensor molecules that may be used to monitor the presence or concentration of various target molecules. Target molecules include a variety of biologically relevant molecules, such as, for example, proteins (including specific post-translationally modified forms of proteins), peptides, nucleic acids, nucleotides, natural products, metabolites, drugs, toxins, biohazards, and ions.

The invention also includes methods by which a change in the activity or conformation of a nucleic acid sensor molecule upon recognition of a specific target molecule can be coupled to a quantifiable, measurable signal. The invention also includes methods which allow one to test the inhibitory activity of one or more compounds simultaneously against one or more enzymes or biochemical targets. Assays can be carried out in a variety of formats, including in vitro biochemical assays, in vitro cellular assays, in vivo cellular assays, in solution, on chips or other substrates, or in vivo animal models. These assays have applications in all phases of drug discovery, including target validation and discovery and development, high throughput screening, biochemical assays, in vitro cellular models and in vivo animal models.

Nucleic acid sensor molecules are RNAs, DNAs, RNA/DNA hybrids, or derivatives or analogs of nucleic acids that catalyze a chemical reaction and/or undergo a conformational change upon the recognition of a specific target molecule. Nucleic acid sensor molecule - based assays can be carried out using all catalytic platforms, which include endonucleases, such as the hammerhead ribozyme, the hairpin ribozyme, the HDV ribozyme, and the VS ribozyme; ligases, such as the L1 ligase, and the class I–III ligases and; group I and group II self-splicing introns.

Catalytic NASMs can be generated or selected by a variety of methods both disclosed herein and known in the art. For examples, see WO98/27104, WO01/96559, and WO 00/26226 Also disclosed herein are optical nucleic acid sensor molecules and methods making them. In general, optical catalytic NASMs generate a detectable optical signal upon recognition of a target molecule. Optical NASMs are generated from catalytic NASMs by addition of an optical signal generating unit.

Also disclosed herein are two new classes of catalytic NASMs (referred to as one-piece or cis ligases) and two piece ligases and methods of generating them.

In general, catalytic NASMs can be used, e.g., to detect target molecules either by generation of an optical signal or an amplicon detectable, e.g., by RT-PCR, size gel purification procedures and any other means of seperating variously sized or conformed nucleic acid molecules. Optical NASMs, on the other hand, can be used, e.g., to detect target molecules by generation of an optical signal.

Optical signals can be generated by optical NASMs in a number of ways. In some embodiments the signal is an optical signal generated, e.g., by the fluorescence of a fluorescent dye. In other embodiments, the signal is an optical signal generated by molecules in close proximity to the nucleic acid sensor molecule whose optical or electrochemical properties are affected by the presence of the target molecule bound nucleic acid sensor molecule. In some embodiments the nucleic acid sensor molecules comprise at least one signaling moiety. In other embodiments, the nucleic acid sensor molecules comprise first and second signaling moieties whose optical properties change in response to the binding of a target molecule through changes in the proximity of the first and second signaling moieties. Thus, detection can be direct or indirect.

In one embodiment, a plurality of nucleic acid sensor molecules are provided, either in solution, or immobilized on a substrate, generating a biosensor. In a further embodiment, a diagnostic system is provided which comprises at least one biosensor in optical communication with a optical signal detector. Methods of using the diagnostic system are also provided, as well as kits for performing the method.

In other embodiments, the NASMs are used to detect the presence of target molecules in vivo.

In order to more clearly and concisely describe and point out the subject matter of the claimed invention, the following definitions are provided for specific terms which are used in the following written description and the appended claims.

As defined herein, a "oligonucleotide" is used interchangeably with the term "nucleic acid" and includes RNA or DNA (or RNA/DNA) sequences of more than one nucleotide in either single strand or double-stranded form. A "modified oligonucleotide" includes at least one residue with any of: an altered internucleotide linkage(s), altered sugar(s), altered base(s), or combinations thereof.

As defined herein, a "target molecule" is any molecule to be detected. The term "target molecule" refers to, any molecule for which nucleic acid sensor molecule exists or can be generated and can be naturally occurring or artificially created.

As defined herein, a "signature target molecule" is a target molecule whose expression is correlatable with a trait.

As used herein, a "diagnostic signature target molecule" is a signature target molecule whose expression is, by itself or in combination with other signature target molecules, diagnostic of a trait.

As used herein, a "pathway target molecule" is a target molecule involved in a biological or metabolic pathway and whose accumulation and/or activity is dependent on other target molecules in the same biological or metabolic pathway, or whose accumulation and/or activity affects the accumulation and/or activity of other target molecules in the same biological or metabolic pathway.

As used herein, a "diagnostic pathway target molecule" is a pathway target molecule whose expression/activity and/or structural properties, by itself or in combination with other pathway target molecules, is diagnostic of a particular trait.

As used herein, a "profiling nucleic acid sensor molecule" is a nucleic acid sensor molecule that recognizes a signature target molecule, a diagnostic signature target molecule, a pathway target molecule, and/or a diagnostic pathway target molecule.

As defined herein, a "biosensor" comprises a plurality of nucleic acid sensor molecules.

As defined herein, a "profiling biosensor" comprises a plurality of profiling nucleic acid sensor molecules.

As used herein, a molecule which "naturally binds to DNA or RNA" is one which is found within a cell in an organism found in nature.

As defined herein, a "target modulation domain" is the portion of a nucleic acid sensor molecule which recognizes a target molecule. The target modulation domain is also sometimes referred to herein as the "target activation site" or "effector modulation domain".

As used herein a "catalytic domain" is the portion of a nucleic acid sensor molecule possessing catalytic activity which is modulated in response to binding of a target molecule to the target modulation domain.

As used herein, a "linker region" or "linker domain" is a portion of a nucleic acid sensor molecule by or at which the "target modulation domain" and "catalytic domain" are joined. Linker regions include, but are not limited to oligonucleotides of varying length, baseparring phosphodiester, phosphothiolate, and other covalent bonds, chemical moieties (e.g., PEG), PNA, formacetal, bismaleimide, disulfide, and other bifunctional linker reagents. The linker domain is also sometimes referred to herein as a "connector" or "stem".

As used herein, a "random sequence" or a "randomized sequence" is a segment of a nucleic acid having one or more regions of fully or partially random sequences. A fully random sequence is a sequence in which there is an approximately equal probability of each base (A, T, C, and G) being present at each position in the sequence. In a partially random sequence, instead of a 25% chance that an A, T, C, or G base is present at each position, there are unequal probabilities.

As defined herein, "a fixed region" is a nucleic acid sequence which is known.

As defined herein, "amplifying" means any step or process or any combination of steps or processes that increases the amount or number of copies of a molecule or class of molecules.

As defined herein, a "catalytic nucleic acid sensor molecule" is a nucleic acid molecule 20 comprising a target modulation domain, a linker region, and a catalytic domain.

As defined herein, an "optical nucleic acid sensor molecule" is a catalytic nucleic acid sensor molecule wherein the catalytic domain has been modified to emit an optical signal as a result of and/or in lieu of catalysis by the inclusion of an optical signal generating unit.

As defined herein, a "nucleic acid sensor molecule" or "NASM" refers to either or both of a catalytic nucleic acid sensor molecule and an optical nucleic acid sensor molecule.

As used herein, a "signal" is a detectable physical quantity, impulse or object.

As used herein, an "optical signal" is a signal the optical properties of which can be detected.

As defined herein, an "optical signal generating unit" is a portion of a nucleic acid sensor molecule comprising one or more nucleic acic sequences and/or non-nucleic acid molecular entities, which change optical or electrochemical properties or which change the optical or electrochemical properties of molecules in close proximity to them in response to a change in the conformation or the activity of the nucleic acid sensor molecule following recognition of a target molecule by the target modulation domain.

As defined herein, a nucleic acid sensor molecule which "recognizes a target molecule" is a nucleic acid molecule whose activity is modulated upon binding of a target molecule to the TMD a greater extent than it is by the binding of any non-target molecule or in the absence of the target molecule. The recognition event between the nucleic acid sensor molecule and the target molecule need not be permanent during the time in which the resulting allosteric modulation occurs. Thus, the recognition event can be transient with respect to the ensuing allosteric modulation (e.g., conformational change) of the nucleic acid precursor molecule or nucleic acid sensor molecule.

As defined herein, an "array" or "microarray" refers to a biosensor comprising a plurality of nucleic acid sensor molecules immobilized on a substrate.

As defined herein, a "substrate" refers to any physical supporting surface, whether rigid, flexible, solid, porous, gel-based, or of any other material or composition.

As defined herein, an "amplicon" is the sequence of a nucleic acid sensor molecule with ligase activity covalently ligated to an oligonucleotide substrate.

As defined herein, a "cleavage substrate" is an oligonucleotide or portion of an oligonucleotide cleaved upon target molecule recognized by a target modulation domain of an endonucleolytic nucleic acid sensor molecule.

As defined herein, an "oligonucleotide substrate" is an oligonucleotide that is acted upon by the catalytic domain of a nucleic acid sensor molecule.

As defined herein, an "effector oligonucleotide" is an oligonucleotide that base pairs with the effector oligonucleotide binding domain of a nucleic acid sensor molecule with ligase activity.

As defined herein, an "effector oligonucleotide binding domain" is the portion of the nucleic acid sensor molecule with ligase activity which is complementary to the effector oligonucleotide.

As defined herein, a "capture oligonucleotide" is an oligonucleotide that is used to attach a nucleic acid sensor molecule to a substrate by complementarity and/or hybridization.

As defined herein, an "oligonucleotide substrate binding domain" is the portion on the nucleic acid sensor molecule with ligase activity that is complementary to and can base pair with an oligonucleotide substrate.

As defined herein, a "oligonucleotide supersubstrate" is an oligonucleotide substrate that is complementary to and can base pair with the oligonucleotide substrate binding domain and to the effector oligonucleotide binding domain of a nucleic acid sensor molecule with ligase activity. The oligonucleotide supersubstrate may or may not carry an affinity tag.

As defined herein, a "oligonucleotide supersubstrate binding domain" is the region of a nucleic acid sensor molecule with ligase activity that is complementary to and can base pair with the oligonucleotide supersubstrate.

As defined herein, "stem selection" refers to a process performed on a pool of nucleic molecules comprising a target modulation domain, a catalytic domain and an oligonucleotide linker region wherein the linker region is fully or partially randomized.

As defined herein, "rational design/engineering" refers to a technique used to construct nucleic acid sensor molecules in which a non-conserved region of a ribozyme is replaced with a target modulation domain and joined to the catalytic domain of the ribozyme by an oligonucleotide linker region.

As defined herein, "amplicon dependent nucleic acid amplification" refers to a technique by which one can amplify the signal of a nucleic acid sensor molecule by use of standard RT/PCR or Real-Time RT-PCR methods."

As defined herein, "switch factor" is the enhancement observed in the catalytic activity and/or catalytic initial rate of a nucleic acid sensor molecule upon recognition of a target molecule by the target modulation domain.

As defined herein, a "cis-ligase ribozyme" is a ligase ribozyme that ligates its 3' end to its 5' end. The cis-ligase ribozyme is also referred herein as "1-piece ligase" and is a 1-component system where oligonucleotide substrate, oligonucleotide substrate binding domain, catalytic domain, effector oligonucleotide and effector oligonucleotide binding domains are fused in the format shown in FIG. 39.

As defined herein, a "trans-ligase ribozyme" is a ligase ribozyme that ligates its 5' end to the 3' end of an oligonucleotide substrate.

As defined herein, a "2-piece ligase" is a 2-component trans-ligase ribozyme. The first component consists of the catalytic domain, the linker region, the target modulation domain, the substrate binding domain and the effector oligonucleotide binding domain. The second component is the oligonucleotide substrate that is complementary to the substrate binding domain and the effector oligonucleotide binding domain. This system follows the format shown in FIG. 41.

As defined herein, a "3-piece ligase" is a 3-component trans-ligase ribozyme. The first component consists of the catalytic domain, the linker, the target modulation domain, the substrate binding domain and the effector oligonucleotide binding domain. The second component is the effector oligonucleotide that is complementary to the effector oligonucleotide binding domain. The third component is the oligonucleotide substrate that is complementary to the substrate binding domain. This system follows the format of the 3-piece ligase platform shown in FIG. 39.

1. Generating a Target Specific Nucleic Acid Sensor Molecule

Catalytic nucleic acid sensor molecules (NASMs) are selected which have a target molecule-sensitive catalytic activity (e.g., ligation or self-cleavage) from a pool of randomized oligonucleotides. The catalytic NASMs have a target modilation domain to which the target molecule specifically binds and a catalytic domain for mediating a catalytic reaction. Binding of a target molecule to the target modulation domain triggers a conformation change and/or change in catalytic activity in the nucleic acid sensor molecule. In one embodiment, by modifying (e.g., removing) at least a portion of the catalytic domain and coupling it to an optical signal generating unit, an optical nucleic acid sensor molecule is generated whose optical properties change upon binding of a target molecule to the target modulation domain. In one embodiment, the pool of randomized oligonucleotides comprises the catalytic site of a ribozyme.

A. Selection and Generation of Catalytic Nucleic Acid Sensor Molecules

In one embodiment, a heterogeneous population of oligonucleotide molecules comprising randomized sequences is screened to identify a nucleic acid sensor molecule having a catalytic activity which is modified (e.g., activated) upon interaction with a target molecule. Each oligonucleotide in the population comprises a random sequence and at least one fixed sequence at its 5' and/or 3' end. In one embodiment, the fixed sequence comprises at least a portion of a catalytic site. In the embodiments shown in FIGS. 1 and 4, the random sequence is flanked at both ends with fixed sequences.

In one embodiment, the random sequence portion of the oligonucleotide is about 15–70 (e.g., 30–40) nucleotides in length and can comprise ribonucleotides and/or deoxyribonucleotides. Random oligonucleotides can be synthesized from phosphodiester-linked nucleotides using solid phase oligonucleotide synthesis techniques well known in the art (see, e.g., Froehler, et al., 1986a; 1986b. Oligonucleotides can also be synthesized using solution phase methods such as triester synthesis methods (see, e.g., Sood, et al., 1977, and Hirose, et al., 1978). Typical syntheses carried out on automated DNA synthesis equipment yield $10^{15}$–$10^{17}$ molecules. Sufficiently large regions of random sequence in the sequence design increases the likelihood that each synthesized molecule is likely to represent a unique sequence.

To synthesize randomized sequences, mixtures of all four nucleotides are added at each nucleotide addition step during the synthesis process, allowing for random incorporation of nucleotides. In one embodiment, random oligonucleotides comprise entirely random sequences; however, in other embodiments, random oligonucleotide can comprise stretches of nonrandom or partially random sequences. Partially random sequences can be created by adding the four nucleotides in different molar ratios at each addition step.

To generate oligonucleotide populations which are resistant to nucleases and hydrolysis, modified oligonucleotides can be used and can include one or more substitute intemucleotide linkages, altered sugars, altered bases, or combinations thereof. In one embodiment, oligonucleotides are provided in which the P(O)O group is replaced by P(O)S ("thioate"), P(S)S ("dithioate"), P(O)NR$_2$ ("amidate"), P(O) R, P(O)OR', CO or CH$_2$ ("formacetal") or 3'-amine (—NH—CH$_2$—CH$_2$—), wherein each R or R' is independently H or substituted or unsubstituted alkyl. Linkage groups can be attached to adjacent nucleotide through an —O—N—, or —S— linkage. Not all linkages in the oligonucleotide are required to be identical.

In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2'-modified sugars are described in Sproat, et al., 1991; Cotten, et al., 1991; and Hobbs, et al., 1973. The use of 2-fluoro-ribonucleotide oligomer molecules can increase the sensitivity of a nucleic acid sensor molecule for a target molecule by ten-to one hundred-fold over those generated using unsubstituted ribo- or deoxyribooligonucleotides (Pagratis, et al., 1997), providing additional binding interactions with a target molecule and increasing the stability of the nucleic acid sensor molecule's secondary structure(s) (Kraus, et al., 1998; Pieken, et al., 1991; Lin, et al., 1994; Jellinek, et al. 1995; Pagratis, et al., 1997).

Figure 4:
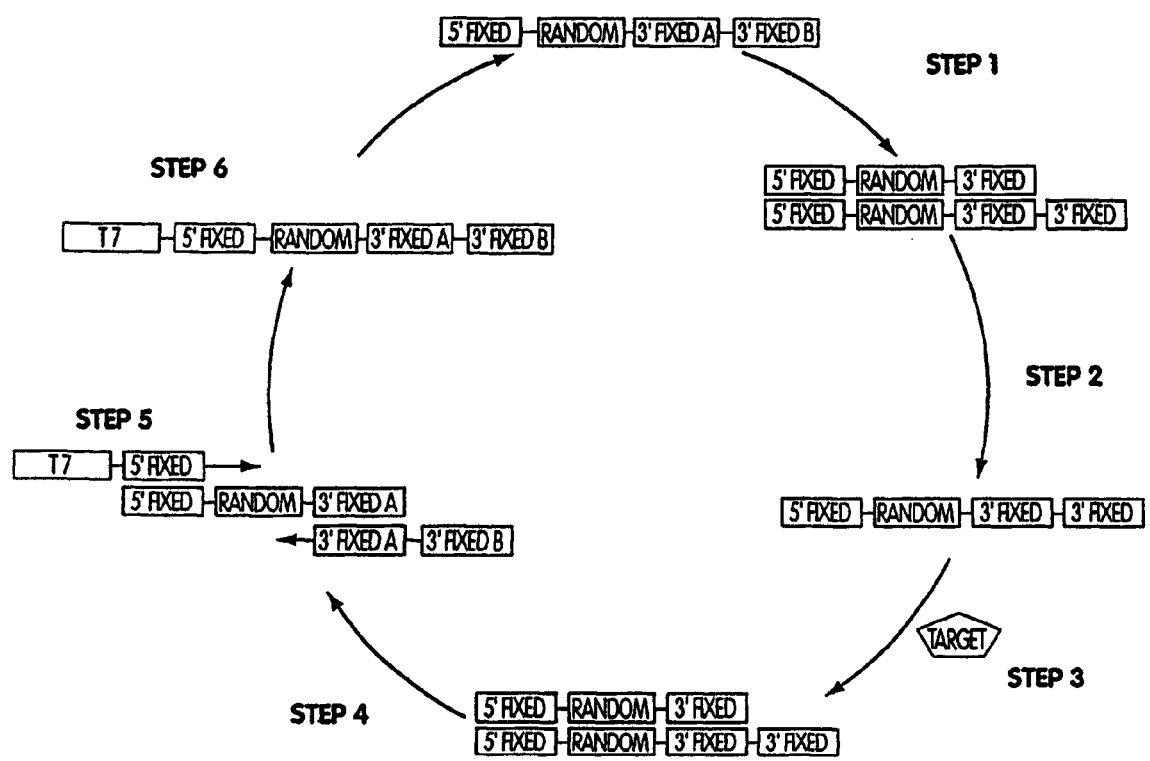
FIG. 4 is a flow diagram showing a method for selecting nucleic acid sensor molecules having a target molecule activatable self-cleavage activity according to one embodiment.

In the embodiments shown in FIGS. 1 and 4, the random sequence portion of the oligonucleotide is flanked by at least one fixed sequence which comprises a sequence shared by all the molecules of the oligonucleotide population. Fixed sequences include sequences such as hybridization sites for PCR primers, promoter sequences for RNA polymerases (e.g., T3, T4, T7, SP6, and the like), restriction sites, or homopolymeric sequences, such as poly A or poly T tracts, catalytic cores (described further below), sites for selective binding to affinity columns, and other sequences to facilitate cloning and/or sequencing of an oligonucleotide of interest. In one embodiment, the fixed sequence is approximately 50 nucleotides in length.

In a preferred embodiment, the fixed sequence comprises at least a portion of a catalytic site of an oligonucleotide molecule (e.g., a ribozyme) capable of catalyzing a chemical reaction. Catalytic sites are well known in the art and include, e.g. a ligase site (see FIG. 2), the catalytic sites of Group I or Group II introns (see, e.g., U.S. Pat. No. 5,780,272), the catalytic core of a hammerhead ribozyme (see, e.g., U.S. Pat. No. 5,767,263 and U.S. Pat. No. 5,700,923, and FIG. 5, herein) or a hairpin ribozyme (see, e.g., U.S. Pat. No. 5,631,359. Other catalytic sites are disclosed in U.S. Pat. No. 6,063,566, Koizumi et al., FEBS Lett. 239: 285–288 (1988), Haseloff and Gerlach, Nature 334: 585–59 (1988), Hampel and Tritz, Biochemistry 28: 4929–4933 (1989), Uhlenbeck, Nature, 328: 596–600 (1987), and Fedor and Uhlenbeck, Proc. Natl. Acad. Sci. USA 87: 1668–1672 (1990)).

Figure 1B:
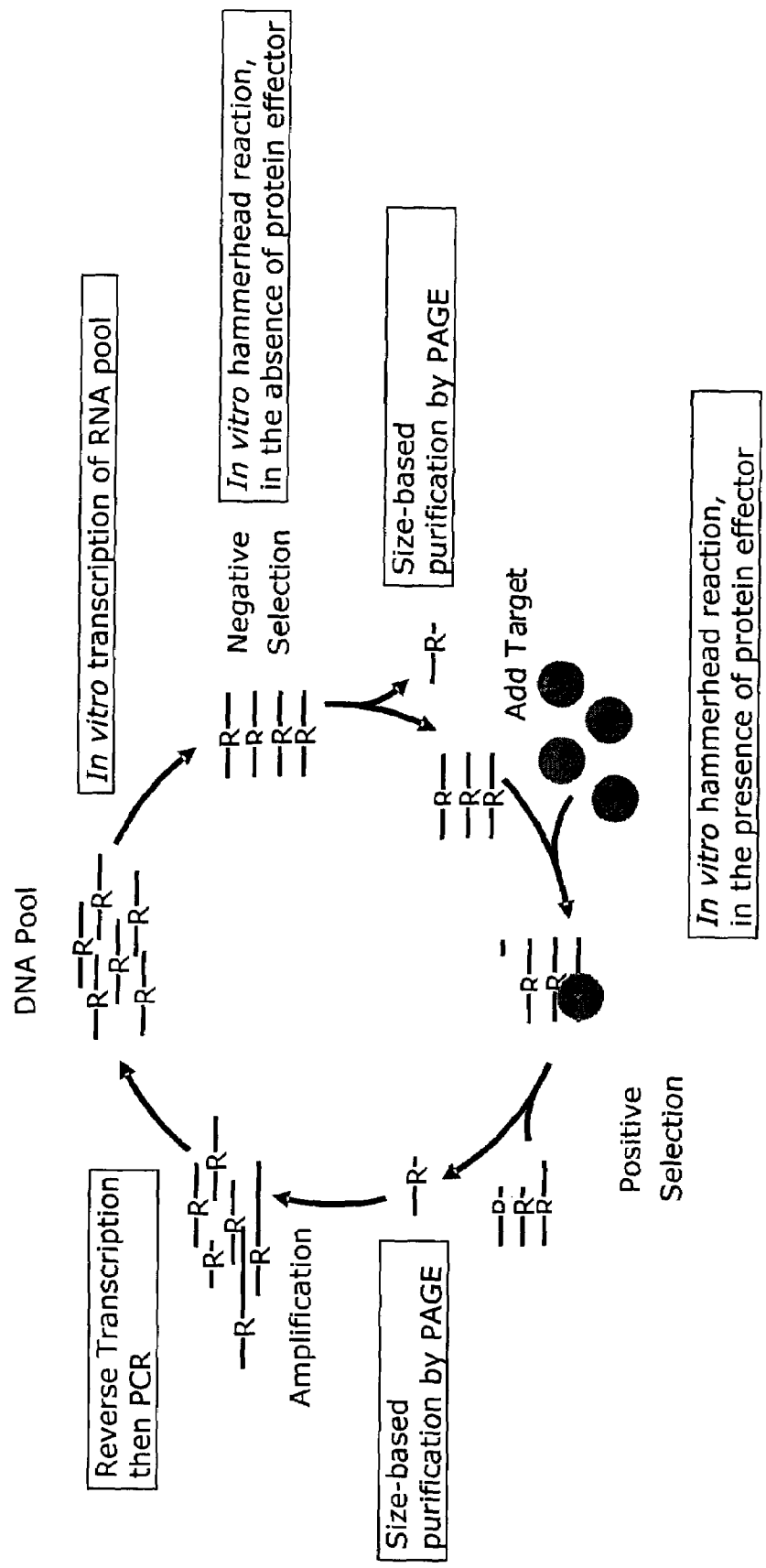
FIG. 1B is a flow diagram showing a gel-based method for selecting nucleic acid sensor precursor molecules having a target molecule activatable endonuclease activity according to one embodiment.

Nucleic acid sensor molecules are generally selected in a 5 to 20 cycle procedure. In one embodiment, heterogeneity is introduced only in the initial selection stages and does not occur throughout the replicating process. FIG. 1A shows a schematic diagram in which the oligonucleotide population is screened for a nucleic acid sensor molecule which comprises a target molecule activatable ligase activity. FIG. 1B shows the hammerhead nucleic acid sensor molecule selection methodology. Each of these methods are readily modified for the selection of NASMs with other catalytic activities.

In the embodiment shown in FIG. 1A, the ligation reaction involves covalent attachment of an oligonucleotide substrate to the 5'-end of the NASM through formation of a phosphodiester linkage. Other ligation chemistries can form the basis for selection of NASMs (e.g., oligonucleotide ligation to the 3'-end, alkylation's (Wilson & Szostak), peptide bond formation (Zhang & Czech), Diels-Alder reactions to couple alkenes and dienes (Seelig & Jaschke), etc.). For some chemistries, the chemical functional groups that constitute the reactants in the ligation reaction may not naturally appear within nucleic acids. Thus, it may be necessary to synthesize an RNA pool in which one of the ligation reactants is covalently attached to each member of the pool (e.g., attaching a primary amine to the 5'-end of an RNA to enable selection for peptide bond formation).

In this embodiment, the oligonucleotide population from which the NASMs will be selected is initially screened in a negative selection procedure to eliminate any molecules which have ligase activity even in the absence of target molecule binding. A solution of oligonucleotides (e.g., 100 pM) comprising a 5' and 3' fixed sequence ("5'-fixed: random: 3'fixed") is denatured with a 3' primer sequence ("3' prime") (e.g., 200 pM) which binds to at least a portion of the 3' fixed sequence. In one embodiment, the 5'-fixed: random:3'-fixed sequence is

```
                                              (SEQ ID NO:1)
GGACUUCGGUCCAGUGCUCGUGCACUAGGCCGUUCGACC-N30-50

CUUAGACAGGAGGUUAGGUGCCUCGUGAUGUCCAGUCGC-3',
``` where N represents a random sequence having 30 to 50 nucleotides and the 3' primer sequence used is

```
5'-GCGACTGGACATCACGAG-3'.   (SEQ ID NO:2)
```

Ligation buffer (e.g., 30 mM Tris HCl, pH 7.4, 600 mM NaCl, 1 mM EDTA, 1% NP-40, 60 mM $MgCl_2$) and a tagged oligonucleotide substrate sequence ("tag-substrate") (e.g., Tag-UGCCACU) are added and the mixture is incubated for about 16 to about 24 hours at 25° C. in the absence of target molecule (STEP 1). Tags encompassed within the scope include, e.g., radioactive labels, fluorescent labels, a chemically reactive species such as thiophosphate, the first member of a binding pair comprising a first and second binding member, each member bindable to the other (e.g., biotin, an antigen recognized by an antibody, or a tag nucleic acid sequence). The reaction is stopped by the addition of EDTA. Alternatively, the reaction can be terminated by removal of the substrate or addition of denaturants (e.g. urea, formamide).

Ligated molecules are removed from pool of selectable molecules (STEP 2), generating a population of oligonucleotides substantially free of ligated molecules (as measured by absence of the tag sequence in the solution). In the embodiment shown in FIG. 1A, the tag is the first member of a binding pair (e.g., biotin) and the ligated molecules ("biotin-oligonucleotide substrate:5'-fixed:random:3'-fixed") are physically removed from the solution by contacting the sample to a solid support to which the second member of the binding pair is bound ("S") (e.g., streptavidin). The eluant collected comprises a population of oligonucleotides enriched for non-ligated molecules (5'-fixed: random:3'-fixed). This step can be repeated multiple times until the oligonucleotide population is substantially free of molecules having target-insensitive ligase activity.

This step allows for suppression of the ability of constitutively active molecules to be carried through to the next cycle of selection. Physical separation of ligated and unligated molecules is one mechanism by which this can be achieved. Alternatively, the negative selection step can be configured such that catalysis converts active molecules to a form that blocks their ability to be either retained during the subsequent positive selection step or to be amplified for the next cycle of selection. For example, the oligonucleotide substrate used for ligation in the negative selection step can be synthesized without a capture tag. Target-independent ligases covalently self-attach the untagged oligonucleotide substrate during the negative selection step and are then unable to accept a tagged form of the oligonucleotide substrate provided during the positive selection step that follows. In another embodiment, the oligonucleotide substrate provided during the negative selection step has a different sequence from that provided during the positive selection step. When PCR is carried out using a primer complementary to the positive selection oligonucleotide substrate, only target-activated ligases will be capable of amplification.

A positive selection phase follows. In this phase, more 3' primer and tagged oligonucleotide substrate are added to the pool resulting from the negative selection step. Target molecules are then added to form a reacted solution and the reacted solution is incubated at 25 ° C. for about 2 hours (STEP 3). Target molecules encompassed within the scope include, e.g., proteins or portions thereof (e.g., receptors, antigen, antibodies, enzymes, growth factors), peptides, enzyme inhibitors, hormones, carbohydrates, polysaccharides, glycoproteins, lipids, phospholipids, metabolites, metal ions, cofactors, inhibitors, drugs, dyes, vitamins, nucleic acids, membrane structures, receptors, organelles, and viruses. Target molecules can be free in solution or can be part of a larger cellular structure (e.g., such as a receptor embedded in a cell membrane). In one embodiment, a target molecule is one which does not naturally bind to nucleic acids.

In one embodiment, nucleic acid sensor molecules are selected which are activated by target molecules comprising molecules having an identified biological activity (e.g., a known enzymatic activity, receptor activity, or a known structural role); however, in another embodiment, the biological activity of at least one of the target molecules is unknown (e.g., the target molecule is a polypeptide expressed from the open reading frame of an EST sequence, or is an uncharacterized polypeptide synthesized based on a predicted open reading frame, or is a purified or semi-purified protein whose function is unknown).

Although in one embodiment the target molecule does not naturally bind to nucleic acids, in another embodiment, the target molecule does bind in a sequence specific or non-specific manner to a nucleic acid sensor molecule. In a further embodiment, a plurality of target molecules binds to the nucleic acid sensor molecule. Selection for NASMs specifically responsive to a plurality of target molecules (i.e. not activated by single targets within the plurality) may be achieved by including at least two negative selection steps in which subsets of the target molecules are provided.

In still a further embodiment, nucleic acid sensor molecules are selected which bind specifically to a modified target molecule but which do not bind to non-modified target molecules. Targeted modifications include, e.g., post-translational modifications of a protein, such as phosphorylation, ribosylation, methylation (Arg, Asp, N, S, or 0-directed), prenylation (e.g., farnesyl, geranylgeranyl, and the like), acetylation, acylation, allelic variations within a protein (e.g., single amino acid changes in a protein) and cleavage sites in a protein. In another embodiment, intermediates in a chemical synthesis pathway can be targeted, as well as starting and final products. In still a further embodiment, stereochemically distinct species of a molecules can be targeted.

The reacted solution is enriched for ligated molecules (biotin-oligonucleotide substrate: 5'- fixed :random:3'-fixed) by removing non-tagged molecules (5'-fixed:random:3'-fixed) from the solution. For example, in one embodiment, the tagged oligonucleotide substrate comprises a biotin tag and ligated molecules are isolated by passing the reacted solution over a solid support to which streptavidin (S) is bound (STEP 4). Eluant containing non-bound, non-ligated molecules (5'-fixed:random:3'-fixed) is discarded and bound, ligated molecules (biotin-oligonucleotide substrate: 5'-fixed:random:3'-fixed) are identified as nucleic acid sensor molecules and released from the support by disrupting the binding pair interaction which enabled capture of the catalytically active molecules. For example, heating to 95° C. in the presence of 10 mM biotin allows release of biotin-tagged catalysts from an immobilized streptavidin support. In another embodiment, the captured catalysts remain attached to a solid support and are directly amplified (described below) while immobilized. Multiple positive selection phases can be performed (STEPS 3 and 4). In one embodiment, the stringency of each positive selection phase is increased by decreasing the incubation time by one half.

Physically removing inactive species from the pool adds stringency to the selection process. However, to the extent that the ligation reaction increases the amplification potential of the NASMs, this step may be omitted. In the illustrated embodiment, for example, ligation of an oligonucleotide to the active species provides a primer binding site that enables subsequent PCR amplification using an oligonucleotide substrate complementary to the original oligonucleotide substrate. Unligated species do not necessarily need to be physically separated from other species because they are less likely to amplify in the absence of a covalently tethered primer binding site. Selected nucleic acid sensor molecules are amplified (or in the case of RNA molecules, first reverse transcribed, then amplified) using an oligonucleotide substrate primer ("S primer") (e.g., 5 '-AAAAAATGCACTG-GACT-3' (SEQ ID NO:3)) which specifically binds to the litgated oligonucleotide substrate sequence (STEP 5). In one embodiment, amplified molecules are further amplified with a nested PCR primer that regenerates a T7 promoter ("T7 Primer") from the 5' fixed and the litigated oligonucleotide substrate sequence (STEP 6). Following transcription with T7 RNA polymerase (STEP 7), the oligonucleotide pool may be further selected and amplified to eliminate any remaining unligated sequences (5'-fixed:random:3'-fixed) by repeating STEPS 3–7. It should be obvious to those of skill in the art that in addition to PCR, and RT-PCR, any number of amplification methods can be used (either enzymatic, chemical, or replication-based, e.g., such as by cloning), either singly, or in combination. Exemplary amplification methods are disclosed in Saiki, et al., 1985; Saiki, et al., 1988, Kwoh, et al., 1989; Joyce, 1989; and Guatelli, et al., 1990.

Because the 3' primer (3' prime) (see STEP 3 in FIG. 1A) is included in the ligation mixture, selected nucleic acid sensor molecules may require this sequence for activation. In cases where this is undesirable, the 3' primer may be omitted from the mix. Alternatively, the final nucleic acid sensor molecule can be modified by attaching the 3' primer via a short sequence loop or a chemical linker to the 3' end of the nucleic acid sensor molecule, thereby eliminating the requirement for added primer, allowing 3' primer sequence to self-prime the molecule.

As shown in FIG. 1B, selection of a nucleic acid sensor molecule begins with the synthesis of a ribozyme sequence on a DNA synthesizer. Random nucleotides are incorporated generating pools of roughly $10^{16}$ molecules. Most molecules in this pool are non-functional, but a handful will respond to a given target and be useful as nucleic acid sensor molecules. Sorting among the billions of species to find the desired molecules starts from the complex sequence pool. Nucleic acid sensor molecule are isolated by an iterative process: in addition to the target-activated ribozymes that one desires, the starting pool is usually dominated by either constitutively active or completely inactive ribozymes. The selection process removes both types of contaminants. In the following amplification stage, thousands of copies of the surviving sequences are generated to enable the next round of selection. During amplification, random mutations can be introduced into the copied molecules—this 'genetic noise' allows functional NASMs to continuously evolve and become even better adapted as target-activated molecules. The entire experiment reduces the pool complexity from $10^{16}$ down to <100.

Pool preparation. The starting library of DNA sequences is generated by automated chemical synthesis on a DNA synthesizer. This library of sequences is transcribed in vitro into RNA using T7 RNA polymerase and subsequently purified.

Negative selection incubation. In the absence of the desired target molecule of interest, the RNA library is incubated together with the binding buffer alone. During this incubation, non-allosteric (or non-target activated) ribozymes are expected to undergo cleavage.

Size-based Purification. Undesired members of the hammerhead pool, those that are constitutively active in the absence of the target molecule, are removed from the unreacted members by PAGE-chromatography; 7M Urea, 8% acrylamide, 1×TBE. Higher molecular weight species are eluted as a single broad band from the gel matrix into TBE buffer, then purified for subsequent steps in the selection cycle.

Positive selection incubation. The remaining RNA pool is then incubated under identical conditions but now in the presence of the target molecule of interest in binding buffer.

Size-based Purification. In this step, desired members of the hammerhead pool, those that are only active in the presence of the target molecule, are removed from the remaining unreacted members by PAGE-chromatography; 7M Urea, 8% acrylamide, 1×TBE. In this step, lower molecular weight species are eluted as a single broad band from the gel matrix into TBE buffer, then purified for subsequent steps in the selection cycle.

Amplification. RT-PCR amplified DNA is purified and transcribed to yield an enriched pool for a subsequent round of reselection.

Iteratively repeat. Rounds of selection and amplification (steps 2–5) are repeated until functional members sufficiently dominate the resultant library.

In another embodiment, as shown in FIG. 4, an oligonucleotide population is screened for a nucleic acid sensor molecule which comprises a target molecule having activatable self-cleaving activity. In this embodiment, the starting population of oligonucleotide molecules comprises 5' and 3' fixed regions ("5'-fixed and 3' fixed A-3'fixed B") and at least fixed regions, in this example, the 3' fixed region, comprises a ribozyme catalytic core including a self cleavage site (the junction between 3' fixed A-3 ' fixed B). In one embodiment, the 5'-fixed: random:3' fixed A-3'-fixed B molecule is GGGCGACCCUGAUGAGCCUGG-$N_{20\text{-}50}$-UUAGAC-GAAACGGUGAAAGCCGUAGGUUGCCC (SEQ ID NO:4), where $N_{20\text{-}50}$ is a random sequence of 20–50 nucleotides.

The population of oligonucleotide molecules comprising random oligonucleotides flanked by fixed 5' and 3' sequences (5'-fixed:random:3'-fixed A: 3' fixed B) are negative selected to remove oligonucleotides which self-cleave (i. e., 5'-fixed:random:3'-fixed-A molecules) even in the absence of target molecules. The oligonucleotide pool is incubated in reaction buffer (e.g., 50 mM Tris HCl, pH 7.5, 20 mM $MgCl_2$) for 5 hours at 25° C., punctuated at one hour intervals by incubation at 60° C. for one minutes (STEP 1). In one embodiment, the uncleaved fraction of the oligonucleotide population (containing 5'-fixed and 3' fixed A-3'-fixed B molecules) is purified by denaturing 10% polyacrylamide gel electrophoresis (PAGE) (STEP 2). Target molecule dependent cleavage activity is then selected in the presence of target molecules in the presence of reaction buffer by incubation at 23° C. for about 30 seconds to about five minutes (STEP 3). Cleaved molecules (5'-fixed:random:3'fixed-A molecules) are identified as nucleic acid sensor molecules and are purified by PAGE (STEP 4).

Amplification of the cleaved molecule is performed using primers which specifically bind the 5'-fixed and the 3'-fixed A sequences, regenerating the T7 promoter and the 3'-fixed B site (STEP 5), and the molecule is further amplified further by RNA transcription using T7 polymerase (STEP 6). In one embodiment, the process (STEPS 1–6) is repeated until the nucleic acid sensor precursor population is reduced to about one to five unique sequences.

Alternative methods for separating cleaved from uncleaved RNAs can be used. Tags can be attached to the 3'-fixed B sequence and separation can be based upon separating tagged sequences from non-tagged sequences at STEP 4. Chromatographic procedures that separate molecules on the basis of size (e.g., gel filtration) can be used in place of electrophoresis. One end of each molecule in the RNA pool can be attached to a solid support and catalytically active molecules isolated upon release from the support as a result of cleavage. Alternate catalytic cores may be used. These alternate catalytic cores and methods using these cores are also are encompassed within the scope of the invention.

Nucleic acid sensor molecules which combine both cleavage and ligase activities in a single molecule can be isolated by using one or a combination of both of the selection strategies outlined independently above for ligases and endonucleases. For example, the hairpin ribozyme is known to catalyze cleavage followed by ligation of a second oligonucleotide substrate (Berzal-Herranz et al.). Target activated sensor precursors based on the hairpin activity can be isolated from a pool of randomized sequence RNAs prepared as described previously with a sequence of the form 5'-GGAGTTACCTAACAAGAAACAGNgaagtcaaccagNgaaacNCACGGAGACGTGNNaNattaNct ggt$(N_{20}\text{-}N_{50})$GGACCTACTGAGCTGACAGTCCT-GTTTGATGCATACCGAGTAAGTG-3' (SEQ ID NO:36) where N indicates any nucleotide, lower case letters represent doped nucleotides, and uppercase letters represent fixed nucleotides. Hairpin-based NASMs can be isolated on the basis of target molecule dependent release of the fragment 5'-GUCCUGUUUGAUGCAUACCGAGUAAGUG-3' (SEQ ID NO:74) in the same way that hammerhead-based NASMs are isolated (e.g.,. target molecule dependent increase in electrophoretic mobility or target molecule dependent release from a solid support). Alternatively, nucleic acid sensor molecules can be selected on the basis of their ability to substitute the 3'-sequence released upon cleavage for another sequence as described in an target molecule independent manner by Berzal-Heranz et al. In this scheme, the original 3'-end of the NASM is released in an initial cleavage event-and an exogenously provided oligonucleotide substrate with a free 5'-hydroxyl is ligated back on. The newly attached 3'-end provides a primer binding site that can form the basis for preferential amplification of catalytically active molecules. Constitutively active molecules that are not activated by a provided target molecule can be removed from the pool by (1) separating away molecules that exhibit increased electrophoretic mobility in the absence of an exogenous oligonucleotide substrate or in the absence of target molecule, or (2) capturing molecules that acquire an exogenous oligonucleotide substrate (e.g., using a 3'-biotinylated substrate and captured re-ligated species on an avidin column.

Like the hairpin ribozyme, the group I intron self-splicing ribozymes combine cleavage and ligation activities to promote ligation of the exons that flank it. In the first step of group I intron-catalyzed splicing, an exogenous guanosine cofactor attacks the 5'-splice site. As a result of an intron-mediated phosphodiester exchange reaction, the 5'-exon is released coincident with attachment of the guanosine cofactor to the ribozyme. In a second chemical step, the 3'-hydroxyl at the end of the 5'-exon attacks the phosphodiester linkage between the intron and the 3'-exon, leading to ligation of the two exons and release of the intron. Group I intron-derived NASMs can be isolated from degenerate sequence pools by selecting molecules on the basis of either one or both chemical steps, operating in either a forward or reverse direction. NASMs can be isolated by specifically enriching those molecules that fail to promote catalysis in the absence of target molecule but which are catalytically active in its presence. Specific examples of selection schemes follow. In each case, a pool of RNAs related in sequence to a representative group I intron (e.g., the Tetrahymena thermophila pre-rRNA intron or the phage T4 td intron) serves as the starting point for selection. Random sequence regions can be embedded within the intron at sites known to be important for proper folding and activity (eg., substituting the P5abc domain of the Tetrahymena intron, Williams et al.). Intron nucleic acid sensor molecules, in this case, sensitive to thio-GMP can be generated as follows.

First step, forward direction

The intron is synthesized with a short 5'-exon. In the negative selection step, a guanosine cofactor is provided and constitutively active molecules undergo splicing. In the positive selection step, the target molecule is provided together with thio-GMP. Molecules responsive to the target undergo activated splicing and as a result acquire a unique thiophosphate at their 5'-termini. Thio-tagged NASMs can be separated from untagged ribozymes by their specific retention on mercury gels or activated thiol agarose columns.

First step, reverse direction

The method is performed as described in Green & Szostak. An intron is synthesized with a 5'-guanosine and no 5'-exon. An oligonucleotide substrate complementary to the 5'-internal guide sequence is provided during the negative selection step and constitutively active molecules ligate the substrate to their 5'-ends, releasing the original terminal guanosine. A second oligonucleotide substrate with a different 5'-sequence is provided together with target in the positive selection step. NASMs specifically activated by the target molecule ligate the second oligonucleotide substrate to their 5'-ends. PCR amplification using a primer corresponding to the second substrate can be carried out to preferentially amplify target molecule sensitive nucleic acid sensor molecules.

Second step, reverse direction

The method is performed as described in Robertson & Joyce. The intron is synthesized with no flanking exons. During the negative selection step, pool RNAs are incubated together with a short oligonucleotide substrate under conditions which allow catalysis to proceed. During the positive selection step, a second oligonucleotide substrate with a different 3'-sequence is provided together with the sensor target. NASMs are activated and catalyze ligation of the 3'-end of the second substrate. Reverse transcription carried out using a primer complementary to the 3'-end of the second substrate specifically selects NASMs for subsequent amplification.

Once nucleic acid sensor molecules are identified, they can be isolated, cloned, sequenced, and/or resynthesized using natural or modified nucleotides. Accordingly, synthesis intermediates of nucleic acid sensor molecules are also encompassed within the scope, as are replicatable sequences (e.g., plasmids) comprising nucleic acid sensor precursor molecules and nucleic acid sensor molecules.

Figure 47:
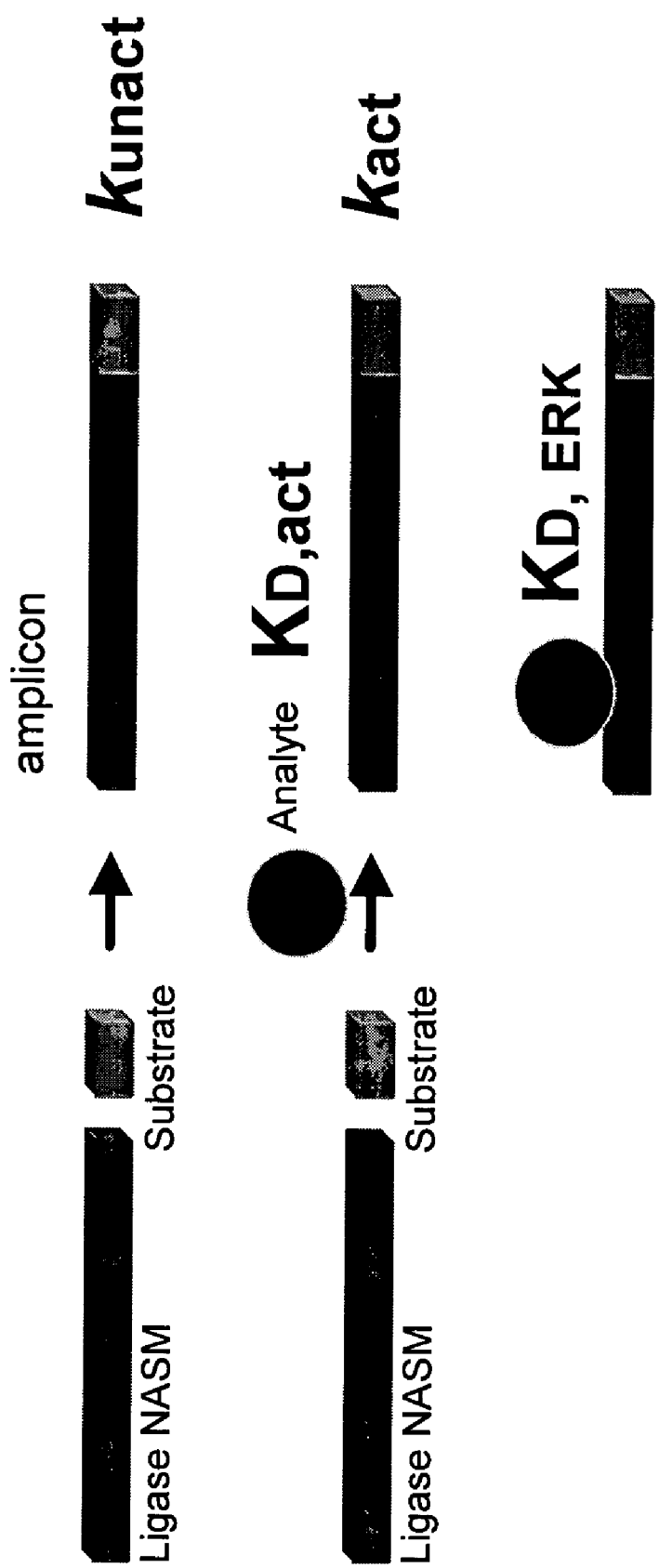
FIG. 47 shows a schematic describing a mechanism used by nucleic acid sensor molecules to transduce signal and the kinetic constants used to characterize NASMs.

B. Converting a Catalytic Nucleic Acid Sensor Molecule to an Optical Nucleic Acid Sensor Molecule The nucleic acid sensor molecules identified above through in vitro selection comprise a catalytic domain (i.e., a signal generating moiety), coupled to a target modulation domain, (i.e., a domain which recognizes a target molecule and which transduces that molecular recognition event into the generation of a detectable signal). In general, the target modulation domain is defined by the minimum number of nucleotides sufficient to create a three-dimensional structure which recognizes a target molecule. In addition, the nucleic acid sensor molecules of the present invention use the energy of molecular recognition to modulate the catalytic or conformational properties of the nucleic acid sensor molecule. The selection process as described in detail in the present invention identifies novel nucleic acid sensor molecules through target modulation of the catalytic core of a ribozyme. Hence, the in vitro selection procedures described herein are distinct from those previously described for affinity-based aptamer selections (e.g., SELEX) in that we show that selective pressure on the starting population of NASMs (starting pool size is as high as $10^{14}$ to $10^{17}$ molecules) results in nucleic acid sensor molecules with enhanced catalytic properties, but not in enhanced binding properties, FIG. 59. Specifically, the NASM selection procedures place selective pressure on catalytic effectiveness of potential NASMS by modulating both target concentration and reaction time-dependence. Either parameter, when optimized throughout the selection, can lead to nucleic acid molecular sensor molecules which have custom-designed catalytic properties, e.g., NASMs that have high switch factors (FIG. 47 and FIG. 59), and or NASMs that have high specificity (FIG. 57). The kinetic properties of the NASMs of the present invention are consistent with that obtained from a nucleoprotein-selection reported previously by Robertson and Ellington (2001) in which the resulting ribozyme (switch factor equal to 1,700 fold) has the same affinity for RNA (1 µM) as did the starting pool.

In the examples described above, the catalytic site is a known sequence (a ligase site or a hammerhead catalytic core) and is at least a portion of either the 5' and/or 3' fixed region (the other portion being supplied by the random sequence), or is a complete catalytic site. However, in other embodiments, the catalytic site may be selected along with the target molecule binding activity of oligonucleotides within the oligonucleotide pool.

Figure 5:
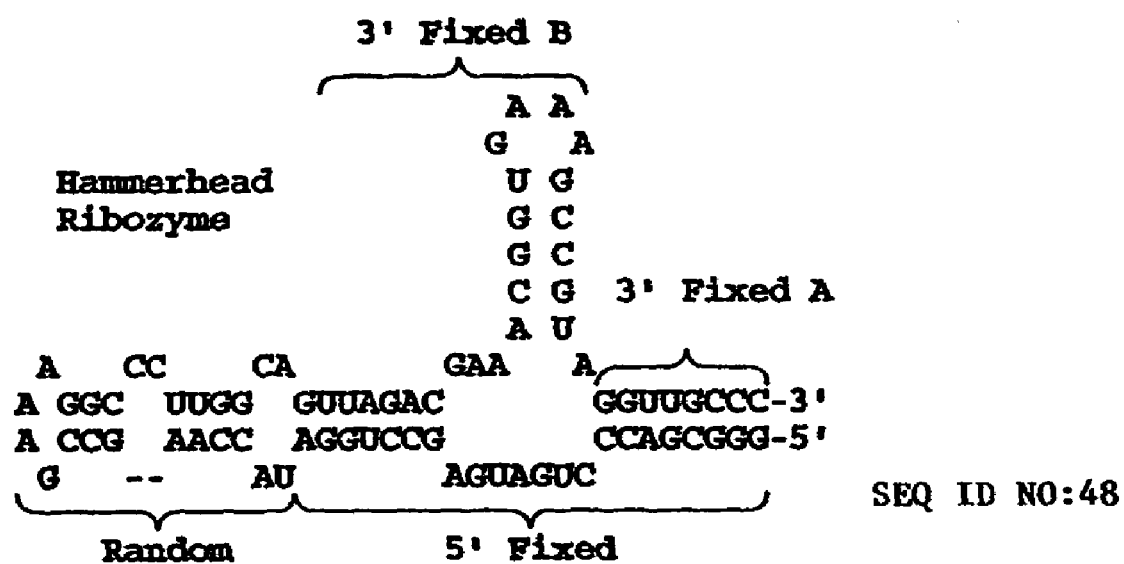
FIGS. 5A and B show a nucleic acid sensor molecule according to one embodiment, in which the catalytic site includes a self-cleavage site which is the catalytic core of a hammerhead ribozyme.
FIG. 5B shows the conformation of the non-target bound form of the nucleic acid sensor molecule (SEQ ID NO:48).

In one embodiment, in order to convert a catalytic nucleic acid sensor molecule into an optical nucleic acid sensor molecule, at least a portion of the catalytic domain is modified (e.g., deleted). In one embodiment, the deletion enhances the conformational stability of the optical nucleic acid sensor molecule in either the bound or unbound forms. In one embodiment, shown in FIGS. 6A and B, deletion of the entire catalytic domain of the catalytic NASM shown in FIG. 5 is shown to stabilize the unbound form of the nucleic acid sensor molecule. In another embodiment, the deletion may be chosen so as to take advantage of the inherent fluorescence-quenching properties of unpaired guanosine (G) residues (Walter, N. G. and Burke, J. M., "Real-time monitoring of hairpin ribozyme kinetics through base-specific quenching of fluorescein-labeled substrates", RNA 3:392 (1997).)

In another embodiment, the target modulation domain from a previously identified nucleic acid sensor molecule is incorporated into an oligonucleotide sequence that changes conformation (e.g., from a duplexed hairpin to a G-quadruplex) upon target binding. Optical Nucleic acid sensor molecules of this type can be derived from allosteric ribozymes, such as those derived from the hammerhead, hairpin, L1 ligase, or group 1 intron ribozymes and the like, all of which transduce molecular recognition into a detectable signal. For example, 3',5'-cyclic nucleotide monophosphate (cNMP)-dependent hammerhead ribozymes were reengineered into (RNA) optical nucleic acid sensor molecules which specifically bound to cNMP (Garretta et al., 2001). The catalytic cores for hammerhead ribozymes were removed and replaced with 5-base duplex forming sequences. The binding of these reengineered RNA optical NASMs to c-NMP was then confirmed experimentally. By adjusting the duplex length, they can be redesigned to undergo significant conformational changes. The conformational changes can be coupled to detection via FRET or simply changes in fluorescence intensity (as in the case of a molecular beacon). For example, by adding an appropriate probe on the each end of the duplex, the stabilization of duplex by target binding can be monitored with the change in fluorescence.

While the above experimental example is performed in solution and utilizes a cuvette-based fluorescence spectrometer, in alternative embodiments the methods are performed in microwell multiplate readers (e.g., the Packard Fusion, or the Tecan Ultra) for high-throughput solution phase measurements.

In another embodiment, a nucleic acid sensor molecule is bound to a surface by a linker attached to one end of the molecule. For example, a nucleic acid sensor molecule is modified to include a 12 carbon linker terminated with an amine group. This free amine group allows the NASM to be attached to an aldehyde-derivatized glass surface via standard protocols for Schiff base formation and reduction. The nucleic acid sensor molecules can be bound in discrete regions or spots to form an array or uniformly distributed to cover an extended area. In the absence of target molecule, the optical nucleic acid sensor molecule forms a stem-loop conformation with duplex formation along the stem due to the complementarity of the nucleotides at the 3' and 5' ends of the molecule. In the presence of the target molecule, the optical nucleic acid sensor molecule undergoes a conformational rearrangement. In some embodiments, this conformational rearrangement results in a change in the distance between the fluorophore attached to the 5' end and the quencher attached to the 3' end. With the quencher separated from the fluorophore, the detected fluorescence emission intensity from the fluorophore increases sharply. The detected increase in fluorescence intensity with target molecule concentration can be used to detect and quantify the amount of target present in a sample solution introduced onto the surface. A sample solution can be laterally confined about the sensor surface by a coverslip, microwell, incubation chamber seal, or flowcell.

In one embodiment, after deletion of at least a portion of the catalytic site from a catalytic nucleic acid sensor molecule, an optical signaling unit is either added to, or inserted within, the nucleic sensor molecule, generating a sensor molecule whose optical properties change in response to binding of the target molecule to the target modulation domain. In one embodiment, the optical signaling unit is added by exposing at least a 5' or 3' nucleotide that was not previously exposed. The 5' nucleotide or a 5' subterminal nucleotide (e.g., an internal nucleotide) of the molecule is couplable to a first signaling moiety while the 3' nucleotide or 3' subterminal nucleotide is couplable to a second signaling moiety. Target molecule binding to the optical nucleic acid sensor molecule alters the proximity of the 5' and 3' nucleotide (or subterminal nucleotides) with respect to each other, and when the first and second signaling moieties are coupled to their respective nucleotides, this change in proximity results in a target sensitive change in the optical properties of the nucleic acid sensor molecule. Detection of changes in the optical properties of the nucleic acid sensor molecule can therefore be correlated with the presence and/or quantity of a target molecule in a sample.

In another embodiment optical NASMs are generated by adding first and second signaling moieties, that are coupled to the 5' terminal or subterminal sequences, and 3'-terminal and subterminal sequences respectively, of the catalytic NASM. Signaling molecules can be coupled to nucleotides which are already part of the nucleic acid sensor molecule or may be coupled to nucleotides which are inserted into the nucleic acid sensor molecule, or can be added to a nucleic acid sensor molecule as it is synthesized. Coupling chemistries to attach signaling molecules are well known in the art (see, for example, The Molecular Probes Handbook, R. Haughland). Suitable chemistries include, e.g., derivatization of the 5-position of pyrimidine bases (e.g., using 5'-amino allyl precursors), derivatization of the 5'-end (e.g., phosphoroamidites that add a primary amine to the 5'-end of chemically-synthesized oligonucleotide) or the 3'-end (e.g., periodate treatment of RNA to convert the 3'-ribose into a dialdehyde which can subsequently react with hydrazide-bearing signaling molecules).

In another embodiment, a single signaling moiety is either added to, or inserted within, the catalytic nucleic sensor molecule. In this embodiment, binding of the target molecule results in changes in both the conformation and physical aspect (e.g., molecular volume, and thus rotational diffusion rate, etc.) of the optical nucleic acid sensor molecule. Conformational changes in the optical nucleic acid sensor molecule upon target binding will modify the chemical environment of the signaling moiety, while changes in the physical aspect of the nucleic acid, sensor molecule will alter the kinetic properties of the signaling moiety. In both cases, the result will be a detectable change in the optical properties of the nucleic acid sensor molecule.

In one embodiment, the optical nucleic acid sensor molecule is prepared without a quencher group. Instead of a quencher group a moiety with a free amine group can be added. This free amine group allows the sensor molecule to be attached to an aldehyde-derivatized glass surface via standard protocols for Schiff base formation and reduction. The nucleic acid sensor molecules can be bound in discrete regions or spots to form an array, or uniformly distributed to cover an extended area. In the absence of target, the optical nucleic acid sensor molecule will diffusionally rotate about its point of attachment to the surface at a rate characteristic of its molecular volume and mass. After target binding, the optical NASM-target complex will have a correspondingly larger volume and mass. This change in molecular volume (mass) will slow the rate of rotational diffusion, and result in a measurable change in the polarization state of the fluorescence emission from the fluorophore.

In one embodiment of the invention, a single signaling moiety is attached to a portion of a catalytic NASM that is released as a result of catalysis (e.g., either end of a self-cleaving ribozyme or the pyrophosphate at the 5'-end of a ligase). Target molecule-activated catalysis leads to release of the signaling moiety from the optical NASM to generate a signal correlated with the presence of the target. Release can be detected by either (1) changes in the intrinsic optical properties of the signaling moiety (e.g., decreased fluorescence polarization as the released moiety is able to tumble more freely in solution), or (2) changes in the partitioning of the signaling moiety (e.g., release of a fluorophore from a chip containing immobilized ribozymes such that the total fluorescence of the chip is reduced following washing).

In another embodiment of the invention, the catalytic nucleic acid sensor molecule is unmodified and the optical signaling unit is provided as a substrate for the NASM. One example of this embodiment includes a fluorescently tagged oligonucleotide substrate which can be joined to a NASM with ligase activity. In a heterogeneous assay using the ligase as a sensor molecule, analyte-containing samples are incubated with the fluorescent oligonucleotide substrate and the ligase under conditions that allow the ligase to function. Following an incubation period, the ligase is separated from free oligonucleotide substrate (e.g., by capturing ligases onto a solid support on the basis of hybridization to ligase-specific sequences or by pre-immobilizing the ligases on a solid support and washing extensively).

Quantitation of the captured fluorescence signal provides a means for inferring the concentration of analyte in the sample. In a second example of this embodiment, catalytic activity alters the fluorescence properties of a oligonucleotide substrate without leading to its own modification. Fluorophore pairs or fluorophore/quencher pairs can be attached to nucleotides flanking either side of the cleavage site of an oligonucleotide substrate for a trans-acting endonuclease ribozyme (Jenne et al.). Target activated cleavage of the substrate leads to separation of the pair and a change in its optical properties.

In another embodiment of the invention, the ligase catalytic NASM and its oligonucleotide substrates are unmodified and detection relies on catalytically-coupled changes in the ability of the NASM to be enzymatically amplified. In one example, a target-activated ligase is incubated together with oligonucleotide substrate and an analyte-containing sample under conditions which allow the ligase to function. Following an incubation period, the reaction is quenched and the mixture subjected to RT/PCR amplification using a primer pair that includes the oligo sequence corresponding to the ligation substrate. Amplification products can be detected by a variety of generally practiced methods (e.g. Taqman®). Only those ribozymes that have self-ligated an oligonucleotide substrate are capable of amplification under these conditions and will generate a signal that can be coupled to the concentration of the sensor target.

i. Proximity Dependent Signaling Moieties

Many proximity dependent signaling moieties are known in the art and are encompassed within the scope of the present invention (see, e.g., Morrison, 1992, in Nonisotopic DNA Probe Techniques, Kricka, ed., Academic Press, Inc., San Diego, Calif., chapter 13; and Heller and Morrison, 1985, in Rapid Detection and Identification of Infectious Agents, Academic Press, Inc., San Diego, Calif., pages 245–256). Systems using these signaling moieties rely on the change in fluorescence that occurs when the moieties are brought into close proximity. Such systems are described in the literature as fluorescence energy transfer (FET), fluorescence resonance energy transfer (FRET), nonradiative energy transfer, long-range energy transfer, dipole-coupled energy transfer, or Forster energy transfer (see, e.g., U.S. Pat. No. 5,491,063, Wu, and Brand, 1994).

Other proximity-dependent signaling systems that do not rely on direct energy transfer between signaling moieties are also known in the art and can be used in the methods described herein. These include, e.g., systems in which a signaling moiety is stimulated to fluoresce or luminesce upon activation by the target molecule. This activation may be direct (e.g., as in the case of scintillation proximity assays (SPA), via a photon or radionuclide decay product emitted by the bound target), or indirect (e.g., as in the case of AlphaScreen™ assays, via reaction with singlet oxygen released from a photosensitized donor bead upon illumination). In both scenarios, the activation of detected signaling moiety is dependent on close proximity of the signaling moiety and the activating species. In general, for both fluorescence, fluorescence polarization, and scintillation-proximity-type assays, the nucleic acid sensor molecule may be utilized in either solution-phase or solid-phase formats. That is, in functional form, the nucleic acid sensor molecule may be tethered (directly, or via a linker) to a solid support or free in solution.

In one embodiment, a scintillation proximity assay (SPA) is used. In this embodiment, the nucleic acid sensor molecules, ligate on oligonucleotide substrate in the presence of a target molecule (see FIGS. 2A and B), are bound to a scintillant-impregnated microwell plate (e.g., FlashPlates, NEN Life Sciences Products, Boston, Mass.) coated with, for example, streptavidin via a (biotin) linker attached to the 5' end of the effector oligonucleotide sequence (for example, GCGACTGGACATCACGAG (SEQ ID NO:51) in FIG. 2A). The various plate-sensor coupling chemistries are determined by the type and manufacturer of the plates, and are well-known in the art. Upon the addition of a solution containing target molecule and excess radiolabeled (e.g., with $^{32}P$ or $^{35}S$) oligonucleotide substrate in ligation buffer, the NASMs hybridize and ligate the substrate oligonucleotide. Some fraction of the radiolabeled oligonucleotide substrate will be ligated to surface-immobilized NASMs on the plate, while unligated oligonucleotide substrate will be free in solution. Only those oligonucleotide substrates ligated to surface-immobilized NASMs on the plate will be in close enough proximity to the scintillant molecules embedded in the plate to excite them, thereby stimulating luminescence which can be easily detected using a luminometer (e.g., the TopCount luminescence plate reader, Packard Biosciences, Meriden, Conn.). This type of homogeneous assay format provides straightforward, real-time detection, quantification, and kinetic properties of target molecule binding.

In another embodiment, a similar SPA assay format is performed using scintillant-impregnated beads (e.g., Amersham Pharmacia Biotech, Inc., Piscataway, N.J.). In this embodiment, the NASMs which ligate on oligonucleotide substrate in the presence of a target molecule (see FIGS. 2A and B) are coupled to scintillant-impregnated beads which are suspended in solution in, for example, a microwell plate. The various bead-sensor coupling chemistries are determined by the type and manufacturer of the beads, and are well-known in the art. Upon the addition of a solution containing target molecule and excess radiolabeled (e.g., with $^{32}P$ or $^{35}S$) oligonucleotide substrate in ligation buffer, the NASMs hybridize and ligate the oligonucleotide substrate. Some fraction of the radiolabeled substrate will be ligated to surface-immobilized NASMs on the beads, while unligated substrate will be free in solution. Only those substrates ligated to surface-immobilized NASMs on the beads will be in close enough proximity to the scintillant molecules embedded in the beads to excite them, thereby stimulating luminescence which can be easily detected using a luminometer (e.g., the TopCount luminescence plate reader, Packard Biosciences, Meriden, Conn.). In addition to enabling real-time target detection and quantification, this type of homogeneous assay format can be used to investigate cellular processes in situ in real time. This could be done by culturing cells directly onto a microwell plate and allowing uptake of scintillant beads and radioisotope by cells. Biosynthesis, proliferation, drug uptake, cell motility, etc. can then be monitored via the luminescence signal generated by beads in presence of selected target molecules (see Cook et al.,1992, or Heath et al., 1992).

Figure 11:
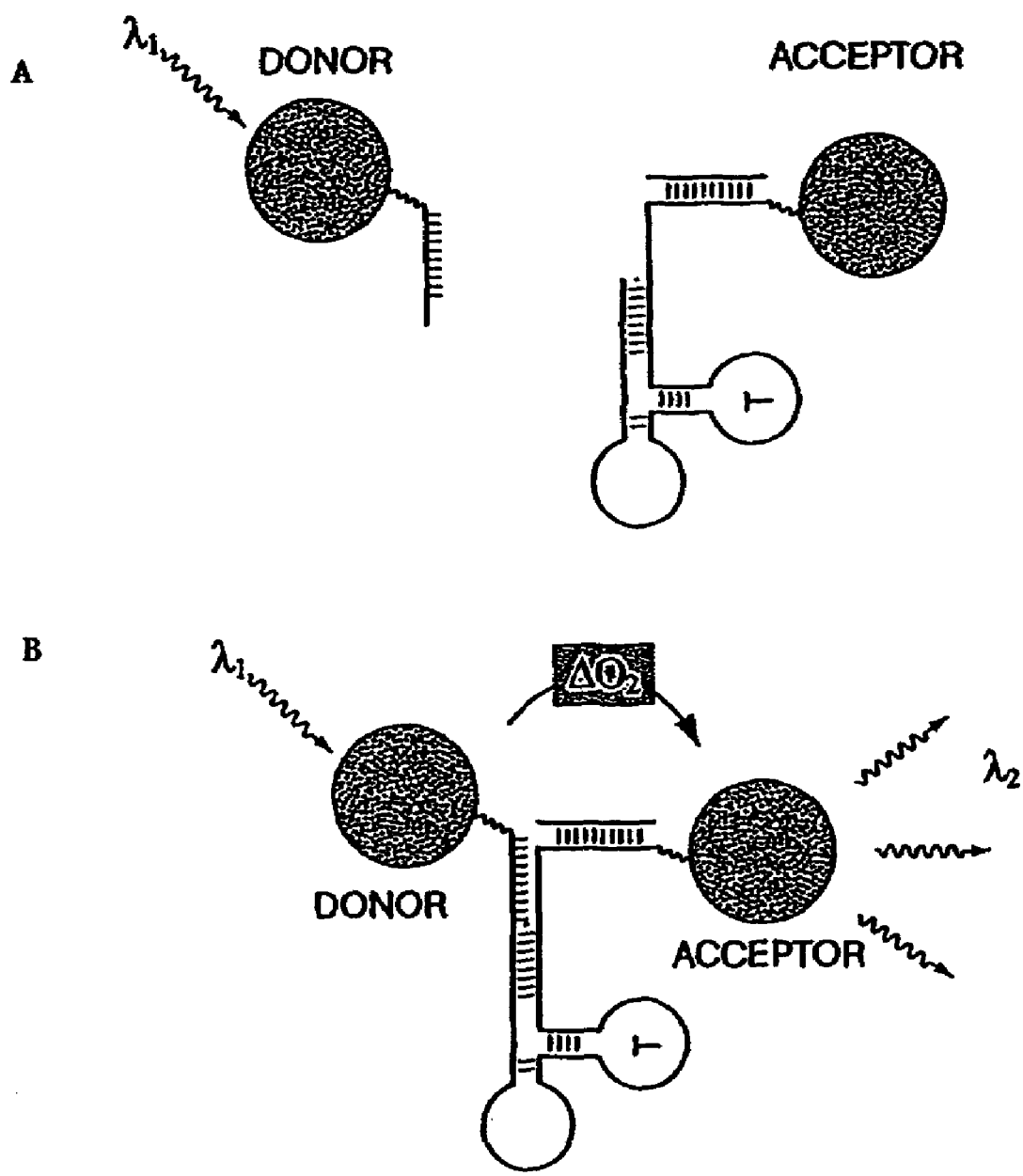
FIG. 11 illustrates the use of beads in a homogeneous assay format utilizing a self-ligating nucleic acid sensor.

FIGS. 11A and B show an exemplary embodiment of a non-isotopic proximity assay based on nucleic acid sensor molecules used in conjunction with AlphaScreenTm beads (Packard Biosciences, Meriden, Conn.). In this embodiment, the nucleic acid sensor molecules, which ligate on oligonucleotide substrate in the presence of a target molecule (see FIGS. 2A and B), are 5 bound to a chemiluminescent compound-impregnated acceptor bead coated with, for example, streptavidin, via a (biotin) linker attached to the 5' end of the effector oligonucleotide sequence (GCGACTG- GACATCACGAG (SEQ ID NO:5 1) in FIG. 2A). The various bead-sensor coupling chemistries are determined by the type and manufacturer of the beads, and are well-known in the art. The oligonucleotide substrate is coupled to a photosensitizer-impregnated donor bead coated with, for example, streptavidin, via a (biotin) linker attached to the 3' end of the substrate. The donor (substrate) and acceptor (ribozyme) beads and target molecules are then combined in solution in a microwell plate, some of the NASMs hybridize and ligate the oligonucleotide substrate, bringing the donor and acceptor beads into close proximity (<200 nm). Upon illumination at 680 nm, the photosensitizer in the donor bead converts ambient oxygen into the singlet state at a rate of approximately 60,000/second per bead. The singlet oxygen will diffuse a maximum distance of approximately 200 nm in solution; if an acceptor bead containing a chemiluminescent compound is within this range, i.e., if ligation has occurred in the presence of the target molecule, chemiluminescence at 370 nm is generated. This radiation is immediately converted within the acceptor bead to visible luminescence at 520–620 nm with a decay half-life of 0.3 sec. The visible luminescence at 520–620 nm is detected using a time-resolved fluorescence/luminescence plate reader (e.g., the Fusion multifuinction plate reader, Packard Biosciences, Meriden, Conn.). This type of nonisotopic homogeneous proximity assay format provides highly sensitive detection and quantification of target molecule concentrations in volumes <25 microliters for high throughput screening (see Beaudet et al. 2001).

Suitable fluorescent labels are known in the art and commercially available from, for example, Molecular Probes (Eugene, Oreg.). These include, e.g., donor/acceptor (i.e., first and second signaling moieties) molecules such as: fluorescein isothiocyanate (FITC) /tetramethylrhodamine isothiocyanate (TRITC), FITC/Texas Red TM Molecular Probes), FITC/N-hydroxysuccinimidyl 1 -pyrenebutyrate (PYB), FITC/eosin isothiocyanate (EITC), N-hydroxysuccinimidyl 1 -pyrenesulfonate (PYS)/FITC, FITC/ Rhodamine X (ROX), FITC/tetramethylrhodamine (TAMRA), and others. In addition to the organic fluorophores already mentioned, various types of nonorganic fluorescent labels are known in the art and are commercially available from, for example, Quantum Dot Corporation, Inc. Hayward Calif.). These include, e.g., donor/acceptor (i.e., first and second signaling moieties) semiconductor nanocrystals (i.e., 'quantum dots') whose absorption and emission spectra can be precisely controlled through the selection of nanoparticle material, size, and composition (see, for example, Bruchez et al., 1998, Chan and Nie, 1998, Han et al., 2001).

The selection of a particular donor/acceptor pair is not critical to practicing the invention provided that energy can be transferred between the donor and the acceptor. P-(dimethyl aminophenylazo) benzoic acid (DABCYL) is one example of a non-fluorescent acceptor dye which effectively quenches fluorescence from an adjacent fluorophore, e.g., fluorescein or 5-(2'-aminoethyl) aminonaphthalene (EDANS).

FIGS. 3A and B and 6A and B show exemplary optical nucleic acid sensor molecules derived from catalytic nucleic acid molecules (FIGS. 2A and B and 5, respectively), according to two embodiments. FIG. 3 shows a catalytic nucleic acid sensor molecule obtained from an oligonucleotide pool in which the catalytic site was a ligase site. FIG. 6 shows a catalytic nucleic acid sensor molecule obtained from an oligonucleotide pool in which the catalytic site was a site mediating self-cleavage.

In the embodiment shown in FIGS. 3A and B, a catalytic nucleic acid sensor molecule from which a portion of a ligase site (e.g., the AGUCG sequence at the 3' end of the nucleic acid sensor precursor molecule, as shown in FIG. 2) has been removed is coupled to a first signaling moiety (F) at a first nucleotide (1) and to a second signaling moiety (D) at a second nucleotide (2). In a further embodiment, the first and second signaling moieties molecules are attached to non-terminal sequences. The position of the non-terminal sequences coupled to signaling moieties is limited to a maximal distance from the 5' or 3' nucleotide which still permits proximity dependent changes in the optical properties of the molecule. Coupling chemistries are routinely practiced in the art, and oligonucleotide synthesis services provided commercially (e.g., Integrated DNA Technologies, Coralville, Iowa) can also be used to generate labeled molecules. In a further embodiment, the nucleic acid sensor molecule is used, either tethered to a solid support or free in solution, to detect the presence and concentration of target molecules in a complex biological fluid.

In the embodiment shown in FIGS. 3A and B, the first signaling moiety (F) is a fluorescein molecule coupled to the 5' end and the second signaling molecule (D) is a DABCYL molecule (a quenching group) coupled to the 3' end. Because of the nearly complete base pairing of the non-target molecule activated form (see FIG. 3B), this is the favored form of the nucleic acid sensor molecule in the absence of the target molecule. When the nucleic acid sensor molecule is not activated by target molecule, the fluorescent group and the quenching group are in close proximity and little fluorescence is detectable from the fluorescent group. Addition of target molecule causes a change in the conformation of the optical nucleic acid sensor molecule shown in FIG. 3B to that shown in FIG. 3A. When the molecule assumes the conformation shown in FIG. 3A, the first and second signaling moieties (F and D, respectively) are no longer in sufficient proximity for the quenching group to quench the fluorescence of the fluorescent group, resulting in a detectable fluorescent signal being produced upon recognition of the target molecule.

In one embodiment, the target modulation domain sequence from a previously identified nucleic acid sensor molecule is incorporated into a separate oligonucleotide sequence which changes conformation upon target recognition as shown in FIGS. 6A and B. During or after synthesis, an optical signal generating unit is either added or inserted into the oligonucleotide sequence comprising. the derived nucleic acid sensor molecule. As noted previously, nucleic acid sensor molecules of this type can be derived from allosteric ribozymes, such as those derived from the hammerhead, hairpin, L1 ligase, or group 1 intron ribozymes and the like (see Soukup et al., 2001, or Hamaguchi et al., 2001), all of which transduce molecular recognition into a detectable optical signal.

Figure 9:
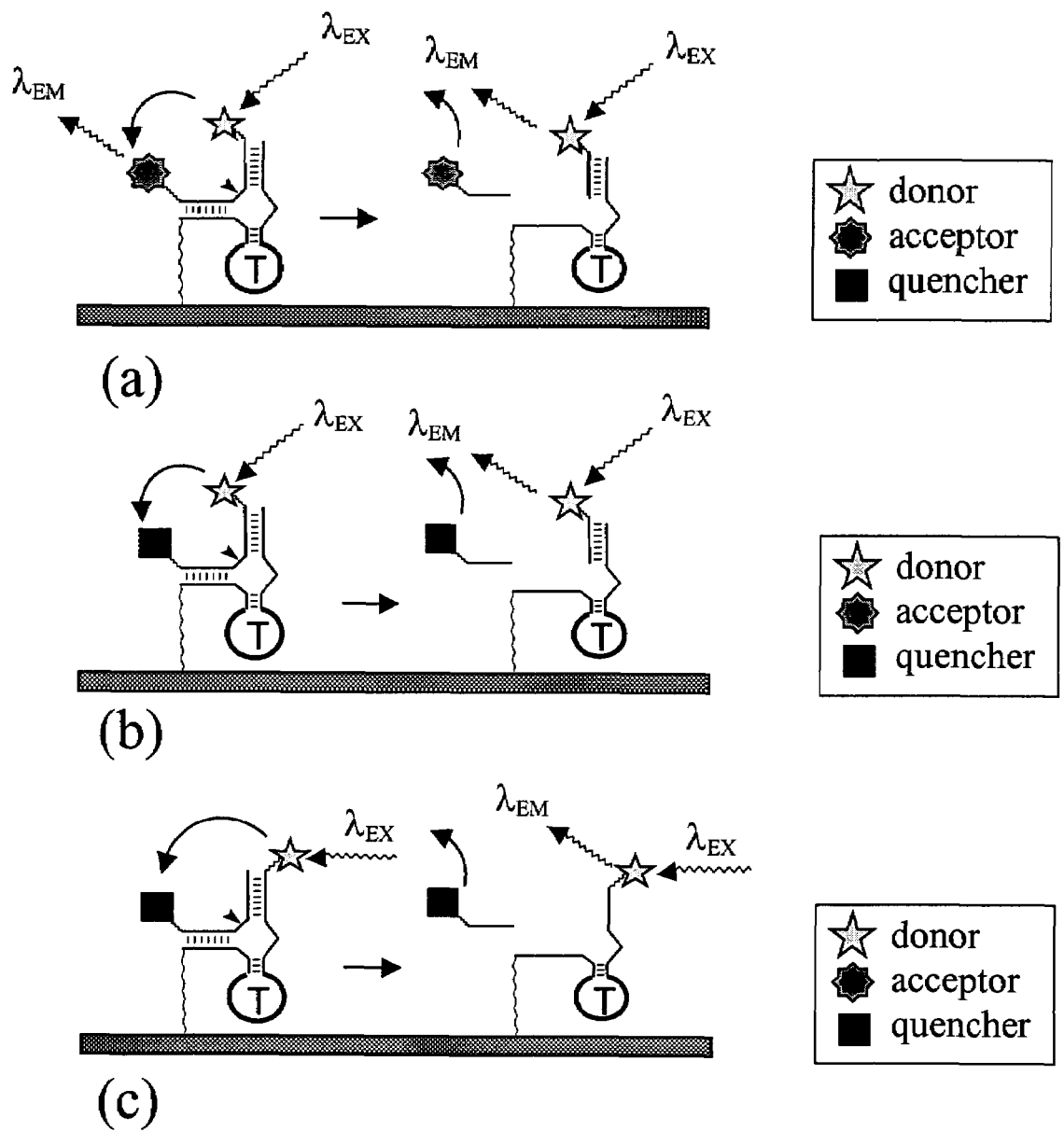
FIG. 9A shows an example of a self-cleaving nucleic acid sensor bound to a solid support when used in an epi-illuminated FRET detection scheme.
FIG. 9B shows the same sensor in an epi-illuminated beacon configuration, with the acceptor fluorophore replaced by a quencher group.
FIG. 9C shows the same sensor in an TIR-illuminated beacon configuration.

In the embodiment shown in FIGS. 9A, B, and C, a self-cleaving ribozyme such as the hammerhead (in this case attached to a solid support via a linker molecule is shown) is labeled with a fluorphore. In FIG. 9A, the labeled NASM in the unactivated state comprises two oligonucleotide including a transacting cleavage substrate which bears a second fluorescent label. In the unactivated state, i.e., in the absence of target molecule, the donor fluorophore (on one oligonucleotide NASM) and the acceptor fluorophore (on the cleavage substrate) are in sufficiently close proximity for FRET to occur; thus, minimal fluorescent emission is detected from the donor fluorophore at wavelength 3, $\lambda 3$, upon epi-illumination excitation at wavelength 1, $\lambda 1$. Upon target molecule recognition, the cleavage fragment of the cleavage substrate bearing the acceptor fluorophore dissociates from the ribozyme-target complex. Once separated from the acceptor fluorophore, the donor fluorophore can no longer undergo de-excitation via FRET, resulting in a detectable increase in its fluorescent emission at wavelength 2, $\lambda 2$ (see, for example, Singh. et al., 1999; Wu, and Brand, 1994; Walter and Burke, 1997; Walter et al., 1998). In a further embodiment, the change in the polarization state of the fluorescent emission from the donor fluorophore (due to the increased diffusional rotation rate of the smaller cleavage fragment) can be detected/monitored in addition to changes in fluorescent emission intensity (see, for Singh, 2000). In a further embodiment, the NASMs are free in solution.

In another embodiment, shown in FIG. 9B, the acceptor fluorophore attached to the cleavage substrate is replaced by a quencher group. This replacement will also result in minimal fluorescent donor emission at wavelength 2, $\lambda 2$, when the NASM is in the unbound state under epi-illumination excitation at wavelength 1, $\lambda 1$. Upon target molecule recognition, the cleavage fragments of the cleavage substrate bearing the donor and quencher groups dissociate from the NASM-target molecule complex. Once separated from the quencher, the donor fluorophore will exhibit a detectable increase in its fluorescent emission at wavelength 2, $\lambda 2$. In a further embodiment, the change in the polarization state of the fluorescent emission from the donor fluorophore (due to the increased diffusional rotation rate of the smaller cleavage fragment) can be detected/monitored in addition to changes in fluorescent emission intensity. In a further embodiment, NASMs are free in solution.

In a different embodiment, the optical configuration is designed to provide excitation via total internal reflection (TIR)-illumination, as shown in FIG. 9C. Also, the donor fluorophore is attached to the NASM body while the quencher is attached to the cleavage substrate. In this configuration, with the surface-immobilized NASM in the unbound state, the fluorescent donor emission at wavelength 2, $\lambda 2$, will be minimal. Upon target module recognition, the cleavage fragment of the cleavage substrate bearing the quencher group dissociates from the NASM-target module complex. Once separated from the quencher, the donor fluorophore will exhibit a detectable increase in its fluorescent emission at wavelength 2, $\lambda 2$. In an alternative embodiment to that shown in shown in FIG. 9C, the quencher group can be replaced with an acceptor fluorophore. In yet another alternative embodiment to those shown in FIGS. 9A, B, and C, the donor fluorophore is coupled to the cleavage fragment of the cleavage substrate and the acceptor fluorophore or quencher group is deleted. Upon target molecule recognition and dissociation of the cleavage fragment, the polarization state of the fluorescent emission from the donor fluorophore will undergo a detectable change due to the difference in the diffusional rotation rates of the surface-bound ribozyme-target complex and the free cleavage fragment.

In one embodiment, a universal FRET trans-substrate is synthesized for all NASMs derived from self-cleaving allosteric ribozymes. This substrate would have complementary optical signaling units (i.e., donor and acceptor groups) coupled to opposite ends of the synthetic oligonucleotide sequence. Such a universal substrate would obviate the need for coupling optical signaling units to the sensor (i.e., ribozyme) molecule itself.

The relative stabilities of the activated and unactivated forms of the nucleic acid sensor molecules is optimized to achieve the highest sensitivity of detection of target molecule. In one embodiment, the nucleic acid sensor molecule is further engineered to enhance the stability of one form over another. In one embodiment, the boxed UA in FIGS. 3A and B is changed to a CC, favoring the formation of the target molecule activated form. Because these bases do not form base pairs when the nucleic acid sensor molecule is unactiaved, the unactivated form is not stabilized.

In addition to the herein described methods, any additional proximity dependent signaling system known in the art can be used to practice the method according to the invention, and are encompassed within the scope.

A number of methods can be used to evaluate the relative stability of different conformations of the nucleic acid sensor molecule. In one embodiment, the free energy of the structures formed by the nucleic acid sensor molecule is determined using software programs such as mfold®, which can be found on, the Rensselaer Polytechnic Institute (RPI) web site (www.rpi.edu/dept.).

In another embodiment, a gel assay is performed which permits detection of different conformations of the nucleic acid sensor molecule. In this embodiment, the nucleic acid sensor molecule is allowed to come to equilibrium at room temperature or the temperature at which the nucleic acid sensor molecule will be used. The molecule is then cooled to 4° C. and electrophoresed on a native (non-denaturing) gel at 4° C. Each of the conformations formed by the nucleic acid sensor molecule will run at a different position on the gel, allowing visualization of the relative concentration of each conformation. Similarly, the conformation of nucleic acid sensor molecules which form in the presence of target molecule is then determined by a method such as circular dichroism (CD). By comparing the conformation of the nucleic acid sensor molecule formed in the presence of target molecule with the conformations formed in the absence of target molecule, the conformation which corresponds to the activated conformation can be identified in a sample in which there is no target molecule. The nucleic acid sensor molecule can then be engineered to minimize the formation of the activated conformation in the absence of target molecule. The sensitivity and specificity of nucleic acid sensor molecule can be further tested using target molecule modulation assays with known amounts of target molecules.

In another embodiment, shown in FIGS. 6A and B, a catalytical nucleic acid sensor molecule from which a portion of a self-cleaving site has been removed, is coupled to a first signaling moiety (F) at a first nucleotide and to a second signaling moiety,(D) at a second nucleotide. In this embodiment, the entire catalytic site of the catalytic nucleic acid molecule (see FIG. 5) has been removed. In one embodiment (FIGS. 6A and B), additional bases (e.g., UGGUAU) are added to one end of the portion of the nucleic acid sensor molecule comprising the modulation domain, to stabilize the unbound form of the nucleic acid sensor molecule (FIG. 6B). These bases are selected to be complementary to bases at the opposite end of the nucleic acid sensor molecule (ACCAUA). Additional bases may be added to either the 5' or the 3' end of the nucleic acid sensor molecule.

Modifications to stabilize one conformation of the nucleic sensor molecule over another may be identified using the mfold program or native gel assays discussed above. A labeled nucleic acid sensor molecule is generated by coupling a first signaling moiety (F) to a first nucleotide and a second signaling moiety (D) to a second nucleotide as discussed above. As above, the sensitivity and specificity of the nucleic acid sensor molecule can be further assayed by using target molecule modulation assays with known amounts of target molecules.

ii. Optical Signal Generating Units With Single Signaling Moieties

In one embodiment, the optical nucleic acid sensor molecule comprises an optical signaling unit with a single signaling moiety introduced at either an internal or terminal position within the nucleic acid sensor molecule. In this embodiment, binding of the target molecule results in changes in both the conformation and physical aspect (e.g., molecular volume or mass, rotational diffuision rate, etc.) of the nucleic acid sensor molecule. Conformational changes in the nucleic acid sensor molecule upon target recognition will modify the chemical environment of the signaling moiety. Such a change in chemical environment will in general change the optical properties of the signaling moiety. Suitable signaling moieties are described in Jhaveri, et al, 2000, and include, e.g., fluorescein, acridine, and other organic and nonorganic fluorophores.

In one embodiment, a signaling moiety is introduced at a position in the catalytic nucleic acid molecule near the target activation site (identifiable by footprinting studies, for example). Binding of the target molecule will (via a change in conformation of the nucleic acid molecule) alter the chemical environment and thus affect the optical properties of the signaling moiety in a detectable manner.

Recognition of the target molecule by the NASM will result in changes in the conformation and physical aspect of the nucleic acid sensor molecule, and will thus alter the kinetic properties of the signaling moiety. In particular, the changes in conformation and mass of the sensor-target complex will reduce the rotational diffusion rate for the sensor-target complex, resulting in a detectable change in the observed steady state fluorescence polarization (FP) from the signaling moiety. The expected change in FP signal with target concentration can be derived using a modified form of the well-known Michaelis-Menten model for ligand binding kinetics (Lakowicz, 1999). FP is therefore a highly sensitive means of detecting and quantitatively determining the concentration of target molecules in a sample solution (Jameson and Sawyer, 1995; Jameson and Seifried, 1999; Jolley, 1999; Singh, 2000; Owicki et al., 1997). FP methods are capable of functioning in both solution- and solid-phase implementations.

Numerous additional methods can be used that, e.g., make use of a single fluorescent label and an unpaired guanosine residue (instead of a quencher group), to enable the use of FRET in target detection and quantitation as described in the embodiments above (see Walter and Burke, 1997).

Figure 10:
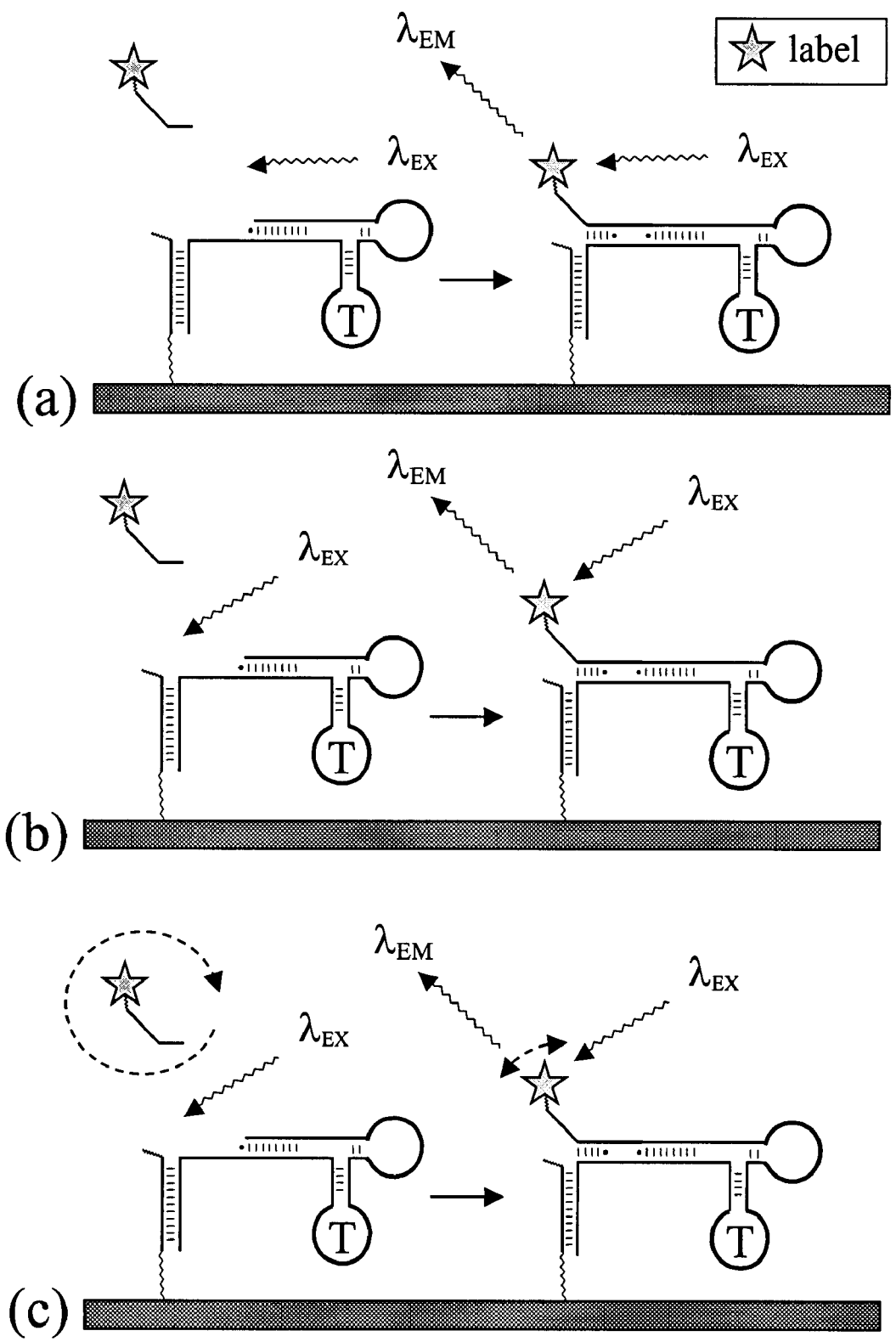
FIG. 10A shows an example of a self-ligating nucleic acid sensor bound to a solid support when used in a TIR-illuminated detection scheme where there is a signal increase upon target binding.
FIG. 10B shows the same sensor in an epi-illuminated configuration, where target binding is detected by monitoring changes of the fluorophore bound to the substrate at the surface of the array.
FIG. 10C shows the same epi-illuminated configuration, where target binding is detected by monitoring changes in the fluorescence polarization.

In a further embodiment, shown in FIGS. 10A, B, and C an unlabeled ligating ribozyme such as the lysozyme-dependent L1 ligase is shown (see, for example, Robertson, M. P. and Ellington, A. D, 2000). In the unactivated state, i.e., in the absence of target, no fluorescent emission is detected from the surface-bound ribozymes under total internal reflection (TIR)-illumination (see FIG. 10A), or epi-illumination (see FIG. 10B). Upon recognition of target molecules in the presence of an oligonucleotide substrate with a tag (where the tag is capable of binding to a subsequently added fluorescent label via interactions including, but not limited to, biotin/streptavidin, amine/aldehyde, hydrazide, thiol, or other reactive groups) those oligonucleotide substrates hybridized to NASMs will undergo ligation and become covalently bonded to the thereto. In order to maximize the probability of hybridization for a given NASM, oligonucleotide substrate can be added in excess relative to NASM, the temperature of the ambient solution in which the reaction takes place can be kept below room temperature (e.g., 4° C.), and agitation of the reaction vessel can be employed to overcome the kinetic limitation of diffusion-limited transport of species in solution. Given the above conditions, as well as sufficient time for maximal hybridization and subsequent ligation to occur, fluorescent label with the appropriate reactive group to bind the substrate tag is added to the reaction mixture. Again, the degree of substrate-label binding can be maximized through control of label concentration, solution temperature, and agitation. Once the fluorescent label has bound to all available ligated substrate-ribozyme-target complex, the solution temperature can be raised to drive off all of the hybridized but unligated substrate. With TIR-illumination, the spatial extent of the excitation region above the solid substrate surface to which the ribozymes are bound is only on the order of 100 nm. Therefore, the bulk solution above the substrate surface is not illuminated and the detected fluorescent emission will be primarily due to fluorophores which are bound to ligated oligonucleotide substrate-NASM- target molecule complexes tethered to the substrate surface. The fluorescence emission from surface-bound NASM-target molecule complexes in this homogeneous solid phase assay format represents an easily detectable optical signal. In another embodiment, the fluorescence polarization (FP) of the labeled substrate can be monitored, as shown in FIG. 10C. Upon ligation, the steady state fluorescence polarization signal from the substrate-NASM complex will increase detectably relative to the FP signal from the free labeled oligonucleotide substrate in solution, due to the difference in the diffusional rotation rates between the free and ligated forms.

In another embodiment, an unlabeled ligating ribozyme such as the lysozyme-dependent Li ligase (see, for example, Robertson, M. P. and Ellington, A. D, 2000) is bound to a solid surface. In this embodiment, the oligonucleotide substrate is coupled to an enzyme-linked luminescent moiety, such as horse radish peroxidase (HRP) by a tag (where the tag is capable of binding to a subsequently added label via interactions including, but not limited to, biotin/streptavidin, amine/aldehyde, hydrazide, thiol, or other reactive groups). In the absence of target molecule, no luminescent emission is detected from the surface-bound ribozymes. Upon recognition of target molecules in the presence of labeled oligonucleotide substrate, those oligonucleotide substrates hybridized to NASMs will undergo ligation and become covalently bonded to the NASMs. After removal of excess, unbound oligonucleotide substrate, the activation empty for the enzyme-linked luminescent label is added to the reaction volume. The resulting luminescent signal (e.g., from HRP, luciferase, etc.) is easily detectable using standard luminometers (e.g., the Fusion multifunction plate reader, Packard Bioscience). In a further embodiment, the activated solution can be precipitated, followed by calorimetric detection. In a particular embodiment, the enzyme linked signal amplification, TSA, (sometimes referred to as CARD-catalyzed reporter deposition) is an ultrasensitive detection method. The technology uses turnover of multiple tyramide substrates per horseradish peroxidase (HRP) enzyme to generate high-density labeling of a target protein or nucleic acid probe in situ. Tyramide signal amplification is a combination of three elementary processes: (1) Ligation (or not) of a biotinylated ligase oligonucleotide substrate oligo, followed by binding (or not) of a streptavidin-HRP to the probe; (2) HRP-mediated conversion of multiple copies of a fluorescent tyramide derivative to a highly reactive radical; (3)

Covalent binding of the reactive, short lived tyramide radicals to nearby nucleophilic residues, greatly reducing diffusion-related signal loss.

2. Generating Biosensors

Optical nucleic acid sensor molecules for the detection of a target molecule of interest are generated by first selecting catalytic nucleic acid molecules with catalytic activity modifiable (e.g., activatable) by a selected target molecule. In one embodiment, at least a portion of the catalytic site of the catalytic NASM is then removed and an optical signal generating unit is either added or inserted. Recognition of the target molecule by the nucleic acid sensor molecule activates a change in the properties of the optical signaling unit.

In one embodiment, a biosensor is provided which comprises a plurality of optical nucleic acid sensor molecules labeled with first and second signaling moieties specific for a target molecule. In another embodiment, the optical NASMs are labeled with a single signaling moiety. In one embodiment, the labeled nucleic acid sensor molecules are provided in a solution (e.g., a buffer). In another embodiment, the labeled nucleic acid sensor molecules are attached directly or indirectly (e.g., through a linker molecule) to a substrate. In further embodiments, nucleic acid sensor molecules can be synthesized directly onto the substrate. Suitable substrates which are encompassed within the scope include, e.g., glass or quartz, silicon, encapsulated or unencapsulated semiconductor nanocrystal materials (e.g., CdSe), nitrocellulose, nylon, plastic, and other polymers. Substrates may assume a variety of configurations (e.g., planar, slide shaped, wafers, chips, tubular, disc-like, beads, containers, or plates, such as microtiter plates, and other shapes).

Numerous attachment chemistries, both direct and indirect, can be used to: immobilize the sensor molecules on a solid support. These include, e.g., amine/aldehyde, biotin/streptavidin (avidin, neutravidin), ADH/oxidized 3' RNA. In a particular embodiment, the nucleic acid sensor molecules ligate a substrate in the presence of a target molecule (see FIGS. 2A and B). In this embodiment the ribozymes are bound to a solid substrate via the effector oligonucleotide sequence (for example, GCGACTGGACATCACGAG (SEQ ID NO:51) in FIG. 2A).

In one embodiment, a manual or computer-controlled robotic microarrayer is used to generate arrays of nucleic acid sensor molecules immobilized on a solid substrate. In one embodiment, the arrayer utilizes contact-printing technology (i.e., it utilizes printing pins of metal, glass, etc., with or without quill-slots or other modifications). In a different embodiment, the arrayer utilizes non-contact printing technology (i.e., it utilizes ink jet or capillary-based technologies, or other means of dispensing a solution containing the material to be arrayed). Numerous methods for preparing, processing, and analyzing microarrays are known in the art (see Schena et al., 2000; Mace et al., 2000; Heller et al., 1999; Basararsky et al., 2000; Schermer, 1999). Robotic and manual arrayers are commercially available for example, the SpotArray from Packard Biosciences, Meriden, Conn., and the RA-1 from GenomicSolutions, Ann Arbor, Mich.).

In one embodiment, larger substrates can be generated by combining a plurality of smaller biosensors forming an array of biosensors. In a further embodiment, nucleic acid sensor molecules placed on the substrate are addressed (e.g., by specific linker or effector oligonucleotide sequences on the nucleic acid sensor molecule) and information relating to the location of each nucleic acid sensor molecule and its target molecule specificity is stored within a processor. This technique is known as spatial addressing or spatial multiplexing. Techniques for addressing nucleic acids on substrates are known in the art and are described in, for example, U.S. Pat. No. 6,060,252, U.S. Pat. No. 6,051,380, U.S. Pat. No. 5,763,263, U.S. Pat. No. 5,763,175, and U.S. Pat. No. 5,741,462.

In one embodiment different nucleic acid sensor molecules are immobilized on a streptavidin-derivatized glass substrate via biotin linkers. The individual sensor spots can be manually arrayed. Solution measurements of target molecule concentration can be made by bathing the surface of the biosensor array in a solution containing the targets (analytes) of interest. In practice this is accomplished either by incorporating the array within a microflowcell (with a flow rate of ~25 microliters/min), or by placing a small volume (~6–10 microliters) of the target solution on the array surface and covering it with a cover slip. Detection and quantification of target concentration is accomplished by monitoring changes in the fluorescence polarization (FP) signal emitted from the fluorescein label under illumination by 488 nm laser radiation. The rotational diffusion rate is inversely proportional to the molecular volume; thus the rotational correlation time for the roughly 20-nucleotide unbound sensor (i.e., in the absence of target molecule) will be significantly less than that for the target-NASM complex. The fluorescence emission from the target-NASM complex will therefore experience greater residual polarization due to the smaller angle through which the emission dipole axis of the sensor fluorophore can rotate within its radiative lifetime. In another embodiment, different surface attachment chemistries are used to immobilize the NASMs on a solid substrate. As previously noted, these include, e.g., interactions involving biotin/streptavidin, amine/aldehyde, hydrazide, thiol, or other reactive groups.

The specificity of the biosensors and NASMs according to the invention is determined by the specificity of the target modulation domain of the nucleic acid sensor molecule. In one embodiment, a biosensor is provided in which all of the nucleic acid sensor molecules recognize the same molecule. In another embodiment, a biosensor is provided which can recognize at least two different target molecules allowing for multi-analyte detection. Multiple analytes can be distinguished by using different combinations of first and second signaling molecules. In addition to the wavelength/color and spatial multiplexing techniques previously described, biosensors may be used to detect multiple analytes using intensity multiplexing. This is accomplished by varying the number of fluorescent label molecules on each biosensor in a controlled fashion. Since a single fluorescent label is the smallest integral labeling unit possible, the number of fluorophores (i.e., the intensity from) a given biosensor molecule provides a multiplexing index. Using the combination of 6-wavelength (color) and 10-level intensity multiplexing, implemented in the context of semiconductor nanocrystals derivatized as bioconjugates, would theoretically allow the encoding of million different analyte-specific biosensors (Han et al., 2001).

In one embodiment, multiple single target biosensors can be combined to form a multianalyte detection system which is either solution-based or substrate-based according to the needs of the user. In this embodiment, individual biosensors can be later removed from the system, if the user desires to return to a single analyte detection system (e.g., using target molecules bound to supports, or, for example, manually removing a selected biosensor(s) in the case of substrate-based biosensors). In a further embodiment, nucleic acid sensor molecules binding to multiple analytes are distinguished from each other by referring to the address of the nucleic acid sensor molecule on a substrate and correlating its location with the appropriate target molecule to which it binds (previously described as spatial addressing or multiplexing).

In one embodiment, subsections of a biosensor array can be individually subjected to separate analyte solutions by use of substrate partitions or enclosures that prevent fluid flow between subarrays, and microfluidic pathways and injectors to introduce the different analyte solutions to the appropriate sensor subarray.

3. Nucleic Acid Sensor Molecule and Biosensor Systems

In one embodiment, a nucleic acid sensor molecule or biosensor system is provided comprising a nucleic acid sensor molecule in communication with a detector system. In a further embodiment, a processor is provided to process optical signals detected by the detector system. In still a further embodiment, the processor is connectable to a server which is also connectable to other processors. In this embodiment, optical data obtained at a site where the NASM or biosensor system resides can be transmitted through the server and data is obtained, and a report displayed on the display of the off-site processor within seconds of the transmission of the optical data. In one embodiment, data from patients is stored in a database which can be accessed by a user of the system.

Data obtainable from the biosensors according to the invention include diagnostic data, data relating to lead compound development, and nucleic acid sensor molecule modeling data (e.g., information correlating the sequence of individual sensor molecules with specificity for a particular target molecule). In one embodiment, these data are stored in a computer database. In a further embodiment, the database includes, along with diagnostic data obtained from a sample by the biosensor, information relating to a particular patient, such as medical history and billing information. Although, in one embodiment, the database is part of the nucleic acid sensor molecule system, the database can be used separately with other detection assay methods and drug development methods.

Detectors used with the nucleic acid sensor molecule systems according to the invention, can vary, and include any suitable detectors for detecting optical changes in nucleic acid molecules. These include, e.g., photomultiplier tubes (PMTs), charge coupled devices (CCDs), intensified CCDs, and avalanche photodiodes (APDs). In one embodiment, a nucleic acid sensor molecule comprising labeled nucleic acid sensor molecules is excited by a light source in communication with the biosensor. In a further embodiment, when the optical signaling unit comprises first and second signal moieties that are donor/acceptor pairs (i.e., signal generation relies on the fluorescence of a donor molecule when it is removed from the proximity of a quencher acceptor molecule), recognition of a target molecule will cause a large increase in fluorescence emission intensity over a low background signal level. The high signal-to-noise ratio permits small signals to be measured using high-gain detectors, such as PMTs or APDs. Using intensified CCDs, and PMTs, single molecule fluorescence measurements have been made by monitoring the fluorescence emission, and changes in fluorescence lifetime, from donor/acceptor FRET pairs (see Sako, et al., 2000; Lakowicz et al, 1991)).

Light sources include, e.g., filtered, wide-spectrum light sources, (e.g., tungsten, or xenon arc), laser light sources, such as gas lasers, solid state crystal lasers, semiconductor diode lasers (including multiple quantum well, distributed feedback, and vertical cavity surface emitting lasers (VC-SELs)), dye lasers, metallic vapor lasers, free electron lasers, and lasers using any other substance as a gain medium. Common gas lasers include Argon-ion, Krypton-ion, and mixed gas (e.g., Ar–Kr) ion lasers, emitting at 455, 458, 466, 476, 488, 496, 502, 514, and 528 nm (Ar ion); and 406, 413, 415, 468, 476, 482, 520, 531, 568, 647, and 676 nm (Kr ion). Also included in gas lasers are Helium Neon lasers emitting at 543, 594, 612, and 633 mn. Typical output lines from solid state crystal lasers include 532 nm (doubled Nd:YAG) and 408/816 nm (doubled/primary from Ti:Sapphire). Typical output lines from semiconductor diode lasers are 635, 650, 670, and 780 mm.

Excitation wavelengths and emission detection wavelengths will vary depending on the signaling moieties used. In one embodiment, where the first and second signaling moieties are fluorescein and DABCYL, the excitation wavelength is 488 nm and the emission wavelength is 514 mn. In the case of semiconductor nanocrystal-based fluorescent labels, a single excitation wavelength or broadband UV source may be used to excite several probes with widely spectrally separated emission wavelengths (see Bruchez et al., 1998; Chan et al., 1998).

In one embodiment, detection of changes in the optical properties of the nucleic acid sensor molecules is performed using any of a cooled CCD camera, a cooled intensified CCD camera, a single-photon-counting detector (e.g., PMT or APD), or other light sensitive sensor. In one embodiment, the detector is optically coupled to the nucleic acid sensor molecule through a lens system, such as in an optical microscope (e.g., a confocal microscope). In another embodiment, a fiber optic coupler is used, where the input to the optical fiber is placed in close proximity to the substrate surface of a biosensor, either above or below the substrate. In yet another embodiment, the optical fiber provides the substrate for the attachment of nucleic acid sensor molecules and the biosensor is an integral part of the optical fiber.

In one embodiment, the interior surface of a glass or plastic capillary tube provides the substrate for the attachment of nucleic acid sensor molecules. The capillary can be either circular or rectangular in cross-section, and of any dimension. The capillary section containing the biosensors can be integrated into a microfluidic liquid-handling system which can inject different wash, buffer, and analyte-containing solutions through the sensor tube. Spatial encoding of the sensors can be accomplished by patterning them longitudinally along the axis of the tube, as well as radially, around the circumference of the tube interior. Excitation can be accomplished by coupling a laser source (e.g., using a shaped output beam, such as from a VCSEL) into the glass or plastic layer forming the capillary tube. The coupled excitation light will undergo TIR at the interior surface/solution interface of the tube, thus selectively exciting fluorescently labeled biosensors attached to the tube walls, but not the bulk solution. In one embodiment, detection can be accomplished using a lens-coupled,or proximity-coupled large area segmented (pixelated) detector, such as a CCD. In a particular embodiment, a scanning (i.e., longitudinal/axial and azimuthal) microscope objective lens/emission filter combination is used to image the biosensor substrate onto a CCD detector. In a different embodiment, a high resolution CCD detector with an emission filter in front of it is placed in extremely close proximity to the capillary to allow direct imaging of the biosensors. In a different embodiment, highly efficient detection is accomplished using a mirrored tubular cavity that is elliptical in cross-section. The sensor tube is placed along one focal axis of the cavity, while a side-window PMT is placed along the other focal axis with an emission filter in front of it. Any light emitted from the biosensor tube in any direction will be collected by the cavity and focused onto the window of the PMT.

In still another embodiment, the optical properties of a nucleic acid sensor molecule are analyzed using a spectrometer (e.g., such as a luminescence spectrometer) which is in communication with the biosensor. The spectrometer can perform wavelength discrimination for excitation and detection using either monochromators (i.e., diffraction gratings), or wavelength bandpass filters. In this embodiment, biosensor molecules are excited at absorption maxima appropriate to the signal labeling moieties being used (e.g., acridine at 450 nm, fluorescein at 495 nm) and fluorescence intensity is measured at emission wavelengths appropriate for the labeling moiety used (e.g., acridine at 495 nm; fluorescein at 515 nm). Achieving sufficient spectral separation (i.e., a large enough Stokes shift) between the excitation wavelength and the emission wavelength is critical to the ultimate limit of detection sensitivity. Given that the intensity of the excitation light is much greater than that of the emitted fluorescence, even a small fraction of the excitation light being detected or amplified by the detection system will obscure a weak biosensor fluorescence emission signal. In one embodiment, the biosensor molecules are in solution and are pipetted (either manually or robotically) into a cuvette or a well in a microtiter plate within the spectrometer. In a further embodiment, the spectrometer is a multifinction plate reader capable of detecting optical changes in fluorescence or luminescence intensity (at one or more wavelengths), time-resolved fluorescence, fluorescence polarization (FP), absorbance (epi and transmitted), etc., such as the Fusion multi-function plate reader system (Packard Biosciences, Meriden, Conn.). Such a system can be used to detect optical changes in biosensors either in solution, bound to the surface of microwells in plates, or immobilized on the surface of solid substrate (e.g., a biosensor microarray on a glass substrate). This type of multiplate/multisubstrate detection system, coupled with robotic liquid handling and sample manipulation, is particularly amenable to high-throughput, low-volume assay formats.

In embodiments where nucleic acid sensor molecules are attached to substrates, such as a glass slide or in microarray format, it is desirable to reject any stray or background light in order to permit the detection of very low intensity fluorescence signals. In one embodiment, a small sample volume (~10 nL) is probed to obtain spatial discrimination by using an appropriate optical configuration, such as evanescent excitation or confocal imaging. Furthermore, background light can be minimized by the use of narrow-bandpass wavelength filters between the sample and the detector and by using opaque shielding to remove any ambient light from the measurement system.

Figure 12:
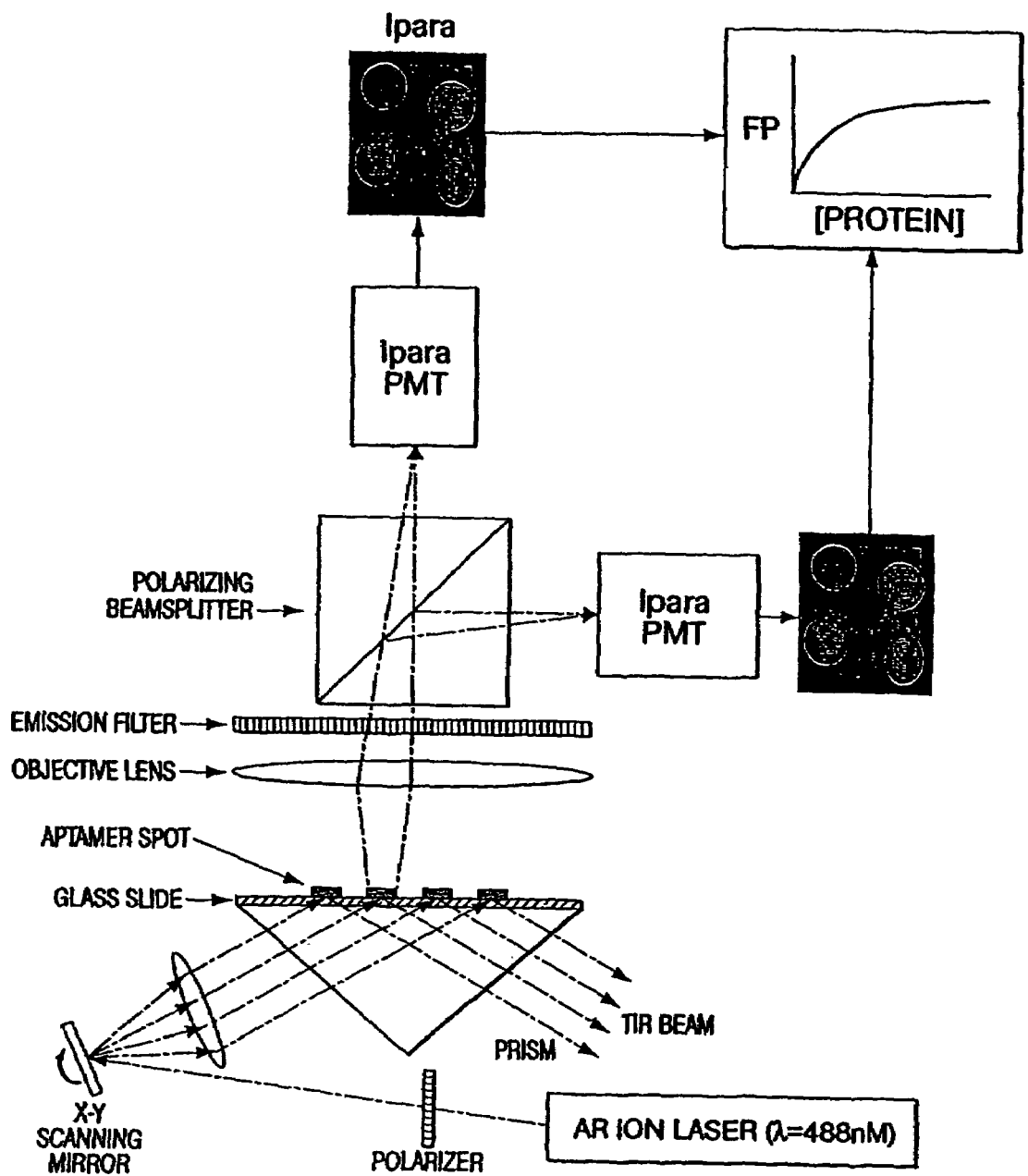
FIG. 12 shows a schematic of a previously constructed scanning detection system utilizing TIR laser evanescent wave excitation in either large area illumination/CCD imaging mode, or scanned spot/PMT imaging mode. The schematic shows how an array can be scanned and FP or fluorescence intensity data extracted.

In one embodiment, spatial discrimination of nucleic acid sensor molecules attached to a substrate in a direction normal to the interface of the substrate (i.e., excitation of only a small thickness of the solution layer directly above and surrounding the plane of attachment of the biosensor molecules to the substrate surface) is obtained by evanescent wave excitation. This is illustrated in FIG. 12. Evanescent wave excitation utilizes electromagnetic energy that propagates into the lower-index of refraction medium when an electromagnetic wave is totally internally reflected at the interface between higher and lower-refractive index materials. In this embodiment a collimated laser beam is incident on the substrate/solution interface (at which the biosensors are immobilized) at an angle greater than the critical angle for total internal reflection (TIR). This can be accomplished by directing light into a suitably shaped prism or an optical fiber. In the case of a prism, as shown in FIG. 12, the substrate is optically coupled (via index-matching fluid) to the upper surface of the prism, such that TIR occurs at the substrate/solution interface on which the biosensors are immobilized. Using this method, excitation can be localized to within a few hundred nanometers of the substrate/solution interface, thus eliminating autofluorescence background from the bulk analyte solution, optics, or substrate. Target recognition is detected by a change in the fluorescent emission of the nucleic acid sensor, whether a change in intensity or polarization. Spatial discrimination in the plane of the interface (i.e., laterally) is achieved by the optical system.

In one embodiment, a large area of the biosensor substrate is uniformly illuminated, either via evanescent wave excitation or epi-illumination from above, and the detected signal is spatially encoded through the use of a pixelated detector, such as CCD camera. An example of this type of uniform illumination/CCD detection system (using epi-illumination)) for the case of microarrayed biosensors on solid substrates is the GeneTAC 2000 scanner (GenomicSolutions, Ann Arbor, Mich.). In a different embodiment, a small area (e.g., 10×10 microns to 100×100 microns) of the biosensor substrate is illuminated by a micro-collimated beam or focused spot. In one embodiment, the excitation spot is rastered in a 2-dimensional scan across the static biosensor substrate surface and the signal detected (with an integrating detector, such as a PMT) at each point correlated with the spatial location of that point on the biosensor substrate (e.g., by the mechanical positioning system responsible for scanning the excitation spot). Two examples of this type of moving spot detection system for the case of microarrayed biosensors on solid substrates are: the DNA-Scope scanner (confocal, epi-illumination, GeneFocus, Waterloo, ON, Canada), and the LS IV scanner (non-confocal, epi-illumination, GenomicSolutions, Ann Arbor, Mich.). In yet another embodiment, a small area (e.g., 10×10 microns to 100×100 microns) of the biosensor substrate is illuminated by a stationary micro-collimated beam or focused spot, and the biosensor substrate is rastered in a 2-dimensional scan beneath the static excitation spot, with the signal detected (with an integrating detector, such as a PMT) at each point correlated with the spatial location of that point on the biosensor substrate (e.g., by the mechanical positioning system responsible for scanning the substrate). An example of this type of moving substrate detection (using confocal epi-illumination) system for the case of microarrayed biosensors on solid substrates is the ScanArray 5000 scanner (Packard Biochip, Billerica, Mass.).

In the embodiment shown in FIG. 12, a TIR evanescent wave excitation optical configuration is implemented, with a static substrate and dual-capability detection system. The detection system is built on the frame of a Zeiss universal fluorescence microscope. The system is equipped with 2 PMTs on one optical port, and an intensified CCD camera (Cooke, St. Louis, Mo.) mounted on the other optical port. The optical path utilizes a moveable mirror which can direct the collimated, polarized laser beam through focusing optics to form a spot, or a beam expander to form a large (>1 cm) beam whose central portion is roughly uniform over the field of view of the objective lens. Another movable mirror can direct the light either to the intensified CCD camera when using large area uniform illumination, or to the PMTs in the scanned spot mode. In spot scanning mode, a polarizing beamsplitter separates the parallel and perpendicular components of the emitted fluorescence and directs each to its designated PMT. An emission filter in the optical column rejects scattered excitation light from either type of detector. In CCD imaging mode, manually adjusted polarizers in the optical column of the microscope must be adjusted to obtain parallel and perpendicular images from which the fluorescence polarization or anisotropy can be calculated. A software program interfaces with data acquisition boards in a computer which acquires the digital output data from both PMTs and CCD. This program also controls the PMT power, electromechanical shutters, and galvanometer mirror scanner, calculates and plots fluorescence polarization in real time, and displays FP and intensity images.

In another embodiment, the detection system is a single photon counter system (see, e.g., U.S. Pat. No. 6,016,195 and U.S. Pat. No. 5,866,348) requiring rastering of the sensor substrate to image larger areas and survey the different binding regions on the biosensor.

In another embodiment of the invention, the biosensor is used to detect a target molecule through changes in the electrochemical properties of the nucleic acid sensor moleculeor molecules in close proximity to it which occur upon recognition of the NASM to the target molecule.

Figure 15:
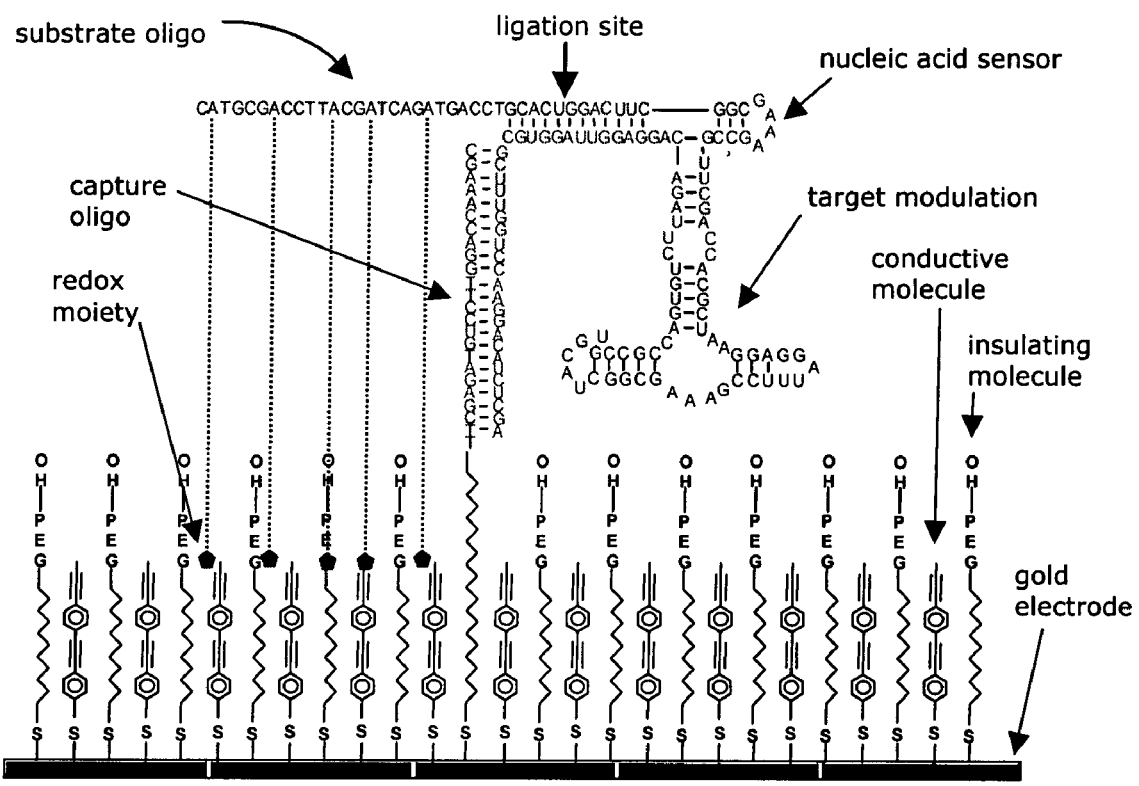
FIG. 15 is a schematic showing a ligase nucleic acid sensor molecule sensor system. It shows SEQ ID NO:76 across the top, and SEQ ID NO:77 hybridized to a portion of SEQ ID NO:76 and bound to an insulating moiety.

In a preferred embodiment, the biosensor system would consist of three major components: One, optical nucleic acid sensor molecules immobilized on an array of independently addressable gold electrodes. The nucleic acid sensor molecules immobilized on each electrode may be modulated by the same or different target molecules, including proteins, metabolites and other small molecules, etc.; two, an oligonucleotide substrate which acts as a signaling probe, hybridizing to the oligonucleotide substrate binding domain of the ligase sensor and forming a covalent phosphodiester bond with the nucleic acid sensor molecule nucleotide adjacent to its 3' terminus in the presence of the appropriate target. This oligonucleotide substrate is typically a nucleic acid sequence containing one or more modified nucleotides conjugated to redox active metallic complexes, e.g., ferrocene moieties, which can act as electron donors; and three, an immobilized mixed self-assembled surface monolayer (SAM), comprised of conductive species separated by insulating species, covering the surface of the electrodes. Examples of conductive species include thiol-terminated linear molecules, such as oligophenylethyl molecules, while examples of nonconductive thiol-terminated linear molecules, include alkane-thiol molecules terminated with polyethylene glycol (PEG). All immobilized species can be covalently attached to the electrode surface by terminal thiol groups. FIG. 15 schematically shows the structure of the mixed self-assembled surface monolayer (SAM) coating the gold electrode, as well as the immobilized nucleic acid sensor molecule (NASM) with a ligated oligonucleotide substrate conjugated to several redox active moieties. Upon recognition of the target molecule by the target modulation domain and subsequent ligation of the oligonucleotide substrate at the site indicated in the figure, the redox active signaling moieties coupled to the substrate oligo will be brought into close proximity to the conductive surface layer, resulting in a detectable increase in electronic surface signal.

Figure 16:
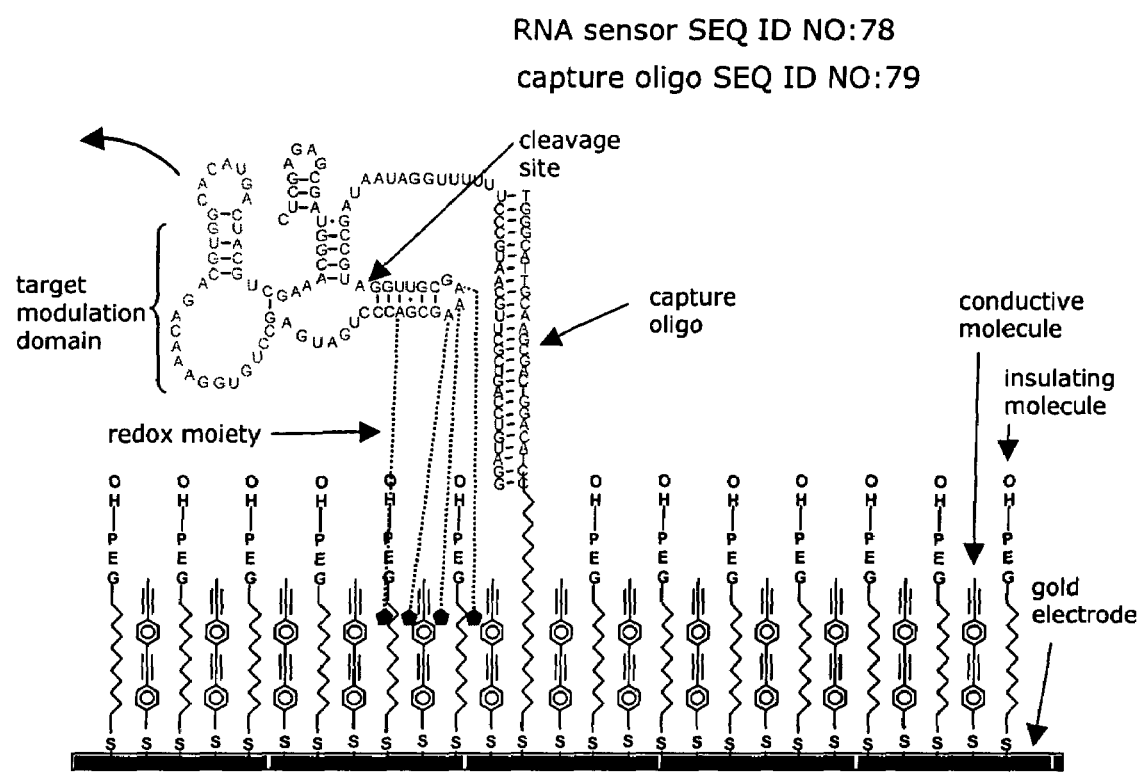
FIG. 16 is a schematic showing a hammerhead (endonuclease) Nucleic acid sensor molecule sensor system. It has a nucleic acid sensor molecule sensor (SEQ ID NO:78), and SEQ ID NO:79 hybridizing to a portion of the sensor and bound to an insulating moiety.

In another preferred embodiment, the biosensor system would consist of two major components: (1) Optical nucleic acid sensor molecules immobilized on an array of independent addressable gold electrodes. The nucleic acid sensor molecules immobilized on each electrode may be modulated by the same or different target molecules, including proteins, metabolites and other small molecules, etc. The NASM will contain one or more nucleotides conjugated to redox active metallic complexes, e.g., ferrocene moieties, which can act as electron donors; and (2) an immobilized mixed self-assembled surface monolayer (SAM), comprised of conductive species separated by insulating species, covering the surface of the electrodes. Examples of conductive species include thiol-terminated linear molecules, such as oligophenylehtynyl molecules, while examples of nonconductive thiol-terminated linear molecules include alkane-thiol molecules terminated with polyethylene glycol (PEG). FIG. 16 shows the SAM-coated molecule immobilized via a capture oligonucleotide. In this case, the redox active signaling moieties are coupled to the body of the NASM, as shown in the figure. Upon recognition of the target molecule by the target modulation domain and subsequent cleavage at the site indicated in the figure, the bulk of the NASM, including the nucleotides coupled to the redox active signaling moieties will dissociate from the surface, resulting in a detectable loss of electronic current signal.

Figure 17:
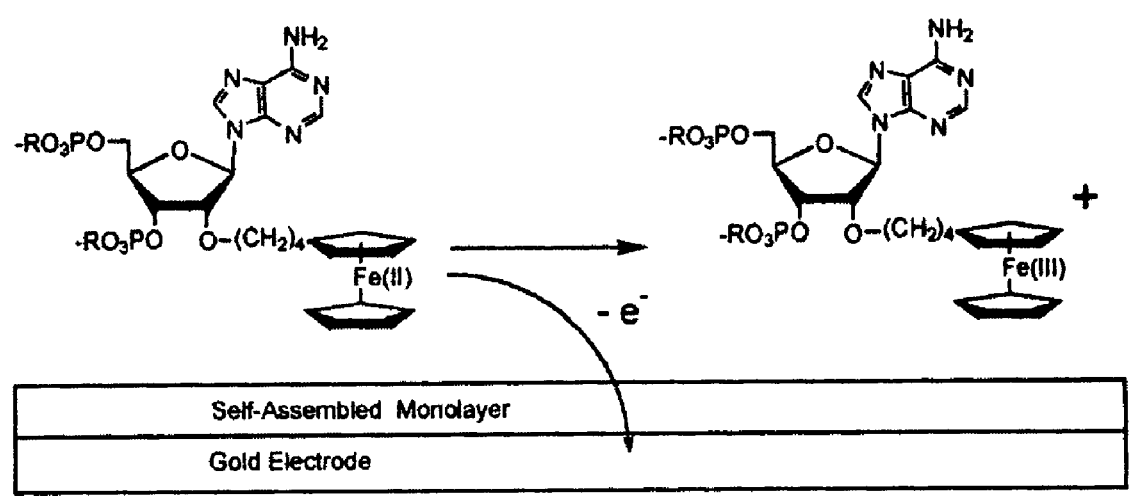
FIG. 17 is a schematic of the net electron transfer to or from the electrode.

In another embodiment, the array would be subjected, e.g., by an integrated microfluidic flowcell, to an analyte solution containing the target(s) of interest at some unknown concentration. The range of possible sample analyte solutions may include standard buffers, biological fluids, and cell or tissue extracts. The sample solution will also contain the signaling probe at a saturating concentration relative to the immobilized nucleic acid sensor molecule. This ensures that at any given time during analysis, there is a high probability that each nucleic acid sensor molecule will have a signaling probe hybridized to it. In the presence of the target molecules in the sample solution, the nucleic acid sensor molecule will form a covalent phosphodiester bond, i.e., ligate, with the signaling probe, thus immobilizing it with its redox active electron donor species in electrical contact with the conductive molecules within the mixed self-assembled surface monolayer. After some integration time, during which signal probe ligation occurs, it may be necessary to denature the hybridized but unligated signaling probes. This denaturation step, which effectively removes 'background' signaling probes and their associated redox moieties from the vicinity of the electrode, can be accomplished by a small temperature increase (e.g., from 21° C. to 25° C.), or by a brief negative voltage spike applied to the sensor electrodes followed by the application of a large positive DC voltage to a separate electrode that would collect unligated signaling. For the case of a sufficiently short hybridization region, e.g., 5 base-pairs, on the signaling probe, a separate denaturation step may not be necessary. In either case, following nucleic acid sensor molecule activation by target molecules, a linear electrical potential ramp is applied to the electrodes. The redox species conjugated to the immobilized signaling probe-nucleic acid sensor molecule will be electrochemically oxidized, liberating one or more electrons per moiety. The conductive molecules within the surface monolayer will provide an electrical path for the liberated electrons to the electrode surface, as shown in FIG. 17.

Figure 18:
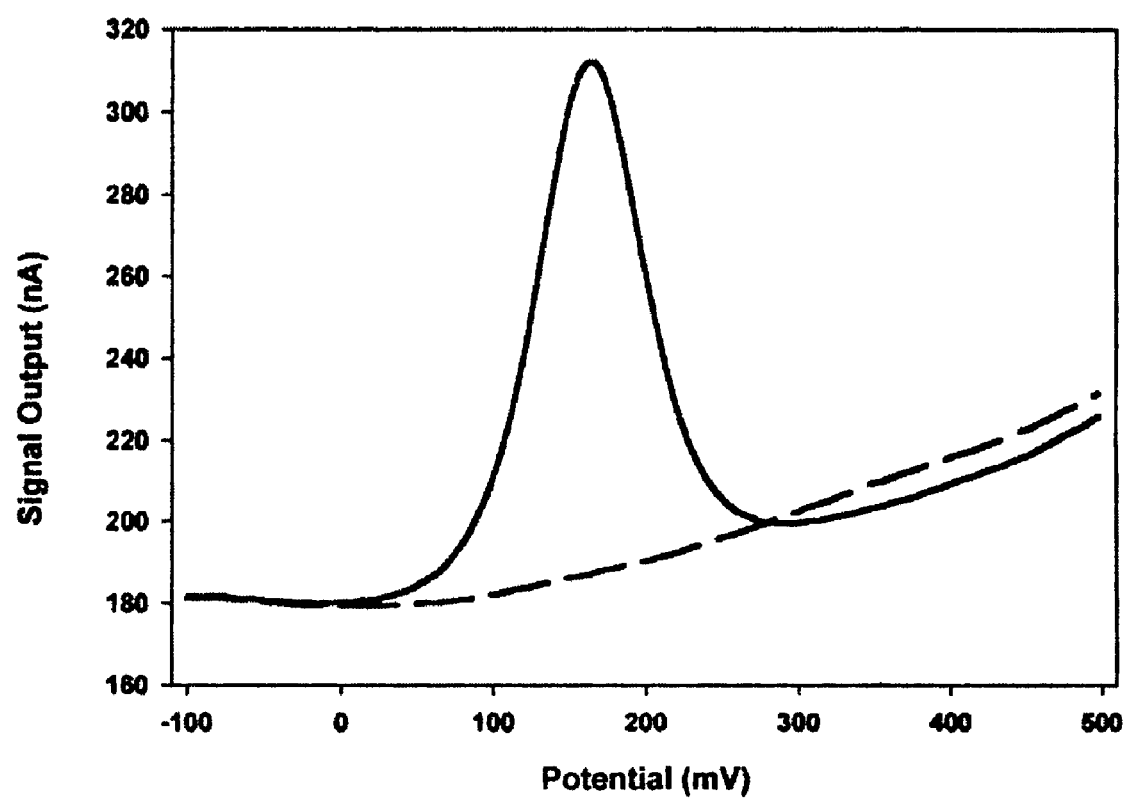
FIG. 18 is a schematic of a peak in the faradaic current, centered at the redox potential of the electron donor species (specified for a given reference electrode) and superposed on top of the capacitive current baseline which is observed in the absence of surface-immobilized signaling probes.

The net electron transfer to or from the electrode will be measured as a peak in the faradaic current, centered at the redox potential of the electron donor species (specified for a given reference electrode) and superposed on top of the capacitive current baseline which is observed in the absence of surface-immobilized signaling probes. This is shown schematically in FIG. 18.

Quantitative analysis of the sensor signal, and therefore accurate determination of target molecule concentration, is based on the fact that the measured faradaic peak height is directly proportional to number of redox moieties immobilized at the electrode, that is, the number of nucleic acid sensor molecules ligated to signaling probes times the multiplicity of redox moieties per signaling probe molecule. Signal generation by the nucleic acid sensor molecules is thus amplified by virtue of multiple redox species per signaling probe. In addition, if an alternating current (AC) bias voltage is applied (superposed) on top of the DC linear voltage ramp applied to the sensor electrodes, i.e., in the case of AC voltammetry, signal amplification would result from the cyclic repetition of the signal-generating redox reaction.

The system described above for the case of a surface-immobilized nucleic acid sensor molecule which ligates a signaling probe containing one or more modified nucleotides conjugated to redox active species suggests a general method and instrumentation for the detection and quantitation of an arbitrary target molecule in solution in real time. Detection of a particular target would require development of a nucleic acid sensor molecule against that recognizes the target molecule. Additionally, nucleic acid sensor molecules have been developed which are activated only in the presence of two different target molecules. Such dual-effector sensors could be used to detect the simultaneous presence of two or more targets, or could be used in conjunction with single-target molecule sensors to form biological logic (i.e., AND, OR, etc.) circuits.

Multiplexed detection of multiple target molecules simultaneously in a complex sample solution could be accomplished by immobilizing nucleic acid sensor molecules against the target molecules of interest on separate electrodes within a two-dimensional array of electrodes. A complex sample solution containing multiple target molecules and a common signaling probe could then be introduced to the array. All nucleic acid sensor molecules would be exposed simultaneously to all targets, with the target-activated nucleic acid sensor molecule response(s) being observed and recorded only at the spatial location(s) known to contain a nucleic acid sensor molecule specific for the target molecules present in the (unknown) sample. The utility of such a nucleic acid sensor molecule array would be greatly enhanced by the integration of a microfluidic sample and reagent delivery system. Such an integrated microfluidic system would allow the application of reagents and samples to the sensor array to be automated, and would allow the reduction of sample volume required for analysis to <1 uL.

The sensor array electrodes may be of any configuration, number, and size. In a preferred embodiment, the sensor and reference electrodes would be circular gold pads on the order of 100–500 uM in diameter, separated by a center-to center distance equal to twice their diameter. Each electrode would be addressed by separate electrical interconnects. The application of electrical signals to the sensor electrodes can be accomplished using standard commercially available AC and DC voltage sources. Detection of faradaic electrical signals from the sensor electrodes can be accomplished easily using standard commercially available data acquisition boards mounted within and controlled by a microcomputer. Specifically, the raw sensor current signals would need to be amplified, and then converted to a voltage and analyzed via a high resolution (i.e., 16 bit) analog to digital converter (ADC). It is possible to reduce the signal background and to increase the signal to noise ratio (SNR) by using the common technique of phase-sensitive detection. In this detection method, an alternating current (AC) bias voltage (at a frequency between, for example, 100 to 1000 Hz) is superposed on top of the DC linear voltage ramp applied to the sensor electrodes. The frequency of the applied bias voltage is called the fundamental frequency. It can be shown that the sensor response signal contains multiple frequency components, including the fundamental frequency and its harmonics (integral multiples of the fundamental frequency). It can further be shown that the nth harmonic signal is proportional to the nth derivative of the signal. Detecting these derivative signals (by means of a lock-in amplifier) minimizes the effects of constant or sloping backgrounds, and can enhance sensitivity by increasing the signal to noise ratio and allowing the separation of closely spaced signal peaks. It should be noted that digital, computer-controlled AC and DC voltage sources (i.e., digital to analog converters, DACs), current preamplifiers, analog to digital converters (ADCs), and lock-in amplifiers are all available as integrated signal generation/acquisition boards that can be mounted within and controlled by a single microcomputer.

In a preferred embodiment, an integrated nucleic acid sensor molecule system with electrochemical detection would include the following elements one, a independently addressable multielement electrode array with immobilized surface layer composed of conductive species separated by insulating species and sensors; two, optical nucleic acid sensor molecules immobilized on the electrode array; three, an oligonucleotide substrate/signaling probe which ligates with the nucleic acid sensor molecule in the presence of the appropriate target; four, an automated or semi-automated microfluidic reagent and sample delivery system; and five, a reader instrument/data acquisition system consisting of a microcomputer controlling the appropriate voltage sources, current and lock-in amplifiers, data acquisition boards, and software interface for instrument control and data collection.

In another embodiment, the change in activity of the nucleic acid sensor molecule can be detected by watching the change in fluorescence of a nucleic acid sensor molecule when it is immobilized on a chip. A ligase can be attached to a chip and its ligase activity monitored. Ligase ERK nucleic acid sensor molecules, labeled with one fluorophore, e.g., Cy3 is attached via an amino modification to an aldehyde chip. The initial Cy3 fluorescence indicates the efficiency of immobilization of the nucleic acid sensor molecules. Next, the chip is exposed to a substrate labeled with a second fluorophore, e.g., Cy5, with or without the ERK protein target. In the presence of ERK the nucleic acid sensor molecule ligates the substrate to itself, and becomes Cy5-labeled. Without ERK, the ligation does not occur.

The use of a labeled effector oligonucleotide does not change the rate of ligation of the nucleic acid sensor molecule whether ERK is present or not. When using nucleic acid sensor molecules in the context of a chip based system, in one embodiment, an effector oligonucleotide is used to attach the nucleic acid sensor molecule to the chip. Whether one uses effector oligonucleotide or not, the TaqMan (real-time PCR)traces obtained in the presence or absence of target (ERK) for ERK dependent ligases are identical. The presence or absence of this effector oligonucleotide does not affect the activity of the nucleic acid sensor molecule.

Figure 82:
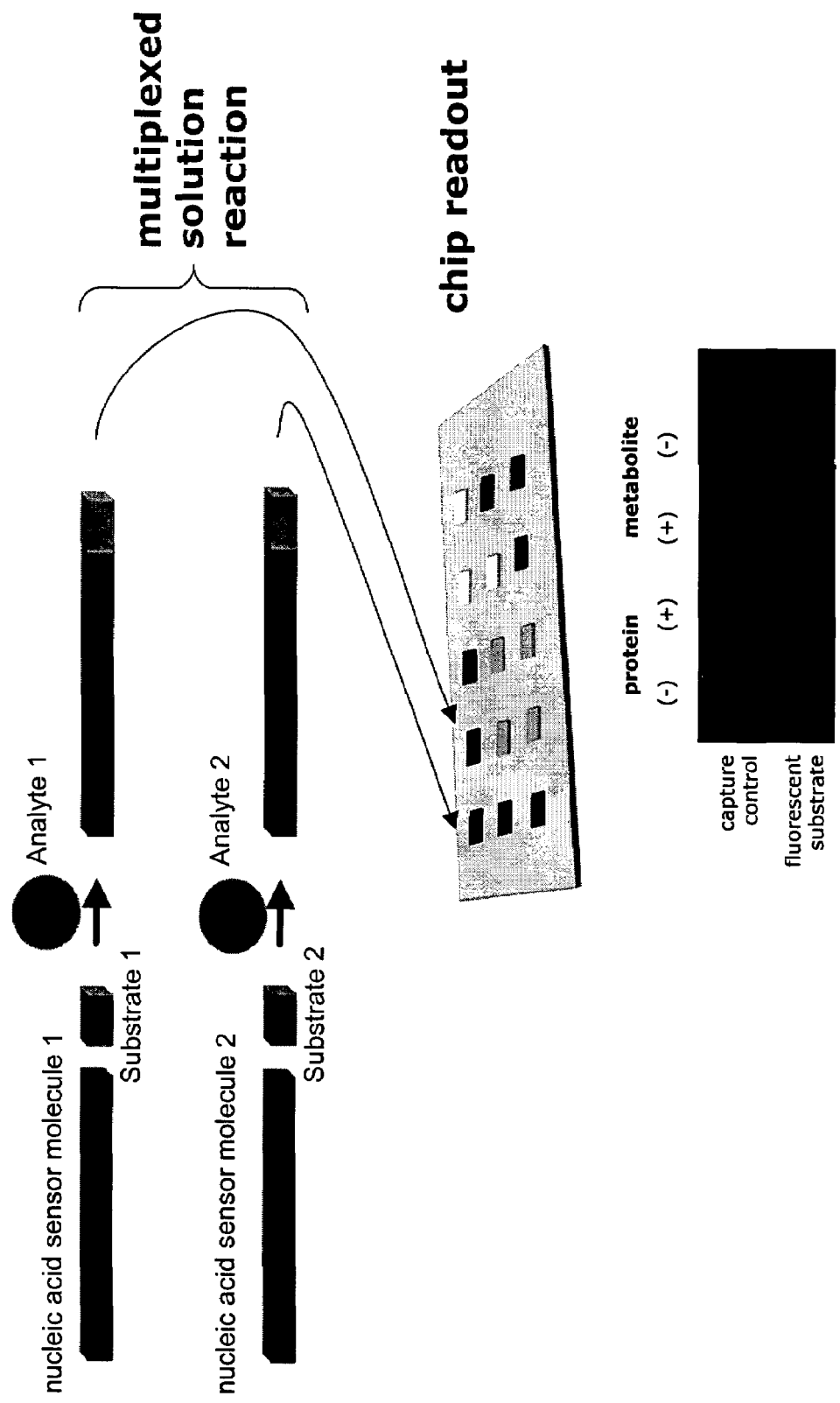
FIG. 82 shows a schematic describing multiplexed chip assays.

In another embodiment, a hammerhead nucleic acid sensor molecule could be used to measure the concentration of an analyte through the use of fluorescence. FIG. 82 shows how many nucleic acid sensor molecules with different effector molecules and/or analytes could be integrated onto one chip to study the concentration of many molecules at once.

Any optical method known in the art, in addition to those described above can be used in the detection and/or quantification of all targets of interest in all sensor formats, in both biological and nonbiological media. These targets include, e.g., those listed in Table 1, below.

Any other detection method can also be used in the detection and/or quantification of targets. For example, radioactive labels could be used, including $^{32}P$, $^{33}P$, $^{14}C$, $^{3}H$, or $^{125}I$. Also enzymatic labels can be used including horse radish peroxidase or alkaline phosphatase. The detection method could also involve the use of a capture tag for the bound nucleic acid sensor molecule.

4. Methods of Using Nucleic Acid Sensor Molecules

A. Diagnostic Assays

The nucleic acid sensor molecules according to the invention can be used to detect virtually any target molecule. In one embodiment, the target molecule is a target molecule associated with a pathological condition and detection of changes in the optical properties of the nucleic acid sensor molecules of the biosensor provides a means of diagnosing the condition. Target molecules which are contemplated within the scope include, e.g. proteins, modified forms of proteins, metabolites, organic molecules, and metal ions, as discussed above. Because signal generation in this system is reversible, washing of the biosensor(s) in a suitable buffer will allow the biosensor(s) to be used multiple times, enhancing the reproducibility of the any diagnostic assay since the same reagents can be used over and over. Suitable wash buffers include, e.g., binding buffer without target or, for faster washing, a high salt buffer or other denaturing conditions, followed by re-equilibration with binding buffer.

Re-use of the biosensor is enhanced by selecting optimal fluorophores. For example, Alexa Fluor 488, produced by Molecular Probes, has similar optical characteristics compared to fluorescein, but has a much longer lifetime. However, in one embodiment, a site recognized by a nuclease is engineered proximal to the signal generating site, and sequences comprising signaling moieties are removed from the biosensor and replaced by new sequences, as needed.

Profiling Biosensors for Use in Diagnostic Assays

In one embodiment, the expression pattern of a plurality of target molecules is determined to obtain a profile of target molecules associated with a trait in an individual to determine an expression pattern which is diagnostic of that trait. In this embodiment, combinations of biosensors targeted to individual target molecules are selected until a signature optical profile is determined which is characteristic of a trait. Traits include, e.g., a disease, a genetic alteration, a combination of genetic alterations (e.g., a polygenic disorder), a physiological reaction to an environmental condition, or a wild type state (e.g., of an organism or of an organ system). The target molecules which generate the signature optical profile are identified (based on the type of biosensors used) as signature target molecules. The expression of the signature target molecules can thereafter be determined to identify the presence of the trait in a patient.

The expression of the target molecules can be identified using any molecular detection system known in the art; however, in a preferred embodiment, the detection system comprises optical nucleic acid sensor molecules and the trait is identified by detecting the signature optical profile. In one embodiment, data relating to the signature optical profile is stored in the memory of a computer. Signature optical profiles can be generated for individual patients or can be generated for populations of individuals. In the latter embodiment, data relating to a composite signature profile (e.g., comprising normalized data) is stored in the memory of a computer or in a computer program product.

Because the biological function of the target molecules does not need to be known, biosensors according to the invention can be generated which are diagnostic of diseases/traits whose biological basis is not yet known or are the result of complex polygenic interactions and/or of environmental influences. In one embodiment, nucleic acid sensor molecules are identified which are activatable by synthetic polypeptides obtained from putative open reading frames identified in the human genome project and/or in other sequencing efforts. Combinations of these activatable nucleic acid sensor molecules (along with activatable nucleic acid sensor molecules specific for target molecules with known functions) are identified which generate a diagnostic optical signal, and signature target molecules are in turn identified which are linked to a particular trait, allowing a biological-activity to be associated with a previously uncharacterized molecule.

Data relating to signature target molecules or to the optical signals generated upon activation of nucleic acid sensor molecules upon binding to signature target molecules is stored in a database, which can include further information such as sequence information or chemical structure information relating to the signature target molecule. A signature profile relating to a particular trait is generated based on normalized data from a plurality of tests. In one embodiment, a signature profile is obtained by determining any or all of the level, chemical structure, or activity, of signature target molecules associated with a disease in samples from a population of healthy individuals to determine a signature profile corresponding to a healthy state. In a further embodiment, signature profiles are obtained using data from subsets of populations which are divided into groups based on sex, age, exposure to environmental factors, ethnic background, and family history of a disease.

B. Drug Discovery

Generally, methods of drug discovery comprise steps of 1) identifying target(s) molecules associated with a disease; 2) validating target molecules (e.g., mimicking the disease in an animal or cellular model); 3) developing assays to identify lead compounds which affect that target (e.g., such as using libraries to assay the ability of a compound to bind to the target); 4) prioritizing and modifying lead compounds identified through biochemical and cellular testing; 5) testing in animal models; and 6) testing in humans (clinical trials). Through the power of genomics and combinatorial chemistry, large numbers of lead compounds can be identified in high throughput assays (step 3); however, a bottleneck occurs at step 4 because of the lack of efficient ways to prioritize and optimize lead compounds and to identify those which actually offer potential for clinical trials. The target activatable nucleic acid sensor molecules according to the present invention offer a way to solve this problem by providing reagents which can be used at each step of the drug development process. Most importantly, the target activatable nucleic acid sensor molecules according to the present invention offer a way to correlate biochemical data, from in vitro biochemistry and cellular assays, with the effect of a drug on physiological response from a biological assay.

In one embodiment of invention, a method for identifying a drug compound is provided, comprising identifying a profile of target molecules associated with a disease trait in a patient, administering a candidate compound to the patient, and monitoring changes in the profile. In another embodiment, the monitored profile is compared with a profile of a healthy patient or population of healthy patients, and a compound which generates a profile which is substantially similar to the profile of target molecules in the healthy patient(s) (based on routine statistical testing) is identified as a drug. In a further embodiment, both the profiling and the drug identification step is performed using at least one nucleic acid sensor molecule whose properties change upon binding to a target molecule.

In a further embodiment, a method for identifying a drug compound comprises identifying a plurality of pathway target molecules, each belonging to a pathway, monitoring the level, chemical structure, and/or activity of pathway target molecules in a patient having a disease trait, administering a candidate compound to the patient, and monitoring changes in the level, chemical structure, and/or activity of the pathway target molecules. In another embodiment, the monitored level, chemical structure, and/or activity of the pathway target molecules is compared to the level, chemical structure, and/or activity of pathway target molecules in a wild type patient or patients. In a further embodiment, both profiling and the identification of drug compounds is performed using at least one nucleic acid sensor molecule whose properties change upon binding to a pathway target molecule.

Properties according to this aspect include, e.g., optical properties, change in sequence, chemical structure, catalytic activity, and/or molecular weight. In a preferred embodiment, sensor molecules are target activated optical nucleic acid sensor molecules.

i. Nucleic Acid Sensor Molecules for Use in Identifying Lead Compounds

In one embodiment, biosensors activatable by signature target molecules, identified as described above, are provided and are validated by testing against multiple patient samples in vitro to verify that the optical signal generated by these molecules is diagnostic of a particular disease. Validation can also be performed ex vivo, e.g., in cell culture, (using microscope-based detection systems and other optical systems as described in U.S. Pat. No. 5,843,658, U.S. Pat. No. 5,776,782, U.S. Pat. No. 5,648,269, and U.S. Pat. No. 5,585,245) and/or in vivo, for example, by providing a profile biosensor in communication with an optical fiber.

The incorporation of biosensors into fiber optic waveguides is known in the art (see, e.g., U.S. Pat. No. 4,577,109, U.S. Pat. No. 5,037,615, U.S. Pat. No. 4,929,561, U.S. Pat. No. 4,822,746, and U.S. Pat. No. 4,762,799). The selection of fluorescent energy transfer molecules for in vivo use is described in EP-A 649848, for example. In this embodiment, nucleic-acid based biosensors are introduced into the body by any suitable medical access device, such as an endoscope or a catheter. The optical fiber is provided within a working lumen of the access device and is in communication with an optical imaging system.

In one embodiment, the same methods which are used to validate the diagnostic value of particular sets of target molecule/nucleic acid sensor molecule combinations are used to identify lead compounds which can function as drugs. Thus, in one embodiment, the effects of a compound on target dependent optical signaling is monitored to identify changes in a signature profile arising as a result of treatment with a candidate compound.

In one embodiment, samples from a treated patient are tested in vitro; however, samples can also be tested ex vivo or in vivo. When the diagnostic profile identified by the biosensor changes from a profile which is a signature of a disease to one which is substantially similar to the signature of a wild type state (e.g., as determined using routine statistical tests), the lead compound is identified as a drug.

Target molecules which activate the biosensor can comprise molecules with characterized activity and/or molecules with uncharacterized activity. Because large number of target molecules can be monitored simultaneously, the method provides a way to assess the affects of compounds on multiple drug targets simultaneously, allowing identification of the most sensitive drug targets associated with a particular trait (e.g., a disease or a genetic alteration).

Examples of suitable target molecules include, e.g., nuclear hormone receptor (NHR) polypeptides; G-coupled protein receptor (GPCR) polypeptides, phosphodiesterase (PDE), and protein kinases.

NHR Polypeptides

Included in the invention are methods of identifying nucleic acid sensor molecules for detection of conformational isoforms of nuclear hormone receptors, as well as the nucleic acid sensor molecules identified by the methods described herein.

Nuclear hormone receptors (NHRs) act as ligand-inducible transcription factors by directly interacting as monomers, homodimers, or heterodimers in complex with DNA response elements of target genes. The activation of these transcription regulators is induced by the change in conformation of the NHR upon complex formation with ligand.

Provided are methods for generating unique NASMs for each NHR ligand binding domain (LBD). The NASMs described herein can include, e.g., those derived from the hammerhead, hairpin, L1 ligase or group 1 intron ribozymes and the like, any of which transduce molecular recognition into a detectable signal.

Also provided is a direct mechanistic assay for the action of small molecule ligand-agonism, -antagonism and partial antagonism of members of the NHR family. The mechanistic assays function in both in vitro biochemical as well as with in vitro cell-based settings. In the in vitro assay setting, the nucleic acid sensor molecules are designed to recognize one conformational isomer of the NHR. In one embodiment, the nucleic acid sensor molecule recognizes the unique conformation that exists for the agonist bound form of a hormone receptor; such as that observed for the estrogen receptor ligand binding domain ER-LBD when bound to estrogen (Shiau A K, Barstad D, Loria P M, Cheng L, Kushner P J, Agard D A, Greene G L. Cell. 1998;95(7):927–37) and then produces a detectable signal, such as release of fluorescently labeled oligonucleotide, radiolabeled oligonucleotide, or reveals a change in nucleic acid sensor molecule conformation driven by ligand binding through a change in fluorescence or the like. Hence, in this embodiment, the nucleic acid sensor molecule transduces molecular recognition of the ER-LBD-estrogen agonist complex into a detectable signal. The level of the signal is then used to quantify the amount of ER-LBD-estrogen agonist complex present in solution. In another embodiment, the ER-LBD-estrogen specific nucleic acid sensor molecule is used as a screening tool in assays designed to detect inhibitors of ER-LBD-estrogen complex formation. These screening tools can be used to determine the inhibition potency of compounds in in vitro biochemical assays or in in vitro cell-based assays. Inhibitors of estrogen binding to ER-LBD are useful as anti-proliferative agents for treatment of breast cancers (e.g., tamoxifen) and other estrogen dependent diseases. In another embodiment, nucleic acid sensor molecules are introduced into cell lines by known methods of electroporation, transfection or coupling to peptide translocating agents such as tat or antennapedia peptides. In another embodiment, the ER-LBD-estrogen complex specific nucleic acid sensor molecule is an allosteric intron imbedded in a reporter gene such as GFP or luciferase or the like. When the intron derived nucleic acid sensor molecule is inserted into the reporter gene it renders reporter gene expression effector dependent. Thus, in one embodiment functional GFP protein is expressed only when the ER-LBD-estrogen complex is present in the cell, and inhibitors of ER-LBD-estrogen complex formation thus block functional GFP protein expression in appropriate mammalian, such as MCF7 or T47D, yeast or bacterial cell lines. In a further embodiment, the MCF7 or T47D tumor cell lines transfected with GFP-ER-LBD-estrogen nucleic acid sensor molecule sensitive construct are used to form tumor xenografts in nude mice. Thus, the transfected tumor xenograft cell lines can be used to form tumors in mice which are not only estrogen dependent but also regulate reporter gene expression in ER-LBD-estrogen dependent manner. These cell lines and tumor models are used to discover inhibitors of ER-LBD-estrogen complex formation in vivo.

NHR ligand binding domains bind antagonists, forming additional conformational isomers. When antagonists are bound to the receptor a new conformer results such as that observed upon tamoxifen binding to the estrogen receptor to form a stable ER-LBD-tamoxifen complex (Shiau A K, Barstad D, Loria P M, Cheng L, Kushner P J, Agard D A, Greene G L. Cell. 1998 Dec 23;95(7):927–37). Accordingly, the invention includes use of an ER-LBD-tamoxifen specific nucleic acid sensor molecule that is used to detect the levels of antagonist specific complex in both in vitro biochemical, cell-based and, in in vivo assays as described above.

Nucleic acid sensor molecules can be developed that are specific for the ligand binding domains of all NHRs. In addition, it should be clear that nucleic acid sensor molecules for agonist, antagonist, dimeric or multimeric forms of NHR LBDs can be used to screen for inhibitors of LBD function and therefore for inhibitors of NHR dependent transcriptional activation or repression. It should be clear to one skilled in the art that nucleic acid sensor molecules specific for individual LBD complexes can be used to screen for agents that modify NHR function in in vitro and in in vivo assays.

NHRs are multidomain proteins containing a variable $NH_2$-terminal region (A/B), a conserved DNA binding domain (DBD) or region (C), a linker region (D), and a conserved region (E) that contains the ligand binding domain (LBD). NHRs also contain regions required for transcriptional activation, of particular interest is the region AF-2 which is located in the COOH-terminus and whose function is strictly ligand dependent. Provided herein is a method for generating unique nucleic acid sensor molecules to each of the 63 known human NHR LBDs. In addition, methods are described that enable the generation of nucleic acid sensor molecules capable of recognizing the activated state of the NHR by selection for nucleic acid sensor molecules geometries which signal the presence of either the activated or inactivated conformation (NHR with bound ligand), but whose signaling action is quiescent in the presence of other forms of the NHR.

The nucleic acid sensor molecules allow the direct, simultaneous, and rapid detection of the activation states of all NHRs. This tool can be used in in vitro assays for receptor activation with agonists and antagonists, and can be used to generate cell lines and animal models that report on the activation state of such receptors in a biological setting and as a function of drug or drug lead.

GPCR Nucleic Acid Sensor Molecules

Also provided by the invention are nucleic acid sensor molecules for detection of conformational isoforms of G-protein coupled receptors.

G-protein coupled receptors (GPCRs) play fundamental roles in regulating the activity of virtually every cell. Upon binding of extracellular ligands, GPCRs interact with a specific subset of heterotrimeric G-proteins that can then, in their activated forms, inhibit or activate various effector enzymes and/or ion channels. Molecular cloning studies have identified multiple human GPCRs, and have identified the ligands for many of these.

GPCRs include three domains: an extracellular N-terminus, a central domain of seven trans-membrane helices connected by unstructured loops, and a cytoplasmic C-terminus. Activation of GPCRs is induced by ligand binding, which causes a conformational change in the receptor transmitting a signal across the plasma membrane to intracellular members of a signaling pathway. The methods described herein allow for generating unique nucleic acid sensor molecules to any GPCR. In addition, methods are described that enable the generation of nucleic acid sensor molecules capable of recognizing the activated state of the GPCR by selecting for nucleic acid sensor molecule geometries which signal the presence or absense of the activated conformation of the receptor through recognition of one or all of the mobile domains, but whose signaling action is quiescent in the presence of other forms of the GPCR. The biosensors described herein include nucleic acid sensor molecules such as allosetric ribozymes (AR), including those derived from the hammerhead, hairpin, LI ligase, or group 1 intron ribozymes and the like. Nucleic acid sensor molecules may also be derived from aptamer beacons or signaling aptamers which transduce molecular recognition into a detectible signal.

Upon the activation by an extracellular ligand or stimuli, G-protein coupled receptor(GPCR) polypeptides activate intracellular Gec-protein. A single GPCR can activate a number of Gα-proteins. For example, adrenergic receptors activate Gi, which inhibit adenylyl cyclases, Gs, which stimulate adenylyl cyclases, and Gq, which regulate cellular Calcium-ion level (Wenzel-Seifert and Seifert 2000). Thus, it is highly desirable to distinguish which class of Gα-proteins are activated through the GPCR of interest in cells.

The initial drug screening of the GPCRs is normally performed by competition assay with radiolabeled ligands. For a cell based GPCR assay, incorporation of radiolabeled GTP can be measured to detect the coupling of Gα-protein and GPCR, however this assay does not distinguish the type of Gα-proteins involved. The assays for the effect on individual effectors, such as the $Ca^{++}$ flow or cellular cAMP level, are also commonly used, but only one downstream signal can be measured at a time using these assays.

Upon activation, a Gα-protein undergoes significant conformational change which results in release of GDP and association with GTP (Coleman and Sprang 1998). The Gα-protein also dissociates from its βγ-subunits. This activated form of Gα-protein then becomes capable of interacting with its effector (Li, Stemweis et al. 1998). The well-characterized conformation change takes place in three switches; switch I (residues 177–187 in Giα1), switch II (residues 199–219 in Giα1), and switch III (residues 231–242 in Giα1). The sequences and the conformational changes in these switches are well conserved among Gα-proteins.

Ras is a member of the small GTPase protein family, which shares significant similarity with other family members. GTP-bound ras and GDP-bound ras can be distinguished by the RBD (ras binding domain) of Raf-1 (Taylor, Resnick et al. 2001). The activated state of Raf-1 can be identified by RaIRDS (Franke, Akkerman et al. 1997). This indicates significant change in the surface of the protein, and the effector binding surface are only available for interaction in GTP complex form.

The invention provides methods for selecting nucleic acid sensor molecules which recognize the conformational change upon GTP binding and/or specifically interact with newly exposed G-protein effector binding sites upon the activation. Class-specific activated Gα-protein nucleic acid sensor molecules recognize the activated Gα-proteins or its effector binding site, which allow us to interpret the multiple type of downstream signal affect by the GPCR. It can used in both in vitro HTS (high throughput screening) and cell-based HTS.

Also described is a method for developing a direct mechanistic assay of the action of small molecule ligand-agonism, -antagonism, and partial antagonism of members of the GPCR family. The mechanistic assays function in both in vitro biochemical and in vitro cell-based settings. In the in vitro assay setting, the nucleic acid sensor molecules are designed to recognize one conformational isomer of the GPCR.

In one embodiment, the nucleic acid sensor molecule recognizes the unique conformation that exists for the activated state when in complex with ligand, e.g., such as that observed for the beta-2 adrenergic receptor when in complex with the artificial ligand isoproterenol (Ghanouni et al., PNAS USA, 98:5997–6002(2001)) and then produces a detectable signal, e.g., by release of a fluorescently labeled oligonucleotide, release of a radiolabeled oligonucleotide, or a change in conformation of the NASM driven by ligand binding through a change in fluorescence or the like. Hence, in this embodiment, the nucleic acid sensor molecule transduces molecular recognition of the beta-2 adrenergic receptor—in complex with epinephrine, norepinephrine or an artificial ligand such as isoproterenol into a detectible signal. The level of the signal is then used to quantify the amount of beta-2 adrenergic receptor-agonist complex present in solution.

In another embodiment, the beta-2 adrenergic-agonist nucleic acid sensor molecule is used as a screening tool in assays designed to detect agonists of the beta-2 adrenergic receptor. These screening tools can be used to determine the activation potency of compounds in in vitro biochemical assays or in in vitro cell-based assays. Agonists of the beta-2 receptor are useful in the treatment of asthma (Robinson, et al. Lancet 357:2007–2011(2001)). In another embodiment, nucleic acid sensor molecules are introduced into cell lines by known methods of electroporation, transfection, or coupling to peptide translocating agents such as tat or antennapedia peptides.

In another embodiment, the beta-2 adrenergic receptor-agonist complex specific nucleic acid sensor molecule is an allosteric intron imbedded in a reporter gene such as GFP or luciferase or the like. When the intron-derived reporter is inserted into the reporter gene it renders reporter gene expression effector dependent. Thus, in one embodiment functional GFP protein is expressed only when the beta-2 adrenergic receptor-agonist complex is present in the cell, and inhibitors of beta-2 adrenergic receptor-agonist complex formation block functional GFP protein expression in appropriate cells such as mammalian human peripheral blood leukocytes, yeast, insect, or bacterial cell lines.

In a further embodiment, Chinese hamster fibroblasts, which do not express beta-adrenergic receptors (Sheppard, et al., PNAS USA 80:233–236(1983)), are transfected with both the nucleic acid sensor molecule and the gene coding for the beta-adrenergic receptor under a constitutive promoter, and are used to create a model cell line suitable for HTS screening of candidate beta-2 agonists. Furthermore, cells can be caused to express known allelic variants, such as gln27-to-glu associated with obesity (Large, et al., J Clin. Invest 100:3005–3013), to create cells lines which model specific disease states. Furthermore, chimeric mice can be created by "knock-in" (Monroe et al., Immunity 11:201–212 (1999)) which will express the nucleic acid sensor molecule in every cell as the result of blastocyst fusion (Chen et al., PNAS USA 90:4528–4532(1993)), and used for pharmokinetic or bioavailability studies in which the GPCR activation states of various tissues in the organism are of concern.

GPCRs bind antagonists, which cause the GPCRs to become resistant to conformational changes, or result in conformations not susceptible to activation, or blockade the ligand binding domain from interaction with the appropriate ligand and thus prevent activation of the GPCR, such as the beta-2 adrenergic receptor antagonist butoxamine (Horinouchi et al., Pharmacology 62:98–102(2001)). Hence, the invention also provides a method for using a nucleic acid sensor molecule to detect conformers which result from binding of GPCRs to antagonists. Furthermore, when the cell line described above is transfected with a mutant variants of GPCRs which spontaneously adopt the active conformation, such as lys272-to-ala (Pei, et al., PNAS USA 91:2699–2702(1994) and references therein) the nucleic acid sensor molecule can be employed in a screen for compounds which are beta-2 antagonists (Ramsay et al, Br J Pharmacol 133:315–323(2001)). Antagonists of the beta-2 receptor are useful in the treatment of cardiovascular diseases (Nagatomo, et al., Cardiovasc Drug Rev 19:9–24 (2001)). The invention accordingly provides a method for using a Beta-2 adrenergic receptor—butoxamine complex-specific nucleic acid sensor molecule that is used to detect the levels of an antagonist specific complex in both in vitro biochemical, cell-based, and in vivo assays as described above.

Nucleic acid sensor molecules can also be developed that are specific for the occupancy state of the ligand-binding domains of all GPCRs. In addition, nucleic acid sensor molecules for the agonist, antagonist, dimeric, or multimeric forms of all GPCRs can be used to screen for inhibitors or activators of GPCR function and therefore for inhibitors or activators of GPCR-dependent cell signaling pathways. Nucleic acid sensor molecules specific for individual GPCR complexes can be additionally used to screen for agents that modify GPCRs in in vitro and in vivo assays.

Phosphodiesterase-specific Nucleic Acid Sensor Molecules

Multiple classes of phosphodiesterases (PDEs) have been identified in humans. These enzymes catalyze a reaction that converts second messenger cAMP and cGMP into 5'-AMP and 5'-GMP. Different class of PDEs have different substrate specificity as well as different physiological function. For example, PDE4s are specific for cAMP and PDE5 are specific for cGMP.

The invention provides multiple classes of PDE nucleic acid sensor molecules. The first class of nucleic acid sensor molecules can distinguish cAMP vs. 5' AMP (cGMP vs 5'GMP) (Koizumi, Kerr et al. 1999) (Koizumi, Soukup et al. 1999). The second class of nucleic acid sensor molecule binds to the active site of PDE in a class specific manner and inhibits PDE catalytic activity. This class of nucleic acid sensor molecule can be raised using PDEs in the presence and absence of high affinity known inhibitors (e.g., Ropalim for PDE4). The third class of nucleic acid sensor molecule recognizes PDE in a class-specific (e.g., PDE1–11) or sub-class-specific (PDE4A–D) manner.

Protein Kinase-specific Nucleic Acid Sensor Molecules

The invention also provides nucleic acid sensor molecules raised against protein kinases. In one embodiment, the invention provides nucleic acid sensor molecules that are modulated by the phosphorylation state in a given peptide sequence. Alternatively, native proteins can be used with different phosphorylation states in order to raise nucleic acid sensor molecules that can distinguish the different phosphorylation states. For example, ERK1/2 and phosphorylated ERK1/2 can be distinguished by specific nucleic acid sensor molecules (Seiwert, Stines Nahreini et al. 2000). The nucleic acid sensor molecule also can be a competitive inhibitor for a kinase by binding at ATP or substrate binding sites.

Alternatively, an ADP-dependent nucleic acid sensor molecule can be obtained at lower pH. These nucleic acid sensor molecules can be used to detect the production of ADP.

ii. Pathway Profiling Biosensors

Figure 7:
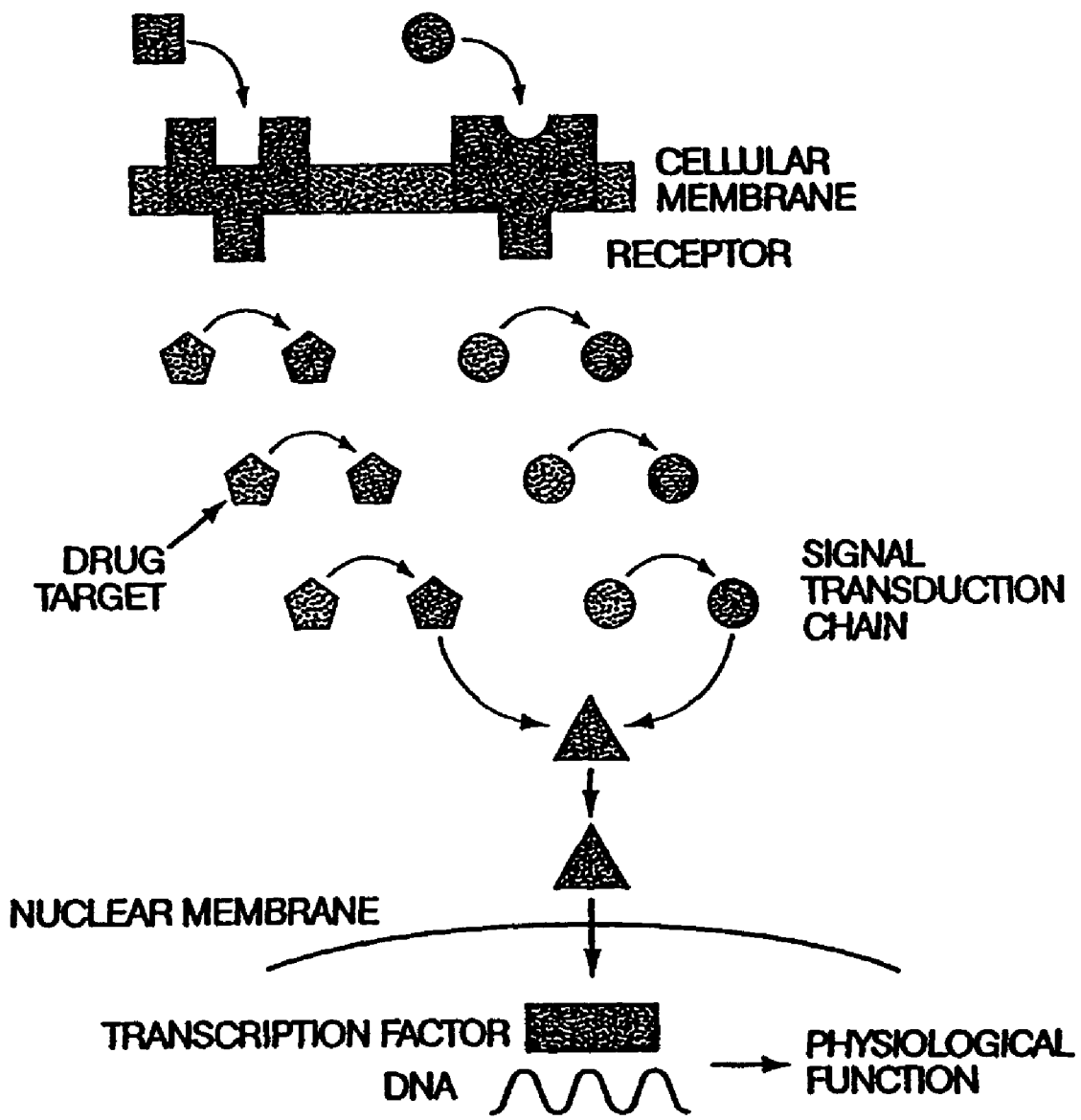
FIG. 7 is a schematic diagram illustrating pathway target molecules according to one embodiment.

As shown in FIG. 7, physiological function is modulated by complex pathways, each of which may have multiple overlapping and intersecting steps. Furthermore, the proteins involved in these pathways are highly homologous and can have overlapping substrates and drug specificities. Using current techniques, it is possible only to monitor the response of single elements of a pathway. These techniques are inadequate to understand the mechanism of drug interactions. For example, a particular drug found to have a particular in vitro activity against a single target in biochemical assays might interact with other proteins in the same pathway, or in other unrelated pathways. Consequently, physiological function is often uncorrelated with the results of biochemical assays of a single target.

The nucleic acid sensor molecules according to the invention provide reagents to simultaneously quantify the level and chemical state of all components in a molecular pathway As used herein, "pathway target molecules" are target molecules involved in the same pathway and whose accumulation and/or activity is dependent on other pathway target molecules, or whose accumulation and/or activity affects the accumulation and/or activity of other pathway target molecules. Pathway target molecules according to the invention include, e.g., proteins, such as enzymes, modified forms of proteins, such as phosphorylated, sulfated, ribosylated proteins, methylated proteins (Arg, Asp; N, S or O directed), prenylated proteins (such as by farnesyl, geranylgeranyl, and other types of prenylation) acetylated or acylated proteins, cleaved or clipped proteins, bound or unbound forms of proteins, allelic variants of a protein (e.g., proteins differing from each other by single amino acid changes in a protein), as well as substrates, intermediates, and products of enzymes (including both protein and non-protein molecules).

In another embodiment, diagnostic pathway target molecules are identified by pre-selecting a plurality of nucleic acid sensor molecules activatable by pathway-specific target molecules. In one embodiment, a profiling biosensor is provided comprising at least one nucleic acid sensor molecule specific for every molecular species within a pathway (e.g., a signaling pathway), to generate a biosensor which can monitor the levels, chemical structure, and/or activity of every molecular species in the pathway.

Because of the finite number of target molecules (as determined from data obtained from the Human Genome Project) and the high throughput of the biosensors of the instant invention (greater than 10,000 target molecules can be monitored simultaneously), the profiling biosensors of the instant invention make it feasible to evaluate the response of all the components of a pathway to a drug compound simultaneously.

In one embodiment, a profiling biosensor reactive to the components of an entire pathway, is contacted with a sample from a patient having a disease, and ani optical signal corresponding to a disease state is determined to identify diagnostic pathway target molecules which are diagnostic of that disease. Samples from a plurality of patients are obtained and tested using the profiling biosensor to identify a pathway profile that is diagnostic of the disease, the pathway profile comprising normalized data relating to any or all of the level, structure, and activity, of the signature pathway molecules. A pathway profile corresponding to a wild type state is determined by testing the profiling biosensor molecules against samples from a population of healthy patients, or subsets of populations of healthy patients. In one embodiment, data relating to the optical signals generated by nucleic acid sensor molecules activated by the diagnostic pathway target molecules is stored within the memory of a computer or within a computer program product.

The pathway profiles can be used in diagnostic testing as discussed above. In one embodiment, a profiling biosensor is used in which the pathway is one which is known or suspected of being disrupted in patients having a particular trait (e.g., having a particular disease or genetic alteration(s)). For example, in one embodiment, one profiling biosensor used to evaluate samples from a patient with cardiovascular disease is a cholesterol metabolism pathway profiling biosensor. However, random combinations of profiling biosensors can be used to assess the physiological state of a patient, to identify diagnostic pathway profiles which are diagnostic of diseases whose molecular basis has not yet been identified or characterized.

In one embodiment, profiling biosensors according to the invention are used to assess the affect of a candidate drug on any or all of the level, chemical structure, or activity of diagnostic pathway target molecules to generate a drug treatment pathway profile. In this embodiment, a profiling biosensor is contacted with a sample from a cell or physiological system (e.g., a group of cells, a tissue system, an organ system, or a patient), and changes in optical signals are obtained which are correlated to any, or all of, the level, chemical structure, or activity of a particular pathway target molecule by relating the optical signal obtained to the address of the nucleic acid sensor molecule, as described above. In one embodiment, a drug treatment profile which is substantially similar to a diagnostic pathway profile obtained from a healthy population of patients (as determined by observing no significant differences in the profile by routine statistical testing, to within 95% confidence levels) is used to identify a candidate drug as one which is suitable for further testing. The profile produced by such a drug is used to produce an effective drug treatment profile, against which other candidate drugs can be compared.

In another embodiment, a candidate drug is tested against a plurality of profiling biosensors including the one which will generate a diagnostic signature profile, to identify drugs which produce an effective drug treatment profile without effecting significant changes in other pathway profiles. In this embodiment, the systemic effects of a candidate drug can be predicted.

In further embodiments, it is desirable to use a biosensor representing less than an entire pathway. In one embodiment, a biosensor is provided comprising nucleic acid sensor molecules diagnostic pathway target molecules. In a further embodiment, a biosensor is provided which comprises nucleic acid sensor molecules necessary to evaluate particular components of a pathway suspected of being involved in a disease. For example, compounds being screened to identify candidate drugs that affect diseases relating to defective DNA repair can be tested against a pathway biosensor comprising only S phase cell cycle target molecule reactive nucleic acid sensor molecule.

Exemplary pathway target molecules include various proteins and modified form thereof. Modifications include post-translational modifications such as phosphorylation, prenylation, glycosylation, methionine removal, N-acetylation, acylation, acylation of cysteines, myristoylation, alkylation, ubiquitinylation, prolyl-4-hydroxylation, carboxylation of glutaminyl residues, advanced glycoslylation (e.g., of hemoglobin), deamination of glutamine and asparagine, addition of glycophosphatidylinositol, disulfide bond formation, hydroxylation, and lipidation. Examples of such proteins include ERK and phosphorylated ERK, CDK and phosphorylated CDK, modified cyclin A, cyclin D, cyclin E, k-Ras, h-Ras, Rho A, MEK-1, MEKK-1, Raf-1, Raf-A, JNK, PKA, ATK, PTEN, p53, P16, and INK4. Other proteins include those listed in Table 1 as well as post-translationally modified forms thereof.

TABLE 1

| | | |
|---|---|---|
| apoptotic pathways | | Bcl, Bak, ICE proteases, Ich-1, CrmA, CPP32, APO-1/Fas, DR3, FADD containing proteins, perform, p55 tumor necrosis factor (TNF) receptor, NAIP. TAP, TRADD-TRAF2 and TRADD-FADD, TNF, D4-GDI, NF-kB, CPP32/apopain, CD4O, IRF-i, p53, apoptin |
| blood clotting pathways | | thrombin, fibrinogen, factor V, Factor VIII-FVa, FVIIIa, Factor XI, Factor Xia, Factors IX and X, thrombin receptor, thrombomodulin (TM), protein C (PC) to activated protein C (aPC). aPC, plasminogen activator inhibitor-i (PAT-i), tPA (tissue plasminogen activator) |
| calcium signaling pathways | | calmodulin, calcineurin, |
| Cell cycle Pathway | G0 | MPS, CYTOSTATIC FACTOR (CSF) (INCLUDING MOS) |
| | G1 | mid GI phase: cdk4/cycin D1–3 and cdk6/cyclin D1–3 late G 1 phase: cdk2/cycin E others: p53, p21, p16, Rb, p2'1, E2F, Cdc25A, Cdc25B |
| | S | cyclin A/CDK2, cyclin B/Cdc2, SPA-i, Cdc25A, Cdc25B |
| | G2 | G2/M transition phase: cdk1/cyclin B 1–3, cdk1/cyclin A, Cdc25A, Cdc25B, Cdc25C. PIN!, Chki, Myt 1, Wee 1 |
| | M | Cdc2/cyclin B, P1k, Cdc25C, |
| Cholesterol metabolism pathway | | LDL, LDL-receptor, VLDL, HDL, cholesterol acyltransferase, apoprotein E, Cholesteryl esters, ApoA-I and A-I1, HMGCoA reductase, cholesterol |
| Flt-3 pathway | | flt-3 pathway flt-3, GRP-2, SHP-2, SHIP, She |
| JAK/STATS signaling pathway | | Jak1, Jak2, IL-2, IL-4 and IL-7, Jak3, Ptk-2, Tyk2, EPO, GH, prolactin, IL-3, GM-CSF, G-CSF, IFN gamma, LW, OSM, IL-12 and IL-6, IFNR-alpha, IFNR-gamma, IL-2R beta, IL-6R, CNTFR, Stat 1 alpha, Stat 1 beta, and Stats2–6 |
| MAP kinase signaling pathways | | flt-3, ras, raf, Grb2, Erk-i, Erk-2, and Src, Erb2, gpl3O, MEK-1, MEK-2, hsp 90, JNK, p38, Sin!, Styi/Spcl, MKK's, MAPKAP kinase-2, JNK, SAPK |
| P53 pathway | | bax, bid, caspases, cytochrome c |
| PI 3 kinase pathway | | SHIP, Akt |
| ras activation pathways | | p120-Ras GAP, neurofibromin, Gapl, Ra!-GDS, Rsbs 1, 2, and 4, Rinl, MEKK-1, and phosphatidylinositol-3-OH kinase (P13K), ras |
| SIP signaling pathways | | GRB2, SIP, ras, P1 3-kinase |
| SHC signaling pathways | | trkA, trkb, NGF, BDNF, NT-4/5, trkC, fNT-3, Shc, PLC gamma 1, P1–3 kinase, SNT, ras, rafi, MEK and MAP kinase |
| TGF-13 signaling pathways | | BMP, Smad 2, Smad4, activin, TGF |
| T-cell receptor complex | | lck, fyn, CD4, CD8, T cell receptor proteins |
| MHC-I pathways | | TAP proteins, LMP 2, LMP 7, gp 96, HSP 90, HSP 70 |

If desired, nucleic acid sensor molecules can be raised against particular amino acid sequences in the polypeptides. Some representative peptide regions are presented in Table 2.

TABLE 2

| Sequence | | Enzyme |
|---|---|---|
| L-R-A-S-L-G | (SEQ ID NO:52) | PKA |
| A-A-K-I-Q-A-S-F-R-G-H-M-A-R-K-K | (SEQ ID NO:53) | PKC |
| P-K-T-P-K-K-A-K-K-L | (SEQ ID NO:54) | cdc2 |
| E-P-P-L-S-Q-E-A-F-A-D-L-W-K-K | (SEQ ID NO:55) | DNA-PK |
| D-D-D-E-E-S-I-T-R-R | (SEQ ID NO:56) | CK-1 |
| R-R-R-E-E-T-E-E-E | (SEQ ID NO:57) | CK-2 |
| K-K-A-L-R-R-Q-E-T-V-D-A-L | (SEQ ID NO:58) | CaM KII |
| S-T-K-V-P-Q-T-P-L-H-T-S-R-V | (SEQ ID NO:59) | P38 |
| R-R-R-S-I-I-F-I | (SEQ ID NO:60) | PKA |
| R-R-R-R-K-G-S-F-R-R-K-A | (SEQ ID NO:61) | PKCα |
| R-K-L-K-R-K-G-S-F-R-R-K-A | (SEQ ID NO:62) | PKCβ I, II |
| R-R-R-R-K-G-S-F-K-K-F-A | (SEQ ID NO:63) | PKCγ |
| A-A-R-K-R-K-G-S-F-F-Y-G-G | (SEQ ID NO:64) | PKCδ |
| Y-Y-X-K-R-K-M-S-F-F-E-F-D | (SEQ ID NO:65) | PKCε |
| A-R-L-R-R-R-S-F-R-R-X-R | (SEQ ID NO:66) | PKCη |
| R-R-F-K-R-Q-G-S-F-F-Y-F-F | (SEQ ID NO:67) | PKCζ |
| A-A-L-V-R-Q-M-S-V-A-F-F-F | (SEQ ID NO:68) | PKCμ |
| K-R-Q-Q-S-F-D-L-F | (SEQ ID NO:69) | CaM KII |
| F-R-M-M-S-F-F-L-F | (SEQ ID NO:70) | Phosphorylase kinase |
| R-R-F-G-S-L-R-R-F | (SEQ ID NO:71) | SLK1 |
| R-R-R-H-S-R-R-R-R | (SEQ ID NO:72) | SRPK2 |
| R-K-R-X-R-T-Y-S-F-G | (SEQ ID NO:73) | AKT/PKB |

In one embodiment, a profiling biosensor array is generated comprising target activatable nucleic acid sensor molecules which are activatable by components of a cell cycle pathway. In this embodiment, a cell cycle biosensor is generated comprising nucleic acid nucleic acid sensor 10 molecules activatable by at least two members selected from the group consisting of: MPS, Cytostatic factor (CSF) (including Mos), cdk4, cyclins D1–3, cdk6, cdk2, cyclin E, p53, p21, p16, Rb, p27, E2F, cyclin A, cyclin B, cdkl, cyclin B1–3, Cdc2, SPA-1, and other biomolecules involved in cell cycle regulation.

In another embodiment, the cell cycle biosensor array generated is used to evaluate samples from patients suspected of having a disorder affecting cell proliferation (e.g., cancer) and a signature target molecule profile is determined which is diagnostic of this disorder. Changes in the signature target molecule profile upon treatment with a candidate compound are subsequently monitored by any or all of in vitro, ex vivo, and in vivo methods, as described above, to identify and/or validate lead compounds for use in cancer therapies.

In further embodiments, a cell cycle biosensor is provided comprising a plurality of locations, each location comprising a set of nucleic acid sensor molecules activatable by target molecules which identify a different portion of the cell cycle.

Thus, in one embodiment, a cell cycle biosensor comprises at a first location, nucleic acid sensor molecules activatable by G0 specific target molecules (e.g., MPS, Cytostatic factor (CSF) (including Mos)), at a second location, nucleic acid sensor molecules activatable by G1 specific target molecules (cdk4, cyclin D1–3, cdk6, cdk2, cyclin E, p53, p21, p16, Rb, p27, E2F), at a third location, nucleic ac molecules which are activatable by S specific target molecules (e.g., cyclin A/CDK2, cyclin B/Cdc2, SPA-), at a fourth location, nucleic acid sensor molecules activatable by G2 specific target molecules-(e.g., cdk1, cyclin B 1–3, cyclin A), and at a fifth location, nucleic acid sensor molecules activatable by M specific target molecules (e.g., Cdc2, cyclin B). In this way the effects of diseases and/or drugs on specific phases of the cell cycle can be assessed.

Similarly, pathway specific biosensors can be generated for any of apoptotic pathways, blood clotting pathways, calcium regulation pathways, cholesterol metabolism pathways, the JAK/STATS signaling pathway, MAP kinase signaling pathways, p53 pathway, PI 3 kinase pathway, ras activation pathways, SIP signaling pathways, SHC signaling pathways, TGF-13 signaling pathways, T-cell receptor complex, and MHC-I pathways, using exemplary target molecules listed above, or other target molecule components of the respective pathways.

It should be apparent to those of ordinary skill in the art, that many other pathways exist whose components have been characterized and that target molecules within these pathways are also encompassed within the scope of the present invention (e.g., including, but not limited to, phosphatase pathways, transcription factor pathways, hormone dependent pathways, as well as intermediary metabolism pathways, and developmental pathways). Further, additional pathways can be identified using the nucleic acid based biosensor profiling techniques discussed above (e.g., identifying pathway molecules involved in the functioning of a wild type or diseased organ system, such as the cardiovascular system, central nervous system, digestive system, reproductive system, pulmonary system, skin system, and the like), and these also are encompassed within the scope of the invention.

Alternatively, or additionally, pathway specific molecules can be identified by other techniques known in the art (see, e.g., U.S. Pat. No. 6,087,4717, U.S. Pat. No. 6,054,558, U.S. Pat. No. 6,048,709, and U.S. Pat. No. 6,046, 165) and used to engineer additional pathway target activatable nucleic acid sensor molecules. Because there is a finite number of pathway target molecules in each pathway (constrained by the absolute number of gene products which have been identified) (see, e.g., Drews, Science 287: 1960–1964), it is feasible using the target activatable nucleic acid sensor molecules to generate biosensors representative of an entire pathway.

In further embodiments, sets of profiling biosensors are used to monitor the expression/activity of target molecules representing complex systems. Thus, for example, the effect of target molecules on the cardiovascular system and pulmonary system can be monitored simultaneously. In one embodiment, an array representative of a plurality of systems in the human body is used in methods to assess the effects of drug compounds on multiple systems in the body.

iii. Using Pathway Nucleic Acid Sensor Molecules in Drug Optimization

Figure 8:
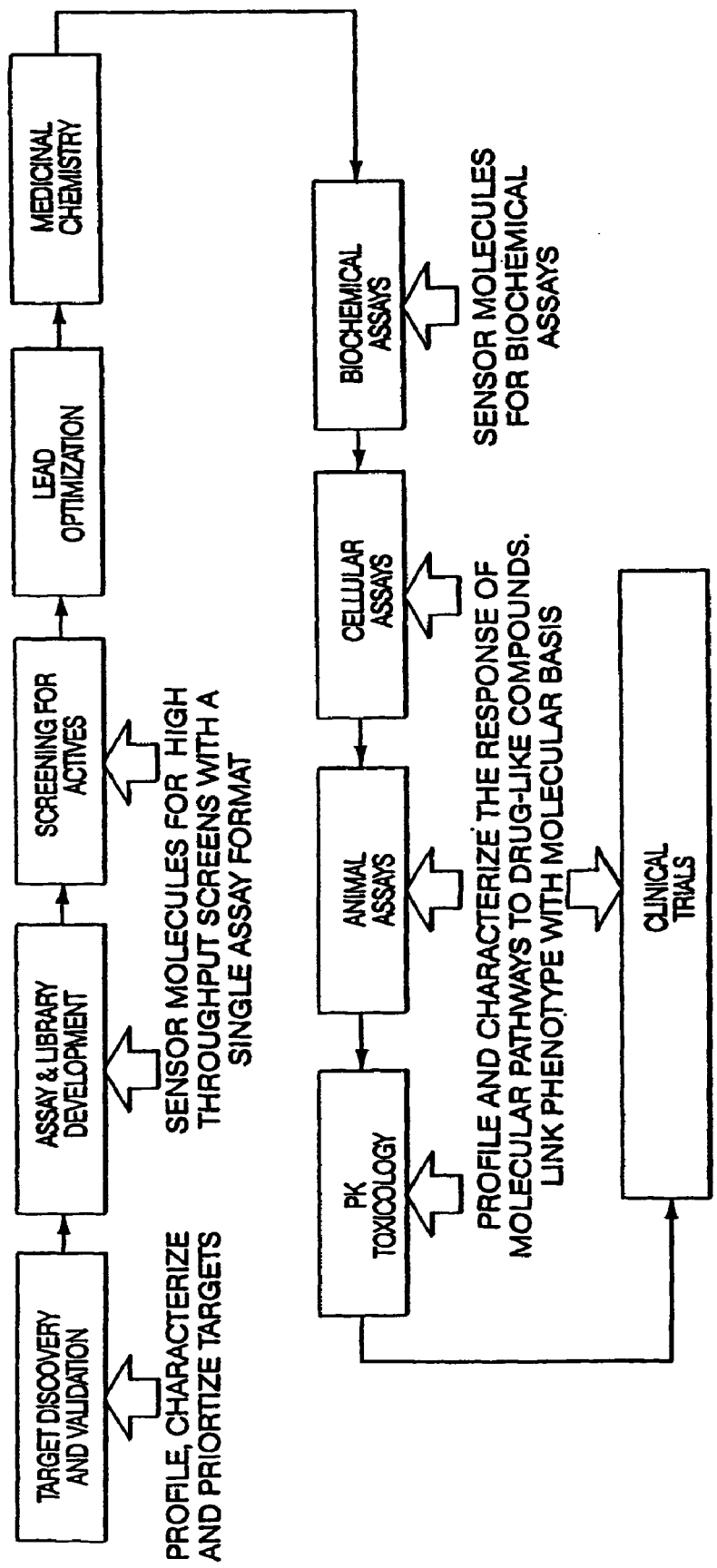
FIG. 8 is a flow chart showing steps in a drug optimization method according to one embodiment, in which nucleic acid sensor molecules are used at each step in the method.

The profiling nucleic acid sensor molecules according to the invention can be used in every step of a drug optimization process, as shown in FIG. 8, and are suitable reagents for use in conventional high throughput screening systems making them extremely adaptable for use alone, or in conjunction with, other drug development assays.

Step 1. Drug Target Discovery or Drug Target Validation

As discussed above, profiling nucleic acid sensor molecules can be used to identify signature target molecules which are correlatable to particular traits, such as disease. Signature target molecules are drug targets whose levels, structure, and/or activity can be used to evaluate the efficacy of compounds. A large number of signature drug targets, both characterized and uncharacterized, can be identified simultaneously using a single profiling biosensor according to one embodiment. In one embodiment, a profiling biosensor recognizes and is independently activated by about 1–5,000 molecules. In another embodiment, a profiling biosensor recognizes and is independently activated by about 500–10,000 molecules, and in another embodiment, by greater than 10,000 molecules.

Step 2. High Throughput Screening

In one embodiment, the drug targets identified in step 1 are evaluated in high throughput screening assays, using either solution-based biosensors or substrate-based biosensors, to characterize the biological activity of a drug target. For example, in one embodiment, nucleic acid sensor molecules are used to assess levels of substrate, product and intermediates produced by an enzyme in a wild type vs. a disease state, to identify other components of a pathway that would be affected by a drug acting on that target (i.e., secondary drug targets). In another embodiment, the levels, structure, and/or activity of all of the modified forms of a drug target, or the active and inactive forms of a drug target (e.g., a receptor) is determined in a wild type vs. a disease state, to further develop a diagnostic profile of a diagnostic pathway target molecule and to evaluate changes of that profile in the presence of a drug.

In a further embodiment, the same type of profiling biosensor used to identify a diagnostic profile is contacted with samples from patients exposed to a compound. A compound-treated sample which produces substantially similar levels, structure, and/or activity of target and secondary drug targets in a sample from a healthy patient is used to identify a compound as a candidate drug. Because this testing is done in a high throughput format, a single dose of a candidate drug is evaluated in any given test.

Step 3. In vitro Biochemical Assays

In one embodiment, the nucleic acid sensor molecules used in step 2, are tested in an in vitro biochemical assay to determine compound potency. In this embodiment, a preliminary dosing effect is determined to identify the IC50 of candidate drug. In one embodiment, multiple biosensors of the type used in step 2 are contacted with samples from patients exposed to different doses of the candidate drugs identified in step 2, to identify candidate drugs with the highest potency (e.g., requiring the least amount of drug to generate a wild type profile or an effective drug profile.

Step 4. Cellular Assays

In one embodiment, nucleic acid sensor molecules are used in cellular assays where the effect of adding a compound on cell physiology is known and the researcher wants to determine that the drug is in fact acting through the drug target selected in steps 1–3. Here a candidate drug is added to a physiological system (e.g., cell(s), tissue(s), organ(s), or a patient). Cells from the physiological system are lysed and the substrate or product of an enzyme reaction is monitored using the nucleic acid sensor molecule either in an ELISA format or other solid support-based format (e.g., a profiling array) or a solution phase format. In another embodiment, cell lysates are contacted with a profiling biosensor specific for a target or pathway of interest to determine the profile of target molecules in the lysed sample. The profile is then compared to the wild type profile and the disease profile to determine if the drug is operating in vivo to restore a cell to its wild type state. Thus, the physiological effect of a candidate drug on a physiological system is correlated with the in vivo mechanism of action of the candidate drug.

In a preferred embodiment, pathway profiling arrays comprised of nucleic acid sensor molecules affixed to a solid support are used in cellular assays to determine the selectivity of a compound for one target in a pathway relative to other candidate targets in a signal transduction pathway(s) or in another biochemical pathway(s). This data can be used to validate a drug lead or drug target.

In one embodiment, nucleic acid sensor molecules are expressed in vivo or intracellularly using plasmids, viruses or other extra-chromosomal DNA vectors and the cellular nucleic acid sensor molecules are extracted and used to determine the activity of a drug or drug target. These cellular assays can also determine the selectivity of a compound for one target in a pathway relative to other candidate targets in a signal transduction pathway(s) or in another biochemical pathway(s). This data can be used to validate a drug lead or drug target.

In vivo Detection:

With (Amersham) SPA scintillant beads coupled to nucleic acid sensor molecules, one can look at cellular processes in situ in real time, by culturing cells directly onto a microtiter plate and allowing uptake of scintillant beads and radioisotope by cells. One can then monitor biosynthesis, proliferation, drug uptake, cell motility, etc. via luminescence generated by beads in the presence of selected target.

Step 5. Medicinal Chemistry

In one embodiment, drug-lead potency, specificity, and/or in vivo activity is optimized by an iterative repetition of any or all of steps 1–4. In one embodiment, steps 1–4 are repeated until the desired potency, selectivity and in vivo mechanism of action of a candidate drug is obtained. Potency can range from picomolar affinity to nanomolar affinity as measured by in vitro IC50 values. The desired selectivity of a drug candidate for its target can vary from 2 to a million-fold, and can be obtained by measuring the potency (IC50) of a drug lead toward the drug target, versus the drug's potency (IC50) values against other pertinent targets (target pertinence is determined by the requirements of the biological system under investigation). A drug lead is deemed optimal when the parameters of potency, selectivity and cellular action are optimized with respect to each other.

In another embodiment, known drug leads from Steps 1–4 are found to be specific for targets that were not known to the researcher in step 2. This is also termed target discovery and validation, and occurs when steps 1–4 are repeated in an iterative fashion of any or all steps and the drug target is identified by the profiling array to, in fact, exist in an alternative signal transduction pathway, or to be a novel protein or enzyme in the pathway originally under investigation. Thus, MPP arrays can identify the site of action of a drug lead, and can determine the relative selectivity of a drug for one drug target of a drug target pathway.

Step 6. Animal Model Assays

In this embodiment, target cells (e.g., tissue(s)) are removed from an animal model of the disease being targeted for treatment and lysed for testing. The lysate is contacted with nucleic acid sensor molecules either in a solid phase assay, a solution phase assay, or in a pathway profiling biosensor array format to assess the in vivo biological activity of a candidate drug identified by any of the previous steps or by some other method, on a target or pathway. Thus, in this embodiment, the physiological effect of a drug on a diseased or normal tissue is correlated with the in vivo mechanism of action of the drug.

Step 7. Optimization of the Drug Lead

In one embodiment, drug-lead potency, specificity, and/or in vivo activity are optimized by an iterative repetition of any or all of steps 1–6. In one embodiment, steps 1–5 are repeated until the desired potency, selectivity and in vivo mechanism of action of a candidate drug are obtained.

Step 8. Pharmacokinetic Studies

In one embodiment, the nucleic acid sensor molecules are used in pharmaco-kinetic studies, where the effect of a drug on the physiology of a cell, group of cells, tissue(s), organ(s), or animal model is assessed by obtaining blood, plasma, tissue, or a cell, and contacting this material with nucleic acid sensor molecules either in a solid phase (e.g., ELISA), solution or array format to assess the in vivo pharmacological or toxicological activity of a compound. In this embodiment, the nucleic acid sensor molecules used are developed against the candidate drug itself, its metabolic products, and/or the metabolic products of proteins and small ligands involved in a xenobiotic or toxicological response to drug treatment.

In one embodiment, nucleic acid sensor molecules are employed to follow the fate of a drug or its metabolic by-products. In this embodiment, nucleic acid sensor molecules are generated to the drug and its metabolites. The drug is administered to the test animal either subcutaneously, intraperitoneally or by gavage. Subsequent to administration, the blood plasma or disease tissue is removed and its contents are screened for the remaining drug by Liquid chromatography (LC) or LC-mass spectrometry. Drug exposure is then determined as a function of time, dose and method of administration and is reported in values of half-life, bioavailability, AUC and Cmax. Metabolic products of a drug lead can be similarly followed.

Nucleic acid sensor molecules generated against enzymes or proteins known to those skilled in the art to be involved in drug metabolism (P450 enzymes, multi-drug transporter) can be used to follow the effect of a drug on xenobiotic or toxicological response to drug treatment.

Step 9. Optimization of the Drug Lead

In one embodiment, drug-lead potency, specificity, and/or in vivo activity, and pharmacokinetic, or toxological properties are optimized by an iterative repetition repetition of any or all of steps 1–7. In one embodiment, steps 1–7 are repeated until the desired potency, selectivity and in vivo activity and pharmaco-kinetic, or toxicological properties of a candidate drug are obtained.

Step 10. Clinical Trials

In one embodiment, nucleic acid sensor molecules are used in clinical trials to determine the fate of a drug in human or animal models, or used to follow the effect of drug treatment on a target or molecular pathway of choice, as described above. In one embodiment, the nucleic acid sensor molecules, in a solid phase assay (e.g., ELISA format), a solution phase assay, or in a pathway profiling biosensor array format, are used to assess the in vivo biological activity of a drug being tested using lysed cell samples as described above.

In another embodiment, the appropriate profiling biosensor is used in vivo, to monitor the effects of the compound on the patient, for example, by providing the biosensor in communication with a fiber optic probe inserted into the patient, or ex vivo, monitoring optical signals in a cell using a microscope based detection system. In another embodiment, an in vivo assay is done by introducing a nucleic acid sensor molecule which retains its catalytic activity into a physiological system (e.g., by injection at a target site in the body, through liposome carriers, and other means of administration routinely used in the art), obtaining cells from the physiological system and detecting the effect of the compound on the catalytic activity of the nucleic acid sensor molecule (e.g., by evaluating the sequence of the nucleic acid sensor molecule) as a means of determining the level, structure, or activity of a drug target, and relating the level, structure, or activity or the target molecules to the efficacy of the drug.

Step 11. Optimization of the Drug Lead

In one embodiment, any or all of steps 1–10 are repeated to further optimize the properties of the candidate drug.

Step 12. Diagnostic Applications

In one embodiment, individuals who would be suitable for treatment with the candidate drugs identified steps 1–11, are identified using nucleic acid sensor molecules in the diagnostic assays discussed previously.

Step 13. Chemical Genomics

In one embodiment, nucleic acid sensor molecules are used in chemical genomic assays in which a drug or plurality of drug leads, with known or unknown physiological effects, and with unknown targets, are contacted with a physiological system and the site of action of the drug or plurality of drugs is determined using a plurality of the profiling biosensors described previously. Drug optimization then occurs as in steps 1–11.

5. Use of a Profilinz Biosensor in Target Molecule Separation

In addition to, or instead of, their use in detection methods, and drug discovery methods, the nucleic acid sensor molecules according to the invention can also be used to retrieve the target molecules which they specifically recognize. Additional embodiments exploiting the recognition capacity of the biosensors disclosed are contemplated and encompassed within the scope.

6. Reagents for Generating and Using Nucleic Acid Sensor Molecules

In one embodiment, reagents are provided for generating and using nucleic acid sensor molecules. In one embodiment, a kit is provided comprising standardized reagents for making and/or using the nucleic acid sensor molecules according to the invention. In one embodiment, the kit comprises at least a first optical nucleic acid sensor molecule whose optical properties change upon recognition of a target molecule. In another embodiment, the kit additionally comprises any of: a control target molecule, a second nucleic acid sensor molecule which recognizess a different target molecule, suitable buffers, printed instructions, and combinations thereof. In a further embodiment, a nucleic acid sensor molecule is provided with reagents for attaching a label and/or quencher or with reagents for attaching charge transfer molecules to the nucleic acid sensor molecule, which can sensitize the optical properties of the nucleic acid molecule to the presence of a target molecule.

In another embodiment, a composition is provided comprising a target molecule and a nucleic acid sensor molecule. The composition provides a reference against which to compare modified nucleic acid sensor molecules which recognizes to the same target, in order to select those with preferred cataytic activity or conformational change in the presence of the target. In a further embodiment, sets of complexes are provided. In still a further embodiment, a set of pathway target molecules and nucleic acid sensor molecules are provided. In another embodiment, a set of profiling target molecules and nucleic acid sensor molecules are provided. In still a further embodiment, solid supports are provided for isolation of target molecules from nucleic acid sensor molecules.

In yet another embodiment, a computer program product is provided comprising stored data relating to optical signals generated by profiling and or pathway target molecules. In another embodiment, a means to compare this data to other optical signals is provided. In a further embodiment, the memory comprises data relating to patient information or chemical structure information relating to either target molecules or nucleic acid sensor molecules.

The nucleic acid sensor molecules and biosensors according to the invention are amenable for use with high throughput screening systems and methods and the use of the nucleic acid sensor molecules and biosensors in these systems and methods is encompassed within the scope. In one embodiment, the system is a robotic workstation, comprising, at least one of an: arrayer, microplate or microarray feeders, stackers, washers, and dispensers, an optical system, a carousel, a conveyer for conveying microplates or microarrays from one part of the system to another (in a vertical or horizontal direction), a shaker system or other mixing system, a temperature control system, a synthesizer, a solid phase extraction system, and sample concentrators. Components of the robotic workstation can be part of a single integrated. system or can be provided separately for use at any stage of the drug optimization process according to the invention. In a further embodiment, the system comprises a processor connectable to the network which comprises or can access applications comprising stored data relating to profiling information obtained using nucleic acid sensor molecules according to the invention, and/or statistical applications, applications for performing structure/activity analysis of target molecules and nucleic acid sensor molecules, applications for performing nucleic acid sequence alignment and simultaneous structure superposition of proteins (e.g., MOE-Align'TM), applications for predicting binding conformations of molecules to receptor structures, and applications for controlling the processing functions of the robotic workstations.

The invention is further illustrated in the following non-limiting examples.

EXAMPLE

Example 1

General Procedures

A. Generation nucleic acid sensor molecules from pools of ribozymes comprised of randomized linker and target modulation domains.

Direct selection of nucleic acid sensor molecules. Target modulated nucleic acid sensor molecules are isolated by in vitro selection. Pool of partially randomized ribozymes with $10^{15}$–$10^{17}$ unique sequences serve as the starting point for in vitro selection. As with the engineering approach, both the L1 ligase and hammerhead ribozyme are used as platforms for the selection of allosterically-controlled molecules. Selections are designed to yield ribozymes that specifically respond to any target. Nucleic acid sensor molecules with cross-specificity (i.e. modulated by alternate target molecules, or by alternate ligand-bound states, or by alternate post-translationally modified forms of protein or peptides) are selected against by including the undesired form of the target in an initial negative selection step. The specific sequence of operations comprising the selection experiment is outlined in FIG. 1A and 1B for ligase and hammerhead-based selections, respectively 1. Pool preparation. The starting library of DNA sequences is generated by automated chemical synthesis on a DNA synthesizer. This library of sequences is transcribed in vitro into RNA using T7 RNA polymerase, purified, and captured onto beads using an oligonucleotide tag complementary to the 3'-end.
2. Negative selection incubation. In the absence of the desired modulator (target), the RNA library are incubated together with the undesired form of the modulator and an arbitrary sequence oligonucleotide substrate (substrate 1). (During this incubation, non-modulated ribozymes undergo ligation (FIG. 1A) or cleavage (FIG. 1B).
3. Positive selection incubation. The undesired form of the modulator and oligonucleotide substrate 1 are removed by washing. The immobilized RNA pool is then incubated under identical conditions but now in the presence of the intended modulator and a second biotinylated oligonucleotide substrate (substrate 2), in the case of ligase selections (FIG. 1A).

4. Partitioning on the basis of activity (coupled to amplification). Ligases active only in the presence of the desired modulator are isolated using streptavidin capture and selective PCR amplification (relying on sequence differences between substrates 1 and 2 to distinguish allosteric and non-allosteric activities). Hammerheads active only in presence of the desired modulator are isolated by gel electrophoresis.

5. Purification. PCR amplified DNA are purified and transcribed to yield an enriched pool for subsequent reselection.

6. Iteratively repeat. Rounds of selection and amplification (steps 2–5) are repeated until functional members sufficiently dominate the resultant library.

Once NASMs have been selected as described above, they are characterized as follows:

Nucleic acid sensor molecules which are derived from in vitro selection are tested as target modulated biosensors. The pool of NASMs is cloned into various plasmids that contain a T7 promoter transformed into E. coli. Individual NASM encoded DNA clones are isolated, linearized and the NASM is transcribed in vitro to generate NASM RNA. The NASM RNAs are then tested in target modulation assays which determine the rate or extent of ribozyme modulation. For hammerhead NASMs, the extent of target dependent and independent reaction is determined by quantifying the extent of endonucleolytic cleavage of an oligonucleotide substrate. The extent of reaction can be followed by electrophoresing the reaction products on a denaturing PAGE gel, and subsequently analyzed by standard radiometric methods. For Ligase NASMs, the extent of target dependent and independent reaction is determined by quantifying the extent of ligation of an oligonucleotide substrate, resulting in an increase in NASM molecular weight, as determined in denaturing PAGE gel electrophoresis.

Individual NASM clones which display high target dependent switch factor values, or high $k_{act}$ rate values are subsequently chosen for further modification and evaluation.

Hammerhead derived NASM clones are then further modified to render (the NASM sequences) them suitable for the optical detection applications that are described in detail below. In brief, these NASMs are used as fluorescent biosensors affixed to solid supports, as fluorescent biosensors in homogeneous FRET-based assays, and as biosensors in SPR applications.

Ligase derived NASM clones are further modified to render them suitable for a number of detection platforms and applications; including, but not limited to, the PCR and nucleotide amplification detection methods; fluorescent-based biosensors detectable in solution and chip formats; and as in vivo, intracellular detection biosensors.

The various detection applications of hammerhead ligase and intron-based NASMs are described in detail below.

B. Preparation of an array of immobilized effector oligonucleotides or NASMs

The following protocol describes a method for preparing an array of immobilized effector oligonucleotides with terminal amine groups attached to a solid substrate derivatized with aldehyde groups. The resulting array can then be used to spatially address (i.e., the sequence of nucleotides for each effector oligonucleotide can be synthesized as a cognate to the effector oligonucleotide binding domain of a nucleic acid sensor molecule specific for a particular target molecule) and immobilize the nucleic acid sensor molecules prior to their use in a solid-phase assay (see, e.g., Zammatteo et al., 2000):

Protocol for Attachment of Effector Oligonucleotides to Aldehyde Derivatized Substrate (www.arrayit.com):

1. Print discrete spots of solution containing effector oligonucleotides with amine-reactive terminal groups or linkers with terminal amine groups using microarraying pins, pipette, etc.
2. Allow spotted substrate to dry for 12 hrs. at room temperature and <30% relative humidity.
3. Rinse substrate 2 times in dH$_2$O with 0.2% SDS for 2 min. with vigorous agitation at room temperature.
4. Rinse substrate 1 time in dH$_2$O for 2 min. with vigorous agitation at room temperature.
5. Transfer substrate to boiling (100° C.) dH$_{2O\ for}$ 3 min. to denature DNA.
6. Dry substrate by centrifugation at 500×g for 1 min.
7. Treat substrate in 0.1 M NaBH$_4$ in phosphate buffered saline (PBS, pH 7) for 5 min. with mild agitation at room temperature.
8. Rinse substrate 2 times in dH$_2$O with 0.2% SDS for 1 min. with vigorous agitation at room temperature.
9. Rinse substrate 1 time in dH$_2$0 for 2 min. with vigorous agitation at room temperature.
10. Transfer substrate to boiling (100 degrees C) dH$_2$0 for 10 sec. to denature DNA.
11. Dry substrate by centrifugation at 500×g for 1 min.
12. Store effector oligonucleotide-bound substrate at 4° C prior to hybridization.

The nucleic acid sensor molecules can be, e.g., those which possess either ligating or cleaving activity in the presence of a target molecule. (See, e.g., FIGS. 2A and B for the ligater, FIG. 5 for the cleaver).

In the case where it is desirable to immobilize an array of NASMs by direct attachment to a solid surface, the nucleic acid sensor molecules are bound to a solid substrate directly via their 3' termini. The attachment is accomplished by oxidation (using, e.g., Na periodate) of the 3' vicinal diol of the nucleic acid sensor molecule to an aldehyde group. This aldehyde group will react with a hydrazide group to form a hydrazone bond. The hydrazone bond is quite stable to hydrolysis, etc., but can be further reduced (for example, by treatment with NaBH$_4$ or NaCNBH$_3$). The use of adipic acid dihydrazide (ADH, a bifunctional linker) to derivatize an aldehyde surface results in a hydrazide-derivatized surface which provides a linker of approximately 10 atoms between the substrate surface and point of biomolecular attachment (see Ruhn et al., 1994; O'Shaughnessy, 1990; Roberston et al., 1972, Schluep et al., 1999; Chan et al., 1998). Preparation of a hydrazide-terminated surface via ADH treatment can be accomplished by treating an aldehyde-derivatized substrate according to the following protocol:

Protocol for ADH treatment of aldehyde substrate:

1. To 50 mL of 0.1 M phosphate buffer (pH 5) add 100-fold excess of adipic acid dihydrazide (ADH) relative to concentration of aldehyde groups on substrate surface.
2. Place substrate in a 50 mL tube containing the ADH in phosphate buffer and shake mixture for 2 hrs.
3. Remove the substrate and wash 4 times with 0.1 M phosphate buffer (pH 7).

4. Reduce free aldehyde groups on substrate surface by placing substrate in a 50 mL tube containing a 25-fold excess of NaBH$_4$ or NaCNBH$_3$ in 0.1 M phosphate buffer.
5. Shake the mixture for 90 min.
6. Wash 4 times with 0.1 M phosphate buffer (pH 7).
7. Store ADH-treated substrates in 0.1 M phosphate buffer (pH 7) at 4° C.

Preparation of the nucleic acid molecules for specific coupling to the ADH-terminated surface via their 3' termini can be accomplished according to the following protocol (see, Proudnikov et al., 1996; Wu et al., 1996):

Protocol for Periodate oxidation of RNA:
1. Dissolve up to 20 micrograms of RNA in 5 microliters of H20 at 20° C.
2. Add 1 ML of 0.1 M NaIO$_4$ (~20-fold excess relative to RNA).
3. Incubate for 30 min. in a light-tight tube or enclosure.
4. Add 1 ML of 0.2 M Na sulphite (~2-fold excess relative to NaIO$_4$) to stop reaction.
5. Incubate for 30 min. at room temperature.
6. Ethanol precipitate or use spin-separation column to recover oxidized RNA.

Example 2

Selection for a Nucleic Acid Sensor Molecule Selective for the Estrogen Receptor LBD A nucleic acid sensor molecule which is modulated by the estrogen receptor (ER) ligand binding domain (LBD) is obtained by in vitro selection methods to identify candidate nucleic acid sensor molecules that are modulated by an estrogen receptor LBD.

The full length gene for the estrogen receptor is known. One source of the full-length estrogen receptor clone is Acc. No. M12674 (see also Greene et al., Science 231:1150–54, 1986). The clone includes a 2092 nucleotide mRNA with the sequence presented in Table 3 below:

TABLE 3

```
   1 gaattccaaa attgtgatgt ttcttgtatt tttgatgaag gagaaatact gtaatgatca   (SEQ ID NO:9)
  61 ctgtttacac tatgtacact ttaggccagc cctttgtagc gttatacaaa ctgaaagcac
 121 accggaccog caggctcccg gggcagggcc ggggccagag ctcgcgtgtc ggcgggacat
 181 gcgctgcgtc gcctctaacc tcgggctgtg ctcttttttcc aggtggcccg ccggtttctg
 241 agccttctgc cctgcgggga cacggtctgc accctgcccg cggccacgga ccatgaccat
 301 gaccctccac accaaagcat ctgggatggc cctactgcat cagatccaag ggaacgagct
 361 ggagcccctg aaccgtccgc agctcaagat cccctggag cggccctgg gcgaggtgta
 421 cctggacagc agcaagcccg ccgtgtacaa ctaccccgag ggcgccgcct acgagttcaa
 481 cgccgcggcc gccgccaacg cgcaggtcta cggtcagacc ggcctcccct acggccccgg
 541 gtctgagqct gcggcgttcg gctccaacgg cctgggggt ttcccccac tcaacagcgt
 601 gtctccgagc ccgctgatgc tactgcaccc gccgccgcag ctgtcgcctt tcctgcagcc
 661 ccacggccag caggtgccct actacctgga gaacgagccc agcggctaca cggtgcgcga
 721 ggccggcccg ccggcattct acaggccaaa ttcagataat cgacgccagg gtggcagaga
 781 aagattggcc agtaccaatg acaagggaag tatggctatg gaatctgcca aggagactgg
 841 ctactgtgca gtgtgcaatg actatgcttc aggctaccat tatggagtct ggtcctgtga
 901 gggctgcaag gccttcttca agagaagtat tcaaggacat aacgactata tgtgtccagc
 961 caccaaccag tgcaccattg ataaaaacag gaggaagagc tgccaggcct gccggctccg
1021 caaatgctac gaagtgggaa tgatgaaagg tgggatacga aaagaccgaa gaggagggag
1081 aatgttgaaa cacaagcgcc agagagatga tggggagggc agggtgaag tggggtctgc
1141 tggagacatg agagctgcca acctttggcc aagcccgctc atgatcaaac gctctaagaa
1201 gaacagcctg gccttgtccc tgacggccga ccagatggtc agtgccttgt tggatgctga
1261 gcccccata ctctattccg agtatgatcc taccagaccc ttcagtgaag cttcgatgat
1321 gggcttactg accaacctgg cagacaggga gctggttcac atgatcaact gggcgaagag
1381 ggtgccaggc tttgtggatt tgaccctcca tgatcaggtc caccttctag aatgtgcctg
1441 gctagagatc ctgatgattg gtctcgtctg gcgctccatg gagaacceag tgaagctact
1501 gttttgctcct aacttgctct tggacaggaa ccagggaaaa tgtgtagagg gcatggtgga
```

TABLE 3-continued

```
1561  gatcttcgac atgctgctgg ctacatcatc tcggttccgc atgatgaatc tgcagggaga 1621  ggagtttgtg tgcctcaaat ctattatttt gcttaattct ggagtgtaca catttctgtc 1681  cagcaccctg aagtctctgg aagagaagga ccatatccac cgagtcctgg acaagatcac 1741  agacactttg atccacctga tggccaaggc aggcctgacc ctgcagcagc agcaccagcg 1801  gctggcccag ctcctcctca tcctctccca catcaggcac atgagtaaca aaggcatgga 1861  gcatctgtac agcatgaagt gcaagaacgt ggtgcccctc tatgacctgc tgctggagat 1921  gctggacgcc caccgcctac atgcgcccac tagccgtgga ggggcatccg tggagggagac 1981  ggaccaaagc cacttggcca ctgcgggctc tacttcatcg cattccttgc aaaagtatta 2041  catcacgggg gaggcagagg gtttccctgc cacagtctga gagctccctg ga
```

The polynucleotide encodes a polypeptide with the amino acid sequence presented in Table 4 below:

TABLE 4

MTMTLHTKASGMALLHQIQGNELEPLNRPQLKIPLERPLEGEVYLDSSKPAVYNYPEGAAYEFNAAAAANAQVYGQTG  (SEQ ID NO:10)

LPYGPSGSEAAAFGSNGLGGFPPLNSVSPSPLMLLHPPPQLSPFLQPHGQQVPYYLENEPSGYTVREAGPPAFYRPNS

DNRRQGGRERLASTNDKGSMAMESAKETRYCAVDNDYASGYHYGVWSCEGCKAFFKRSIQGHNDYMCPATNQCTIDK

NRRKSCQACRLRKCYEVGMMKGGIRKDRRGGRMLKHKRQRDDGEGRGEVGSAGMRAANLWPSPLMIKRSKKNSLAL

SLTADQMVSALLDAEPPILYSEYDPTRPFSEASMMGLLTNLADRELVHMINWAKRVPGFVDLTLHDQVHLLECAWLE

ILMIGLVWRSMEHPVKLLFAPNLLLDRNQGKCVEGMVEIFDMLLATSSRFRMMNLQGEEFVCLKSIILLNSGVYTFL

SSTLKSLEEKDHIHRVLDKITDTLIHLMAKAGLTLQQQHQRLAQLLLILSHIRHMSNKGMEHLYSMKCKNVVPLYDL

LLEMLDAHRLHAPTSRGGASVEETDQSHLATAGSTSSHSLQKYYITGEAEGFPATV

---

The gene encoding either full length ER or the ligand binding domain is cloned and expressed in BL21 (DE3)-pLysS *E. coli* cells [Shiau A K, Barstad D, Loria P M, Cheng L, Kushner P J, Agard D A, Greene G L. Cell. 1998 Dec. 23;95(7):927–37]. Human ER alpha LBD (residues 297–554) are purified from estradiol-sepharose column by published procedures [Shiau A K, Barstad D, Loria P M, Cheng L, Kushner P J, Agard D A, Greene G L. Cell. 1998 Dec. 23;95(7):927–37].

Selection of nucleic acid sensor molecules which are activated by ER-LBD not bound to ligand: A library of up to $10^{17}$ variants of in vitro synthesized (1 ,µM) nucleic acid sensor molecules is allowed to react with purified apo-ER-LBD at a final concentration of 1 uM. Selection of catalytic nucleic acid sensor molecules and optionally, generation of an optical NASM, is carried out by procedures outlined in prior examples and elsewhere herein.

Selection of Nucleic Acid Sensor Molecules which are Modulated by the ER-LBD-Estradiol Complex:

Stable complexes of ER-LBD and estradiol ligand are formed with from 1–10 equivalents of ligand. A library of up to $10^{17}$ variants of in vitro synthesized ribozymes is then allowed to react with purified ER-LBD-Estradiol at a final complex concentration of luM. Selection of allosterically activated ribozymes is carried out by procedures outlined the detailed description. Selection of nucleic acid sensor molecules which are modulated by the ER-LBD-Tamoxifen complex stable complexes of ER-LBD and tamoxifen ligand are formed with from 1–10 equivalents of ligand. A library of up to $10^{17}$ variants of in vitro synthesized ribozymes (1 µM containing a plurality of potential target modulation domains and linker domains coupled to the catalytic domain of the ribozyme, is then allowed to react with purified ER-LBD-Tamoxifen at a final complex concentration of 1uM. Selection of catalytic nucleic acid sensor molecules target modulated ribozymes (nucleic acid sensor molecules) is carried out by procedures outlined in prior examples.

Example 3

Selection for a Library of Nucleic Acid Sensor Molecules which Signal the Presence of all Known Nuclear Hormone Receptor LBDs:

A wide variety of nuclear hormone receptor ("NHR") ligand binding domains and their ligands, many of which are described in Table 5 below, are known for which a nucleic acid sensor molecule can be selected.

TABLE 5

| Symbol | Description | Ligand |
|---|---|---|
| AIB3 | nuclear receptor coactivator RAP250; peroxisome proliferator-activated receptor interacting protein; thyroid hormone receptor binding protein | thyroid hormone |
| AR | androgen receptor (dihydrotestosterone receptor; testicular feminization; spinal and bulbar muscular atrophy; Kennedy disease) | dihydroxytestosteron |
| C1D | nuclear DNA-binding protein | |
| ESR1 | estrogen receptor 1 | estrogen |
| ESR2 | estrogen receptor 2 (ER beta) | estrogen |
| ESRRA | estrogen-related receptor alpha | estrogen and TFIIB |
| ESRRB | estrogen-related receptor beta | estrogen and TFIIB |
| ESRRG | estrogen-related receptor gamma | estrogen and TFIIB |
| HNF4A | hepatocyte nuclear factor 4, alpha | |
| HNF4G | hepatocyte nuclear factor 4, gamma similar to retinoid X receptor, alpha (*H. sapiens*) similar to nuclear receptor subfamily 1, group D, member 1 (*H. sapiens*) | |
| NCOA1 | nuclear receptor coactivator 1 | Binds to steroid hormone receptors |
| NCOR1 | nuclear receptor co-repressor 1 | Thyroid hormone receptor without TH |
| NCOR2 | nuclear receptor co-repressor 2 | RXR without retinoic acid and THR without TH |
| NR0B1 | nuclear receptor subfamily 0, group B, member 1 | |
| NR0B2 | nuclear receptor subfamily 0, group B, member 2 | |
| NR1D1 | nuclear receptor subfamily 1, group D, member 1 | |
| NR1H2 | nuclear receptor subfamily 1, group H, member 2 | |
| NR1H3 | nuclear receptor subfamily 1, group H, member 3 | Interacts with RXR |
| NR1H4 | nuclear receptor subfamily 1, group H, member 4 | Bile acid, farnesol, or chenodoxycholic acid |
| NR1I2 | nuclear receptor subfamily 1, group I, member 2 | pregnane |
| NR1I3 | nuclear receptor subfamily 1, group I, member 3 | androstane S |
| NR2C1 | nuclear receptor subfamily 2, group C, member 1 | |
| NR2C2 | nuclear receptor subfamily 2, group C, member 2 | |
| NR2E1 | nuclear receptor subfamily 2, group E, member 1 | |
| NR2E3 | nuclear receptor subfamily 2, group E, member 3 | |
| NR2F1 | nuclear receptor subfamily 2, group F, member 1 | |
| NR2F2 | nuclear receptor subfamily 2, group F, member 2 | |
| NR2F6 | nuclear receptor subfamily 2, group F, member 6 | Thyroid hormone |
| NR3C1 | nuclear receptor subfamily 3, group C, member 1 | glutocorticoid receptor, cortisol, corticosterone |
| NR3C2 | nuclear receptor subfamily 3, group C, member 2 | Aldosterone |
| NR4A1 | nuclear receptor subfamily 4, group A, member 1 | |
| NR4A2 | nuclear receptor subfamily 4, group A, member 2 | |
| NR4A3 | nuclear receptor subfamily 4, group A, member 3 | |
| NR5A1 | nuclear receptor subfamily 5, group A, member 1 | |
| NR5A2 | nuclear receptor subfamily 5, group A, member 2 | |
| NR6A1 | nuclear receptor subfamily 6, group A, member 1 | |
| PAX8 | paired box gene 8 | |
| PGR | progesterone receptor | progesterone |
| PPARA | peroxisome proliferative activated receptor, alpha | nafenopin, clofibrate, WY14643 |
| PPARBP | PPAR binding protein | binds to PPAR gamma |
| PPARD | peroxisome proliferative activated receptor, delta | WY1463 |
| PPARG | peroxisome proliferative activated receptor, gamma | 9-HODE, 13-HODE |
| PTHR1 | parathyroid hormone receptor 1 | parathyroid hormone |
| RARA | retinoic acid receptor, alpha | retinoic acid |
| RARB | retinoic acid receptor, beta | retinoic acid |
| RARG | retinoic acid receptor, gamma | retinoic acid |
| RORA | RAR-related orphan receptor A | |
| RORB | RAR-related orphan receptor B | |
| RORC | RAR-related orphan receptor C | |
| RXRA | retinoid X receptor, alpha | 9-cis retonoic acid, complexes with activated VDR and THR |
| RXRB | retinoid X receptor, beta | 9-cis retonoic acid, complexes with activated VDR and THR |
| RXRG | retinoid X receptor, gamma | 9-cis retonoic acid, complexes with activated VDR and THR |
| SMAP | thyroid hormone receptor coactivating protein | activated THR |
| THRA | thyroid hormone receptor, alpha (avian erythroblastic leukemia viral (v-erb-a) oncogene homolog) | thyroid hormone |
| THRB | thyroid hormone receptor, beta (avian erythroblastic leukemia viral (v-erb-a) oncogene homolog 2) | thyroid hormone |

TABLE 5-continued

| Symbol | Description | Ligand |
|---|---|---|
| TNRC11 | trinucleotide repeat containing 11 (THR-associated protein, 230 kDa subunit) | activated THR |
| TRAP150 | thyroid hormone receptor-associated protein, 150 kDa subunit | activated THR |
| TRAP240 | thyroid hormone receptor-associated protein, 240 kDa subunit | activated THR |
| TRAP95 | thyroid hormone receptor-associated protein, 95-kD subunit | activated THR |
| TRIP13 | thyroid hormone receptor interactor 13 | inactive THR |
| VDR | vitamin D (1,25-dihydroxyvitamin D3) receptor | vitamin D |

N-terminally GST-tagged or N-/C-terminally His-tagged nuclear hormone receptor ligand binding domains, defined on the basis of structural homology are cloned and expressed in BL21 (DE3)-pLysS E. coli cells, or are cloned and expressed in standard baculovirus expression systems.

Human NHR LBDs (homologous to ER-alpha residues including the region aa 297–554) are purified from GSH-sepharose or nickel affinity columns by published procedures available from the manufacturers. LBDs are produced in a either a parallel or serial fashion and the purified proteins are stored in buffer containing 50 mM TrisHCl, 1 mM EDTA, 1 mM DTT and 50–250 NaCl/SCN salt, pH 7 to pH 8.5, 10% glycerol or other stabilizing agent. Protein sequence and MW is verified by electrospray LC-MS mass spectrometry.

1. Selection of nucleic acid sensor molecules which are modulated by NHR-LBD not bound to ligand: A library of up to $10^{17}$ variants of in vitro synthesized ribozymes (1 µM) containing a plurality of potential target modulation domains and linker domains coupled to the catalytic domain of the ribozyme, is allowed to react with purified apo-NHR-LBDs at a final concentration of 1 uM LBD. Selection of catalytic nucleic acid sensor molecules is carried out by procedures outlined in the Detailed Description. Selections are carried out in parallel fashion. Selections can also be carried out in mixed pools of anywhere from 5–10 NHR-LBDs. In the final rounds of nucleic acid sensor molecule selection, the RNA pools may separated into aliquots which may then be used to carry out in vitro selection against single NHR-LBD proteins to yield unique nucleic acid sensor molecules selective for multiple NHR-LBDs.

2. Selection of nucleic acid sensor molecules which are activated by ligand bound forms of NHR-LBDs.

Stable complexes of each NHR-LBD are formed with from 1 –10 equivalents of ligand. A library of up to $10^{17}$ variants of in vitro synthesized ribozymes (1 µM) containing a plurality of potential target modulation domainsland linker domains coupled to the catalytic domain of the ribozyme is then allowed to react with purified NHR-LBD-Ligand complexes at a final complex concentration of 1uM. Selection of catalytic nucleic acid sensor molecules is carried out by procedures outlined in the Detailed Description and Example 1 below. Selections are carried out in parallel fashion. Selections can also be carried out in mixed pools of anywhere from 5–10 NHR-LBD-Ligand complexes. In the final rounds of nucleic acid sensor molecule selection, the RNA pools may separated into aliquots which may then be used to carry out in vitro selection against single NHR-LBD-Ligand complexes to yield unique nucleic acid sensor molecules selective for all NHR-LBDs, bound to their ligands.

Thus, the invention provides an in vitro selection protocol against purified LBDs, bound to their ligands or not, for each known NHR. In vitro selections can be carried out with less than 1 mg of the purified forms of the LBDs. In addition the selection of nucleic acid sensor molecules can be done in vitro with mixed pools of LBD and subsequently deconvoluted after selection is complete. Alternatively, the final selection can be carried out with fractionally purified extracts containing a slight excess of recombinant LBD. In one embodiment the LBD is expressed in E. coli, or insect cell lines or mammalian cell lines. In another embodiment, the selection is carried out in cell free lysates in which the LBD is expressed in an in vitro transcription-translation procedure such as is described in the literature or can be purchased using common reagents from Roche or Promega. In another embodiment, the fractionated or purified LBDs are combined with known ligands, (as described above) agonist, antagonists or partial agonist/antagonists to form stable complexes, and these complexes are then used for in vitro selection of nucleic acid sensor molecules. Upon interaction of the nucleic acid sensor molecule with the NHR-LBD, a signal will be generated detectable to an external monitoring device. In this manner, the activation state of any or all NHRs can be monitored in vivo or in vitro as will be described in detail in subsequent examples.

Example 4

Selection for a Nucleic Acid Sensor Molecule Selective for the Beta-2 Adrenergic Receptor.

The full-length gene for the Beta-2 adrenergic receptor is described (Emorine et al., Proc.

Natl. Acad. Sci. USA 84:6995–99, 1987) and is available at Acc. No. AAA88017. The nucleic acid sequence is set forth in Table 6 below:

TABLE 6

GCACCGCGAGCCCCTAGCACCCGACAAGCTGAGTGTGCAGGACGAGTCCCCACCACACCC  (SEQ ID NO:11)

ACACCACAGCCGCTGAATGAGGCTTCCAGGCGTCCGCTCGCGGCCCGCAGAGCCCCGCCG

TGGGTCCGCCCGCTGAGGCGCCCCCAGCCAGTGCGCTTACCTGCCAGACTGCGCGCCATG

TABLE 6-continued

```
GGGCAACCCGGGAACGGCAGCGCCTTCTTGCTGGCACCCAATGGAAGCCATGCGCCGGAC

CACGACGTCACGCAGGAAAGGGACGAGGTGTGGGTGGTGGGCATGGGCATCGTCATGTCT

CTCATCGTCCTGGCCATCGTGTTTGGCAATGTGCTGGTCATCACAGCCATTGCCAAGTTC

GAGCGTCTGCAGACGGTCACCAACTACTTCATCACTTCACTGGCCTGTGCTGATCTGGTC

ATGGGCCTGGCAGTGGTGCCCTTTGGGCCGCCCATATTCTTATGAAAATGTGGACTTTT

GGCAACTTCTGGTGCGAGTTTTGGACTTCCATTGATGTGCTGTGCGTCACGGCCAGCATT

GAGACCCTGTGCGTGATCGCAGTGGATCGCTACTTTGCCATTACTTCACCTTTCAAGTAC

CAGAGCCTGCTGACCAAGAATAAGGCCCGGGTGATCATTCTGATGGTGTGGATTGTGTCA

GGCCTTACCTCCTTCTTGCCCATTCAGATGCACTGGTACCGGGCCACCCACCAGGAAGCC

ATCAACTGCTATGCCAATGAGACCTGCTGTGACTTCTTCACGAACCAAGCCTATGCCATT

GCCTCTTCCATCGTGTCCTTCTACGTTCCCCTGGTGATCATGGTCTTCGTCTACTCCAGG

GTCTTTCAGGAGGCCAAAAGGCAGCTCCAGAAGATTGACAAATCTGAGGGCCGCTTCCAT

GTCCAGAACCTTAGCCAGGTGGAGCAGGATGGGCGGACGGGGCATGGACTCCGCAGATCT

TCCAAGTTCTGCTTGAAGGAGCACAAAGCCCTCAAGACGTTAGGCATCATCATGGGCACT

TTCACCCTCTGCTGGCTGCCCTTCTTCATCGTTAACATTGTGCATGTGATCCAGGATAAC

CTCATCCGTAAGGAAGTTTACATCCTCCTAAATTGGATAGGCTATGTCAATTCTGGTTTC

AATCCCCTTATCTACTGCCGGAGCCCAGATTTCAGGATTGCCTTCCAGGAGCTTCTGTGC

CTGCGCAGGTCTTCTTTGAAGGCCTATGGGAATGGCTACTCCAGCAACGGCAACACAGGG

GAGCAGAGTGGATATCACGTGGAACAGGAGAAAGAAAATAAACTGCTGTGTGAAGACCTC

CCAGGCACGGAAGACTTTGTGGGCCATCAAGGTACTGTGCCTAGCGATAACATTGATTCA

CAAGGGAGGAATTGTAGTACAAATGACTCACTGCTGTAAAGCAGTTTTTCTACTTTTAAA

GACCCCCCCCCCCCAACAGAACACTAAACAGACTATTTAACTTGAGGGTAATAAACTTA

GAATAAAATTGTAAAAATTGTATAGAGATATGCAGAAGGAAGGGCATCCTTCTGCCTTTT

TTATTTTTTTAAGCTGTAAAAAGAGAGAAAACTTATTTGAGTGATTATTTGTTATTTGTA

CAGTTCAGTTCCTCTTTGCATGGAATTTGTAAGTTTATGTCTAAAGAGCTTTAGTCCTAG

AGGACCTGAGTCTGCTATATTTTCATGACTTTTCCATGTATCTACCTCACTATTCAAGTA

TTAGGGGTAATATATTGCTGGTAATTTGTATCTGAAGGAGATTTTCCTTCCTACACCCTT

GGACTTGAGGATTTTGAGTATCTCGGACCTTTCAGCTGTGAACATGGACTCTTCCCCCAC

TCCTCTTATTTGCTCACACGGGGTATTTTAGGCAGGGATTTGAGGAGCAGCTTCAGTTGT

TTTCCCGAGCAAAGGTCTAAAGTTTACAGTAAATAAAATGTTTGACCATG
```

The amino acid sequence of the polypeptide encoded by the nucleic acid sequence is set forth in Table 7 below:

TABLE 7

```
  1 mgqpgngsaf llapngshap dhdvtqqrde vwvvgmgivm slivlaivfg nvlvitaiak   (SEQ ID NO:12)

61 ferlqtvtny fitslacadl vmglavvpfg aahilmkmwt fgntwcefwt sidvlcvtas 121 ietlcviavd ryfaitspfk yqslltknka rviilmvwiv sgltsflpiq mhwyrathqe 181 aincyanetc cdfftnqaya iassivsfyv plvimvfvys rvfqeakrql qkidksegrf 241 hvqnlsqveq dgrtghglrr sskfclkehk alktlgiimg tftlcwlpff ivnivhviqd
```

TABLE 7-continued

```
301 nlirkevyil lnwigyvnsg fnpliycrsp dtriatqell clrrsslkay gngyssngnt
361 geqsgyhveq ekenkliced lpgtedfvgh qgtvpsdnid sqgrncstnd sil
```

The gene encoding either the full-length Beta-2 adrenergic receptor or cytoplasmic loop II or III or helix VII is cloned, expressed and purified from *E. coli* or baculovirus infected cells (Hampe, et al., J Biotechnol 77:219–234 (2000)) according to published procedures, and incorporated into detergent micelles to simulate the cellular milieu (Min, et al., J Biol Chem 268:9400–9404 (1993)). A library of up to $10^{17}$ variants of in vitro synthesized ribozymes (1 µM) containing a plurality of potential target modulation domains and linker domains coupled to the catalytic domain of the ribozyme is allowed to react with purified Beta-2 adrenergic receptor at a final concentration of 1 uM. Selection of catalytic nucleic acid sensor molecules is carried out by procedures outlined in Example 1.

Selection of nucleic acid sensor molecules which are activated by the butoxamine- Beta-2 adrenergic complex. 1:1 complexes of butoxamine and purified Beta-2 adrenergic receptor are formed and selection of catalytic nucleic acid sensor molecules is carried out by procedures outlined in Example 1.

Selection of nucleic acid sensor molecules which are activated by the isoproterenol- Beta-2 adrenergic complex is accomplished as follows. 1:1 complexes of isoproterenol and purified Beta-2 adrenergic receptor are formed and selection of catalytic nucleic acid sensor molecules is carried out by procedures outlined in Example 1 and the Detailed Description.

Example 5

Selection for a Library of Nucleic Acid Sensor Molecules which Signal the Presence of all Known GPCRs The full-length gene sequences for over 400 G-protein coupled receptors ("GPCR") is known. GPCR polypeptides, peptides and peptide fragments are also know as set forth in Table 8 and Table 9 below. The entire gene, or peptides derived from these sequences, is N-terminally tagged or N-/C- terminally His-tagged and cloned, expressed, and purified, or synthesized by chemical means. All 400 plus GPCRs are produced in either a serial or parallel fashion and the purified proteins or peptides stored in buffer containing 50 mM Tris-HCl, 1 mM EDTA, 1 mM DTT, and 50–250 mM NaCl/SCN salt, pH 7 to pH 8.5, 10% glycerol or other stabilizing agent.

TABLE 8

| | |
|---|---|
| refNP_006134.1 | G protein-coupled receptor 19 [*Homo sapiens*] |
| refXP_049562.1 | G protein-coupled receptor 19 [*Homo sapiens*] |
| refNP_004876.1 | neuropeptide G protein-coupled receptor; n . . . |
| refXP_011102.1 | 46228 [*Homo sapiens*] >gi|14723215|refXP_0 . . . |
| refNP_057624.1 | G protein-coupled receptor 72; reserved; G . . . |
| refXP_011520.3 | orexin receptor 2 [*Homo sapiens*] |
| refNP_001517.1 | orexin receptor 2 [*Homo sapiens*] |
| refNP_001471.1 | galanin receptor 1; Galanin receptor [*Homo* . . . |
| refNP_071429.1 | neuropeptide FF 1; RFamide-related peptide . . . |
| refXP_005747.4 | tachykinin receptor 2 [*Homo sapiens*] |
| refNP_001048.1 | tachykinin receptor 2; Tachykinin receptor . . . |
| refNP_000901.1 | neuropeptide Y receptor Y2 [*Homo sapiens*] . . . |
| refNP_003848.1 | galanin receptor 2 [*Homo sapiens*] >gi|1365 . . . |
| refXP_004030.2 | adrenergic, beta-2-, receptor, surface [Ho . . . |

TABLE 8-continued

| | |
|---|---|
| refNP_000015.1 | adrenergic, beta-2-, receptor, surface [Ho . . . |
| refNP_001777.1 | orexin receptor 1 [*Homo sapiens*] |
| refXP_011871.3 | neuropeptide FF 1; RFamide-related peptide . . . |
| refNP_001516.1 | orexin receptor 1 [*Homo sapiens*] |
| refNP_001041.1 | somatostatin receptor 2 [*Homo sapiens*] >gi . . . |
| refNP_001040.1 | somatostatin receptor 1 [*Homo sapiens*] >gi . . . |
| refNP_001044.1 | somatostatin receptor 5 [*Homo sapiens*] |
| refXP_012565.1 | somatostatin receptor 5 [*Homo sapiens*] |
| refNP_115940.1 | G protein-coupled receptor; G protein-coup . . . |
| refXP_037563.1 | G protein-coupled receptor [*Homo sapiens*] |
| refNP_001050.1 | tachykinin receptor 3; NK-3 receptor; neur . . . |
| refXP_011942.1 | prolactin-releasing hormone receptor [*Homo* . . . |
| refXP_017624.1 | G protein-coupled receptor 58 [*Homo sapiens*] |
| refXP_004239.1 | prolactin-releasing hormone receptor [*Homo* . . . |
| refNP_071640.1 | histamine receptor H2; gastric receptor 1 . . . |
| refNP_055441.1 | G protein-coupled receptor 58 [*Homo sapiens*] |
| refXP_009594.2 | somatostatin receptor 4 [*Homo sapiens*] |
| refNP_003605.1 | galanin receptor 3; galanin receptor, fami . . . |
| refNP_001049.1 | tachykinin receptor 1, isoform long; Tachy . . . |
| refXP_039747.1 | opioid receptor, mu 1 [*Homo sapiens*] >gi|1 . . . |
| refNP_000905.1 | opioid receptor, mu 1 [*Homo sapiens*] |
| refXP_004341.2 | 53355 [*Homo sapiens*] |
| refXP_052174.1 | 50635 [*Homo sapiens*] |
| refXP_052175.1 | 5-hydroxytryptamine (serotonin) receptor 4 . . . |
| refXP_052165.1 | 5-hydroxytryptamine (serotonin) receptor 4 . . . |
| refXP_052164.1 | 50636 [*Homo sapiens*] >gi|14732317|refXP_0 . . . |
| refNP_000861.1 | 5-hydroxytryptamine (serotonin) receptor 4 . . . |
| refNP_001043.1 | somatostatin receptor 4 [*Homo sapiens*] |
| refNP_000721.1 | cholecystokinin A receptor [*Homo sapiens*] . . . |
| refNP_006670.1 | putative opioid receptor, neuromedin K (ne . . . |
| refNP_055442.1 | G protein-coupled receptor 57 [*Homo sapiens*] |
| refNP_000698.1 | arginine vasopressin receptor 1B; arginine . . . |
| refNP_001718.1 | bombesin-like receptor 3 [*Homo sapiens*] >g . . . |
| refXP_040306.1 | similar to SOMATOSTATIN RECEPTOR TYPE 2 (S . . . |
| refNP_056542.1 | tachykinin receptor 1, isoform short; Tach . . . |
| refNP_001042.1 | somatostatin receptor 3 [*Homo sapiens*] >gi . . . |
| refNP_000722.1 | cholecystokinin B receptor [*Homo sapiens*] |
| refNP_000789.1 | dopamine receptor D5; Dopamine receptor D1 . . . |
| refNP_000612.1 | 5-hydroxytryptamine (serotonin) receptor 2 . . . |
| refNP_004215.1 | G protein-coupled receptor 50 [*Homo sapiens*] |
| refXP_010228.2 | G protein-coupled receptor 50 [*Homo sapiens*] |
| refNP_000907.1 | oxytocin receptor [*Homo sapiens*] |
| refXP_052179.1 | oxytocin receptor [*Homo sapiens*] >gi|14725 . . . |
| refNP_005192.1 | chemokine (C-C motif) receptor 8; chemokin . . . |
| refNP_000670.1 | adrenergic, alpha-1B-, receptor; adrenergi . . . |
| refXP_046588.1 | G protein-coupled receptor slt [*Homo sapie* . . . |
| refNP_000671.1 | adrenergic, alpha-1A-, receptor; adrenergi . . . |
| refNP_110411.1 | brain expressed G-protein-coupled receptor . . . |
| refXP_003199.2 | growth hormone secretagogue receptor [*Homo* . . . |
| refXP_017623.1 | G protein-coupled receptor 57 [*Homo sapiens*] |
| refNP_005949.1 | melatonin receptor 1A; melatonin receptor . . . |
| refNP_115892.1 | G protein-coupled receptor slt; melanin-co . . . |
| refNP_000903.1 | opioid receptor, kappa 1; Opiate receptor, . . . |
| refNP_000900.1 | neuropeptide Y receptor Y1; Neuropeptide Y . . . |
| refXP_011716.2 | similar to opioid receptor, kappa 1; Opiat . . . |
| refXP_011707.2 | adrenergic, alpha-1A-, receptor [*Homo sapi* . . . |
| refXP_048085.1 | adrenergic, alpha-1A-, receptor [*Homo sapi* . . . |
| refXP_048084.1 | adrenergic, alpha-1A-, receptor [*Homo sapi* . . . |
| refNP_000785.1 | dopamine receptor D1 [*Homo sapiens*] |
| refXP_048082.1 | adrenergic, alpha-1A-, receptor [*Homo sapi* . . . |
| refNP_003292.1 | thyrotropin-releasing hormone receptor [Ho . . . |
| refNP_005305.1 | gastrin-releasing peptide receptor [*Homo s* . . . |
| refXP_006335.4 | dopamine receptor D2 [*Homo sapiens*] |
| refXP_006334.3 | dopamine receptor D2longer [*Homo sapiens*] |
| refNP_000786.1 | dopamine receptor D2 [*Homo sapiens*] >gi|14 . . . |
| refXP_036647.1 | dopamine receptor D2 [*Homo sapiens*] >gi|14 . . . |
| refXP_041422.1 | similar to dopamine receptor D2 (*H. sapien* . . . |
| refNP_057658.1 | dopamine receptor D2longer [*Homo sapiens*] . . . |

TABLE 8-continued

| | |
|---|---|
| ref|NP_000697.1| | arginine vasopressin receptor 1A; V1a vaso ... |
| ref|NP_002502.1| | neuromedin B receptor [*Homo sapiens*] |
| ref|XP_018475.1| | neuromedin B receptor [*Homo sapiens*] |
| ref|NP_062874.1| | 5-hydroxytryptamine receptor 7, isoform b; ... |
| ref|NP_000730.1| | cholinergic receptor, muscarinic 2; muscar ... |
| ref|NP_062873.1| | 5-hydroxytryptamine receptor 7, isoform d; ... |
| ref|NP_000863.1| | 5-hydroxytryptamine receptor 7, isoform a; ... |
| ref|NP_000667.1| | adenosine A2b receptor [*Homo sapiens*] >gi| ... |
| ref|NP_000675.1| | beta-1-adrenergic receptor [*Homo sapiens*] |
| ref|NP_005963.1| | pancreatic polypeptide receptor 1 [*Homo sa* ... |
| ref|NP_000732.1| | cholinergic receptor, muscarinic 4; muscar ... |
| ref|XP_039923.1| | 44527 [*Homo sapiens*] |
| ref|NP_000787.1| | dopamine receptor D3 [*Homo sapiens*] |
| ref|XP_011027.3| | dopamine receptor D3 [*Homo sapiens*] |
| ref|NP_061822.1| | G protein-coupled receptor 14 [*Homo sapiens*] |
| ref|NP_000731.1| | cholinergic receptor, muscarinic 3; muscar ... |
| ref|NP_000669.1| | adrenergic, alpha-1D-, receptor; adrenergi ... |
| ref|NP_005282.1| | G protein-coupled receptor 17 [*Homo sapien* ... |
| ref|XP_048332.1| | similar to purinergic receptor (family A g ... |
| ref|XP_041897.1| | similar to G protein-coupled receptor 17 ( ... |
| ref|NP_005152.1| | angiotensin receptor-like 1 [*Homo sapiens*] ... |
| ref|NP_000016.1| | adrenergic, beta-3-, receptor [*Homo sapien* ... |
| ref|NP_001286.1| | chemokine (C-C motif) receptor 1; macropha ... |
| ref|NP_000902.1| | opioid receptor, delta 1 [*Homo sapiens*] |
| ref|NP_005758.1| | purinergic receptor (family A group 5) [Ho ... |
| ref|XP_006296.1| | cholinergic receptor, muscarinic 4 [*Homo s* ... |
| ref|XP_006058.1| | similar to MUSCARINIC ACETYLCHOLINE RECEPT ... |
| ref|NP_000729.1| | cholinergic receptor, muscarinic 1; muscar ... |
| ref|NP_000904.1| | opiate receptor-like 1; opiod receptor-lik ... |
| ref|NP_006630.1| | cysteinyl leukotriene receptor 1 [*Homo sap* ... |
| ref|NP_001828.1| | chemokine (C-C motif) receptor 3 [*Homo sap* ... |
| ref|NP_000530.1| | rhodopsin; rhodopsin (retinitis pigmentosa ... |
| ref|NP_009154.1| | putative G protein coupled receptor [*Homo* ... |
| ref|XP_009882.2| | adenosine A2a receptor [*Homo sapiens*] |
| ref|XP_045486.1| | adrenergic, alpha-1D-, receptor [*Homo sapi* ... |
| ref|NP_000397.1| | gonadotropin-releasing hormone receptor; g ... |
| ref|NP_000666.2| | adenosine A2a receptor; adenosine A2 recep ... |
| ref|XP_002299.1| | G protein-coupled receptor 45 [*Homo sapiens*] |
| ref|NP_003958.1| | putative neurotransmitter receptor [*Homo s* ... |
| ref|NP_000854.1| | 5-hydroxytryptamine (serotonin) receptor 1 ... |
| ref|XP_001811.2| | opioid receptor, delta 1 [*Homo sapiens*] >g ... |
| ref|NP_005950.1| | melatonin receptor 1B; melatonin receptor ... |
| ref|NP_001548.1| | interleukin 8 receptor, beta [*Homo sapiens*] |
| ref|NP_064552.1| | neuromedin U receptor 2 [*Homo sapiens*] |
| ref|NP_009158.1| | G protein-coupled receptor 45 [*Homo sapiens*] |
| ref|NP_000625.1| | interleukin 8 receptor, alpha; chemokine ( ... |
| ref|XP_017622.1| | putative neurotransmitter receptor [*Homo s* ... |
| ref|NP_036257.1| | cholinergic receptor, muscarinic 5; muscar ... |
| ref|NP_000743.1| | leukotriene b4 receptor (chemokine recepto ... |
| ref|NP_000788.1| | dopamine receptor D4 [*Homo sapiens*] |
| ref|XP_006145.2| | dopamine receptor D4 [*Homo sapiens*] |
| ref|NP_001543.1| | G protein-coupled receptor 52 [*Homo sapiens*] |
| ref|XP_009663.1| | G protein-coupled receptor 8 [*Homo sapiens*] |
| ref|XP_007212.1| | purinergic receptor (family A group 5) [Ho ... |
| ref|NP_006165.1| | neuropeptide Y receptor Y5 [*Homo sapiens*] |
| ref|NP_002522.1| | neurotensin receptor 1 [*Homo sapiens*] |
| ref|XP_003692.2| | 5-hydroxytryptamine (serotonin) receptor 1 ... |
| ref|XP_009612.2| | neurotensin receptor 1 [*Homo sapiens*] |
| ref|NP_005277.1| | G protein-coupled receptor 8 [*Homo sapiens*] |
| ref|NP_000515.1| | 5-hydroxytryptamine (serotonin) receptor 1 ... |
| ref|NP_001707.1| | Burkitt lymphoma receptor 1, isoform 1; C- ... |
| ref|NP_005675.1| | G protein-coupled receptor 52 [*Homo sapiens*] |
| ref|NP_000852.1| | histamine receptor H1; histamine receptor, ... |
| ref|NP_000639.1| | chemokine (C-C motif) receptor 2; chemokin ... |
| ref|NP_116743.1| | Burkitt lymphoma receptor 1, isoform 2; C- ... |
| ref|NP_006574.1| | retinal pigment epithelium-derived rhodops ... |
| ref|NP_031395.1| | G-protein coupled receptor [*Homo sapiens*] ... |
| ref|XP_009373.1| | formyl peptide receptor-like 2 [*Homo sapie* ... |
| ref|NP_076917.1| | 5-hydroxytryptamine (serotonin) receptor 5 ... |
| ref|XP_005280.2| | G protein-coupled receptor 7 [*Homo sapiens*] |
| ref|XP_039818.1| | G protein-coupled receptor 91 [*Homo sapien* ... |
| ref|NP_006164.1| | neuropeptide Y receptor Y6 (pseudogene) [H ... |
| ref|XP_012748.2| | galanin receptor 1 [*Homo sapiens*] >gi|476 ... |
| ref|NP_000862.1| | 5-hydroxytryptamine (serotonin) receptor 6 ... |
| ref|NP_005281.1| | G protein-coupled receptor 15 [*Homo sapiens*] |
| ref|XP_010406.1| | angiotensin receptor 2 [*Homo sapiens*] >gi| ... |
| ref|NP_001328.1| | chemokine (C-X3-C) receptor 1; chemokine ( ... |
| ref|NP_002554.1| | purinergic receptor P2Y, G-protein coupled ... |
| ref|NP_004942.1| | EBV-induced G protein-coupled receptor 2; ... |
| ref|NP_000672.1| | adrenergic, alpha-2A-, receptor [*Homo sapi* ... |
| ref|XP_005827.3| | beta-1-adrenergic receptor [*Homo sapiens*] |
| ref|NP_005288.1| | G protein-coupled receptor 24 [*Homo sapien* ... |
| ref|NP_002021.2| | formyl peptide receptor-like 2 [*Homo sapie* ... |
| ref|NP_005276.1| | G protein-coupled receptor 7 [*Homo sapiens*] |
| ref|XP_010009.2| | similar to somatostatin receptor-like prot ... |
| ref|NP_003458.1| | chemokine (C-X-C motif), receptor 4 (fusin ... |
| ref|NP_000673.1| | adrenergic, alpha-2B-, receptor [*Homo sapi* ... |
| ref|XP_051229.1| | similar to C-X-C CHEMOKINE RECEPTOR TYPE 4 ... |
| ref|NP_001453.1| | formyl peptide receptor-like 1; lipoxin A4 ... |
| ref|NP_006047.1| | G protein-coupled receptor 66 [*Homo sapien* ... |
| ref|NP_000856.1| | 5-hydroxytryptamine (serotonin) receptor 1 ... |
| ref|XP_048737.1| | 41064 [*Homo sapiens*] |
| ref|NP_005499.1| | chemokine (C-C motif) receptor 4; chemokin ... |
| ref|NP_000638.1| | chemokine (C-C motif) receptor 2; chemokin ... |
| ref|XP_009664.1| | opiate receptor-like 1 [*Homo sapiens*] >gi| ... |
| ref|NP_005285.1| | G protein-coupled receptor 21 [*Homo sapien* ... |
| ref|XP_009561.2| | 34426 [*Homo sapiens*] |
| ref|NP_004063.1| | chemokine-like receptor 1 [*Homo sapiens*] > ... |
| ref|XP_035769.1| | chemokine-like receptor 1 [*Homo sapiens*] |
| ref|NP_000855.1| | 5-hydroxytryptamine (serotonin) receptor 1 ... |
| ref|NP_000045.1| | arginine vasopressin receptor 2 [*Homo sapi* ... |
| ref|NP_064445.1| | opsin 1 (cone pigments), long-wave-sensiti ... |
| ref|XP_048964.1| | similar to PROBABLE G PROTEIN-COUPLED RECE ... |
| ref|NP_000665.1| | adenosine A1 receptor [*Homo sapiens*] >gi| ... |
| ref|XP_011880.1| | similar to pancreatic polypeptide receptor ... |
| ref|NP_000676.1| | angiotensin receptor 1; angiotensin recept ... |
| ref|NP_000674.1| | adrenergic, alpha-2C-, receptor [*Homo sapi* ... |
| ref|NP_002705.3| | G protein-coupled receptor 17 [*Homo sapiens*] |
| ref|NP_000677.1| | angiotensin receptor 2 [*Homo sapiens*] |
| ref|XP_004279.1| | chemokine (C-C motif) receptor 6 [*Homo sap* ... |
| ref|NP_000504.1| | opsin 1 (cone pigments), medium-wave-sensi ... |
| ref|XP_033840.1| | similar to chemokine (C-C motif) receptor ... |
| ref|NP_002555.1| | purinergic receptor P2Y, G-protein coupled ... |
| ref|XP_006367.1| | purinergic receptor P2Y, G-protein coupled ... |
| ref|NP_004358.1| | chemokine (C-C motif) receptor 6; chemokin ... |
| ref|XP_045851.1| | opsin 1 (cone pigments), short-wave-sensit ... |
| ref|NP_057641.1| | orphan seven-transmembrane receptor, chemo ... |
| ref|NP_003251.1| | chemokine (C-C motif) receptor 9 [*Homo sap* ... |
| ref|NP_001699.1| | opsin 1 (cone pigments), short-wave-sensit ... |
| ref|XP_002838.5| | similar to C-C CHEMOKINE RECEPTOR TYPE 11 ... |
| ref|NP_000570.1| | chemokine (C-C motif) receptor 5; chemokin ... |
| ref|NP_006632.2| | chemokine (C-C motif) receptor 9, isoform ... |
| ref|NP_000859.1| | 5-hydroxytryptamine (serotonin) receptor 2 ... |
| ref|NP_115942.1| | putative purinergic receptor [*Homo sapiens* ... |
| ref|NP_001497.1| | G protein-coupled receptor 32 [*Homo sapien* ... |
| ref|NP_061843.1| | G protein-coupled receptor 85; super conse ... |
| ref|NP_006555.1| | G protein-coupled receptor [*Homo sapiens*] ... |
| ref|NP_065110.1| | cysteinyl leukotriene CysLT2 receptor; cDN ... |
| ref|NP_004113.1| | growth hormone secretagogue receptor [*Homo* ... |
| ref|NP_055137.1| | opsin 3 (encephalopsin) [*Homo sapiens*] |
| ref|XP_001515.3| | opsin 3 (encephalopsin) [*Homo sapiens*] >gi ... |
| ref|NP_005274.1| | G protein-coupled receptor 5 [*Homo sapiens* ... |
| ref|NP_061842.1| | super conserved receptor expressed in brai ... |
| ref|NP_005291.1| | G protein-coupled receptor 34 [*Homo sapien* ... |
| ref|NP_037477.1| | G protein-coupled receptor [*Homo sapiens*] ... |
| ref|XP_003126.1| | chemokine binding protein 2 [*Homo sapiens*] ... |
| ref|XP_007392.1| | G protein-coupled receptor 65 [*Homo sapiens*] |
| ref|NP_005284.1| | G protein-coupled receptor 20 [*Homo sapiens*] |
| ref|NP_005287.1| | G protein-coupled receptor 23 [*Homo sapien* ... |
| ref|NP_009195.1| | adrenomedullin receptor; G-protein-coupled ... |
| ref|NP_003941.1| | coagulation factor II (thrombin) receptor- ... |
| ref|NP_000701.1| | bradykinin receptor B1 [*Homo sapiens*] |
| ref|NP_000857.1| | 5-hydroxytryptamine (serotonin) receptor 1 ... |
| ref|NP_057652.1| | G-protein coupled receptor SALPR; somatost ... |
| ref|XP_012745.1| | histamine H4 receptor [*Homo sapiens*] >gi| ... |
| ref|NP_000858.1| | 5-hydroxytryptamine (serotonin) receptor 2 ... |
| ref|NP_003599.1| | G protein-coupled receptor 65; T-cell deat ... |
| ref|NP_001499.1| | G protein-coupled receptor 39 [*Homo sapien* ... |
| ref|XP_007275.2| | bradykinin receptor B1 [*Homo sapiens*] |

TABLE 8-continued

| | |
|---|---|
| ref\|XP_006230.3\| | G protein-coupled receptor 72 [Homo sapien . . . |
| ref\|XP_037208.1\| | histamine receptor H3 [Homo sapiens] |
| ref\|XP_010168.2\| | arginine vasopressin receptor 2 [Homo sapi . . . |
| ref\|XP_009163.1\| | histamine receptor H3; G protein-coupled r . . . |
| ref\|XP_037209.1\| | 34432 [Homo sapiens] >gi\|14786758\|ref\|XP_0 . . . |
| ref\|NP_005273.1\| | G protein-coupled receptor 4 [Homo sapiens . . . |
| ref\|NP_000668.1\| | adenosine A3 receptor [Homo sapiens] >gi\|1 . . . |
| ref\|XP_001499.1\| | endothelial differentiation, sphingolipid . . . |
| ref\|NP_114142.1\| | G protein-coupled receptor 61 [Homo sapiens] |
| ref\|NP_002020.1\| | formyl peptide receptor 1 [Homo sapiens] > . . . |
| ref\|XP_007108.2\| | endothelin receptor type B, isoform 1 [Hom . . . |
| ref\|NP_000106.1\| | endothelin receptor type B, isoform 1 [Hom . . . |
| ref\|NP_003982.1\| | endothelin receptor type B isoform 2 [Homo . . . |
| ref\|XP_007276.2\| | bradykinin receptor B2 [Homo sapiens] >gi\| . . . |
| ref\|NP_000614.1\| | bradykinin receptor B2 [Homo sapiens] >gi\| . . . |
| ref\|XP_001907.1\| | G protein-coupled receptor 25 [Homo sapiens] |
| ref\|XP_051522.1\| | G protein-coupled receptor [Homo sapiens] |
| ref\|NP_003476.1\| | G protein-coupled receptor 68; Ovarian can . . . |
| ref\|NP_001498.1\| | G protein-coupled receptor 38 [Homo sapien . . . |
| ref\|NP_073625.1\| | platelet ADP receptor [Homo sapiens] >gi\|1 . . . |
| ref\|NP_039226.1\| | olfactory receptor, family 10, subfamily H . . . |
| ref\|XP_040869.1\| | similar to cannabinoid receptor 1 (brain) . . . |
| ref\|NP_004145.1\| | pyrimidinergic receptor P2Y, G-protein cou . . . |
| ref\|NP_057167.1\| | central cannabinoid receptor, isoform a; C . . . |
| ref\|NP_062813.1\| | seven transmembrane receptor BLTR2; leukot . . . |
| ref\|NP_149046.1\| | olfactory receptor, family 2, subfamily B, . . . |
| ref\|NP_000943.1\| | platelet-activating factor receptor [Homo . . . |
| ref\|XP_008010.2\| | similar to MELANOCYTE STIMULATING HORMONE . . . |
| ref\|NP_063950.1\| | olfactory receptor, family 2, subfamily S, . . . |
| ref\|NP_001831.1\| | central cannabinoid receptor, isoform a; C . . . |
| ref\|XP_003761.3\| | 48895 [Homo sapiens] >gi\|14724697\|ref\|XP_0 . . . |
| ref\|NP_002377.2\| | melanocortin 1 receptor (alpha melanocyte . . . |
| ref\|XP_032638.1\| | neuromedin U receptor 2 [Homo sapiens] |
| ref\|NP_005270.1\| | G protein-coupled receptor 1 [Homo sapiens] |
| ref\|NP_005293.1\| | G protein-coupled receptor 37 (endothelin . . . |
| ref\|NP_004092.1\| | coagulation factor II (thrombin) receptor- . . . |
| ref\|NP_005289.1\| | G protein-coupled receptor 25 [Homo sapiens] |
| ref\|NP_001727.1\| | complement component 5 receptor 1 (C5a lig . . . |
| ref\|XP_002667.1\| | 41743 [Homo sapiens] |
| ref\|XP_008392.1\| | CC chemokine receptor 10 [Homo sapiens] >g . . . |
| ref\|NP_001496.1\| | G protein-coupled receptor 30; chemokine r . . . |
| ref\|NP_057686.1\| | CC chemokine receptor 10 [Homo sapiens] |
| ref\|NP_001829.1\| | chemokine (C-C motif) receptor 7; Chemokin . . . |
| ref\|XP_016412.1\| | 28082 [Homo sapiens] >gi\|14721034\|ref\|XP_0 . . . |
| ref\|NP_006009.1\| | putative chemokine receptor; GTP-binding p . . . |
| ref\|NP_000136.1\| | follicle stimulating hormone receptor; ova . . . |
| ref\|NP_002541.1\| | olfactory receptor, family 3, subfamily A, . . . |
| ref\|XP_002212.2\| | follicle stimulating hormone receptor [Hom . . . |
| ref\|NP_004769.1\| | G protein-coupled receptor 44; chemoattrac . . . |
| ref\|XP_015921.1\| | similar to putative chemokine receptor; GT . . . |
| ref\|XP_015923.1\| | putative chemokine receptor; GTP-binding p . . . |
| ref\|NP_055380.1\| | olfactory receptor, family 1, subfamily A, . . . |
| ref\|NP_065133.1\| | putative G protein-coupled receptor 92 [Ho . . . |
| ref\|XP_008716.1\| | melanocortin 4 receptor [Homo sapiens] |
| ref\|NP_039225.1\| | olfactory receptor, family 11, subfamily A . . . |
| ref\|NP_002556.1\| | pyrimidinergic receptor P2Y, G-protein cou . . . |
| ref\|NP_005903.1\| | melanocortin 4 receptor [Homo sapiens] |
| ref\|NP_005297.1\| | G protein-coupled receptor 43 [Homo sapien . . . |
| ref\|XP_012667.1\| | olfactory receptor, family 1, subfamily A, . . . |
| ref\|NP_112221.1\| | olfactory receptor, family 12, subfamily D . . . |
| ref\|NP_039227.1\| | olfactory receptor, family 10, subfamily H . . . |
| ref\|NP_059976.1\| | olfactory receptor, family 7, subfamily C, . . . |
| ref\|NP_005279.1\| | G protein-coupled receptor 12 [Homo sapien . . . |
| ref\|NP_001948.1\| | endothelin receptor type A [Homo sapiens] |
| ref\|NP_005904.1\| | melanocortin 5 receptor [Homo sapiens] >gi . . . |
| ref\|NP_110401.1\| | prostate specific G-protein coupled recept . . . |
| ref\|NP_004758.1\| | endothelin type b receptor-like protein 2 . . . |
| ref\|NP_003544.1\| | olfactory receptor, family 1, subfamily E, . . . |
| ref\|NP_000520.1\| | melanocortin 2 receptor; Melanocortin-2 re . . . |
| ref\|NP_036492.1\| | olfactory receptor, family 1, subfamily F, . . . |
| ref\|NP_002557.1\| | purinergic receptor P2Y, G-protein coupled . . . |
| ref\|XP_030219.1\| | gonadotropin-releasing hormone receptor [H . . . |
| ref\|XP_009029.4\| | purinergic receptor P2Y, G-protein coupled . . . |
| ref\|NP_036284.1\| | endothelial cell differentiation gene 7; c . . . |
| ref\|NP_039228.1\| | olfactory receptor, family 10, subfamily H . . . |
| ref\|NP_036484.1\| | olfactory receptor, family 1, subfamily A, . . . |
| ref\|XP_012668.1\| | olfactory receptor, family 1, subfamily A, . . . |
| ref\|NP_001983.1\| | coagulation factor II receptor precursor; . . . |
| ref\|NP_036501.1\| | olfactory receptor, family 2, subfamily F, . . . |
| ref\|NP_055694.1\| | putative G-protein-coupled receptor; G pro . . . |
| ref\|XP_004852.1\| | olfactory receptor, family 2, subfamily F, . . . |
| ref\|NP_000949.1\| | prostaglandin E receptor 4 (subtype EP4) [ . . . |
| ref\|NP_072093.1\| | putative leukocyte platelet-activating fac . . . |
| ref\|NP_110503.1\| | olfactory receptor, family 5, subfamily V . . . |
| ref\|NP_003907.1\| | coagulation factor II receptor precursor [ . . . |
| ref\|XP_004216.1\| | similar to olfactory receptor 89 (H. sapie . . . |
| ref\|NP_112167.1\| | olfactory receptor, family 2, subfamily J, . . . |
| ref\|NP_002542.1\| | olfactory receptor, family 3, subfamily A, . . . |
| ref\|NP_036505.1\| | olfactory receptor, family 3, subfamily A, . . . |
| ref\|NP_005292.1\| | G protein-coupled receptor 35 [Homo sapiens] |
| ref\|XP_004045.1\| | complement component 3a receptor 1; comple . . . |
| ref\|NP_005290.1\| | G protein-coupled receptor 31 [Homo sapiens] |
| ref\|NP_005233.2\| | coagulation factor II (thrombin) receptor- . . . |
| ref\|NP_003546.1\| | olfactory receptor, family 1, subfamily G, . . . |
| ref\|XP_003671.3\| | coagulation factor II (thrombin) receptor- . . . |
| ref\|NP_112163.1\| | olfactory receptor, family 7, subfamily A, . . . |
| ref\|NP_039229.1\| | olfactory receptor, family 10, subfamily C . . . |
| ref\|NP_002539.1\| | olfactory receptor, family 1, subfamily D, . . . |
| ref\|XP_037263.1\| | similar to coagulation factor II (thrombin . . . |
| ref\|NP_067647.1\| | leucine-rich repeat-containing G protein-c . . . |
| ref\|NP_065103.1\| | inflammation-related G protein-coupled rec . . . |
| ref\|NP_055314.1\| | putative purinergic receptor [Homo sapiens . . . |
| ref\|NP_036509.1\| | olfactory receptor, family 7, subfamily C, . . . |
| ref\|NP_036507.1\| | olfactory receptor, family 52, subfamily A . . . |
| ref\|XP_035507.1\| | similar to NONE_RETURNED (H. sapiens) [Hom . . . |
| ref\|NP_004280.1\| | G protein-coupled receptor 31 [Homo sapiens] |
| ref\|NP_003545.1\| | olfactory receptor, family 1, subfamily E, . . . |
| ref\|XP_036497.1\| | olfactory receptor, family 1, subfamily F, . . . |
| ref\|NP_061844.1\| | super conserved receptor expressed in brai . . . |
| ref\|NP_063941.1\| | melanocortin 3 receptor [Homo sapiens] |
| ref\|NP_009091.1\| | olfactory receptor, family 2, subfamily H, . . . |
| ref\|XP_008678.2\| | olfactory receptor, family 1, subfamily D, . . . |
| ref\|NP_003543.1\| | olfactory receptor, family 1, subfamily D, . . . |
| ref\|XP_011731.3\| | similar to adrenergic, beta-3-, receptor ( . . . |
| ref\|XP_009545.1\| | melanocortin 3 receptor [Homo sapiens] |
| ref\|NP_076403.1\| | G protein-coupled receptor 86 [Homo sapiens] |
| ref\|XP_042200.1\| | G protein-coupled receptor 86 [Homo sapiens] |
| ref\|NP_004711.2\| | endothelial differentiation, lysophosphati . . . |
| ref\|NP_037440.1\| | platelet activating receptor homolog [Homo . . . |
| ref\|NP_005217.1\| | endothelial differentiation, sphingolipid . . . |
| ref\|NP_005295.1\| | G protein-coupled receptor 41 [Homo sapien . . . |
| ref\|NP_005296.1\| | G protein-coupled receptor 42 [Homo sapiens] |
| ref\|NP_115943.1\| | putative chemokine receptor [Homo sapiens] . . . |
| ref\|NP_055381.1\| | olfactory receptor, family 1, subfamily D, . . . |
| ref\|XP_042826.1\| | luteinizing hormone/choriogonadotropin rec . . . |
| ref\|XP_010797.3\| | luteinizing hormone/choriogonadotropin rec . . . |
| ref\|NP_000224.1\| | luteinizing hormone/choriogonadotropin rec . . . |

TABLE 9

```
>G(S)-1 mgclgnskte dqrneekaqr eankkiekql qkdkqvyrat hrllllgage sgkstivkqm    (SEQ ID NO:13)
rilhvngfng eggeedpqaa rsnsdgekat kvqdiknnlk eaietivaam snlvppvela
npenqfrvdy ilsvmnvpdf dfppefyeha kalwedegvr acyersneyq lidcaqyfld
kidvikqady vpsdqdllrc rvltsgifet kfqvdkvnfh mfdvggqrde rrkwiqcfnd
vtaiifvvas ssynmvired nqtnrlqeal nltksiwnnr wlrtisvilf lnkqdllaek
vlagkskied yfpefarytt pedatpepge dprvtrakyf irdefirist asgdgrhycy
phftcavdte nirrvfndcr diiqrmhlrq yell.

>G(S)-2 mgclgnskte dqrneekaqr eankkiekql qkdkqvyrat hrllllgage sgkstivkqm    (SEQ ID NO:14)
rilhvngfng eggeedpqaa rsnsdgseka tkvqdiknnl keaietivaa msnlvppvel
anpenqfrvd yiisvmnvpd fdfppefyeh akalwedegv racyersney qlidcaqyfl
dkidvikqad yvpsdqdllr crvltsgife tkfqvdknf hmfdvggqrd errkwiqcfn
dvtaiifvva sssynmvire dnqtnrigea lnlfksiwnn rwlrtisvil flnkqdilae
kviagkskie dyfpefaryt tpedatpepg edprvtraky firdeflris tasgdgrhyc
yphftcavdt enirrvfndc rdiiqrmhlr qyell.

>G(S)-3 mgclgnskte dqrneekaqr eankkiekqi qkdkqvyrat hrllllgage sgkstivkqm    (SEQ ID NO:15)
rilhvngfng dekatkvqdi knnikeaiet ivaamsnlvp pveianpenq frvdyilsvm
nvpdfdfppe fyehakalwe degvracyer sneyqiidca qyflakidvi kqadyvpsdq
dllrcrvlts gifetkfqvd kvnfhmfdvg gqrderrkwi qcfndvtaii fvvasssynm
virednqtnr iqeainifks iwnnrwlrti svilflnkqd llaekviagk skiedyfpef
aryttpedat pepgedprvt rakyfirdef lristasgdg rhycyphftc avdtenirrv
fndcrdiiqr mhirqyell.

>G(S)-4 mgclgnskte dqrneekaqr eankkiekql qkdkqvyrat hrlillgage sgkstivkqm    (SEQ ID NO:16)
rilhvngfng dsekatkvqd iknnlkeaie tivaamsnlv ppveianpen qfrvdyilsv
mnvpdfdfpp efyehakalw edegvracye rsneyqlidc aqyfidkidv ikqadyvpsd
qdllrcrvit sgifetkfqv dkvnfhmfdv ggqrderrkw iqcfndvtai ifvvasssyn
mvirednqtn riqealnifk siwnnrwlrt isvilflnkq dliaekvlag kskiedyfpe
faryttpeda tpepgedprv trakyfirde firistasgd grhycyphft cavdtenirr
vfndcrdiiq rmhirqyeli.

>G(s)-xl meisgppfei gsapagvddt pvnmdsppia ldgppikvsg apdkreraer ppveeeaaem    (SEQ ID NO:17)
egaadaaegg kvpspgygsp aagaasadta araapaapad pdsgatpedp dsgtapadpd
sgafaadpds gaapaapadp dsgaapdapa dpdsgaapda papdagaap eapaapaaae
traahvapaa pdagaptapa asatraaqvr raasaapasg arrkihlrpp speiqaadpp
tprptrasaw rgksessrgr rvyydegvas sdddssgdes ddgtsgclrw fqhrrnrrrr
kpqrnilrnf ivqafggcfg rsespqpkas rsikvkkvpi aekrrqmrke alekraqkra
ekkrsklidk qlqdekmgym cthrlllll.

>g-olf mgclggnskt tedqgvdeke rreankkiek qiqkerlayk athrllllga gesgkstivk    (SEQ ID NO:18)
qmriihvngf npeekkqil dirknvkdai vtivsamsti ippvplanpe nqfrsdyiks
iapitdfeys qeffdhvkkl wddegvkacf ersneyqlid caqyflerid svsivdytpt
dqdllrcrvl tsgifetrfq vdkvnfhmfd vggqrderrk wiqcfndvta iiyvaacssy
nmvirednnt nriresidlf esiwnnrwir tisijifink qdmlaekvia gkskiedyfp
eyanytvped atpdagedpk vtrakffird lflristatg dgkhycyphf tcavdtenir
rvfndcrdii qrmhlkqyel l.

>I1 mgctisaedk aaverskmid rniredgeka arevkilllg agesgkstiv kqmkiiheag    (SEQ ID NO:19)
yseeeckqyk avvysntiqs iiaiiramgr lkidfgdsar addarqifvi agaaeegfmt
aelagvikri wkdsgvqacf nrsreyqlnd saayylndld riaqpnyipt qqdvlrtrvk
ttgivethft fkdihfkmfd vggqrserkk wihcfegvta iifcvalsdy dlvlaedeem
nrmhesmklf dsicnnkwft dtsiiiflnk kdlfeekikk spiticypey agsntyeeaa
ayiqcqfedi nkrkdtkeiy thftcatdtk nvqfvfdavt dviiknnikd cglf.

>I2 mgctvsaedk aaaerskmid kniredgeka arevkllіig agesgkstiv kqmkiihedg    (SEQ ID NO:20)
yseeecrqyr avvysntiqs imaivkamgn iqidfadpsr addarqifal sctaeeqgvi
pddlsgvirr iwadhgvqac fgrsreyqln dsaayyindl eriaqsdyip tqqdvlrtrv
kttgivethf ttkdlhfkmf dvggqrserk kwihcfegvt aiifcvalsa ydlviaedee
mnrmhesmki fdsicnnkwf tdtsiiifin kkdifeekit hspiticfpe ytganykydea
asyiqskfed inkrkdtkei ythftcatdt knvqfvfdav tdviiknnik dcgif.
```

TABLE 9-continued

>I3

```
mgctisaedk aaverskmid rniredgeka akevkiilig agesgkstiv kqmkiihedg    (SEQ ID NO:21)
ysedeckqyk vvvysntiqs iiaiiramgr lkidfgeaar addarqifvi agsaeegvmt
peiagvikri wrdgqvqacf srsreyqlnd sasyyindid risqsnyipt qqdvirtrvk
ttgivethft fkdlyfkmfd vggqrserkk wihcfegvta iifcvalsdy dlviaedeem
nrmhesmkif dsicnnkwft etsiiiflnk kdifeekikr spiticypey tgsntyeeaa
ayiqcqfedi nrrkdtkeiy thftcatdtk nvqfvfdavt dviiknnike ogly.
```

>G01

```
mgctlsaeer aaierskaie knikedgisa akdvkiiiig agesgkstiv kqmkiihedg    (SEQ ID NO:22)
fsgedvkqyk pvvysntiqs laaivramdt lgieygdker kadakmvcdv vsrmedtepf
saeilsammr iwgdsgiqec fnrsreyqln dsakyyidsi drigaadyqp teqdilrtrv
kttgivethf tfknihfrif dvggqrserk kwihcfedvt aiifcvaisg ydqvlhedet
tnrmheslmi fdsicnnkff idtsiilfin kkdlfgekik kspliticfpe ytgpntyeda
aayiqaqtes knrspnkeiy chmtcatdtn niqvvfdavt diiiannlrg cgly.
```

>g02

```
mgctvsaedk aaaerskmid kniredgeka arevkiillg agesgkstiv kqmkiihedg    (SEQ ID NO:23)
yseeecrqyr avvysntiqs imaivkamgn lqidfadpsr addarqlfal sctaeeqgvl
pddisgvirr iwadhgvqac fgrsreyqln dsaayyindl eriaqsdyip tqqdvlrtrv
kttgivethf tfkdihfkmf dvggqrserk kwihcfegvt aiifcvalsa ydiviaedee
mnrmhesmkl fdsicnnkwf tdtsiilfin kkdlfeekit hspliticfpe ytganykydea
asyiqskfed inkrkdtkei ythftcatdt knvqfvfdav tdviiknnlk dogif.
```

>G(T-1)

```
mgagasaeek hsieiekkik edaekdartv kililgages gkstivkqmk iihqdgysle    (SEQ ID NO:24)
eclefiaiiy gntlqsilai vramttlniq ygdsarqdda rklmhmadti eegtmpkems
diiqrlwkds giqacteras eyqindsagy ylsdierlvt pgyvpteqdv lrsrvkttgi
ietqfsfkdl nfrmfdvggq rserkkwihc fegvtciifi aaisaydmvl veddevnrmh
eslhitnsic nhryfattsi vifinkkdvf fekikkahis icfpdydgpn tyedagnyik
vqflelnmrr dvkeiyshmt catdtqnvkf vfdavtdiii kenikdcglf.
```

>G(T-2)

```
mgsgasaedk elakrskele kklqedadke aktvkiiiig agesgkstiv kqmkiihqdg    (SEQ ID NO:25)
yspeeciefk aiiygnviqs iiaiiramtt igidyaepsc addgrqinni adsieegtmp
pelvevirrl wkdggvqacf eraaeyqlnd sasyylnqle ritdpeylps eqdvirsrvk
ttgiietkfs vkdinfrmfd vggqrserkk wihcfegvtc iifcaaisay dmvlveddev
nrmheslhlf nsicnnhkffa atsivlfink kdlfeekikk vhisicfpey dgnnsyddag
nyiksqfldl nmrkdvkeiy shmtcatdtq nvkfvfdavt diiikenlkd cgif.
```

>G(Z)

```
mvflsgnasd ssnctqppap vniskaillg viiggiilfg vignilvils vachrhihsv    (SEQ ID NO:26)
thyyivnlav adllltstvl pfsaifevlg ywafgrvfcn iwaavdvicc tasimglcii
sidryigvsh plryptivtq rrglmalicv waisivisig pifgwrqpap edeticqine
epgyvifsal gsfylpiaii lvmycrvyvv akresrgiks glktdksdse qvtlrihrkn
apaggsgmas aktkthfsvr likfsrekka aktigivvgc fvlcwlpffl vmpigsffpd
fkpsetvfki vfwlgyinsc inpiiypcss qefkkafqnv iriqclcrkq sskhalgytl
hppsqavegq hkdmvripvg sreafygisr tdgvcewkff ssmprgsari tvskdqssct
tarvrsksfl qvcccvepst psldknhqvp tikvhtisis engeev.
```

>G(Q)

```
macclseeak earrindeje rqlrrdkrda rrelkllllg tgesgkstfi kqmriihgsg    (SEQ ID NO:27)
ysdedkrgft kivyqnitta mqamiramdt lkipykyehn kahaqlvrev dvekvsafen
pyvdaiksiw ndpgiqecyd rrreyqisds tkyylndldr vadpaylptq qdvlrvrvpt
tgiieypfdl qsvifrmvdv gggrserrkw ihcfenvtsi mflvalseyd qvlvesdnen
rmeeskaifr tiitypwfqn ssvilflnkk dileekimys hivdyfpeyd gpqrdaqaar
efilkmfvdl npdsdkiiys hftcatdten irfvfaavkd tilqlnlkey nay.
```

>G(Y-11)

```
mtlesmmacc isdevkeskr inaeiekqlr rdkrdarrel kllllgtges gkstfikqmr    (SEQ ID NO:28)
iihgagysee dkrgftklvy qniftamqam irametikil ykyeqnkana llirevdvek
vtttehqyvs aiktlwedpg iqecydrrre yqlsdsakyy itdvdriatl gyiptqqdvl
rvrvpttgii eypfdlenii frmvdvggqr serrkwihcf envtsimflv aiseydqviv
esdnenrmee skaifrtiit ypwfqnssvi lflnkkdlle dkilyshlvd yfpefdgpqr
daqaarefii kmfvdlnpds dkiiyshfto atdtenirfv faavkdtilq lnlkeynlv.
```

>G(Y-12)

```
msgvvrtisr cilpaeagga rerragsgar daerearrrs raidailare rravrrlvki    (SEQ ID NO:29)
illgagesgk stfikqmrii hgrefdqkai lefrdtifdn ilkgsrvlvd ardkigipwq
```

TABLE 9-continued

```
ysenekhgmf imafenkagi pvepatfqiy vpalsalwrd sgireafsrr sefqlgesvk
yfidnidrig qinyfpskqd iilarkatkg ivehdfvikk ipfkmvdvgg qrsqrqkwfq
cfdgitsilf mvssseydqv lmedrrtnrl vesmnifeti vnnkiffnvs iilfinkmdi
ivekvktvsi kkhfpdfrgd phqiedvqry ivqcfdrkrr nrskplfhhf ttaidtenvr
fvfhavkdti iqenikdiml q.
```

\>G(Y-13)

```
madflpsrsv lsvcfpgcii tsgeaeqqrk skeidkclsr ektyvkrivk illlgagesg    (SEQ ID NO:30)
kstflkqmri ihgqdfdqra reefrptiys nvikgmrvlv darekThipw gdnsnqqhgd
kmmsfdtrap maaqgmvetr vfiqyipair alwadsgiqn aydrrrefqi gesvkyfldn
ldklgepdyi psqqdiilar rptkgiheyd feiknvpfkm ldvggqrser krwfecfdsv
tsilfivsss efdqvimedr itnrltesln ifetivnnrv fsnvsiilfl nktdileekv
qivsikdyfl efegdphcir dvqkfivecf rnkrrdqqqk piyhhfttai ntenirivfr
dvkdtilhdn ikqimiq.
```

\>G(Y-14)

```
magccclsae ekesqrisae ierqlrrdkk darrelklll lgtgesgkst fikqmriihg    (SEQ ID NO:31)
sgysdedrkg ftkivyqnif tamqamiram dtlriqyvce qnkenaqiir evevdkvsml
sreqveaikq iwqdpgiqec ydrrreyqls dsakyyltdi driatpsfvp tqqdvlrvrv
pttgiieypf dieniifrmv dvggqrserr kwihcfesvt siifivaise ydqvlaecdn
enrmeeskai fktiitypwf lnssvilfin kkdileekim yshiisyfpe ytgpkqdvra
ardfilklyq dqnpdkekvi yshftcatdt dnirfvfaav kdtilqlnlr efnlv.
```

\>G(Y-15)

```
marsitwrcc pwcltedeka aarvdqeinr illeqkkqdr gelklllgp gesgkstfik    (SEQ ID NO:32)
qmriihgagy seeerkgfrp ivyqnifvsm ramieameri qipfsrpesk hhaslvmsqd
pykvttfekr yaaamqwlwr dagiracyer rrefhlidsa vyylshieri teegyvptaq
dvlrsrmptt gineycfsvq ktnlrivdvg gqkserkkwi hcfenviali ylaslseydq
cieennqenr mkeslalfgt iielpwfkst sviifinktd iieekiptsh latyfpsfqg
pkqdaeaakr fiidmytrmy tgcvdgpegs kkgarsrrif shytcatdtq nirkvfkdvr
dsviaryide mu.
```

\>Gusducin

```
mfdvggqrse rkkwihcfeg vtciifcaal saydmvlved eevnrmhesl hlfnsicnhk    (SEQ ID NO:33)
yfsttsivif inkkdifqek vtkvhlsicf peytgpntfe dagnyiknqf ldlnikkedk
eiyshmtcat dtqnvkfvfd avtdiiiken lkdcglf.
```

1. Selection of nucleic acid sensor molecules which are activated by GPCRs not bound to ligand:

A library of up to $10^{17}$ variants of in vitro synthesized ribozymes is allowed to react with purified GPCRs at a final concentration of luM GPCR. Selection of catalytic nucleic acid sensor molecules is carried out by procedures outlined in prior examples. Selections are carried out in parallel fashion. Selections can also be carried out in mixed pools of anywhere from 5–10 GPCRs. In the final rounds of nucleic acid sensor molecule selection, the RNA pools may separated into aliquots which may then be used to carry out in vitro selection against single GPCR proteins to yield unique nucleic acid sensor molecules selective for all 400 plus GPCRs.

2. Selection of nucleic acid sensor molecules which are activated by ligand bound GPCRs.

Stable complexes of each GPCR and corresponding -ligand are formed with from 1–10 equivalents of ligand. Selection of catalytic nucleic acid sensor molecules is carried out by procedures outlined in the Detailed Description. Selections are carried out in parallel fashion. Selections can also be carried out in mixed pools of anywhere from 5–10 GPCR-ligand complexes. In the final rounds of nucleic acid sensor molecule selection, the RNA pools may separated into aliquots which may then be used to carry out in vitro selection against single GPCR-ligand complexes to yield unique nucleic acid sensor molecules selective for all GPCR-ligand complexes.

Selection of nucleic acid sensor molecules using peptide fragments of GPCRs Nucleic acid sensor molecules that specifically recognize conformational isoforms of GPCRs that are revealed upon ligand binding can also be selected for using the methods described herein.

Molecular cloning studies have identified over 400 human GPCRs, and have identified the ligands for 120. GPCRs consist of three domains: an extracellular N-terminus, a central domain of seven trans-membrane helices, and a cytoplasmic C-terminus. Activation of GPCRs is induced by ligand binding, which causes a conformational change in the receptor transmitting a signal across the plasma membrane to intracellular members of a signaling pathway. This method provides for generation of unique biosensors for each GPCR.

A library of up to $10^{17}$ variants of in vitro synthesized ribozymes is allows to react with peptide fragments of the GPCRs comprising regions of the GPCR that are exposed upon activation. Nucleic acid sensor molecules which recognize these domains are then capable of recognizing them within the context of the full length protein and hence recognize the activated state of the GPCR. Examples of the use of peptide fragments to generate nucleic acid sensor molecules which recognize the full length protein are known in the art and are incorporated herein. See, for example, data on nucleic acid sensor molecule selection and recognition of HIV rev peptide and full length protein [Michael Robertson, 2001, University of Texas, Austin, Ph.D. Dissertation]. In the case of HIV rev, unique peptide sequences are recognized both as free peptides and in the context of the full protein.

Nucleic acid sensor molecules specific for GPCRs are generated by in vitro selection for recognition of peptide fragments of the GPCRs comprising regions of the GPCR that are exposed to the inside face of the plasma membrane when ligand binds to the GPCR. Exemplary suitable GPCR peptide fragments are presented in Table 9. Nucleic acid sensor molecules which recognize these peptides are then capable of recognizing them within the context of the full length protein and hence recognize the activated state of the GPCR.

Example 6
Nucleic Acid Sensor Molecule Specific to Phosphodiesterase (PDE) for Target Validation Likewise, different classes of PDE (PDE1–11) are expressed in a tissue-specific manner and play different physiological roles (Conti 2000), and the subcellular localization of PDE regulates their activity. Accordingly, the nucleic acid sensor molecule can be used to determine the subcellular localization of each PDE from fractionated cell extracts (Bolger, Erdogan et al. 1997), or in situ hybridization technique (Sirinarumitr, Paul et al. 1997).

Figures 65A, 65B:
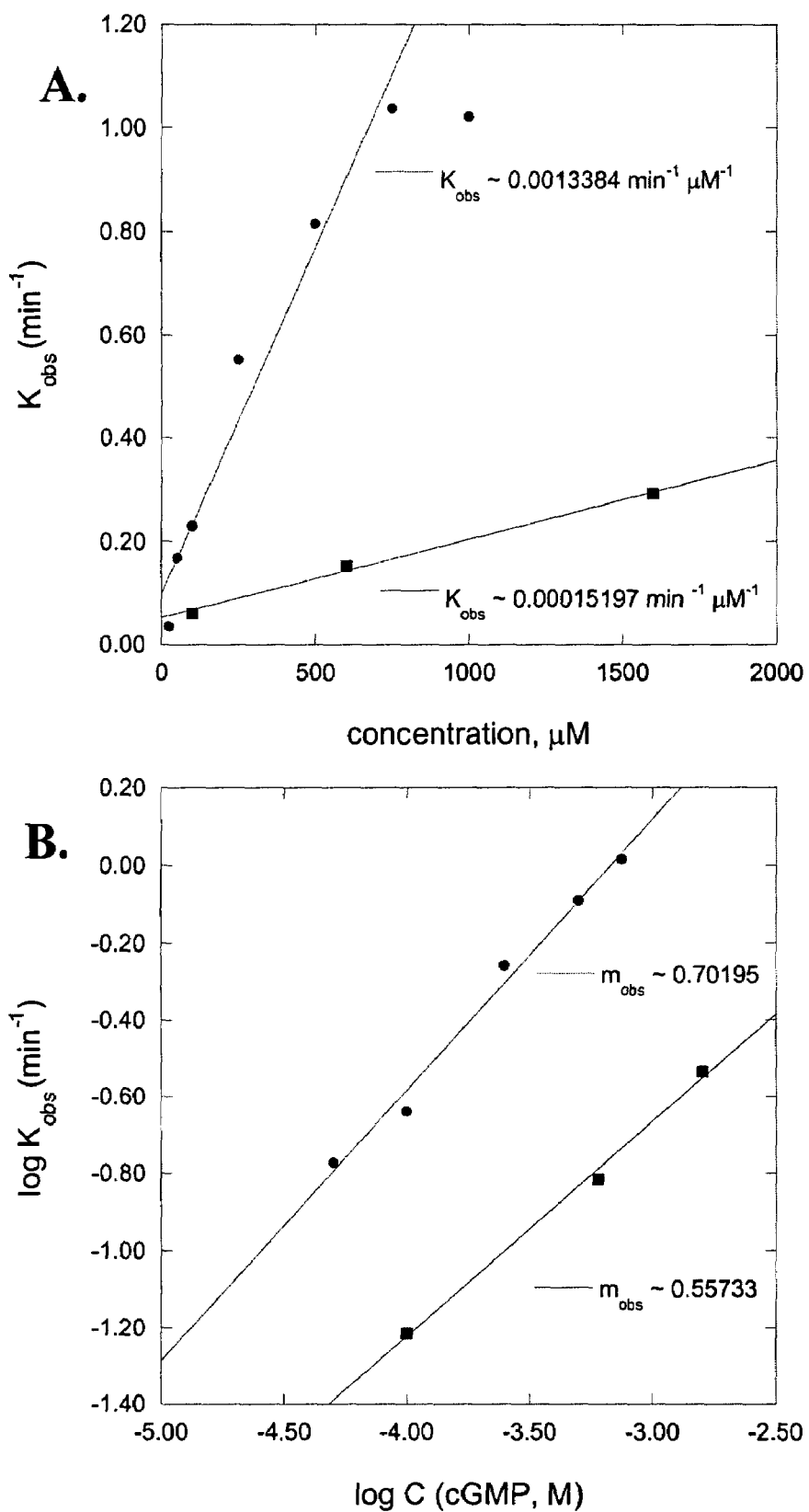
FIGS. 65A and 65B compare the observed pseudo-first order rate constants from solution- and solid-phase FRET sensor constructs.

The nucleotide sequences of a cAMP-dependent PDE nucleic acid sensor molecule and cGMP-dependent nucleic acid sensor molecule are presented in Table 10. Allosteric domains are 15 shown in bold font and the cleavage site nucleotide is underlined. CGMP modulated NASMs that are configured for homogeneous, solution based fluorescence assays (FRET) are shown the FIG. 62. Multiplexed camp and cGMP-modulated FRET-sensor NASM-based assays are shown in FIG. 65B. The optical NASMs modulated by cAMP and cGMP are used in PDE assays as described in detail below.

TABLE 10 cAMP-Hammerhead RNA seq:

5'-GGGC GAC CC UGA UGA GCC UGU GGA AAC AGA CGU GGC ACA UGA CUA CGU CGA AAC   (SEQ ID NO:34)
GGU GAA AGC CGU <u>A</u>GG UUG   CCC -3' cGMP-Hammerhead RNA seq:

5'-GGGC GAC CC UGA UGA GCC CUG CGA UGC AGA AAG GUG CUG ACG ACA CAU CGA AAC   (SEQ ID NO:35)
GGU GAA AGC CGU <u>A</u>GG UUG   CCC -3'

Nucleic acid sensor molecules are generated to be specific to various subclasses of PDEs are used for understanding the role of PDE subclasses in the molecular pathology of disease, and as PDE target validation. For example, nucleic acid sensor molecules which are modulated by each of four PDE4 subtypes have specific utility in understanding the role of PDE4 in human disease. The four subclasses of PDE4 are differentially localized between cell type and also the PDE4 isozymes differ with respect to their intracellular localization. This differential localization, together with the transcriptional regulation and post-translational modification, controls the cAMP level in cells in response to the cells' environment (Muller, Engels et al. 1996).

The cDNAs for four PDE4 subtypes are cloned from human blood leukocyte cDNA library as described (Wang, Myers et al. 1997). Each subclass of PDE4 is expressed as recombinant protein fused with a His-tag in E. coli or SF9 insect cells (Richter, Hermsdorf et al. 2000) (Wang, Myers et al. 1997). The expressed proteins are purified through Ni$^{++}$ columns according to established procedures. Catalytic nucleic acid sensor molecules modulated by the four subclasses of PDE4 are then selected as described above. The nucleic acid sensor molecules are tested for their subclass specificity, by determining the switch factor.

Tissue samples from different organs can be prepared, and the cell extract can be tested against a panel of PDE4 subclass-specific nucleic acid sensor molecules to determine the protein level of each PDE in the organ. Thus, one can obtain more precise information about PDE4 levels relative to methods based on measuring the mRNA level (Bloom and Beavo 1996) (Obernolte, Ratzliff et al. 1997) (Nagaoka, Shirakawa et al. 1998).

The cAMP and cGMP-dependent nucleic acid sensor molecules were added to a solution containing various amounts of PDE and the corresponding cyclic nucleotide (cAMP or cGMP). A decreasing amount of the cyclic nucleotide was found to correspond to the increasing amount of PDE. These results demonstrate that the cyclic nucleotide-dependent nucleic acid sensor molecules can be used to measure PDE activity.

The calmodulin activated PDE specific for cGMP was used under the following enzyme assay conditions: Assay conditions (10 mM Tris, 20 mM MgCl$_2$, 100 FM CaCl$_2$) 200 nM cGMP-NASM; the assay is quenched with 0.1% SDS and then 200 nM cGMP-NASM is added to the mixture. Remaining cGMP was determined by the amount of conversion of nucleic acid sensor molecule to product using a gel based radioactive product-release (gel-shift) assay format. The nucleic acid sensor molecule is active in a variety of formats and is not inhibited by GMP produced by the components of the PDE assay. Similarly, the cAMP nucleic acid sensor molecule is active in a variety of assay formats and is not inhibited by GMP produced by the components of the PDE assay. The conversion of cGMP to GMP is followed by the optical NASM formats described in FIGS. 62–72.

High Throughput Screening (HTS) Assays Using cAMP-dependent PDE Nucleic Acid Sensor Molecules:

A cAMP-dependent nucleic acid sensor molecule is used in HTS assays for PDEs (PDE1, PDE2, PDE3, PDE4, PDE7, PDE8, PDE10, and PDE11). Similarly, cGMP-dependent-nucleic acid sensor molecules can be used in HTS assays for PDEs (PDE5, PDE9, PDE10, and PDE I1). Representative cAMP-dependent and cGMP-dependent PDE nucleic acid sensor molecules are shown above, and in FIGS. 62–72 for all solution and chip-based NASM assay configurations.

Each class of PDE can be isolated from human tissue (Ballard, Gingell et al. 1998), or expressed as recombinant proteins in various system (e.g. *E coli*, SF9 cells). Thus, the nucleic acid sensor molecule monitors the PDE activity in the presence and the absence of candidate drugs. For example, PDE and its substrate (i.e., cAMP and/or cGMP) are incubated at predetermined durations in a multiwell chamber (e.g., 96, 384 well) with various concentration of compounds for screening, and the reaction is terminated by changing the buffer conditions (e.g., addition of sufficient amount of EGTA, shifting buffer pH), or by separating enzyme and substrate (e.g., filtration). Next, the nucleic acid sensor molecules are added to measure the altered concentration of the substrate, cAMP and cGMP. Alternatively, optical nucleic acid sensor molecules can be added without terminating the PDE activity. CAMP and cGMP modulated these HTS assays, as described in FIG. 62 and FIG. 63.

cAMP- or cGMP-dependent nucleic acid sensor molecules can also be used to characterize the IC50 of the drug in vitro. A PDE assay is performed with serial dilutions of a compound of interest. Purified PDE or, alternatively, soluble extract from cells (Moreland, Goldstein et al. 1998) can be used for the assay. The assay can be performed as described herein.

Alternatively, cAMP- or cGMP-dependent nucleic acid sensor molecules (FIGS. 62, 33, and 64) are used to characterize the IC50 values of drug candidate in vitro by analyzing cAMP-or cGMP synthesized by adenyl and guanyl cyclases. Adenylate and guanylate cyclase assays are set up with serial dilution of a compound of interest. Membrane fractions containing adenylate and guanylate cyclases are used for the assay. The assay can be setup as described in the literature using ATP or GTP as the substrate.

Competitive Assays using PDE Nucleic Acid Sensor Molecules:

Nucleic acid sensor molecules are generated that interact with the active sites of PDEs. PDE4 proteins are obtained as described above. The nucleic acid sensor molecules are selected against PDE4 with negative selection in the presence of PDE4 complexed with subnanomolar inhibitor (e.g., Rolipram). Thus, the nucleic acid sensor molecule is modulated by free, uncomplexed PDE4, the PDE nucleic acid sensor molecules compete for PDE binding with inhibitors.

The direct inhibition by the nucleic acid sensor molecules can be tested using commercially available PDE assay kits (Amersham SPA assay kit for cAMP, Molecular Devices HEEP cAMP assay kit). In drug screening, the competition is performed by monitoring the signal from the nucleic acid sensor molecules in the presence of various inhibitors. Purified PDE or soluble cell extract from appropriate source (e.g., Wistar rat brain (Andersson, Gemalmaz et al. 1999) ) is incubated with nucleic acid sensor molecules (100 rtM) in the presence and the absence of compounds in 10 mM Tris buffer pH 7.5 containing 10 mM $MgCl_2$. The changes in the initial rate of each nucleic acid sensor molecule response in the presence and the absence of the drug can be monitored in homologous system. Multiple PDEs can be tested against a same compound in the same well. This assay is expanded if desired to determine the tissue specific interaction of each class of PDE and any compounds.

Cell-based Assays using Cyclic Nucleotide-dependent PDE Nucleic Acid Sensor Molecules Nucleic acid sensor molecules are used to monitor the cellular cAMP and cGMP level in response to the injection of drugs in tissue or rat cell lines. For example, strips of human corpus collasum (HCC) tissue or rat HCC cell lines (N1S1 and McA-RH7777 cells) can be incubated in the presence and absence of a drug against PDE5 (Min, Kim et al. 2000) (Arora, de Groen et al. 1996), and the cGMP specific nucleic acid sensor molecule can be used to measure the amount of cGMP in soluble extract from the tissue or cell sample as described above.

Alternatively, the cAMP, and cGMP-dependent nucleic acid sensor molecules are incorporated into a reporter-gene plasmid as described above. This construct is introduced in cell lines by standard transfection (e.g. lipid-mediated transfection, calcium-phosphate co-precipitation, microinjection, electroporation, retroviral infection). The level of cGMP or camp in the cell is measured by the expression of the reporter gene.

Class Specific PDE Assay:

Nucleic acid sensor molecules are selected for the catalytic domains of each class of PDE1–11 are prepared. These nucleic acid sensor molecules are then used for target validation as described above.

Alternatively, the nucleic acid sensor molecules are used in competitive inhibition assays. Competitive nucleic acid sensor molecules are used in in vitro assays to screen compounds against multiple PDEs in multiplex assays, as described above.

Example 7

Pharmacokinetics Studies using Nucleic Acid Sensor Molecules

Nucleic acid sensor molecules modulated by drug leads or drug compounds used in preclinical testing and clinical trial for pharmacokinetics studies are selected and identified as described in the Detailed Description. A human serum sample with or without the administration of a drug or other therapeutic agent is prepared (Berzas Nevado, Rodriguez Flores et al. 2001). The nucleic acid sensor molecule is added to the sample. The nucleic acid sensor molecule is then used in optical or PCR based detection methods as described in later examples, thereby quantifying the drug concentration in the whole serum or extract from the serum.

The nucleic acid sensor molecule modulated by various drugs or leads can also be used to determine the drug distribution in an animal model system. For example, a drug can be administrated in animals (e.g., Sprague Dawley rats, New Zealand white rabbit) by IV or orally (Andersson, Gemalmaz et al. 1999) (Jeremy, Ballard et al. 1997). At various time intervals after drug administration, the animal is sacrificed. Various organs are tested for the drug distribution by in situ hybridization using the drug-dependent nucleic acid sensor molecule. Alternatively, each organs/serum is prepared for pharmacokinetic studies.

Example 8

Cell-permeability Studies using Nucleic Acid Sensor Molecules

Nucleic acid sensor molecules against a test compound are used to test cell permeability of the compound. These nucleic acid sensor molecules can be incorporated into a reporter gene construct, if desired, to make a drug-sensitive reporter gene system as described above. This construct is introduced in established cell lines (e.g. HELA cells, 293 cell, CHO cell). The cells are cultured in various concentrations of drug in media, and the expression of the reporter gene is monitored.

Example 9

Expression and Purification of Recombinant MAPKs

All protein ORFs were obtained from Upstate Biotech, and cloned into pRSET (Invitrogen), except for ERK which was cloned directly downstream from a hexahistidine tag into pRSET from which the leader sequence had been removed. Constructs were sequence verified before transformation into Rosetta plys(S) cells (Novagen). After growth and induction as described below, cells were washed in 10 ml PBS per liter of culture and resuspended in 7.5 ml Lysis Buffer (500 mM KCl, 20 mM Tris-Cl, pH 8.0, 10% glycerol, 0.5% NP-40, supplemented with 1 Complete EDTA-Free Protease Inhibitor tablet (Roche) per 50 ml) per liter of culture. Cells were frozen in liquid nitrogen and stored at −80° C. Lysis and clarification was accomplished by rapid thawing in a 40° C. bath for 10 minutes, incubation at 4° C. for thirty minutes, and centrifugation for 60 minutes at 100,000×g. As a standard first step, metal chelate affinity chromatography (MCAC) was performed as follows: cell lysate was diluted 1:2 with Buffer A (500 mM KCl, 20 mM Tris-Cl, pH 8.0, 10% glycerol) and applied to a 5 ml HiTrap Chelating column (Amersham Biosciences) charged with nickel. The column was washed with 10 column volumes of Buffer A, and eluted stepwise with 10 column volumes of Buffer A plus 16, 56, 167 and 500 mM imidazol, pH 8.0 at a flow rate of 1.5 ml/min and collecting 5 ml fractions. MAPKs eluted in either the 167 or 500 mM imidazol fractions. After the purification described below, proteins were essentially pure as determined by silver staining of SDS-PAGE gels.

For purification of ERK, cells were grown to an OD600 of 0.7 at 37° C. and induced with 1 mM IPTG for 2 hours at 37° C. The MCAC fraction was diluted tenfold with Buffer B (20 mM HEPES 8.0, 1 mM DTT, 1 mM EDTA, 10% glycerol) and loaded onto a 5 ml HiTrap Q column (Amersham Biosciences) previously equilibrated with Buffer B plus 50 mM KCl. ERK was eluted in a 10 column gradient to Buffer B plus 500 mM KCl, at a flow rate of 1.5 ml/min, taking 2.5 ml fractions.

For purification of Jnk1, stationary phase culture was diluted to OD600 of 0.7 and grown at 37° C. for one hour, and induced with 0.5 mM IPTG for 2 hours at 37° C. MCAC fractions containing Jnk1 were pooled and desalted into Buffer C (20 mM HEPES 7.0, 1 mM DTT, 1 mM EDTA, 10% glycerol) plus 100 mM NaCl by passage over a PD-10 column (Amersham Biosciences). PD-10 eluate was diluted 1:5 with buffer C immediately before loading on a 1 ml HiTrap SP column (Amersham Biosciences) equilibrated in Buffer C. The column was washed with 5 column volumes Buffer C, 5 column volumes Buffer C plus 50 mM NaCl, eluted with a 7 column volume gradient to Buffer C plus 300 mM NaCl, and finished with 5 column volumes of Buffer C plus 300 mM NaCl. The SP column was run at 0.5 ml/min collecting 0.5 ml fractions.

Ion-exchange chromatograpy conditions for p38gamma, h-Ras, and RhoA were identical to ERK, except KCl was substituted for NaCl in Buffer D additions. For purification of p38gamma, cultures were grown to an OD600 of 0.8 and induced with 0.5 mM IPTG for 3 hours at 30° C. For purification of RhoA and h-Ras, cells were grown at 37° C. to an OD600 of 0.8 at 37 ° C., and induced with 0.5 mM IPTG for 3 hours. MCAC fractions were diluted two fold with ddH$_2$O, and dialyzed into Buffer D (20 mM HEPES 7.4, 1 mM DTT, 1 mM EDTA, 10% glycerol) plus 50 mM NaCl. Dialysate was applied to a 1 ml HiTrap Q column (Amersham Biosciences), washed with 5 column volumes Buffer D plus 50 mM NaCl, eluted with 8 column volumes to Buffer D plus 500 mM NaCl, and flushed with 3 column volumes Buffer D plus 500 mM NaCl. Column flow rate and fractionation parameters were identical to Jnk1 purification.

For purification of p38delta, cells were grown at 37° C. to OD600 1.0 and induced with 0.5 mM IPTG for 2 hours. MCAC fractions were dialysed against Buffer B plus 100 mM KCl, then diluted threefold with Buffer B immediately before loading on a 1 ml HiTrap SP column. The column was washed with 5 column volumes of Buffer B plus 50 mM KCl, and eluted with 10 column volumes to Buffer B plus 500 mM KCl, at a flow rate of 0.5 ml/min taking 0.5 ml fractions.

For purification of Mek1, a fresh transformation was grown for 12 hours at 30° C., split 1:100 into fresh media, and grown to OD600 0.7 at 37° C., then induced with 1 mM IPTG for 3 hours. MCAC fractions were desalted on a PD-10 column into Buffer E (40 mM HEPES, pH 7.4, 1 mM EDTA, 1 mM DTT, 10% glycerol) and applied to a 1 ml HiTrap Q column. The column was washed with 10 CV Buffer E and MekI was eluted in a single step of Buffer E plus 85 mM NaCl. Q column run parameters were as for Jnk1; fractions containing Mek1 were collected and dialyzed into Buffer F (150 mM NaCl, 10 mM HEPES, pH 7.5, 1 mM DTT, 1 mM EDTA) and applied to a Superdex 75 column (Amersham Biosciences). The Superdex 75 column was run at 1 ml/min and 1 ml fractions were collected. Fractions containing Mekl were pooled and concentrated tenfold on a Centricon YM-10 (Amicon), and glycerol was added to 10% v/v before proteins were frozen in liquid nitrogen.

For purification of Mek1-DD (Huand and Erikson, 1994), cells were grown to OD600 of 0.7 at 37C and induced with 0.5 mM IPTG for 3 hours. Purification conditions were identical to RhoA and H-ras.

Example 10

Activation of ERK and Generation of ppERK.

Recombinant ERK and Mek1-DD were mixed in a 20:1 molar ratio in 1×Kinase Activation Buffer (100 mM NaCl, 10 mM MgCl$_2$, 10 mM HEPES, pH 8.0, 10% glycerol). ATP was added to 1 mM and the mixture incubated for 30 minutes at 23° C. Excess ATP was removed from the reaction by desalting on a PD-10 column into Buffer G (20 mM HEPES, pH 8.0, 2 mM DTT, 10% glycerol) plus 25 mM NaCl. The eluate was loaded on a 1 ml HiTrap Q column and washed with 20 column volumes of Buffer G plus 100 mM NaCl. ppERK was eluted with a 60 column volume gradient to Buffer G plus 300 mM NaCl at 0.5 ml/min, collecting 0.5 ml fractions. Activated ERK eluted at 176 mM NaCl, while inactivated ERK eluted at 228 mM NaCl. Fractions containing ppERK were diluted six fold with buffer G and reapplied to a 1 ml HiTrapQ column. The column was washed with 50 mM NaCl, and the ppERK was eluted with a single step of Buffer G plus 500 mM NaCl.

Example 11

In Vitro Selection of Cis-hammerhead Derived ERK and ppERK NASMs

Figure 19:
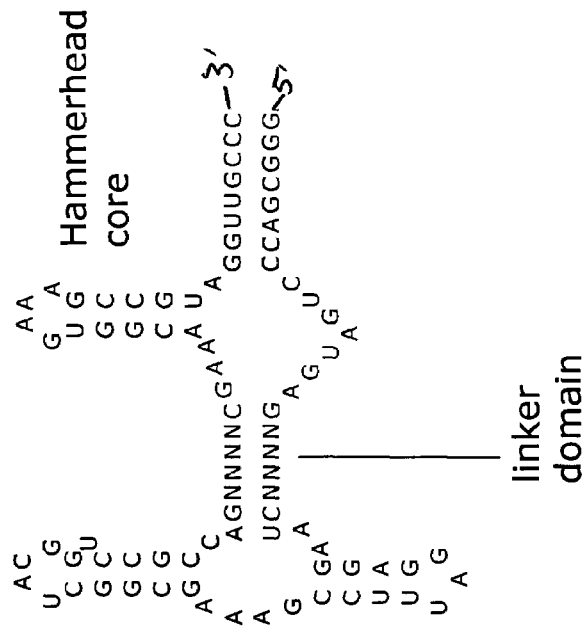
FIG. 19 is the sequence of the entire ERK2 activated allosteric ribozyme (SEQ ID NO:80). Also shown are the sequences of the Stem II connector domain for selective clones.

Library design. FIG. 1B, illustrates an RNA ribozyme library derived from a hammerhead sequence pool consisting of up to $10^{17}$ variants of randomized sequences appended to the hammerhead ribozyme motif (FIG. 19). The ribozyme library is prepared on DNA synthesizer. Random nucleotides are incorporated during the synthesis to generate pools of roughly $10^{17}$ molecules. FIG. 19 illustrates linker scanning library designed to identify cis-hammerhead NASMs that are modulated by the protein kinase ERK. The linker library was generated by appending an ERK target modulation domain to the randomized linker domain to create a library of potential ERK-modulated cis-hammerhead NASMs. The linker library of ERK-modulated cis-hammerhead NASMs consists of up to 65,000 variants. Most molecules in the randomized NASM pools are non-functional NASMs.

Selection of NASMs. Sorting among the billions of NASMs to find the desired molecules starts from the complex sequence pool, whereby desired target-modulated NASMS are isolated through an iterative in vitro selection process: in addition to the target-activated ribozymes that one desires, the starting pool is usually dominated by either constitutively active or completely inactive ribozymes. The selection process removes both types of contaminants. In a following amplification stage, thousands of copies of the surviving sequences are generated to enable the next round of selection. During amplification, random mutations can be introduced into the copied molecules—this 'genetic noise' allows functional nucleic acid sensor molecules to continuously evolve and become even better adapted as target-activated enzymes. The entire experiment reduces the pool complexity from 1017 molecules down to around 100 NASMs that require detailed characterization.

In vitro Selection Method. Negative selections were set up in which 100 gl reactions containing the library (c.f. FIG. 19, where the linker library of ERK NASMs consists of up to 65,000 variants, alternatively the library consists of up to $10^{17}$ variants of randomized sequences appended to the hammerhead ribozyme motif) of target modulated ribozymes containing randomized target modulation domains and randomized linker regions (1 µM), were incubated at 72° C., 5 seconds, followed by 25° C. for lhr in a reaction buffer containing KCl (0–150 mM), HEPES pH 7.5 (20 mM), $MgCl_2$ (20 mM), EDTA (0.5 mM). Cleaved RNA molecules (radiolabeled internally) were then removed from the mixture by electrophoresis through a 7M urea, 8% PAGE gel, followed by cutting the uncleaved band from the gel. Detection of cleaved and uncleaved RNAs were carried out using a phosphor-imager system. The uncleaved hammerhead-derived RNAs were then subjected to a round of positive selection for ERK, or ppERK, target modulation, by incubating the pool of RNA in selection to which the protein target (50 nM to 1 µM ERK, or 50 nM to 1 µM ppERK) were added, and the mixture was further incubated at 37° C. for 30 minutes. Cleaved RNA molecules (radiolabeled internally) were then isolated and removed from the mixture by electrophoresis through a 7M urea, 8% PAGE gel, followed by cutting the cleaved band from the gel. incubated with reverse transcription mix at 65° C. for 1 hour using a thermostable reverse transcriptase. The pool was subsequently separated from the reverse transcription mixture by filtration and was then amplified using PCR first with the substrate 3-specific 5'-PCR primer and the library-specific 3'-PCR primer, and secondly with the regeneration 5'-PCR primer and the library-specific 3 '-PCR primer in order to add the T7 promoter. Transcriptions were performed with these PCR products directly and after denaturing PAGE purification the entire process was repeated for several rounds with assays run after every round.

Cleavage Assays

Cleavage assays were performed using radiolabeled RNA and analytical denaturing polyacrylamide gel elecrophoresis (PAGE) (gel-based assays). Assays were performed upon both the library and clonal sequences. In a representative gel-based assay transcription was performed in the presence of alpha-$^{32}$P-labelled UTP, and the resultant transcripts were gel-purified using denaturing PAGE. Assay mixtures were then made in which 10 µl reactions containing RNA (1u µM), and protein target (1 µM) were incubated at 37° C. for between 15 min and 16 h in a reaction buffer containing buffer containing KCl (0–150 mM), HEPES pH 7.5 (20 mM), $MgCl_2$ (20 mM), EDTA (0.5 mM). The resultant samples are quenched by the addition of EDTA and the relative extents of cleavage measured by comparison of the intensity of the corresponding bands on a denaturing PAGE observed by reading a phosphorimager plate that had been exposed to the gel.

See general Example 1A for a discussion of the cloning, sequencing and characterization of individual NASMs.

Example 12

Nucleic Acid Sensor Molecules Modulated by ERK and Phosphorylated ERK Generated by Engineering Target Modulation Domains into Hammerhead Catalytic Domains.

ERK and ppERK modulated nucleic acid sensor molecules were generated by a strategy combining both engineering and in vitro selection, FIG. 19. Target modulation domains selected for binding to ERK and to the phosphorylated form of ERK (ppERK) are the starting point of the engineering efforts (Seiwert et al. 2000). These target modulation domains when isolated as discrete aptamers specifically recognize ERK but do not detectably interact with other mitogen-activated protein kinases such as Jun N-terminal kinase or p38 (as monitored by the ability to inhibit kinase activity). An aptamer (target modulation domain) selected for ppERK binding efficiently discriminates between phosphorylated and non-phosphorylated forms of the protein, binding ppERK with a $K_D$ of 4.7 nM and ERK with a $K_D$ of 50 nM (Seiwert et al. 2000). Simply engineering an ERK aptamer sequence onto a stably duplexed linker domain appended to the hammerhead ribozyme motif as shown in FIG. 21, results in non-functional NASMs, e.g., certain ribozyme NASMs, derived through direct engineering, when assayed as described above, exhibit little or no cleavage activity in the absence of ERK and no detectable ERK-modulation of cleavage activity in the presence of ERK. Inactive NASMs remained unresponsive to added ERK protein in concentrations ranges tested from 50 nM to 5 uM. Hence, ERK concentrations greater than 1000 fold over the aptamer $K_D$ values does not result in target modulation of the NASM, suggesting that functional NASM activity will require more than a finctional target modulation domain appended to a ribozyme motif.

In vitro selection of cis-hammerhead NASMs based on the 65,000 member ERK target modulated ribozyme library shown in FIG. 19, were performed as described in Example lA. In vitro selection of hammerhead derived ERK and ppERK NASMs, and the subsequently identified and characterized a series of ERK-modulated NASMs are shown in FIG. 19, and in Table 11. The detailed methods for the analysis ERK-modulated NASM clones is given in Example 1A Cloning, sequencing and characterization of individual NASMs.

Example 13. In vitro selection of L1-ligase derived ERK and ppERK NASMs

Figure 31:
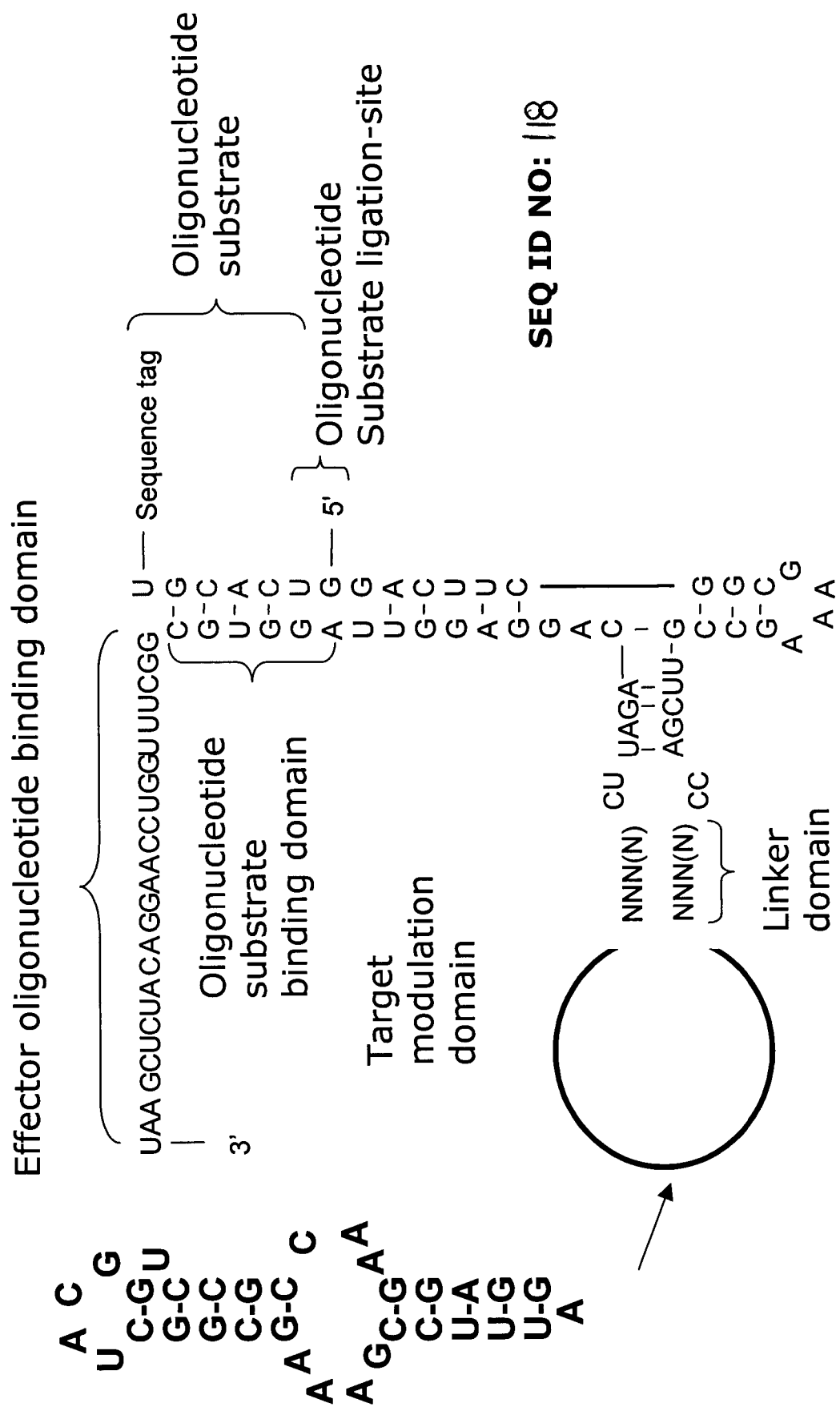
FIG. 31 is a schematic showing the construct design for an ERK dependent 3-piece ligase nucleic acid sensor molecule (SEQ ID NO:118).

Starting from a random linker domain library of L1-ligase derived NASMs as shown in FIG. 31, we carried out in vitro selection to identify ERK-modulated and or ppERK-modulated L1-ligase NASMs. Negative selections were set up in which 100 µl reactions containing the library of ribozymes (1 µM), effector oligonucleotide (1.5 µM) and substrate 3 (5 µM) were incubated at 25° C. for between 16 and 160 h in a reaction buffer containing KCl (150 mM), HEPES (20 mM), MgCl$_2$ (10 mM), EDTA (1 mM), DTT (1 mM), tRNA (0.1 mg/ml) and glycerol (10% w/v). Ligated RNA molecules were then removed from the mixture by incubation with immobilized neutravidin. The flow through was collected by filtration and to this was added more substrate 3 (2 µM), protein target (1 µM ERK or ppERK) and RNase inhibitor were added and the mixture was further incubated at 25 ° C for between 15 minutes and 1 hour. Ligated RNA molecules were then captured by incubation with immobilized neutravidin and, after washing, the matrix was incubated with reverse transcription mix at 65° C. for 1 hour using a thermostable reverse transcriptase. The matrix was subsequently separated from the reverse transcription mixture by filtration and was then amplified using PCR first with the substrate 3-specific 5'-PCR primer and the library-specific 3'-PCR primer, and secondly with the regeneration 5'-PCR primer and the library-specific 3'-PCR primer in order to add the T7 promoter. Transcriptions were performed with these PCR products directly and after denaturing PAGE purification the entire process was repeated for several rounds with assays run after every round.

Ligation Assays

Ligation assays were performed using radiolabeled RNA and analytical denaturing polyacrylamide gel elecrophoresis (PAGE) (gel-based assays), or by PCR utilizing the substrate 3-specific 5'-PCR primer (PCR-based assay). Assays were performed upon both the library and clonal sequences. In a representative gel-based assay transcription was performed in the presence of alpha-$^{32}$P-labelled UTP, and the resultant transcripts were gel-purified using denaturing PAGE. Assay mixtures were then made in which 10 µl reactions containing RNA (1u µM), effector oligonucleotide (1.5 µM), substrate 3 (5 µM) and optionally RNase-inhibitor and protein target (1 µM) were incubated at 25° C. for between 15 min and 16 h in a reaction buffer containing protein target (1 µM ERK or ppERK), KCl (150 mM), HEPES (20 mM), MgCl2 (10 mM), EDTA (1 mM), DTT (1 mM), tRNA (0.1 mg/ml) and glycerol (10% w/v) . The resultant samples were quenched by the addition of EDTA and the relative extents of ligation were measured by comparison of the intensity of the corresponding bands on a denaturing PAGE observed by reading a phosphorimager plate that had been exposed to the gel. PCR assays were performed using the same reaction mixture except that the relative extents of ligation in different samples were compared by observing the relative rates of appearance of PCR products using the substrate 3-specific 5'-PCR primer and the library-specific 3'-PCR primers. The detailed methods for the analysis ERK-modulated NASM clones is given in Example 1A, Cloning, sequencing and characterization of individual NASMs.

Example 14. Rational design and Engineering of ERK dependent ligases.

ERK-dependent ligase ribozymes were built on the catalytic core of the L1 ligase ribozyme of Robertson and Ellington (2000; NAR 28, 1751–1759) in which the non-conserved, stem C element was replaced with the ERK-interacting domain and joined to the catalytic core by a 2–4 base pair helical element, or "communication module". Ten different ribozymes were designed, identical in sequence except for the bases in the linker domain (FIG. 32). (SEQ ID NOs:109–1 16)

Templates for transcription by T7 RNA polymerase were prepared for each ribozyme by PCR amplification using a set of three overlapping primer oligonucleotides. The forward, or 5' primer TAATACGACTCACTATAGGACTTCGGC-GAAAGCCGTTCGACC (SEQ ID NO:315), included the T7 RNA polymerase promoter and sequence corresponding to the 5'-proximal region of the L1 ligase catalytic core. The other two primers corresponded to sequences spanning the 3'-proximal portion of the L1 ligase core ATTCGAGAT-GTCCTTGGACCAAAGCCGCACCTAAC-CTCCTGTCTAAG (SEQ ID NO:316) and the ERK interacting domain (including sequences), respectively. RNA was synthesized by in vitro transcription (Milligan & Uhlenbeck (1989) Methods Enzymol 180, 51 –62) using the T7-MEGAshortscript™ transcription kit from Ambion, and purified by gel-filtration (to remove transcription buffer components) and/or polyacrylamide gel electrophoresis (PAGE). The purified RNAs were then quantified by their absorbance at 260 nm, and stored in TE buffer (10 mM Tris-HCI, 1 mM EDTA, pH 8.0) at −20 ° C. Radiolabeled RNAs were prepared exactly as described above, except that a-$^{32}$P-UTP was included in the in vitro transcription reaction.

Example 15. Rational design and Engineering of ppERK dependent ligases.

ppERK-dependent ligase ribozymes were built on the catalytic core of the L1 ligase ribozyme of Robertson and Ellington (2000; NAR 28, 1751–1759) in which the non-conserved, stem C element was replaced with the ERK-interacting domain and joined to the catalytic core by a 2–4 base pair helical element, or "communication module". Fourteen different ribozymes were designed, identical in sequence except for the bases in the linker domain (FIG. 41) (SEQ ID NO:352).

Templates for transcription by T7 RNA polymerase were prepared for each ribozyme by PCR amplification using a set of three overlapping primer oligonucleotides. The forward, or 5' primer TAATACGACTCACTATAGGACTTCGGC-GAAAGCCGTTCGACC (SEQ ID NO:315), included the T7 RNA polymerase promoter and sequence corresponding to the 5'-proximal region of the L1 ligase catalytic core. The other two primers corresponded to sequences spanning the 3'-proximal portion of the L1 ligase core ATTCGAGAT-GTCCTTGGACCAAAGCCGCACCTAAC-CTCCTGTCTAAG (SEQ ID NO:316) and the ppERK target modulation domain (including sequences), respectively. RNA was synthesized by in vitro transcription (Milligan & Uhlenbeck (1989) Methods Enzymol 180, 51–62) using the T7-MEGAshortscript™ transcription kit from Ambion, and purified by gel-filtration (to remove transcription buffer components) and/or polyacrylamide gel electrophoresis (PAGE). The purified RNAs were then quantified by their absorbance at 260 nm, and stored in TE buffer (10 mM Tris-HCI, 1 mM EDTA, pH 8.0) at −20° C. Radiolabeled RNAs were prepared exactly as described above, except that α-$^{32}$P-UTP was included in the in vitro transcription reaction.

Example 16

Linker-region Selection of Effector-dependent Ligases Oligonucleotides

Synthetic DNA and the DNA-RNA chimeric substrates were synthesized using standard solid-phase methodology and purified by denaturing (8M urea) polyacrylamide gel electrophoresis (PAGE). Random-sequence regions of synthetic DNA were generated using a single mixed "N" bottle on the DNA synthesizer that contains all four nucleotide phosphoramidites mixed in proportions. Variable-length regions of synthetic DNA were generated by interrupting the synthesis and removing part of the reaction mixture, re-starting the synthesis and then replacing the removed material after a subsequent interruption. Templates for transcription were generated by PCR, and the transcripts thus generated were also purified by denaturing (8M urea) polyacrylamide gel electrophoresis (PAGE). Gel-purification is followed by the localization of nucleic acids within the gel by UV-shadowing, nucleic-acid containing gel pieces are excised and the purified nucleic acids are recovered by electroelution. The following synthetic oligonucleotides were utilized:

Example 17

Nucleic Acid Sensor Molecules Modulated by Native ERK Enzyme.

Hammerhead-derived nucleic acid sensor molecules (88 nucleotides in length) were selected from populations of nucleic acid molecules with randomized linker domain in stem II, as shown in FIG. 19. The Table in FIG. 19 depicts illustrative linker-domain sequences of several of the ERK-modulated nucleic acid sensor molecules isolated from in vitro selection linker randomized clones (described in detail in Example 11). Each NASM displays a varying degree of modulation driven by addition of equal amounts (1 uM) native ERK. Individual ERK-modulated cis-hammerhead nucleic acid sensor molecules are shown in FIG. 19. Clones 1-14, 1-13, 1-2, 1-6, 2-7, 2-2, 2-3, 2-13, 2-14, and 2-20 were tested in target modulation assays as described previously. The NASM's relative dependence on ERK is denoted in the Table in FIG. 19 by the extent of activity of the ribozyme in the presence of ERK protein.

The time course of signal generation in the presence of nonphosphorylated ERK, phosphorylated ERK, and in the absence of protein is determined by measuring signal

Figure 20A:
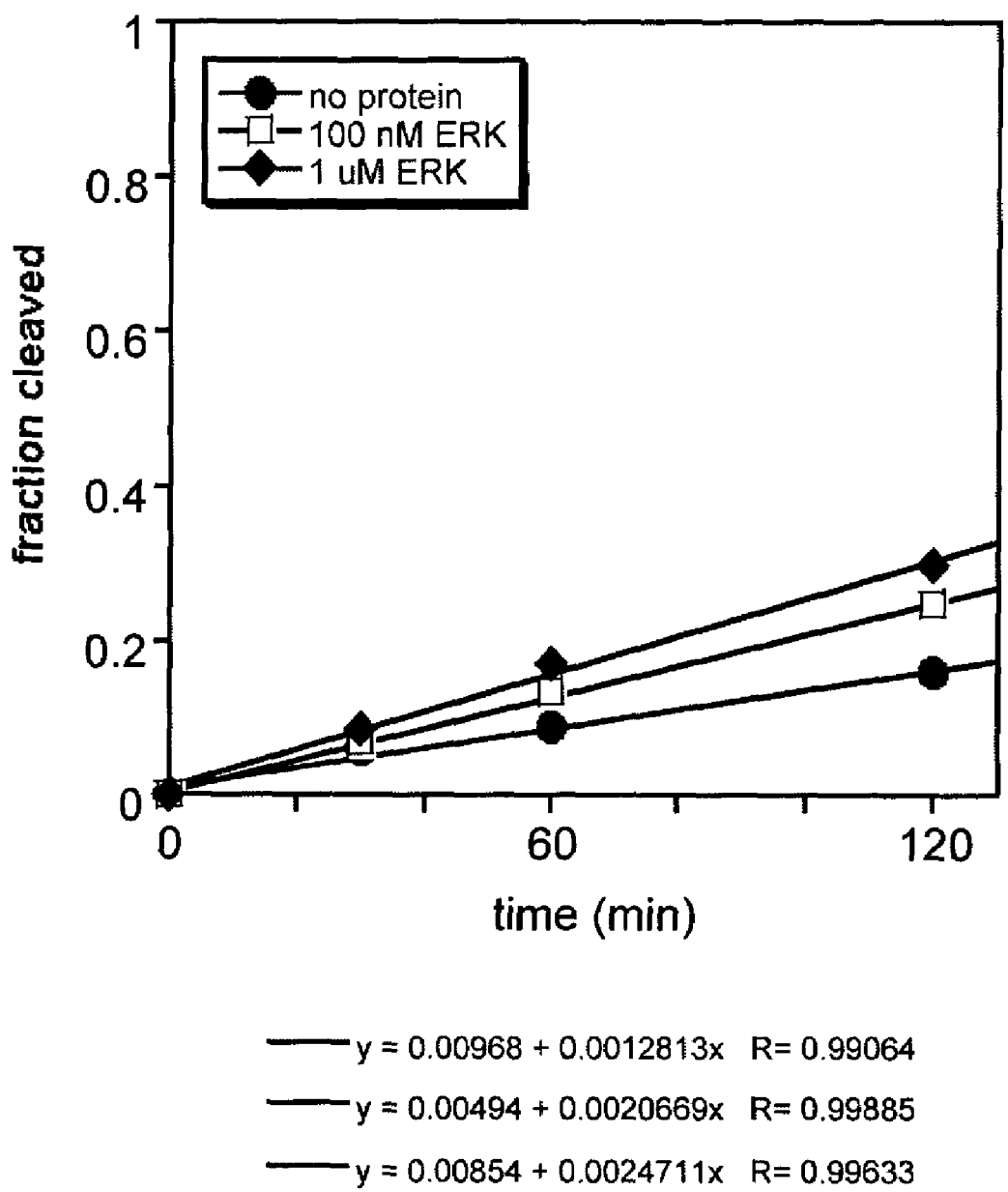
FIG. 20A is a chart showing measurement of cis-hammerhead cleavage.
Figure 20B:
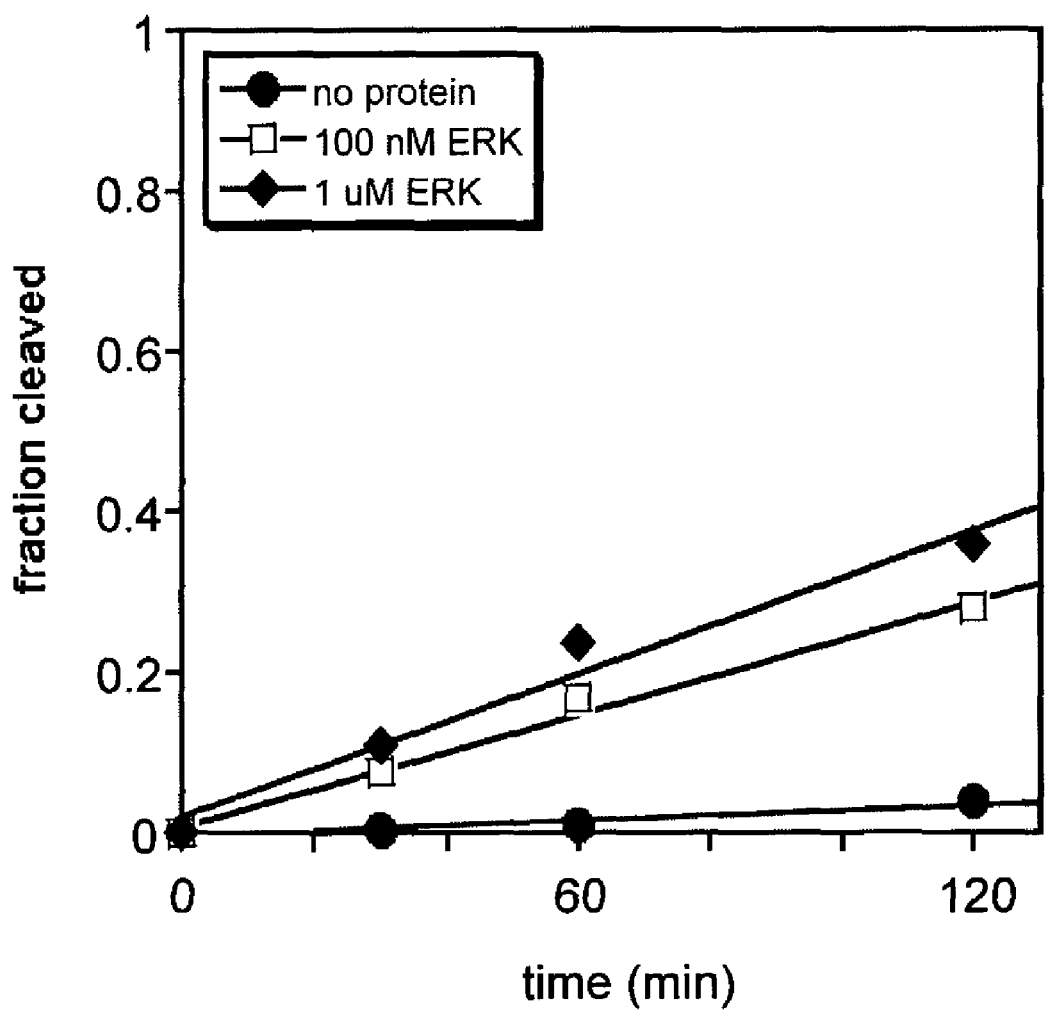
FIG. 20B shows a chart showing measurement of cis-hammerhead cleavage.
Figure 20C:
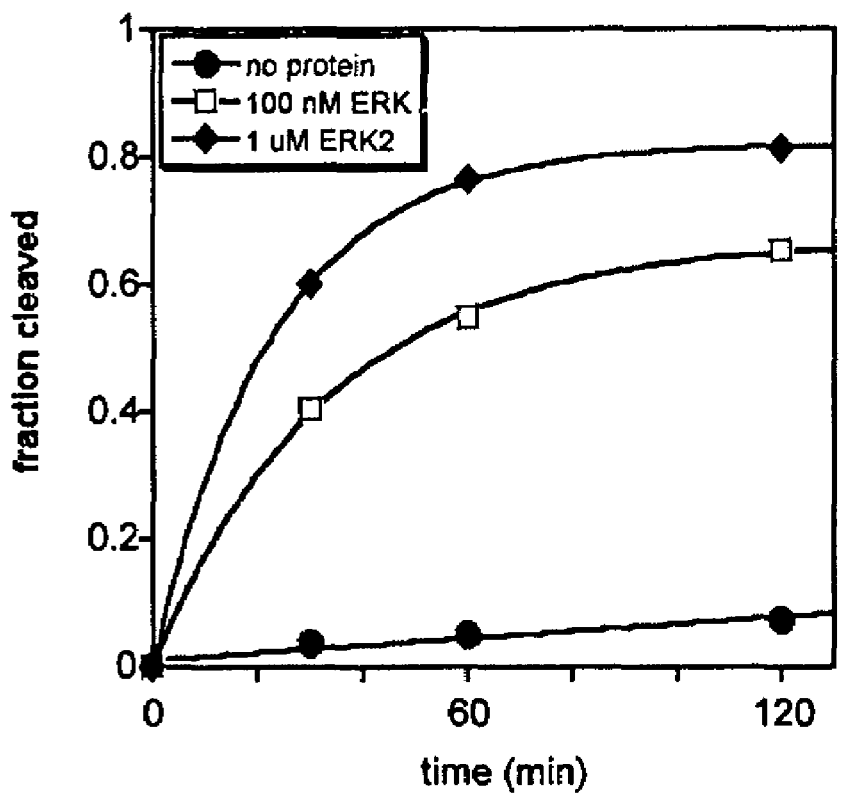
FIG. 20C is a chart showing measurement of cis-hammerhead cleavage.

```
Oligonucleotides common to all selections:

Substrate 3 (DNA, RNA underlined)                                         (SEQ ID NO:321)
Biotin-TEG-CATGCGACCTTACGATCAGATGACCTUGCACU Substrate 3-specific 5'-PCR primer                                        (SEQ ID NO:322)
CATGCGACCTTACGATCAGAT Regeneration 5'-PCR primer                                                (SEQ ID NO:323)
TCTAATACGACTCACTATAGGACTTCGGCGAAAGC ERK selection-specific oligonucleotides:

Library (DNA) (random regions 3-5 nucleotides in length)                  (SEQ ID NO:324)
GGACTTCGGCGAAAGCCGTTCGACCNNN(N)(N)AAGGAGGATTTCCGAAAGCGGCTA
CGGTCCGCCNNN(N)(N)CTTAGACAGGAGGTTAGGTGCGTAGGTAACCGATAGTTCC
G Effector (2'-O-methyl DNA), 3'-PCR primer (DNA) and RT primer (DNA)       (SEQ ID NO:325)
CGGAACTATCGGTTACCTAC B ppERK selection-specific oligonucleotides:

Library                                                                   (SEQ ID NO:326)
GGACTTCGGCGAAAGCCGTTCGACCNNNN(N)(N)CAGACGCTAGCGAATTGGTTCCT
CGAAAGGGGAAAGCGTTATTAAGAAACCAAAATGNNNN(N)(N)CTTAGACAGGAGG
TTAGGTGCGTCAATGCTGCAAGTTACTG Effector (2'-O-methyl DNA), 3'-PCR primer (DNA) and RT primer (DNA)       (SEQ ID NO:327)
CAGTAACTTGCAGCATTGAC bFGF selection-specific oligonucleotides:

Library (random regions 5-7 nucleotides in length)                        (SEQ ID NO:328)
GGACTTCGGCGAAAGCCGTTCGACCNNNNN(N)(N)GCAACGCTACAGACAAG
TGCANNNNN(N)(N)CTTAGACAGGAGGTTAGGTGCCCGAGTTGTTCGAACGAGAC Effector (2'-O-methyl DNA), 3'-PCR primer (DNA) and RT primer (DNA)       (SEQ ID NO:329)
GTCTCGTTCGAACAACTCGG Thrombin selection-specific oligonucleotides Library                                                                   (SEQ ID NO:330)
GGACTTCGGCGAAAGCCGTTCGACCNNNN(N)(N)ATCGAAGTTAGTAGGNNN(N)(N)C
TTAGACAGGAGGTTAGGTGCGTCAATCGATTGCAGATCCG Effector (2'-O-methyl DNA), 3'-PCR primer (DNA) and RT primer (DNA)       (SEQ ID NO:331)
CGGATCTGCAATCGATTGAC
``` released over time by a radiolabeled nucleic acid sensor molecule. Significant amounts signal, corresponding to cleavage of the nucleic acid sensor molecule is observed over time only with the nonphosphorylated ERK. Clones1-2, 1-13 and 1-14 all display sensitivity to ERK concentration, as shown in FIGS. 20A, B and C. However, of these three clones, clone 1-14 displays the greatest enhancement in activity upon addition of ERK. Clone 1-14 is able to differentiate between varying concentrations of ERK, as indicated by the dose-dependent change in the activity of clone-14 upon the addition of 5, 10, 20, 50 and 100 nM ERK (FIG. 21).

Example 18

ERK-modulated NASM-based Competitive Inhibition Assays, & Target-protein Specific Profiling Biosensors.

Figure 22A:
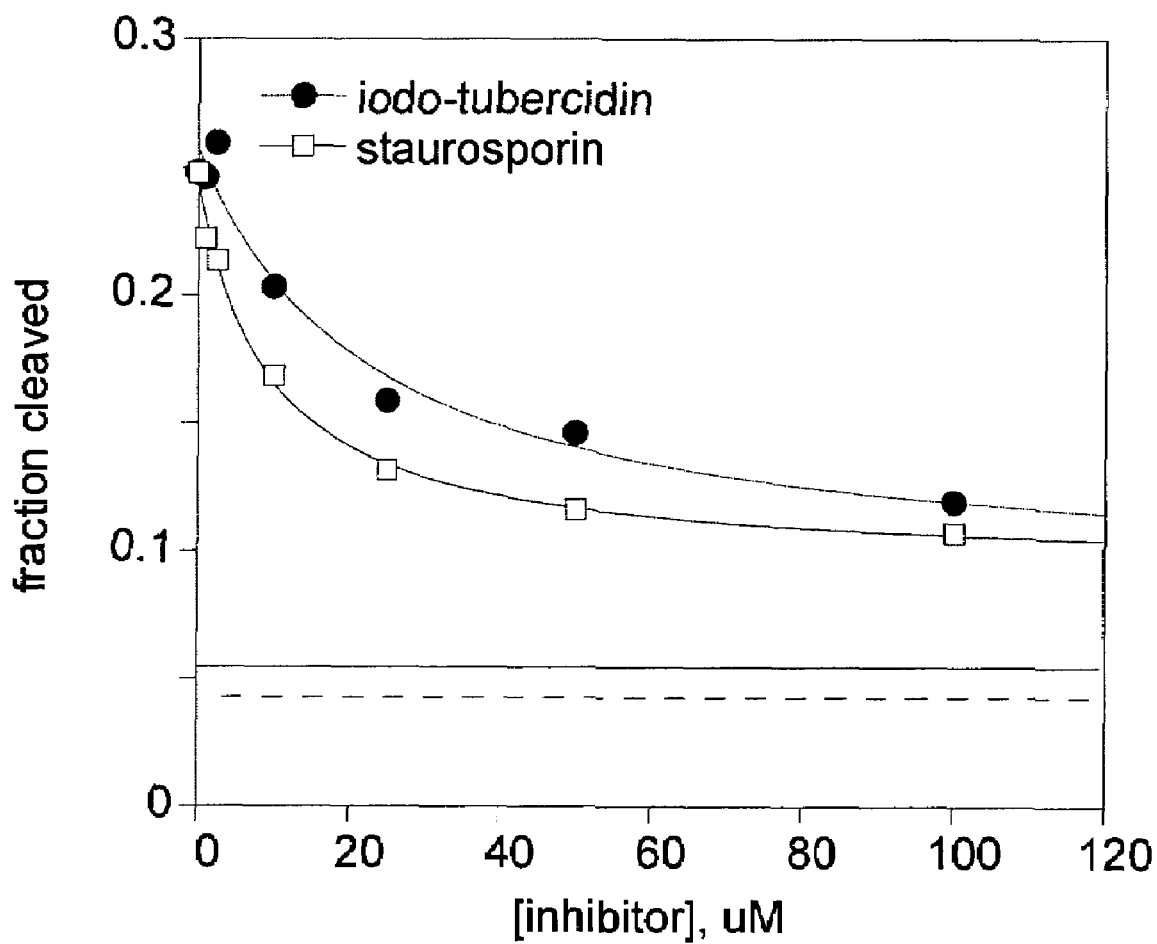
FIG. 22A is a chart showing the measurement of ERK2-inhibitor IC50 values by nucleic acid sensor molecule.

The specificity of the interaction between clone 1-14 and ERK was assessed by measuring the activity of clone 1-14 in the presence of 50 nM ERK and increasing concentrations of known protein kinase inhibitors. The kinase inhibitors staurosporine and 5-iodo-tubercidin are compounds that are known bind to in an ATP-substrate competitive manner to ERK and to modulate ERK kinase catalytic activity, decreasing its ability to phosphorylate other proteins. We tested whether kinase inhibitors would compete directly for the ATP-binding site in ERK, and thereby block NASM activation by ERK. As shown in FIG. 22A, increasing concentrations of the compounds staurosporin and or ITU disrupt the interaction between clone 1-14 and ERK protein, suppressing the activation of the nucleic acid sensor molecule. We have used NASM-based assay to confirm the known kinase-inhibitory IC50 values of staurosporin and ITU (5 and 1 uM, respectively). This result indicates that clone 1-14 recognizes free unliganded ERK and is not modulated by the ERK-stuaroporine or ERK-ITU complex. Since, staurosporin or ITU (ATP analogs) are general kinase inhibitors, and bind to the active/ATP binding sites of kinases, these data suggest that the NASMs either bind directly to the kinase active site, or are exquisitely sensitive to the conformational state of the enzyme. Hence, when saturating levels of the kinase inhibitors are present (10 uM) in the NASM-assay, along with uM levels of ERK, the nucleic acid sensor molecule does not signal the presence of ERK protein. Thus, the ERK-modulated NASMs are used as general HTS screening reagents for the discovery of small molecule drug leads.

Figure 58:
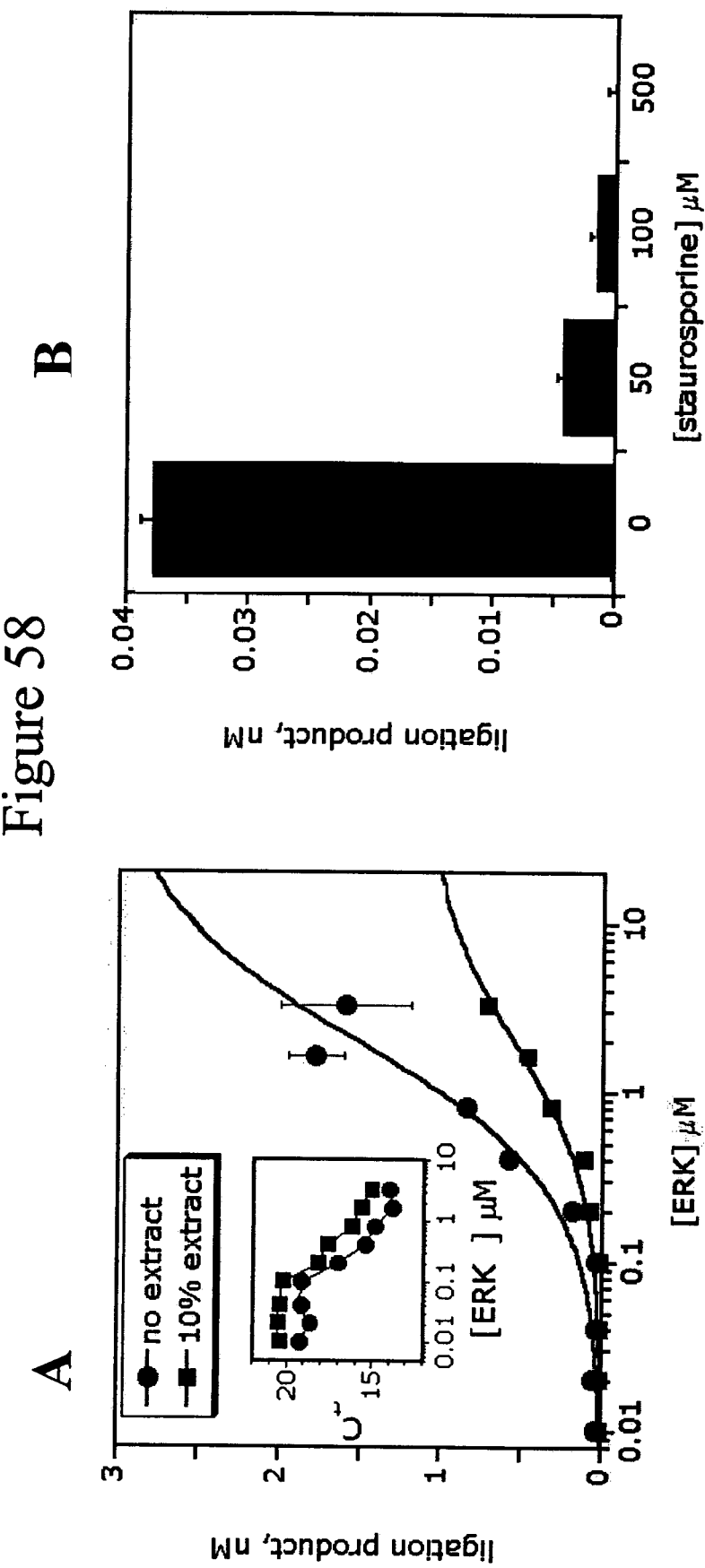
FIG. 58 shows a graph describing the activity of an ERK modulated nucleic acid sensor molecule in the presence of 10% 293 cell extract in the left panel. The right panel shows the activity of an ERK modulated nucleic acid sensor molecule in the presence of increasing concentrations of staurosporine. Both panels show data determined using quantitive PCR methods (ADNA).

Similar results to those described above for the hammerhead-derived NASMs of FIG. 19 have been obtained with ERK-modulated L1-ligase NASMs described in detail in Example 13. FIG. 58, shows additional staurosporine competitive NASM assay results using an L1-ligase-derived NASM which is also modulated by ERK protein. Additional modifications of the 3-piece L1-ligase NASM (c.f., FIG. 36, constructs 27 and constructs 28) render these biosensors suitable for cellular assays as intracellular biosensors (c.f., FIG. 37 and the detailed description of the 3-piece, and 1-piece ligases described in detail in Example 22). Thus, ERK-modulated nucleic acid sensor molecules are used for cell-based drug discovery and drug candidate screening.

Figure 22B:
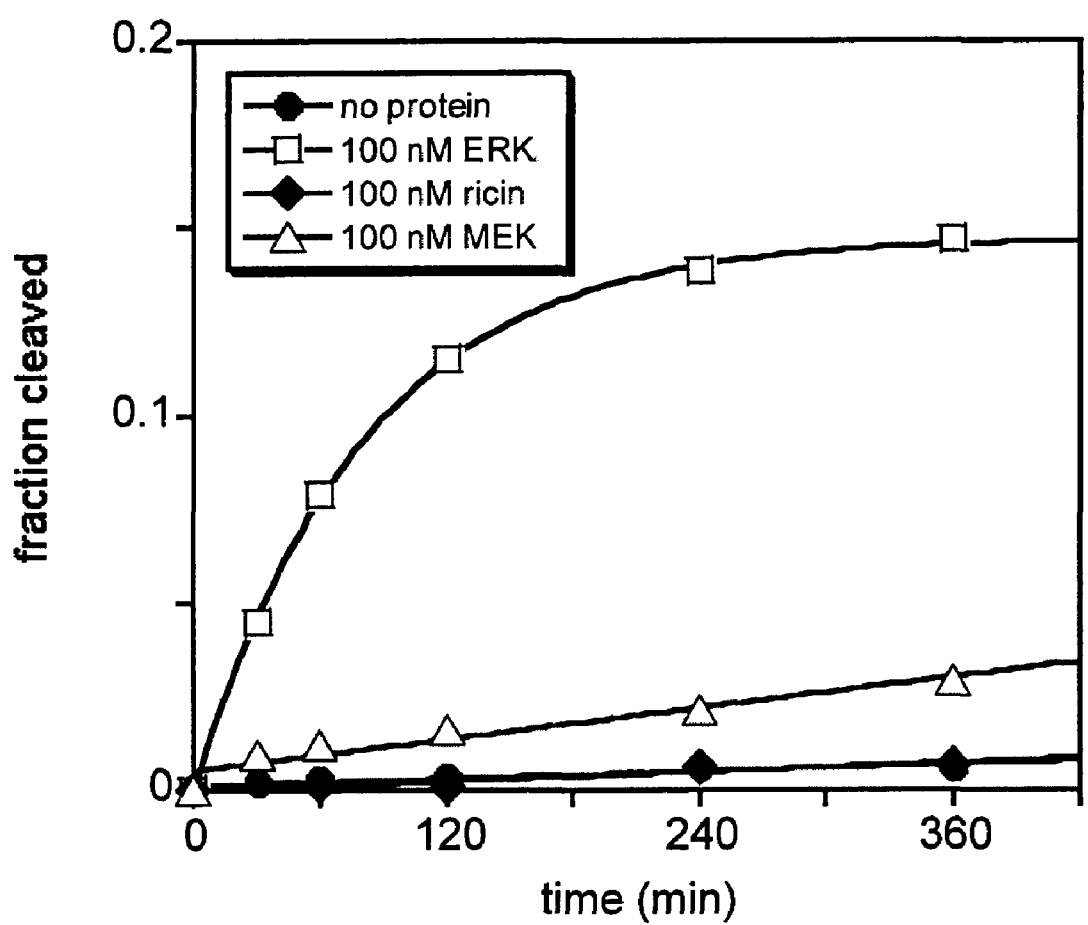
FIG. 22B is a chart showing the fraction of construct I-14 cleaved in the presence of 100 nM ERK2, ricin, or MEK, or with no protein.

The data in FIG. 22B and FIGS. 57A and 57B indicates that ERK NASMs (clone 1-14 and constructs 27 and 28) are modulated specifically by ERK only in its fully active, and not by ppERK, or by related homologues and MAP Kinase pathway molecules, For example clone 1-14 recognizes only ERK, and not related kinase MEK. Hence, NASMs and more specifically, the ERK and ppERK NASMs, are shown here to be useful specific protein profiling biosensors.

A compilation of novel hammerhead ERK-modulated nucleic acid sensor molecule sequences are disclosed in Table 11.

TABLE 11

Cis-hammerhead nucleic acid sensor molecules
Sequences of 157 ERK activated cis-hammerhead clones.

| Sequence | SEQ ID NO: |
|---|---|
| GGGCGACCCUGAUGAGUCGGGCUAAGGAGGAUUUCCGAAAGCGGCUACGGUCCGCCAGUAAUACGAAACGGUGAAAGCCGUAGGUUGCC | 140 |
| GGGCGACCCUGAUGAGGGAGGCUAAGGAGGAUUUCCGAAAGCGGCUACGGUCCGCCAGUUGCGCGAAACGGUGAAAGCCGUAGGUUGCC | 141 |
| GGGCGACCCUGAUGAGGGUUGCUAAGGAGGAUUUCCGAAAGCGGCUACGGUCCGCCAGUGGCCAAACAGNGAAANNNGNANGUGGNC | 142 |
| GGGCGACCCUGAUGAGUACGGCUAAGGAGGAUUUCCGAAAGCGGCUACGGUCCGCCAGUAGAACGAAACGGUGAAAGCCGUAGGUUGCC | 143 |
| GGGCGACCCUGAUGAGNCAUGCUAAGGAGGAUUUCCGAAAGCGGCUACGGUCCGCCAGUAACNCGAAACGGUGAAAGCCGUAGGUUGCC | 144 |
| GGGCGACCCUGAUGAGUUGCGCUAAGGAGGAUUUCCGAAAGCGGCUACGGUCCGCCAGUAUAACGAAACGGUGAAAGCCGUAGGUUGCC | 145 |
| GGGCGACCCUGAUGAGUGUUGCUAAGGAGGAUUUCCGAAAGCGGCUACGGUCCGCCAGUUCUACGAAACGGUGAAAGCCGUAGGUUGCC | 146 |
| GGGCGACCCUGAUGAGUAAUGCUAAGGAGGAUUUCCGAAAGCGGCUCGGGCCGCCAGUUAGGCCAAACGGNGAAAGCCCGUANGNUGCC | 147 |
| GGGCGACCCUGAUGAGCUCUGCUAAGGAGGAUUUCCGAAAGCGGCUACGGUCCGCCAGUAUGGCCGAAACGGUGAAAGCCGUAGGUUGCC | 148 |
| GGGCGACCCUGAUGAGGCAUGCUAAGGAGGAUUUCCGAAAGCGGCUACGGUCCGCCAGUGCGGCGAAACGGUGAAAGCCGUAGGUUGCC | 149 |
| GGGCGACCCUGAUGAGCCCCGCUAAGGAGGAUUUCCGAAAGCGGCUACUGGUCCGCCAGUUGAGCGAAACGGUGAAAGCCGUAGGUUGCC | 150 |
| GGGCGACCCUGAUGAGUACGGCUNAGGAGGAUUUCCGAAGCGGNUACUGGUCCGNCAGUNANACGAAACNGNGAAAGCCGUAGGUUGCC | 151 |
| GGGCGACCCUGAUGAGCCAUGCUAAGGAGGAUUUCCGAAAGCGGCUACUGGUCCGCCAGUACUACAGAAACGGUGAAAGCCGUAGGUUGCC | 152 |

TABLE 11-continued

Cis-hammerhead nucleic acid sensor molecules
Sequences of 157 ERK activated cis-hammerhead clones.

| Sequence | SEQ ID NO: |
| --- | --- |
| GGGCGACCCUGAUGAGUGACGCUAAGGAGGAUUUCCGAAAGCGGCUACUGGUCCGCCAGUUGCGCGAAACGGUGAAAGCCGUAGGUUGCC | 153 |
| GGGCGACCCUGAUGAGUCUGGCUAAGGAGGAUUUCCGAAAGCGGCUACUGGUCCGCCAGUUUCGCGAAACGGUGAAAGCCGUAGGUUGCC | 154 |
| GGGCGACCCUGAUGAGNANCGCUAAGGAGGAUUUCCGAAAGCGGCUACUGGUCCGCCAGUGAUACGAAACGGUGAAAGCCGUAGGUUGCC | 155 |
| GGGNGACCCUGANGANNGACGCUNAAGAGGAUUUCCGAAAGCGGCUACUAGUCCNCAUUGNACCGAAACGGCUAAAGCCGGAGGUUGCC | 156 |
| GGGCGACCCUGAUGAGAUACGCUAAGGAGGAUUUCCGAAAGCCGGNUACGGUCCGACAGUCUAGCCCAAACGGUGAAAGCCGUAGGUUGUCC | 157 |
| GGGCGACCCUGAUGAGUGGCGCUAAGGAGGAUUUCCGAAAGCGGCUACGGUCCGCCAGUUCAACGAAACGGUGAAAGCCGUAGGUUGCC | 158 |
| GGGCGACCCUGAUCAGCUGUGCUAAGGAGGAUUUCCGAAAGCGGCUACGGUCCGCCAGUUCGACGAAACGGUGAAAGCCGUAGGUUGCC | 159 |
| GGGCGACCCUGAUGAGGCUGGCUAAGGAGGAUUUCCGAAAGCGGCUACGGUCCGCCAGUUAGACGAAACGGUGAAAGCCGUAGGUUGCC | 160 |
| GGGCGACCCUGAUGAGAACUGCUAAGGAGGAUUUCCGAAAGCGGCUACGGUCCGUCAGUACUCGAAACGGUGAAAGCCGUAGGUUGCC | 161 |
| GGGCGACCCUGAUGAGNGCUGCUAAGGAGGAUUUCCGAAAGCGGCUACGGUCCGCCAGUGCUGCGAAACGGUGAAAGCCGUAGGUUGCC | 162 |
| GGGCGACCCUGAUGAGNANGGCUAAGGAGGAUUUCCGAAAGCGGCUACGGUCCGCCAGUAAUGCGAAACGGUGAAAGCCGUAGGUUGCC | 163 |
| GGGCGACCCUGAUGAGNUNUGCUAAGGAGGAUUUCCGAAAGCGCUUNCGGCCNCACNACNCCGAAACNGNGAAANNCCGNANGUGGNC | 164 |
| GGGCGACCCUGAUGAGGAGUGCUAAGGAGGAUUUCCGAAAGCGGCUACGGUCCGCCAGUUAUACGAAACGGUGAAAGCCGUAGGUUGCC | 165 |
| GGGCGACCCUGAUGAGACCUGCUAAGGAGGAUUUCCGAAAGCGGCUACGGUCCGCCAGUCNCACGAAACGGUGAAAGCCGUAGGUUGCC | 166 |
| GGGCGACCCUGAUGAGGCGCGCUAAGGAGGAAUUCCGAAAGCGGCUACGGUCCGCCAGUGUAACGAAACGGUGAAAGCCGUAGGUUGCC | 167 |
| GGGCGACCCUGAUGAGUAACGCUAAGGAGGAUUUCCGAAAGUCGGGUACGGUCCGCCAGUUUAUCGAAACGGNGAAAGCCGUAGGUUGCC | 168 |
| GGGCGACCCUGAUGAGNUACGCUAAGGAGGAUUUCCGAAAGCGGCUACGGUCCGCCAGUGUCACGAAACGGUGAAAGCCGUAGGUUGCC | 169 |
| GGGCGACCCUGAUGAGUUGCGCUAAGGAGGAUUUCCGAAAGCGGCUACGGUCCGCCAGUUACGCGAAACGGUGAAAGCGUANGNUGCC | 170 |
| GGGCGACCCUGAUGAGUNUNGCUAAGGAGGAUUUCCGAAAGCGGCUACGGUCCGCCAGUNNUACGAAACGGUGAAAGCCGUAGGUUGCC | 171 |
| GGGCGACCCUGAUGAGACUG-CUAAGGAGGAUUUCCGAAAGCGGCUACGGUCCGCCAGUUGGACGAAACGGUGAAAGCCGUAGGUUGCC | 172 |
| GGGCGACCCUGAUGAGGUGCGCUAAGGAGGAUUUCCGAAAGCGGCUACGGUCCGCCAGACGUCGAAACGGUGAAAGCCGUAGGUUGCC | 173 |
| GGGCGACCCUGAUGAGUAUUGCUAAGGAGGAUUUCCGAAAGCGGCUACGGUCCGCCAGUUUAGCGAAACGGUGAAAGCCGUAGGUUGCC | 174 |
| GGGCGACCCUGAUGAGUGGCGCUAAGGAGGAUUUCCGAAAGCGGCUACGGUCCGCCAGUUAACCGAAACGGUGAAAGCCGUAGGUUGCC | 175 |
| GGGCGACCCUGAUGAGCUCAGCUAAGGAGGAUUUCCGAAAGCGGCUACGGUCCGCCAGUUUGGCGAAACGGUGAAAGCCGUAGGUUGCC | 176 |
| GGGCGACCCUGAUGAGCCUNGCUAAGGAGGAUUUCCGAAAGCGGCUACGGUCCGCCAGUNACUGCGAAACGGUGAAAGCCGUAGGUUGCC | 177 |
| GGGCGACCCUGAUGAGUCAUGCUAAGGAGGAUUUCCGAAAGCGGCUACGGUCCGCCAGUUUUGCGAAACGGUGAAAGCCGUAGGUUGCC | 178 |
| GGGCGACCCUGAUGAGAACCGCUAAGGAGGAUUUCCGAAAGCGGCUACGGUCCGCCAGUUAUGCGAAACGGUGAAAGCCGUAGGUUGCC | 179 |
| GGGCGACCCUGAUGAGGGNGGCUAAAGAGGAUUUCCGAAAGCGGCUACGGUCCGCCAGUUACACGAAACGGUGAAAGCCGUAGGUUGCC | 180 |
| GGGCGACCCUGAUGAGUGACGCUAANGAGGAUUUCCGAAAGCGGCUACGGUCCNCCAGUUUAACGAAACGGUGAAAGCCGUANGUUGCC | 181 |
| GGGCGACCCUGAGAGUACNNGCUAAGGAGGAUUUCCGAA-GCGGCUACGGUCCGCCAGUNNAACGAAACGGUGAAAGCCGUAGGUUGCC | 182 |
| GGGCGACCCUGAGGAGCUCAGCUAAGGAGGAUUUCCGAAAGCGGCUACGGUCCGCCAGUCAGUACGAAACGGUGAAAGCCGUAGGUUGCC | 183 |
| GGGCGACCCUGAGAGGAUA-GCUAAGGAGGAUUUCCGAA-GCGGCUACGGUCCGCCAGUACAACGAAACGGUGAAAGCCGUAGGUUGCC | 184 |
| GGGCGACCCUGAUGAGUAGUGCUAAGGAGGAUUUCCGAAAGCGGCUACGGUCCGCCAGUGUGACGAAACGGUGAAAGCCGUAGGUUGCC | 185 |
| GGGCGACCCUGAUGAGUCGUGCUAAGGAGGAUUUCCGAAAGCGGCUACGGUCCGCCAGUUGAACGAAACGGUGAAAGCCGUAGGUUGCC | 186 |
| GGGCGACCCUGNNGAGAACUGCUAAGGAGGAUUUCCGAAAGCGGCUACGGUCCGCCAGUUAUGCGAAACGGUGAAAGCCGUANGUUGCC | 187 |
| GGGCGACCCUGANGAGNUCNGCUNAGGAGGAUUUCCGAAAGCGGCUACGGAGCCGUCAGUAUUGCGAAACGGCGAAAGCCGUAGGUUGNC | 188 |
| GGGCGACCCUGAUGAGUAACGCUAAGGAGGAUUUCCGAAAGCGGCUACGGUCCGCCAGUAUUGCGAAACGGUGAAAGCCGUAGGUUGCC | 189 |

TABLE 11-continued

Cis-hammerhead nucleic acid sensor molecules
Sequences of 157 ERK activated cis-hammerhead clones.

| Sequence | SEQ ID NO: |
|---|---|
| GGGCGACCCUGAUGAGCUUAGCUAAGGAGGAUUUCCGAAAGCGGCUACGGUCCGCCAGUGAAACGAAACGGUGAAAGCCGUAGGUUGCC | 190 |
| GGGCGACCCUGAUGAGNCCAGCUAAGGAGGAUUUCCGAAAGCGGCUACGGNCCGCCAGUUACCCGAAACGGNGAAAGCCGUANGUUGCC | 191 |
| GGGCGACCCUGAUGAGNNCAGCUAAGGAGGAUUUCCGAAAGCGGCUACGGNCCGCCAGUUACCCGAAACGGNGAAAGCCGUAGGUUGCC | 192 |
| GGGCGACCCUGAUGAGCUUCGCUAAGGAGGAUUUCCGAAAGCGGCUACGGUCCGCCAGUUAGUCGAAACGGUGAAAGCCGUAGGUUGCC | 193 |
| GGGCGACCCUGAUGAGCNNNGCUAAGGAGGAUUUCCGAAAGCGGCUACGGUCCGCCAGUUNUCGAAACGGUGAAAGCCGUAGGUUGCCU | 194 |
| GGGCGACCCUGAUGAGACCUGCUAAGGAGGAUUUCCGAAAGCGGCUACGGUCCGCCAGUUAAUCGAAACGGUGAAAGCCGUAGGUUGCC | 195 |
| GGGCGACCCUGAUGAGCACUGCUAAGGAGGAUUUCCGAAAGCGGCUACGGUCCGCCAGUCGCGCGAAACGGUGAAAGCCGUAGGUUGCC | 196 |
| GGGCGACCCUGAUGAGAUCUGCUAAGGAGGAUUUCCGAAAGCGGCUACGGUCCGCCAGUNACGCGAAACGGUGAAAGCCGUAGGUUGCC | 197 |
| GGGCGACCCUGA-GAGUUUUGCUAAGGAGGAUUUCCGAA-GCGGCUACGGUCCGCCAGUAAUCCGAAACGGUGAAAGCCGUAGGUUGCC | 198 |
| GGGCGACCCUGN-GAGUUUAGCUAAGGAGGAUUUCCGAA-GCGGCUACGGUCCGCCAGUUUAGCGAAACGGUGAAAGCCGUAGGUUGCC | 199 |
| GGGCGACCCUGNNGAGGCGUGCUAAGGAGGAUUUCCGAA-GCGGCUACGGUCCGCCAGUUAGACGAAACGGUGAAAGCCGUAGGUUGCC | 200 |
| GGGCGACCCUGAUGAGUACUGCUAAGGAGGAUUUCCGAA-GCGGCUACGGUCCGCCAGUACUACGAAACGGUGAAAGCCGUAGGUUGCC | 201 |
| GGGCGACCCUGAUGAGCAGAGCUAAGGAGGAUUUCCGAAAGCGGCUACGGUCCGCCAGUUUUACGAAACGGUGAAAGCCGUAGGUUGCC | 202 |
| GGGCGACCCUGAUGAGCAUAGCUAAGGAGGAUUUCCGA-AGCGGCUACGGUCCGCCAGUUGCACGAAACGGUGAAAGCCGUAGGUUGCC | 203 |
| ---------UGNAGAGCGUUGCUAAGGAGGAUUUCCGAAAGC-GCUACGUCCGCCAGUAACACGAAACGGUGAAAGCCGUAGGUUGCCUU | 204 |
| GGGCGACCCUGAUGAGCAACGCUAAGGAGAAUUUCCGAAAGCGGCUACGGUCCGCCAGUUACCCGAAACGGUGAAAGCCGUAGGUUGCC | 205 |
| GGGCGACCCUGAUGAGGGAGGCUAAGGAGGAUUUCCGAAAUCGGCUACGGUCCGCCAGUCAUACGAAACGGUGAAAGCCGUAGGUUGCC | 206 |
| GGGCGACCNUGAUGAGCUUCGCUAAGGAGGAUUUCCGAAAGCGGNUACGGUCCGCCAGUGAUUCGAAACGGUGAAAGCCGUAGGUUGCC | 207 |
| GGGCGACCCUGAUGAGACCGGCUAAGGAGGAUUUCCGAAAGCGGNUACGGUCCGCCAGUCUAUCGAAACGGUNAAAGCCGUAGGUUGCC | 208 |
| GGGCGACCNUGAUGAGUUAUGCUAAGGAGGAUUUCCGAAAGCGGNUACGGUCCGCCAGUGAAUCGAAACGGUGAAAGCCGUAGGUUGCC | 209 |
| GGGCGACCNUGAUGAGUAUAGCUAAGGAGGAUUUCCGAAAGCGGNUACGGUCCGCCAGUCAGACGAAACGGUGAAAGCCGUAGGUUGCC | 210 |
| GGGCGACCNUGAUGAGUNGCGCUAAGGAGGAUUUCCGUAAGCGGCUACGGUCCGCCAGUUUAUNCGAAACGGUGAAAGCCGUAGGUUGCC | 211 |
| GGGCGACCCUGAUGAGCAACGCUAAGGAGGAUUUCCGAAAGCGGCUACGGUCCGCCAGUACCACGAAACGGUGAAAGCCGUAGGUUGCC | 212 |
| GGGCGACCCUGAUGAGUCGCGCUAAGGAGGAUUUCCGAAAGCGGCUACGGUCCGCCAGUNAACGAAACGGUGAAAGCCGUAGGUUGCC | 213 |
| GGGCGACCCUGAUGAGUCACGCUAAGGAGGAUUUCCGAAAGCGGNUACGGUCCGCCAGUUACACGAAACGGUGAAAGCCGUAGGUUGCC | 214 |
| GGGCNACCUCUGAGUAGCAGGCUAAGNAGNAUUUCCGNAACGGNUACGGUCNGCCAGUAUGACGAAACGGUNAAAGCCGUAGGUUGCC | 215 |
| GGGCGACCCUGAUGAGCUGUGCUAAGGAGGAUUUCCGAAAGCGGNNACGGUCCGCCAGUUUCCCGAAACGGUGAAAGCCGUAGGUUGCC | 216 |
| GGGCNACCUUGAUGAGCANNGCUAAGNAGUAUUUCCNNAACGGAUACGGUCCGCCAGUNNNNCGNAACGGUNAAAGCCGUAGGUUGCC | 217 |
| GGGCGACCCUGAUGAGCAUAGCUAAGGAGGAUUUCCGAAAGCGGCUACGGUCCGCCAGUACGACGAAACGGUGAAAGCCGUAGGUUGCC | 218 |
| GGGCGACCNUGAUGAGCUCUGCUAAGGAGGAUUUCCGAAAGCGGNUACGGUCCGCCAGUUCAACGAAACGGUGAAAGCCGUAGGUUGCC | 219 |
| GGGCGACCCUGAUGAGACCAGCUAAGGAGGAUUUCCGAAAGCGGCUACGGUCCGCCAGUGAUUCGAAACGGUGAAAGCCGUAGGUUGCC | 220 |
| GGGCGACCNUGAUGAGCNUGGCUAAGGAGGAUUUCCGAAAGCGGNUACGGUCCGCCAGUGUUACGAAACGGUGAAAGCCGUAGGUUGCC | 221 |
| GGGCGACCNUGAUGAGUCUCGCUAAGGAGGAUUUCCGAAAGCGGNUACGGUCCGCCAGUAAUGCGAAACGGUGAAAGCCGUAGGUUGCC | 222 |
| GGGCNACCUUGAUGAGGUGGGNUAAGGAGUAUUUCCGAAANCGGAUACGGUCCGCCAGUAACCCGAAACGGUNAAAGCCGUAGGUUGCC | 223 |
| GGGNGACCCUGAUGAGUAGGGCUAAGGAGGAUUUCCNAAAGCGGCUACGGUCCGCCANANGUCGAAACGGUGAAAGCCGUAGGUUGCC | 224 |
| GGGNAGACUUGAUGAGUAGCGCUAAGGAGNAUUUCCGAAANCGGNUACGGUCNGCCAGUUGAGCGCAACGGUGAAAGCCGUAGGUUGCC | 225 |

TABLE 11-continued

Cis-hammerhead nucleic acid sensor molecules
Sequences of 157 ERK activated cis-hammerhead clones.

| Sequence | SEQ ID NO: |
|---|---|
| GGGCGACCCUGAUGAGCUCUGCUAAGGAGGAUUUCCGAAAGCGGCUACGGUCCGCCAGUUGGUCGAAACGGUGAAAGCCGUAGGUUGCC | 226 |
| GGGCGACCCUGAUGAGGGCUGCUAAGGAGGAUUUCCGAAAGCGGCUACGGUCCGCCAGUUAAACGAAACGGUGAAAGCCGUAGGUUGCC | 227 |
| GGGNGACCCUGAUGAGCCAUGCUAACGAGNAUUUCUNAAAGCGGC-ACGGUCCGCCAGUUUCGCGAAACGGUGAAAGCCGUAGGUUGCC | 228 |
| GGGCGACCNUGAUGAGUCACGCUAAGGNAGGAUUUCCGAAAGCGGCUACGGUCCGCCAGUCUCACGAAACGGUGAAAGCCGUAGGUUGCC | 229 |
| GGGCGACCCUGAUGAGACUUGGUAAGGAGGAUUUCCGAAANCGNNUACGGUCCGCCAUGUUUAGCGAAACGGUGAAAGCCGUAGGUUGCC | 230 |
| GGGCGACCNUGAUGAGNUUUGCUAAGGAGGAUUUCCGAAAGCGGNUACGGUCCGCCAGUUUAUCGAAACGGUGAAAGCCGUAGGUUGCC | 231 |
| GGGCGACCNUGAUGAGCUACGCUAAGGAGGAUUUCCGAAAGCGGNNACGGUCCGCCAGUUCCACGAAACGGUGAAAGCCGUAGGUUGCC | 232 |
| GGGCGACCNUGAUGAGNNCGNUAAGGAGNAUUUCCGAAAGCGGANACGGUCNGCCAGUNACCGNAACGGUGAAAGCCGUAGGUUGCC | 233 |
| GGGCGACCNUGAUGAGGAAUGCUAAGGAGGAUUUCCGAAAGCGGNUACGGUCCGCCAGUACAGCGAAACGGUGAAAGCCGUAGGUUGCC | 234 |
| GGGCGACCNUGAUGAGUCCUGCUAAGGAGGAUUUCCGAAAGCGGNNACGGUCCGCCAGUAAAGCGAAACGGUGAAAGCCGUAGGUUGCC | 235 |
| GGGCGACCCUGAUGAGUUCUGCUAAGGAGGAUUUCCGAAAGCGGNUACGGUCCGCCAGUUUUACGAAACGGUGAAAGCCGUAGGUUGCC | 236 |
| GGGCGACCNUGAUGAGNAUNGCUAAGGAGGAUUUCCGAAAGCGGCUACGGUCCGCCAGUUANNCGAAACGGUGAAAGCCGUAGGUUGCC | 237 |
| GGGCGACCCUGAUGAGGAAUGCUAAAGAGGAUUUCCGAAAGCGGCUACGGUCCGCCAGUUAAGCGAAACGGUGAAAGCCGUAGGUUGCC | 238 |
| GGGCGACCCUGAUGAGCAGUGCUAAGGAGGAUUUCCGAAAGCGGCUACGGUCCGCCAGUGGAGCGAAACGGUGAAAGCCGUAGGUUGCC | 239 |
| GGGCGACCCUGAUGAGNUAUGCUAAGGAGGAUUUCCGAAAGCGGCUACGGUCCGCCAGUNAGNCGAAACGGUGAAAGCCGUAGGUUGCC | 240 |
| GGGCGACCCUGAUGAGCACUGCUAAGGAGGAUUUCCGAAAGCGGCUACGGUCCGCCAGUGAGACGAAACGGUGAAAGCCGUAGGUUGCC | 241 |
| GGGCGACCCUGAUGAGCUCAGCUAAGGAGGAUU-CCGAAAGCGGCUACGGUCCGCCAGUUUCGCGAAACGGUGAAAGCCGUAGGUUGCC | 242 |
| GGGCGACCCUGAUGAGGCUUGCUAAGGAGGAUUUCCGAAAGCGGCNACGGUCCGCCAGUCCGUCGAAACGGUGAAAGCCGUAGGUUGCC | 243 |
| GGGCGACCCUGAUGAGCUCUGCUAAGGAGGAUUUCCGAAAGCGGCUACGGUCCGCCAGUUCGGCGAAACGGUGAAAGCCGUAGGUUGCC | 244 |
| GGGCGACCCUGAUGAGGCAAGCUAAGGAGGAUUUCCGAAAGCGGCUACGGUCCGCCAGUUCAACGAAACGGUGAAAGCCGUAGGUUGCC | 245 |
| GGGCGACCCUGAUGAGCGUCGCUAAGGAGGAUUUCCGAAAGCGGCUACGGUCCGCCAGUAUCUCGAAACGGUGAAAGCCGUA | 246 |
| GGGCGACCCUGAUGAGCUUCGCUAAGGAGGAUUUCCGAAAGCGGCUACGGUCCGCCAGUUAAACGAAACGGUGAAAGCCGUAGGU | 247 |
| GGGCGACCCUGAUGAGUGGCGCUAAGGAGGAUUUCCGAAAGCGGCUACGGUCCGCCAGUUUAACGAAACGGUGAA | 248 |
| GGGCGACCCUGAUGAGACUCGCUAAGGAGGAUUUCCGAAAGCGGCUACGGUCCGCCAGUGGUACGAAACGGUGAAAGCCGUAGGU | 249 |
| GGGCGACCCUGAUGAGUAUUGCUAAGGAGGAUUUNCCGAAAGCGGCUCACGGUGCCGCCAGUUGAGCGAAACGGUGAAAGCCUAGGUUGCC | 250 |
| GGGCGACCCUGAUGAGCNUCGCUAAGGAGGAUUUCCGAAAGCGGCUACGGUCCGCCAGUAAUACGAAACGGUGAAAGCCGUAGGUUGC | 251 |
| GGGCGACCCUGAUGAGCUNNGCUAAGGAGGAUUUCCGAAAGCGGCUACGGUCCGCCAGUUCNACGAAACGGUGAAAGCCGUAGGUUGCC | 252 |
| GGGCGACCCUGAUGAGUUCGGCUAAGGAGGAUUUCCGAAAGCGGCUACGGUCCGCCAGUGAAGCGAAACGGUGAAAGCCGUAGGU | 253 |
| GGGCGACCCUGAUGAGAUGAGCUAAGGAGGAUUUCCGAAAGCGGCUACGGUCCGCCAGUAAACCGAAACGGUGAAAGCCGUAGGUUGCC | 254 |
| GGGCGACCCUGAUGAGAAUCGCUAAGGAGGAUUUCCGAA-GCG-CUACGGUCCGCCAGUUCCCCGAAACGGUGAAAG | 255 |
| GGGCGACCCUGAUGAGUCACGCUAAGGAGGAUUUCCGAAAGCGGCUACGGUCCGCCAGUUGNCGCGAAACGGUGAAAGCCGUAGGUUGCC | 256 |
| GGGCGACCCUGAUGAGCAUCGCUAAGGAGGAUUUCCGAAAGCGGCUACGGUCCGCCAGUUAAGCGAAACGGUGAAAGCCGUAGGUUGCC | 257 |
| GGGCGACCCUGAUGAGGUCAGCUAAGGAGGAUUUCCGAAAGCGGCUACGGUCCGCCAGUUCAGCGAAACGGUGAAAGCCGUAGG | 258 |
| GGGCGACCCUGAUGAGAAGCGCUAAGGAGGAUUUCCGAAAGCGGCUACGGUCCGCCAGUCUAGCGAAACGGUGAAAGCC | 259 |
| GGGCGACCCUGAUGAGGCUUGCUAAGGAGGAUUUCCGAAAGCGGCUACGGUCCGCCACUUGAUCGAAACGGUGAAAGCCGUGAGGUUGCC | 260 |
| GGGCGACCCUGAUGAGGCUGGCUAAGGAGGAUUUCCGAAAGCGGCUCACGGUCCGCCAGUCCUAACGAAACGGUGAAAGCCGUAGGUUGCC | 261 |
| GGGCGACCCUGAUGAGCCUUGCUAAGGAGGAUUUCCGAAAGCGGCUACGGUCCGCCAGUUAGUCGAAACGGUGAAAGCCGUAGGUUGC | 262 |

TABLE 11-continued

Cis-hammerhead nucleic acid sensor molecules
Sequences of 157 ERK activated cis-hammerhead clones.

| Sequence | SEQ ID NO: |
|---|---|
| GGGCGACCCUGAUGAGUCACGCUAAGGAGGAUUUCCGAAAGCGGCUACGGUCCGCCAGUUNCGCGAA | 263 |
| GGGCGACCCUGAUGAGAACUGCUAAGGAGGAUUUACCGAAAGCGGCUACGGUCCGCCAGUUGCGCGAAACGGUGAAAGCCGUAGGUUGCC | 264 |
| GGGCGACCCUGAUGAGCGACGCUAAGGAGGAUUUCCGAAAGCGGCUACGGUCCGCCAGUUGGGCGAAACGGUGAAAGCCGUAGG | 265 |
| GGGCGACCCUGAUGAGUAACGCUAAGGAGGAUUUCCGAAAGCGGCUACGGUCCGCCAGUCAGACGAAACGGUGAAAGCCGUAGGU | 266 |
| GGGCGACCCUGAUGAGGACUGCUAAGGAGGAUUUCCGAAAGCGGCUACGGUCCGCCAGUUACUCGAAACGGUGAAAGCCGUAGGU | 267 |
| GGGCGACCCUGAUGAGCCGGGCUAAGGAGGAUUUCCGAAAGCGGCUACGGUCCGCCAGUUGAGCGAAACGGUGAAAGCCGUAGGUUGCC | 268 |
| GGGCGACCCUGAUGAGCANAGCUAAGGAGGAUUUCCGAAAG | 269 |
| GGGCGACCCUGAUGAGUUGCGCUAAGGAGGAUUUCCGAAAGCGGCUACGGUCCGCCAGUUUAGCGAAACGGUGAAAGCCGUAGGU | 270 |
| GGGCGACCCUGAUGAGCAGCGCUAAGGAGGAUUUCCGAAAGCGGCUAGGUCCGCCAGUCUUCGAAACGGUGAAAGCCGUAGGUUG | 271 |
| GGGCGACCCUGAUGAGUAAGGCUAAGGAGGAUUUCCGAAAGCGGCUACGGUCCGCCAGUGUUGCGAAACGGUGAA | 272 |
| GGGCGACCCUGAUGAGCACCGCUAAGGAGGAUUUCCGAAAGCGGCUACGGUCCGCCAGUUACGCGAAACGGUGAAAGCCGUAGGUUGCC | 273 |
| GGGCGACCCUGAUGAGGCAUGCUAAGGAGGAUUUCCGAAAGCGGCUACGGUCCGCCAGUAAGGCGAAACGGUGAAAGCCGUA | 274 |
| GGGCGACCCUGAUGAGUUUAGCUAAGGAGGAUUUCCGAAAGCGGCUACGGUCCGCCAGUAGACCGAAACGGUGAAAG | 275 |
| GGGCGACCCUGAUGAGAAGCGCUAAGGAGGAUUUCCGAAAGCGGCUACGGUCCGCCAGUAAUGCGAAACGGUGAAAG | 276 |
| GGGUGACCUCUGAUAGUGUUGCUAAGGAGGGAUUUCCGAAAGCGGNUACGGUCCGCCAGUAGAGCGAAACGGUGAAAGCCGUAGGUUGCC | 277 |
| GGGCGACCNUGAUGAGCANGCGCUAAGGAGGAUUUCCGAAAGCGGNUACGGUCCGCCAGUGACUCGAAACGGUGAAAGCCGUAGGUUGCC | 278 |
| GGGCGACCCUGAUAGUAGCGCUAAGUAAGGAUNUUCCGAAAGCGCGCUCACGGUCCGCCAGUCUCACGANNCGGUNAAAG | 279 |
| GGGNGACCCUGAUGAGUAUNAGCUAAGGAGGAUUUCCGAAAGCGGCUACGGNCCGCCAGUAAUGNGAAACGGUGAAAGCCGUAGGUUGCC | 280 |
| GCGCGACCUUGAUGAAGGNCAGNUAAGGAGGAUUUCCGAAAGCGGNUACGGUCAGCCAGUGGCACGAAACGGUGAAAGCCGUAGGUUGCC | 281 |
| GGGCGACCCUGAUGAGCAUGCUAAGGAGGAUUUCCGAAAGCGGCUACGGUCCGCCAGUUAGUCGAAACGGUGAAAGCCGUAGGUUGCC | 282 |
| GGGCGACCCUGAUGANNGCUGNUAGGAGGAUUUCCGAAANUGCUUCUGGCCCGCANUUANNCCGAACGGGCNAAANCGAANGGUGNC | 283 |
| GGGCGACCCUGAUGAGUAGGCUAAGGAGGAUUUCGAAAGCGGCUACGGUCCGCCAGUGUGCCGAA | 284 |
| GGGCGACCCUGCUGAGCNACGCUANGAGGAUUUCCGAAAGCGGCUACGGNCCGCCAGUCNGACGAAACGGUGAAAGCCGUAGGUUGCC | 285 |
| Construct 1-14<br>GGGCGACCCUGAUGAGGGUCGCUAAGGAGGAUUUCCGAAAGCGGCACGGUCCGCCAGACGUCGAAACGGUGAAAGCCGUAGGUUGCC | 286 |
| Construct 1-13<br>GGGCGACCCUGAUGAGUCUUCUAAGGAGGAUUUCCGAAAGCGGCACGGUCCGCCAGUACGUCGAAACGGUGAAAGCCGUAGGUUGCC | 287 |
| Construct 1-2<br>GGGCGACCCUGAUGAGCCUUCUAAGGAGGAUUUCCGAAAGCGGCACGGUCCGCCAGACGUCGAAACGGUGAAAGCCGUAGGUUGCC | 288 |
| Construct 1-6<br>GGGCGACCCUGAUGAGUCAUGCUAAGGAGGAUUUCCGAAAGCGGCACGGUCCGCCAGACGUCGAAACGGUGAAAGCCGUAGGUUGCC | 289 |
| Construct 2-7<br>GGGCGACCCUGAUGAGCCUUGCUAAGGAGGAUUUCCGAAAGCGGCACGGUCCGCCAGUCAGUCGAAACGGUGAAAGCCGUAGGUUGCC | 290 |
| Construct 2-2<br>GGGCGACCCUGAUGAGCCUCGCUAAGGAGGAUUUCCGAAAGCGGCACGGUCCGCCAGCUAGCGAAACGGUGAAAGCCGUAGGUUGCC | 291 |
| Construct 2-3<br>GGGCGACCCUGAUGAGAACUGCUAAGGAGGAUUUCCGAAAGCGGCACGGUCCGCCAGUUUAACGAAACGGUGAAAGCCGUAGGUUGCC | 292 |
| Construct 2-13<br>GGGCGACCCUGAUGAGUAAAGCUAAGGAGGAUUUCCGAAAGCGGCACGGUCCGCCAGUCUGGCGAAACGGUGAAAGCCGUAGGUUGCC | 293 |

TABLE 11-continued

Cis-hammerhead nucleic acid sensor molecules
Sequences of 157 ERK activated cis-hammerhead clones.

| Sequence | SEQ ID NO: |
|---|---|
| Construct 2-14<br>GGGCGACCCUGAUGAGUUUUGCUAAGGAGGAUUUCCGAAAGCGGCACGGUCCGCCAGUGAUCCGAAACGGUGAAAGCCGUAGGUUGCC | 294 |
| Construct 2-20<br>GGGCGACCCUGAUGAGGCGAGCUAAGGAGGAUUUCCGAAAGCGGCACGGUCCGCCAGUUUAACGAAACGGUGAAAGCCGUAGGUUGCC | 295 |

These results demonstrate that the nucleic acid sensor molecule is specific for the non-phosphorylated form of the ERK.

Example 19

Cis-hammerhead-derived Nucleic Acid Sensor Molecules Activated by ppERK

Figure 23A:
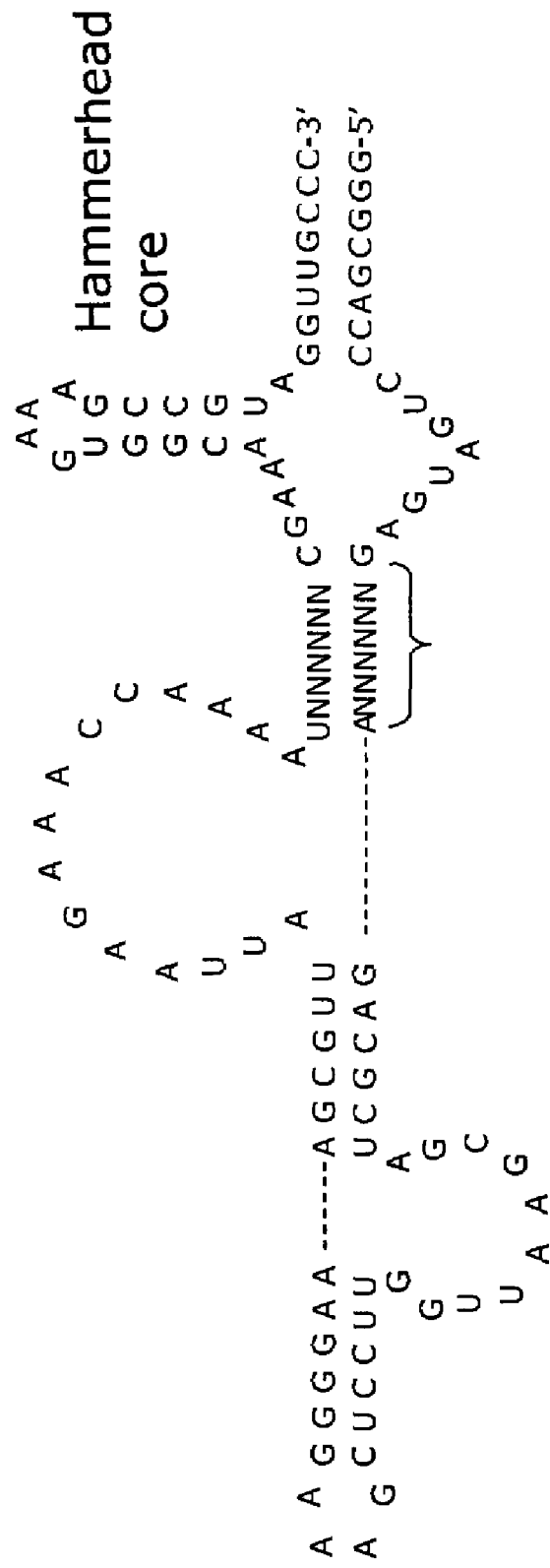
FIG. 23A shows a ppERK cis-hammerhead nucleic acid sensor molecule construct (SEQ ID NO:353).

A stem-selection library of hammerhead-derived nucleic acid sensor molecules modulated by ppERK is shown in FIG. 23A. ppERK-modulated nucleic acid sensor molecules were designed to by joining ppERK a target modulation domain (TMD) to a hammerhead core sequence via a linker region. FIG. 23A shows the general structure of ppERK-modulated hammerhead ribozyme with the linker region depicted as a randomized sequence (N6). Individual ppERK dependent cis hammerhead RNA sequences are shown in FIG. 23B.

FIG. 24 is a table displaying different properties of the cis hammerhead ERK sensors shown in FIG. 23B. Each construct displays variability in its sequence, its activity and its stability.

Figure 25:
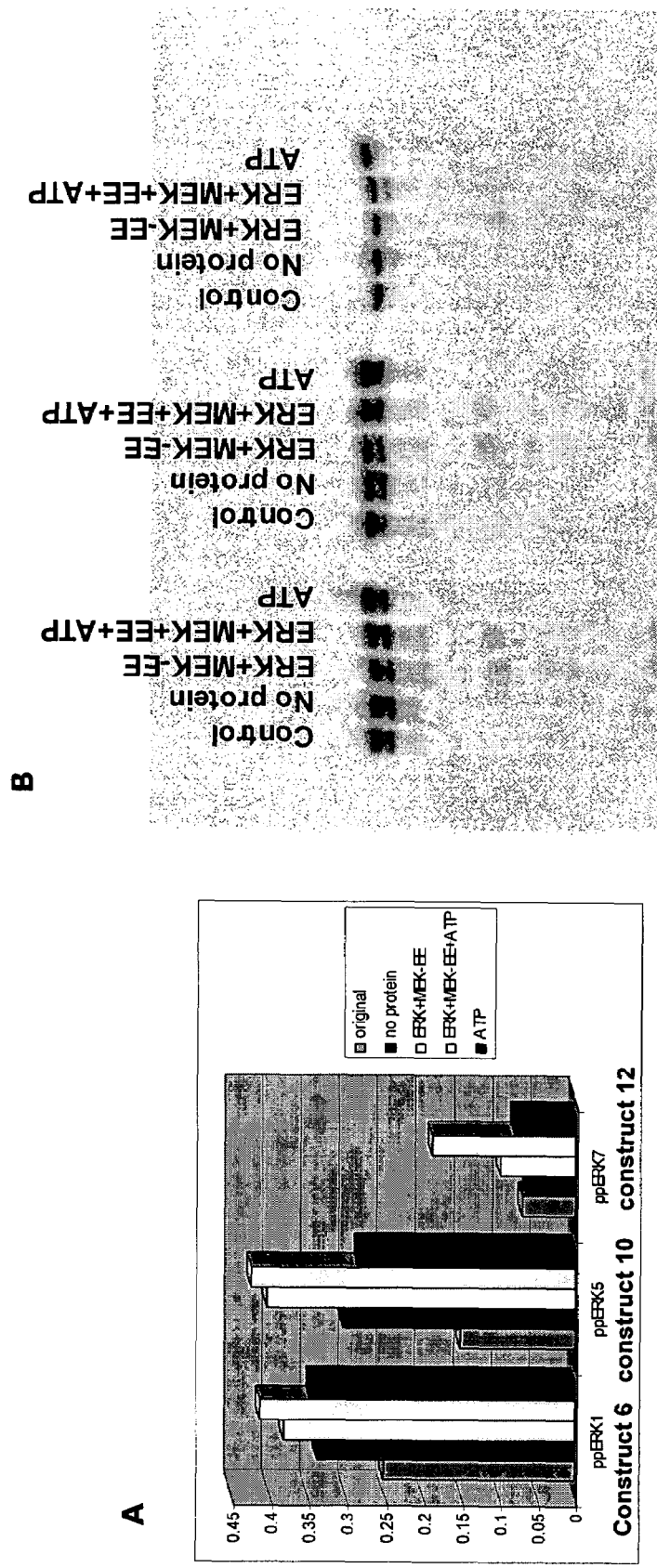
FIGS. 25A and B show a bar graph and corresponding radiograph demonstrating the relative pp ERK dependence of constructs 6, 10, and 12.

FIG. 25 shows data for the ppERK-NASMs that have been tested in target modulation assays using in situ generated ppERK (using constitutively activated MEK activate to generate ppERK from native ERK). ppERK has been generated in situ by direct phosphorylation of ERK with constitutively active MEK mutant, MEK-EE in the presence of $MgCl_2$ and ATP. FIG. 25 also shows data for radiolabeled nucleic acid sensor molecules for ppERK-hammerhead NASM constructs 6, 10, and that were incubated at 37° C. for 30 minutes in the absence of protein; in the presence of 2 µM ERK, 0.14 µM constitutively active MEK (MEK-EE); in the presence of 2 µM ERK, 0.14 µM constitutively active MEK-EE, 1 mM ATP; in the presence of 1 mM ATP only. All these reactions were performed in the following buffer of 20 mM HEPES (pH 7.5), 10 mM MgCl2, and 0.1 mM EDTA. The mixtures of ERK, ERK+MEK–EE, and ERK+MEK+EE with ATP were incubated in the presence of 10 mM MgCl2 prior to mixing with radiolabeled nucleic acid sensor molecule. After the incubation, the nucleic acid sensor molecule reaction mixtures were subjected to 5% acrylamide gel containing 8 M Urea as shown in panel B of FIG. 25, in order to examine the NASM endonuclease activity. Three constructs displayed an increase in endonuclease activity in the presence of ERK+MEK+EE with ATP as shown in FIG. 25. These data indicate general methods for a NASM-based ERK activation assay: as shown in FIG. 25, NASMs are used to directly detect MEK conversion of ERK to ppERK as detected by ppERK-modulation of nucleic acid sensor molecules.

Example 20

Characterization of the ERK and ppERK Modulated L1-Ligase Derived NASMs

Figure 33:
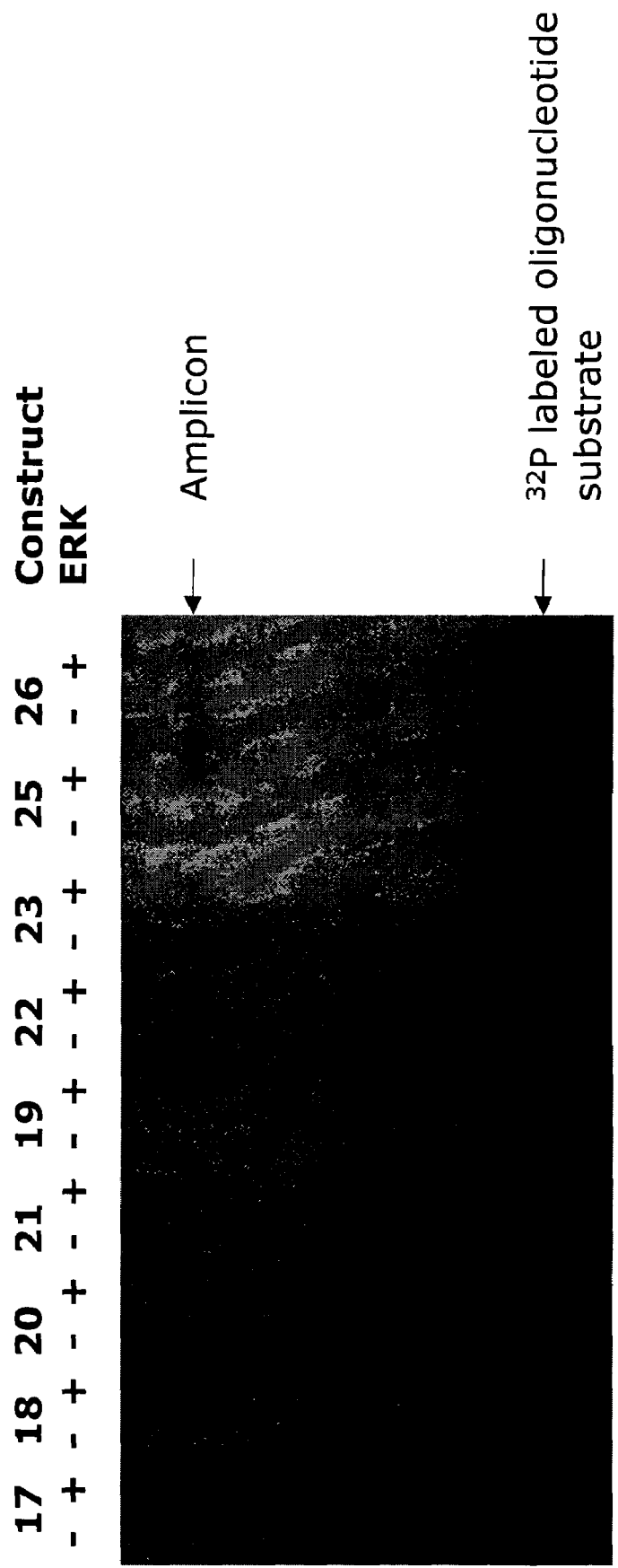
FIG. 33 shows the ERK dependent activity of constructs 17 (A), 18 (B), 20 (C), 21 (D), 19 (E), 22 (F), 23 (G), 25 (H), and 26 (I).
Figure 34:
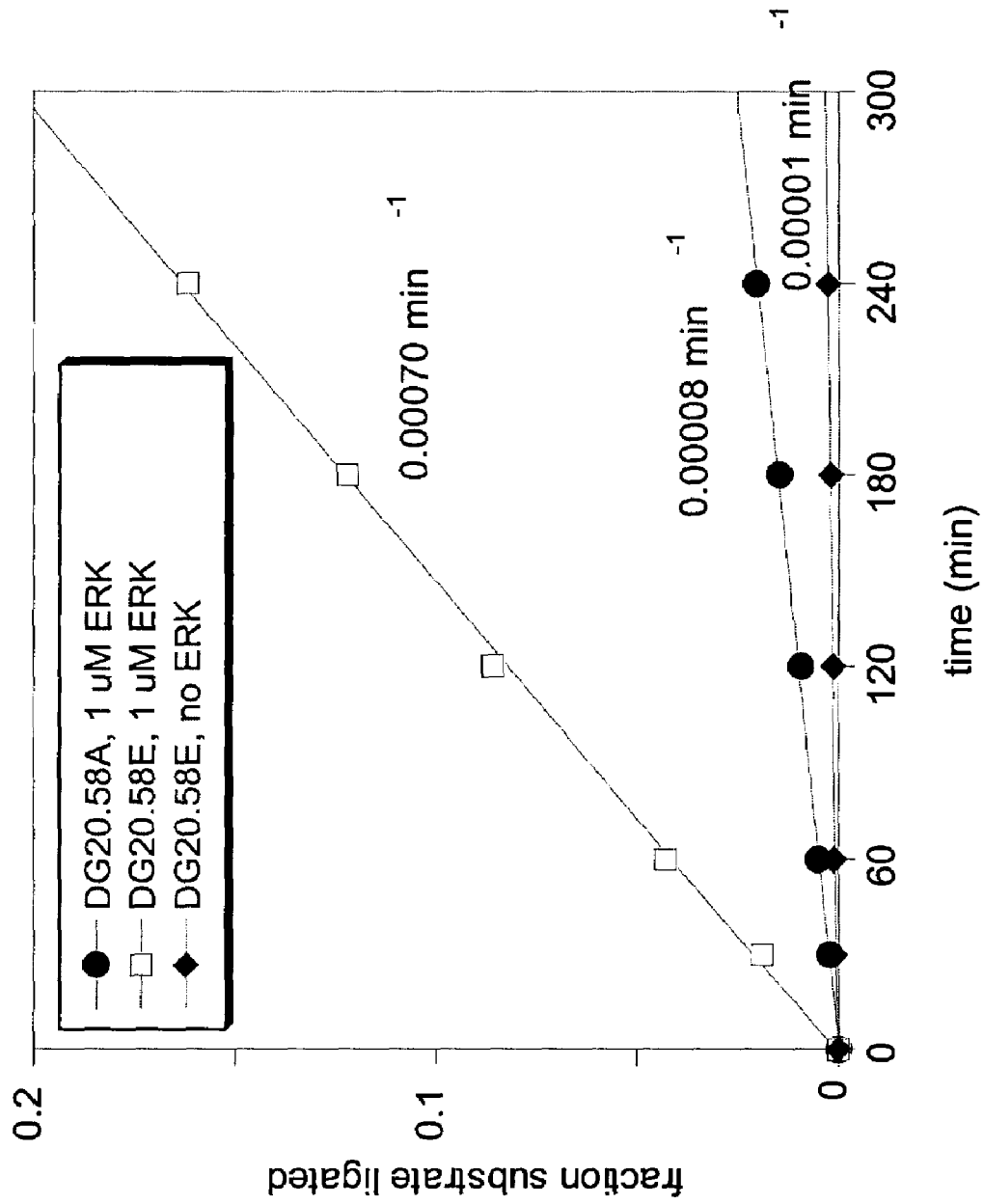
FIG. 34 is a graph that shows ligase time-dependent activity assays for construct 17 (clone A) (SEQ ID NO:109) and construct 19 (clone E) (SEQ ID NO:111).
Figure 35:
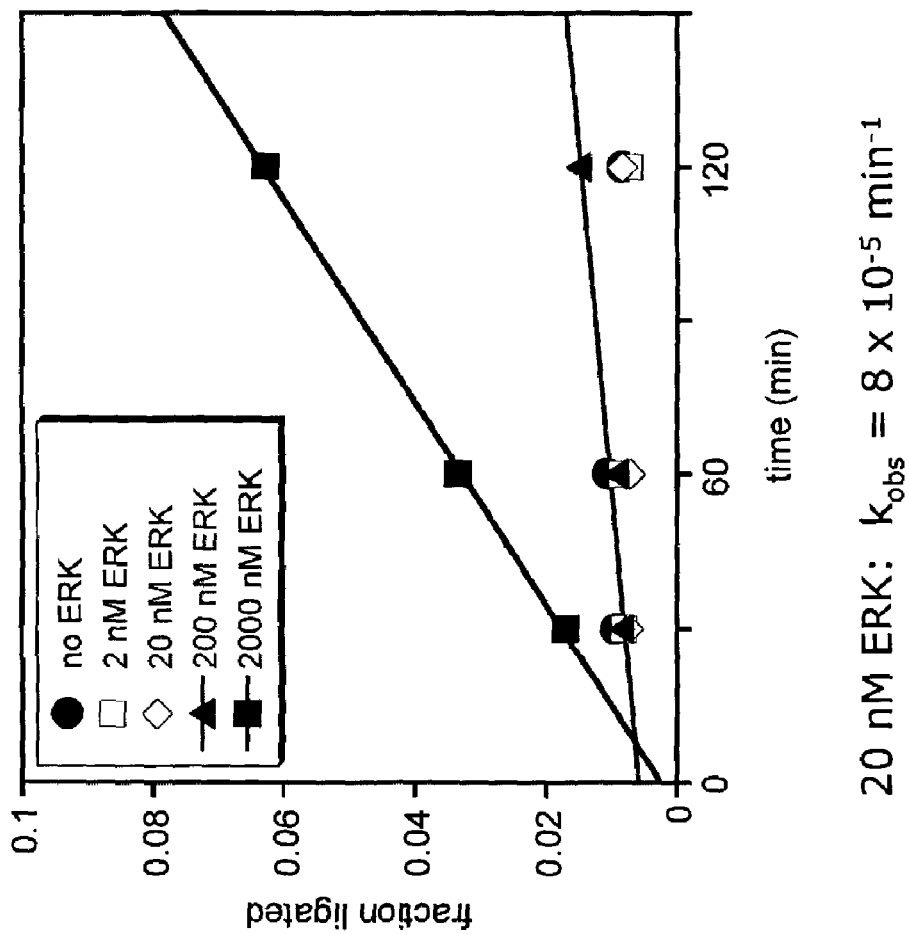
FIG. 35 shows a graph showing the time-dependent activity of construct 19 (clone E) (SEQ ID NO:111) with varying concentrations of ERK2.
Figure 37:
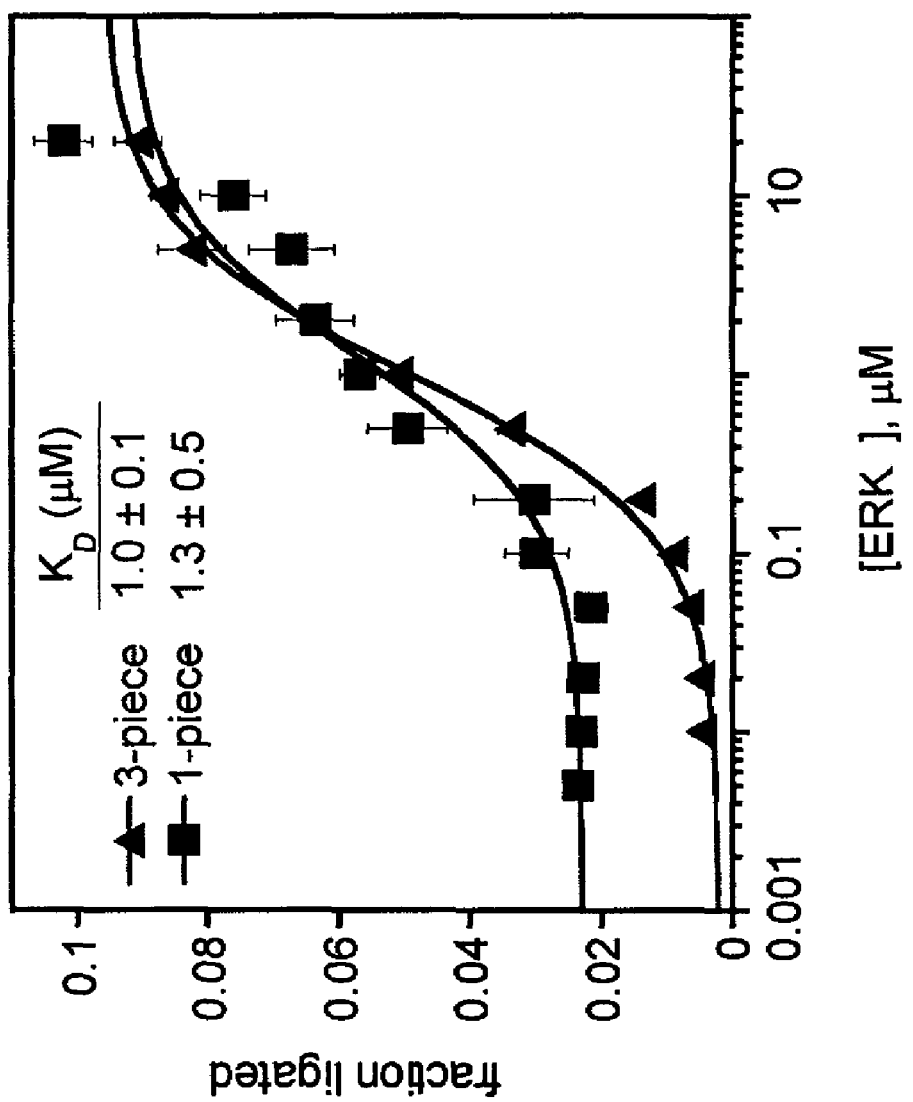
FIG. 37 shows a graph demonstrating continued ERK2 dependence of a nucleic acid sensor molecule in the 3-piece and 1-piece formats (constructs 19 and 28, respectively).
Figure 38:
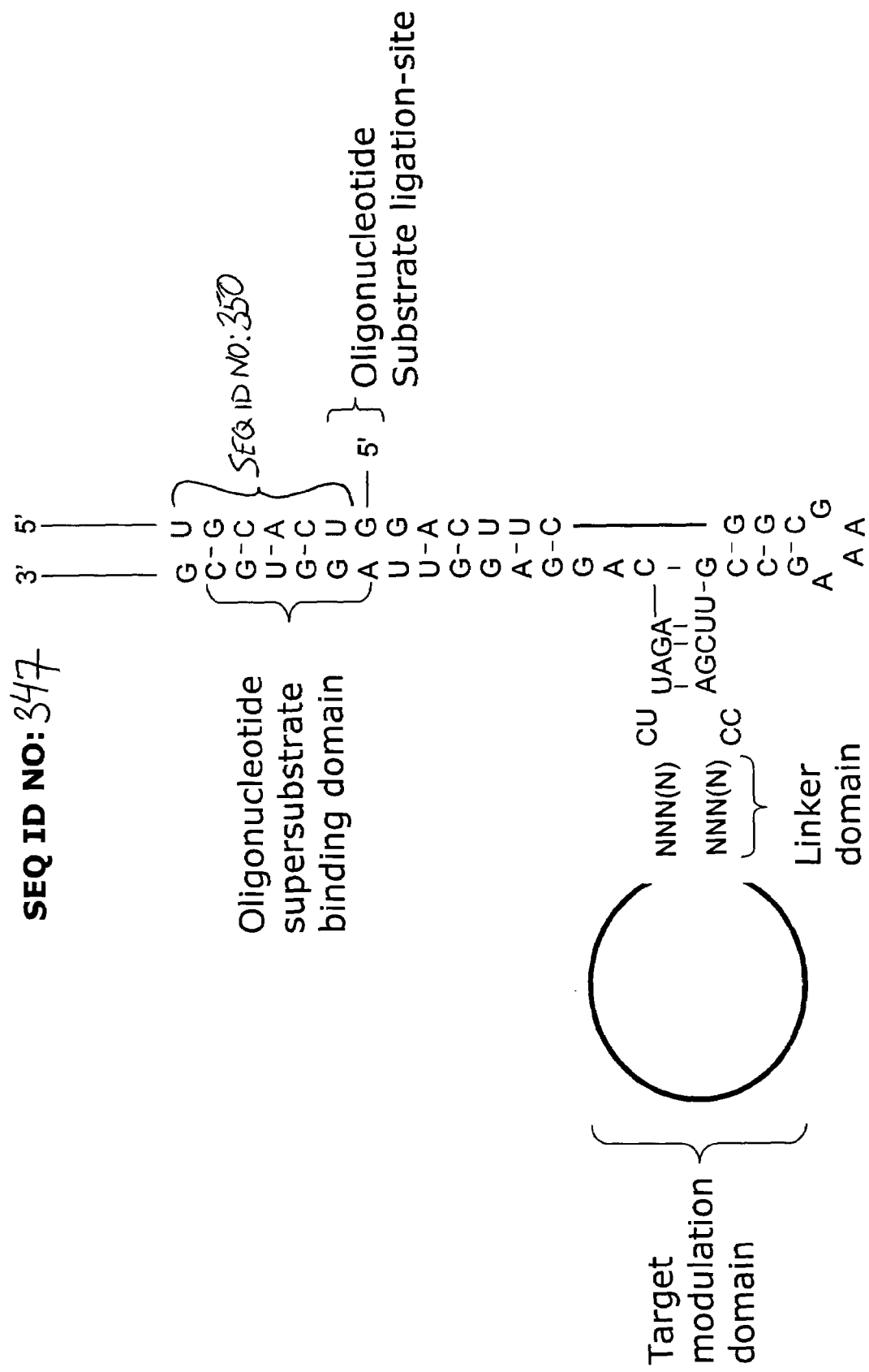
FIG. 38 shows a secondary structure representation of the 2-piece ERK dependent ligase platform (SEQ ID NO:347), and its oligonucleotide substrate (SEQ ID NO:350).
Figure 39A:
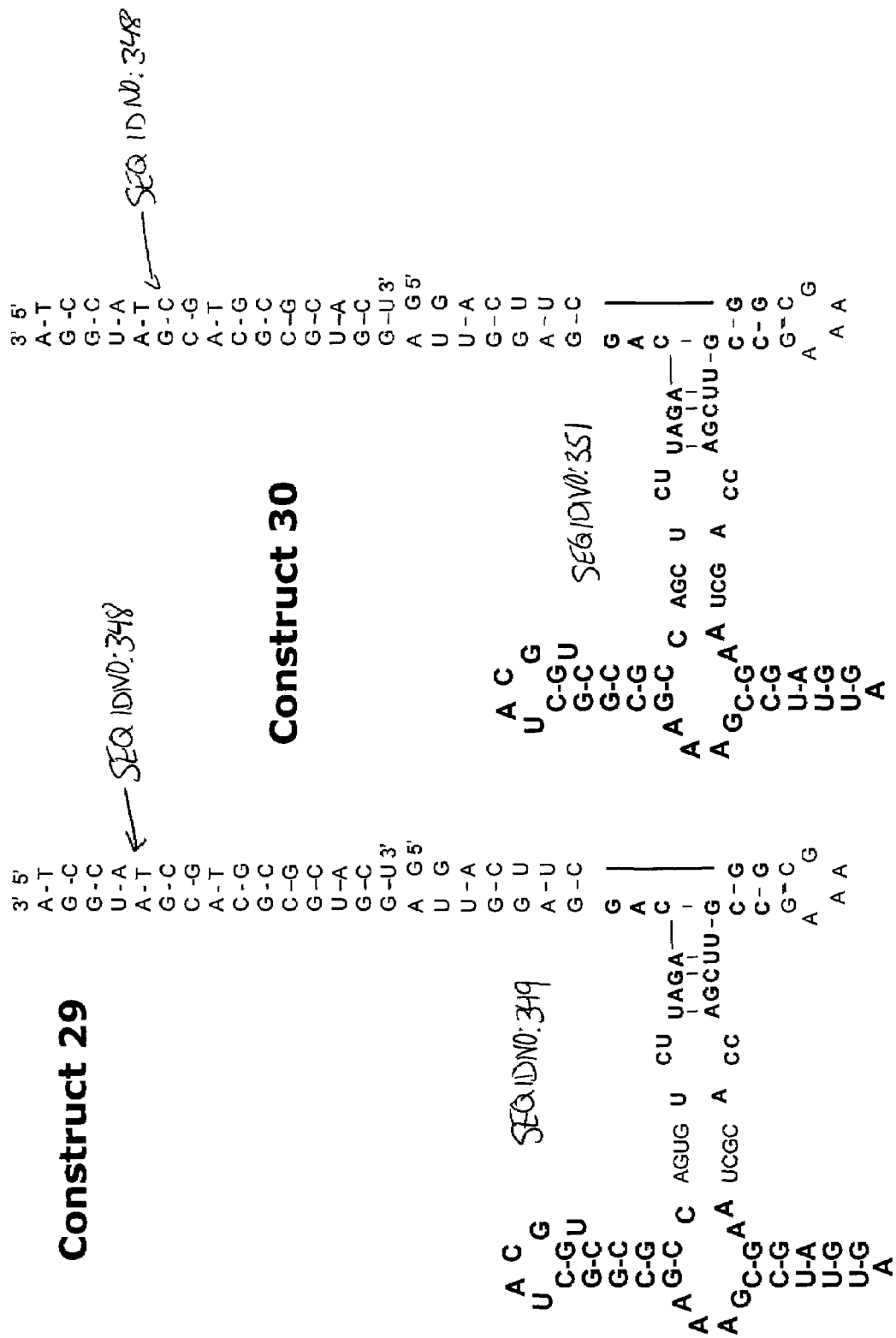
FIG. 39A shows a secondary structure representation of two 2-piece ERK-modulated nucleic acid sensor molecules: construct 29 (SEQ ID NO:349), and construct 30 (SEQ ID NO:351), with their oligonucleotide substrate (SEQ ID NO:348).

A template for an ERK dependent ligase is shown in FIG. 31. FIG. 32 discloses the different clones of ERK dependent ligases based on this template. The ERK dependence of these clones is shown in FIG. 33. Constructs 17 and 19 are particularly sensitive to 2µM ERK. Construct 19, also known as Clone E, was tested to see if it could be used to detect increasing concentrations of ERK. Construct 19 was found to have a distinct signal at 1 µM, 100 nM, and 10 nM ERK. Time dependency was also tested for Construct 19 as shown in FIG. 34. Increasing signal from Construct 19 could be seen at 1, 2, 3, and 4 hours. Concentration dependence of Construct 19 (Clone E) is also shown in the graph in FIG. 35. Construct 19 can differentiate between different concentrations of ERK. Two formats that can be used with nucleic acid sensor molecule ligases are the 3-piece ligase platform, and the 1-piece ligase platform, both shown in FIG. 36. The different platforms allow the nucleic acid sensor molecules to be used in different applications. For example, the 3-piece could be used in vitro, while the 1-piece could be used in vivo, even intracellularly. The performance of these two formats is shown in FIG. 37. There is also a 2-piece platform shown generally in FIG. 38 and shown as ERK regulated 2-piece ligases as shown in FIG. 39A. The 2-piece platform of Construct 19 is also ERK dependent as shown in FIG. 39B.

Figure 40:
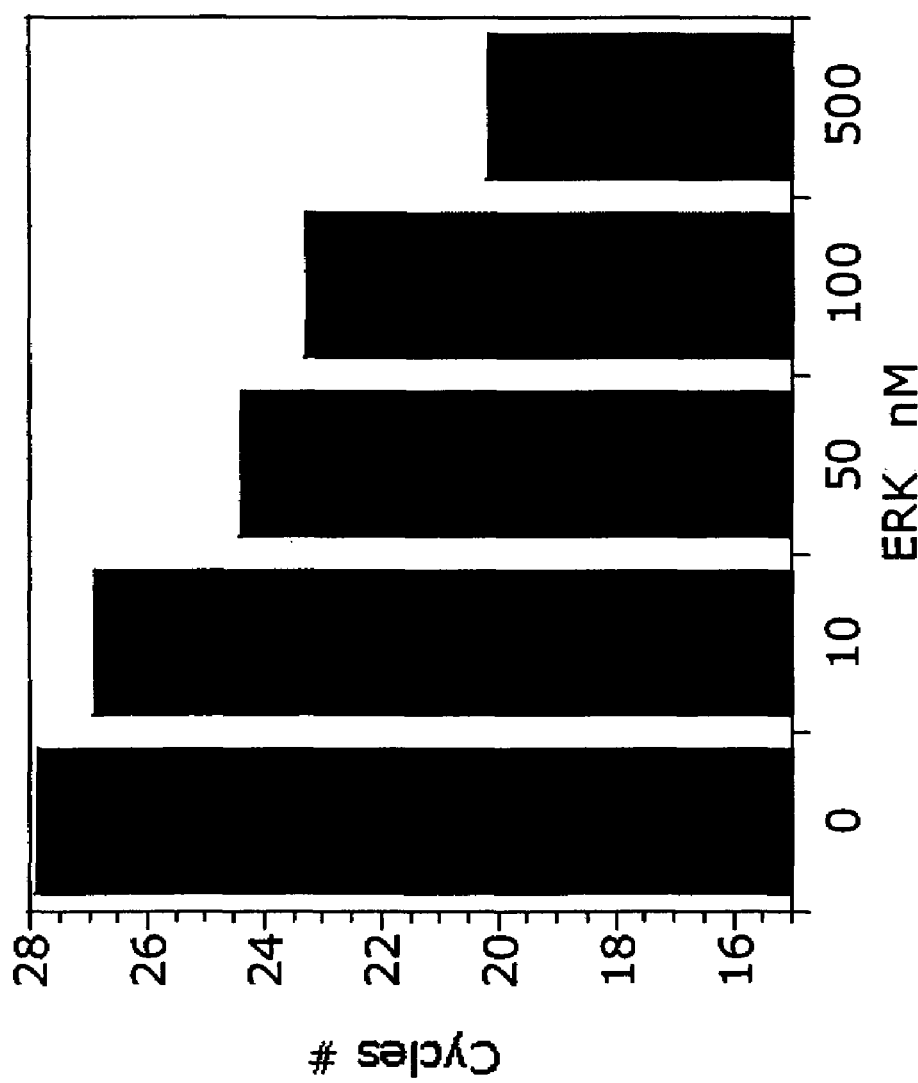
FIG. 40 shows the ligation efficiency of ERK nucleic acid sensor molecule construct 19 (SEQ ID NO:111) detected with quantiative-PCR (Taqman®). All incubation with various concentration of ERK were performed in the presence of 10% 293 extracts with exogenously added 10 mM MgCl$_2$.

Ligase nucleic acid sensor molecules can be used in the presence of cell extracts. Construct 19 shows ERK activation dependence in the presence of 50% HeLa cell extract as shown in FIG. 40.

Ligase based nucleic acid sensor molecules were also found that were specifically activated by ppERK. FIG. 41 shows a template for the ppERK sensitive ligase. FIG. 42 show the specific sequences left generalized in FIG. 41. ppERK sensitivity was shown in the clones described FIG. 57 shows activation of 3-piece Construct 19 (DG.20.58E) (ERK2-dependent) (SEQ ID NO:111) and TK.16.118.M (ppERK2-dependent) (SEQ ID NO:123) ligases in the presence of purified proteins. Ligation assays (10 mM $MgCl_2$, 100 mM NaCl, 30 mM Tris, pH 7.5) were performed at room temperature for 1 hour, using 1 µM ligase RNA, 1 µM effector oligonucleotide, 2 µM substrate oligonucleotide and 1 µM protein. RNAs were incubated in the presence of: (A) purified ERK, in either its non-phosphorylated or diphosphorylated form; or (B) other members of the MAP kinase pathway (Ras, MEKI and p38), and ricin. Ligase activity was measured in solution, using real-time RT-PCR detection.

It has been shown that Construct 19 still has activity in low magnesium ion. In one embodiment of the invention, these nucleic acid sensor molecules can be used in cell extracts and intracellularly, to detect ppERK. There is very low magnesium ion concentrations in these environments, so it is important that these nucleic acid sensor molecules maintain function even in low concentrations of magnesium ion.

FIG. 42 shows the full sequences of the different clones of ppERK sensitive nucleic acid sensor molecules in the 3-piece format.

Example 21

Amplicon Detection

Amplicon dependent nucleic amplification is a high-throughput method for cell or tissue profiling of proteins and metabolites. The method can include using real-time PCR to follow the activity of nucleic acid sensor molecules over time to follow the changing concentrations of a protein or metabolite.

Figure 72:
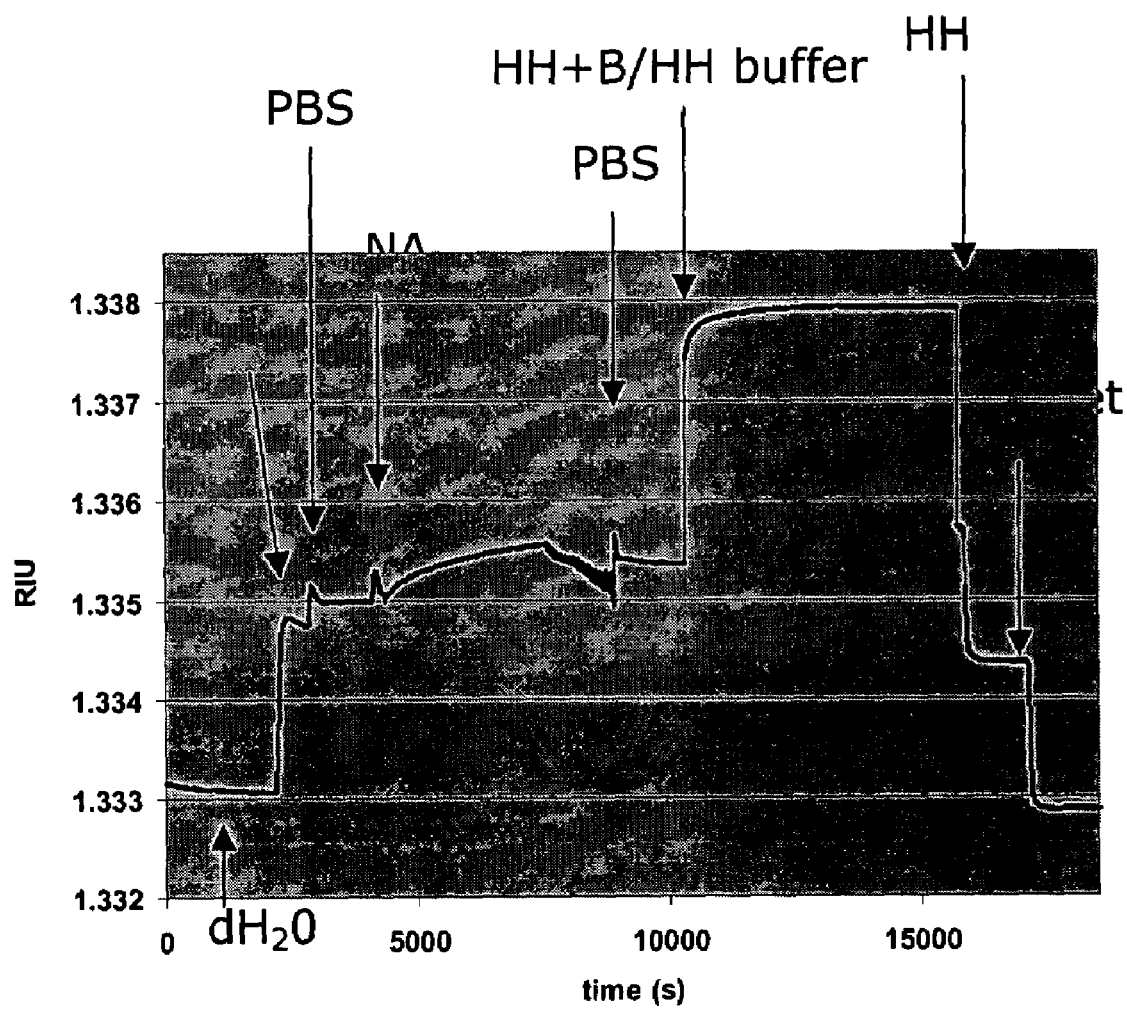
FIG. 72 shows a plot of SPR signal (in refractive index units, RIU) vs. time for a typical SPR sensor array assay: surface cleaning (dH$_2$0, NaOH, PBS), surface loading of the gold SPR layer with neutravidin (NA), requilibration with PBS (PBS), loading of the surface with biotinylated sensor molecules in PBS(HH+B/PBS), requilibration of sensor surface in assay buffer (HH buff), and addition of target in assay buffer (target/HH buff).

The method can also comprise the use of multiplexed chips. A chip can be exposed to a sample solution containing proteins or metabolites to be analyzed. Using multiple nucleic acid sensor molecules on one chip, the concentrations of many analytes can be shown simultaneously. This can also be extended to cellular assays as shown in FIG. 72.

TaqMan can also be used in Protein-PCR, as shown in FIG. 58. FIG. 58 shows solution-based detection of ligase activity using real-time RT-PCR. Ligation reactions (10 mM $MgCl_2$, 100 mM NaCl, 30 mM Tris, pH 7.5) were performed for 0.5–2 hours at room temperature using 1 µM 3-piece construct 19 (DG.20.58E), (SEQ ID NO:111) ligase, 2 µM effector oligonucleotide, 2 µM substrate oligonucleotide and purified ERK protein. Part A shows the effect of 293 cell extracts on the ERK concentration dependence of ligase activity. The increase in ligation product observed with increasing concentrations of ERK (0–3.2 µM) is shown in the presence of buffer only (circles) or buffer containing 10% 293 cell extract (squares). (inset) The ERK2 concentration dependence of ligation is shown as the decrease in cycles of amplification required for detection of ligase product RNA, as measured by real-time RT-PCR. In Panel B ligation in the presence of 1 µM ERK and increasing concentrations of the kinase inhibitor staurosporine is shown. ERK nucleic acid sensor molecules can be used to detect ERK in a concentration dependent manner even in the presence of 293 cell extract. This detection is sensitive to the presence of staurosporine, a kinase inhibitor, which indicates that the activity of ERK is important to the detection of ERK by the nucleic acid sensor molecule.

Amplicon dependent nucleic acid amplification technique can be used to show the downstream effects of EGF and MEK inhibitor administration in a cell. The diphosphorylated ERK is detected in the presence of EGF and not in the presence of the MEK inhibitor as would be expected. This technique can be used to screen other substances for their ability to have ERK phosphorylated. In one embodiment, this technique could be used to screen for carcinogens in certain cell types.

Example 22

Analysis of Radiolabeled Ligation Products in 3,2,1-piece Systems.

The ERK-modulated 3-piece ligase is converted to the 1-piece ligase NASM by displacement of the effector oligonucleotide binding domain by a stable tetraloop, as depicted in FIG. 36. The deletion of the effector oligonucleotide binding domain of construct 27 (in general), and construct 27, specifically, to generate construct 28 has no effect on the switch factor of the 1-piece ligase NASM (in comparison to the 3-piece ligase NASM), nor does it have an effect on the ERK-modulation KD value for the 1-piece ligase NASM (in comparison to the 3-piece ligase NASM), FIG. 37. The exact sequence constraints for the displacement of the effector oligonucleotide binding domain in construct 27 to generate construct 28, were in fact delineated by the analysis obtained from the lysozyme-modulated 1-piece ligase NASMs shown in FIG. 26. The data in FIG. 26 also indicates that the length of the stem region proximal to the tetraloop has a significant effect on ligase (e.g. self-circularization) efficiency. The self-circularizing ligase NASMs are then used as biosensors in intracellular target modulation assays, FIG. 30. Detailed assay conditions are described in subsequent Examples.

Additionally, the ERK-modulated 3-piece ligase is converted to the 2-piece ligase NASM by linking the effector oligonucleotide substrate to the oligonucleotide substrate (FIG. 38), effectively creating the oligonucleotide supersubstrate, which base pairs with both the effector oligonucleotide binding domain and the oligonucleotide substrate binding domain. The 2-piece ligase NASM configuration has particular utility in chip applications, described in detail in subsequent Examples (cf., FIGS. 75 and 79).

Ligation reactions containing $^{32}$P-labeled ligase RNA were analyzed by 8–12% PAGE to separate unligated and ligated products, and quantified using a PhosphorImager (Molecular Dynamics). Initial rates of ligation were calculated by linear regression from plots of the increase in ligation product over time.

Analysis of ligation products can also be performed by amplicon dependent nucleic acid amplification (ADNA). Amplicon dependent nucleic acid amplification (ADNA) was performed using the TaqMan® One-Step RT-PCR protocol from the same Applied Biosystems. In a typical assay, approximately 0.7 nM ligase RNA (diluted from the EDTA-quenched ligation reaction) was mixed in 25 µL of TaqMan® One-Step master mix with 300 nM each of both the forward (5'-GCGACCTTACGATCAGATGAC (SEQ ID NO:317)) and reverse (5'-CCGCACCTAACCTCCT-GTCTAA (SEQ ID NO:318)) PCR primers (Integrated DNA Technologies), and 350 nM TaqMan® fluorescent probe oligonucleotide (ERK-ligase: 5'-6FAM-AAGGAG-GATTTCCGAAAGCGGCTACG-TAMRA (SEQ ID NO:319); ppERK-ligase: 5'-6FAM-CGCTAGCGAATTG-GTTCCTCGAAAGG-TAMRA (SEQ IDNO:320)). RT-PCR amplification was performed in the ABI Prism™ 7000 Sequence Detection System by incubating the reaction mixes at 48° C. for 30 min to generate the cDNA complement of the ligated RNA product, followed by 40 cycles of PCR amplification. The increase in fluorescence upon amplification is quantified in units of $C_T$ (threshold cycles), equal to the number of cycles of amplification required for sample fluorescence to exceed background levels. The molar quantity of ligation product can be calculated from these

Example. 23

Measurement of Affinity Between ERK Protein and ERK-dependent Nucleic Acid Sensor Molecules.

The affinity of the ERK protein target for the ERK-dependent nucleic acid sensor molecule can be measured directly, by a filter-binding assay, or indirectly, by an activity-based assay. In the direct method, increasing concentrations of ERK protein target (0–10 μM) are equilibrated with trace (<1 nM) concentrations of $^{32}$P-labeled, ERK-dependent nucleic acid sensor. The samples are drawn through a sandwich of Protran BA85 nitrocellulose (Schleicher and Schuell) and Hybond P nylon (Amersham-Pharmacia) filter papers, using a 96-well vacuum manifold. Protein and protein-bound RNA species adhere to the nitrocellulose, and free RNA to the nylon. The concentration of ERK protein/sensor complex is plotted as the fraction of the total radioactivity per sample bound to the nitrocellulose versus total ERK protein concentration. The dissociation constant ($K_D$; FIG. 59) is determined as the ERK protein concentration at which 50% of the nucleic acid sensor RNA is bound to protein.

Figure 60:
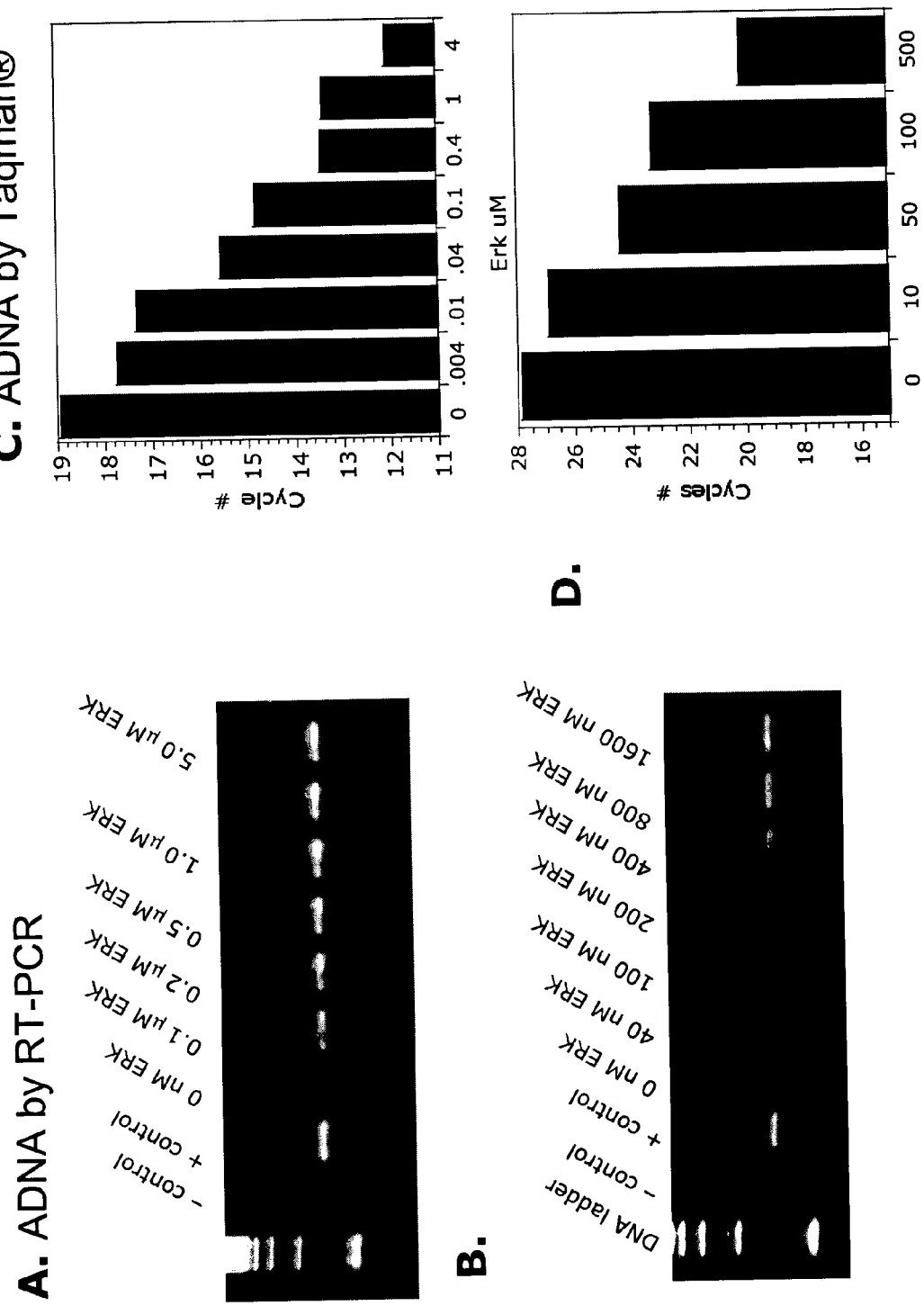
FIG. 60A and B show RT-PCR gels, and C and D corresponding bar graphs showing ERK modulation of a nucleic acid sensor molecule in vitro (panels A and C) and in biological extracts (panels B and D).

In the indirect method, the activity of the ERK-dependent nucleic acid sensor molecule is measured as a function of increasing ERK protein concentration. In a typical measurement, 50 nM nucleic acid biosensor is incubated with ERK protein (0–10 μM) for one hour at room temperature. The extent of ligation at each concentration of ERK protein is determined by real-time RT-PCR (FIG. 60, Panels C and D). The ligation product (nM) is plotted against ERK protein concentration, and the apparent dissociation constant ($K_{act}$) is determined as the protein concentration at which the extent of ligation is half-maximal. Panels A and B show ERK-dependent ligation is determined by RT-PCR on an agarose gel containing ethidium bromide.

Example 24

High Throughput Screening (HTS) Assays Using ppERK Nucleic Acid Sensor Molecules The competitive inhibitor nucleic acid sensor molecule can be used in a HTS assay. A nucleic acid sensor molecule specific for phosphorylated ERK is used as a competitive inhibitor for ATP binding (Seiwert, Stines Nahreini et al. 2000). A competitive assay for compounds is established by incubating ERK with 10 nM nucleic acid sensor molecule in the presence of various concentrations of the inhibitors in 10 mM Tris buffer pH 7.5 containing 0.5 μg/μl tRNA and 10 mM MgCl$_2$. The reactions are terminated by addition of EDTA and the amount of reacted nucleic acid sensor molecule has been determined.

In other embodiment, the nucleic acid sensor molecules that are sensitive for the phosphorylation state of peptides (or protein substrates) can be used in HTS assays for kinase activity. The nucleic acid sensor molecules can be generated to be specific for the phosphorylation state of substrates or its peptides. HTS assay can be performed using these substrate (Mansour, Candia et al. 1996). For example, MEK can be expressed as GST-tagged protein and purified by a standard method. The activity are measured at 30° C. under standard reaction conditions of 20 mM HEPES (pH 7.4), 2 mM dithiothreitol, 0.01% Triton X-100, 10 mM MgCl$_2$, 0.1 mM ATP, and 1M His-tagged ERK, at concentrations of MEK, 0.5 nM, in the presence of various concentration of compounds. After incubation, the reaction is terminated by absorbing MEK with GST-column. Phosphorylation of ERK is quantified by nucleic acid sensor molecule. Alternatively, the nucleic acid sensor molecule can be used in western-blotting format (Bianchini, Radrizzani et al. 2001).

The nucleic acid sensor molecule specific for phosphoERK (ppERK) described above binds to ppERK, presumably in a competitive manner at the active site of the kinase enzyme, and inhibits the phosphorylation of the ppERK substrate by ppERK enzyme. Up to 200 nM nucleic acid sensor molecule inhibits up to 80% of the ppERK phosphorylation of ERK substrate.

Example 25

In Vivo Assays Using Phosphorylation State-sensitive Nucleic Acid Sensor Molecules The phosphorylation state sensitive ppERK nucleic acid sensor molecule is used to determine drug efficacy in vivo (e.g., tissue and cell culture). For example, T84 cells on glass coverslips are incubated in the presence and the absence of the MEK kinase inhibitor, and cells are fixed by 4% paraformaldehyde and permeabilized using 0.3% Triton X-100. The slides are incubated with FRET nucleic acid sensor molecule (Bianchini, Radrizzani et al. 2001). The localization of phosphorylated substrate can be observed using a confocal microscope.

Alternatively, phosphorylation-state-sensitive nucleic acid sensor molecule are incorporated into reporter-gene constructs. These constructs are introduced into cells, and phosphorylation of the substrates is monitored.

Nucleic acid sensor molecules made of nuclease resistant forms of hammerhead, -ligase or -hairpin ribozymes are transfected into mammalian cells using standard lipofectamine reagents or liposomal solutions known to effect internalization an cellular uptake of polynucleotides. If desired, the nucleic acid sensor molecules are attached to polypeptides such as tat or antennapoedia or the like and are transported into mammalian cells by methods known in the art.

The activity of nucleic acid sensor molecule systems is followed by changes in fluorescence if the nucleic acid sensor molecule is fluorescently tagged, i.e., is an optical nucleic acid sensor molecule or by changes in size as determined by RT-PCR.

Example 26

Detection of Analytes in Crude Biological Samples.

Figure 56:
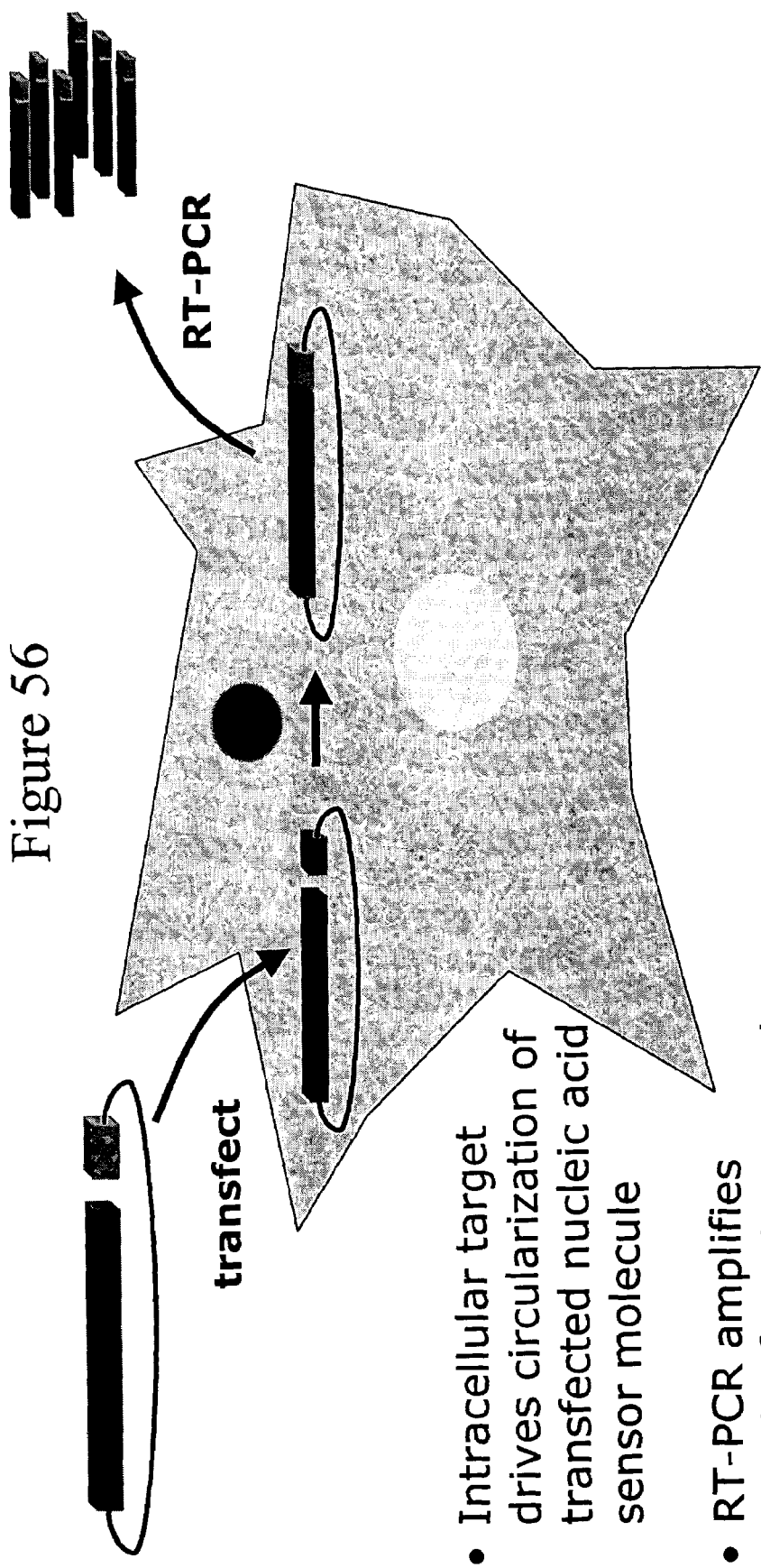
FIG. 56 shows a schematic describing cellular assays using 1-piece ligase nucleic acid sensor molecules.

Nucleic acid sensor molecules can also be used to detect the presence of and measure the concentration of non-nucleic acid analytes in crude biological samples as shown in FIG. 56.

As noted above, nucleic acid sensor molecules can be created whose activity is activated in the presence of a specific target molecule. These nucleic acid sensor molecules together with any required substrates, can be combined with a complex mixture of biological origin and allowed to undergo reaction. Subsequent quantification of the product of the reaction can be used to infer the concentration of the analyte in the sample.

Figure 50:
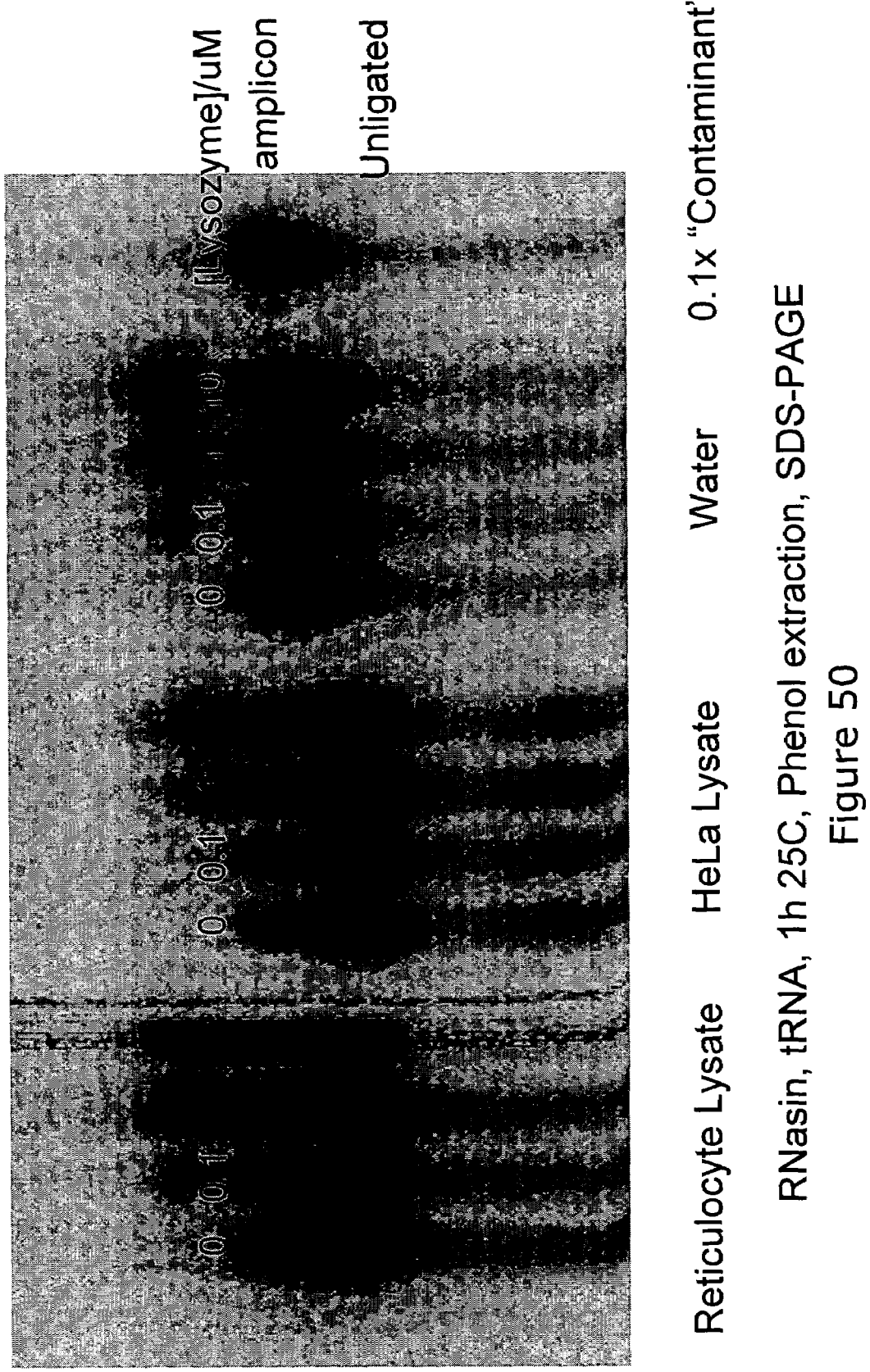
FIG. 50 shows a radiograph demonstrating lysozyme sensitive ligase nucleic acid sensor molecule activity in reticulocyte and HeLa cell extract.

In a preferred embodiment, the crude biological sample is human serum or mammalian cell extract. The nucleic acid sensor molecule catalyzes self-ligation with an oligonucleotide substrate. RNAse-inhibitors such as ribonucleoside vanadyl complex can be used to prevent degradation of the product. The product of catalysis can be measured by a variety of means (e.g., a gel mobility shift assay as shown in FIG. 50).

Figure 51:
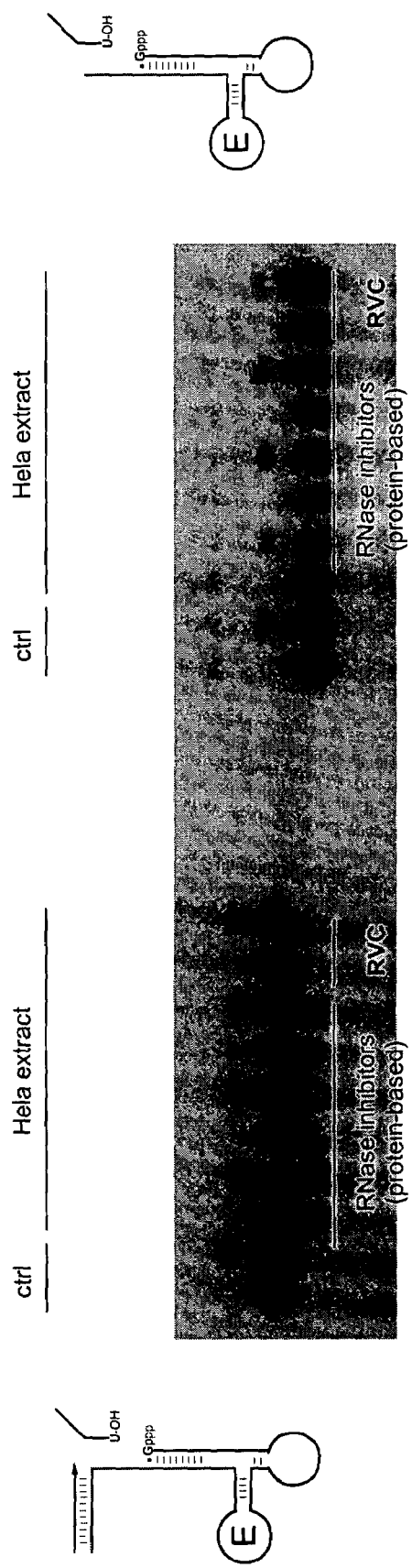
FIG. 51 shows a radiograph showing that ligase activity is relatively unchanged in the presence of cell lysate and various RNase inhibitors.
Figure 52:
FIG. 52 shows a radiograph of a lysozyme modulated nucleic acid sensor molecule in the presence of human serum.
Figure 53:
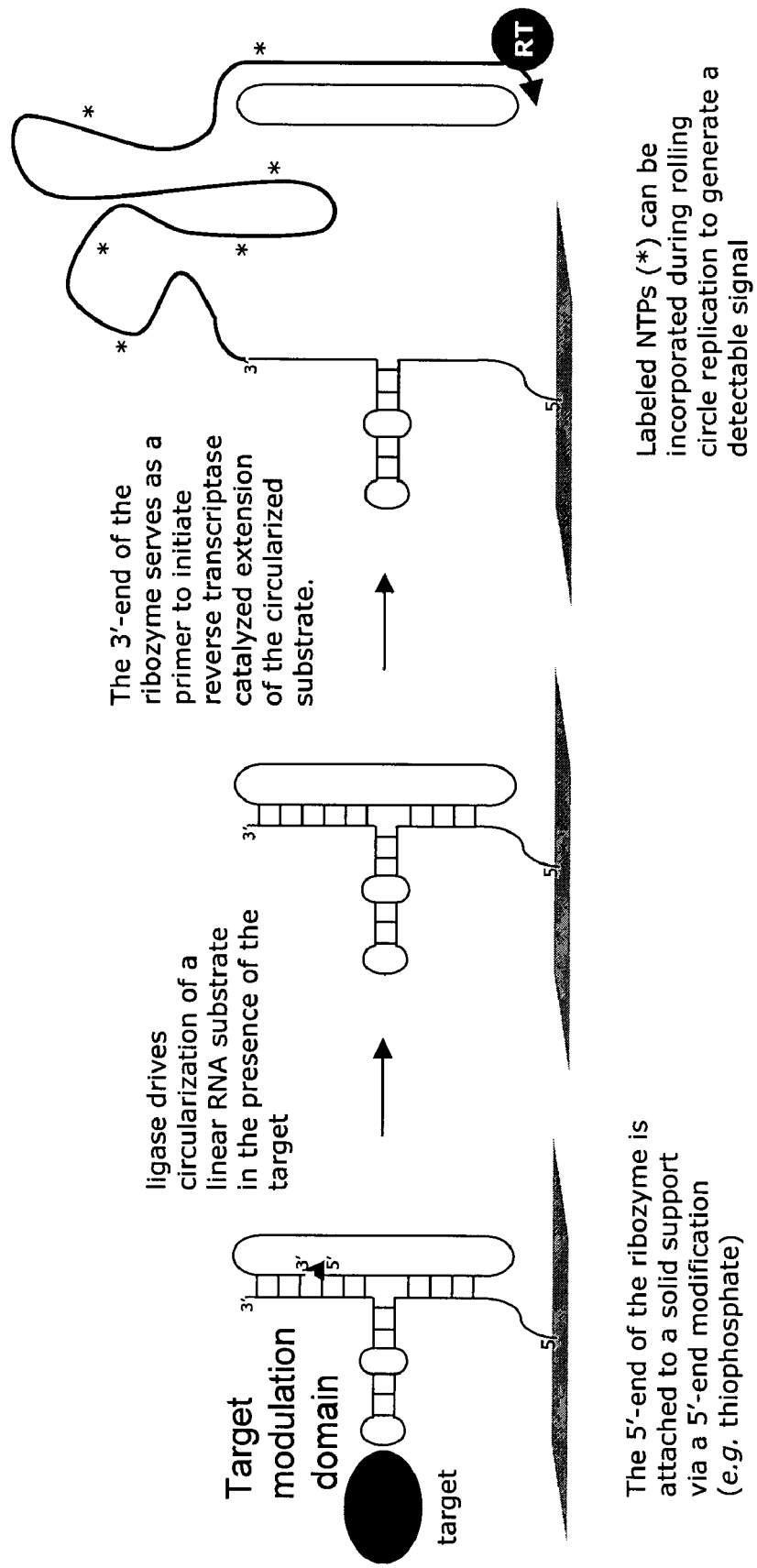
FIG. 53 shows a schematic describing rolling circle amplification of an amplicon derived from immobilized trans-acting ligase nucleic acid sensor molecules.

Ribonucleoside vanadyl complex (RVC) can be used as a general purpose inhibitor of endogenous RNAses to enable the use of allosteric ribozymes in assays of samples containing RNAse activity (e.g. human serum, mammalian cell extracts, bacterial extracts). RVC inhibits RNA degradation mediated by generic RNAses as well as RNAse H-like activities that specifically target RNA-DNA hybrids. Inhibition of RNAse activity prevents degradation of the reaction product generated by ribozyme action that ultimately forms the basis for readout in a ribozyme-based assay. In a specific example, a lysozyme-dependent nucleic acid sensor molecule RNA with the sequence 5' GGACCUCGGC-GAAAGCUAACGUCUCAUGGCUAAAUUGC-CAUGUUGCUACAAAU GAUAUGACUAGAGAGG-UUAGGUGCCUCGUGAUGUCCAGUCGC (SEQ ID NO:312) is prepared through transcription off a double-stranded DNA template using T7 polymerase (Ambion MegaShortscript kit, Ambion, Austin, Tex.), including trace amounts of [alpha-$^{32}$P]UTP. For the ligation reaction, 1 µM nucleic acid sensor molecule RNA, 2 µM DNA effector oligo 5' GCGACTGGACATCACGAG (SEQ ID NO:313) and 2 µM oligonucleotide substrate 5' GTACGATGCGAT-GCTAGCGATTGTTgugcacu (SEQ ID NO:314) (DNA: upper case; RNA: lower case) were incubated in the presence or absence of 1 µM hen egg white lysozyme in reaction buffer (50 mM Tris pH 7.4, 100 mM KCl, 10 mM MgCl$_2$) as previously described (Robertson M P & Ellington A D, Nature Biotechnol. 2001, 19, 650–655). HeLa extract is added to some of the samples (10% v/v), plus one of various RNase inhibitors (human placenta RNase inhibitor (Sigma, St. Louis, Mo.), RNasin (Ambion, Austin, Tex.) and vanadyl ribonucleoside complex, RVC, (Sigma, St. Louis, Mo.)). After 60 min at room temperature, the reaction is stopped by addition of loading buffer containing formamide, and the samples are analyzed by electrophoresis on a 6% denaturing gel, followed by Phosphorimager scanning (FIG. 51, left). The HeLa extract samples that contain protein-based RNase inhibitors show significant broadening of the precursor RNA band compared to a buffer-only control, suggesting RNase H degradation where the RNA is bound to the DNA effector oligonucleotide. The sample containing the VRC RNase inhibitor does not show any significant degradation. All of the samples show lysozyme-dependent product formation. To further test this hypothesis, additional test are done with an analog of the nucleic acid sensor molecules where the oligonucleotide effector domain is deleted (5' GGACCUCG-GCGAAAGCUAACGUCUCAUGGCUAAA-UUGCCAUGUUGCUACAAAU GAUAUGACUA-GAGAGGUUAGGUGC) (SEQ ID NO:332) under otherwise identical conditions (FIG. 51, right). No broadening of the RNA bands is observed, suggesting that the RNase activity was indeed specific to the RNA/DNA hybrid region. In a series of related experiments the above described reactions with the lysozyme-dependent nucleic acid sensor molecule are done in buffer to which 10% v/v human serum is added (FIG. 53). Without the addition of RVC complete degradation of the RNA is observed. In the presence of VRC, however, no difference in RNA stability and lysozyme-dependent product formation is observed.

By inactivating endogenous RNAse H-like activity, it is possible to carry out allosteric ribozyme assays in which the ribozymes have been immobilized on a chip surface through hybridization with a tethered DNA probe.

Example 27

Formatting an ERK Nucleic Acid Sensor Molecule Chip

Immobilization of nucleic acid sensor molecules on a substrate provides a straightforward mechanism for carrying out multiple arrays in parallel. Initially, the optimal attachment chemistries were determined to be used to immobilize these molecules on a solid substrate. These molecules are were further configured such that their activity and allosteric behavior is maintained following immobilization. Generally, the chip is configured such that it may be placed at the bottom of a sample holder and overlaid with sample solution, target (ERK and ppERK) (and substrate oligonucleotide). Following an incubation to allow ERK and pERK present within the sample to activate catalysis, the sample is washed away and the extent of ribozyme catalysis quantified.

Detection. Immobilized nucleic acid sensor molecules for ERK and pERK are prepared as described in the following section and are assayed for activity by monitoring either retention of end-labeled oligonucleotide substrate (for L1 ligase-based ribozymes) or release of end-labeled ribozyme (for endonucleases as originally described by (Seetharaman et al. 2001). Radioactive tracers are used for labeling RNAs and substrates. To the extent that different attachment chemistries do not interfere, both fluorescent and biotin labels are used in end-labeling the oligo substrate.

Attachment chemistries. One advantage of using nucleic acid sensor molecule arrays as opposed to protein arrays is the relative ease with which nucleic acid sensor molecules can be attached to chip surfaces. Several different chemistries for attaching nucleic acid sensor molecules to solid supports were tested and optimized, such as:

1. Conventional DNA arrays using aldehyde coated slides and 5'-amino modified oligonucleotides. The attached oligonucleotide serves as a capture tag that specifically hybridizes to a 3'-end extension on the ribozyme.
2. Nucleic acid sensor molecule RNA treated with periodate to specifically introduce an aldehyde modification at the 3'-end. Modified RNA can be used in two different ways:

Subsequent reaction with biotin hydrazide enables RNA capture on commercially-available streptavidin coated slides.

Subsequent reaction with adipic acid dihydrazide enables RNA capture on commercially-available aldehyde coated slides.

3. (Endonuclease) Nucleic acid sensor molecules are generated by transcription in the presence of γ-thio-GTP (introducing a unique thiol at their 5'-end) and subsequently attached to a thiol-reactive surface (e.g gold-coated polystyrene as described by Seetharaman et al.).

Attachment methodologies are evaluated on the basis of the following criteria:

efficiency—what is the yield of nucleic acid sensor molecule capture?

capacity—what is the maximum concentration of nucleic acid sensor molecules that can be localized in a given spot size?

stability—are ribozymes efficiently retained under a variety of solution conditions and during long-term storage?

detection—do immobilization chemistries interfere with the ability to generate a detectable signal?

Reconfiguring ribozymes for activity in solid phase applications. To the extent, that allosteric activity for immobilized ERK and pERK nucleic acid sensor molecules is diminished, three different strategies are possible:
1. Immobilization chemistries. A variety of different immobilization chemistries are compared on the basis of their ability to maintain allosteric behavior. To the extent that they leave different surfaces available for protein effectors to interact with, that they tether different ends of the nucleic acid sensor molecules, and that they position the NASM either directly at the surface or displaced from the surface (in the case of streptavidin capture), different behaviors are observed depending upon the immobilization method. Protein-target activated NASMs have been shown to function in both direct and indirect attachment scenarios.
2. Blocking chemistries. Blocking agents (e.g., carrier proteins) are tested to determine whether losses in allosteric responsiveness are due to non-specific interactions between the allosteric activators and the chip surface.
3. Tethers. Steric effects may cause decreased catalytic activity upon direct end attachment to a solid support. Arbitrary sequence tethers are added as needed to increase the spacing between the attachment end and the core of the ribozyme.

While endogenous activators and nucleases do not appear to be an issue for the lysozyme-responsive nucleic acid sensor molecules, the following strategies are used in the eventuality that they are a problem for the ERK/pERK (or other) nucleic acid sensor molecules.

Nucleic acid sensor molecule pre-screening. As noted above, individual clones isolated from the selection experiment are tested early for allosteric activation in the presence of ERK-depleted extracts. Molecules that respond to endogenous non-specific activators are eliminated from further consideration.

Negative selection with depleted extracts. To the extent that all isolated nucleic acid sensor molecules are activated by ERK-depleted extracts, depleted extracts are included in the negative selection step of the selection process.

Nuclease inhibition. Commercially available RNase inhibitors and competing RNAse substrates (e.g. tRNA) are added to test samples.

Kinetic considerations. RNAse-mediated degradation of the nucleic acid sensor molecule proceeds at a rate in competition with the rate of nucleic acid sensor molecule catalysis. As such, nucleic acid sensor molecules with fast turnover rates can be assayed for shorter times and are thus less susceptible to RNAse problems. Nucleic acid sensor molecules with fast turnover can be obtained by (1) reducing the length of the incubation during the positive selection step, and/or (2) choosing fast nucleic acid sensor molecules (potentially with less favorable allosteric activation ratios) when screening individual clones emerging from the selection experiment.

Nuclease-Resistant Nucleic acid sensor molecules. By carrying out selection in the presence of nucleases (e.g. by including depleted extracts during the negative selection step), the experiment intrinsically favors those molecules that are resistant to degradation.

Modified RNA. Covalent modifications to RNA that can render it highly nuclease-resistant are performed. Several of these modifications, including for example 2'-O-methylation, are compatible with hammerhead cleavage activity and are used to minimize non-specific cleavage in the presence of biological samples (Usman and Blatt 2000).

Example 28

Rolling Circle Amplification.

A circularized nucleic acid product generated by the target-activated ligase nucleic acid sensor molecule serves as a template to promote rolling circle replication. In most cases, rolling circle replication initially requires that an oligonucleotide primer be annealed to the circular nucleic acid template. This oligonucleotide primer may be provided subsequent to the nucleic acid sensor molecule reaction that generates the circular template. Alternatively, the primer may be present during the nucleic acid sensor molecule reaction as either a separate oligonucleotide or as part of the nucleic acid sensor molecule itself (FIG. 53). Also, the primer may exist free in solution or be tethered either covalently (e.g., via 5'-end modification) or non-covalently (e.g., association of biotinylated primer with immobilized streptavidin or through base-pairing with complementary immobilized oligonucleotide) to a solid support. In a preferred embodiment for solid-state (e.g., chip) applications, an immobilized nucleic acid sensor molecule serves directly as the primer for rolling circle amplification as illustrated in FIG. 53. Immobilization makes it possible to confine the signal generated through the rolling circle reaction to a specific spatial location, enabling the development of arrays in which each element in the array is composed of a different target-activated nucleic acid sensor molecules. In another embodiment, an immobilized primer is used for rolling circle extension, also leading to a spatially localized signal. Preferably, the primer is at least 10 nucleotides long and it hybridizes to a unique site on the circular template.

Rolling circle amplification may proceed using either a DNA-directed or RNA-directed polymerase, depending upon the nature of the circular template generated by the target-activated nucleic acid sensor molecules. Concatamers generated from primarily DNA templates can be generated by an enzyme preferably from the following group: Taq DNA polymerase, Tth DNA polymerase, Klenow fragment of E. coli DNA polymerase, bacteriophage O29 DNA Polymerase, or Bst DNA polymerase. More preferably, the polymerase enzyme is Bst DNA Polymerase. Concatamers generated from primarily RNA templates can be generated by an enzyme preferably from the following group: AMV reverse transcriptase, MMLV reverse transcriptase, or Q-beta replicase. More preferably, the polymerase enzyme is MMLV reverse transcriptase.

The rolling circle amplification reaction requires a supply of nucleotide triphosphates for incorporation to generate the nucleic acid product. Quantification of the rolling circle amplification reaction may be facilitated by using nucleotides containing fluorescent or radioactive labels or affinity tags as described below.

Figure 54:
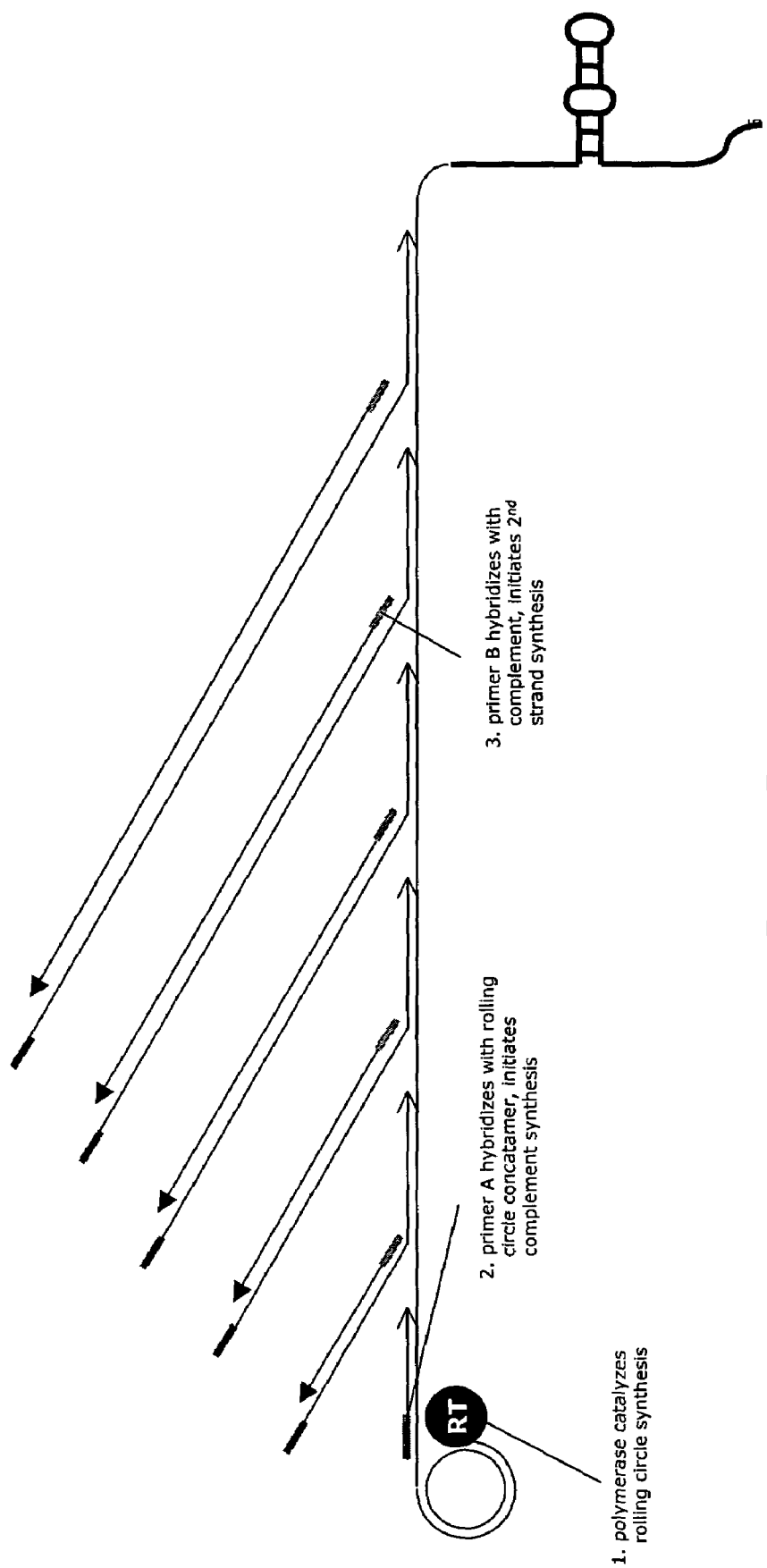
FIG. 54 shows a schematic describing exponential amplification of an amplicon.

The rolling circle amplification reaction may be made to proceed exponentially by the addition of a linear oligonucleotide primer containing all or part of the circular template sequence (FIG. 54). The uncircularized form of the ligase substrate can perform this function. As such, in the preferred embodiment, the detection reaction is carried out with excess oligonucleotide substrate.

Detection

The rolling circle amplification reaction generates single- and double-stranded DNA. The amount of the rolling circle amplification product generated can be determined by the variety of methods outlined below. The signal measured by each method can be directly related to a corresponding analyte concentration by constructing a standard curve in which a range of known concentrations of the analyte are analyzed in parallel.

Figure 55:
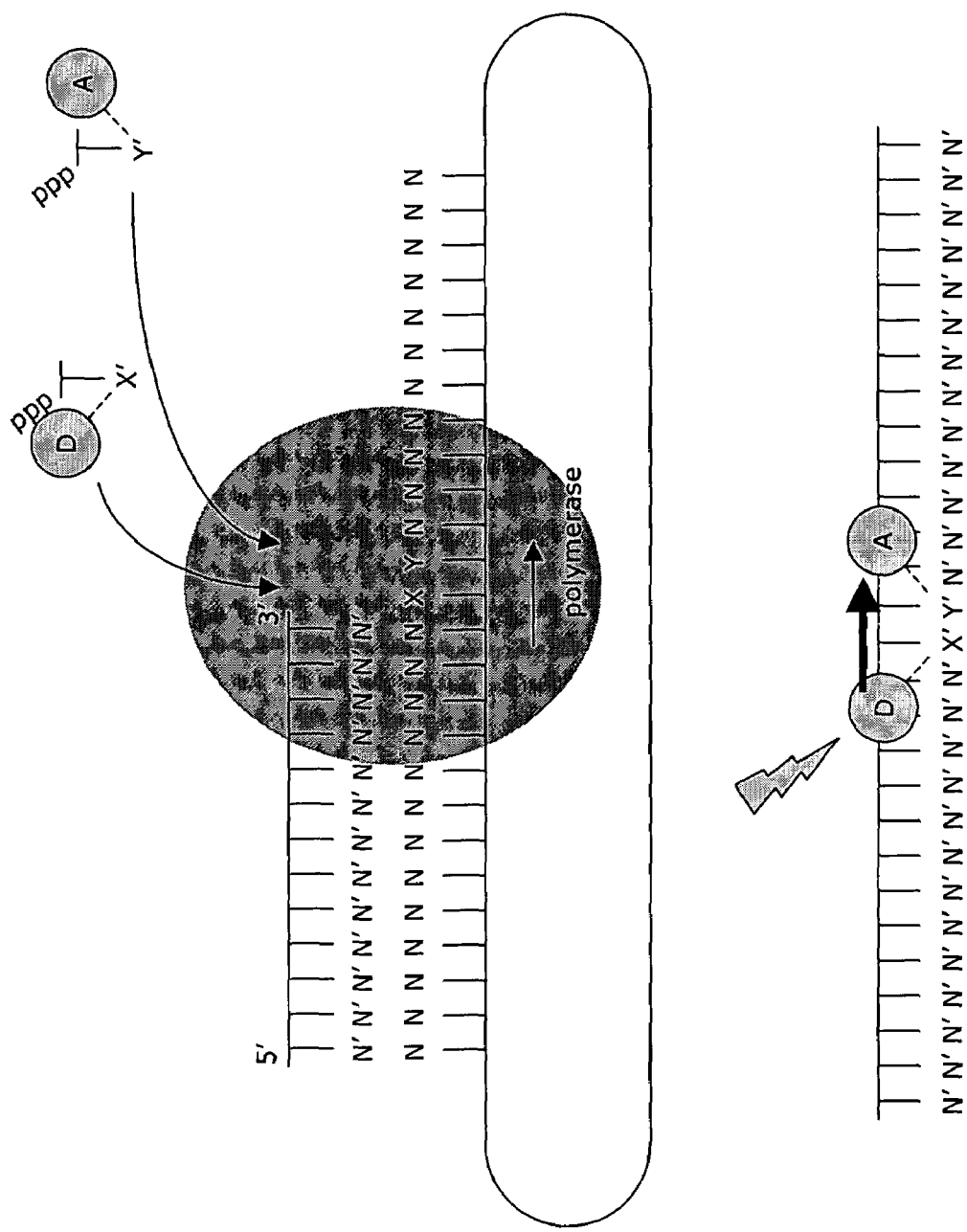
FIG. 55 shows a schematic describing FRET-based signal generation coupled to nucleic acid synthesis of nucleic acid sensor molecules.

Fluorescent detection. Products of the rolling circle amplification reaction may be detected fluorescently by the following methods:

a. Intercalating dyes. The fluorescence intensity of several dyes is known to increase upon their binding to DNA. The yield from the rolling circle amplification reaction may be measured by including one of these dyes during the reaction and using a fluorimeter to monitor the change in fluorescence intensity as the reaction proceeds. For this, a variety of nucleic acid stains is readily available (see Handbook of Fluorescent Probes and Research Products, Chapter 8, Molecular Probes, OR).

b. Labeled nucleotides. Fluorescent labels may be attached to the nucleotides that serve as substrates for the rolling circle amplification reaction. Fluorescent nucleotides incorporated into the newly synthesized DNA can be detected by two different mechanisms:

Homogeneous assays: nucleotides with appropriate fluorescence donor and acceptor pairs may be combined such that their sequential incorporation into a polynucleotide increases their spatial proximity and, correspondingly, the efficiency of fluorescence resonance energy transfer (FRET) (FIG. 55). The resulting FRET signal may be read using a fluorimeter. The strength of this signal may be maximized by appropriate design of the ligase substrate such that its sequence contains many acceptor-donor dinucleotides. A similar process using a fluorescent UTP and a biotin-CTP derivative, followed by addition of an fluorescence-acceptor streptavidin conjugate has been described for labeling of RNA (Alpha-Bazin et al. Anal. Biochem. (2000) 286, 17–25).

Heterogeneous assays: unincorporated nucleotides may be physically removed by covalently or non-covalently capturing the rolling circle amplification reaction product (e.g. by pre-immobilization of the rolling circle amplification primer or by hybridization to an immobilized capture probe) and followed by washing. Fluorescent nucleotides retained with the immobilized nucleic acid product can be detected and quantified (e.g. using a confocal scanner) to obtain an estimate of the extent of the rolling circle amplification reaction.

Sequence-specificfluorescent hybridization probes. Hybridization of a complementary, fluorescently labeled probe with the rolling circle amplification reaction product is used in a variety of ways to generate a fluorescent signal. Strategies include (1) physical retention of a fluorescent probe by captured/immobilized RCA product, (2) co-immobilization of a fluorophore acceptor-donor oligonucleotide pair (FRET), (3) 5'-nuclease induced cleavage of a fluorophore-quencher oligonucleotide (Taqman™) and (4) conformational changes in a fluorescent probe induced by hybridization which change its fluorescent properties. In a related aspect, the fluorescent probe may be attached to the primer that is used, leading to a conformational change during transcription (e.g. Ampliflour™, Intergen, NY)

Proximity Assays: In addition to the aforementioned methods that rely on inducing physical proximity of two fluorophores through hybridization of probes with rolling circle amplification products (e.g., FRET, molecular beacons, Taqman™ etc.), other proximity-based assays may be used. This includes, but is not limited to, luminescence-based assays such as Amplified Luminescent Proximity Homogeneous Assay (AlphaScreen, Packard Bio-Science, CT) and Bioluminescence Resonance Energy Transfer (BRET, Packard BioScience, CT). Radiometric read-out. By using appropriate radioactively labeled nucleotides in the rolling circle amplification reaction (e.g. alpha-$P^{32}$-ATP), the resulting rolling circle amplification product becomes radioactive and may be quantified using instrumentation that detects radioisotope decay (e.g. phosphorimagers, x-ray film, scintillation counters). In the preferred embodiment, nucleotides provided for the rolling circle amplification reaction are labeled with tritium and the primer for the rolling circle amplification reaction is immobilized on a solid support that contains a scintillant. Co-localization of the radioactively-labeled RCA product on the scintillant surface generates the signal readily detected by a scintillation counter (scintillation proximity assay, SPA).

Surface Plasmon Resonance (SPR). The primer used to initiate the rolling circle amplification reaction is immobilized on the gold surface of a detection element in an SPR detector (e.g. Biacore). As the rolling circle amplification reaction proceeds, the effective mass of the primer increases, generating a signal that can be detected due to the change in surface plasmon resonance.

Coagulation: Microspheres bearing a hybridization probe complementary to the rolling circle amplification product or the primers for the rolling circle amplification reaction can lead to coagulation as the reaction progresses. Coagulation can be readily detected by means that include measurement of changes in refractive index or turbidity.

Others. Rolling circle amplification is capable of generating very long polynucleotides that are very likely to lead to significant changes in the sample's physical properties. Examples include, but are not limited to, changes in viscosity, refractive index, turbidity, and electrophysical properties such as conductivity. In general, any kind of method that can detect these chances can likely be used to monitor the rolling circle amplification reaction.

Example 29

High Throughput Screening (HTS) Assay using G Protein Nucleic Acid Sensor Molecules Activated Gα-protein dependent nucleic acid sensor molecules are used in vitro to test the efficacy of the agonists and inverse agonists for any GPCR. Giα-protein cDNA can be obtained (Guthrie cDNA resource Center) and expressed in E. coli as His-tagged protein (Lee, Linder et al. 1994). GDP or GTP-γS are added during the purification to avoid degradation. GDP-complex Giα-protein and GTP-complex Giα-protein are used to generate nucleic acid sensor molecules.

GTP-complex Giα-protein (activated-Giα-protein)-dependent nucleic acid sensor molecules are tested in a target modulation assay to screen the selected nucleic acid sensor molecules with desirable properties. For example, membrane fraction of C6 glioma cells in 12-well plates are loaded for 16 h in the presence and the absence of adrenaline. Cell lysate can be tested for activated Giα-protein-dependent nucleic acid sensor molecule response. Alternatively, the competitive modulation by for adenylyl cyclase is tested following the inhibition of adenylyl cyclase activity by activated Giα-protein in the presence of nucleic acid sensor molecules by a modified assay based on a previously described assay (Burt, Sauté et al. 1998).

Adenylyl cyclase activity is measured as described in the presence and the absence of nucleic acid sensor molecules (Kozasa and Gilman 1995). Cell membranes from HeLa cells transfected with human cloned 5-HT$_{1A}$ receptors resuspended in buffer are used to screen compounds. The membranes are incubated with 30 M GDP and decreasing concentrations of test drugs (from 100 pM to 0.1 nM) or decreasing concentrations of 5-HT, from 100 M to 0.1 nM (reference curve) for 20 min at 30° C. in a final volume of about 0.5 mL (Stanton and Beer 1997). Then samples are added with GTPS and the nucleic acid sensor molecules and then incubated for a further 30 min at 30° C.

Alternatively, nucleic acid sensor molecules are generated that depend on the presence of Gβ-protein uncomplexed with Gα-protein. There are four known classes of Gβ-protein. Gβ-protein complex with Gγ-protein can also play important roles in the signal transduction. After dissociation from alpha subunit, this complex is known to regulate various target protein, such as GRKs, Raf kinase, adenylyl cyclase, PLCs and ion channels. Producing nucleic acid sensor molecules that block the complex keep the GPCR's from activating their effectors.

Example 30

Cell-based Assays Using GPCR Nucleic Acid Sensor Molecules

GPCR nucleic acid sensor molecules are used in cell-based assay using modifications of previously described GPCR assays (Hun, Ellington et al. 2001). For example, β-adrenergic receptor can be expressed in CHO cells. CHO cells are grown in multiwell tissue culture plates in Dulbecco's modified Eagle media (DMEM) with 10% fetal bovine serum. On the day of assay, medium is replaced with 0.2 mL treatment medium containing DMEM media containing 250 M IBMX (isobutyl-1-methylxantine) plus 1 mM ascorbic acid with test compound dissolved in DMSO. Test compounds are added at a desired concentration range (e.g. $10^{-9}$ to $10^{-4}$ M). Isoproterenol ($10^{-5}$ M) is used as an internal standard for comparison of activity. Cells were incubated at 37° C. on a rocker for 15–30 min. Then cells are lysed and the level of the activated Gα-protein is measured by the nucleic acid sensor molecule. The antagonist is screened in the same format in the presence of the known agonist by detecting the decreasing amount of the activated Gα-protein.

Alternatively, the agonism and the antagonism of compounds for specific or general GPCR is measured using the nucleic acid sensor molecule. For example, evaluation of compounds for antagonism can be performed using Sprague Dawley rats. The aorta from animal is isolated and freed of adhering connective tissue. Desmethylimipramine (0.1 M) and corticosterone (1 M) to block neuronal and extraneuronal uptake of noradrenaline, (±)-propranolol (1M) to block β-receptors, and yohimbine (0.1 M) to block γ-receptors are added. Aortic strips are incubated with various concentration of compounds in the presence and the absence of 10 M noradrenaline. Then the cell extract is prepared and the activated Giα-protein level in the cell is measured with the nucleic acid sensor molecules (Barlocco, Cignarella et al. 2001).

Example 31

In Vitro Assay for GPCR Activation by Following Liberation of Gα-protein with Gα-protein Dependent Nucleic Acid Sensor Molecules.

Nucleic acid sensor molecules generated against Gα-protein subunits are used to test the efficacy of agonists and inverse agonists for any GPCR in vitro using activated G-protein. For example, Giα-protien cDNA can be obtained (Guthrie cDNA resource Center) and expressed in *E coli* as His-tagged protein (Lee, Linder et al. 1994). GDP or GTP-γS are added during the purification to avoid degradation. GDP-complex Giα-protein and GTP-complex Giα-protein are used to generate nucleic acid sensor molecules. GTP-complex Giα-protein (activated-Giα-protein)-dependent nucleic acid sensor molecule can be tested for the binding assay to screen the selected nucleic acid sensor molecules with desirable properties. For example, membrane fraction of C6 glioma cells in 12-well plates were loaded for 16 h in the presence and the absence of adrenaline. Cell lysate can be tested for activated Giα-protein-dependent nucleic acid sensor molecule response. Alternatively, the competitive binding for adenylyl cyclase can be tested following the inhibition of adenylyl cyclase activity by activated Giα-protein in the presence of nucleic acid sensor molecules by a modified assay based on a previously described assay (Burt, Sautel et al. 1998).

Adenylyl cyclase activity can be measured as described in the presence and the absence of nucleic acid sensor molecules (Kozasa and Gilman 1995). Cell membranes from HeLa cells transfected with human cloned 5-hydroxytryptamine 1A (5-HT$_{1A}$) receptors resuspended in buffer can be used to screen compounds. The membranes are incubated with 30 mM GDP and decreasing concentrations of test drugs or decreasing concentrations of 5-HT, from 100 M to 0.1 nM (reference curve) for 20 min at 30° C. in a final volume of about 0.5 mL (Stanton and Beer 1997). Then samples are added with GTPS and the nucleic acid sensor molecules and then incubated for a further 30 min at 30° C.

Nucleic acid sensor molecules can also be generated that depend on the presence of Gβ-protein uncomplexed with G60-protein. There are four known class of Gβ-protein. Gβ-protein complex with Gγ-protein can also play important roles in the signal transduction. After dissociation from alpha subunit, this complex is known to regulate various target protein, such as GRKs, Raf kinase, adenylyl cyclase, PLCs and ion channels. Producing nucleic acid sensor molecules that block the complex keep the GPCR's from activating their effectors.

Example 32

Multiplex Assay for Gα Proteins

Nucleic acid sensor molecules are also generated whose activity is dependent on multiple activated G-proteins. Human G-protein cDNAs are obtained from publicly available databases or are cloned by RT-PCR from polka-RNA pool of appropriate source. They can be expressed as described above and use to select nucleic acid sensor molecules. The readouts for multiplex assay system are discussed above.

Example 33

Nucleic Acid Sensor Molecules Activated by Native Lysozyme.

Figure 26:
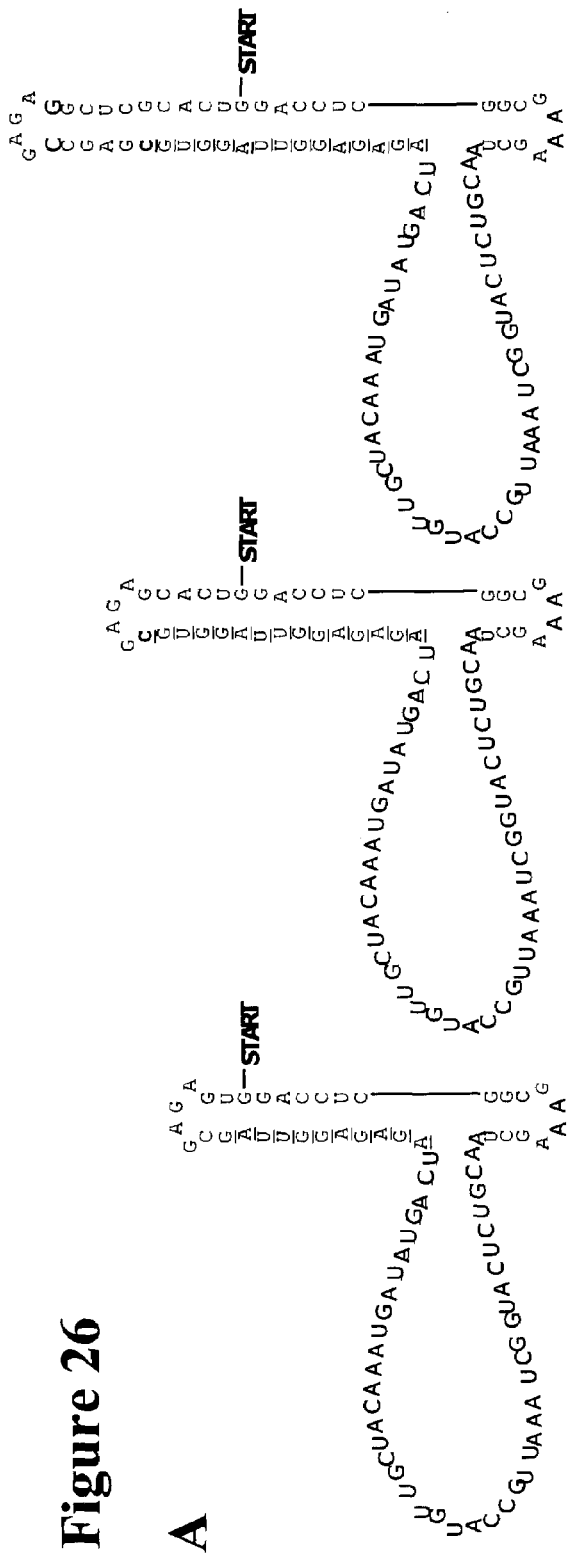
FIG. 26 shows the sequences for lysozyme modulated ligase nucleic acid sensor molecules C.lys.L1.A (SEQ ID NO:105), C.lys.L1.B (SEQ ID NO:106), and C.lys.L1.C (SEQ ID NO:107).

Lysozyme activated nucleic acid sensor molecules lys.L1.A, B, and C are disclosed in FIG. 26. Stems above the ligation junction varied in length from 2, 5 and 10 base pairs. The unimolecular NASMs were generated by PCR of the original lysozyme NASM with 5' primer (TCTAATAC- GACTCACTATAGGACCTCGGCGAAAGC) (SEQ ID NO:296) and the following 3' primers: A ACTCTCGCTAACCTCTCTAGTCATA (SEQ ID NO:297), (B) AGTGCTCTCGCACCTAACCTCTCTAGT (SEQ ID NO:298) or (C) AGTGCGAGCCTCTCGGCTCGCAC-CTAACCTCTCTAGT (SEQ ID NO:299) using Taq polymerase (Invitrogen) following the manufacturer's protocol. RNAs were generated with Ampliscribe T7 transcription kits following the manufacturer's protocol. RNA was heated in water for 3 min at 70° C. and then brought to room temperature before adding 5×buffer (5×buffer: 150 mM Tris, 50 mM MgCl2, pH 7.5) and lysozyme (1 uM or absent). Ligations were performed at room temperature for one hour then quenched with stop dye [formamide, 0.1% bromophenol blue, xylene cyanol] and anaylzed on a 6% acrylamide gel. Self-ligation was increased in the presence of lysozyme for constructs B and C. No ligation was observed for construct A, suggesting that the stem length above the ligation junction is critical.

Figure 27:
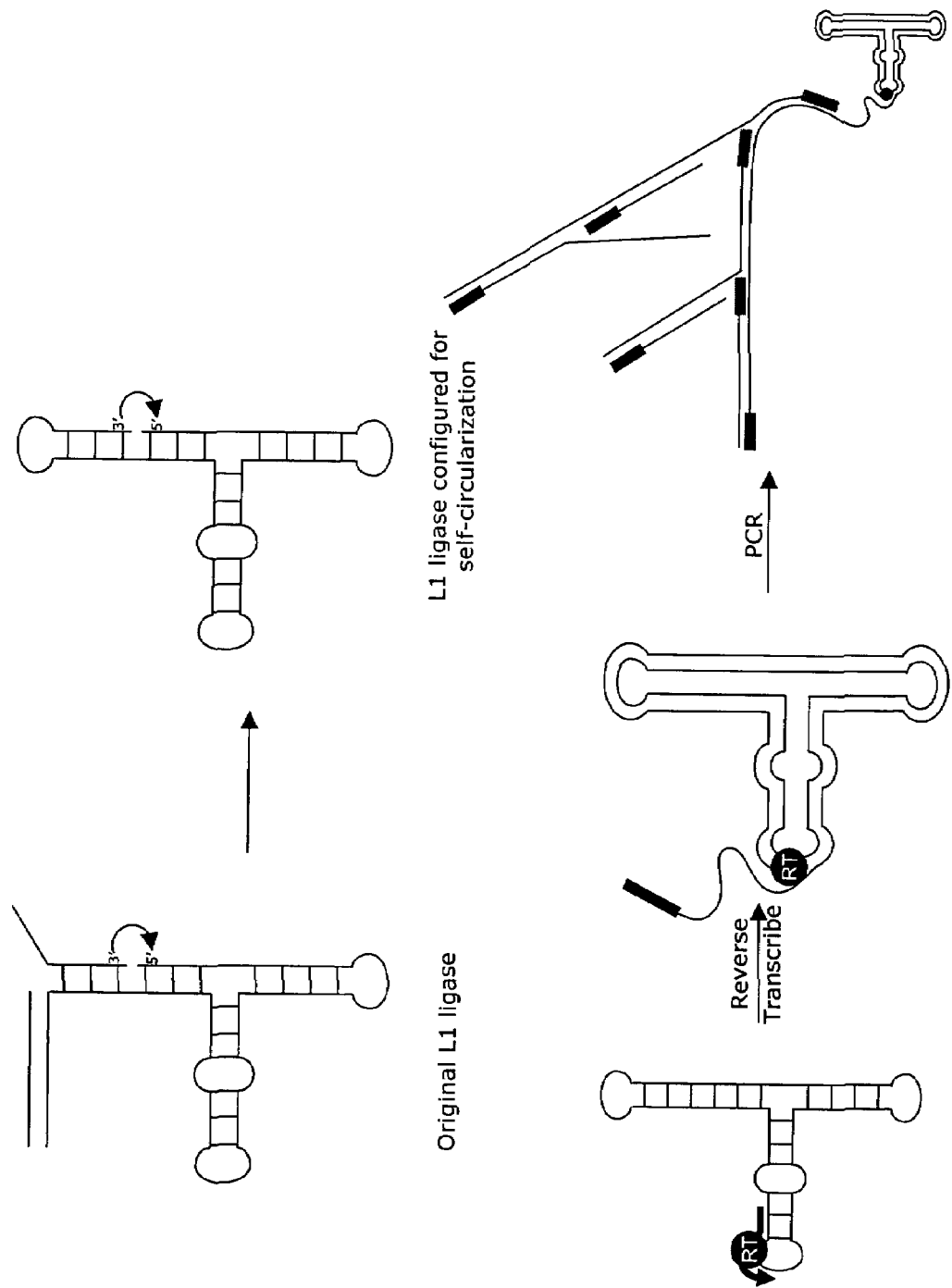
FIG. 27 is a schematic of how an L1 ligase is configured for self-circularization, and how its self-circularization can be detected using RT-PCR.
Figure 28:
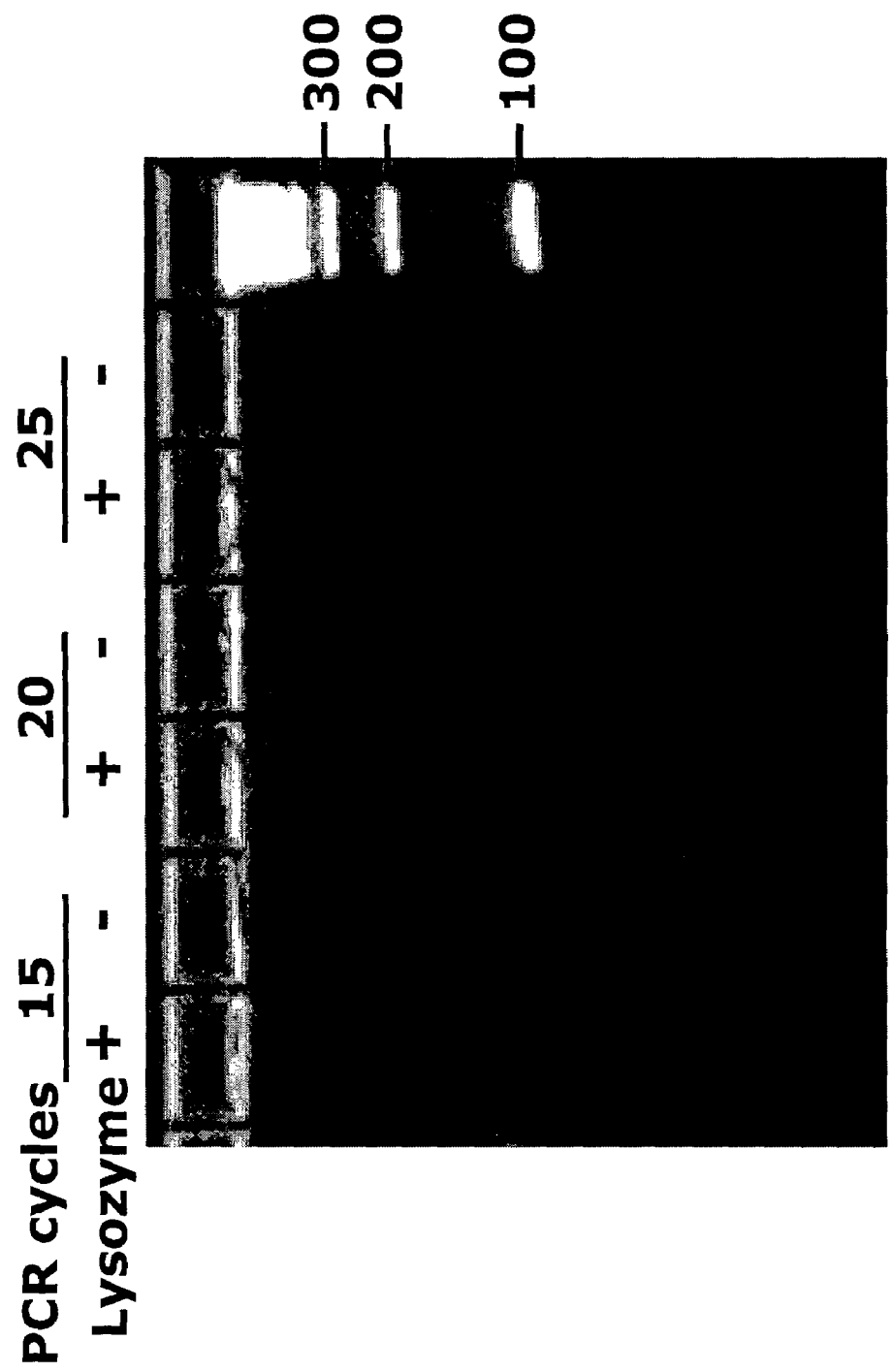
FIG. 28 shows increases in amplification of circularized C.lys.L1.B (SEQ ID NO:106) in response to the addition of lysozyme. The signal is strengthened as additional cycles of PCR are performed.

This circularization can be detected using PCR across the ligation site as shown in FIG. 27. Activation of (clone B is shown in FIG. 28. Protocols from the supplier were followed for Superscript RT and recombinant Taq Polymerase (Invitrogen). All RNA samples were reverse transcribed and PCR amplified separately with two different sets of primers. The first set was designed to amplify the total NASM RNA that was used as input into in vitro (TCTAATACGACTCAC-TATAGGACCTCGGCGAAAGC (SEQ ID NO:300) and AGTGCTCTCGCACCTAACCTCTCTAGT (SEQ ID NO:301)). The second set of primers was designed to selectively amplify the RNAs that circularized (GTTGCTA-CAAATGATATGAC (SEQ ID NO:302)and ATGGCAATT-TAGCCATGAGA (SEQ ID NO:303)). Following amplification with RT/PCR the circularized species display a ladder like pattern as a result of strand displacement. The ladder can be avoided by the use of a reverse transcriptase with RNase H activity. The gel shows in FIG. 28 that after 25 cycles of PCR, a circularization signal appears. This signal allows for quantitation of the degree of activation of ligase in response to their target molecules.

Figure 29:
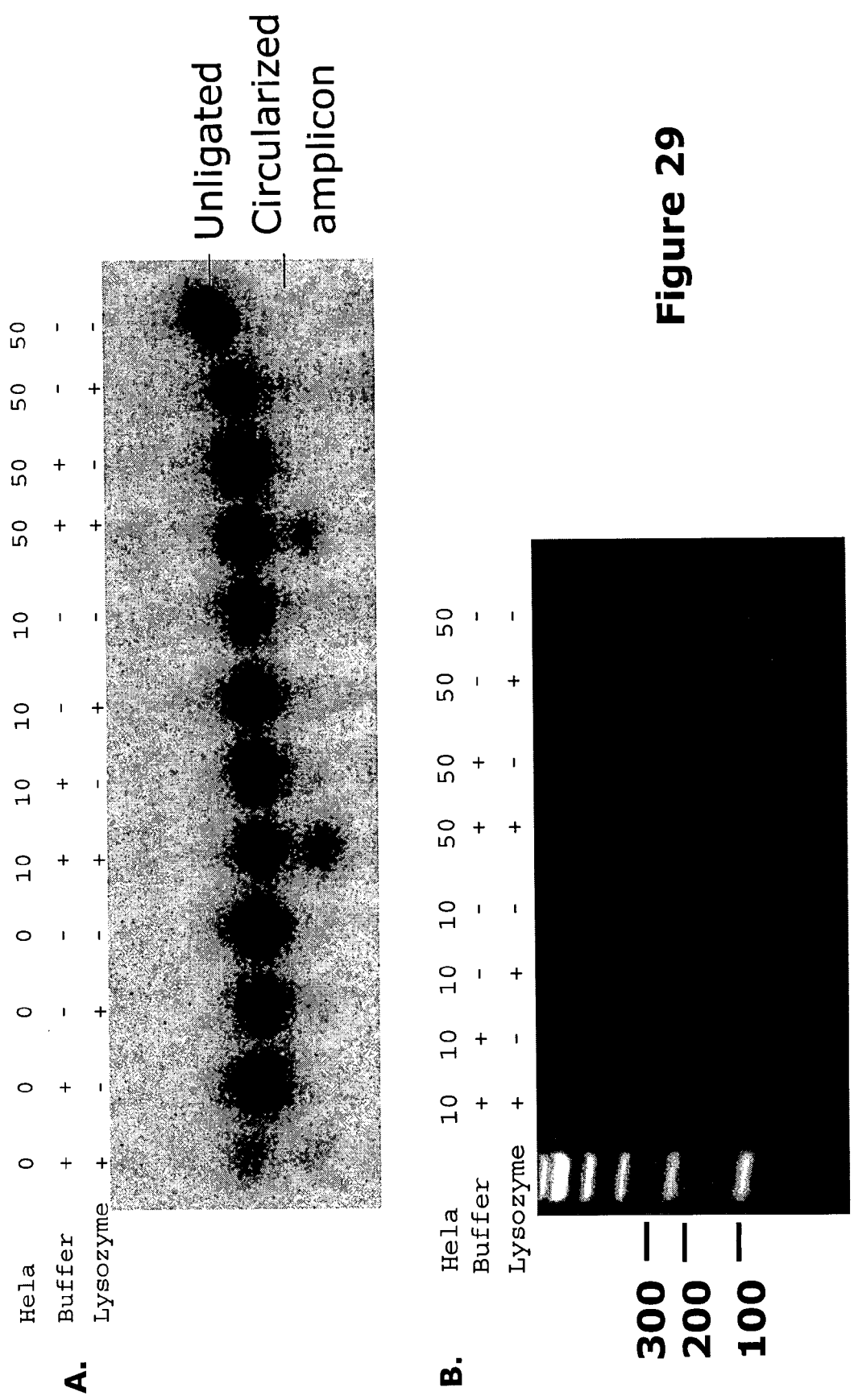
FIG. 29 shows that the ligase nucleic acid sensor molecule C.lys.L1.B (SEQ ID NO:106) still self ligates in response to the presence of lysozyme, even in the presence of HeLa cell extract, demonstrating the stability of this nucleic acid sensor molecule.

Ligase nucleic acid sensor molecules are also able to detect their targets in cell extracts. In FIG. 29, (clone B is combined with lysozyme, and increasing amounts of HeLa cell extracts. Experiments were carried at as described for FIG. 28 with HeLa cell extract added in place of water. Even at the highest HeLa cell extract concentration, activation of clone B by lysozyme is still detectable.

Lysosyme-dependent ligase (lys11–2 from Nature Biotechnology 19, 650–655 (2001)) incubated in the presence of effector oligonucleotide 18.90a (ibid.), substrate S28A (ibid.), optionally 10% cellular lysate (HeLa cells or reticulocyte lysate) and various concentrations of lysozyme at 25° C. for 1 hour, as shown in FIG. 50. Ligation is observable at 100 nM and is ~30% at 1 µM. Ligation yield is unaffected by the presence of 10% reticulocyte lysate or 10% HeLa lysate.

Figure 30:
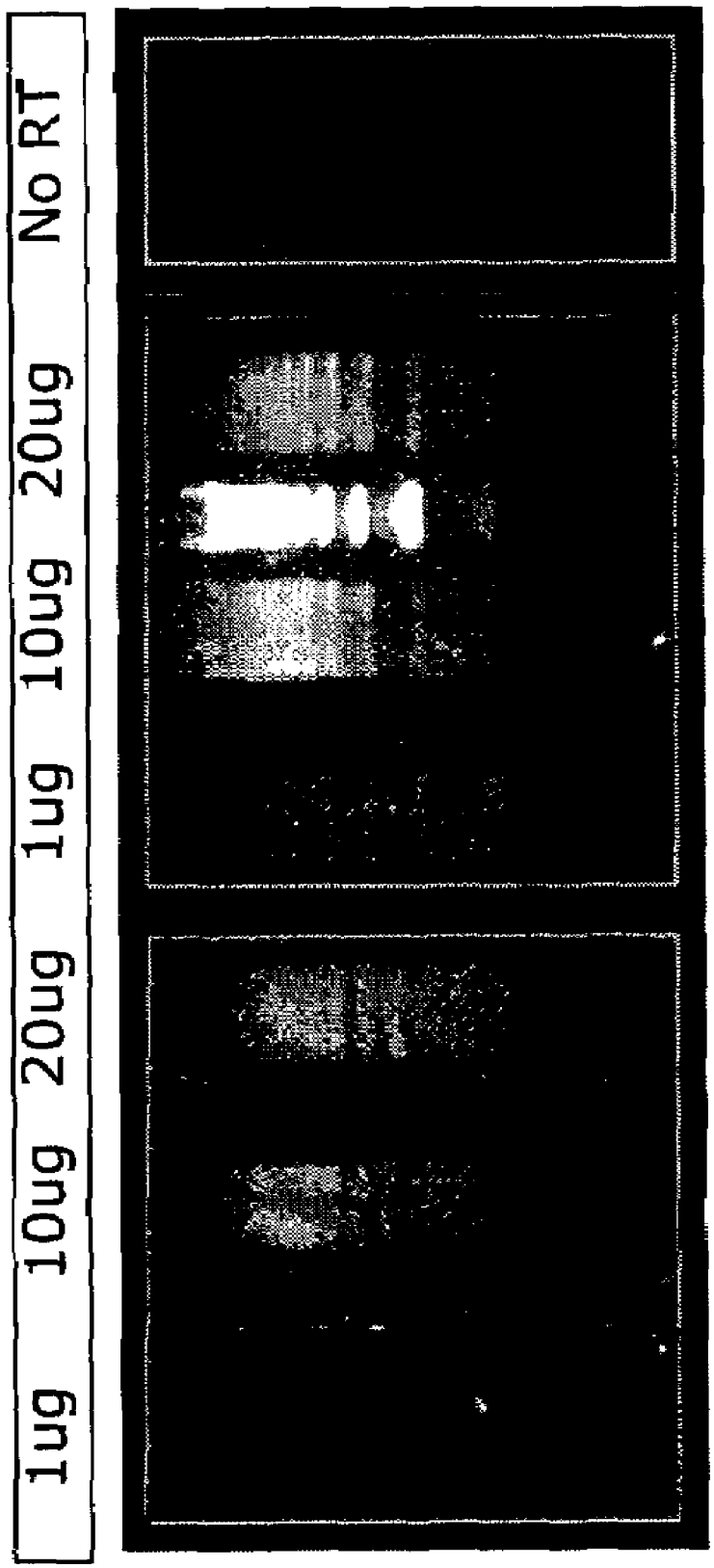
FIG. 30 shows modulation of a 1-piece ligase nucleic acid sensor molecule in vivo.

Ligase nucleic acid sensor molecules are also able to detect their targets in vivo. Mammalian cells were electroporated with 1, 5, 10 and 25 µg RNA. The RNA was brought to a total volume of 30 ul in the presence of 20 ug salmon sperm DNA. Cells were trypsinized, counted, pelleted and resuspended in 250 ul of media. The ligase biosensor/ Salmon sperm DNA mixture was added to the cells, mixed gently and incubated at room temperature for 5 minutes. The cells were electroporated and diluted in pre-warmed media and incubated at ambient temperature for 5 minutes. Subsequently, the cells were plated and transferred to a 37° C. incubator and allowed to recover for 6 hours. Following recovery, the cells were trypsinized, pelleted, washed with PBS and pelleted again. Cells were resuspended in an ice cold mixture of 150 mM NaCl, 1 µl of 10% NP-40 and 6 µl 10% SDS, 28 µl10 mM Tris-HCl, pH 8.0 solution and added to a mixture of 40 Proteinase K (20 mg/ml). The lysate was passed through a 1 ml 26G 5/8 syringe 20 times. Lysates were incubated at 37° C. for 2 hours. Following the incubation the slurry was phenol/chloroform/isoamyl alcohol extracted two times, the aqueous phase was removed and ethanol precipitated RT-PCR reactions were carried as described for FIG. 30. Extent of ligation and circularization was determined by RT-PCR as shown in FIG. 30B, the cells that were cotransfected with lysozyme showed an increased circularization.

Example 34

RT-PCR Analysis of Ligase Nucleic Acid Sensor Molecules/ amplicon-dependent Nucleic Acid Amplification.

Figure 46:
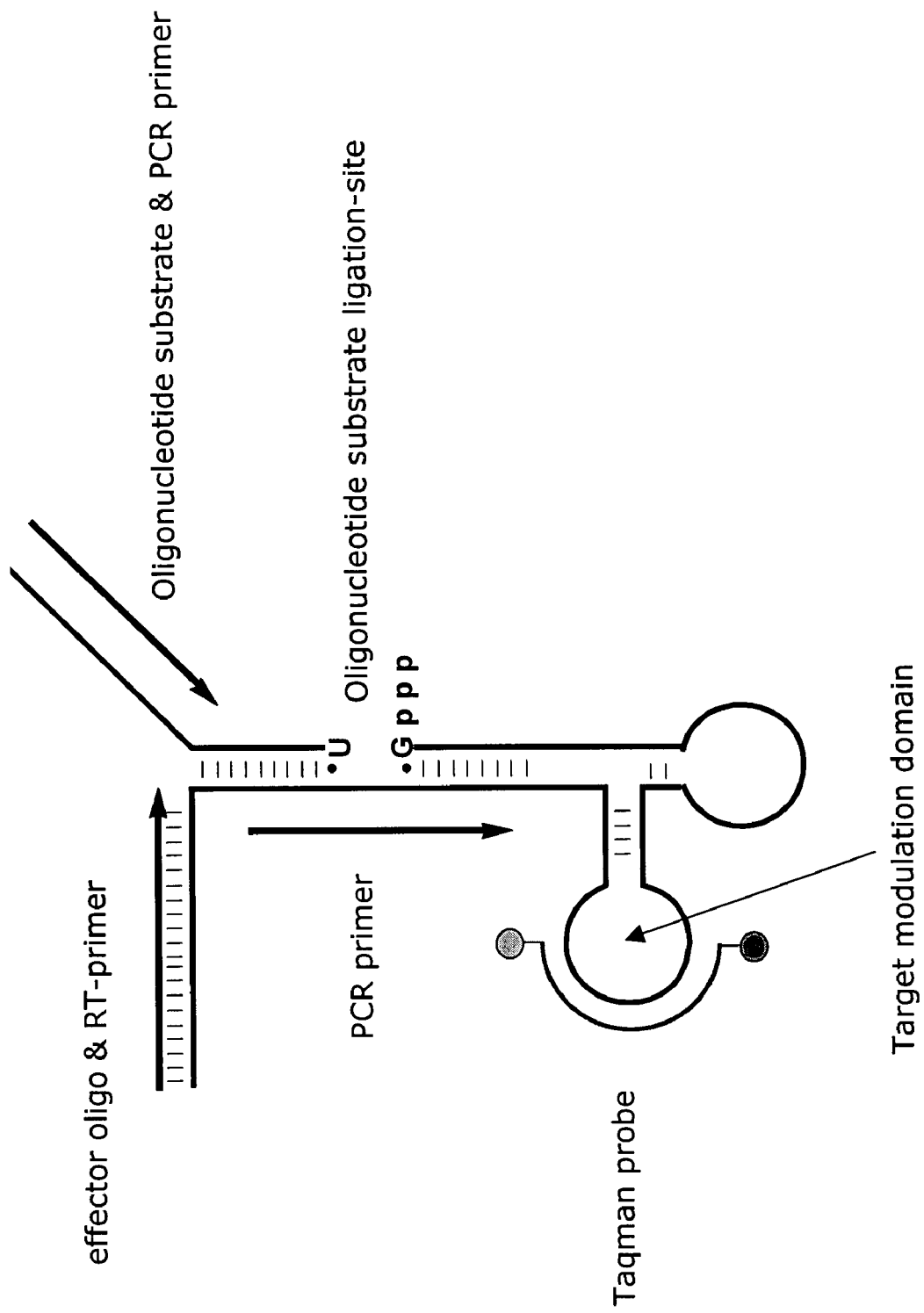
FIG. 46 shows a schematic demonstrating amplicon-dependent nucleic acid amplification (ADNA).

RT-PCR is a quantitative method that can be used to measure the activity of a ligase nucleic acid sensor molecule. As shown in FIG. 46, PCR primers are used that hybridize to sequences of the ligase nucleic acid sensor molecule that are only joined after self-ligation. After ligation occurs the nucleic acid sensor molecule can be amplified, and the PCR product can be detected on an agarose gel, using ethidium bromide or other nucleic acid staining techniques. Alternatively, the progress of the PCR reaction can be monitored using real-time detection techniques including, but not limited to, Taqman (Applied Biosystems, Foster City, Calif.), SYBR Green (Molecular Probes, Eugene, Ore. and Applied Biosystems, Foster City, Calif.), Scorpion (Eurogentec, Liege, Belgium), Amplifluor (Serologicals, Norcross, Ga.) or related systems.

Figure 48:
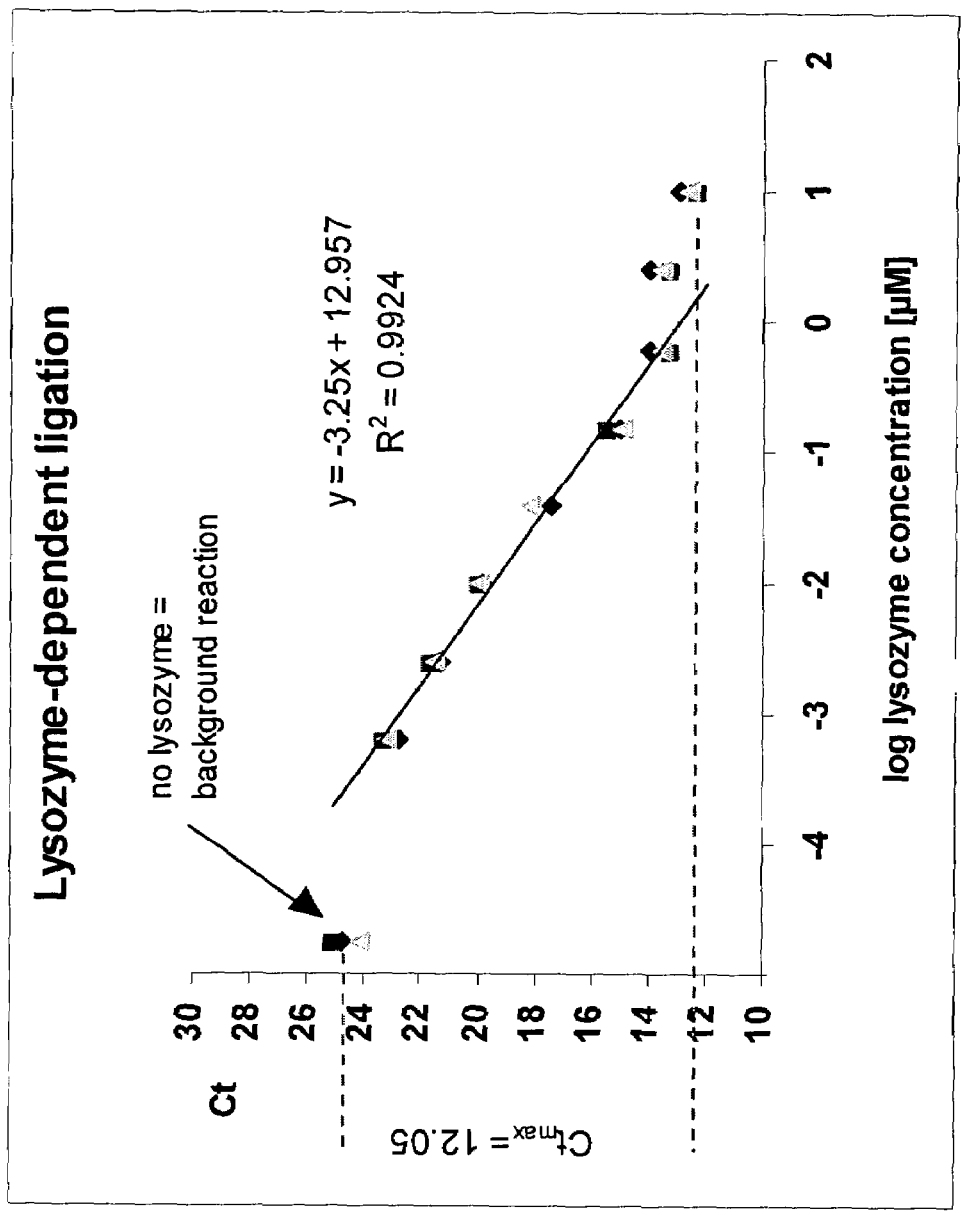
FIG. 48 shows a graph demonstrating the determination of threshold cycle versus log of target molecule concentration using amplicon-dependent nucleic acid amplification via quantitative PCR analysis.
Figure 49:
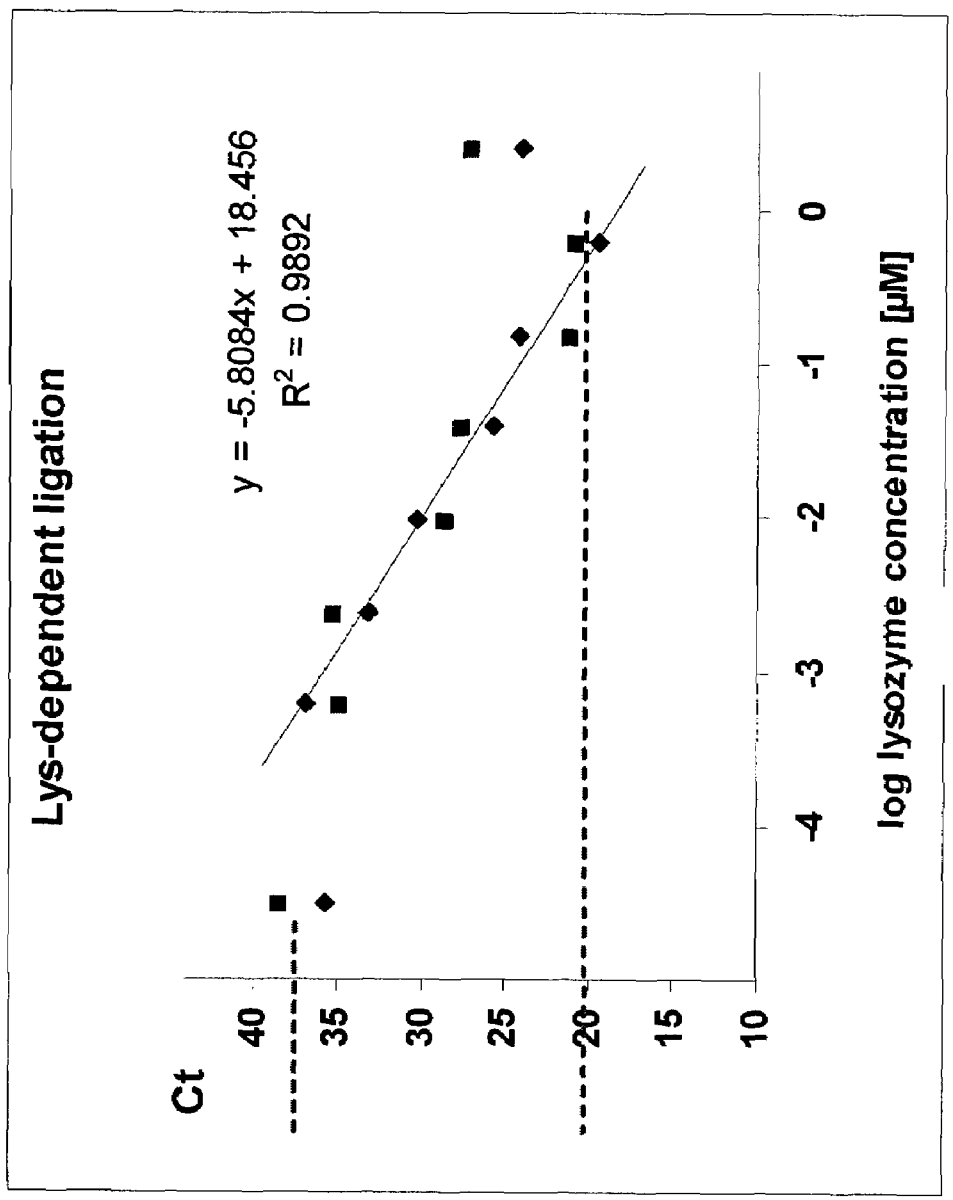
FIG. 49 shows a graph demonstrating the determination of threshold cycle versus log of target molecule concentration using amplicon-dependent nucleic acid amplification via SYBR-green analysis.

A specific example of a lysozyme-dependent ligase nucleic acid sensor molecule is as follows:

The ligase RNA has the sequence 5'GGACCUCGGC-GAAAGCUAACGUCUCAUGGCUAAAUUGC-CAUGUUGCUACAAAU GAUAUGACUAGAGAGG-UUAGGUGCAUCUUCAUGUCCAGUCGCUUGCA AUGCCC (SEQ ID NO:304) and is prepared through transcription off a double-stranded DNA template using T7 polymerase (Ambion MegaShortscript kit, Ambion, Austin, Tex.). For the ligation reaction, 200 nM nucleic acid sensor molecule RNA,1 ,µM DNA RT primer 5'GGGCATTG-CAAGCGACTGGACAT (SEQ ID NO:305) and 1 µM substrate oligo 5'ACTGAACCTGACCGTACAAAGATg-cacu (SEQ ID NO:306) (DNA: upper case; RNA: lower case) are incubated with 1 nM-10 µM hen egg white lysozyme in reaction buffer (50 mM Tris pH 7.4, 100 mM KCl, 10 mM $MgCl_2$) as previously described (Robertson M P & Ellington A D, Nature Biotechnol. 2001, 19, 650–655). After 15 min at room temperature, the reaction is stopped by diluting 300-fold with 1 mM EDTA. Of this, 5 µL are transferred into 25 µL of a RT-PCR reaction mix (Applied Biosystems, Foster City, Calif.) that contains 300 nM DNA forward primer 5'ACTGAACCTGACCGTACAAAGA (SEQ ID NO:307) and DNA reverse primer 5'TTTGTAG-CAACATGGCAATTTA (SEQ ID NO:308) plus 350 nM Taqman probe 5'6FAM-CGGCGAAAGCTAACGTCT-CATGG-TAMRA (SEQ ID NO:309) (Applied Biosystems, Foster City, Calif.). Reverse transcription is performed through incubation for 30 min at 48° C. The sample is then denatured for 10 min at 95° C. followed by 40 PCR cycles (15 sec at 95° C., 1 min at 60° C.). The amplification process is monitored using a ABI 7000 instrument (Applied Biosystems, Foster City, Calif.), and threshold cycle values are calculated using the instrument software. Plotting the Ct against the logarithm of the lysozyme concentration reveals a largely linear relationship (FIG. 48). The linear dynamic range spans about three orders of magnitude from ~1 nM to ~1 μM. A control reaction without the addition of lysozyme gives a threshold cycle values of ~24.5. This value defines the upper limit for threshold cycle values, and is due to the small amount of product that is inevitably generated through the background ligation. On the opposite end, the lower plateau of threshold cycle values is reached with lysozyme >~1 PM. This concentration is close to the apparent Kd (1.5 μM), and the nucleic acid sensor molecule target modulation domain is beginning to be saturated by lysozyme, triggering a reaction at maximum catalytic rate. Another specific example describes the use of the SYBR Green RT-PCR amplification detection system (Applied Biosystems, Foster City, Calif.). Ligation reactions are run as described above, and analysis is done through transferring 5 μL of the reaction into 25 μL of a SYBR-Green RT-PCR reaction mix (Applied Biosystems, Foster City, Calif.) that contains 100 nM DNA forward primer 5'ACTGAACCTGACCGTACAAAGA (SEQ ID NO:310) and DNA reverse primer 5'TTTGTAG-CAACATGGCAATTTA (SEQ ID NO:311). Reverse transcription is performed through incubation for 30 min at 48° C. The sample is then denatured for 10 min at 95° C. followed by 40 PCR cycles (15 sec at 95° C., 1 min at 60° C.). The amplification process is monitored using a ABI 7000 instrument(Applied Biosystems, Foster City, Calif.), and threshold cycle values are calculated using the instrument software as above (FIG. 49). The threshold cycle values are directly proportional to the logarithm of the lysozyme concentration between ~1 nM to ~1 μM. A melting profile confirms that a uniform amplification product was obtained, without the appearance of artifacts such as primer-dimers.

Example 35

Ligation Reactions in 3 or 2 Piece Systems.

Ligation reactions with varying volumes depending on the application type were performed in buffer 1, [30 mM Tris-HCl, pH 7.5, 10 mM MgCl$_2$, 50 μg/mL tRNA type X (Sigma)], or buffer 2 [20 mM HEPES, pH 7.4, 10% glycerol, 150 mM KCl, 10 mM MgCl$_2$, 1 mM EDTA, 1 mM DTT, 0.5 mg/ml tRNA, 2 U/μL RNaseOUT™ (Invitrogen)]. Ligation reactions performed in the presence or absence of crude cell lysates contained 200 nM or 50 nM ligase RNA, respectively. Ligase RNA was pre-annealed with a 2-fold molar excess of effector oligonucleotide by incubation for 3 min at 70° C., followed by the addition of 5×reaction buffer at 25° C. The appropriate concentration of protein and/or cell lysate was added to the RNA and incubated for an additional 15 min at room temperature. Ligation reactions were then initiated by the addition of this mixture to a 10×solution of the substrate oligonucleotide TK.04.82.C ACGTAGCAT-AGCATCGATAGCTGTTGugcacu (SEQ ID NO:357) (small letters correspond to RNA nucleotides) final concentration=1 μM). The reactions were incubated at 25° C., and small aliquots (2–10 μL) of reaction mix were quenched by dilution in EDTA.

Example 36

Transfection of Ligase Biosensors into Mammalian Cells by Electroporation.

HEK 293, 3T3 or HeLa cells were grown in DMEM medium containing 10% fetal bovine serum to 85–90% confluency, and harvested by trypsinization. Aliquots of approximately 250,000 cells were pelleted by centrifugation (3 min at 2000 rpm), resuspended in 250 μL of growth medium, and gently mixed with 30 μL of nucleic acid mix containing 20 μg of salmon sperm DNA (carrier) and 1, 5, 10 or 25 μg nucleic acid sensor molecule ligase RNA. This mixture was incubated at room temperature for exactly 5 minutes without agitation, and transferred to electroporator cuvettes. An electric field pulse was applied to the cells at ambient temperature using a Gene Pulser II power supply (BioRad; settings: 250V, 0.975 μF high capacitance). The cells were plated in pre-warmed growth medium, incubated at 37° C. for varying periods, and harvested. Cells were washed with PBS, pelleted, and immediately subjected to total, cytoplasmic, or nuclear RNA isolation procedures or flash-frozen in liquid nitrogen and stored at −80° C. for further analysis.

Purification of total RNA from mammalian cells Pelleted cells were resuspended in ice old buffer (150 mM NaCl, 10 mM Tris HCl, pH 8.0) and added to 40 μl of 10% SDS, 28 μl of 10% NP40 and 6 μl of Proteinase K (20 μg/ ml). The mixture was drawn into a 1 ml syringe and passed through a 26 gauge needle at least 20 times, and then incubated at 37° C. for 2 hours. Following incubation, the slurry phenol/chloroform/isoamyl alcohol extracted two-times, the aqueous phase was removed and ethanol precipitated. The sample was 70% ethanol washed, and dried. The RNA pellets were resuspended and the yield was quantified based on OD 260. The cleanliness of the prep was assessed based on 260/280 ratio. All RNA samples were stored at −80° C.

Example 37

Analysis of Ligation and/or Circularization by RT/PCR:

Protocols from the supplier were followed for reverse transcription and PCR. Either Superscript RT or AMV RT, and recombinant Taq Polymerase (Invitrogen) were used.

In order to avoid any occurrence of ligation in the detection phase of experiments, all reverse transcriptions were performed at 48° C. All RNA samples were reverse transcribed and PCR amplified separately with two different sets of primers. First set was designed to amplify the total RNA that was used as input into in vitro or ex vivo assays. The second set of primers were designed to selectively amplify the RNAs that were ligated to the substrate oligo (resulting in a higher molecular weight) or were ligated to their 5' end and became circularized without molecular weight change. two and three-piece ligase platforms give rise to higher molecular weight products as a result of target dependent ligation. One piece ligase platform circularize as a result of target dependent ligation. When observed directly with gel based assays the circularized form has a different mobility than the linear RNA. Following amplification with RT/PCR the circularized species display a ladder like pattern as a result of strand displacement that happens in the reverse transcription phase. The ladder like pattern can be avoided by the use of a reverse transcriptase with RNase H+ activity.

Example 38

Preparation of Extracts from Mammalian Cell Cultures:

After stimulation with the reagent that regulates target levels, mammalian cells were rinsed briefly in cold TBS and then lysed in TBS lysis buffer (137 mM NaCl, 20 mM Tris, pH 8.0, 1% vol/vol NP-40, and 10% vol/vol glycerol; Knusel et al. 1994) or Brij Lysis buffer (150 mM NaCl, 10 mM Tris, pH 7.5, 2 mM EDTA, 0.125% vol/vol NP-40, 0.875% vol/vol Brij and 10% vol/vol glycerol). Lysis buffers were supplemented with Mini Complete protease inhibitor cocktail (Boehringer Mannheim Corp.) and 1.5 mM sodium vanadate. Lysates were scraped into Eppendorf tubes and rocked for 30 min at 4° C. Samples were then cleared by centrifugation at 10,000 xg fro 10 min at 4° C. Protein concentration was determined by the BCA assay (Pierce Chemical Co.) using BSA as a standard.

Example 39

Intron-based Catalytic NASMs

Figure 61:
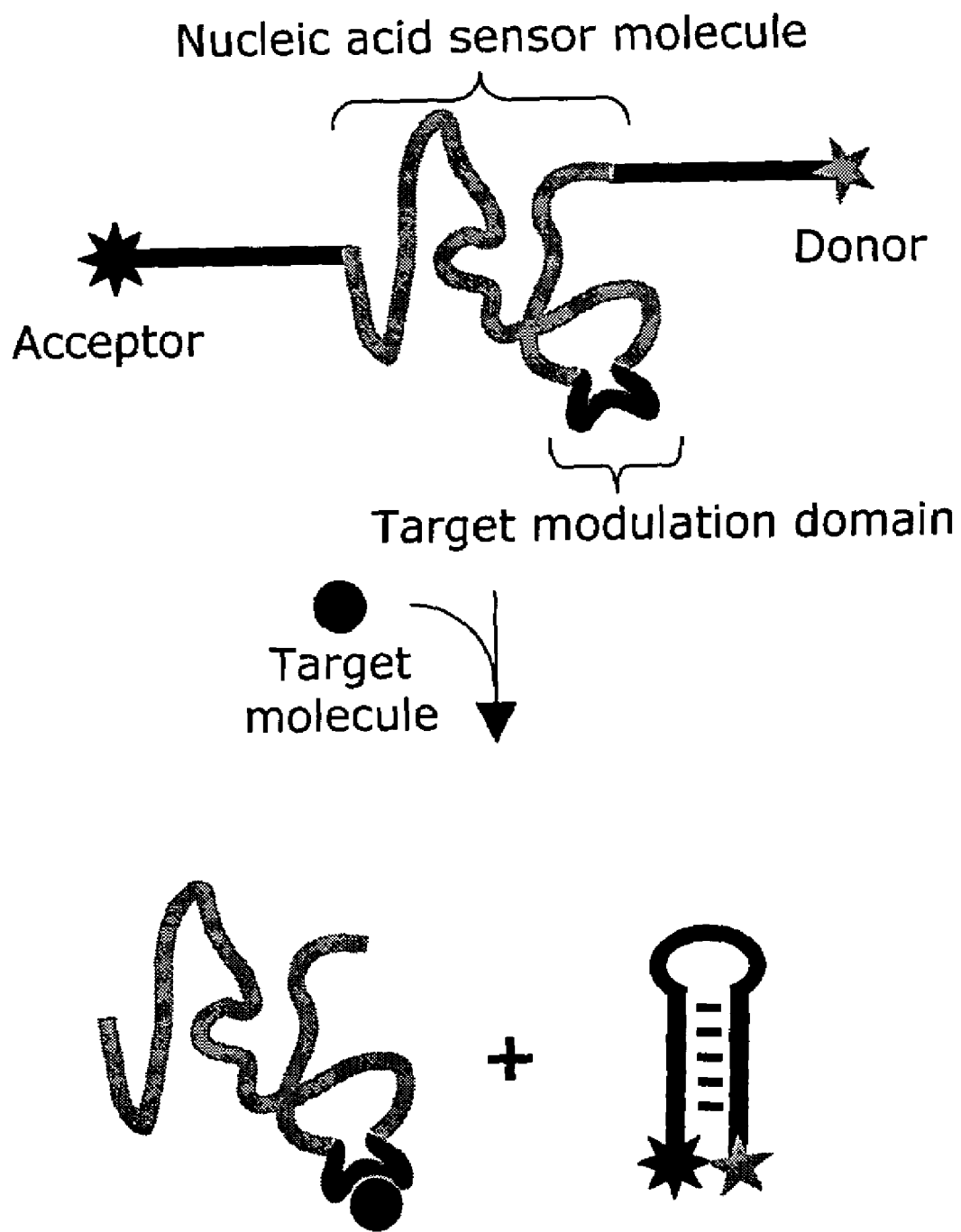
FIG. 61 shows a schematic describing optical detection based on the modulation of an intron-derived nucleic acid sensor molecule.

FIG. 61 illustrates an optical NASM derived from an intron-based catalytic NASM. The optical nucleic acid sensor molecule derived from the group I intron splices in vitro such that it excises itself from a larger nucleic acid sequence and subsequently ligates, or joins together the two terminal portions of the RNA molecule (i.e., the 5' and 3' exons). The distal termini of the 5' and 3' exons are modified to incorporate the donor and acceptor components of a FRET signaling pair. In the absence of target modulation, fluorescence emission will be observed only from the donor fluorophore which is being directly excited optically. Splicing and ligation of the 5' and 3' exons brings the donor and acceptor molecules on the exons into close proximity, resulting in efficient fluorescence energy transfer (FRET) and thus a measurable increase in the fluorescence emission signal from the acceptor fluorophore (with a corresponding decrease in fluorescence emission from the donor fluorophore). In an alternative embodiment (not shown), the acceptor molecule may be replaced with a quencher molecule (i.e., an acceptor species which absorbs but does not re-radiate fluorescent energy). In this case, the splicing and ligation event will only result in a measurable decrease in the fluorescence emission signal from the donor fluorophore.

The thymidylate synthase ("td") intron (Construct 41) (SEQ ID NO:358) -TAATTGAGGCCTGAGTATAAGGT-GACTTATACTTGTAATCTATCTAAACGGG GAAC-CTCTCTAGTAGACAATCCCGTGCTAAATTGTAG GACTGCCCGGGTTCTACATAAATGC CTAACGAC-TATCCCTTTGGGGAGTAGGGTCAAGT-GACTCGAAACGATAGACAACTT GCTTTAACAAGT-TGGAGATATAGTCTGCTCTGCATGGTGACATGC AGCTGGATATAA TTCCGGGGTAAGATTAACGACCT-TATCTGAACATAATG—is a group I intron sequence of 265 nucleotides in length. Other lengths and their sequences are known in the art and can used as described herein in lieu of SEQ ID NO:358 above.

An example of an intron-derived optical NASM that is modulated by target recognition is the theophylline dependent td group I intron which splices itself out of a thymidylate synthase gene. The intron sequence of this optical NASM is as follows:
TAATTGAGGCCTGAGTATAAGGTGACT-TATACTTGTAATCTATCTAAACGGGG AAC-CTCTCTAGTAGACAATCCCGTGCTAAAT-TGATACCAGCATCGTCTTGATGCCC TTGGCAGCATAAATGCCTAACGACTATC-CCTTTGGGGAGTAGGGTCAAGTGACTCG AAAC-GATAGACAACTTGCTTTAACAAGTTG-GAGATATAGTCTGCTCTGCATGGTGAC ATGCAGCTGGATATAATTCCGGGGTAA-GATTAACGACCTTATCTGAACATAATG (construct 42) (SEQ ID NO:359) wherein the bolded nucleotides represent a target modulation domain that recognizes theophylline.

The complete optical NASM comprises the intron sequence described above and the 5' and 3' exons attached thereto. Exon 1, the 5'-exon - TTTCTTGGGT (construct 43)(SEQ ID NO:360)—is designed to contain a first fluorescent donor molecule, such as Cy3 (Amersham Biosciences) coupled to a nucleotide in the vicinity (i.e., within no more than about 15 nucleotides) of the 3' terminus of the 5' exon. The 5'-exon length can vary with a minimum of 6 nucleotides of complementarity to P10. Exon 2, the 3'-exon—CTACCGTTTA (construct 43)(SEQ ID NO:361)—is designed to contain a second fluorescent molecule, such as Cy5 (Amersham Biosciences) coupled to a nucleotide in the vicinity (i.e., no more than about 15 nucleotides) of the 5' terminus of the 3' exon. The 3'-exon length can vary with a minimum of 2 nucleotides of complementarity to P10.

Intron Splicing conditions are as follows: the intron (500 nM) is heated in $H_2O$ to 70° C. for 3 minutes then put on ice for 1 minute. Splicing buffer (20 mM Tris-HCl, pH 7.5, 100 mM KCl, 3 mM $MgCl_2$), is added and the reaction is incubated on ice for an additional 15 minutes. At this time a 4.5 µl aliquot is removed for a time zero point and quenched with 5 µl stop dye (95% formamide, 20 mM EDTA, 0.5% xylene cyanol, and 0.5% bromophenol blue). GTP (50 µM) is added to the remaining reaction (4.5 µl) to start the splicing reaction. The reaction is incubated at 37° C. for 1 hour and then terminated with stop dye (5 µl). The reactions are heated to 70° C. for 3 minutes. Splicing of full length RNA transcripts is detected by gel analysis of labeled RNA.

The theophylline-dependent optical NASM splices in vitro under the same conditions as described for the intron splicing reaction, but with theophylline added to a final concentration 1.5 mM in the splicing buffer. The theophylline-dependent optical NASM (500 nM) is heated in $H_2O$ to 70° C. for 3 minutes then put on ice for 1 minute. Splicing buffer (20 mM Tris-HCl, pH 7.5, 100 mM KCl, 3 mM $MgCl_2$) and theophylline (1.5 mM) are added and the reaction is incubated on ice for an additional 15 minutes. At this time a 4.5 µl aliquot is removed for a time zero point and quenched with 5 µl stop dye (95% formamide, 20 mM EDTA, 0.5% xylene cyanol, and 0.5% bromophenol blue) (95% formamide, 20 mM EDTA, 0.5% xylene cyanol, and 0.5% bromophenol blue). GTP (50 µM) is added to the remaining reaction (4.5 µl) to start the splicing reaction. The reaction is incubated at 37° C. for 1 hour.

Target dependent modulation of the intron-derived optical NASM is followed by fluorescence measurement as described herein.

Example 40

Solid-phase Nucleic Acid Sensor Array for Assays with Fluorescent Detection-FRET Chip This example describes a general method for implementing a FRET-based (fluorescence resonance energy transfer) assay utilizing nucleic acid sensor molecules. (in this case, cGMP-dependent hammerhead nucleic acid sensor molecule) wherein the nucleic acid sensor molecule is immobilized on a solid substrate, e.g., within a microtiter plate well, on a membrane, on a glass or plastic microscope slide, etc.

In the specific embodiment described here, a first oligonucleotide of the nucleotide sensor molecule is 3'-labeled with an acceptor or quencher fluorophore, such as TAMRA, AlexaFluor 568, or DABCYL, via specific periodate oxidation (see Example 34. for specific protocol). A second oligonucleotide of the nucleic acid sensor molecule, complementary to at least part of the first oligo portion of the NASM, is labeled with a 3' biotin and a 5' donor fluorophore, such as fluorescein (FAM, FITC, etc.). These two nucleic oligonucleotides are heat-denatured in solution and allowed to anneal/hybridize during cooling to room temperature. After hybridization, the NASM solution is applied to a surface which has been coated with some type of avidin (streptavidin, neutravidin, avidin, etc.). This surface could include a microtiter plate well, a streptavidin-impregnated membrane, a glass or plastic microscope slide, etc. In any case, the ribozyme-oligo complex is specifically immobilized via the 3' biotin on the donor oligo, leaving the binding domain free to interact with the target effector molecule.

Figure 62:
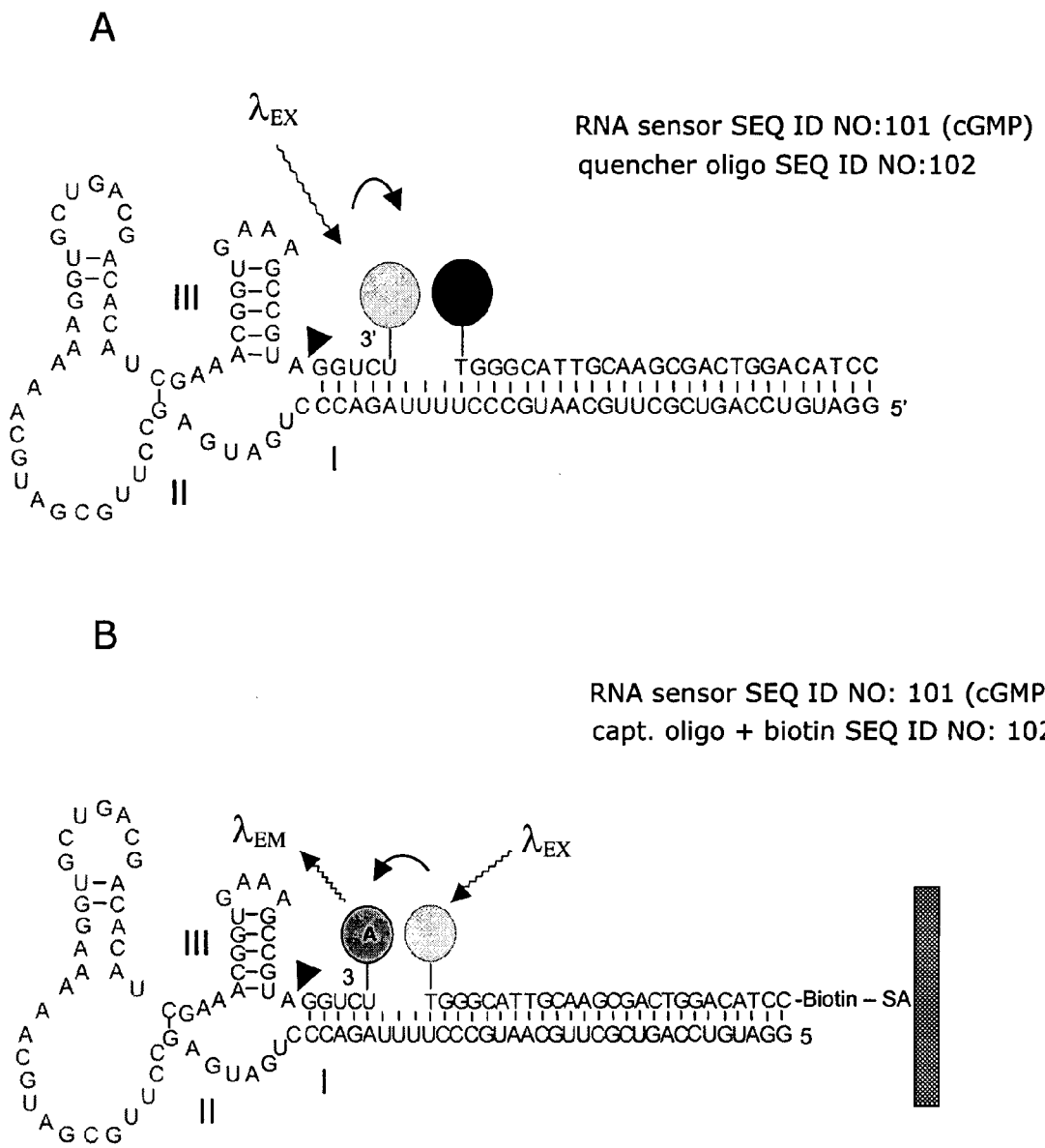
FIG. 62 shows the original solution-phase cGMP-dependent hammerhead nucleic acid sensor molecule FRET construct (SEQ ID NO:101) and its effector/capture oligo (SEQ ID NO:102) from which the solid-phase FRET sensor was derived. In the solution-phase construct shown in FIG. 62A, the fluorophore (F) and quencher (Q) are FAM and DAB-CYL, respectively. In the solid-phase construct shown in FIG. 62B, the donor fluorophore (D) and acceptor fluorophore (A) are FAM and AlexaFluor 568, respectively.

FIG. 62 shows the solution-phase FRET construct (upper panel) from which the solid-phase nucleic acid sensor molecule construct (lower panel) was derived. In the figure, the species labeled 'A' and 'D' represent the acceptor and donor fluorophores, respectively; similarly, the species labeled 'F' and 'Q' represent the donor and quencher fluorophores, respectively.

Figure 63:
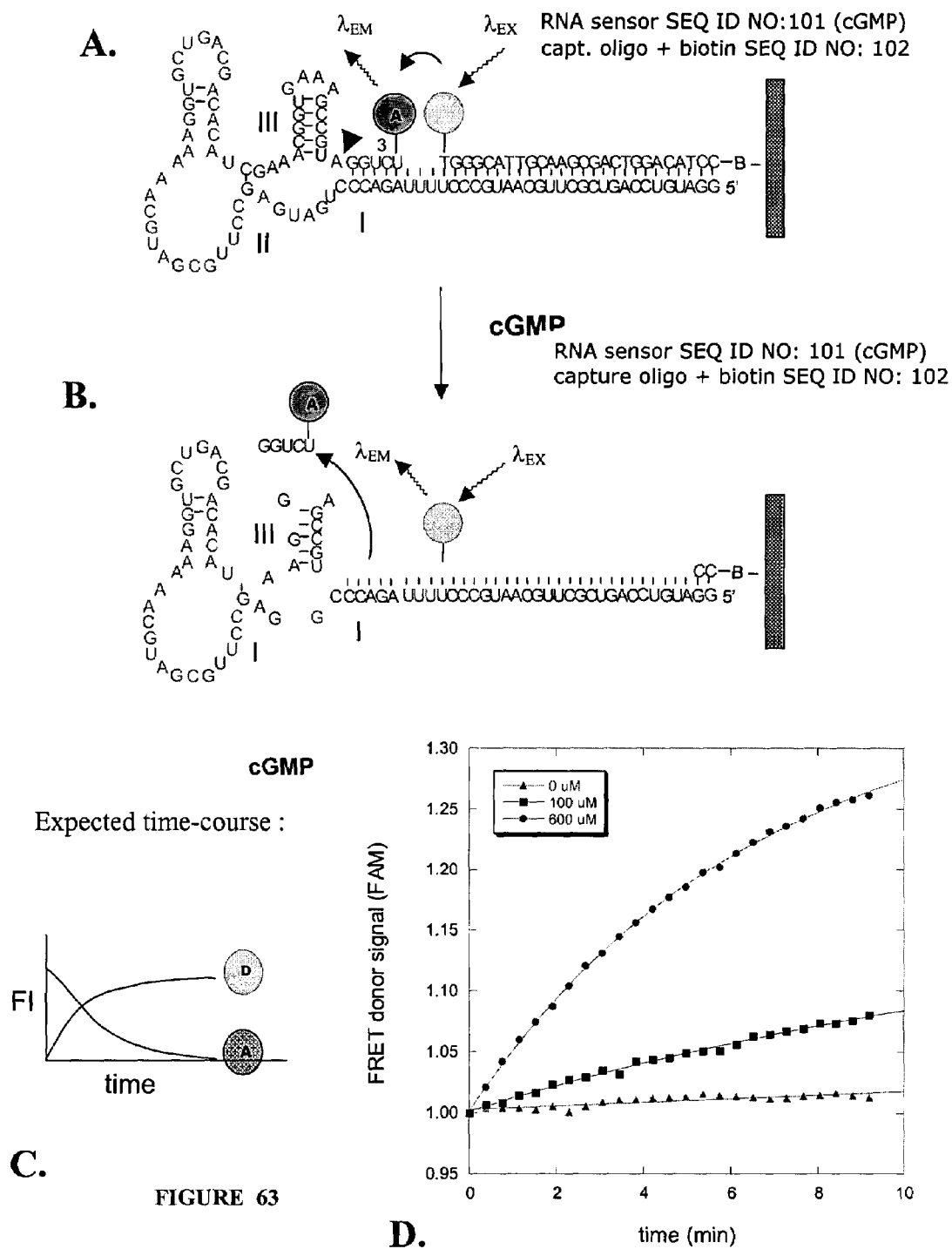
FIG. 63A shows the surface-immobilized FRET sensor before.
FIG. 63B shows after, exposure to the activating target molecule (cGMP), followed by subsequent cleavage and dissociation of the sequence fragment containing the acceptor fluorophore (A).
FIG. 63C shows the expected kinetic time course signals and FIG. 63D shows the actual kinetic time course signals observed from these sensors in the presence of various concentrations of target.

As shown in FIG. 62 (lower panel), the donor and acceptor fluorophores form an efficient FRET-pair; that is, upon excitation of the donor fluorophore near its spectral absorption maxima, the incident electromagnetic energy is efficiently transferred (nonradiatively) via resonant electric dipole coupling from the donor fluorophore to the acceptor fluorophore. The efficiency of this resonant energy transfer is strongly dependent on the separation between the donor and acceptor fluorophores, the transfer rate being proportional to $1/R^6$, where R is the intermolecular separation. Therefore, when the donor and acceptor are in close proximity, i.e., a few bond-lengths or roughly 10–50 Angstroms, the fluorescent emission from donor species will be reduced relative to its output in an isolated configuration, while the emission from the acceptor species, through indirect excitation by the donor, will be detectable. Upon separation of the donor and acceptor, the donor fluorescence emission signal will increase strongly, while the acceptor emission signal will show a commensurate decrease in intensity. These effects are shown in FIG. 63 (upper panel) for the cGMP-dependent NASM system (SEQ ID: NO. 102).

The black arrow shown in the uppermost panel of FIG. 63 indicates the site of phosphodiester bond cleavage, which occurs upon modulation fo the target modulation domain (TMD) by a cGMP, to the TMD. The melting temperature, $T_m$, of the remaining 5-base pair sequence (GGUCU in the figure) is ~25° C. Thus, after effector-mediated cleavage at room temperature, the 5-base pair cleavage fragment will rapidly dissociate from the ribozyme body and diffuse away into solution, as shown in the upper panel of FIG. 63.

This target-activated nucleic acid sensor molecule system constitutes a highly sensitive real-time sensor for detecting and quantitating the concentration of the target molecule present in an unknown sample solution. The ultimate limit of detection (LOD) for this system is determined by the switch factor, defined as the ratio of the catalytic rate (in this example, the rate of cleavage) of the ribozyme sensor in the presence of its target to that of the ribozyme in the absence of its target. The dynamic range of the ribozyme sensor will be determined by the dissociation constant, $K_d$, for the interaction of the ribozyme binding domain with the target molecule. In theory, the effective dynamic range over which the rate-response of the NASM is linear in the target concentration has $K_d$ as an upper bound. The lower panel of FIG. 63 shows experimental data from the surface-immobilized cGMP-activated NASM. The data shown in the figure represents the FRET signal from the donor fluorophore with the sensor exposed to concentrations of 0, 100 uM, and 600 uM cGMP. The upper panel of FIG. 64 shows both donor and acceptor fluorescence signals for the FRET system in the presence of 200 uM cGMP. Note that the experimental data exhibits the behavior expected, as shown in the lower panel of FIG. 63. The lower panel of FIG. 64 shows the donor signal form the plot in the upper panel fitted to a pseudo-first order rate equation. As shown by the closeness of the data fit, the kinetic response of this sensor system closely approximates a pseudo-first order reaction.

Figure 65C:
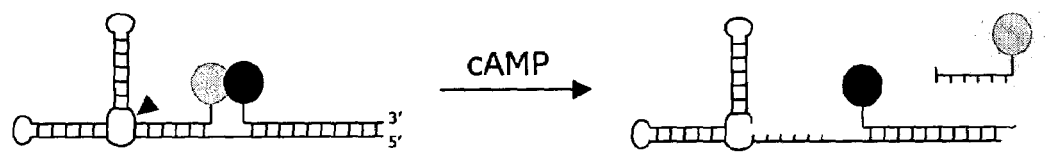
FIG. 65C, D, and E shows experimental data and constructs for multiplexed detection using solution-phase cGMP and cAMP FRET.
Figure 65D:
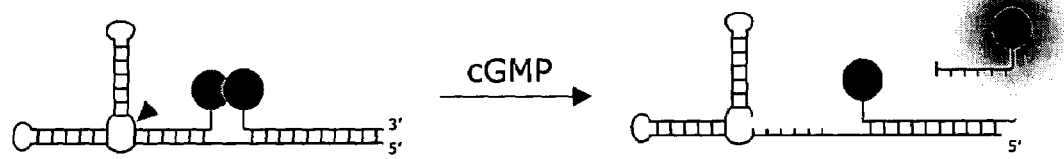
Figure 65E:
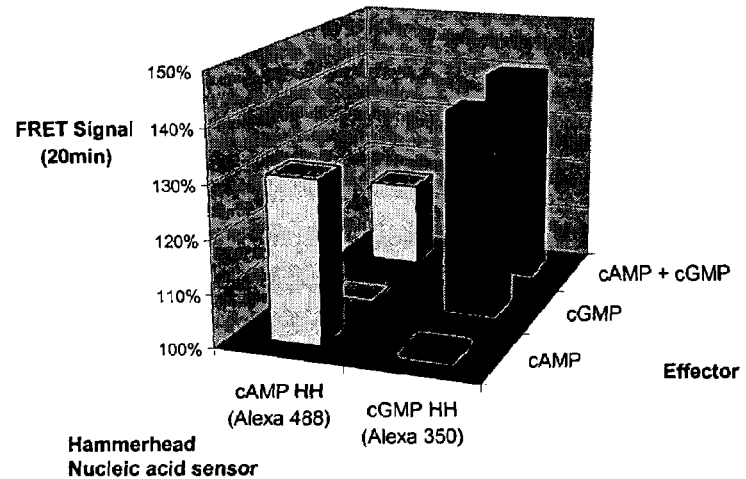

The measured dissociation constant for this cGMP-activated NASM with cGMP is approximately 200–500 uM. In practice, concentration measurements up to 1 mM are possible with this sensor in solution-phase measurements. The absolute precision of measurements made with this NASM will depend on the amount of background catalytic activity (i.e., in the absence of target) and baseline drift of the fluorescence signals from both sample and controls due to physical factors, such as liquid handling errors, reagent adhesion, evaporation, or mixing. After some optimization, run-to-run CVs of a few percent are possible with similar FRET-based NASMs measured in solution. Immobilization of the NASM does not degrade its catalytic activity, although it may limit the effective availability of the target-binding domain for interaction with target molecules. The locally high concentration of surface-immobilized NASM will tend to offset this effect by driving the equilibrium for the association (and subsequent catalytic) reactions toward formation of ribozyme-target complex. The net result is a reduction in the observed catalytic rate of approximately 4-fold at $K_d$ (200–500 uM) for the surface-immobilized cGMP-dependent hammerhead NASM, relative to the observed rate for the same sensor system in solution. This effect is shown in the experimental data presented in FIG. 65A, which shows linear (Panel A) and logarithmic (Panel B) plots of the observed catalytic rate constant versus cGMP concentration for the cGMP-dependent hammerhead NASM in both solution and surface-immobilized ('solid') configurations. The upper panel plots the observed rate as a function of target (cGMP) concentration on linear axes, while the lower plot plots the same rate data on log-log axes. The observed rate constant (at a given concentration) for the immobilized solid-phase sensor is roughly 10-fold lower than that for the solution-phase sensor. The practical effect of this is that, while the solution-phase sensor's linear dynamic range is limited to about 0–600 uM, the solid-phase sensor's linear dynamic range is at least 2 mM. FIGS. 65C, 65D, and 65E shows how this general NASM strategy could be extended to accomplish multiplexed detection of multiple analytes in a sample simultaneously, by using NASMs labeled with fluorophores having different emission wavelengths. Squares are NASMs immobilized on a solid. Circles are NASMs in solution. In this case, the sensors were immobilized in neutravidin-coated microtiter plate wells (96 well plate, volume of 50 uL). Detection of the fluorescent signals was accomplished in this case by a microplate fluorescence reader equipped with the appropriate lamps, optics, filters, and optical detectors (PMT) manufactured by Packard Instrument Co.

This cGMP-dependent hammerhead NASM system was immobilized on streptavidin-impregnated membranes, and target-activated FRET activity observed. The generalization of this application of surface-immobilized NASM with FRET detection to a micro- or macro-arrayed format on an extended substrate such as glass or plastic is easily envisioned. Such a sensor array could be used to detect and quantify the presence of an arbitrary target molecule in a complex solution, e.g., crude cell extract or biological fluid, in real time. In addition, this general NASM strategy could be extended to accomplish multiplexed detection of multiple analytes in a sample simultaneously, by using NASMs labeled with fluorophores having different emission wavelengths. Experimental data for multiplexed detection using solution-phase cGMP and cAMP FRET sensors is shown in FIG. 66B. This NASM, and further extensions of it to include large numbers of unique analyte-sensors, could be used for high throughput screening (HTS) in drug discovery or clonal analysis. In all of these scenarios, optical detection of the FRET signals could be accomplished using a commercially available microarray imager or scanning fluorescence microscope.

The following example contains a sample protocol for the complete process of performing the solid-phase FRET assay described above, including reagent preparation, DNA amplification, RNA transcription, RNA labeling, substrate and instrument set-up, and, finally, assay data acquisition.

Example 41

Protocol for Micotiter Plate-based Solid-phase FRET Assay:

The nucleic acid sensor molecules used in the assays described in Example 33. for the case of the cGMP NASM system were prepared as follows:

The appropriate sequence construct was synthesized and amplified via PCR. This was accomplished using the appropriate DNA template molecule(s) and the corresponding primers:

```
cGMP PCR template:   MK.08.92.A    (SEQ ID NO:333)
5'GCTTGCAAGCCCTTAGACCCTGATGAGCCTTGCGATGCAAAAAGGTGC
TGACGACACAT CGAAACGGTGAAAGCCGTAGGTCT Primer 1:            MK.08.66.B    (SEQ ID:334)
5'AGACCTACGGCTTTCACCGTTTCG Primer 2:            MK.08.130.B   (SEQ ID:335)
5'ATACGACTCACTATAGGATGTCCAGTCGCTTGCAATGCCCTTTTAGAC
CCTGATGAG
```

A trace amount (~100 ng) of template dsDNA was combined with 10–100 picomoles of each primer, e.g., 1 uL each of 100 uM stocks. Using taq DNA polymerase, run 15 cycles of PCR using a typical (95–55–75° C.) temperature-step profile was run. The PCR products were cleaned up using a desalting/size separation column, such as a Qiagen Qiaquick PCR cleanup kit. The resuspended volume of cleaned up PCR products was ~35 uL. The products can be further concentrated, or added directly to a transcription reaction.

After synthesis and amplification of the appropriate sensor construct via PCR, the dsDNA was converted to RNA via in vitro transcription. This was typically accomplished using T7 RNA polymerase and pre-mixed NTPs and buffer, such as are provided in the Epicentre High Yield Transcription Kit. The transcription reaction, consisting of ~16–20 uL of cleaned up PCR products in a 40–50 uL total reaction volume, was typically run at 37° C. for ~8–12 hrs. Following the transcription reaction, the products were usually purified via PAGE or using a desalting/size separation column, such as a Centrisep column (Princeton Separations).

Following production and purification of the RNA NASMs, the fluorescent acceptor labels were attached to the sensor molecules. The fluorescent donor label (in this case a FAM label) was attached to the 5'-biotinylated capture oligo during solid-phase synthesis on a commercial DNA synthesizer, via standard phosphoramidite chemistry. The labeling procedure was accomplished by a specific oxidation of the 3' terminus of the RNA using 20 mM $NaIO_4$, followed by reaction with a hydrazide-conjugated fluorescent label. The resulting covalent bond is extremely stable under the assay conditions. For the oxidation reaction, one typically 15 µL RNA (~200–400 pmoles in reaction), 15 µL 0.3 M NaOAc pH 5.4, and 30 µL 20 mM stock $NaIO_4$ in a were combined 1.5 mL reaction tube, which was then placed on ice in the dark for ~1 hr. After the oxidation reaction, the reaction products were run through a Centrisep desalting column. Alternatively the sample can be ethanol precipitated and resuspended in the original volume.

The oxidized RNA uses then reacted with the dye-(in this example, AlexaFluor 568)-hydrazide conjugate. A typical reaction includes 60 µL oxidized RNA (resuspended in $H_2O$), 60 µL 0.3 M NaOAc pH 5.4, and 10 µL 20 mM stock AlexaFluor 568 hydrazide (made fresh in DMSO). This 130 uL reaction was incubated at room temperature for 2 hrs. After the labeling reaction, the sample was ethanol precipitated, resuspended, gel purified (8% PAGE), and quantitated to determine concentration (using the absorbance at 260 nm). Finally, a 1 uM stock solution of the labeled NASM is prepared in water or buffer.

The substrate and plate-reader/detection system were then prepared for the assay reaction. A typical substrate was a 96 well Pierce Black Neutravidin Plate and a typical plate reader was the Packard Fusion microplate reader (Packard/Perkin-Elmer). Typical settings for this instrument and this assay (as entered in the user interface menus in the instrument control software) are as follows:

2-channel fluorescence assay (ex:FAM*/em:FAM & TAMRA**)
emission detection set to top-read
integration time/well: 1 sec (1 read/well)
25 serial reads of each well, 1 min delay between reads
lamp intensity: 10/20
PMT voltage: 950/1100 V
PMT gain: 1.0/200
*FAM excitation/emission filters: 485 nm/535 nm
**TAMRA/or AlexaFluor 568 emission filters: 590 nm The following reaction mixture of NASM+ biotinylated capture oligo was prepared in a 1.5 mL tube:

| Reagent | Stock conc. | Final conc. |
| --- | --- | --- |
| 1 ul FAM-biotin Probe | 5 uM | 500 nM |
| 1.2 ul Alexa 568 cGMP RNA | 5 uM | 600 nM |
| 7.8 uL dH2O | | |
| 10.0 uL (total volume = 10 uL × # of wells) | | |

The mixture was heat annealed to ~85° C. in 1× annealing buffer (30 mM Tris, 50 mM NaCl), and then cooled to room temperature. The assay reactions were run in the presence/absence of target.

To run a solid-phase FRET assay in a standard 96-well microplate, coated with neutravidin, the following procedure was used:

First, neutravidin plate surfaces were pre-blocked to prevent nonspecific adsorption of sensor molecules:
  pipet 30 ul of PBS preblocking buffer (0.05% tRNA+ 0.025% Tween-20/1×PBS) into wells
  cover and shake for 15 min at room temperature on thermomixer
  rinse wells with PBS from squirt bottle
  invert plate and tap wells dry on absorbent surface
Next assay reagents were added to each well with multichannel pipet to pre-immobilized sensor molecules in plate wells:
  pipet 10 ul of annealed RNA+biotinylated probe into wells
  pipet 30 ul of PBS preblocking buffer (0.05% tRNA+ 0.025% Tween-20/1×PBS) into wells & -mix by serial pipetting ~4×
  cover and shake for 15 min at room temperature on thermomixer
  rinse wells with PBS from squirt bottle
  invert plate and tap wells dry on absorbent surface
Next assay reaction buffers were added:
  1×HH buffer: 50 mM Tris pH 7.5, 20 mM $MgCl_2$, 0.1 mM EDTA Finally, assay reactions were initiated and the plate was loaded into reader/detector:
  start all reactions simultaneously by adding 50 ul of cGMP in IX HH Buffer p1 shake on thermomixer for ~3 sec & load directly into microplate reader Kinetic assay data is assigned as (target-dependent) cleavage reaction proceeds. In the case of the Packard Fusion reader described above, data points were plotted on-screen as they were acquired, giving a real-time readout as the assay proceeds.

Example 42

Real-time Solid-phase Nucleic Acid Sensor Array for Assays with Surface Plasmon Resonance (SPR) Detection—SPR chip:

Surface plasmon resonance (SPR) can be used to detect target-activated ligation/cleavage events of nucleic acid sensor molecules. In SPR, a light beam is directed, via a prism or grating, onto the back surface of a thin metallic layer (typically ~50–100 nm of gold) that has been deposited onto a glass or plastic (dielectric) substrate. The incident beam is s-polarized and directed at an angle of incidence which satisfies the condition for total internal reflection (TIR) at the metal/dielectric interface. At certain angles near the TIR critical angle, electromagnetic energy is coupled from the incident beam into surface plasmon excitation modes in the metallic layer. For a fixed excitation wavelength, the precise angular position of the primary surface plasmon resonance depends very strongly on the index of refraction of the medium (typically a liquid) in contact with the front surface of the metallic layer. By monitoring the intensity of the 25 TIR-reflected incident beam as a function of angle, the angular position of the primary surface plasmon resonance can be found. The adsorption or desorption of molecular species from the front surface of the metallic layer (the SPR sensor surface) will modify the refractive index of the medium in its immediate vicinity (i.e., within ~100 nm); this will result in a measurable angular shift in the position of the surface plasmon resonance. SPR is thus a sensitive technique for detecting the binding (including hybridization, etc.) and/or release of molecular species from a surface. Measurements can be performed in real time, allowing the kinetic characterization of binding events, as shown in FIG. 67 panels C+D. A system utilizing a large collimated incident beam and an area detector (such as a CCD detector) could be used to generate SPR images of two-dimensional arrays of surface-immobilized species, such as nucleic acid sensor molecules.

The demonstration of an SPR assay format utilizing nucleic acid sensor molecules was accomplished by coupling hammerhead (HH) nucleic acid sensor molecules (FIG. 67, Panel B) to the native gold surface of a commercially available integrated single-channel (i.e., non-imaging) SPR module, called SPReeta (see FIG. 67, Panel A). The SPReeta modules are manufactured by Texas Instruments, Inc., and marketed by Nomadics, Inc. (Stillwater, Okla.). The SPReeta is an integrated package comprised of an optical plastic housing, within which is embedded a light emitting diode (LED) with a polarizer, two reflecting surfaces, i.e., the SPR surface and a mirror, and a linear diode array detector, where the mirror directs the TIR-reflected beam onto diode array. The entire package is built onto a printed circuit board (PCB), with standard dual inline pins which allow the sensor module to be plugged directly into another PCB containing preamplifier and signal processing circuits. The real-time processed data is sent to a computer (PC) via a standard serial port connector. A software application logs, analyzes, and displays the data to the user.

Numerous immobilization schemes for nucleic acid sensor molecules are possible on the gold SPR surface substrate: (1) direct attachment to the gold SPR surface of a construct with a closed stem I, and extended 3' and 5' termini on an open stem III, via a terminal 5' gamma-thiol GTP incorporated during transcription (see FIG. 68); (2) direct attachment to a passively adsorbed neutravidin-on-gold layer on the SPR surface using constructs with a truncated, open stem I, and a closed stem III, post-transcriptionally modified by specific periodate oxidation of the 3' terminus, followed by subsequent reaction with biotin-XX-hydrazide to produce a 3' biotinylated hammerhead nucleic acid sensor molecule (see FIG. 69); (3) indirect attachment to the gold SPR surface via hybridization of a nucleic acid sensor molecule to a thiol-modified capture oligo via a 3' terminal extension on an open stem I, with stem III closed (see FIG. 70). The latter two strategies are flexible in terms of application, allowing easy thermal or chemical stripping and recharging of the sensor surface with nucleic acid sensor molecules in situ, whereas direct attachment of the nucleic acid sensor molecules via incorporated thiol-groups would limit the sensor surface to a single use, or require the use of extremely harsh stripping agents.

All of the above nucleic acid sensor molecule constructs were synthesized and/or amplified from existing PCR products. Synthetic DNA templates were prepared by standard solid-phase methods and were purified by denaturing (8 M urea) polyacrylamide gel electrophoresis (PAGE). RNAs were generated by in vitro transcription of the appropriate DNA templates that were generated by PCR.

Standard in vitro transcription reactions were conducted in a total volume of 50 µl containing ~20 pmol template DNA, 50 mM Tris-HCl (pH 7.5 at 23° C.), 10 mM $MgCl_2$, 50 mM dithiothreitol (DTT), 20 mM spermidine, 2 mM each of the four ribonucleoside 5'-triphosphates (NTPs), and 35 units/µl T7 RNA polymerase (T7 RNAP) by incubation at 37° C. for 2 h. 5'-thiol-modified RNA was prepared by in vitro transcription wherein GTP was replaced by guanosine 5'-O-(3-thiotriphosphate) (Sigma Chemical Co., St. Louis, Mo.). 3'-biotinylatedRNA was prepared by post-transcriptionally modification by specific periodate oxidation of the 3' terminus, followed by subsequent reaction with biotin-XX-hydrazide. The resulting RNA products were purified by denaturing 10% PAGE and isolated from the gel by elution with 10 mM Tris-HCl (pH 7.5 at 23° C.), 200 mM NaCl, and 1 mM ethylenediamine tetraacetic acid (EDTA). The recovered RNA was precipitated with ethanol, resuspended in deionized water (dH$_2$O), and stored at −20° C. until use. In addition, the thiol-modified DNA capture oligo was synthesized and purified.

Initial surface immobilization experiments using a kinased (5' 32P-labeled) sample of the thiol-modified DNA capture oligo were conducted on Au/Cr coated microscope slides in order to optimize the thiol-gold coupling procedure. Initial results indicated that blocking of the surface with mercaptohexanol (MCH) and control of pH during the surface coupling reaction were critical. Good surface coupling and binding capacities were observed.

The passive adsorption of neutravidin to the gold sensor surface (via cysteine residues) was investigated, prior to subsequent attachment of a biotinylated hammerhead nucleic acid sensor molecule. Purified neutravidin (Pierce, Rockford, Ill.) was acquired and flowed over the SPReeta sensor surface at a concentration of 50–100 ug/mL. The adsorption of the neutravidin was monitored in real time. cGMP and cAMP hammerhead nucleic acid sensor molecules were generated, amplified, and transcribed with a truncated, open stem I, and a closed stem III. The constructs were then post-transcriptionally modified by specific periodate oxidation of the 3' terminus, followed by subsequent reaction with biotin-XX-hydrazide. These constructs allowed for a maximal cleavage fragment (~65 nt=21.5 kD), and thus maximal dynamic range in the observed SPR signals, with only 5 nt retained on the surface. As with the capture oligo and direct-attachment thiol constructs, the melting temperature, Tm, of the base-paired region retaining the ribozyme body after cleavage is only ~25° C., facilitating rapid dissociation and removal from the SPR sensor surface upon effector-induced cleavage.

After characterizing the SPR signature and kinetic parameters for neutravidin adsorption, the surface immobilization of 3'-biotinylated cGMP nucleic acid sensor molecules (see FIG. 71, Panel A). Initial experiments showed a significant reduction in RIUs upon introduction of excess (1 mM) effector solution was introduced into the flow cell (see FIG. 71, Panel B). For a 65 nt mass change, the maximum expected signal change (i.e., for complete cleavage of all surface-immobilized nucleic acid sensor molecules) was ~2145 RIU; the observed signal change was ~1487 RIU, with a signal to noise ration (SNR)>100. Subsequent negative control experiments (using cAMP) confirmed the effector-dependent origin of the observed signal. The cleavage The cleavage/dissociation time course was fitted to a pseudo-first order rate fimction (correlation coefficient=0.9977), with an observed rate constant of ~1 per minute.

The usual scheme for attachment of the nucleic acid sensor molecule to the capture oligo and subsequent target-induced activity is shown in Panel C of FIG. 71. In order to verify the generality of the surface attachment strategy, as well as the catalytic activity of surface-immobilized nucleic acid sensor molecules, the 3'-biotinylated cGMP-dependent hammerhead was immobilized via neutravidin to a SPREETA sensor chip surface. The cGMP HH Riboreporter surface was then exposed to a range of concentrations of cGMP (0–1 mM) and varying Mg$^{2+}$ concentration in the ambient buffer (2–20 mM). Target-modulated cleavage was observed for Mg$^{2+}$ concentrations>10 mM, and cGMP concentrations greater than ~10 uM. The time-course for a portion of this type of experiment is shown in FIG. 72. This data was generated using a single surface-adsorption step with neutravidin, followed by sequential addition of increasing concentrations of cGMP, with buffer flushes and/or active buffer pumping (peristaltic) in between each cGMP addition. All sample fluids were injected at volumes of ~25–40 uL, while buffer washes were ~100 uL of 1×buffer. For active pumping, volume exchange was ~500 uL of 1×buffer.

Example 43

Figure 66:
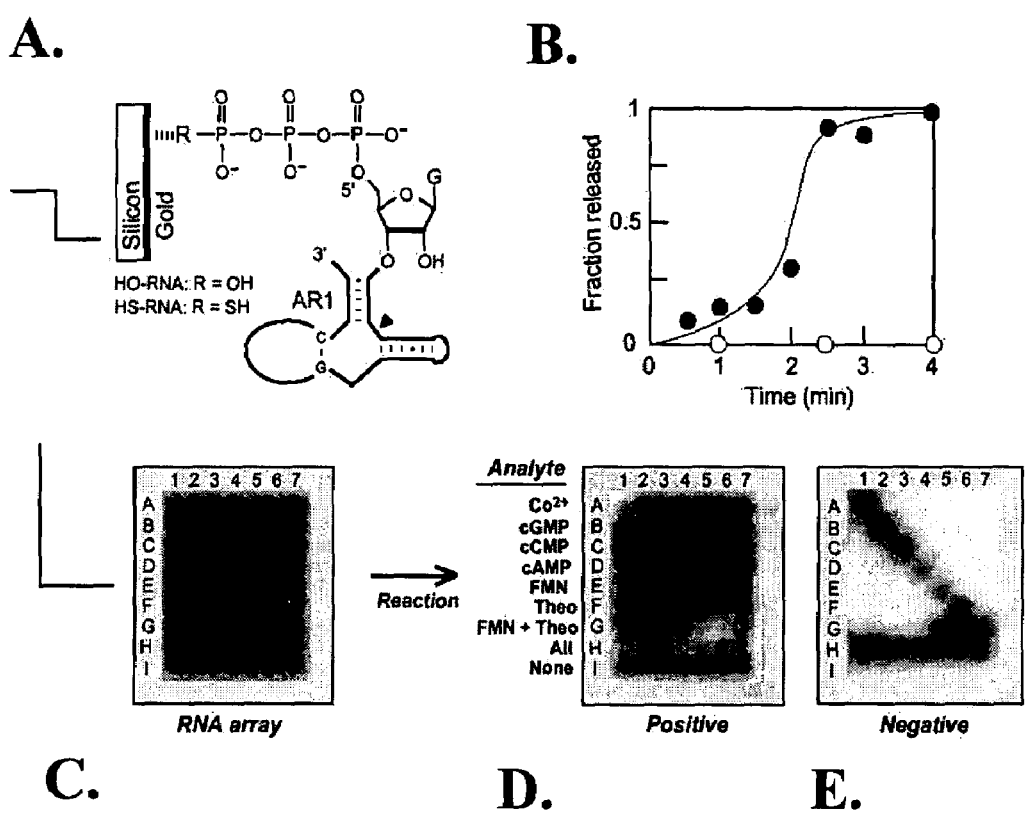
Figure 69:
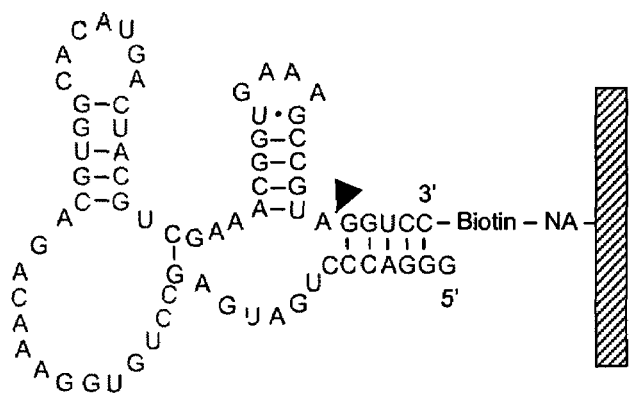
FIG. 69 gives the sequences for three cyclic nucleotide-dependent nucleic acid (hammerhead ribozyme) sensors dependent upon cCMP (SEQ ID NO:138), cAMP (SEQ ID NO:103), and cGMP (SEQ ID NO:139) in a conformation suitable for direct 3' surface attachment. The figure schematic shows the SPR sensor construct intended for direct 3' attachment to a neutravidin surface which has been passively adsorbed onto the gold SPR surface via cysteine residues.

Solid-phase Nucleic Acid Sensor Array for Assays with Fluorescent Detection—Ligase Chip Nucleic acid sensors can be tethered to solid supports while still maintaining their activity, as shown in FIG. 66. The plot in Panel B of FIG. 66 shows the fraction of this endonuclease-based nucleic acid sensor molecule that is released by self-cleavage over time in presence of its analyte. When exposed to its target analyte, the solid-phase nucleic acid sensor molecule increased in activity. In the case of ligase based NASMs, the sensor molecule ligated itself to a labeled oligonucleotide in the presence of target, and the detected signal increase. In the case of the endonucleolytic nucleic acid sensor, the molecule cleave a labeled oligonucleotide from itself, resulting in a decrease in the deleted signal.

Figure 73:
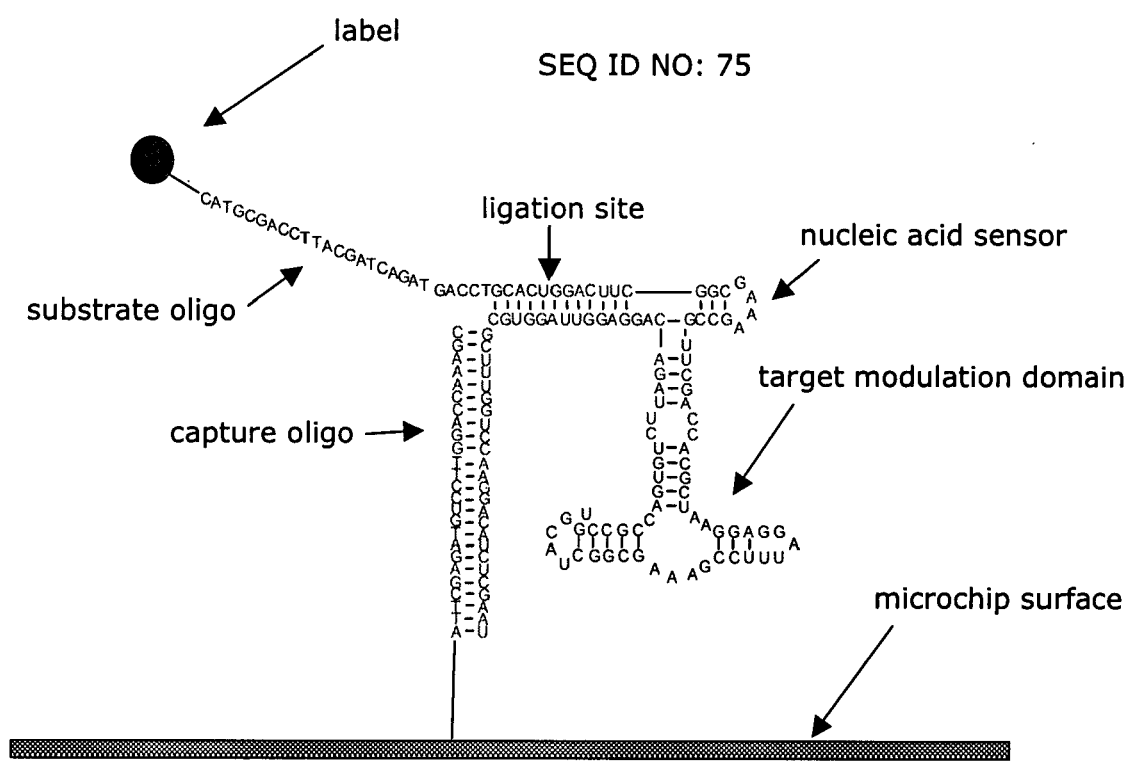
FIG. 73 shows a schematic representation of the secondary structure and components of a ligase-based nucleic acid array sensor. The sensor (SEQ ID NO:75) is shown attached to the chip surface via hybridization to a capture oligo (SEQ ID NO:104), and with an external substrate oligo bearing a fluorescent label already ligated into place. The substrate oligo can be either directly labeled (as shown), or labeled with an affinity tag (e.g., biotin) for subsequent indirect labeling or signal amplification (e.g., via tyramide signal amplification).
Figure 74:
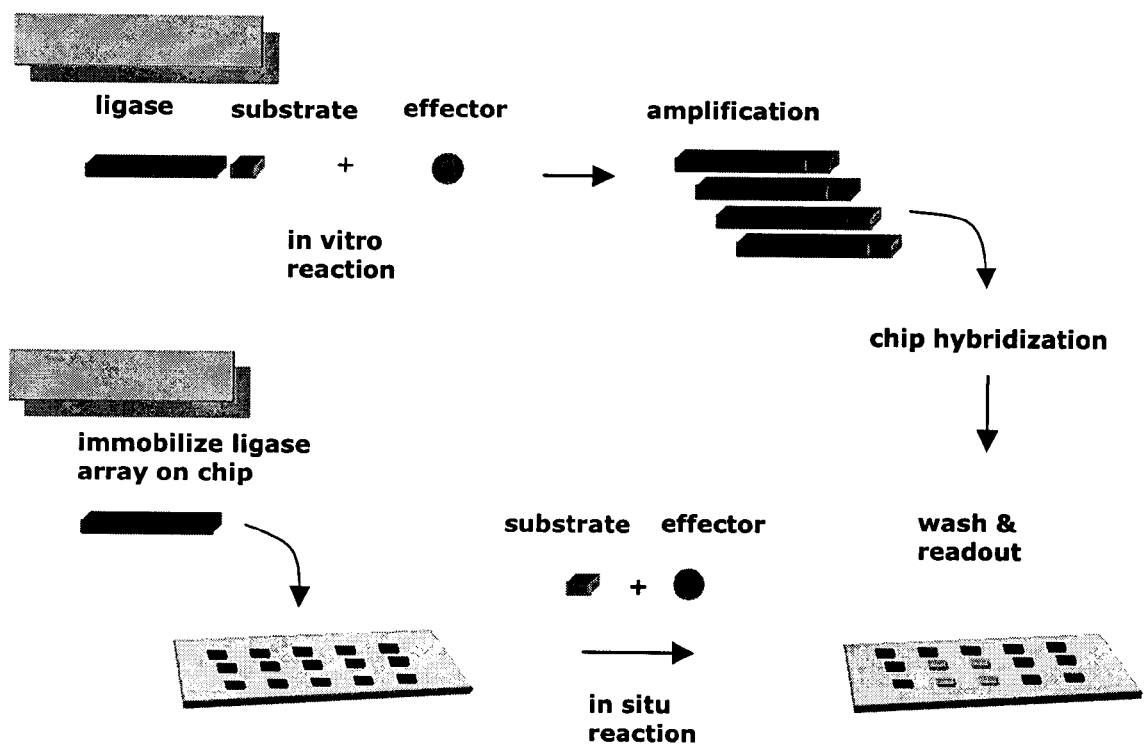
FIG. 74 contrasts the two principal solid-phase array (chip) formats used for ligase-based nucleic acid sensors.

These ligase based nucleic acid sensor molecules can be used in solid-state scintillation proximity assays, membrane assays, chip-based assays with fluorescent detection chip based assays with electrochemical detection, and in assays using intrinsic (non labeled detection such as, surface plasmon resonance. FIG. 74 presents the two principal solid-phase array (chip) formats used for ligase-based nucleic acid sensors. (a) In the capture format, the ligation reaction in the presence of target is performed in vitro, followed by an optional amplification step, hybridization of the reaction products (amplified or not) to a capture oligo array, and finally washing and detection/readout of the array. Here, each capture tag oligonucleotide is a unique sequence address, allowing spatial multiplexing of the assay over numerous different NASM/target combinations. (b) In the in situ format, the ligase sensors are pre-immobilized on the chip via unique capture tags; the ligation reaction in the presence of target is performed in situ on the chip surface, followed by washing and detection/readout of the array. Under ordinary solution-phase reaction conditions for ligase-based nucleic acid sensors, a external effector oligo (the non-immobilized analog of the capture oligo used to immobilize the sensor to a surface) is typically present. In order for the capture chip assay format (i.e., in vitro reaction followed by on-chip capture and readout, as shown in FIG. 74A) to be a viable the case where no isothermal amplification step is performed prior to hybridization, it is necessary either to (a) exclude such a effector oligo form the in vitro reaction, so that the appropriate portion of the sensor sequence would be free to hybridize to the surface-immobilized capture oligo in the subsequent capture step; or (b) to include some form of effector oligonucleotide that could be easily separated or competitively displaced from the sensor molecule after the in vitro reaction, allowing hybridization to the surface-immobilized capture oligo in the subsequent capture step. Both strategies were shown to be viable. In particular, FIG. 73 shows an example, of an ERK-dependent ligase-based nucleic acid sensor system ligase-based NASMs can function effectively in solution-based assays without the presence of a effector oligonucleotide. The ligation signals from 2 separate reactions that were run in the presence of target (ERK) and the presence and absence of an external effector oligonucleotide, respectively; showed i.e., that the reaction products amplified equally in the same number of PCR cycles, that the sensor functions equally well in the presence or absence of a capture effector oligonucleotides. A parallel result is shown for the case of the reactions run in the absence of target (ERK) and the presence and absence of an external passivating capture oligo, respectively. The results, which have been shown to be valid for all ligase-based sensor systems studied (>10 different ligase sensor systems), is that the ligase-based sensors function in solution-based reactions equally well in the presence or absence of a effector oligo. The in vitro reaction steps for all capture chip data shown and referred to in the following examples were all conducted in the absence of a effector oligo.

Figure 14:
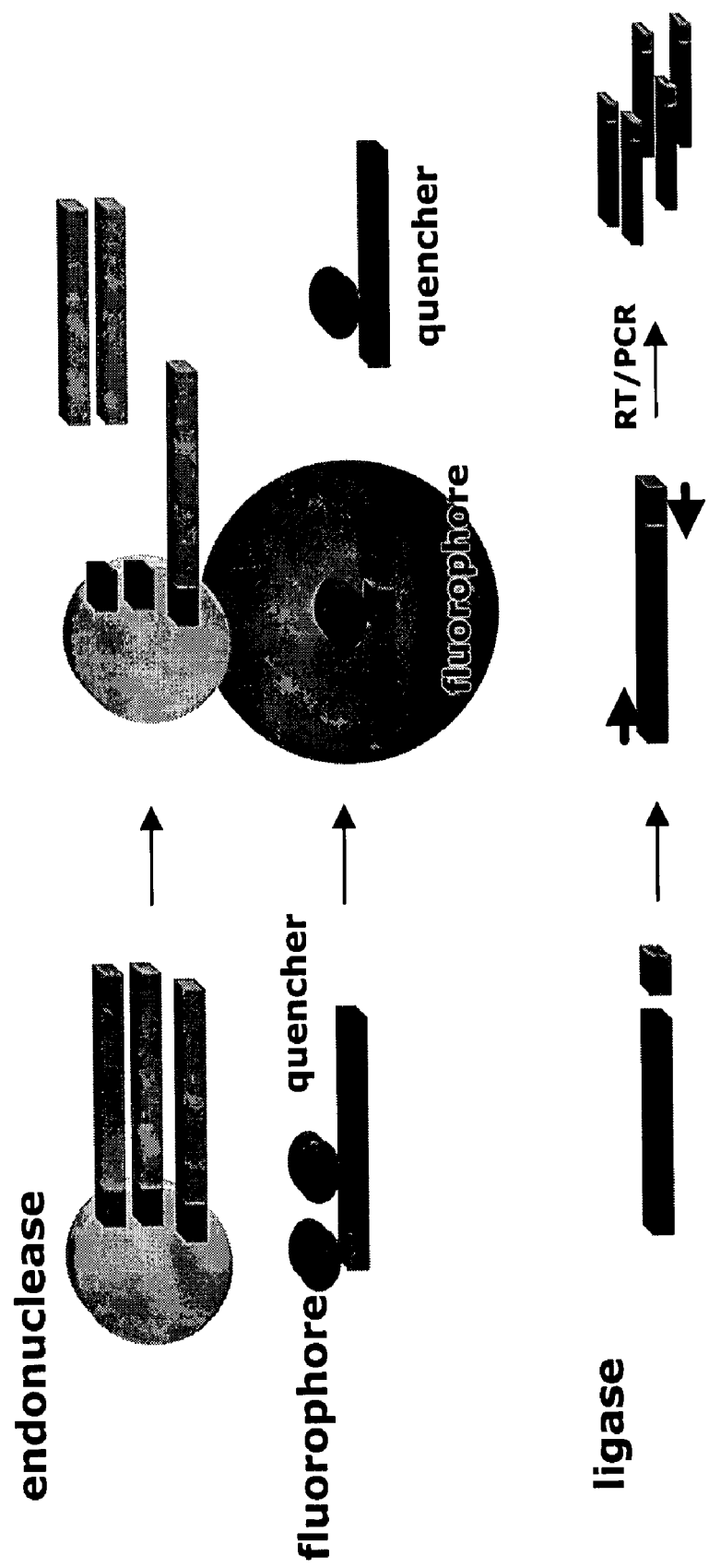
FIG. 14 shows a schematic showing different catalytic platforms for detection methods for nucleic acid sensor molecules.

For chip-based assays, the activity of the nucleic acid sensor molecules can be detected using many methods shown schematically in FIG. 14. In one embodiment of the invention, the nucleic acid sensor molecule has a self cleaving activity. These nucleic acid sensors can be attached to a solid substrate in such a way that cleavage results in the release into solution of a nucleic acid fragment of known size. This fragment can then be detected through the use of agarose gels using stains that bind to nucleic acids, including ethidium bromide. The activity of the nucleic acid sensor molecule with self-cleaving activity could also be detected through attaching a fluorophore and a quencher group to either side of the cleavage site, as detailed above, and in FIG. 62. In another embodiment of the invention, the nucleic acid sensor molecule has ligation activity. The components of a ligase-based nucleic acid sensor molecule immobilized to a chip surface are shown in FIG. 73. The activity of this sensor in the presence of target molecules can be detected through fluorescence, chemiluminescence, radioactivity, or electrochemical means. The labeling of the sensor can be accomplished either during the assay reaction, during a subsequent amplification reaction (e.g., via RT), or after the sensor (as a component of the assay reaction products) has been captured to a microarray chip for read out, as shown in FIG. 74.

FIG. 75 shows a multiplex in situ ligase sensor chip, with pre-immobilized radiolabeled sensors activatable by lysozyme (LYS) and FMN. The left panel shows the pre-hybridized sensor-substrate complexes, in this case immobilized via a biotin linker on the substrate oligo on a streptavidin/glass chip. The right panel shows the array after it has been exposed to target mixtures consisting of lysozyme only, FMN only, and lysozyme plus FMN, as indicated in the figure. Following the in situ ligation reaction, the chip was subjected to a denaturing wash, in order to remove any sensor molecules not ligated to their substrates. Note the retention of labeled sensors only in spots that had been exposed to the corresponding target, and that both protein (lysozyme) and small molecule (FMN) sensors function in the presence of nontarget analytes.

Figure 76:
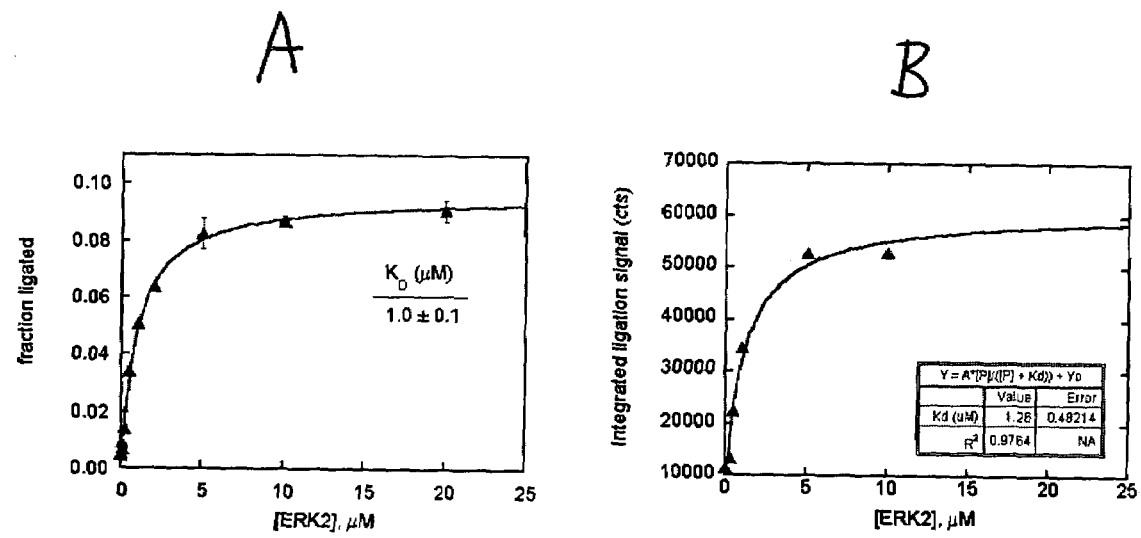
FIG. 76 shows dose-response data for ERK-dependent ligase-based nucleic acid sensors using a gel-assay (panel A) and a capture chip (pane lB).

FIG. 13 shows a solid-phase nucleic acid sensor molecule array on a streptavidin membrane. In this case, 6 different ligase sensors were immobilized on a streptavidin membrane, and assayed in an in situ format, with each NAMS being reacted with an analyte mixture containing all 6 targets. The plot shows the detected retention of ligation signal following target exposure and washing. Here detection was accomplished using a radiolabeled sensor, with the ligase immobilized via a biotin tag on the 5' terminus of the substrate oligo FIG. 76 shows dose-response data for ERK-dependent ligase-based nucleic acid sensor molecules. The data plotted in the left panel was generated from a PAGE-based assay, while the data in the right panel was generated from a capture chip assay (right panel). The reaction incubation time for both assays was approximately 2 hrs. Detection in both cases was via radiolabeled sensors and substrate oligonucleotides. Note that the capture chip assay recapitulates the apparent affinity constant (Kd) of ~1 uM measured from the gel-assay data, indicating that the chip mode of capture and detection accurately reflects all reaction parameters observed in the in vitro case.

Figure 77:
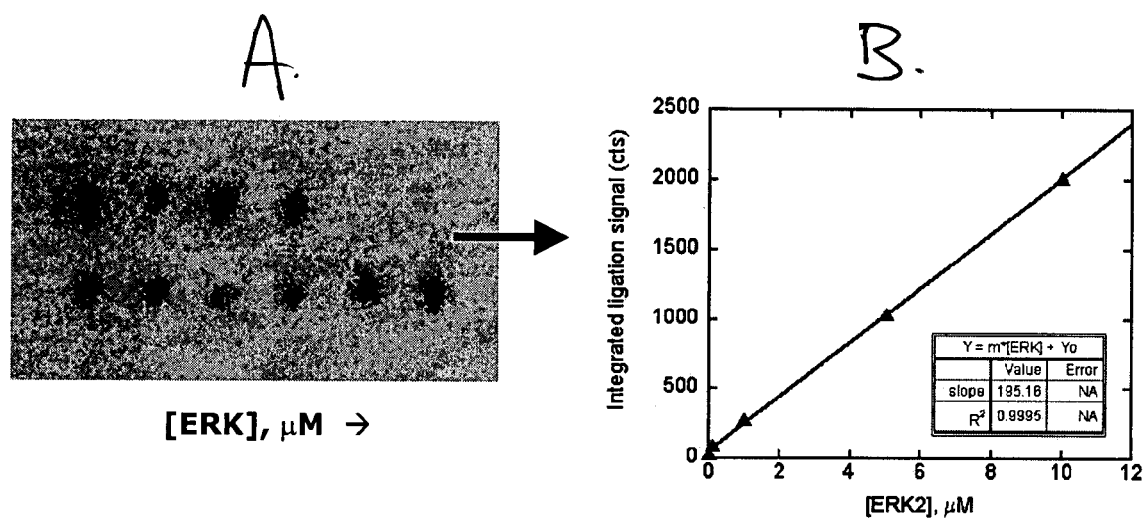
FIG. 77 shows dose-response data for an in situ ligase-based nucleic acid sensor array populated with ERK-dependent unlabeled ligase sensors in FIG. 77A and in FIG. 77B the retained ligation signal from each spot in the concentration profile was plotted vs. its corresponding target concentration.

FIG. 77 shows dose-response data for an in situ ligase-based nucleic acid sensor molecule array populated with ERK-dependent unlabeled ligase sensors. The left panel shows an image of the in situ chip after exposure to target (ERK) plus radiolabeled substrate and subsequent washing to remove unligated substrate. The reaction incubation time for both assays was approximately 2 hrs. Each array spot corresponds to a different concentration of target, giving rise to the observed pattern of positive/negative controls (10/0 uM, respectively), and the concentration profile (0–10 uM) shown. The retained ligation signal from each spot in the concentration profile is plotted vs. its corresponding target concentration in the right panel. The linear dose-response observed here is a result of two effects: (1) the surface-immobilization of the NASM reduces its effective catalytic rate over the rate observed in vitro; and (2) the much higher surface to volume (S/V) ratio in the in situ chip format, relative to the in vitro reaction/capture chip format, has been shown to promote nonspecific interactions of protein targets (e.g., ERK) with the chip surface coating. This leads to a reduced effective target concentration in the reaction volume at each sensor spot.

Figure 78:
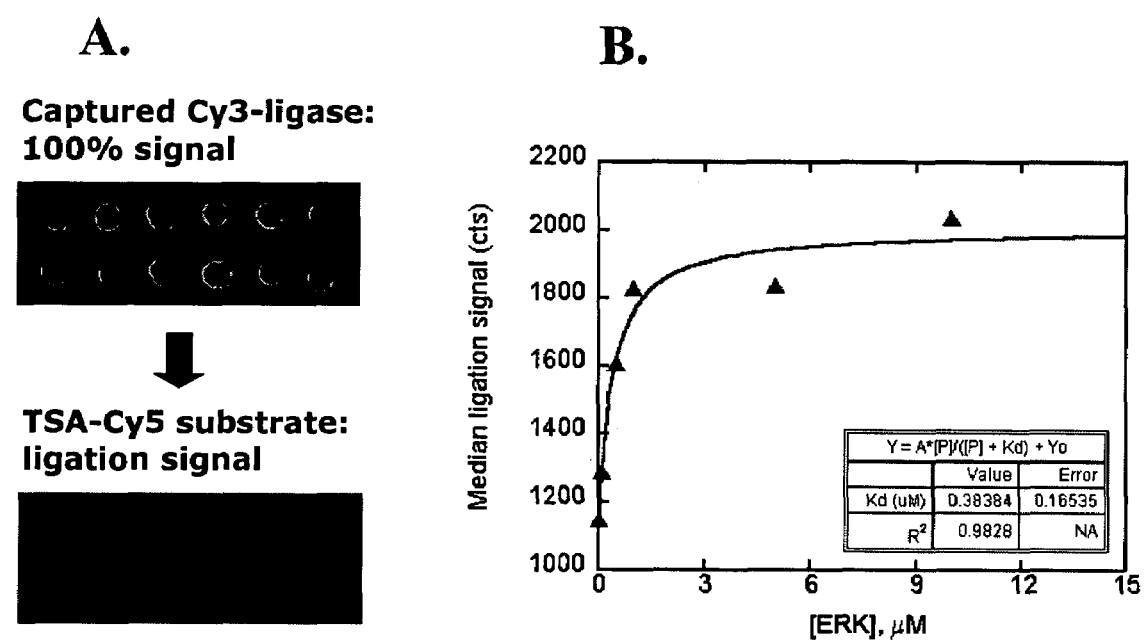
FIG. 78 shows dose-response data for a ERK-dependent ligase-based nucleic acid sensor capture array in FIG. 78A and captured and amplified fluorescent ligation signal for each spot is plotted in FIG. 78B vs. its corresponding target concentration.

FIG. 78 shows the dose-response data for a ERK-dependent ligase-based nucleic acid sensor molecule capture array. The NASMs in this case were fluorescently 3' labeled with Cy3-labeled ligase sensors, and the substrate oligos were 5' labeled with biotin. After 2 hr. in vitro reactions in the presence of varying concentrations of target (ERK), the reaction products were hybridized to the capture array. After hybridization and washing, tyramide signal amplification (TSA) was performed using a streptavidin-conjugated horseradish peroxidase (HRP) pulse Cy5-labeled tryramide HRP substrates. The captured and amplified fluorescent ligation signal for each spot is plotted in the right panel vs. its corresponding target concentration. This data demonstrates the high sensitivity of fluorescence detection for ligase-based nucleic acid sensor molecule arrays in both in situ and capture formats.

Figure 79:
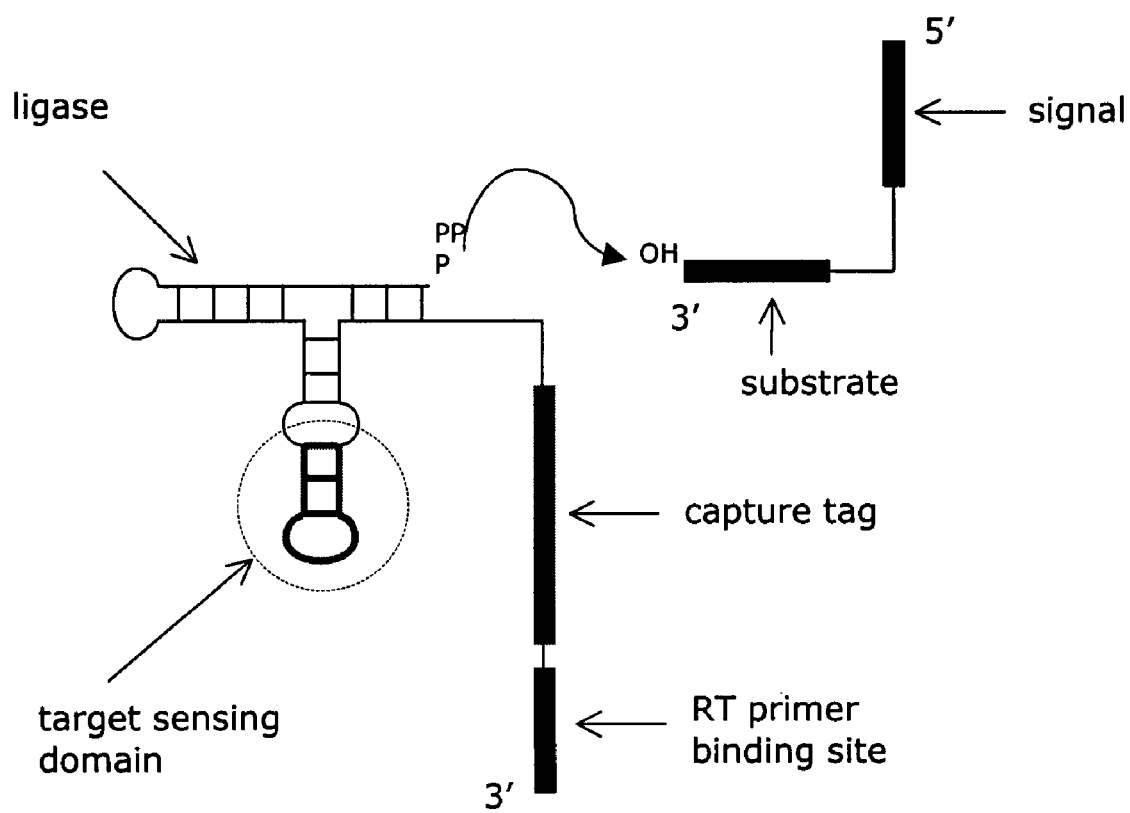
FIG. 79 shows the components of a generalized construct for an amplifiable ligase-based nucleic acid sensor molecule.
Figure 80:
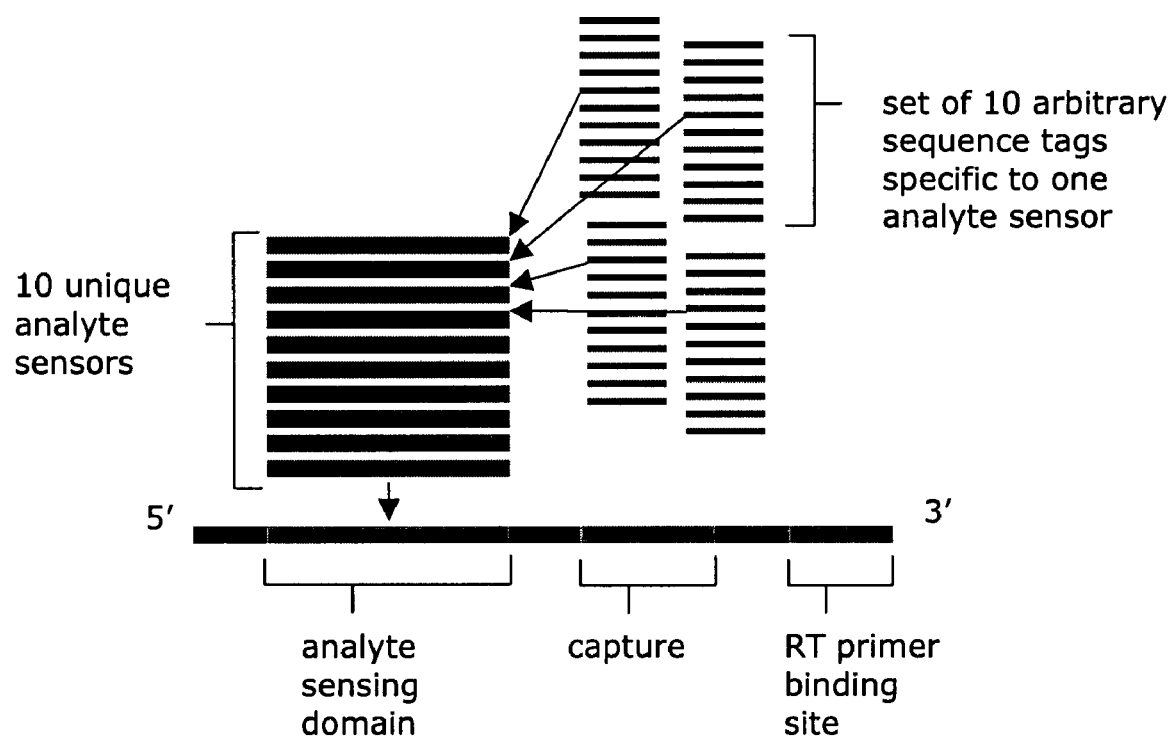
FIG. 80 shows a generalized strategy for performing a multiplexed capture chip formatted assay with ligase-based nucleic acid sensors.
Figure 81:
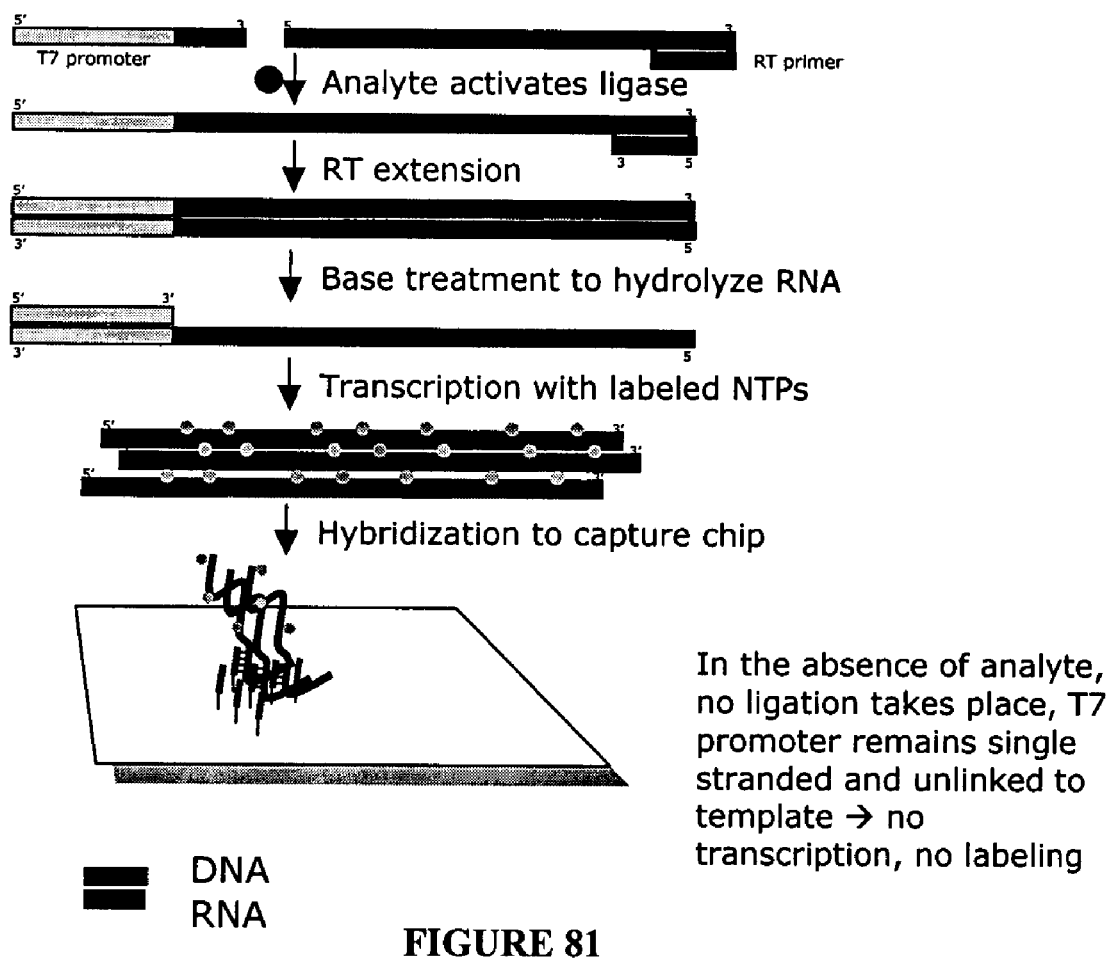
FIG. 81 shows a generalized strategy for performing a highly sensitive capture chip formatted assay with ligase-based nucleic acid sensors.

FIG. 79 shows the components of a generalized construct for an amplifiable ligase-based nucleic acid sensor molecule. Each sensor in an array would have a unique 3' capture tag sequence domain, and a common RT primer binding site. The external substrate oligonucleotide contains a signal generation label, which may comprise a direct label (e.g., fluorescent, radionuclide, enzyme-linked, etc.) or an affinity tag (e.g., biotin) for subsequent indirect labeling or amplification (e.g., via TSA), or a specific sequence (e.g., the T7 RNA polymerase promoter sequence) which will facilitate selective amplification of ligated sensors via RT or RT-PCR. The amplification process (RT or RT-PCR) can also be used to incorporate multiple direct or indirect labels or affinity tags, thus increasing the sensitivity of the sensor system. In one embodiment, detection can be accomplished by using a chimeric (RNA/DNA) external substrate oligonucleotide which contains a DNA sequence that is necessary for subsequent amplification of the nucleic acid, such as the T7 RNA polymerase promoter sequence, as shown in FIG. 79. An arbitrary number (e.g., 10, as shown) of unique analyte-specific sensors are each outfitted (e.g., via PCR) with an arbitrary number (e.g., 10, as shown) of unique sequence capture tags. In the present example, the result would be a panel of 100 uniquely addressed sensors. Thus, ten different targets could be simultaneously assayed under ten different conditions, with the reaction products RT-amplified (and simultaneously labeled with multiple fluorophores per sensor molecule) and spatially sorted by hybridization to a capture array chip, and finally detected using standard techniques, such as fluorescence. Upon ligation of such an external substrate, RT can be performed to synthesize a complementary strand to the sensor, as shown in FIG. 81. A given NASM is reacted in vitro with its corresponding target analyte and a chimeric (i.e., containing both DNA and RNA bases) substrate oligo containing the T7 promoter sequence comprised of DNA bases. Following the ligation reaction, an RT step is performed to synthesize a complementary cDNA strand to the RNA sensor molecule. The NASM is then hydrolyzed or degraded with RNaseH. In the case of NASM that ligated its substrate in the presence of target, this leaves the cDNA strand with the DNA T7 promoter sequence annealed. This complex forms a suitable platform for the T7 RNA polymerase to transcribe multiple copies of those cDNA sequences corresponding to sensors which were triggered by their respective targets. During transcription, NTPs with direct fluorescent labels or affinity tags (e.g., biotin) are multiply incorporated into the transcribed cRNA molecules. After hybridization to the capture array, the amplified cRNA sensors can be detected via their direct labels, or by subsequent staining with a conjugate to the incorporated affinity tags, e.g., streptavidin-phycoerythrin. After hydrolysis of the original RNA sensor strand, the double-stranded DNA portion containing the T7 promoter sequence will allow in vitro transcription of the cDNA to cRNA by standard methods. This transcription step will amplify the sensor sequence, and can be used to simultaneously incorporate nucleotides that contain direct or indirect (e.g., biotin, or other affinity tag) labels for subsequent fluorescence- or luminescence-based detection, as shown in FIG. 80. This detection strategy can be implemented in a multiplexed format by using PCR to incorporate arbitrary sequence capture oligo domains, as well as common RT primer binding domains, to a panel of ligase-based sensors. In particular, FIG. 80 shows a generalized strategy for performing a multiplexed capture chip formatted assay with ligase-based nucleic acid sensors. An arbitrary number (e.g., 10, as shown) of unique analyte-specific sensors are each outfitted (e.g., via PCR) with an arbitrary number (e.g, 10, as shown) of unique sequence capture tags. In the present example, the result would be a panel of 100 uniquely addressed sensors. Thus, 10 different targets could be simultaneously assayed under 10 different conditions, with the reaction products RT-amplified (and simultaneously labeled with multiple fluorophores per sensor molecule) and spatially sorted by hybridization to a capture array chip, and finally detected using standard techniques, such as fluorescence. In one embodiment, shown in FIG. 80, a generalized strategy for performing a highly sensitive capture chip formatted assay with ligase-based nucleic acid sensors. A given sensor molecule is reacted in vitro with its corresponding target analyte and a chimeric (RNA) substrate oligo containing the T7 promoter sequence comprised of DNA bases. Following the ligation reaction, an RT step is performed to synthesize a complementary cDNA strand to the RNA sensor molecule. The RNA sensor molecule is then hydrolyzed or degraded with RNAseH. In the case of a sensor which ligated its substrate in the presence of target, this leaves the cDNA strand with the DNA T7 promoter sequence annealed. This complex forms a suitable platform for the T7 RNA polymerase to transcribe multiple copies of those cDNA sequences corresponding to sensors which were triggered by their respective targets. During transcription, NTPs with direct fluorescent labels or affinity tags (e.g., biotin) are multiply incorporated into the transcribed cRNA molecules. After hybridization to the capture array, the amplified cRNA sensors can be detected via their direct labels, or by subsequent staining with a conjugate to the incorporated affinity tags, e.g., streptavidin-phycoerythrin.

Highly multiplexed in vitro or in situ assays can then be performed, using the specific hybridization of each sensor's unique capture oligo to address its signal to a feature spot whose position on the array is known. The presence or relative concentration of a given analyte can then be determined by the presence/absence of a signal in the expected array position, and the relative concentration determined by comparison of the relative signal intensity to that of other sensor spots in the array.

Listed below are selected DNA template sequences that can be used to generate ligase-based nucleic acid sensor molecules via PCR, as described above:

Synthetic DNA universal templates for 2- & 3-piece ligase constructs (underlined regions = primer annealing regions)

ERK.A.LIG.TMPLT         SEQ ID NO: 109
(DG.20.58A):
5'<u>CTATAGGACTTC</u>GGCGAAAGCCGTTCGACCACGCTAAGGAGGATTTCC
GAAAGCGGCTACGGTCCGCCAGTGTCTTAGACAG<u>GAGGTTAGGTGC</u>

ERK.E.LIG.TMPLT         SEQ ID NO: 111
(DG.20.58E):
5'-<u>CTATAGGACTTC</u>GGCGAAAGCCGTTCGACCAGCTAAGGAGGATTTCC
GAAAGCGGCTACGGTCCGCCAGCTCTTAGACAG<u>GAGGTTAGGTGC</u>

LYS.LIG.TMPLT.L1-       SEQ ID NO: 336
11.2:
5'<u>CTATAGGACTTC</u>GGCGAAAGCTAACGTCTCATGGCTAAATTGCCATGT
TGCTACAAATGATATGACTAGA<u>GAGGTTAGGTGC</u>

FMN.LIG.TMPLT.L1-       SEQ ID: 337
R7C13:
5'<u>CTATAGGACTTC</u>GGTCCAGTGCTCGTGCACTAGGCCGTTCGACCTTCA
GGATATGCTTCGGCAGAAGGGAACTTAGACAG<u>GAGGTTAGGTGC</u>3'

THEO.LIG.TMPLT.L1-      SEQ ID: 338
D1:
5'<u>CTATAGGACTTC</u>GGTCCAGTGCTCGTGCACTAGGCCGTTCGACCATGA
TACCAGCATCGTCTTGATGCCCTTGGCAGCATCTTAGACAG<u>GAGGTTAGG
TGC</u>

For 3-piece system:
5'-primer:              TK.16.32.A    SEQ ID: 339
5'-TTCTAATACGACTCA<u>CTATAGGACTTC</u>

3'-primer (5 nt sub):   TK.16.32.B    SEQ ID: 340
5'-ATTCGAGATGTCCTTGGACCAAAGCC<u>GCACCTAACCTC</u>

3'-primer (15 nt sub):  TK.16.32.15NT SEQ ID NO: 341
5'-ATTCGAGATGTCCTTGGACCAAAGCCTCCATCGTGC<u>GCACCTAACCT
C</u>

-continued

Synthetic DNA universal templates for 2- & 3-piece ligase constructs (underlined regions = primer annealing regions)

| | | |
|---|---|---|
| Substrate (5 nt): | TK.04.82.A | SEQ ID NO: 342 |
| 5'-Biotin/Fluor-CATGCGACCTTACGATCAGATGACCTugcacu | | |
| Substrate (15 nt): | MK.08.125A | SEQ ID NO: 343 |
| 5'-Biotin-TCCATCGTGCGCACu | | |
| For 2-piece system: | | |
| 5' primer: | TK16.32A | SEQ ID NO: 344 |
| 5'-TTCTAATACGACTCA<u>CTATAGGACTTC</u> | | |
| 3' primer: | MK.08.125B | SEQ ID NO: 345 |
| 5'-TCCATCGTGC<u>GCACCTAACCTC</u> | | |
| Substrate: | MK.08.125A | SEQ ID NO: 346 |
| 5'-Biotin-TCCATCGTGCGCACu | | |

Example 43

Conversion of Nucleic Acid Sensor Molecules into Unimolecular Ligase NASMs

The Erk and pERK dependent nucleic acid sensor molecules can be converted to unimolecular ligase NASMs. The engineered NASM ERK B, ERK CW45-33-C08 and ERK CW45-33-D09 were converted by PCR as described for FIG. 28 with primers GGACTTCGGCGAAAGC and AGTGCTCTCGCACCTAACCTCCTGTCT (SEQ ID NO:363). NASMs pERK CW45-33-C04, CW45-33-D05 and CW45-33-H03 were all converted with primers GGACTTCGGC-GAAAGC (SEQ ID NO:364) and AGTGCTCTCGCAC-CTAACCTCCTGTCT (SEQ ID NO:365). Circularization can be detected by RTPCR for ERK B (GCTACGGTC-CGCCAGTTCTT) (SEQ ID NO:366) and CGCTTTCG-GAAATCCTCCTT) (SEQ ID NO:367), ERK CW45-33-C08 (GCTACGGTCCGCCAGGGGCT (SEQ ID NO:368) and CGCTTTCGGAAATCCTCCTT (SEQ ID NO:369)), ERK CW45-33-D09 (GCTACGGTCCGCCAAAAGCT (SEQ ID NO:370) and CGCTTTCGGAAATCCTCCTT (SEQ ID NO:371)) and pERK CW45-33-C04, CW45-33-D05 and CW45-33-H03 (AAGGGGAAAGCGTTATTAAG (SEQ ID NO:372) and TCGAGGAACCAATTCGCTAG (SEQ ID NO:373)).

REFERENCES

Andersson, K. E., H. Gemalmaz, et al. (1999). "The effect of sildenafil on apomorphine-evoked increases in intracavernous pressure in the awake rat." *J Urol* 161(5): 1707–12.

Arora, A. S., P. C. de Groen, et al. (1996). "Hepatocellular carcinoma cells resist necrosis during anoxia by preventing phospholipase-mediated calpain activation." *J Cell Physiol* 167(3): 434–42.

Asher, et al., PCT 98/08974 (1996)

Ballard, S. A., C. J. Gingell, et al. (1998). "Effects of sildenafil on the relaxation of human corpus cavernosum tissue in vitro and on the activities of cyclic nucleotide phosphodiesterase isozymes." *J Urol* 159(6): 2164–71.

Barlocco, D., G. Cignarella, et al. (2001). "Phenylpiperazinylalkylamino substituted pyridazinones as potent alpha (1) adrenoceptor antagonists." *J Med Chem* 44(15): 2403–10.

Basararsky, T. et al., "Overview of a Microarray Scanner: Design Essentials for an Integrated Acquisition and Analysis Platform", in *Microarray Biochip Technology*, ed. by M. Schena, Eaton Publishing Co., 2000, Natick, MA, pp. 265–284.

Beaudet L. et al., "Homogeneous Assays for Single-Nucleotide Polymorphism Typing Using AlphaScreen", *Genome Res.* 11:600 (2001).

Bell, et al., *J. Biol. Chem.* 273: 14309 (1998).

Berzal-Herranz A; Joseph S; Burke J M. In vitro selection of active hairpin ribozymes by sequential RNA-catalyzed cleavage and ligation reactions. *Genes and Development*, 1992 January, 6(1):129–34.

Berzas Nevado, J. J., J. Rodriguez Flores, et al. (2001). "Micellar electrokinetic capillary chromatography for the determination of Viagra and its metabolite (UK-103,320) in human serum." *Electrophoresis* 22(10): 2004–9.

Bianchini, M., M. Radrizzani, et al. (2001). "Specific oligobodies against ERK-2 that recognize both the native and the denatured state of the protein." *J Immunol Methods* 252(1–2): 191–7.

Bloom, T. J. and J. A. Beavo (1996). "Identification and tissue-specific expression of PDE7 phosphodiesterase splice variants." Proc Natl Acad Sci U S A 93(24): 14188–92.

Bock, et al., *Nature,* 355(6360): 564–6 (1992).

Bolger, G. B., S. Erdogan, et al. (1997). "Characterization of five different proteins produced by alternatively spliced mRNAs from the human cAMP-specific phosphodiesterase PDE4D gene." *Biochem J* 328(Pt 2): 539–48.

Breaker,. PCT WO 98/43993 (1998)

Breaker, PCT WO 98/27104 (1998)

Bruchez, M. et al., "Semiconductor Nanocrystals as Fluorescent labels", *Science* 281, 2013 (1998).

Burt, A. R., M. Sautel, et al. (1998). "Agonist occupation of an alpha2A-adrenoreceptor-Gi1alpha fusion protein results in activation of both receptor-linked and endogenous Gi proteins. Comparisons of their contributions to GTPase activity and signal transduction and analysis of receptor-G protein activation stoichiometry." *J Biol Chem* 273(17): 10367–75.

Caceci, et al., *Byte* 9: 340–362 (1984).

Chan, V. et al., Effect of Hydrophobocity and Electrostatics on Adsorption and Surface Diffusion of DNA Oligonucleotides at Liquid/Solid Interfaces", *J. Colloid and Interface Sci.* 203:197 (1998).

Chan, W.C.W and Nie, S., "Quantum Dot Bioconjugates for Ultrasensitive Nonisotopic Detection", *Science* 281: 2016 (1998).

Coleman, D. E. and S. R. Sprang (1998). "Crystal structures of the G protein Gi alpha 1 complexed with GDP and Mg2+: a crystallographic titration experiment." *Biochemistry* 37(41): 14376–85.

Ciesiolka et al., *Methods in Enzymology* 267: 3 15–335 (1996).

Conti, M. (2000). "Phosphodiesterases and cyclic nucleotide signaling in endocrine cells." *Mol Endocrinol* 14(9): 1317–27.

Cook, N.D. et al., "SPA: a revolutionary new technique for drug screening", *Pharmaceutical Manufacturing International,* 1992, pp. 49–53.

Cooper, et al., *Biochemistry* 29: 926 1–9268 (1990).

Cotten, et al., *Nuc. Acid Res.* 19: 2629–2635 (1991).

Cox J C; Rudolph P; Ellington A D. Automated RNA selection. *Biotechnology Progress,* 1998 November-December, 14(6):845–50.

DeRisi et al., *Science* 278: 680–686 (1997).

Ellington and Szostak, *Nature* 346(6287): 818–822 (1990).

Fehrentz, J. A. et al., *Biochem. Biophys. Res. Commun.* 188:865 (1992).

Froehler, et al., *Nucleic Acids Research* 14: 53 99–5467 (1986a).

Froehler, *Tet. Lett.* 27: 5575–5578 (1986b).

Franke, B., J. W. Akkerman, et al. (1997). "Rapid Ca2+-mediated activation of Rap1 in human platelets." *Embo J* 16(2): 252–9.

Gold, et al., *Annual Review of Biochemistry* 64: 763–797 (1995).

Gold, et al., *Proc. Natl. Acad. Sci.* 94: 59–64 (1997).

Griffiths, et al. *EMBO. J* 13: 3245–3260 (1994).

Goueli, S. A., K. Hsiao, et al. (2001). "Assaying activity of individual protein kinases in crude tissue or cellular extracts." *Methods Enzymol* 333: 16–27.

Green R; Szostak J W. Selection of a ribozyme that fuictions as a superior template in a self-copying reaction. *Science*, 1992 Dec 18, 258(5090):1910–15.

Guatelli, et al., *Proc. Nati. Acad. Sci.* 87: 1874 (1990).

Hamaguchi, N. et al., "Aptamer Beacons for the Direct Detection of Proteins", *Anal. Biochem.* 294: 126 (2001).

Han, M. et al., "Quantum-dot-tagged microbeads for multiplexed optical coding of biomolecules", *Nature Biotechnol.* 19, 631 (2001).

Heath, R. et al., "cAMP [$^{125}$I] scintillation proximity assay (SPA)—a homogeneous radioimmunoassay for cAMP", in *Cell Signalling: Experimental Strategies*, ed. Reid, E., Cook, G. M. W., and Luzio, J. R., 1992, pp. 193–194.

Heller and Morrison, in Rapid Detection and Identflcation of Infections Agents, Academic Press, Inc., San Diego, Calif., pages 245–256 (1985).

Heller, R. A. et al., "Gene Chips and microarrays: applications in disease profiles, drug target discovery, drug action and toxicity", in *DNA Microarrays: A Practical Approach*, ed. by M. Schena, Oxford University Press, 1999, Oxford, pp. 187–202.

Hirose, et al., *Tet. Lett.* 28: 2449 (1978).

Hobbs, et al., *Biochemistry* 12: 5138–5145 (1973).

Hu, B., J. Ellingboe, et al. (2001). "(4-Piperidin-1-yl)phenyl amides: potent and selective human beta(3) agonists." *J Med Chem* 44(9): 1456–66.

Jameson, D. M. and Sawyer, W. H., "Fluorescence Anisotropy Applied to Biomolecular Interactions", *Methods in Enzymology* 246:283 (1995).

Jameson, D. M. and Seifried, S. E., "Quantificatin of Protein-Protein Interactions Using Fluorescence Polarization", *METHODS* 19:222 (1999).

Jellinek, et al., *Biochemistry* 34: 11363–11372 (1995).

Jenne A; Hartig J S; Piganeau N; Tauer A; Samarsky D A; Green M R; Davies J; Famulok M. Rapid identification and characterization of hammerhead-ribozyme inhibitors using fluorescence-based technology. *Nature Biotechnology*, 2001 Jan, 19(1):56–61.

Jeremy, J. Y., S. A. Ballard, et al. (1997). "Effects of sildenafil, a type-5 cGMP phosphodiesterase inhibitor, and papaverine on cyclic GMP and cyclic AMP levels in the rabbit corpus cavernosum in vitro." *Br J Urol* 79(6): 958–63.

Jhaveri, et al. *J. Am. Chem. Soc.* 122: 2469–2473 (2000).

Jenison, et al. *Science*, 263(5 152): 1425–9 (1994).

Jolley, M., "Fluorescence Polarization: an analytical tool for immunoassay and drug discovery", *Comb. Chem. High Throughput Screen.* 2(4):177 (1999).

Joyce, in Molecular Biology of RNA: UCLA Symposia on Molecular and Cellular Biology, T. R.Cech (ed.), Liss, N.Y., 1989, pp. 361–371.

Koizumi, M., G. A. Soukup, et al. (1999). "Allosteric selection of ribozymes that respond to the second messengers cGMP and cAMP." *Nat Struct Biol* 6(11): 1062–71.

Koizumi, M., J. N. Kerr, et al. (1999). "Allosteric ribozymes sensitive to the second messengers cAMP and cGMP." *Nucleic Acids Symp Ser* 42: 275–6.

Kozasa, T. and A. G. Gilman (1995). "Purification of recombinant G proteins from Sf9 cells by hexahistidine tagging of associated subunits. Characterization of alpha 12 and inhibition of adenylyl cyclase by alpha z." *J Biol Chem* 270(4): 1734–41.

Kraus, et al., *Journal of Immunology* 160: 5209–52 12 (1998).

Krishnan, et al., *Science* 282(53 88): 484–7 (1998).

Kwoh, et al., *Proc. Natl. Acad. Sci.* 86: 1173 (1989).

Kubik, et al., *Nucleic Acids Res.* 22(13): 2619–26 (1994).

Lakowicz, J. R. and Berndt, K., "Lifetime-selective fluorescence imaging using an rf phase-sensitive camera", *Rev. Sci. Instr.* 62(7):1727 (1991).

Lakowicz, J. R., *Principles of Fluorescence Spectroscopy*, Second Edition, 1999. Kluwer Academic/Plenum Publishers, New York.

Lee, E., M. E. Linder, et al. (1994). "Expression of G-protein alpha subunits in Escherichia coli." *Methods Enzymol* 237: 146–64.

Li, Y., P. M. Stemweis, et al. (1998). "Sites for Galpha binding on the G protein beta subunit overlap with sites for regulation of phospholipase Cbeta and adenylyl cyclase." *J Biol Chem* 273(26): 16265–72.

Lin, et al. *Nucleic Acids Research* 22: 5229–5234 (1994).

Liu, X. and Tan, W., "A fiberoptic evanescent wave DNA biosensor based on novel molecular beacons", *Anal. Chem.* 71:5054 (1999).

Lockhart, et al., *Science,* 274(5287): 6 10–4 (1996).

Mace, M. L. et al., "Novel Microarray Printing and Detection Technologies", in *Microarray Biochip Technology*, ed. by M. Schena, Eaton Publishing Co., 2000, Natick, MA, pp. 39–64.

Morrison, in Nonisotopic DNA Probe Techniques, Kricka, ed., Academic Press, Inc., San Diego, Calif., chapter 13 (1992).

Mansour, S. J., J. M. Candia, et al. (1996). "Interdependent domains controlling the enzymatic activity of mitogen-activated protein kinase kinase 1." *Biochemistry* 35(48): 15529–36.

Min, K., N. N. Kim, et al. (2000). "Sildenafil augments pelvic nerve-mediated female genital sexual arousal in the anesthetized rabbit." *Int J Impot Res* 12 Suppl 3: S32–9.

Moreland, R. B., I. Goldstein, et al. (1998). "Sildenafil, a novel inhibitor of phosphodiesterase type 5 in human corpus cavemosum smooth muscle cells." *Life Sci* 62(20): 309–18.

Morrison, et al., *Anal. Biochem* 183: 23 1–244 (1989).

Muller, T., P. Engels, et al. (1996). "Subtypes of the type 4 cAMP phosphodiesterases: structure, regulation and selective inhibition." *Trends Pharmacol Sci* 17(8): 294–8.

Nagaoka, T., T. Shirakawa, et al. (1998). "Cyclic nucleotide phosphodiesterase 3 expression in vivo: evidence for tissue-specific expression of phosphodiesterase 3A or 3B mRNA and activity in the aorta and adipose tissue of atherosclerosis-prone insulin-resistant rats." *Diabetes* 47(7): 1135–44.

Obata, T., M. B. Yaffe, et al. (2000). "Peptide and protein library screening defines optimal substrate motifs for AKT/PKB." *J Biol Chem* 275(46): 36108–15.

Obernolte, R., J. Ratzliff, et al. (1997). "Multiple splice variants of phosphodiesterase PDE4C cloned from human lung and testis." *Biochim Biolphys Acta* 1353(3): 287–97.

O'Shaughnessy, D. J., "Hydrazido-derivatized supports in affinity chromatography", *J. Chromatography,* 510:13 (1990).

Owicki, J. C. et al., "Application of Fluorescence Polarization Assays in High-Throughput Screening", *Genetic Engineering News* 17(19), 1997.

Pagratis, et al., *Nat Biotechnol* 15: 68–73 (1997).

Pieken, et al., *Science* 253: 314–3 17 (1991).

Pillai, R., K. Kytle, et al. (1993). "Use of a yeast expression system for the isolation and analysis of drug-resistant mutants of a mammalian phosphodiesterase." *Proc Natl Acad Sci U S A* 90(24): 11970–4.

Potyrailo, et al. *Anal Chem,* 70(16): 34 19–25 (1998).

Proudnikov, D. and Mirzabekov, A., "Chemical Methods of DNA and RNA fluorescent labeling", *Nucleic Acids Res.* 24(22):4535 (1996).

Richter, W., T. Hermsdorf, et al. (2000). "Refolding, purification, and characterization of human recombinant PDE4A constructs expressed in Escherichia coli." *Protein Expr Purif* 19(3): 375–83.

Robertson, D. and Davidson, N., "Covalent coupling of ribonucleic acid to agarose", *Biochemistry* 11(4):533 (1972).

Robertson D L; Joyce G F. Selection in vitro of an RNA enzyme that specifically cleaves single-stranded DNA. *Nature,* 1990 Mar 29, 344(6265):467–8.

Robertson, M. P. and Ellington, A. D., "Design and optimization of effector-activated ribozyme ligases", *Nucleic Acids Res.* 28(8):1751 (2000).

Ruhn, P. F. et al., "Development of dihydrazide-activated silica supports for high-performance affinity chromatography", *J. Chromatography A* 669:9 (1994).

Saiki, et al., *Science* 230: 1350–54 (1985).

Saiki, et al., *Science* 239: 487–49 1 (1988).

Sako, Y. et al., "Single-molecule imaging of EGFR signaling on the surface of living cells", *Nature Cell Bio.* 2:168 (2000).

Schena, M. and Davis, R. W, "Technology Standards for Microarray Research", in *Microarray Biochip Technology,* ed. by M. Schena, Eaton Publishing Co., 2000, Natick, MA, pp1–18.

Schermer, M. J., "Confocal scanning microscopy in microarray detection", in *DNA Microarrays: A Practical Approach,* ed. by M. Schena, Oxford University Press, 1999, Oxford, pp. 17–42.

Schluep, T. and Cooney, C. L., "Immobilization of oligonucleotides on a large pore support for plasmid purification by triplex affinity interaction", *Bioseparation* 7:317 (1999).

Seelig B; Jaschke A. A small catalytic RNA motif with Diels-Alderase activity. *Chemistry and Biology,* 1999 Mar, 6(3):167–76.

Seetherman, S., et al., "Immobilized RNA switches for the analysis of complex and biological mixtures", *Nature Biotech.* 19:336 (2001).

Serivce, "Coming soon: the pocket DNA sequencer." *Science* 282, 399–401

Seiwert, S. D., T. Stines Nahreini, et al. (2000). "RNA aptamers as pathway-specific MAP kinase inhibitors." *Chem Biol* 7(11): 833–43.

Simone, et al. *Trends Genet* 14(7): 272–6 (1998).

Singh, K. K. et al., "Rapid kinetic characterization of hammerhead ribozymes by real-time monitoring of fluorescence resonance energy transfer (FRET)", *RNA* 5:1348 (1999).

Singh, K. K., et al., "Fluorescence Polarization for Monitoring Ribozyme Reactions in Real Time", *BioTechniques* 29:344 (2000).

Sirinarumitr, T., P. S. Paul, et al. (1997). "Rapid in situ hybridization technique for the detection of ribonucleic acids in tissues using radiolabelled and fluorescein-labelled riboprobes." *Mol Cell Probes* 11(4): 273–80.

Sokol, et al., *Proc. Natl. Acad. Sci.* 95(20): 11538–43 (1998).

Sood, et al., *Nuci. Acid Res.* 4:2557 (1977).

Soukup, et al. *Journal of Molecular Biology* 298: 623–632 (2000).

Sproat, et al., *Nucl. Acid Res.* 19:733-.738 (1991).

Soukup, G., et al., "Generating new ligand-binding RNAs by affinity maturation and disintegration of allosteric ribozymes", *RNA* 7:524 (2001).

Stanton, M., Hamaguchi, N., and Ellington, A. Poster Presentation at the National Cancer Institute Innovative Molecular Analysis Technologies P1 Meeting, July 6–8, Chantilly, Virginia (2000)

Stanton, J. A. and M. S. Beer (1997). "Characterisation of a cloned human 5-HT1A receptor cell line using [35S]GTP gamma S binding." *Eur J Pharmacol* 320(2–3): 267–75.

Tasset, et al. *J Mol Biol,* 272(5): 688–98 (1997).

Truskey, G. A. et al., "Total internal reflection fluorescence microscopy (TIRFM): Topographical mapping of relative cell/substratum separation distances", *J. Cell Science* 103: 491 (1992).

Tuerk and Gold, *Science* 249: 505(1990)

Taylor, S. J., R. J. Resnick, et al. (2001). "Nonradioactive determination of Ras-GTP levels using activated ras interaction assay." *Methods Enzymol* 333: 333–42.

Tyagi, et al., *Nature Biotechnology* 14: 303–308 (1996).

Usman, N. and L. M. Blatt (2000). "Nuclease-resistant synthetic ribozymes: developing a new class of therapeutics." *J Clin Invest* 106(10): 1197–202.

Walter, N. G. and Burke, J. M., "Real-time monitoring of hairpin ribozyme kinetics through base-specific quenching of fluorescein-labeled substrates", *RNA* 3:392 (1997).

Walter, N. G. et al., "Tertiary structure formation in the hairpin ribozyme monitored by fluorescence resonance energy transfer", *The EMBO Journal* 17(8):2378 (1998).

Wang, P., J. G. Myers, et al. (1997). "Expression, purification, and characterization of human cAMP-specific phosphodiesterase (PDE4) subtypes A, B, C, and D." *Biochem Biophys Res Commun* 234(2): 320–4.

Wenzel-Seifert, K. and R. Seifert (2000). "Molecular analysis of beta(2)-adrenoceptor coupling to G(s)-, G(i)-, and G(q)-proteins." *Mol Pharmacol* 58(5): 954–66.

Williams K P; Imahori H; Fujimoto D N; Inoue T. Selection of novel forms of a functional domain within the Tetrahymena ribozyme. *Nucleic Acids Research,* 1994 Jun 11, 22(11):2003–9.

Wilson C; Szostak JW. In vitro evolution of a self-alkylating ribozyme. Nature, 1995 Apr 27, 374(6525):777–82.

Wu, P. and Brand, L., "Resonance Energy Transfer: Methods and Applications", *Anal. Biochem.* 218:1(1994)

Wu, T. P. et al., "A fluorescent-labeling method for sequencing small RNA on polyacrylamide gel", *Nucleic Acids Res.* 24(17):3472 (1996).

Zammatteo, N. et al., "Comparison between Different Strategies of Covalent Attachment of DNA to Glass Surfaces to Build DNA Microarrays", *Anal. Biochem.* 280:143 (2000).

Zhang B; Cech T R. Peptide bond formation by in vitro selected ribozymes. *Nature,* 1997 Nov 6, 390(6655): 96–100.

Bassi, G. S., de Oliveira, D. M., White, M. F. and Weeks, K. M. (2002) *Proc Natl Acad Sci USA* 99, 128–33.

Chang, L. and Karin, M. (2001) *Nature* 410, 37–40.

Doudna, J. A. and Cech, T. R. (2002) *Nature* 418, 222–8.

English, J. M. and Cobb, M. H. (2002) *Trends Pharm. Sci.* 23, 40–45.

Koizumi, M., Soukup, G. A., Kerr, J. Q. and Breaker, R. R. (1999) *Nat. Struct. Biol.* 6, 1062–71.

Myers, C. A., Kuhla, B., Cusack, S. and Lambowitz, A. M. (2002) *Proc Natl Acad Sci USA* 99, 2630–5.

Pan, T. (1995) *Biochemistry* 34, 902–9.

Robertson, M. P. and Ellington, A. D. (1999) *Nat. Biotech.* 17, 62–66.

Robertson, M. P. and Ellington, A. D. (2000) *Nucleic Acids Res.* 28, 1751–9.

Russell R. and Herschlag, D. (1999) *J. Mol. Biol.* 291, 1155–67.

Sassanfar and Szostak (1993) *Nature* 363, 550–553.

Soukup, G. A. and Breaker, R. R. (1999) *Proc Natl Acad Sci USA* 96, 3584–9.

Soukup, G. A., DeRose, E. C., Koizumi, M. and Breaker, R. R. (2001) *RNA* 7, 524–36.

Tang, J. and Breaker, R. R. (1997) *Chem. Biol.* 4, 453–9.

Walter, N. G., Harris, D. A., Pereira, M. J. and Rueda D. (2001–2) *Biopolymers* 61, 224–42.

Knusel, B., Rabin, S. J., Hefti, F., Kaplan, D. R. 1994. Regulated neurotrophin receptor responsiveness during neuronal migration and early differentiation. *J. Neurosci* 14:1542

Fox, T., Coll, J. T., Xie, Xiaoling, Ford, P. J., Germann, U. A., Porter, M. D., Pazhanisamy, S., Fleming, M. A., Galullo, V., Su, M. S. and Wilson, K. P. (1998). "A single amino acid substitution makes ERK2 susceptible to pyridinyl imidazole inhibitors of p38 MAP kinase". *Protein Science* 7: 2249–55.

Meggio, F., Donella, D. A., Ruzzene, M., Brunati, A. M., Cesaro, L., Guerra, B., Meyer, T., Mett, H., Fabbro, D., Furet, P., et al. (1995). "Different susceptibility of protein kinases to staurosporine inhibition". *Eur J Biochem* 234: 317–22.

Variations, modifications, and other implementations of what is described herein will occur to those of ordinary skill in the art without departing from the spirit and scope as claimed. Accordingly, the invention is to be defined not by the preceding illustrative description but instead by the spirit and scope of the following claims.

---

SEQUENCE LISTING

```
<160> NUMBER OF SEQ ID NOS: 372

<210> SEQ ID NO 1
<211> LENGTH: 128
<212> TYPE: RNA
<213> ORGANISM: Artificial Sequence
<220> FEATURE:
<223> OTHER INFORMATION: Description of Artificial Sequence: 5'
      fixed:random:3'-fixed sequence
<220> FEATURE:
<221> NAME/KEY: misc_feature
<222> LOCATION: (40)..(89)
<223> OTHER INFORMATION: Wherein n is an a or u or c or g, and some may
      be missing.

<400> SEQUENCE: 1
ggacuucggu ccagugcucg ugcacuaggc cguucgaccn nnnnnnnnn nnnnnnnnnn    60 nnnnnnnnnn nnnnnnnnnn nnnnnnnnnc uuagacagga gguuaggugc cucgugaugu   120
ccagucgc                                                            128

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: 3' primer
      sequence

<400> SEQUENCE: 2
gcgactggac atcacgag                                                  18

<210> SEQ ID NO 3
<211> LENGTH: 17
<212> TYPE: DNA
<213> ORGANISM: Artificial Sequence
```

-continued

```
<220> FEATURE:
<223> OTHER INFORMATION: Description of Artificial Sequence: substrate
      primer

<400> SEQUENCE: 3
aaaaaatgca ctggact                                                    17

<210> SEQ ID NO 4
<211> LENGTH: 103
<212> TYPE: RNA
<213> ORGANISM: Artificial Sequence
<220> FEATURE:
<223> OTHER INFORMATION: Description of Artificial Sequence: 5'
      fixed:random:3' fixed A-3'-fixed B molecule
<220> FEATURE:
<221> NAME/KEY: misc_feature
<222> LOCATION: (22)..(71)
<223> OTHER INFORMATION: Wherein n is an a or u or c or g and some may
      be missing.

<400> SEQUENCE: 4
gggcgacccu gaugagccug gnnnnnnnnn nnnnnnnnnn nnnnnnnnnn nnnnnnnnnn     60
nnnnnnnnnn nuuagacgaa acggugaaag ccguagguug ccc                      103

<210> SEQ ID NO 5
<211> LENGTH: 132
<212> TYPE: RNA
<213> ORGANISM: Artificial Sequence
<220> FEATURE:
<223> OTHER INFORMATION: Description of Artificial Sequence: CW45-33-B04
      ERK specific nucleic acid sensor molecule

<400> SEQUENCE: 5
ggacuucggc gaaagccguu cgaccgcaug cagacgcuag cgaauugguu ccucgaaagg     60
gaaagcguua uuaagaaacc aaaaugcgug ucuuagacag gagguaggu gcgucaaugc    120 ugcaaguuac ug                                                        132

<210> SEQ ID NO 6
<211> LENGTH: 133
<212> TYPE: RNA
<213> ORGANISM: Artificial Sequence
<220> FEATURE:
<223> OTHER INFORMATION: Description of Artificial Sequence: CW45-33-D04
      ERK specific nucleic acid sensor molecule

<400> SEQUENCE: 6
ggacuucggc gaaagccguu cgaccgguag cagacgcuag cgaauugguu ccucgaaagg     60
gaaagcguua uuaagaaacc aaaauguuau cgcuuagaca ggagguagg ugcgucaaug    120 cugcaaguua cug                                                       133

<210> SEQ ID NO 7
<211> LENGTH: 134
<212> TYPE: RNA
<213> ORGANISM: Artificial Sequence
<220> FEATURE:
<223> OTHER INFORMATION: Description of Artificial Sequence: CW45-33-F03
      ERK specific nucleic acid sensor molecule

<400> SEQUENCE: 7
ggacuucggc gaaagccguu cgacccugug cagacgcua gcgaauuggu uccucgaaag      60
ggaaagcguu auuaagaaac caaaaugcgc aggcuuagac aggagguag gugcgucaau    120 gcugcaaguu acug                                                      134
```

<210> SEQ ID NO 8
<211> LENGTH: 133
<212> TYPE: RNA
<213> ORGANISM: Artificial Sequence
<220> FEATURE:
<223> OTHER INFORMATION: Description of Artificial Sequence: CW45-33-D01
    ERK specific nucleic acid sensor molecule

<400> SEQUENCE: 8

```
ggacuucggc gaaagccguu cgacccgcaa cagacgcuag cgaauugguu ccucgaaagg    60
gaaagcguua uuaagaaacc aaaauggugu ggcuuagaca ggagguuagg ugcgucaaug   120
cugcaaguua cug                                                     133
```

<210> SEQ ID NO 9
<211> LENGTH: 2092
<212> TYPE: DNA
<213> ORGANISM: Homo sapiens

<400> SEQUENCE: 9

```
gaattccaaa attgtgatgt ttcttgtatt tttgatgaag gagaaatact gtaatgatca    60
ctgtttacac tatgtacact ttaggccagc cctttgtagc gttatacaaa ctgaaagcac   120
accggacccg caggctcccg gggcagggcc ggggccagag ctcgcgtgtc ggcgggacat   180
gcgctgcgtc gcctctaacc tcgggctgtg ctcttttcc aggtggcccg ccggtttctg    240
agccttctgc cctgcgggga cacggtctgc accctgcccg cggccacgga ccatgaccat   300
gaccctccac accaaagcat ctgggatggc cctactgcat cagatccaag gaacgagct    360
ggagcccctg aaccgtccgc agctcaagat cccctggag cggcccctgg gcgaggtgta    420
cctggacagc agcaagcccg ccgtgtacaa ctaccccgag ggcgccgcct acgagttcaa   480
cgccgcggcc gccgccaacg cgcaggtcta cggtcagacc ggcctcccct acggccccgg   540
gtctgaggct gcgcgttcg gctccaacgg cctgggggt tcccccccac tcaacagcgt     600
gtctccgagc ccgctgatgc tactgcaccc gccgccgcag ctgtcgcctt tcctgcagcc   660
ccacggccag caggtgccct actacctgga gaacgagccc agcggctaca cggtgcgcga   720
ggccggcccg ccggcattct acaggccaaa ttcagataat cgacgccagg gtggcagaga   780
aagattggcc agtaccaatg acaagggaag tatggctatg aatctgcca aggagactcg    840
ctactgtgca gtgtgcaatg actatgcttc aggctaccat tatggagtct ggtcctgtga   900
gggctgcaag gccttcttca agagaagtat tcaaggacat aacgactata tgtgtccagc   960
caccaaccag tgcaccattg ataaaaacag gaggaagagc tgccaggcct gccggctccg   1020
caaatgctac gaagtgggaa tgatgaaagg tgggatacga aaagaccgaa gaggagggag   1080
aatgttgaaa cacaagcgcc agagagatga tggggagggc agggtgaag tggggtctgc    1140
tggagacatg agagctgcca acctttggcc aagcccgctc atgatcaaac gctctaagaa   1200
gaacagcctg gccttgtccc tgacggccga ccagatggtc agtgccttgt tggatgctga   1260
gcccccata ctctattccg agtatgatcc taccagaccc ttcagtgaag cttcgatgat    1320
gggcttactg accaacctgg cagacaggga gctggttcac atgatcaact gggcgaagag   1380
ggtgccaggc tttgtggatt tgaccctcca tgatcaggtc caccttctag aatgtgcctg   1440
gctagagatc ctgatgattg gtctcgtctg gcgctccatg gagcacccag tgaagctact   1500
gtttgctcct aacttgctct tggacaggaa ccagggaaaa tgtgtagagg gcatggtgga   1560
gatcttcgac atgctgctgg ctacatcatc tcggttccgc atgatgaatc tgcagggaga   1620
```

```
ggagtttgtg tgcctcaaat ctattatttt gcttaattct ggagtgtaca catttctgtc    1680
cagcaccctg aagtctctgg aagagaagga ccatatccac cgagtcctgg acaagatcac    1740
agacactttg atccacctga tggccaaggc aggcctgacc ctgcagcagc agcaccagcg    1800
gctggcccag ctcctcctca tcctctccca catcaggcac atgagtaaca aaggcatgga    1860
gcatctgtac agcatgaagt gcaagaacgt ggtgcccctc tatgacctgc tgctggagat    1920
gctggacgcc accgcctac atgcgcccac tagccgtgga ggggcatccg tggaggagac    1980
ggaccaaagc cacttggcca ctgcgggctc tacttcatcg cattccttgc aaaagtatta    2040
catcacgggg gaggcagagg gtttccctgc cacagtctga gagctccctg gc            2092
```

<210> SEQ ID NO 10
<211> LENGTH: 595
<212> TYPE: PRT
<213> ORGANISM: Homo sapiens

<400> SEQUENCE: 10

```
Met Thr Met Thr Leu His Thr Lys Ala Ser Gly Met Ala Leu Leu His
 1               5                  10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
```

|     |     |     |     |     | 290 |     |     |     |     | 295 |     |     |     |     | 300 |     |     |     |     |
|-----|-----|-----|-----|-----|-----|-----|-----|-----|-----|-----|-----|-----|-----|-----|-----|-----|-----|-----|-----|
| Ser | Leu | Ala | Leu | Ser | Leu | Thr | Ala | Asp | Gln | Met | Val | Ser | Ala | Leu | Leu |
| 305 |     |     |     |     | 310 |     |     |     |     | 315 |     |     |     |     | 320 |

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
                355                 360                 365

Asp Leu Thr Leu His Asp Gln Val His Leu Leu Glu Cys Ala Trp Leu
370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
        450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
        530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 11
<211> LENGTH: 1970
<212> TYPE: DNA
<213> ORGANISM: Homo sapiens

<400> SEQUENCE: 11
gcaccgcgag cccctagcac ccgacaagct gagtgtgcag gacgagtccc caccacaccc        60
acaccacagc cgctgaatga ggcttccagg cgtccgctcg cggcccgcag agcccgcccg       120
tgggtccgcc cgctgaggcg cccccagcca gtgcgcttac ctgccagact gcgcgccatg       180
gggcaacccg ggaacggcag cgccttcttg ctggcaccca tggaagcca tgcgccggac        240 cacgacgtca cgcaggaaag ggacgaggtg tgggtggtgg gcatgggcat cgtcatgtct       300
ctcatcgtcc tggccatcgt gtttggcaat gtgctggtca tcacagccat tgccaagttc       360

```
gagcgtctgc agacggtcac caactacttc atcacttcac tggcctgtgc tgatctggtc      420
atgggcctgg cagtggtgcc ctttggggcc gcccatattc ttatgaaaat gtggactttt      480
ggcaacttct ggtgcgagtt ttggacttcc attgatgtgc tgtgcgtcac ggccagcatt      540
gagaccctgt gcgtgatcgc agtggatcgc tactttgcca ttacttcacc tttcaagtac      600
cagagcctgc tgaccaagaa taaggcccgg gtgatcattc tgatggtgtg gattgtgtca      660
ggccttacct ccttcttgcc cattcagatg cactggtacc gggccacccca ccaggaagcc     720
atcaactgct atgccaatga cctgctgtg acttcttca cgaaccaagc ctatgccatt        780
gcctcttcca tcgtgtcctt ctacgttccc tggtgatca tggtcttcgt ctactccagg       840
gtctttcagg aggccaaaag gcagctccag aagattgaca atctgaggg ccgcttccat       900
gtccagaacc ttagccaggt ggagcaggat gggcggacgg gcatggact ccgcagatct       960
tccaagttct gcttgaagga gcacaaagcc ctcaagacgt taggcatcat catgggcact      1020
ttcaccctct gctggctgcc cttcttcatc gttaacattg tgcatgtgat ccaggataac      1080
ctcatccgta aggaagttta catcctccta aattggatag ctatgtcaa ttctggtttc       1140
aatccccta tctactgccg gagcccagat ttcaggattg ccttccagga gcttctgtgc       1200
ctgcgcaggt cttctttgaa ggcctatggg aatggctact ccagcaacgg caacacaggg     1260
gagcagagtg gatatcacgt ggaacaggag aaagaaaata aactgctgtg tgaagacctc     1320
ccaggcacgg aagactttgt gggccatcaa ggtactgtgc ctagcgataa cattgattca     1380
caagggagga attgtagtac aaatgactca ctgctgtaaa gcagttttc tacttttaaa     1440
gaccccccc cccccaacag aacactaaac agactattta acttgagggt aataaactta    1500
gaataaaatt gtaaaaattg tatagagata tgcagaagga agggcatcct tctgcctttt    1560
ttattttttt aagctgtaaa aagagagaaa acttatttga gtgattattt gttatttgta    1620
cagttcagtt cctctttgca tggaatttgt aagtttatgt ctaaagagct ttagtcctag   1680
aggacctgag tctgctatat tttcatgact tttccatgta tctacctcac tattcaagta   1740
ttagggtaa tatattgctg gtaatttgta tctgaaggag attttccttc ctacaccctt   1800
ggacttgagg attttgagta tctcggacct ttcagctgtg aacatggact cttcccccac   1860
tcctcttatt tgctcacacg gggtatttta ggcagggatt tgaggagcag cttcagttgt  1920
tttcccgagc aaaggtctaa agtttacagt aaataaaatg tttgaccatg              1970
```

<210> SEQ ID NO 12
<211> LENGTH: 413
<212> TYPE: PRT
<213> ORGANISM: Homo sapiens

<400> SEQUENCE: 12

```
Met Gly Gln Pro Gly Asn Gly Ser Ala Phe Leu Leu Ala Pro Asn Gly
 1               5                   10                  15

Ser His Ala Pro Asp His Asp Val Thr Gln Gln Arg Asp Glu Val Trp
             20                  25                  30

Val Val Gly Met Gly Ile Val Met Ser Leu Ile Val Leu Ala Ile Val
         35                  40                  45

Phe Gly Asn Val Leu Val Ile Thr Ala Ile Ala Lys Phe Glu Arg Leu
     50                  55                  60

Gln Thr Val Thr Asn Tyr Phe Ile Thr Ser Leu Ala Cys Ala Asp Leu
 65                  70                  75                  80

Val Met Gly Leu Ala Val Val Pro Phe Gly Ala Ala His Ile Leu Met
                 85                  90                  95
```

```
Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
            115                 120                 125

Val Asp Arg Tyr Phe Ala Ile Thr Ser Pro Phe Lys Tyr Gln Ser Leu
            130                 135                 140

Leu Thr Lys Asn Lys Ala Arg Val Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
                195                 200                 205

Tyr Val Pro Leu Val Ile Met Val Phe Val Tyr Ser Arg Val Phe Gln
            210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
            275                 280                 285

Phe Phe Ile Val Asn Ile Val His Val Ile Gln Asp Asn Leu Ile Arg
            290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
                325                 330                 335

Gln Glu Leu Leu Cys Leu Arg Arg Ser Ser Leu Lys Ala Tyr Gly Asn
            340                 345                 350

Gly Tyr Ser Ser Asn Gly Asn Thr Gly Glu Gln Ser Gly Tyr His Val
            355                 360                 365

Glu Gln Glu Lys Glu Asn Lys Leu Leu Cys Glu Asp Leu Pro Gly Thr
            370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
                405                 410

<210> SEQ ID NO 13
<211> LENGTH: 394
<212> TYPE: PRT
<213> ORGANISM: Homo sapiens

<400> SEQUENCE: 13

Met Gly Cys Leu Gly Asn Ser Lys Thr Glu Asp Gln Arg Asn Glu Glu
  1               5                  10                  15

Lys Ala Gln Arg Glu Ala Asn Lys Lys Ile Glu Lys Gln Leu Gln Lys
             20                  25                  30

Asp Lys Gln Val Tyr Arg Ala Thr His Arg Leu Leu Leu Leu Gly Ala
         35                  40                  45

Gly Glu Ser Gly Lys Ser Thr Ile Val Lys Gln Met Arg Ile Leu His
```

```
                 50                  55                  60
Val Asn Gly Phe Asn Gly Glu Gly Gly Glu Asp Pro Gln Ala Ala
 65                  70                  75                  80

Arg Ser Asn Ser Asp Gly Glu Lys Ala Thr Lys Val Gln Asp Ile Lys
                 85                  90                  95

Asn Asn Leu Lys Glu Ala Ile Glu Thr Ile Val Ala Ala Met Ser Asn
                100                 105                 110

Leu Val Pro Pro Val Glu Leu Ala Asn Pro Glu Asn Gln Phe Arg Val
                115                 120                 125

Asp Tyr Ile Leu Ser Val Met Asn Val Pro Asp Phe Asp Phe Pro Pro
130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Ala Asp Tyr Val Pro
                180                 185                 190

Ser Asp Gln Asp Leu Leu Arg Cys Arg Val Leu Thr Ser Gly Ile Phe
                195                 200                 205

Glu Thr Lys Phe Gln Val Asp Lys Val Asn Phe His Met Phe Asp Val
210                 215                 220

Gly Gly Gln Arg Asp Glu Arg Arg Lys Trp Ile Gln Cys Phe Asn Asp
225                 230                 235                 240

Val Thr Ala Ile Ile Phe Val Val Ala Ser Ser Tyr Asn Met Val
                245                 250                 255

Ile Arg Glu Asp Asn Gln Thr Asn Arg Leu Gln Glu Ala Leu Asn Leu
                260                 265                 270

Phe Lys Ser Ile Trp Asn Asn Arg Trp Leu Arg Thr Ile Ser Val Ile
                275                 280                 285

Leu Phe Leu Asn Lys Gln Asp Leu Leu Ala Glu Lys Val Leu Ala Gly
                290                 295                 300

Lys Ser Lys Ile Glu Asp Tyr Phe Pro Glu Phe Ala Arg Tyr Thr Thr
305                 310                 315                 320

Pro Glu Asp Ala Thr Pro Glu Pro Gly Glu Asp Pro Arg Val Thr Arg
                325                 330                 335

Ala Lys Tyr Phe Ile Arg Asp Glu Phe Leu Arg Ile Ser Thr Ala Ser
                340                 345                 350

Gly Asp Gly Arg His Tyr Cys Tyr Pro His Phe Thr Cys Ala Val Asp
                355                 360                 365

Thr Glu Asn Ile Arg Arg Val Phe Asn Asp Cys Arg Asp Ile Ile Gln
                370                 375                 380

Arg Met His Leu Arg Gln Tyr Glu Leu Leu
385                 390

<210> SEQ ID NO 14
<211> LENGTH: 395
<212> TYPE: PRT
<213> ORGANISM: Homo sapiens

<400> SEQUENCE: 14

Met Gly Cys Leu Gly Asn Ser Lys Thr Glu Asp Gln Arg Asn Glu Glu
  1               5                  10                  15

Lys Ala Gln Arg Glu Ala Asn Lys Lys Ile Glu Lys Gln Leu Gln Lys
                 20                  25                  30
```

```
Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
 50                  55                  60

Val Asn Gly Phe Asn Gly Glu Gly Gly Glu Asp Pro Gln Ala Ala
 65                  70                  75                  80

Arg Ser Asn Ser Asp Gly Ser Glu Lys Ala Thr Lys Val Gln Asp Ile
                 85                  90                  95

Lys Asn Asn Leu Lys Glu Ala Ile Glu Thr Ile Val Ala Ala Met Ser
                100                 105                 110

Asn Leu Val Pro Pro Val Glu Leu Ala Asn Pro Glu Asn Gln Phe Arg
            115                 120                 125

Val Asp Tyr Ile Leu Ser Val Met Asn Val Pro Asp Phe Asp Phe Pro
130                 135                 140

Pro Glu Phe Tyr Glu His Ala Lys Ala Leu Trp Glu Asp Glu Gly Val
145                 150                 155                 160

Arg Ala Cys Tyr Glu Arg Ser Asn Glu Tyr Gln Leu Ile Asp Cys Ala
                165                 170                 175

Gln Tyr Phe Leu Asp Lys Ile Asp Val Ile Lys Gln Ala Asp Tyr Val
            180                 185                 190

Pro Ser Asp Gln Asp Leu Leu Arg Cys Arg Val Leu Thr Ser Gly Ile
            195                 200                 205

Phe Glu Thr Lys Phe Gln Val Asp Lys Val Asn Phe His Met Phe Asp
210                 215                 220

Val Gly Gly Gln Arg Asp Glu Arg Arg Lys Trp Ile Gln Cys Phe Asn
225                 230                 235                 240

Asp Val Thr Ala Ile Ile Phe Val Val Ala Ser Ser Ser Tyr Asn Met
                245                 250                 255

Val Ile Arg Glu Asp Asn Gln Thr Asn Arg Leu Gln Glu Ala Leu Asn
            260                 265                 270

Leu Phe Lys Ser Ile Trp Asn Asn Arg Trp Leu Arg Thr Ile Ser Val
            275                 280                 285

Ile Leu Phe Leu Asn Lys Gln Asp Leu Leu Ala Glu Lys Val Leu Ala
290                 295                 300

Gly Lys Ser Lys Ile Glu Asp Tyr Phe Pro Glu Phe Ala Arg Tyr Thr
305                 310                 315                 320

Thr Pro Glu Asp Ala Thr Pro Glu Pro Gly Glu Asp Pro Arg Val Thr
                325                 330                 335

Arg Ala Lys Tyr Phe Ile Arg Asp Glu Phe Leu Arg Ile Ser Thr Ala
            340                 345                 350

Ser Gly Asp Gly Arg His Tyr Cys Tyr Pro His Phe Thr Cys Ala Val
            355                 360                 365

Asp Thr Glu Asn Ile Arg Arg Val Phe Asn Asp Cys Arg Asp Ile Ile
370                 375                 380

Gln Arg Met His Leu Arg Gln Tyr Glu Leu Leu
385                 390                 395

<210> SEQ ID NO 15
<211> LENGTH: 379
<212> TYPE: PRT
<213> ORGANISM: Homo sapiens

<400> SEQUENCE: 15

Met Gly Cys Leu Gly Asn Ser Lys Thr Glu Asp Gln Arg Asn Glu Glu
 1               5                  10                  15
```

```
Lys Ala Gln Arg Glu Ala Asn Lys Lys Ile Glu Lys Gln Leu Gln Lys
         20                  25                  30

Asp Lys Gln Val Tyr Arg Ala Thr His Arg Leu Leu Leu Leu Gly Ala
         35                  40                  45

Gly Glu Ser Gly Lys Ser Thr Ile Val Lys Gln Met Arg Ile Leu His
 50                  55                  60

Val Asn Gly Phe Asn Gly Asp Glu Lys Ala Thr Lys Val Gln Asp Ile
 65                  70                  75                  80

Lys Asn Asn Leu Lys Glu Ala Ile Glu Thr Ile Val Ala Ala Met Ser
             85                  90                  95

Asn Leu Val Pro Pro Val Glu Leu Ala Asn Pro Glu Asn Gln Phe Arg
            100                 105                 110

Val Asp Tyr Ile Leu Ser Val Met Asn Val Pro Asp Phe Asp Phe Pro
            115                 120                 125

Pro Glu Phe Tyr Glu His Ala Lys Ala Leu Trp Glu Asp Glu Gly Val
        130                 135                 140

Arg Ala Cys Tyr Glu Arg Ser Asn Glu Tyr Gln Leu Ile Asp Cys Ala
145                 150                 155                 160

Gln Tyr Phe Leu Asp Lys Ile Asp Val Ile Lys Gln Ala Asp Tyr Val
                165                 170                 175

Pro Ser Asp Gln Asp Leu Leu Arg Cys Arg Val Leu Thr Ser Gly Ile
            180                 185                 190

Phe Glu Thr Lys Phe Gln Val Asp Lys Val Asn Phe His Met Phe Asp
        195                 200                 205

Val Gly Gly Gln Arg Asp Glu Arg Arg Lys Trp Ile Gln Cys Phe Asn
210                 215                 220

Asp Val Thr Ala Ile Ile Phe Val Val Ala Ser Ser Ser Tyr Asn Met
225                 230                 235                 240

Val Ile Arg Glu Asp Asn Gln Thr Asn Arg Leu Gln Glu Ala Leu Asn
                245                 250                 255

Leu Phe Lys Ser Ile Trp Asn Asn Arg Trp Leu Arg Thr Ile Ser Val
            260                 265                 270

Ile Leu Phe Leu Asn Lys Gln Asp Leu Leu Ala Glu Lys Val Leu Ala
        275                 280                 285

Gly Lys Ser Lys Ile Glu Asp Tyr Phe Pro Glu Phe Ala Arg Tyr Thr
    290                 295                 300

Thr Pro Glu Asp Ala Thr Pro Glu Pro Gly Glu Asp Pro Arg Val Thr
305                 310                 315                 320

Arg Ala Lys Tyr Phe Ile Arg Asp Glu Phe Leu Arg Ile Ser Thr Ala
                325                 330                 335

Ser Gly Asp Gly Arg His Tyr Cys Tyr Pro His Phe Thr Cys Ala Val
            340                 345                 350

Asp Thr Glu Asn Ile Arg Arg Val Phe Asn Asp Cys Arg Asp Ile Ile
        355                 360                 365

Gln Arg Met His Leu Arg Gln Tyr Glu Leu Leu
    370                 375

<210> SEQ ID NO 16
<211> LENGTH: 380
<212> TYPE: PRT
<213> ORGANISM: Homo sapiens

<400> SEQUENCE: 16

Met Gly Cys Leu Gly Asn Ser Lys Thr Glu Asp Gln Arg Asn Glu Glu
```

```
              1               5                  10                 15
Lys Ala Gln Arg Glu Ala Asn Lys Lys Ile Glu Lys Gln Leu Gln Lys
                     20                  25                 30

Asp Lys Gln Val Tyr Arg Ala Thr His Arg Leu Leu Leu Leu Gly Ala
             35                  40                 45

Gly Glu Ser Gly Lys Ser Thr Ile Val Lys Gln Met Arg Ile Leu His
         50                  55                 60

Val Asn Gly Phe Asn Gly Asp Ser Glu Lys Ala Thr Lys Val Gln Asp
 65                  70                  75                  80

Ile Lys Asn Asn Leu Lys Glu Ala Ile Glu Thr Ile Val Ala Ala Met
                 85                  90                  95

Ser Asn Leu Val Pro Pro Val Glu Leu Ala Asn Pro Glu Asn Gln Phe
             100                 105                110

Arg Val Asp Tyr Ile Leu Ser Val Met Asn Val Pro Asp Phe Asp Phe
         115                 120                 125

Pro Pro Glu Phe Tyr Glu His Ala Lys Ala Leu Trp Glu Asp Glu Gly
     130                 135                 140

Val Arg Ala Cys Tyr Glu Arg Ser Asn Glu Tyr Gln Leu Ile Asp Cys
145                 150                 155                 160

Ala Gln Tyr Phe Leu Asp Lys Ile Asp Val Ile Lys Gln Ala Asp Tyr
                 165                 170                 175

Val Pro Ser Asp Gln Asp Leu Leu Arg Cys Arg Val Leu Thr Ser Gly
             180                 185                 190

Ile Phe Glu Thr Lys Phe Gln Val Asp Lys Val Asn Phe His Met Phe
         195                 200                 205

Asp Val Gly Gly Gln Arg Asp Glu Arg Arg Lys Trp Ile Gln Cys Phe
     210                 215                 220

Asn Asp Val Thr Ala Ile Ile Phe Val Val Ala Ser Ser Ser Tyr Asn
225                 230                 235                 240

Met Val Ile Arg Glu Asp Asn Gln Thr Asn Arg Leu Gln Glu Ala Leu
                 245                 250                 255

Asn Leu Phe Lys Ser Ile Trp Asn Asn Arg Trp Leu Arg Thr Ile Ser
             260                 265                 270

Val Ile Leu Phe Leu Asn Lys Gln Asp Leu Leu Ala Glu Lys Val Leu
         275                 280                 285

Ala Gly Lys Ser Lys Ile Glu Asp Tyr Phe Pro Glu Phe Ala Arg Tyr
     290                 295                 300

Thr Thr Pro Glu Asp Ala Thr Pro Glu Pro Gly Glu Asp Pro Arg Val
305                 310                 315                 320

Thr Arg Ala Lys Tyr Phe Ile Arg Asp Glu Phe Leu Arg Ile Ser Thr
                 325                 330                 335

Ala Ser Gly Asp Gly Arg His Tyr Cys Tyr Pro His Phe Thr Cys Ala
             340                 345                 350

Val Asp Thr Glu Asn Ile Arg Arg Val Phe Asn Asp Cys Arg Asp Ile
         355                 360                 365

Ile Gln Arg Met His Leu Arg Gln Tyr Glu Leu Leu
     370                 375                 380
```

<210> SEQ ID NO 17
<211> LENGTH: 388
<212> TYPE: PRT
<213> ORGANISM: Homo sapiens

<400> SEQUENCE: 17

-continued

```
Met Glu Ile Ser Gly Pro Pro Phe Glu Ile Gly Ser Ala Pro Ala Gly
  1               5                  10                  15

Val Asp Asp Thr Pro Val Asn Met Asp Ser Pro Ile Ala Leu Asp
             20                  25                  30

Gly Pro Pro Ile Lys Val Ser Gly Ala Pro Asp Lys Arg Glu Arg Ala
             35                  40                  45

Glu Arg Pro Pro Val Glu Glu Ala Ala Glu Met Glu Gly Ala Ala
 50                  55                  60

Asp Ala Glu Gly Gly Lys Val Pro Ser Pro Gly Tyr Gly Ser Pro
 65              70                  75                  80

Ala Ala Gly Ala Ala Ser Ala Asp Thr Ala Ala Arg Ala Ala Pro Ala
                 85                  90                  95

Ala Pro Ala Asp Pro Asp Ser Gly Ala Thr Pro Glu Asp Pro Asp Ser
             100                 105                 110

Gly Thr Ala Pro Ala Asp Pro Asp Ser Gly Ala Phe Ala Ala Asp Pro
             115                 120                 125

Asp Ser Gly Ala Ala Pro Ala Ala Pro Ala Asp Pro Asp Ser Gly Ala
 130                 135                 140

Ala Pro Asp Ala Pro Ala Asp Pro Asp Ser Gly Ala Ala Pro Asp Ala
145                 150                 155                 160

Pro Ala Asp Pro Asp Ala Gly Ala Ala Pro Glu Ala Pro Ala Ala Pro
                 165                 170                 175

Ala Ala Ala Glu Thr Arg Ala Ala His Val Ala Pro Ala Ala Pro Asp
             180                 185                 190

Ala Gly Ala Pro Thr Ala Pro Ala Ser Ala Thr Arg Ala Ala Gln
         195                 200                 205

Val Arg Arg Ala Ala Ser Ala Ala Pro Ala Ser Gly Ala Arg Arg Lys
210                 215                 220

Ile His Leu Arg Pro Pro Ser Pro Glu Ile Gln Ala Ala Asp Pro Pro
225                 230                 235                 240

Thr Pro Arg Pro Thr Arg Ala Ser Ala Trp Arg Gly Lys Ser Glu Ser
                 245                 250                 255

Ser Arg Gly Arg Arg Val Tyr Tyr Asp Glu Gly Val Ala Ser Ser Asp
             260                 265                 270

Asp Asp Ser Ser Gly Asp Glu Ser Asp Asp Gly Thr Ser Gly Cys Leu
         275                 280                 285

Arg Trp Phe Gln His Arg Arg Asn Arg Arg Arg Lys Pro Gln Arg
 290                 295                 300

Asn Leu Leu Arg Asn Phe Leu Val Gln Ala Phe Gly Cys Phe Gly
305                 310                 315                 320

Arg Ser Glu Ser Pro Gln Pro Lys Ala Ser Arg Ser Leu Lys Val Lys
                 325                 330                 335

Lys Val Pro Leu Ala Glu Lys Arg Arg Gln Met Arg Lys Glu Ala Leu
             340                 345                 350

Glu Lys Arg Ala Gln Lys Arg Ala Glu Lys Lys Arg Ser Lys Leu Ile
         355                 360                 365

Asp Lys Gln Leu Gln Asp Glu Lys Met Gly Tyr Met Cys Thr His Arg
     370                 375                 380

Leu Leu Leu Leu
385

<210> SEQ ID NO 18
<211> LENGTH: 381
<212> TYPE: PRT
```

<213> ORGANISM: Homo sapiens

<400> SEQUENCE: 18

```
Met Gly Cys Leu Gly Asn Ser Lys Thr Thr Glu Asp Gln Gly Val
  1               5                  10                  15
Asp Glu Lys Glu Arg Arg Glu Ala Asn Lys Lys Ile Glu Lys Gln Leu
                 20                  25                  30
Gln Lys Glu Arg Leu Ala Tyr Lys Ala Thr His Arg Leu Leu Leu Leu
             35                  40                  45
Gly Ala Gly Glu Ser Gly Lys Ser Thr Ile Val Lys Gln Met Arg Ile
         50                  55                  60
Leu His Val Asn Gly Phe Asn Pro Glu Glu Lys Lys Gln Lys Ile Leu
 65                  70                  75                  80
Asp Ile Arg Lys Asn Val Lys Asp Ala Ile Val Thr Ile Val Ser Ala
                 85                  90                  95
Met Ser Thr Ile Ile Pro Pro Val Pro Leu Ala Asn Pro Glu Asn Gln
            100                 105                 110
Phe Arg Ser Asp Tyr Ile Lys Ser Ile Ala Pro Ile Thr Asp Phe Glu
        115                 120                 125
Tyr Ser Gln Glu Phe Phe Asp His Val Lys Lys Leu Trp Asp Asp Glu
    130                 135                 140
Gly Val Lys Ala Cys Phe Glu Arg Ser Asn Glu Tyr Gln Leu Ile Asp
145                 150                 155                 160
Cys Ala Gln Tyr Phe Leu Glu Arg Ile Asp Ser Val Ser Leu Val Asp
                165                 170                 175
Tyr Thr Pro Thr Asp Gln Asp Leu Leu Arg Cys Arg Val Leu Thr Ser
            180                 185                 190
Gly Ile Phe Glu Thr Arg Phe Gln Val Asp Lys Val Asn Phe His Met
        195                 200                 205
Phe Asp Val Gly Gly Gln Arg Asp Glu Arg Arg Lys Trp Ile Gln Cys
    210                 215                 220
Phe Asn Asp Val Thr Ala Ile Ile Tyr Val Ala Ala Cys Ser Ser Tyr
225                 230                 235                 240
Asn Met Val Ile Arg Glu Asp Asn Thr Asn Arg Leu Arg Glu Ser
                245                 250                 255
Leu Asp Leu Phe Glu Ser Ile Trp Asn Asn Arg Trp Leu Arg Thr Ile
            260                 265                 270
Ser Ile Ile Leu Phe Leu Asn Lys Gln Asp Met Leu Ala Glu Lys Val
        275                 280                 285
Leu Ala Gly Lys Ser Lys Ile Glu Asp Tyr Phe Pro Glu Tyr Ala Asn
    290                 295                 300
Tyr Thr Val Pro Glu Asp Ala Thr Pro Asp Ala Gly Glu Asp Pro Lys
305                 310                 315                 320
Val Thr Arg Ala Lys Phe Phe Ile Arg Asp Leu Phe Leu Arg Ile Ser
                325                 330                 335
Thr Ala Thr Gly Asp Gly Lys His Tyr Cys Tyr Pro His Phe Thr Cys
            340                 345                 350
Ala Val Asp Thr Glu Asn Ile Arg Arg Val Phe Asn Asp Cys Arg Asp
        355                 360                 365
Ile Ile Gln Arg Met His Leu Lys Gln Tyr Glu Leu Leu
    370                 375                 380
```

<210> SEQ ID NO 19
<211> LENGTH: 354

```
<212> TYPE: PRT
<213> ORGANISM: Homo sapiens

<400> SEQUENCE: 19

Met Gly Cys Thr Leu Ser Ala Glu Asp Lys Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Ala Gly Tyr Ser Glu Glu
    50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
                100                 105                 110

Ala Ala Glu Glu Gly Phe Met Thr Ala Glu Leu Ala Gly Val Ile Lys
            115                 120                 125

Arg Leu Trp Lys Asp Ser Gly Val Gln Ala Cys Phe Asn Arg Ser Arg
130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
                195                 200                 205

Lys Lys Trp Ile His Cys Phe Glu Gly Val Thr Ala Ile Ile Phe Cys
210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Phe Thr Asp Thr Ser Ile Ile Leu Phe Leu Asn Lys Lys Asp
                260                 265                 270

Leu Phe Glu Glu Lys Ile Lys Lys Ser Pro Leu Thr Ile Cys Tyr Pro
            275                 280                 285

Glu Tyr Ala Gly Ser Asn Thr Tyr Glu Glu Ala Ala Ala Tyr Ile Gln
            290                 295                 300

Cys Gln Phe Glu Asp Leu Asn Lys Arg Lys Asp Thr Lys Glu Ile Tyr
305                 310                 315                 320

Thr His Phe Thr Cys Ala Thr Asp Thr Lys Asn Val Gln Phe Val Phe
                325                 330                 335

Asp Ala Val Thr Asp Val Ile Ile Lys Asn Asn Leu Lys Asp Cys Gly
            340                 345                 350

Leu Phe

<210> SEQ ID NO 20
<211> LENGTH: 355
<212> TYPE: PRT
<213> ORGANISM: Homo sapiens
```

<400> SEQUENCE: 20

| | | | | | | | | | | | | | | |
|---|---|---|---|---|---|---|---|---|---|---|---|---|---|---|
| Met | Gly | Cys | Thr | Val | Ser | Ala | Glu | Asp | Lys | Ala | Ala | Glu | Arg | Ser |
| 1 | | | | 5 | | | | | 10 | | | | | 15 |
| Lys | Met | Ile | Asp | Lys | Asn | Leu | Arg | Glu | Asp | Gly | Glu | Lys | Ala | Ala | Arg |
| | | | 20 | | | | | 25 | | | | | 30 | | |
| Glu | Val | Lys | Leu | Leu | Leu | Gly | Ala | Gly | Glu | Ser | Gly | Lys | Ser | Thr |
| | | 35 | | | | | 40 | | | | | 45 | | |
| Ile | Val | Lys | Gln | Met | Lys | Ile | Ile | His | Glu | Asp | Gly | Tyr | Ser | Glu | Glu |
| | 50 | | | | | 55 | | | | | 60 | | | | |
| Glu | Cys | Arg | Gln | Tyr | Arg | Ala | Val | Val | Tyr | Ser | Asn | Thr | Ile | Gln | Ser |
| 65 | | | | | 70 | | | | | 75 | | | | | 80 |
| Ile | Met | Ala | Ile | Val | Lys | Ala | Met | Gly | Asn | Leu | Gln | Ile | Asp | Phe | Ala |
| | | | | 85 | | | | | 90 | | | | | 95 | |
| Asp | Pro | Ser | Arg | Ala | Asp | Asp | Ala | Arg | Gln | Leu | Phe | Ala | Leu | Ser | Cys |
| | | | 100 | | | | | 105 | | | | | 110 | | |
| Thr | Ala | Glu | Glu | Gln | Gly | Val | Leu | Pro | Asp | Asp | Leu | Ser | Gly | Val | Ile |
| | | | 115 | | | | | 120 | | | | | 125 | | |
| Arg | Arg | Leu | Trp | Ala | Asp | His | Gly | Val | Gln | Ala | Cys | Phe | Gly | Arg | Ser |
| | 130 | | | | | 135 | | | | | 140 | | | | |
| Arg | Glu | Tyr | Gln | Leu | Asn | Asp | Ser | Ala | Ala | Tyr | Tyr | Leu | Asn | Asp | Leu |
| 145 | | | | | 150 | | | | | 155 | | | | | 160 |
| Glu | Arg | Ile | Ala | Gln | Ser | Asp | Tyr | Ile | Pro | Thr | Gln | Gln | Asp | Val | Leu |
| | | | | 165 | | | | | 170 | | | | | 175 | |
| Arg | Thr | Arg | Val | Lys | Thr | Thr | Gly | Ile | Val | Glu | Thr | His | Phe | Thr | Phe |
| | | | 180 | | | | | 185 | | | | | 190 | | |
| Lys | Asp | Leu | His | Phe | Lys | Met | Phe | Asp | Val | Gly | Gly | Gln | Arg | Ser | Glu |
| | | | 195 | | | | | 200 | | | | | 205 | | |
| Arg | Lys | Lys | Trp | Ile | His | Cys | Phe | Glu | Gly | Val | Thr | Ala | Ile | Ile | Phe |
| | 210 | | | | | 215 | | | | | 220 | | | | |
| Cys | Val | Ala | Leu | Ser | Ala | Tyr | Asp | Leu | Val | Leu | Ala | Glu | Asp | Glu | Glu |
| 225 | | | | | 230 | | | | | 235 | | | | | 240 |
| Met | Asn | Arg | Met | His | Glu | Ser | Met | Lys | Leu | Phe | Asp | Ser | Ile | Cys | Asn |
| | | | | 245 | | | | | 250 | | | | | 255 | |
| Asn | Lys | Trp | Phe | Thr | Asp | Thr | Ser | Ile | Ile | Leu | Phe | Leu | Asn | Lys | Lys |
| | | | 260 | | | | | 265 | | | | | 270 | | |
| Asp | Leu | Phe | Glu | Glu | Lys | Ile | Thr | His | Ser | Pro | Leu | Thr | Ile | Cys | Phe |
| | | | 275 | | | | | 280 | | | | | 285 | | |
| Pro | Glu | Tyr | Thr | Gly | Ala | Asn | Lys | Tyr | Asp | Glu | Ala | Ala | Ser | Tyr | Ile |
| | 290 | | | | | 295 | | | | | 300 | | | | |
| Gln | Ser | Lys | Phe | Glu | Asp | Leu | Asn | Lys | Arg | Lys | Asp | Thr | Lys | Glu | Ile |
| 305 | | | | | 310 | | | | | 315 | | | | | 320 |
| Tyr | Thr | His | Phe | Thr | Cys | Ala | Thr | Asp | Thr | Lys | Asn | Val | Gln | Phe | Val |
| | | | | 325 | | | | | 330 | | | | | 335 | |
| Phe | Asp | Ala | Val | Thr | Asp | Val | Ile | Ile | Lys | Asn | Asn | Leu | Lys | Asp | Cys |
| | | | 340 | | | | | 345 | | | | | 350 | | |
| Gly | Leu | Phe |
| | | 355 |

<210> SEQ ID NO 21
<211> LENGTH: 354
<212> TYPE: PRT
<213> ORGANISM: Homo sapiens

<400> SEQUENCE: 21

Met Gly Cys Thr Leu Ser Ala Glu Asp Lys Ala Val Glu Arg Ser
1               5                   10                  15

Lys Met Ile Asp Arg Asn Leu Arg Glu Asp Gly Glu Lys Ala Ala Lys
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Asp Gly Tyr Ser Glu Asp
    50                  55                  60

Glu Cys Lys Gln Tyr Lys Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Glu Ala Ala Arg Ala Asp Asp Ala Arg Gln Leu Phe Val Leu Ala Gly
            100                 105                 110

Ser Ala Glu Glu Gly Val Met Thr Pro Glu Leu Ala Gly Val Ile Lys
        115                 120                 125

Arg Leu Trp Arg Asp Gly Gly Val Gln Ala Cys Phe Ser Arg Ser Arg
    130                 135                 140

Glu Tyr Gln Leu Asn Asp Ser Ala Ser Tyr Tyr Leu Asn Asp Leu Asp
145                 150                 155                 160

Arg Ile Ser Gln Ser Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu Tyr Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
    210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Phe Thr Glu Thr Ser Ile Ile Leu Phe Leu Asn Lys Lys Asp
            260                 265                 270

Leu Phe Glu Glu Lys Ile Lys Arg Ser Pro Leu Thr Ile Cys Tyr Pro
        275                 280                 285

Glu Tyr Thr Gly Ser Asn Thr Tyr Glu Glu Ala Ala Ala Tyr Ile Gln
    290                 295                 300

Cys Gln Phe Glu Asp Leu Asn Arg Arg Lys Asp Thr Lys Glu Ile Tyr
305                 310                 315                 320

Thr His Phe Thr Cys Ala Thr Asp Thr Lys Asn Val Gln Phe Val Phe
                325                 330                 335

Asp Ala Val Thr Asp Val Ile Ile Lys Asn Asn Leu Lys Glu Cys Gly
            340                 345                 350

Leu Tyr

<210> SEQ ID NO 22
<211> LENGTH: 354
<212> TYPE: PRT
<213> ORGANISM: Homo sapiens

<400> SEQUENCE: 22

Met Gly Cys Thr Leu Ser Ala Glu Glu Arg Ala Ala Leu Glu Arg Ser
1               5                   10                  15

```
Lys Ala Ile Glu Lys Asn Leu Lys Glu Asp Gly Ile Ser Ala Ala Lys
             20                  25                  30

Asp Val Lys Leu Leu Leu Gly Ala Gly Glu Ser Gly Lys Ser Thr
             35                  40                  45

Ile Val Lys Gln Met Lys Ile Ile His Glu Asp Gly Phe Ser Gly Glu
 50                  55                  60

Asp Val Lys Gln Tyr Lys Pro Val Val Tyr Ser Asn Thr Ile Gln Ser
 65                  70                  75                  80

Leu Ala Ala Ile Val Arg Ala Met Asp Thr Leu Gly Ile Glu Tyr Gly
                 85                  90                  95

Asp Lys Glu Arg Lys Ala Asp Ala Lys Met Val Cys Asp Val Val Ser
             100                 105                 110

Arg Met Glu Asp Thr Glu Pro Phe Ser Ala Glu Leu Leu Ser Ala Met
             115                 120                 125

Met Arg Leu Trp Gly Asp Ser Gly Ile Gln Glu Cys Phe Asn Arg Ser
130                 135                 140

Arg Glu Tyr Gln Leu Asn Asp Ser Ala Lys Tyr Tyr Leu Asp Ser Leu
145                 150                 155                 160

Asp Arg Ile Gly Ala Ala Asp Tyr Gln Pro Thr Glu Gln Asp Ile Leu
                165                 170                 175

Arg Thr Arg Val Lys Thr Thr Gly Ile Val Glu Thr His Phe Thr Phe
             180                 185                 190

Lys Asn Leu His Phe Arg Leu Phe Asp Val Gly Gly Gln Arg Ser Glu
             195                 200                 205

Arg Lys Lys Trp Ile His Cys Phe Glu Asp Val Thr Ala Ile Ile Phe
 210                 215                 220

Cys Val Ala Leu Ser Gly Tyr Asp Gln Val Leu His Glu Asp Glu Thr
225                 230                 235                 240

Thr Asn Arg Met His Glu Ser Leu Met Leu Phe Asp Ser Ile Cys Asn
                245                 250                 255

Asn Lys Phe Phe Ile Asp Thr Ser Ile Ile Leu Phe Leu Asn Lys Lys
             260                 265                 270

Asp Leu Phe Gly Glu Lys Ile Lys Lys Ser Pro Leu Thr Ile Cys Phe
             275                 280                 285

Pro Glu Tyr Thr Gly Pro Asn Thr Tyr Glu Asp Ala Ala Ala Tyr Ile
290                 295                 300

Gln Ala Gln Phe Glu Ser Lys Asn Arg Ser Pro Asn Lys Glu Ile Tyr
305                 310                 315                 320

Cys His Met Thr Cys Ala Thr Asp Thr Asn Asn Ile Gln Val Val Phe
                325                 330                 335

Asp Ala Val Thr Asp Ile Ile Ile Ala Asn Asn Leu Arg Gly Cys Gly
             340                 345                 350

Leu Tyr

<210> SEQ ID NO 23
<211> LENGTH: 355
<212> TYPE: PRT
<213> ORGANISM: Homo sapiens

<400> SEQUENCE: 23

Met Gly Cys Thr Val Ser Ala Glu Asp Lys Ala Ala Ala Glu Arg Ser
 1               5                  10                  15

Lys Met Ile Asp Lys Asn Leu Arg Glu Asp Gly Glu Lys Ala Ala Arg
             20                  25                  30
```

```
Glu Val Lys Leu Leu Leu Gly Ala Gly Glu Ser Gly Lys Ser Thr
         35                  40                  45

Ile Val Lys Gln Met Lys Ile Ile His Glu Asp Gly Tyr Ser Glu
 50                  55                  60

Glu Cys Arg Gln Tyr Arg Ala Val Tyr Ser Asn Thr Ile Gln Ser
 65                  70                  75                  80

Ile Met Ala Ile Val Lys Ala Met Gly Asn Leu Gln Ile Asp Phe Ala
                 85                  90                  95

Asp Pro Ser Arg Ala Asp Asp Ala Arg Gln Leu Phe Ala Leu Ser Cys
                100                 105                 110

Thr Ala Glu Glu Gln Gly Val Leu Pro Asp Asp Leu Ser Gly Val Ile
            115                 120                 125

Arg Arg Leu Trp Ala Asp His Gly Val Gln Ala Cys Phe Gly Arg Ser
    130                 135                 140

Arg Glu Tyr Gln Leu Asn Asp Ser Ala Ala Tyr Tyr Leu Asn Asp Leu
145                 150                 155                 160

Glu Arg Ile Ala Gln Ser Asp Tyr Ile Pro Thr Gln Gln Asp Val Leu
                165                 170                 175

Arg Thr Arg Val Lys Thr Thr Gly Ile Val Glu Thr His Phe Thr Phe
            180                 185                 190

Lys Asp Leu His Phe Lys Met Phe Asp Val Gly Gly Gln Arg Ser Glu
    195                 200                 205

Arg Lys Lys Trp Ile His Cys Phe Glu Gly Val Thr Ala Ile Ile Phe
210                 215                 220

Cys Val Ala Leu Ser Ala Tyr Asp Leu Val Leu Ala Glu Asp Glu Glu
225                 230                 235                 240

Met Asn Arg Met His Glu Ser Met Lys Leu Phe Asp Ser Ile Cys Asn
                245                 250                 255

Asn Lys Trp Phe Thr Asp Thr Ser Ile Ile Leu Phe Leu Asn Lys Lys
            260                 265                 270

Asp Leu Phe Glu Glu Lys Ile Thr His Ser Pro Leu Thr Ile Cys Phe
    275                 280                 285

Pro Glu Tyr Thr Gly Ala Asn Lys Tyr Asp Glu Ala Ala Ser Tyr Ile
290                 295                 300

Gln Ser Lys Phe Glu Asp Leu Asn Lys Arg Lys Asp Thr Lys Glu Ile
305                 310                 315                 320

Tyr Thr His Phe Thr Cys Ala Thr Asp Thr Lys Asn Val Gln Phe Val
                325                 330                 335

Phe Asp Ala Val Thr Asp Val Ile Ile Lys Asn Asn Leu Lys Asp Cys
            340                 345                 350

Gly Leu Phe
        355

<210> SEQ ID NO 24
<211> LENGTH: 350
<212> TYPE: PRT
<213> ORGANISM: Homo sapiens

<400> SEQUENCE: 24

Met Gly Ala Gly Ala Ser Ala Glu Glu Lys His Ser Arg Glu Leu Glu
  1               5                  10                  15

Lys Lys Leu Lys Glu Asp Ala Glu Lys Asp Ala Arg Thr Val Lys Leu
                 20                  25                  30

Leu Leu Leu Gly Ala Gly Glu Ser Gly Lys Ser Thr Ile Val Lys Gln
            35                  40                  45
```

```
Met Lys Ile Ile His Gln Asp Gly Tyr Ser Leu Glu Glu Cys Leu Glu
 50                  55                  60

Phe Ile Ala Ile Tyr Gly Asn Thr Leu Gln Ser Ile Leu Ala Ile
 65                  70                  75                  80

Val Arg Ala Met Thr Thr Leu Asn Ile Gln Tyr Gly Asp Ser Ala Arg
                 85                  90                  95

Gln Asp Asp Ala Arg Lys Leu Met His Met Ala Asp Thr Ile Glu Glu
            100                 105                 110

Gly Thr Met Pro Lys Glu Met Ser Asp Ile Ile Gln Arg Leu Trp Lys
            115                 120                 125

Asp Ser Gly Ile Gln Ala Cys Phe Glu Arg Ala Ser Glu Tyr Gln Leu
        130                 135                 140

Asn Asp Ser Ala Gly Tyr Tyr Leu Ser Asp Leu Glu Arg Leu Val Thr
145                 150                 155                 160

Pro Gly Tyr Val Pro Thr Glu Gln Asp Val Leu Arg Ser Arg Val Lys
                165                 170                 175

Thr Thr Gly Ile Ile Glu Thr Gln Phe Ser Phe Lys Asp Leu Asn Phe
            180                 185                 190

Arg Met Phe Asp Val Gly Gly Gln Arg Ser Glu Arg Lys Lys Trp Ile
        195                 200                 205

His Cys Phe Glu Gly Val Thr Cys Ile Ile Phe Ile Ala Ala Leu Ser
        210                 215                 220

Ala Tyr Asp Met Val Leu Val Glu Asp Asp Glu Val Asn Arg Met His
225                 230                 235                 240

Glu Ser Leu His Leu Phe Asn Ser Ile Cys Asn His Arg Tyr Phe Ala
                245                 250                 255

Thr Thr Ser Ile Val Leu Phe Leu Asn Lys Lys Asp Val Phe Phe Glu
            260                 265                 270

Lys Ile Lys Lys Ala His Leu Ser Ile Cys Phe Pro Asp Tyr Asp Gly
        275                 280                 285

Pro Asn Thr Tyr Glu Asp Ala Gly Asn Tyr Ile Lys Val Gln Phe Leu
        290                 295                 300

Glu Leu Asn Met Arg Arg Asp Val Lys Glu Ile Tyr Ser His Met Thr
305                 310                 315                 320

Cys Ala Thr Asp Thr Gln Asn Val Lys Phe Val Phe Asp Ala Val Thr
                325                 330                 335

Asp Ile Ile Ile Lys Glu Asn Leu Lys Asp Cys Gly Leu Phe
            340                 345                 350

<210> SEQ ID NO 25
<211> LENGTH: 354
<212> TYPE: PRT
<213> ORGANISM: Homo sapiens

<400> SEQUENCE: 25

Met Gly Ser Gly Ala Ser Ala Glu Asp Lys Glu Leu Ala Lys Arg Ser
  1               5                  10                  15

Lys Glu Leu Glu Lys Lys Leu Gln Glu Asp Ala Asp Lys Glu Ala Lys
                 20                  25                  30

Thr Val Lys Leu Leu Leu Leu Gly Ala Gly Glu Ser Gly Lys Ser Thr
            35                  40                  45

Ile Val Lys Gln Met Lys Ile Ile His Gln Asp Gly Tyr Ser Pro Glu
        50                  55                  60

Glu Cys Leu Glu Phe Lys Ala Ile Ile Tyr Gly Asn Val Leu Gln Ser
```

-continued

```
                65                  70                  75                  80
Ile Leu Ala Ile Ile Arg Ala Met Thr Thr Leu Gly Ile Asp Tyr Ala
                        85                  90                  95

Glu Pro Ser Cys Ala Asp Asp Gly Arg Gln Leu Asn Asn Leu Ala Asp
                100                 105                 110

Ser Ile Glu Glu Gly Thr Met Pro Pro Glu Leu Val Glu Val Ile Arg
                115                 120                 125

Arg Leu Trp Lys Asp Gly Gly Val Gln Ala Cys Phe Glu Arg Ala Ala
                130                 135                 140

Glu Tyr Gln Leu Asn Asp Ser Ala Ser Tyr Tyr Leu Asn Gln Leu Glu
145                 150                 155                 160

Arg Ile Thr Asp Pro Glu Tyr Leu Pro Ser Glu Gln Asp Val Leu Arg
                165                 170                 175

Ser Arg Val Lys Thr Thr Gly Ile Ile Glu Thr Lys Phe Ser Val Lys
                180                 185                 190

Asp Leu Asn Phe Arg Met Phe Asp Val Gly Gly Gln Arg Ser Glu Arg
                195                 200                 205

Lys Lys Trp Ile His Cys Phe Glu Gly Val Thr Cys Ile Ile Phe Cys
210                 215                 220

Ala Ala Leu Ser Ala Tyr Asp Met Val Leu Val Glu Asp Asp Glu Val
225                 230                 235                 240

Asn Arg Met His Glu Ser Leu His Leu Phe Asn Ser Ile Cys Asn His
                245                 250                 255

Lys Phe Phe Ala Ala Thr Ser Ile Val Leu Phe Leu Asn Lys Lys Asp
                260                 265                 270

Leu Phe Glu Glu Lys Ile Lys Lys Val His Leu Ser Ile Cys Phe Pro
                275                 280                 285

Glu Tyr Asp Gly Asn Asn Ser Tyr Asp Asp Ala Gly Asn Tyr Ile Lys
                290                 295                 300

Ser Gln Phe Leu Asp Leu Asn Met Arg Lys Asp Val Lys Glu Ile Tyr
305                 310                 315                 320

Ser His Met Thr Cys Ala Thr Asp Thr Gln Asn Val Lys Phe Val Phe
                325                 330                 335

Asp Ala Val Thr Asp Ile Ile Ile Lys Glu Asn Leu Lys Asp Cys Gly
                340                 345                 350

Leu Phe
```

<210> SEQ ID NO 26
<211> LENGTH: 466
<212> TYPE: PRT
<213> ORGANISM: Homo sapiens

<400> SEQUENCE: 26

```
Met Val Phe Leu Ser Gly Asn Ala Ser Asp Ser Ser Asn Cys Thr Gln
1               5                   10                  15

Pro Pro Ala Pro Val Asn Ile Ser Lys Ala Ile Leu Leu Gly Val Ile
                20                  25                  30

Leu Gly Gly Leu Ile Leu Phe Gly Val Leu Gly Asn Ile Leu Val Ile
                35                  40                  45

Leu Ser Val Ala Cys His Arg His Leu His Ser Val Thr His Tyr Tyr
                50                  55                  60

Ile Val Asn Leu Ala Val Ala Asp Leu Leu Leu Thr Ser Thr Val Leu
65                  70                  75                  80

Pro Phe Ser Ala Ile Phe Glu Val Leu Gly Tyr Trp Ala Phe Gly Arg
```

```
                      85                  90                  95
Val Phe Cys Asn Ile Trp Ala Ala Val Asp Val Leu Cys Cys Thr Ala
                100                 105                 110
Ser Ile Met Gly Leu Cys Ile Ile Ser Ile Asp Arg Tyr Ile Gly Val
                115                 120                 125
Ser His Pro Leu Arg Tyr Pro Thr Ile Val Thr Gln Arg Arg Gly Leu
            130                 135                 140
Met Ala Leu Leu Cys Val Trp Ala Leu Ser Leu Val Ile Ser Ile Gly
145                 150                 155                 160
Pro Leu Phe Gly Trp Arg Gln Pro Ala Pro Glu Asp Glu Thr Ile Cys
                165                 170                 175
Gln Ile Asn Glu Glu Pro Gly Tyr Val Leu Phe Ser Ala Leu Gly Ser
                180                 185                 190
Phe Tyr Leu Pro Leu Ala Ile Ile Leu Val Met Tyr Cys Arg Val Tyr
            195                 200                 205
Val Val Ala Lys Arg Glu Ser Arg Gly Leu Lys Ser Gly Leu Lys Thr
            210                 215                 220
Asp Lys Ser Asp Ser Glu Gln Val Thr Leu Arg Ile His Arg Lys Asn
225                 230                 235                 240
Ala Pro Ala Gly Gly Ser Gly Met Ala Ser Ala Lys Thr Lys Thr His
                245                 250                 255
Phe Ser Val Arg Leu Leu Lys Phe Ser Arg Glu Lys Lys Ala Ala Lys
                260                 265                 270
Thr Leu Gly Ile Val Val Gly Cys Phe Val Leu Cys Trp Leu Pro Phe
            275                 280                 285
Phe Leu Val Met Pro Ile Gly Ser Phe Phe Pro Asp Phe Lys Pro Ser
290                 295                 300
Glu Thr Val Phe Lys Ile Val Phe Trp Leu Gly Tyr Leu Asn Ser Cys
305                 310                 315                 320
Ile Asn Pro Ile Ile Tyr Pro Cys Ser Ser Gln Glu Phe Lys Lys Ala
                325                 330                 335
Phe Gln Asn Val Leu Arg Ile Gln Cys Leu Cys Arg Lys Gln Ser Ser
            340                 345                 350
Lys His Ala Leu Gly Tyr Thr Leu His Pro Pro Ser Gln Ala Val Glu
            355                 360                 365
Gly Gln His Lys Asp Met Val Arg Ile Pro Val Gly Ser Arg Glu Ala
            370                 375                 380
Phe Tyr Gly Ile Ser Arg Thr Asp Gly Val Cys Glu Trp Lys Phe Phe
385                 390                 395                 400
Ser Ser Met Pro Arg Gly Ser Ala Arg Ile Thr Val Ser Lys Asp Gln
                405                 410                 415
Ser Ser Cys Thr Thr Ala Arg Val Arg Ser Lys Ser Phe Leu Gln Val
            420                 425                 430
Cys Cys Cys Val Glu Pro Ser Thr Pro Ser Leu Asp Lys Asn His Gln
        435                 440                 445
Val Pro Thr Ile Lys Val His Thr Ile Ser Leu Ser Glu Asn Gly Glu
    450                 455                 460
Glu Val
465

<210> SEQ ID NO 27
<211> LENGTH: 353
<212> TYPE: PRT
<213> ORGANISM: Homo sapiens
```

<400> SEQUENCE: 27

Met Ala Cys Cys Leu Ser Glu Glu Ala Lys Glu Ala Arg Arg Ile Asn
1               5                   10                  15

Asp Glu Ile Glu Arg Gln Leu Arg Arg Asp Lys Arg Asp Ala Arg Arg
            20                  25                  30

Glu Leu Lys Leu Leu Leu Gly Thr Gly Glu Ser Gly Lys Ser Thr
        35                  40                  45

Phe Ile Lys Gln Met Arg Ile Ile His Gly Ser Gly Tyr Ser Asp Glu
    50                  55                  60

Asp Lys Arg Gly Phe Thr Lys Leu Val Tyr Gln Asn Ile Phe Thr Ala
65                  70                  75                  80

Met Gln Ala Met Ile Arg Ala Met Asp Thr Leu Lys Ile Pro Tyr Lys
                85                  90                  95

Tyr Glu His Asn Lys Ala His Ala Gln Leu Val Arg Glu Val Asp Val
                100                 105                 110

Glu Lys Val Ser Ala Phe Glu Asn Pro Tyr Val Asp Ala Ile Lys Ser
            115                 120                 125

Leu Trp Asn Asp Pro Gly Ile Gln Glu Cys Tyr Asp Arg Arg Arg Glu
130                 135                 140

Tyr Gln Leu Ser Asp Ser Thr Lys Tyr Tyr Leu Asn Asp Leu Asp Arg
145                 150                 155                 160

Val Ala Asp Pro Ala Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
            180                 185                 190

Val Ile Phe Arg Met Val Asp Val Gly Gly Gln Arg Ser Glu Arg Arg
    195                 200                 205

Lys Trp Ile His Cys Phe Glu Asn Val Thr Ser Ile Met Phe Leu Val
210                 215                 220

Ala Leu Ser Glu Tyr Asp Gln Val Leu Val Glu Ser Asp Asn Glu Asn
225                 230                 235                 240

Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
            260                 265                 270

Leu Glu Glu Lys Ile Met Tyr Ser His Leu Val Asp Tyr Phe Pro Glu
        275                 280                 285

Tyr Asp Gly Pro Gln Arg Asp Ala Gln Ala Ala Arg Glu Phe Ile Leu
290                 295                 300

Lys Met Phe Val Asp Leu Asn Pro Asp Ser Asp Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Glu Tyr Asn Ala
            340                 345                 350

Val

<210> SEQ ID NO 28
<211> LENGTH: 359
<212> TYPE: PRT
<213> ORGANISM: Homo sapiens

<400> SEQUENCE: 28

```
Met Thr Leu Glu Ser Met Met Ala Cys Cys Leu Ser Asp Glu Val Lys
  1               5                  10                  15

Glu Ser Lys Arg Ile Asn Ala Glu Ile Glu Lys Gln Leu Arg Arg Asp
             20                  25                  30

Lys Arg Asp Ala Arg Arg Glu Leu Lys Leu Leu Leu Gly Thr Gly
         35                  40                  45

Glu Ser Gly Lys Ser Thr Phe Ile Lys Gln Met Arg Ile Ile His Gly
     50                  55                  60

Ala Gly Tyr Ser Glu Glu Asp Lys Arg Gly Phe Thr Lys Leu Val Tyr
 65              70                  75                  80

Gln Asn Ile Phe Thr Ala Met Gln Ala Met Ile Arg Ala Met Glu Thr
                 85                  90                  95

Leu Lys Ile Leu Tyr Lys Tyr Glu Gln Asn Lys Ala Asn Ala Leu Leu
                100                 105                 110

Ile Arg Glu Val Asp Val Glu Lys Val Thr Thr Phe Glu His Gln Tyr
            115                 120                 125

Val Ser Ala Ile Lys Thr Leu Trp Glu Asp Pro Gly Ile Gln Glu Cys
130                 135                 140

Tyr Asp Arg Arg Arg Glu Tyr Gln Leu Ser Asp Ser Ala Lys Tyr Tyr
145                 150                 155                 160

Leu Thr Asp Val Asp Arg Ile Ala Thr Leu Gly Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Glu Asn Ile Ile Phe Arg Met Val Asp Val Gly Gly
        195                 200                 205

Gln Arg Ser Glu Arg Arg Lys Trp Ile His Cys Phe Glu Asn Val Thr
210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Asp Lys Ile Leu Tyr Ser His Leu
        275                 280                 285

Val Asp Tyr Phe Pro Glu Phe Asp Gly Pro Gln Arg Asp Ala Gln Ala
290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
            340                 345                 350

Leu Lys Glu Tyr Asn Leu Val
        355

<210> SEQ ID NO 29
<211> LENGTH: 381
<212> TYPE: PRT
<213> ORGANISM: Homo sapiens

<400> SEQUENCE: 29

Met Ser Gly Val Val Arg Thr Leu Ser Arg Cys Leu Leu Pro Ala Glu
  1               5                  10                  15
```

```
Ala Gly Gly Ala Arg Glu Arg Ala Gly Gly Ala Arg Asp Ala
             20                  25                  30

Glu Arg Glu Ala Arg Arg Ser Arg Asp Ile Asp Ala Leu Leu Ala
         35                  40                  45

Arg Glu Arg Arg Ala Val Arg Arg Leu Val Lys Ile Leu Leu Gly
         50                  55                  60

Ala Gly Glu Ser Gly Lys Ser Thr Phe Leu Lys Gln Met Arg Ile Ile
 65                  70                  75                  80

His Gly Arg Glu Phe Asp Gln Lys Ala Leu Leu Glu Phe Arg Asp Thr
                 85                  90                  95

Ile Phe Asp Asn Ile Leu Lys Gly Ser Arg Val Leu Val Asp Ala Arg
                100                 105                 110

Asp Lys Leu Gly Ile Pro Trp Gln Tyr Ser Glu Asn Glu Lys His Gly
             115                 120                 125

Met Phe Leu Met Ala Phe Glu Asn Lys Ala Gly Leu Pro Val Glu Pro
         130                 135                 140

Ala Thr Phe Gln Leu Tyr Val Pro Ala Leu Ser Ala Leu Trp Arg Asp
145                 150                 155                 160

Ser Gly Ile Arg Glu Ala Phe Ser Arg Ser Glu Phe Gln Leu Gly
                 165                 170                 175

Glu Ser Val Lys Tyr Phe Leu Asp Asn Leu Asp Arg Ile Gly Gln Leu
             180                 185                 190

Asn Tyr Phe Pro Ser Lys Gln Asp Ile Leu Leu Ala Arg Lys Ala Thr
         195                 200                 205

Lys Gly Ile Val Glu His Asp Phe Val Ile Lys Ile Pro Phe Lys
     210                 215                 220

Met Val Asp Val Gly Gly Gln Arg Ser Gln Arg Gln Lys Trp Phe Gln
225                 230                 235                 240

Cys Phe Asp Gly Ile Thr Ser Ile Leu Phe Met Val Ser Ser Ser Glu
                 245                 250                 255

Tyr Asp Gln Val Leu Met Glu Asp Arg Arg Thr Asn Arg Leu Val Glu
             260                 265                 270

Ser Met Asn Ile Phe Glu Thr Ile Val Asn Asn Lys Leu Phe Phe Asn
         275                 280                 285

Val Ser Ile Ile Leu Phe Leu Asn Lys Met Asp Leu Leu Val Glu Lys
     290                 295                 300

Val Lys Thr Val Ser Ile Lys Lys His Phe Pro Asp Phe Arg Gly Asp
305                 310                 315                 320

Pro His Gln Leu Glu Asp Val Gln Arg Tyr Leu Val Gln Cys Phe Asp
                 325                 330                 335

Arg Lys Arg Arg Asn Arg Ser Lys Pro Leu Phe His His Phe Thr Thr
             340                 345                 350

Ala Ile Asp Thr Glu Asn Val Arg Phe Val Phe His Ala Val Lys Asp
         355                 360                 365

Thr Ile Leu Gln Glu Asn Leu Lys Asp Ile Met Leu Gln
     370                 375                 380

<210> SEQ ID NO 30
<211> LENGTH: 377
<212> TYPE: PRT
<213> ORGANISM: Homo sapiens

<400> SEQUENCE: 30

Met Ala Asp Phe Leu Pro Ser Arg Ser Val Leu Ser Val Cys Phe Pro
```

```
              1               5               10              15
    Gly Cys Leu Leu Thr Ser Gly Glu Ala Glu Gln Gln Arg Lys Ser Lys
                        20                  25                  30
    Glu Ile Asp Lys Cys Leu Ser Arg Glu Lys Thr Tyr Val Lys Arg Leu
                    35                  40                  45
    Val Lys Ile Leu Leu Gly Ala Gly Glu Ser Gly Lys Ser Thr Phe
                 50                  55                  60
    Leu Lys Gln Met Arg Ile Ile His Gly Gln Asp Phe Asp Gln Arg Ala
     65                  70                  75                  80
    Arg Glu Glu Phe Arg Pro Thr Ile Tyr Ser Asn Val Ile Lys Gly Met
                        85                  90                  95
    Arg Val Leu Val Asp Ala Arg Glu Lys Leu His Ile Pro Trp Gly Asp
                    100                 105                 110
    Asn Ser Asn Gln Gln His Gly Asp Lys Met Met Ser Phe Asp Thr Arg
                 115                 120                 125
    Ala Pro Met Ala Ala Gln Gly Met Val Glu Thr Arg Val Phe Leu Gln
        130                 135                 140
    Tyr Leu Pro Ala Ile Arg Ala Leu Trp Ala Asp Ser Gly Ile Gln Asn
    145                 150                 155                 160
    Ala Tyr Asp Arg Arg Arg Glu Phe Gln Leu Gly Glu Ser Val Lys Tyr
                        165                 170                 175
    Phe Leu Asp Asn Leu Asp Lys Leu Gly Glu Pro Asp Tyr Ile Pro Ser
                    180                 185                 190
    Gln Gln Asp Ile Leu Leu Ala Arg Arg Pro Thr Lys Gly Ile His Glu
                 195                 200                 205
    Tyr Asp Phe Glu Ile Lys Asn Val Pro Phe Lys Met Leu Asp Val Gly
        210                 215                 220
    Gly Gln Arg Ser Glu Arg Lys Arg Trp Phe Glu Cys Phe Asp Ser Val
    225                 230                 235                 240
    Thr Ser Ile Leu Phe Leu Val Ser Ser Ser Glu Phe Asp Gln Val Leu
                        245                 250                 255
    Met Glu Asp Arg Leu Thr Asn Arg Leu Thr Glu Ser Leu Asn Ile Phe
                    260                 265                 270
    Glu Thr Ile Val Asn Asn Arg Val Phe Ser Asn Val Ser Ile Ile Leu
                 275                 280                 285
    Phe Leu Asn Lys Thr Asp Leu Leu Glu Glu Lys Val Gln Ile Val Ser
        290                 295                 300
    Ile Lys Asp Tyr Phe Leu Glu Phe Glu Gly Asp Pro His Cys Leu Arg
    305                 310                 315                 320
    Asp Val Gln Lys Phe Leu Val Glu Cys Phe Arg Asn Lys Arg Arg Asp
                        325                 330                 335
    Gln Gln Gln Lys Pro Leu Tyr His His Phe Thr Thr Ala Ile Asn Thr
                    340                 345                 350
    Glu Asn Ile Arg Leu Val Phe Arg Asp Val Lys Asp Thr Ile Leu His
                 355                 360                 365
    Asp Asn Leu Lys Gln Leu Met Leu Gln
        370                 375

<210> SEQ ID NO 31
<211> LENGTH: 355
<212> TYPE: PRT
<213> ORGANISM: Homo sapiens

<400> SEQUENCE: 31
```

```
Met Ala Gly Cys Cys Cys Leu Ser Ala Glu Glu Lys Glu Ser Gln Arg
 1               5                  10                  15

Ile Ser Ala Glu Ile Glu Arg Gln Leu Arg Arg Asp Lys Lys Asp Ala
                 20                  25                  30

Arg Arg Glu Leu Lys Leu Leu Leu Gly Thr Gly Glu Ser Gly Lys
             35                  40                  45

Ser Thr Phe Ile Lys Gln Met Arg Ile Ile His Gly Ser Gly Tyr Ser
         50                  55                  60

Asp Glu Asp Arg Lys Gly Phe Thr Lys Leu Val Tyr Gln Asn Ile Phe
 65                  70                  75                  80

Thr Ala Met Gln Ala Met Ile Arg Ala Met Asp Thr Leu Arg Ile Gln
                 85                  90                  95

Tyr Val Cys Glu Gln Asn Lys Glu Asn Ala Gln Ile Ile Arg Glu Val
             100                 105                 110

Glu Val Asp Lys Val Ser Met Leu Ser Arg Glu Gln Val Glu Ala Ile
         115                 120                 125

Lys Gln Leu Trp Gln Asp Pro Gly Ile Gln Glu Cys Tyr Asp Arg Arg
130                 135                 140

Arg Glu Tyr Gln Leu Ser Asp Ser Ala Lys Tyr Tyr Leu Thr Asp Ile
145                 150                 155                 160

Asp Arg Ile Ala Thr Pro Ser Phe Val Pro Thr Gln Asp Val Leu
                 165                 170                 175

Arg Val Arg Val Pro Thr Thr Gly Ile Ile Glu Tyr Pro Phe Asp Leu
             180                 185                 190

Glu Asn Ile Ile Phe Arg Met Val Asp Val Gly Gly Gln Arg Ser Glu
         195                 200                 205

Arg Arg Lys Trp Ile His Cys Phe Glu Ser Val Thr Ser Ile Ile Phe
210                 215                 220

Leu Val Ala Leu Ser Glu Tyr Asp Gln Val Leu Ala Glu Cys Asp Asn
225                 230                 235                 240

Glu Asn Arg Met Glu Glu Ser Lys Ala Leu Phe Lys Thr Ile Ile Thr
                 245                 250                 255

Tyr Pro Trp Phe Leu Asn Ser Ser Val Ile Leu Phe Leu Asn Lys Lys
             260                 265                 270

Asp Leu Leu Glu Glu Lys Ile Met Tyr Ser His Leu Ile Ser Tyr Phe
         275                 280                 285

Pro Glu Tyr Thr Gly Pro Lys Gln Asp Val Arg Ala Ala Arg Asp Phe
290                 295                 300

Ile Leu Lys Leu Tyr Gln Asp Gln Asn Pro Asp Lys Glu Lys Val Ile
305                 310                 315                 320

Tyr Ser His Phe Thr Cys Ala Thr Asp Thr Asn Ile Arg Phe Val
                 325                 330                 335

Phe Ala Ala Val Lys Asp Thr Ile Leu Gln Leu Asn Leu Arg Glu Phe
             340                 345                 350

Asn Leu Val
         355

<210> SEQ ID NO 32
<211> LENGTH: 374
<212> TYPE: PRT
<213> ORGANISM: Homo sapiens

<400> SEQUENCE: 32

Met Ala Arg Ser Leu Thr Trp Arg Cys Cys Pro Trp Cys Leu Thr Glu
 1               5                  10                  15
```

```
Asp Glu Lys Ala Ala Arg Val Asp Gln Glu Ile Asn Arg Ile Leu
         20                  25                  30

Leu Glu Gln Lys Lys Gln Asp Arg Gly Glu Leu Lys Leu Leu Leu
         35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
             100                 105                 110

Ala Ser Leu Val Met Ser Gln Asp Pro Tyr Lys Val Thr Thr Phe Glu
             115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
            290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Gln Asn Ile
            340                 345                 350

Arg Lys Val Phe Lys Asp Val Arg Asp Ser Val Leu Ala Arg Tyr Leu
            355                 360                 365

Asp Glu Ile Asn Leu Leu
    370

<210> SEQ ID NO 33
<211> LENGTH: 157
<212> TYPE: PRT
<213> ORGANISM: Homo sapiens

<400> SEQUENCE: 33

Met Phe Asp Val Gly Gly Gln Arg Ser Glu Arg Lys Lys Trp Ile His
```

```
                1               5                   10                  15
            Cys Phe Glu Gly Val Thr Cys Ile Ile Phe Cys Ala Ala Leu Ser Ala
                            20                  25                  30

Tyr Asp Met Val Leu Val Glu Asp Glu Val Asn Arg Met His Glu
                        35                  40                  45

Ser Leu His Leu Phe Asn Ser Ile Cys Asn His Lys Tyr Phe Ser Thr
                50                  55                  60

Thr Ser Ile Val Leu Phe Leu Asn Lys Lys Asp Ile Phe Gln Glu Lys
            65                  70                  75                  80

Val Thr Lys Val His Leu Ser Ile Cys Phe Pro Glu Tyr Thr Gly Pro
                            85                  90                  95

Asn Thr Phe Glu Asp Ala Gly Asn Tyr Ile Lys Asn Gln Phe Leu Asp
                        100                 105                 110

Leu Asn Leu Lys Lys Glu Asp Lys Glu Ile Tyr Ser His Met Thr Cys
                        115                 120                 125

Ala Thr Asp Thr Gln Asn Val Lys Phe Val Phe Asp Ala Val Thr Asp
                    130                 135                 140

Ile Ile Ile Lys Glu Asn Leu Lys Asp Cys Gly Leu Phe
            145                 150                 155

<210> SEQ ID NO 34
<211> LENGTH: 75
<212> TYPE: RNA
<213> ORGANISM: Artificial Sequence
<220> FEATURE:
<223> OTHER INFORMATION: Description of Artificial Sequence:
      cAMP-Hammerhead RNA sequence

<400> SEQUENCE: 34
gggcgacccu gaugagccug uggaaacaga cguggcacau gacuacgucg aaacggugaa      60
agccguaggu ugccc                                                      75

<210> SEQ ID NO 35
<211> LENGTH: 75
<212> TYPE: RNA
<213> ORGANISM: Artificial Sequence
<220> FEATURE:
<223> OTHER INFORMATION: Description of Artificial Sequence:
      cGMP-Hammerhead RNA sequence

<400> SEQUENCE: 35
gggcgacccu gaugagcccu gcgaugcaga aaggugcuga cgacacaucg aaacggugaa      60
agccguaggu ugccc                                                      75

<210> SEQ ID NO 36
<211> LENGTH: 164
<212> TYPE: DNA
<213> ORGANISM: Artificial Sequence
<220> FEATURE:
<223> OTHER INFORMATION: Description of Artificial Sequence: Template
      for randomized sequence
<220> FEATURE:
<221> NAME/KEY: misc_feature
<222> LOCATION: (23)
<223> OTHER INFORMATION: Wherein n is t or a or c or g.
<220> FEATURE:
<221> NAME/KEY: misc_feature
<222> LOCATION: (36)
<223> OTHER INFORMATION: Wherein n is a or t or a or c or g.
<220> FEATURE:
<221> NAME/KEY: misc_feature
<222> LOCATION: (42)
<223> OTHER INFORMATION: Wherein n is t or a or c or g.
```

```
<220> FEATURE:
<221> NAME/KEY: misc_feature
<222> LOCATION: (55)..(56)
<223> OTHER INFORMATION: Wherein n is t or a or c or g.
<220> FEATURE:
<221> NAME/KEY: misc_feature
<222> LOCATION: (58)
<223> OTHER INFORMATION: Wherein n is t or a or c or g.
<220> FEATURE:
<221> NAME/KEY: misc_feature
<222> LOCATION: (63)
<223> OTHER INFORMATION: Wherein n is t or a or c or g.
<220> FEATURE:
<221> NAME/KEY: misc_feature
<222> LOCATION: (69)..(118)
<223> OTHER INFORMATION: Wherein n is an a or u or c or g and some may
      be missing.

<400> SEQUENCE: 36
ggagttacct aacaagaaac agngaagtca accagngaaa cncacggaga cgtgnnanat      60
tanctggtnn nnnnnnnnnn nnnnnnnnnn nnnnnnnnnn nnnnnnnnnn nnnnnnnngg     120
acctactgag ctgacagtcc tgtttgatgc ataccgagta agtg                     164

<210> SEQ ID NO 37
<211> LENGTH: 131
<212> TYPE: RNA
<213> ORGANISM: Artificial Sequence
<220> FEATURE:
<223> OTHER INFORMATION: Description of Artificial Sequence: CW45-33-D02
      ERK specific nucleic acid sensor molecule

<400> SEQUENCE: 37
ggacuucggc gaaagccguu cgacccuacu cagacgcuag cgaauugguu ccucgaaagg      60
gaaagcguua uuaagaaacc aaaaugaggg cuuagacagg agguuaggug cgucaaugcu     120
gcaaguuacu g                                                         131

<210> SEQ ID NO 38
<211> LENGTH: 132
<212> TYPE: RNA
<213> ORGANISM: Artificial Sequence
<220> FEATURE:
<223> OTHER INFORMATION: Description of Artificial Sequence: CW45-33-D05
      ERK specific nucleic acid sensor molecule

<400> SEQUENCE: 38
ggacuucggc gaaagccguu cgaccuucuc agacgcuagc gaauugguuc cucgaaaggg      60
aaagcguuau uaagaaacca aaaugaguaa gcuuagacag gagguuaggu gcgucaaugc     120
ugcaaguuac ug                                                        132

<210> SEQ ID NO 39
<211> LENGTH: 133
<212> TYPE: RNA
<213> ORGANISM: Artificial Sequence
<220> FEATURE:
<223> OTHER INFORMATION: Description of Artificial Sequence: CW45-33-E01

<400> SEQUENCE: 39
ggacuucggc gaaagccguu cgacccgcag cagacgcuag cgaauugguu ccucgaaagg      60
gaaagcguua uuaagaaacc aaaaugcggu ggcuuagaca ggagguuagg ugcgucaaug     120
cugcaaguua cug                                                       133

<210> SEQ ID NO 40
<211> LENGTH: 95
```

```
<210> SEQ ID NO 40 (implied continuation)
<212> TYPE: RNA
<213> ORGANISM: Artificial Sequence
<220> FEATURE:
<223> OTHER INFORMATION: Description of Artificial Sequence: cCMP
      nucleic acid sensor molecule

<400> SEQUENCE: 40
ggacccugau gagccuuuag ggccaagugu ggugaaagac acacgucgaa acggugaaag      60
ccguaggucc uugcgugguu cguucccuu cuucg                                  95

<210> SEQ ID NO 41
<211> LENGTH: 94
<212> TYPE: RNA
<213> ORGANISM: Artificial Sequence
<220> FEATURE:
<223> OTHER INFORMATION: Description of Artificial Sequence: cAMP
      nucleic acid sensor molecule

<400> SEQUENCE: 41
ggacccugau gagccugugg aaacagacgu ggcacaugac uacgucgaaa cggugaaagc      60
cguagguccu ugcgugguuc uguucccuuc uucg                                  94

<210> SEQ ID NO 42
<211> LENGTH: 94
<212> TYPE: RNA
<213> ORGANISM: Artificial Sequence
<220> FEATURE:
<223> OTHER INFORMATION: Description of Artificial Sequence: cGMP
      nucleic acid sensor molecule

<400> SEQUENCE: 42
ggacccugau gagccuugcg augcaaaaag gugcugacga cacaucgaaa cggugaaagc      60
cguagguccu ugcgugguuc uguucccuuc uucg                                  94

<210> SEQ ID NO 43
<211> LENGTH: 24
<212> TYPE: RNA
<213> ORGANISM: Artificial Sequence
<220> FEATURE:
<223> OTHER INFORMATION: Description of Artificial Sequence: Capture
      oligo

<400> SEQUENCE: 43
acgcaccaag acaagggaag aagc                                             24

<210> SEQ ID NO 44
<211> LENGTH: 133
<212> TYPE: RNA
<213> ORGANISM: Artificial Sequence
<220> FEATURE:
<223> OTHER INFORMATION: Description of Artificial Sequence: CW45-33-A02
      ppERK nucleic acid sensor molecule

<400> SEQUENCE: 44
ggacuucggc gaaagccguu cgaccgguug cagacgcuag cgaauugguu ccucgaaagg      60
gaaagcguua uuaagaaacc aaaauggaac cgcuuagaca ggagguuagg ugcgucaaug     120
cugcaaguua cug                                                        133

<210> SEQ ID NO 45
<211> LENGTH: 133
<212> TYPE: RNA
<213> ORGANISM: Artificial Sequence
<220> FEATURE:
<223> OTHER INFORMATION: Description of Artificial Sequence:
```

CW-45-33-B04 ppERK nucleic acid sensor molecule

<400> SEQUENCE: 45
ggacuucggc gaaagccguu cgaccgguug cagacgcuag cgaauugguu ccucgaaagg      60
gaaagcguua uuaagaaacc aaaaugugau cgcuuagaca ggagguuagg ugcgucaaug     120
cugcaaguua cug                                                        133

<210> SEQ ID NO 46
<211> LENGTH: 96
<212> TYPE: RNA
<213> ORGANISM: Artificial Sequence
<220> FEATURE:
<223> OTHER INFORMATION: Description of Artificial Sequence: Nucleic
      acid sensor precursor molecule

<400> SEQUENCE: 46
ggcgugaccu gaugagucac gcagacgcua gcgaauuggu uccucaaagg gggaaagcgu      60
uauuaagaaa ccaaaaugug uuuacgaaac guuccc                               96

<210> SEQ ID NO 47
<211> LENGTH: 108
<212> TYPE: RNA
<213> ORGANISM: Artificial Sequence
<220> FEATURE:
<223> OTHER INFORMATION: Description of Artificial Sequence: Nucleic
      acid sensor precursor molecule

<400> SEQUENCE: 47
ggacuucggu ccagugcucg ugcacuaggc cguucgacca ugauaccagc aucgucuuga      60
ugcccuuggc agcaucuuag acaggagguu aggugccucg ugaugcc                   108

<210> SEQ ID NO 48
<211> LENGTH: 79
<212> TYPE: RNA
<213> ORGANISM: Artificial Sequence
<220> FEATURE:
<223> OTHER INFORMATION: Description of Artificial Sequence: Nucleic
      acid sensor precursor molecule

<400> SEQUENCE: 48
gggcgacccu gaugagccug gauaccaagc cgaaaggccc uuggcaguua gacgaaacgg      60
ugaaagccgu agguugccc                                                  79

<210> SEQ ID NO 49
<211> LENGTH: 34
<212> TYPE: RNA
<213> ORGANISM: Artificial Sequence
<220> FEATURE:
<223> OTHER INFORMATION: Description of Artificial Sequence: Nucleic
      acid sensor molecule
<220> FEATURE:
<221> NAME/KEY: misc_feature
<222> LOCATION: (1)
<223> OTHER INFORMATION: First signaling moiety.
<220> FEATURE:
<221> NAME/KEY: misc_feature
<222> LOCATION: (34)
<223> OTHER INFORMATION: Second signaling moiety.

<400> SEQUENCE: 49
nauaccaagc cgaaaggccc uuggcagugg uaun                                 34

<210> SEQ ID NO 50
<211> LENGTH: 21

-continued

```
<212> TYPE: DNA
<213> ORGANISM: Artificial Sequence
<220> FEATURE:
<223> OTHER INFORMATION: Description of Artificial Sequence: Thrombin
      nucleic acid sensor molecule

<400> SEQUENCE: 50
ccaaccggtt ggtgtggttg g                                            21

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Target
      molecule

<400> SEQUENCE: 51
gcgactggac atcacgag                                                18

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: PKA peptide

<400> SEQUENCE: 52

Leu Arg Ala Ser Leu Gly
 1               5

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: PKC peptide

<400> SEQUENCE: 53

Ala Ala Lys Ile Gln Ala Ser Phe Arg Gly His Met Ala Arg Lys Lys
 1               5                  10                  15

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: cdc2
      peptide

<400> SEQUENCE: 54

Pro Lys Thr Pro Lys Lys Ala Lys Lys Leu
 1               5                  10

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: DNA-PK
      peptide

<400> SEQUENCE: 55

Glu Pro Pro Leu Ser Gln Glu Ala Phe Ala Asp Leu Trp Lys Lys
 1               5                  10                  15

<210> SEQ ID NO 56
```

```
<211> LENGTH: 10
<212> TYPE: PRT
<213> ORGANISM: Artificial Sequence
<220> FEATURE:
<223> OTHER INFORMATION: Description of Artificial Sequence: CK-1
      peptide

<400> SEQUENCE: 56

Asp Asp Asp Glu Glu Ser Ile Thr Arg Arg
  1               5                  10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: CK-2
      peptide

<400> SEQUENCE: 57

Arg Arg Arg Glu Glu Glu Thr Glu Glu Glu
  1               5                  10

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Cam KII
      peptide

<400> SEQUENCE: 58

Lys Lys Ala Leu Arg Arg Gln Glu Thr Val Asp Ala Leu
  1               5                  10

<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: p38 peptide

<400> SEQUENCE: 59

Ser Thr Lys Val Pro Gln Thr Pro Leu His Thr Ser Arg Val
  1               5                  10

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: PKA peptide

<400> SEQUENCE: 60

Arg Arg Arg Arg Ser Ile Ile Phe Ile
  1               5

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence: PKA alpha
      peptide

<400> SEQUENCE: 61

Arg Arg Arg Arg Arg Lys Gly Ser Phe Arg Arg Lys Ala
  1               5                  10
```

```
<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: PKC beta
      I, II peptide

<400> SEQUENCE: 62

Arg Lys Leu Lys Arg Lys Gly Ser Phe Arg Arg Lys Ala
 1               5                  10

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: PKC gammaI
      peptide

<400> SEQUENCE: 63

Arg Arg Arg Arg Arg Lys Gly Ser Phe Lys Lys Phe Ala
 1               5                  10

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: PKC delta
      peptide

<400> SEQUENCE: 64

Ala Ala Arg Lys Arg Lys Gly Ser Phe Phe Tyr Gly Gly
 1               5                  10

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence: PKC epsilon
      peptide
<220> FEATURE:
<221> NAME/KEY: VARIANT
<222> LOCATION: (3)
<223> OTHER INFORMATION: Wherein Xaa is any amino acid.

<400> SEQUENCE: 65

Tyr Tyr Xaa Lys Arg Lys Met Ser Phe Phe Glu Phe Asp
 1               5                  10

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence: PKC eta
      peptide
<220> FEATURE:
<221> NAME/KEY: VARIANT
<222> LOCATION: (12)
<223> OTHER INFORMATION: Wherein Xaa is any amino acid.

<400> SEQUENCE: 66

Ala Arg Leu Arg Arg Arg Arg Ser Phe Arg Arg Xaa Arg
 1               5                  10
```

```
<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: PKC zeta
      peptide

<400> SEQUENCE: 67

Arg Arg Phe Lys Arg Gln Gly Ser Phe Phe Tyr Phe Phe
 1               5                  10

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence: PKC mu
      peptide

<400> SEQUENCE: 68

Ala Ala Leu Val Arg Gln Met Ser Val Ala Phe Phe Phe
 1               5                  10

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Cam KII
      peptide

<400> SEQUENCE: 69

Lys Arg Gln Gln Ser Phe Asp Leu Phe
 1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence:
      phosphorylase kinaseI peptide

<400> SEQUENCE: 70

Phe Arg Met Met Ser Phe Phe Leu Phe
 1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: SLK1
      peptide

<400> SEQUENCE: 71

Arg Arg Phe Gly Ser Leu Arg Arg Phe
 1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: SPRK2
      peptide
```

```
<400> SEQUENCE: 72

Arg Arg Arg His Ser Arg Arg Arg Arg
 1               5

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: AKT/PKB
      peptide
<220> FEATURE:
<221> NAME/KEY: VARIANT
<222> LOCATION: (4)
<223> OTHER INFORMATION: Wherein Xaa is any amino acid.

<400> SEQUENCE: 73

Arg Lys Arg Xaa Arg Thr Tyr Ser Phe Gly
 1               5                   10

<210> SEQ ID NO 74
<211> LENGTH: 28
<212> TYPE: RNA
<213> ORGANISM: Artificial Sequence
<220> FEATURE:
<223> OTHER INFORMATION: Description of Artificial Sequence: Effector
      dependent release factor

<400> SEQUENCE: 74
guccuguuug augcauaccg aguaagug                                          28

<210> SEQ ID NO 75
<211> LENGTH: 146
<212> TYPE: DNA
<213> ORGANISM: Artificial Sequence
<220> FEATURE:
<223> OTHER INFORMATION: Description of Combined DNA/RNA Molecule:
      Substrate oligonucleotide
<220> FEATURE:
<223> OTHER INFORMATION: Description of Artificial Sequence: ERK
      specific ligase nucleic acid sensor molecule

<400> SEQUENCE: 75
uaagcucuac aggaaccugg uuuucgcgug gauuggagga cagauucugu gaccgccgug       60
caucggcgaa agccuuuagg aggaaucgca ccagcuugcc gaaagcggcu ucaggucacg      120
tccagtagac tagcattcca gcgtac                                          146

<210> SEQ ID NO 76
<211> LENGTH: 145
<212> TYPE: DNA
<213> ORGANISM: Artificial Sequence
<220> FEATURE:
<223> OTHER INFORMATION: Description of Artificial Sequence: Ligase
      nucleic acid sensor molecule

<400> SEQUENCE: 76
catgcgacct tacgatcaga tgacctgcac uggacuucgg cgaaagccgu ucgaccacgc       60
uaaggaggau uuccgaaagc ggcuacgugc cgccaguguc uuagacagga gguuaggugc      120
gcuuuggucc aaggacaucu cgaau                                           145

<210> SEQ ID NO 77
<211> LENGTH: 25
<212> TYPE: DNA
<213> ORGANISM: Artificial Sequence
<220> FEATURE:
```

-continued

<223> OTHER INFORMATION: Description of Artificial Sequence: Capture
     oligo

<400> SEQUENCE: 77
attcgagatg uccttggacc aaagc                                        25

<210> SEQ ID NO 78
<211> LENGTH: 121
<212> TYPE: RNA
<213> ORGANISM: Artificial Sequence
<220> FEATURE:
<223> OTHER INFORMATION: Description of Artificial Sequence: Hammerhead
     (endonuclease) nucleic acid sensor molecule

<400> SEQUENCE: 78
cucgagagcg auggcaaagc ugcaucagua cacggugcag acaaaggugu ccgaguaguc   60
ccagcgaaag cguuggaugc cgauaauagg uuuuucccg uaacguucgc ugaccuguag   120
g                                                                  121

<210> SEQ ID NO 79
<211> LENGTH: 26
<212> TYPE: DNA
<213> ORGANISM: Artificial Sequence
<220> FEATURE:
<223> OTHER INFORMATION: Description of Artificial Sequence: Capture
     oligo

<400> SEQUENCE: 79
cctacaggtc agcgaacgtt acgggt                                       26

<210> SEQ ID NO 80
<211> LENGTH: 88
<212> TYPE: RNA
<213> ORGANISM: Artificial Sequence
<220> FEATURE:
<223> OTHER INFORMATION: Description of Artificial Sequence: ERK2
     activated nucleic acid sensor
<220> FEATURE:
<221> NAME/KEY: misc_feature
<222> LOCATION: (17)..(20)
<223> OTHER INFORMATION: Wherein n is a or u or c or g or nothing.
<220> FEATURE:
<221> NAME/KEY: misc_feature
<222> LOCATION: (58)..(61)
<223> OTHER INFORMATION: Wherein n is a or u or c or g or nothing.

<400> SEQUENCE: 80
gggcgacccu gaugagnnnn cuaaggagga uuccgaaag cggcuacggu ccgccagnnn    60
ncgaaacggu gaaagccgua gguugccc                                     88

<210> SEQ ID NO 81
<211> LENGTH: 110
<212> TYPE: RNA
<213> ORGANISM: Artificial Sequence
<220> FEATURE:
<223> OTHER INFORMATION: Description of Artificial Sequence:  ppERK
     sensitive cis-hammerhead nucleic acid sensor
     molecule construct 6

<400> SEQUENCE: 81
gggcgacccu gaugagucac gcagacgcua gcgaauuggu uccucgaaag gggaaagcgu   60
uauuaagaaa ccaaaaugug uuacgaaacg gugaaaggcc guagguagcc             110

<210> SEQ ID NO 82
<211> LENGTH: 108

```
<212> TYPE: RNA
<213> ORGANISM: Artificial Sequence
<220> FEATURE:
<223> OTHER INFORMATION: Description of Artificial Sequence: ppERK
      sensitive cis-hammerhead nucleic acid sensor
      molecule construct 7

<400> SEQUENCE: 82
gggcgacccu gaugagucac gagacgcuag cgaauugguu ccucgaaagg ggaaagcguu      60
auuaagaaac caaaauuguu acgaaacggu gaaaggccgu agguagcc                 108

<210> SEQ ID NO 83
<211> LENGTH: 108
<212> TYPE: RNA
<213> ORGANISM: Artificial Sequence
<220> FEATURE:
<223> OTHER INFORMATION: Description of Artificial Sequence: ppERK
      sensitive cis-hammerhead nucleic acid sensor
      molecule construct 8

<400> SEQUENCE: 83
gggcgacccu gaugagcacg cagacgcuag cgaauugguu ccucgaaagg ggaaagcguu      60
auuaagaaac caaaaugugu ucgaaacggu gaaaggccgu agguagcc                 108

<210> SEQ ID NO 84
<211> LENGTH: 108
<212> TYPE: RNA
<213> ORGANISM: Artificial Sequence
<220> FEATURE:
<223> OTHER INFORMATION: Description of Artificial Sequence: ppERK
      sensitive cis-hammerhead nucleic acid sensor
      molecule construct 9

<400> SEQUENCE: 84
gggcgacccu gaugagucag cagacgcuag cgaauugguu ccucgaaagg ggaaagcguu      60
auuaagaaac caaaauguuu acgaaacggu gaaaggccgu agguagcc                 108

<210> SEQ ID NO 85
<211> LENGTH: 110
<212> TYPE: RNA
<213> ORGANISM: Artificial Sequence
<220> FEATURE:
<223> OTHER INFORMATION: Description of Artificial Sequence: ppERK
      sensitive cis-hammerhead nucleic acid sensor
      molecule construct 10

<400> SEQUENCE: 85
gggcgacccu gaugagucac gcagacgcua gcgaauuggu uccucgaaag gggaaagcgu      60
uauuaagaaa ccaaaaugug uugcgaaacg gugaaaggcc guagguagcc               110

<210> SEQ ID NO 86
<211> LENGTH: 104
<212> TYPE: RNA
<213> ORGANISM: Artificial Sequence
<220> FEATURE:
<223> OTHER INFORMATION: Description of Artificial Sequence: ppERK
      sensitive cis-hammerhead nucleic acid sensor
      molecule construct 11

<400> SEQUENCE: 86
gggcgacccu gaugagugca gacgcuagcg aauuguucc ucgaaagggg aaagcguuau       60
uaagaaacca aaugugcga acggugaaa ggccguaggu agcc                       104

<210> SEQ ID NO 87
```

```
<211> LENGTH: 110
<212> TYPE: RNA
<213> ORGANISM: Artificial Sequence
<220> FEATURE:
<223> OTHER INFORMATION: Description of Artificial Sequence: ppERK
      sensitive cis-hammerhead nucleic acid sensor
      molecule construct 12

<400> SEQUENCE: 87
gggcgacccu gaugagccuu gcagacgcua gcgaauuggu uccucgaaag gggaaagcgu        60
uauuaagaaa ccaaaaugua cgucgaaacg gugaaaggcc guagguagcc                  110

<210> SEQ ID NO 88
<211> LENGTH: 110
<212> TYPE: RNA
<213> ORGANISM: Artificial Sequence
<220> FEATURE:
<223> OTHER INFORMATION: Description of Artificial Sequence: ppERK
      sensitive cis-hammerhead nucleic acid sensor
      molecule construct 13

<400> SEQUENCE: 88
gggcgacccu gaugagucug gcagacgcua gcgaauuggu uccucgaaag gggaaagcgu        60
uauuaagaaa ccaaaauguc auacgaaacg gugaaaggcc guagguagcc                  110

<210> SEQ ID NO 89
<211> LENGTH: 110
<212> TYPE: RNA
<213> ORGANISM: Artificial Sequence
<220> FEATURE:
<223> OTHER INFORMATION: Description of Artificial Sequence: ppERK
      sensitive cis-hammerhead nucleic acid sensor
      molecule construct 14

<400> SEQUENCE: 89
gggcgacccu gaugagucug gcagacgcua gcgaauuggu uccucgaaag gggaaagcgu        60
uauuaagaaa ccaaaauguc uuacgaaacg gugaaaggcc guagguagcc                  110

<210> SEQ ID NO 90
<211> LENGTH: 131
<212> TYPE: RNA
<213> ORGANISM: Artificial Sequence
<220> FEATURE:
<223> OTHER INFORMATION: Description of Artificial Sequence: CW45-33-F08
      ERK specific nucleic acid sensor molecule

<400> SEQUENCE: 90
ggacuucggc gaaagccguu cgaccuacuc agacgcuagc gaauugguuc cucgaaaggg        60
aaagcguuau uaagaaacca aaaugaguag cuuagacagg agguuaggug cgucaaugcu       120
gcaaguuacu g                                                           131

<210> SEQ ID NO 91
<211> LENGTH: 132
<212> TYPE: RNA
<213> ORGANISM: Artificial Sequence
<220> FEATURE:
<223> OTHER INFORMATION: Description of Artificial Sequence: CW45-33-H08
      ERK specific nucleic acid sensor molecule

<400> SEQUENCE: 91
ggacuucggc gaaagccguu cgaccccugu cagacgcuag cgaauugguu ccucgaaagg        60
gaaagcguua uuaagaaacc aaaaugacaa gcuuagacag gagguuaggu gcgucaaugc       120
ugcaaguuac ug                                                          132
```

<210> SEQ ID NO 92
<211> LENGTH: 132
<212> TYPE: RNA
<213> ORGANISM: Artificial Sequence
<220> FEATURE:
<223> OTHER INFORMATION: Description of Artificial Sequence: CW45-33-H09
ERK specific nucleic acid sensor molecule

<400> SEQUENCE: 92
ggacuucggc gaaagccguu cgaccucgcu cagacgcuag cgaauugguu ccucgaaagg    60
gaaagcguua uuaagaaacc aaaaugagcg acuuagacag gagguuaggu gcgucaaugc   120
ugcaaguuac ug                                                      132

<210> SEQ ID NO 93
<211> LENGTH: 131
<212> TYPE: RNA
<213> ORGANISM: Artificial Sequence
<220> FEATURE:
<223> OTHER INFORMATION: Description of Artificial Sequence: CW45-33-A10
ERK specific nucleic acid sensor molecule

<400> SEQUENCE: 93
ggacuucggc gaaagccguu cgaccaacuc agacgcuagc gaauugguuc cucgaaaggg    60
aaagcguuau uaagaaacca aaauggguug cuuagacagg agguuaggug cgucaaugcu   120
gcaaguuacu g                                                       131

<210> SEQ ID NO 94
<211> LENGTH: 131
<212> TYPE: RNA
<213> ORGANISM: Artificial Sequence
<220> FEATURE:
<223> OTHER INFORMATION: Description of Artificial Sequence: CW45-33-F09
ERK specific nucleic acid sensor molecule

<400> SEQUENCE: 94
ggacuucggc gaaagccguu cgaccuguuc agacgcuagc gaauugguuc cucgaaaggg    60
aaagcguuau uaagaaacca aaaugaacag cuuagacagg agguuaggug cgucaaugcu   120
gcaaguuacu g                                                       131

<210> SEQ ID NO 95
<211> LENGTH: 132
<212> TYPE: RNA
<213> ORGANISM: Artificial Sequence
<220> FEATURE:
<223> OTHER INFORMATION: Description of Artificial Sequence: CW45-33-G08
ERK specific nucleic acid sensor molecule

<400> SEQUENCE: 95
ggacuucggc gaaagccguu cgacccuucu cagacgcuag cgaauugguu ccucgaaagg    60
gaaagcguua uuaagaaacc aaaaugagaa gcuuagacag gagguuaggu gcgucaaugc   120
ugcaaguuac ug                                                      132

<210> SEQ ID NO 96
<211> LENGTH: 134
<212> TYPE: RNA
<213> ORGANISM: Artificial Sequence
<220> FEATURE:
<223> OTHER INFORMATION: Description of Artificial Sequence: CW45-33-G02
ppERK specific nucleic acid sensor molecule

<400> SEQUENCE: 96

```
ggacuucggc gaaagccguu cgaccauuug ucagacgcua gcgaauuggu uccucgaaag    60
ggaaagcguu auuaagaaac caaaauggca gaucuuagac aggagguuag gugcgucaau   120
gcugcaaguu acug                                                    134

<210> SEQ ID NO 97
<211> LENGTH: 134
<212> TYPE: RNA
<213> ORGANISM: Artificial Sequence
<220> FEATURE:
<223> OTHER INFORMATION: Description of Artificial Sequence: CW45-33-G03
      ppERK specific nucleic acid sensor molecule

<400> SEQUENCE: 97
ggacuucggc gaaagccguu cgaccuuuag ucagacgcua gcgaauuggu uccucgaaag    60
ggaaagcguu auuaagaaac caaaaugauu agacuuagac aggagguuag gugcgucaau   120
gcugcaaguu acug                                                    134

<210> SEQ ID NO 98
<211> LENGTH: 131
<212> TYPE: RNA
<213> ORGANISM: Artificial Sequence
<220> FEATURE:
<223> OTHER INFORMATION: Description of Artificial Sequence: CW45-33-H03
      ppERK specific nucleic acid sensor molecule

<400> SEQUENCE: 98
ggacuucggc gaaagccguu cgacccgcuc agacgcuagc gaauugguuc cucgaaaggg    60
aaagcguuau uaagaaacca aaaugaucgg cuuagacagg agguuaggug cgucaaugcu   120
gcaaguuacu g                                                       131

<210> SEQ ID NO 99
<211> LENGTH: 130
<212> TYPE: RNA
<213> ORGANISM: Artificial Sequence
<220> FEATURE:
<223> OTHER INFORMATION: Description of Artificial Sequence: CW45-33-H1
      ppERK specific nucleic acid sensor molecule

<400> SEQUENCE: 99
ggacuucggc gaaagccguu cgaccguugc agacgcuagc gaauugguuc cucgaaaggg    60
aaagcguuau uaagaaacca aaaugcaauc uuagacagga gguuaggugc gucaaugcug   120
caaguuacug                                                         130

<210> SEQ ID NO 100
<211> LENGTH: 130
<212> TYPE: RNA
<213> ORGANISM: Artificial Sequence
<220> FEATURE:
<223> OTHER INFORMATION: Description of Artificial Sequence: CW45-33-B05
      ppERK specific nucleic acid sensor molecule

<400> SEQUENCE: 100
ggacuucggc gaaagccguu cgaccuuagc agacgcuagc gaauugguuc cucgaaaggg    60
aaagcguuau uaagaaacca aaaugcuaac uuagacagga gguuaggugc gucaaugcug   120
caaguuacug                                                         130

<210> SEQ ID NO 101
<211> LENGTH: 98
<212> TYPE: RNA
```

<213> ORGANISM: Artificial Sequence
<220> FEATURE:
<223> OTHER INFORMATION: Description of Artificial Sequence: cGMP
    specific hammerhead nucleic acid sensor molecule

<400> SEQUENCE: 101
ggauguccag ucgcuugcaa ugcccuuuua gacccugaug agccugugga aacagacgug    60
gcacaugacu acgucgaaac ggugaaagcc guaggucu                            98

<210> SEQ ID NO 102
<211> LENGTH: 26
<212> TYPE: DNA
<213> ORGANISM: Artificial Sequence
<220> FEATURE:
<223> OTHER INFORMATION: Description of Artificial Sequence: Capture
    oligo

<400> SEQUENCE: 102
tgggcattgc aagcgactgg acatcc                                         26

<210> SEQ ID NO 103
<211> LENGTH: 70
<212> TYPE: RNA
<213> ORGANISM: Artificial Sequence
<220> FEATURE:
<223> OTHER INFORMATION: Description of Artificial Sequence: cAMP
    specific nucleic acid sensor molecule

<400> SEQUENCE: 103
gggacccuga ugagccugug gaaacagacg uggcacauga cuacgucgaa acggugaaag    60
ccguaggucc                                                           70

<210> SEQ ID NO 104
<211> LENGTH: 24
<212> TYPE: DNA
<213> ORGANISM: Artificial Sequence
<220> FEATURE:
<223> OTHER INFORMATION: Description of Combined DNA/RNA Molecule:
    nucleic acid sensor molecule ligase
<220> FEATURE:
<223> OTHER INFORMATION: Description of Artificial Sequence: Capture
    oligo

<400> SEQUENCE: 104
cgaaaccagg ttccgtagag ctta                                           24

<210> SEQ ID NO 105
<211> LENGTH: 81
<212> TYPE: RNA
<213> ORGANISM: Artificial Sequence
<220> FEATURE:
<223> OTHER INFORMATION: Description of Artificial Sequence: C.lys.L1.A
    lysozyme sensitive ligase nucleic acid sensor

<400> SEQUENCE: 105
ggaccucggc gaaagcuaac gucucauggc uaaauugcca uguugcuaca aaugauauga    60
cuagagaggu uagcgagagu g                                              81

<210> SEQ ID NO 106
<211> LENGTH: 87
<212> TYPE: RNA
<213> ORGANISM: Artificial Sequence
<220> FEATURE:
<223> OTHER INFORMATION: Description of Artificial Sequence: C.lys.L1.B
    ligase nucleic acid sensor molecule

```
<400> SEQUENCE: 106
ggaccucggc gaaagcuaac gucucauggc uaaauugcca uguugcuaca aaugauauga      60
cuagagaggu uaggugcgag agcacug                                          87

<210> SEQ ID NO 107
<211> LENGTH: 98
<212> TYPE: RNA
<213> ORGANISM: Artificial Sequence
<220> FEATURE:
<223> OTHER INFORMATION: Description of Artificial Sequence: C.lys.L1.C
      ligase nucleic acid sensor molecule

<400> SEQUENCE: 107
ggaccucggc gaaagcuaac gucucauggc uaaauugcca uguugcuaca aaugauauga      60
cuagagaggu uaaggugcga gccgagaggc ucgcacug                              98

<210> SEQ ID NO 108
<211> LENGTH: 119
<212> TYPE: RNA
<213> ORGANISM: Artificial Sequence
<220> FEATURE:
<223> OTHER INFORMATION: Description of Artificial Sequence: ERK
      dependent ligase nucleic acid sensor molecule
<220> FEATURE:
<221> NAME/KEY: misc_feature
<222> LOCATION: (33)..(36)
<223> OTHER INFORMATION: Wherein n is a or u or t or g or nothing.
<220> FEATURE:
<221> NAME/KEY: misc_feature
<222> LOCATION: (70)..(73)
<223> OTHER INFORMATION: Wherein n is a or u or c or g or nothing.

<400> SEQUENCE: 108
ugcacuggac uucggcgaaa gccguucgac cagcuaagga ggauuuccga aagcggcuac      60
gugccgccag cucuuagaca ggagguuagg ugccguccga cugaucucgg aguuaaacg      119

<210> SEQ ID NO 109
<211> LENGTH: 121
<212> TYPE: RNA
<213> ORGANISM: Artificial Sequence
<220> FEATURE:
<223> OTHER INFORMATION: Description of Artificial Sequence: ERK
      depedent ligase nucleic acid sensor molecule construct 17

<400> SEQUENCE: 109
ugcacuggac uucggcgaaa gccguucgac cacgcuaagg aggauuuccg aaagcggcua      60
cgugccgcca gugucuuaga caggagguua ggugccgucc gacugaucuc ggaguuaaac    120
g                                                                    121

<210> SEQ ID NO 110
<211> LENGTH: 119
<212> TYPE: RNA
<213> ORGANISM: Artificial Sequence
<220> FEATURE:
<223> OTHER INFORMATION: Description of Artificial Sequence: ERK
      depedent ligase nucleic acid sensor moleucle construct 18

<400> SEQUENCE: 110
ugcacuggac uucggcgaaa gccguucgac cagcuaagga ggauuuccga aagcggcuac      60
gugccgccag uucuuagaca ggagguuagg ugccguccga cugaucucgg aguuaaacg      119

<210> SEQ ID NO 111
<211> LENGTH: 119
```

```
<210> SEQ ID NO 111
<211> LENGTH: 119
<212> TYPE: RNA
<213> ORGANISM: Artificial Sequence
<220> FEATURE:
<223> OTHER INFORMATION: Description of Artificial Sequence: ERK
      depedent ligase nucleic acid sensor moleucle construct 19

<400> SEQUENCE: 111
ugcacuggac uucggcgaaa gccguucgac cagcuaagga ggauuuccga aagcggcuac      60
gugccgccag cucuuagaca ggagguuagg ugccguccga cugaucucgg aguuaaacg     119

<210> SEQ ID NO 112
<211> LENGTH: 121
<212> TYPE: RNA
<213> ORGANISM: Artificial Sequence
<220> FEATURE:
<223> OTHER INFORMATION: Description of Artificial Sequence: ERK
      depedent ligase nucleic acid sensor moleucle construct 20

<400> SEQUENCE: 112
ugcacuggac uucggcgaaa gccguucgac cacgguaagg aggauuuccg aaagcggcua     60
cgugccgcca uugucuuaga caggagguua ggugccgucc gacugaucuc ggaguuaaac    120
g                                                                    121

<210> SEQ ID NO 113
<211> LENGTH: 121
<212> TYPE: RNA
<213> ORGANISM: Artificial Sequence
<220> FEATURE:
<223> OTHER INFORMATION: Description of Artificial Sequence: ERK
      depedent ligase nucleic acid sensor moleucle construct 21

<400> SEQUENCE: 113
ugcacuggac uucggcgaaa gccguucgac caccuuaagg aggauuuccg aaagcggcua     60
cgugccgcca cguucuuaga caggagguua ggugccgucc gacugaucuc ggaguuaaac    120
g                                                                    121

<210> SEQ ID NO 114
<211> LENGTH: 119
<212> TYPE: RNA
<213> ORGANISM: Artificial Sequence
<220> FEATURE:
<223> OTHER INFORMATION: Description of Artificial Sequence: ERK
      depedent ligase nucleic acid sensor moleucle construct 22

<400> SEQUENCE: 114
ugcacuggac uucggcgaaa gccguucgac ccgcuaagga ggauuuccga aagcggcuac     60
gugccgccag ugcuuagaca ggagguuagg ugccguccga cugaucucgg aguuaaacg    119

<210> SEQ ID NO 115
<211> LENGTH: 117
<212> TYPE: RNA
<213> ORGANISM: Artificial Sequence
<220> FEATURE:
<223> OTHER INFORMATION: Description of Artificial Sequence: ERK
      depedent ligase nucleic acid sensor moleucle construct 23

<400> SEQUENCE: 115
ugcacuggac uucggcgaaa gccguucgac cgcuaaggag gauuuccgaa agcggcuacg    60
ugccgccagu cuuagacagg agguuaggug ccguccgacu gaucucggag uuaaacg      117

<210> SEQ ID NO 116
<211> LENGTH: 117
```

```
<212> TYPE: RNA
<213> ORGANISM: Artificial Sequence
<220> FEATURE:
<223> OTHER INFORMATION: Description of Artificial Sequence: ERK
      depedent ligase nucleic acid sensor moleucle construct 24

<400> SEQUENCE: 116
ugcacuggac uucggcgaaa gccguucgac cgcuaaggag gauuuccgaa agcggcuacg      60
ugccgccagc cuuagacagg agguuaggug ccguccgacu gaucucggag uuaaacg       117

<210> SEQ ID NO 117
<211> LENGTH: 119
<212> TYPE: RNA
<213> ORGANISM: Artificial Sequence
<220> FEATURE:
<223> OTHER INFORMATION: Description of Artificial Sequence: ERK
      depedent ligase nucleic acid sensor moleucle construct 26

<400> SEQUENCE: 117
ugcacuggac uucggcgaaa gccguucgac cccuuaagga ggauuuccga aagcggcuac      60
gugccgccac gucuuagaca ggagguuagg ugccguccga cugaucucgg aguuaaacg     119

<210> SEQ ID NO 118
<211> LENGTH: 118
<212> TYPE: RNA
<213> ORGANISM: Artificial Sequence
<220> FEATURE:
<223> OTHER INFORMATION: Description of Artificial Sequence: 3-piece ERK
      dependent ligase
<220> FEATURE:
<221> NAME/KEY: misc_feature
<222> LOCATION: (32)..(35)
<223> OTHER INFORMATION: Wherein n is a or u or c or g or nothing.
<220> FEATURE:
<221> NAME/KEY: misc_feature
<222> LOCATION: (68)..(71)
<223> OTHER INFORMATION: Wherein n is a or u or c or g or nothing.

<400> SEQUENCE: 118
ugcacuggac uucggcgaaa gccguucgac cnnnnaagga ggauuuccga aagcggcuac      60
ggccgccnnn ncuuagacag gagguuaggu gccguccgac ugaucucgga guuaaacg      118

<210> SEQ ID NO 119
<211> LENGTH: 95
<212> TYPE: RNA
<213> ORGANISM: Artificial Sequence
<220> FEATURE:
<223> OTHER INFORMATION: Description of Artificial Sequence: 1-piece ERK
      dependent kinase

<400> SEQUENCE: 119
ggacuucggc gaaagccguu cgaccagcua aggaggauuu ccgaaagcgg cuacggccgc      60
cagcucuuag acaggagguu aggugcgaga gcacu                                 95

<210> SEQ ID NO 120
<211> LENGTH: 96
<212> TYPE: RNA
<213> ORGANISM: Artificial Sequence
<220> FEATURE:
<223> OTHER INFORMATION: Description of Artificial Sequence: ppERK
      dependent ligase nucleic acid sensor molecule template
<220> FEATURE:
<221> NAME/KEY: misc_feature
<222> LOCATION: (1)..(13)
<223> OTHER INFORMATION: Wherein n is an a or u or c or g or nothing
<220> FEATURE:
<221> NAME/KEY: misc_feature
```

```
<222> LOCATION: (83)..(96)
<223> OTHER INFORMATION: Wherein n is an a or u or c or g or nothing

<400> SEQUENCE: 120
nnnnnnnnnn nnngucacgc agacgcuagc gaauugguuc cucgaaaggg gaaagcguua      60
uuaagaaacc aaaauguguu acnnnnnnnn nnnnnn                               96

<210> SEQ ID NO 121
<211> LENGTH: 139
<212> TYPE: DNA
<213> ORGANISM: Artificial Sequence
<220> FEATURE:
<223> OTHER INFORMATION: Description of Artificial Sequence: ppERK
      dependent ligase nucleic acid sensor molecule
      template

<400> SEQUENCE: 121
ggacttcggc gaaagccgtt cgaccacgct cagacgctag cgaattggtt cctcgaaagg      60
ggaaagcgtt attaagaaac caaaatgagt gtcttagaca ggaggttagg tgcggctttg     120
gtccaaggac atctcgaat                                                  139

<210> SEQ ID NO 122
<211> LENGTH: 137
<212> TYPE: DNA
<213> ORGANISM: Artificial Sequence
<220> FEATURE:
<223> OTHER INFORMATION: Description of Artificial Sequence:  ppERK
      dependent ligase nucleic acid sensor molecule
      construct TK.16.118.L

<400> SEQUENCE: 122
ggacttcggc gaaagccgtt cgaccagctc agacgctagc gaattggttc ctcgaaaggg      60
gaaagcgtta ttaagaaacc aaaatgagtt cttagacagg aggttaggtg cggctttggt     120
ccaaggacat ctcgaat                                                    137

<210> SEQ ID NO 123
<211> LENGTH: 139
<212> TYPE: DNA
<213> ORGANISM: Artificial Sequence
<220> FEATURE:
<223> OTHER INFORMATION: Description of Artificial Sequence:  ppERK
      dependent ligase nucleic acid sensor molecule
      construct TK.16.118.M

<400> SEQUENCE: 123
ggacttcggc gaaagccgtt cgaccacggt cagacgctag cgaattggtt cctcgaaagg      60
ggaaagcgtt attaagaaac caaaatgatt gtcttagaca ggaggttagg tgcggctttg     120
gtccaaggac atctcgaat                                                  139

<210> SEQ ID NO 124
<211> LENGTH: 139
<212> TYPE: DNA
<213> ORGANISM: Artificial Sequence
<220> FEATURE:
<223> OTHER INFORMATION: Description of Artificial Sequence:  ppERK
      dependent ligase nucleic acid sensor molecule
      construct TK.16.118.N

<400> SEQUENCE: 124
ggacttcggc gaaagccgtt cgaccacctt cagacgctag cgaattggtt cctcgaaagg      60
ggaaagcgtt attaagaaac caaaatgacg ttcttagaca ggaggttagg tgcggctttg     120
```

-continued

```
gtccaaggac atctcgaat                                              139
```

<210> SEQ ID NO 125
<211> LENGTH: 137
<212> TYPE: DNA
<213> ORGANISM: Artificial Sequence
<220> FEATURE:
<223> OTHER INFORMATION: Description of Artificial Sequence: ppERK
      dependent ligase nucleic acid sensor molecule
      construct TK.16.118.O

<400> SEQUENCE: 125

```
ggacttcggc gaaagccgtt cgaccagctc agacgctagc gaattggttc ctcgaaaggg    60
gaaagcgtta ttaagaaacc aaaatgagct cttagacagg aggttaggtg cggctttggt   120
ccaaggacat ctcgaat                                                  137
```

<210> SEQ ID NO 126
<211> LENGTH: 137
<212> TYPE: DNA
<213> ORGANISM: Artificial Sequence
<220> FEATURE:
<223> OTHER INFORMATION: Description of Artificial Sequence: ppERK
      dependent ligase nucleic acid sensor molecule
      construct TK.16.118.P

<400> SEQUENCE: 126

```
ggacttcggc gaaagccgtt cgacccgctc agacgctagc gaattggttc ctcgaaaggg    60
gaaagcgtta ttaagaaacc aaaatgagtg cttagacagg aggttaggtg cggctttggt   120
ccaaggacat ctcgaat                                                  137
```

<210> SEQ ID NO 127
<211> LENGTH: 135
<212> TYPE: DNA
<213> ORGANISM: Artificial Sequence
<220> FEATURE:
<223> OTHER INFORMATION: Description of Artificial Sequence: ppERK
      dependent ligase nucleic acid sensor molecule
      construct TK.16.118.Q

<400> SEQUENCE: 127

```
ggacttcggc gaaagccgtt cgaccgctca gacgctagcg aattggttcc tcgaaagggg    60
aaagcgttat taagaaacca aaatgagtct tagacaggag gttaggtgcg gctttggtcc   120
aaggacatct cgaat                                                    135
```

<210> SEQ ID NO 128
<211> LENGTH: 137
<212> TYPE: DNA
<213> ORGANISM: Artificial Sequence
<220> FEATURE:
<223> OTHER INFORMATION: Description of Artificial Sequence: ppERK
      dependent ligase nucleic acid sensor molecule
      construct TK.16.118.R

<400> SEQUENCE: 128

```
ggacttcggc gaaagccgtt cgacccggtc agacgctagc gaattggttc ctcgaaaggg    60
gaaagcgtta ttaagaaacc aaaatgattg cttagacagg aggttaggtg cggctttggt   120
ccaaggacat ctcgaat                                                  137
```

<210> SEQ ID NO 129
<211> LENGTH: 137
<212> TYPE: DNA
<213> ORGANISM: Artificial Sequence

```
<220> FEATURE:
<223> OTHER INFORMATION: Description of Artificial Sequence:  ppERK
      dependent ligase nucleic acid sensor molecule
      construct TK.16.118.S

<400> SEQUENCE: 129
ggacttcggc gaaagccgtt cgaccccttc agacgctagc gaattggttc ctcgaaaggg      60
gaaagcgtta ttaagaaacc aaaatgacgt cttagacagg aggttaggtg cggctttggt     120
ccaaggacat ctcgaat                                                    137

<210> SEQ ID NO 130
<211> LENGTH: 135
<212> TYPE: DNA
<213> ORGANISM: Artificial Sequence
<220> FEATURE:
<223> OTHER INFORMATION: Description of Artificial Sequence:  ppERK
      dependent ligase nucleic acid sensor molecule
      construct TK.16.118.T

<400> SEQUENCE: 130
ggacttcggc gaaagccgtt cgaccgctca gacgctagcg aattggttcc tcgaaagggg      60
aaagcgttat taagaaacca aaatgagcct tagacaggag gttaggtgcg gctttggtcc     120
aaggacatct cgaat                                                     135

<210> SEQ ID NO 131
<211> LENGTH: 132
<212> TYPE: RNA
<213> ORGANISM: Artificial Sequence
<220> FEATURE:
<223> OTHER INFORMATION: Description of Artificial Sequence: CW45-33-C08
      ERK specific nucleic acid sensor molecule

<400> SEQUENCE: 131
ggacuucggc gaaagccguu cgaccccucu cagacgcuag cgaauugguu ccucgaaagg      60
gaaagcguua uuaagaaacc aaaaugaggg gcuuagacag gagguuaggu cgucaaugc     120 ugcaaguuac ug                                                        132

<210> SEQ ID NO 132
<211> LENGTH: 131
<212> TYPE: RNA
<213> ORGANISM: Artificial Sequence
<220> FEATURE:
<223> OTHER INFORMATION: Description of Artificial Sequence: CW45-33-C09
      ERK specific nucleic acid sensor molecule

<400> SEQUENCE: 132
ggacuucggc gaaagccguu cgaccugauc agacgcuagc gaauugguuc cucgaaaggg      60
aaagcguuau uaagaaacca aaaugaacag cuuagacagg agguuaggug cgucaaugcu     120
gcaaguuacu g                                                         131

<210> SEQ ID NO 133
<211> LENGTH: 131
<212> TYPE: RNA
<213> ORGANISM: Artificial Sequence
<220> FEATURE:
<223> OTHER INFORMATION: Description of Artificial Sequence: CW45-33-D09
      ERK specific nucleic acid sensor molecule

<400> SEQUENCE: 133
ggacuucggc gaaagccguu cgaccuuuuc agacgcuagc gaauugguuc cucgaaaggg      60
aaagcguuau uaagaaacca aaaugaaaag cuuagacagg agguuaggug cgucaaugcu     120
```

```
gcaaguuacu g                                                   131

<210> SEQ ID NO 134
<211> LENGTH: 108
<212> TYPE: DNA
<213> ORGANISM: Artificial Sequence
<220> FEATURE:
<223> OTHER INFORMATION: Description of Artificial Sequence: ppERK
      Sensitive nucleic acid sensor

<400> SEQUENCE: 134
ggcaacctac ggcctttcac cgtttcgtaa cacattttgg tttcttaata acgctttccc    60
ctttcgagga accaattcgc tagcgtctgc gtgactcatc agggtcgc                108

<210> SEQ ID NO 135
<211> LENGTH: 90
<212> TYPE: RNA
<213> ORGANISM: Artificial Sequence
<220> FEATURE:
<223> OTHER INFORMATION: Description of Artificial Sequence: cGMP
      specific nucleic acid sensor molecule

<400> SEQUENCE: 135
ggauaauagc cguagguugc gaaagcgacc cugaugagcc cugcgaugca gaaaggugcu    60
gacgacacau cgaaacggua gcgagagcuc                                    90

<210> SEQ ID NO 136
<211> LENGTH: 88
<212> TYPE: RNA
<213> ORGANISM: Artificial Sequence
<220> FEATURE:
<223> OTHER INFORMATION: Description of Artificial Sequence: cCMP
      specific nucleic acid sensor molecule

<400> SEQUENCE: 136
ggauaauagc cguagguugc gaaagcgacc cugaugaccu guggaaacag acguggcaca    60
ugacuacgug aaacgguagc gagagcuc                                      88

<210> SEQ ID NO 137
<211> LENGTH: 88
<212> TYPE: RNA
<213> ORGANISM: Artificial Sequence
<220> FEATURE:
<223> OTHER INFORMATION: Description of Artificial Sequence: cAMP
      specific nucleic acid sensor molecule

<400> SEQUENCE: 137
ggauaauagc cguagguugc gaaagcgacc cugaugaccu ugcgaugcaa aaaggugcug    60
acgacacaug aaacgguagc gagagcuc                                      88

<210> SEQ ID NO 138
<211> LENGTH: 71
<212> TYPE: RNA
<213> ORGANISM: Artificial Sequence
<220> FEATURE:
<223> OTHER INFORMATION: Description of Artificial Sequence: cCMP
      specific nucleic acid sensor molecule

<400> SEQUENCE: 138
gggacccuga ugagccuuua gggccaagug uggugaaaga cacacgucga aacggugaaa    60
gccguagguc c                                                        71
```

```
<210> SEQ ID NO 139
<211> LENGTH: 70
<212> TYPE: RNA
<213> ORGANISM: Artificial Sequence
<220> FEATURE:
<223> OTHER INFORMATION: Description of Artificial Sequence: cGMP
      specific nucleic acid sensor molecule

<400> SEQUENCE: 139
gggacccuga ugagccuugc gaugcaaaaa ggugcugacg acacaucgaa acggugaaag    60
ccguaggucc                                                          70

<210> SEQ ID NO 140
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 140
gggcgacccu gaugagucgg gcuaaggagg auuuccgaaa gcggcuacgg uccgccagua    60
auacgaaacg gugaaagccg uagguugcc                                     89

<210> SEQ ID NO 141
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 141
gggcgacccu gaugagggag gcuaaggagg auuuccgaaa gcggcuacgg uccgccaguu    60
gcgcgaaacg gugaaagccg uagguugcc                                     89

<210> SEQ ID NO 142
<211> LENGTH: 87
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (70)
<223> OTHER INFORMATION: Wherein n is an a or u or c or g or nothing
<220> FEATURE:
<221> NAME/KEY: misc_feature
<222> LOCATION: (75)..(77)
<223> OTHER INFORMATION: Wherein n is an a or u or c or g or nothing
<220> FEATURE:
<221> NAME/KEY: misc_feature
<222> LOCATION: (79)
<223> OTHER INFORMATION: Wherein n is an a or u or c or g or nothing
<220> FEATURE:
<221> NAME/KEY: misc_feature
<222> LOCATION: (81)
<223> OTHER INFORMATION: Wherein n is an a or u or c or g or nothing
<220> FEATURE:
<221> NAME/KEY: misc_feature
<222> LOCATION: (86)
<223> OTHER INFORMATION: Wherein n is an a or u or c or g or nothing

<400> SEQUENCE: 142
gggcgacccu gaugaggguu gcuaaggagg auuuccgaaa gcggcuacgg uccgccagug    60
gccaaacagn gaaanngna nguggnc                                        87
```

<210> SEQ ID NO 143
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 143
gggcgacccu gaugaguacg gcuaaggagg auuuccgaaa gcggcuacgg uccgccagua    60
gaacgaaacg gugaaagccg uagguugcc                                     89

<210> SEQ ID NO 144
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (17)
<223> OTHER INFORMATION: Wherein n is an a or u or c or g or nothing
<220> FEATURE:
<221> NAME/KEY: misc_feature
<222> LOCATION: (63)
<223> OTHER INFORMATION: Wherein n is an a or u or c or g or nothing

<400> SEQUENCE: 144
gggcgacccu gaugagncau gcuaaggagg auuuccgaaa gcggcuacgg uccgccagua    60
acncgaaacg gugaaagccg uagguugcc                                     89

<210> SEQ ID NO 145
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 145
gggcgacccu gaugaguugc gcuaaggagg auuuccgaaa gcggcuacgg uccgccagua    60
uaacgaaacg gugaaagccg uagguugcc                                     89

<210> SEQ ID NO 146
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 146
gggcgacccu gaugaguguu gcuaaggagg auuuccgaaa gcggcuacgg uccgccaguu    60
cuacgaaacg gugaaagccg uagguugcc                                     89

<210> SEQ ID NO 147
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (71)

```
<223> OTHER INFORMATION: Wherein n is an a or u or c or g or nothing
<220> FEATURE:
<221> NAME/KEY: misc_feature
<222> LOCATION: (83)
<223> OTHER INFORMATION: Wherein n is an a or u or c or g or nothing
<220> FEATURE:
<221> NAME/KEY: misc_feature
<222> LOCATION: (85)
<223> OTHER INFORMATION: Wherein n is an a or u or c or g or nothing

<400> SEQUENCE: 147
gggcgacccu gaugaguaau gcuaaggagg auuuccgaaa gcggcucggg ccgccaguua      60
ggccaaacgg ngaaagcccg uangnugcc                                        89

<210> SEQ ID NO 148
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 148
gggcgacccu gaugagcucu gcuaaggagg auuuccgaaa gcggcuacgg uccgccagua      60
uggccgaaac ggugaaagcc guagguugcc                                       90

<210> SEQ ID NO 149
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 149
gggcgacccu gaugaggcau gcuaaggagg auuuccgaaa gcggcuacgg uccgccagug      60
cggcgaaacg gugaaagccg uagguugcc                                        89

<210> SEQ ID NO 150
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 150
gggcgacccu gaugagcccc gcuaaggagg auuuccgaaa gcggcuacug guccgccagu      60
ugagcgaaac ggugaaagcc guagguugcc                                       90

<210> SEQ ID NO 151
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (24)
<223> OTHER INFORMATION: Wherein n is an a or u or c or g or nothing
<220> FEATURE:
<221> NAME/KEY: misc_feature
<222> LOCATION: (45)
<223> OTHER INFORMATION: Wherein n is an a or u or c or g or nothing
<220> FEATURE:
<221> NAME/KEY: misc_feature
```

```
<222> LOCATION: (56)
<223> OTHER INFORMATION: Wherein n is an a or u or c or g or nothing
<220> FEATURE:
<221> NAME/KEY: misc_feature
<222> LOCATION: (61)
<223> OTHER INFORMATION: Wherein n is an a or u or c or g or nothing
<220> FEATURE:
<221> NAME/KEY: misc_feature
<222> LOCATION: (61)
<223> OTHER INFORMATION: Wherein n is an a or u or c or g or nothing
<220> FEATURE:
<221> NAME/KEY: misc_feature
<222> LOCATION: (63)
<223> OTHER INFORMATION: Wherein n is an a or u or c or g or nothing
<220> FEATURE:
<221> NAME/KEY: misc_feature
<222> LOCATION: (71)
<223> OTHER INFORMATION: Wherein n is an a or u or c or g or nothing
<220> FEATURE:
<221> NAME/KEY: misc_feature
<222> LOCATION: (73)
<223> OTHER INFORMATION: Wherein n is an a or u or c or g or nothing

<400> SEQUENCE: 151
gggcgacccu gaugaguacg gcunaggagg auuuccgaaa gcggnuacug guccgncagu       60
nanacgaaac ngngaaagcc guagguugcc                                       90

<210> SEQ ID NO 152
<211> LENGTH: 91
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 152
gggcgacccu gaugagccau gcuaaggagg auuuccgaaa gcggcuacug guccgccagu       60
acuacagaaa cggugaaagc cguagguugc c                                     91

<210> SEQ ID NO 153
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 153
gggcgacccu gaugagugac gcuaaggagg auuuccgaaa gcggcuacug guccgccagu       60
ugcgcgaaac ggugaaagcc guagguugcc                                       90

<210> SEQ ID NO 154
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 154
gggcgacccu gaugagucug gcuaaggagg auuuccgaaa gcggcuacug guccgccagu       60
uucgcgaaac ggugaaagcc guagguugcc                                       90

<210> SEQ ID NO 155
<211> LENGTH: 90
<212> TYPE: RNA
<213> ORGANISM: Artificial Sequence
```

```
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (17)
<223> OTHER INFORMATION: Wherein n is an a or u or c or g or nothing
<220> FEATURE:
<221> NAME/KEY: misc_feature
<222> LOCATION: (19)
<223> OTHER INFORMATION: Wherein n is an a or u or c or g or nothing

<400> SEQUENCE: 155
gggcgacccu gaugagnanc gcuaaggagg auuuccgaaa gcggcuacug guccgccagu      60
gauacgaaac ggugaaagcc guagguugcc                                      90

<210> SEQ ID NO 156
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (4)
<223> OTHER INFORMATION: Wherein n is an a or u or c or g or nothing
<220> FEATURE:
<221> NAME/KEY: misc_feature
<222> LOCATION: (13)
<223> OTHER INFORMATION: Wherein n is an a or u or c or g or nothing
<220> FEATURE:
<221> NAME/KEY: misc_feature
<222> LOCATION: (16)..(17)
<223> OTHER INFORMATION: Wherein n is an a or u or c or g or nothing
<220> FEATURE:
<221> NAME/KEY: misc_feature
<222> LOCATION: (24)
<223> OTHER INFORMATION: Wherein n is an a or u or c or g or nothing
<220> FEATURE:
<221> NAME/KEY: misc_feature
<222> LOCATION: (54)
<223> OTHER INFORMATION: Wherein n is an a or u or c or g or nothing
<220> FEATURE:
<221> NAME/KEY: misc_feature
<222> LOCATION: (60)
<223> OTHER INFORMATION: Wherein n is an a or u or c or g or nothing

<400> SEQUENCE: 156
gggngacccu ganganngac gcunaagagg auuuccgaag cggcuacuag uccncauugn      60
accgaaacgg ccuaaagccg gagguugcc                                       89

<210> SEQ ID NO 157
<211> LENGTH: 92
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (46)
<223> OTHER INFORMATION: Wherein n is an a or u or c or g or nothing

<400> SEQUENCE: 157
gggcgacccu gaugagauac gcuaaggagg auuuccgaaa gccggnuacg guccgacagu      60
cuagccgaaa cggugaaagc cguagguugu cc                                   92

<210> SEQ ID NO 158
<211> LENGTH: 89
```

```
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 158
gggcgacccu gaugaguggc gcuaaggagg auuuccgaaa gcggcuacgg uccgccaguu      60
caacgaaacg gugaaagccg uagguugcc                                       89

<210> SEQ ID NO 159
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 159
gggcgacccu gaugagcugu gcuaaggagg auuuccgaaa gcggcuacgg uccgccaguu      60
cgacgaaacg gugaaagccg uagguugcc                                       89

<210> SEQ ID NO 160
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 160
gggcgacccu gaugaggcug gcuaaggagg auuuccgaaa gcggcuacgg uccgccaguu      60
agacgaaacg gugaaagccg uagguugcc                                       89

<210> SEQ ID NO 161
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (59)
<223> OTHER INFORMATION: Wherein n is an a or u or c or g or nothing

<400> SEQUENCE: 161
gggcgacccu gaugagaacu gcuaaggagg auuuccgaaa gcggcuacgg uccgucagnu      60
acucgaaacg gugaaagccu guagguugcc                                      90

<210> SEQ ID NO 162
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (17)
<223> OTHER INFORMATION: Wherein n is an a or u or c or g or nothing

<400> SEQUENCE: 162
gggcgacccu gaugagngcu gcuaaggagg auuuccgaaa gcggcuacgg uccgccagug      60
cugcgaaacg gugaaagccg uagguugcc                                       89
```

<210> SEQ ID NO 163
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (17)
<223> OTHER INFORMATION: Wherein n is an a or u or c or g or nothing
<220> FEATURE:
<221> NAME/KEY: misc_feature
<222> LOCATION: (19)
<223> OTHER INFORMATION: Wherein n is an a or u or c or g or nothing

<400> SEQUENCE: 163
gggcgacccu gaugagnang gcuaaggagg auuuccgaaa gcggcuacgg uccgccagua      60
augcgaaacg gugaaagccg uagguugcc                                        89

<210> SEQ ID NO 164
<211> LENGTH: 88
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (17)
<223> OTHER INFORMATION: Wherein n is an a or u or c or g or nothing
<220> FEATURE:
<221> NAME/KEY: misc_feature
<222> LOCATION: (19)
<223> OTHER INFORMATION: Wherein n is an a or u or c or g or nothing
<220> FEATURE:
<221> NAME/KEY: misc_feature
<222> LOCATION: (53)
<223> OTHER INFORMATION: Wherein n is an a or u or c or g or nothing
<220> FEATURE:
<221> NAME/KEY: misc_feature
<222> LOCATION: (57)
<223> OTHER INFORMATION: Wherein n is an a or u or c or g or nothing
<220> FEATURE:
<221> NAME/KEY: misc_feature
<222> LOCATION: (60)
<223> OTHER INFORMATION: Wherein n is an a or u or c or g or nothing
<220> FEATURE:
<221> NAME/KEY: misc_feature
<222> LOCATION: (68)
<223> OTHER INFORMATION: Wherein n is an a or u or c or g or nothing
<220> FEATURE:
<221> NAME/KEY: misc_feature
<222> LOCATION: (70)
<223> OTHER INFORMATION: Wherein n is an a or u or c or g or nothing
<220> FEATURE:
<221> NAME/KEY: misc_feature
<222> LOCATION: (75)..(76)
<223> OTHER INFORMATION: Wherein n is an a or u or c or g or nothing
<220> FEATURE:
<221> NAME/KEY: misc_feature
<222> LOCATION: (80)
<223> OTHER INFORMATION: Wherein n is an a or u or c or g or nothing
<220> FEATURE:
<221> NAME/KEY: misc_feature
<222> LOCATION: (82)
<223> OTHER INFORMATION: Wherein n is an a or u or c or g or nothing
<220> FEATURE:
<221> NAME/KEY: misc_feature
<222> LOCATION: (87)
<223> OTHER INFORMATION: Wherein n is an a or u or c or g or nothing

<400> SEQUENCE: 164

```
gggcgacccu gaugagnunu gcuaaggagg auuuccgaaa gcgcuucngg ccncacnacn    60
ccgaaacngn gaaanncegn anguggnc                                       88
```

<210> SEQ ID NO 165
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 165

```
gggcgacccu gaugaggagu gcuaaggagg auuuccgaaa gcggcuacgg uccgccaguu    60
auacgaaacg gugaaagccg uagguugcc                                      89
```

<210> SEQ ID NO 166
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (61)
<223> OTHER INFORMATION: Wherein n is an a or u or c or g or nothing

<400> SEQUENCE: 166

```
gggcgacccu gaugagaccu gcuaaggagg auuuccgaaa gcggcuacgg uccgccaguc    60
ncacgaaacg gugaaagccg uagguugcc                                      89
```

<210> SEQ ID NO 167
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 167

```
gggcgacccu gaugaggcgc gcuaaggagg aauuccgaaa gcggcuacgg uccgccagug    60
uaacgaaacg gugaaagccg uagguugcc                                      89
```

<210> SEQ ID NO 168
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (73)
<223> OTHER INFORMATION: Wherein n is an a or u or c or g or nothing

<400> SEQUENCE: 168

```
gggcgacccu gaugaguaac gcuaaggagg auuuccgaaa gucggguacg guccgccagu    60
uuaucgaaac ggngaaagcc guagguugcc                                     90
```

<210> SEQ ID NO 169
<211> LENGTH: 89
<212> TYPE: RNA
<213> ORGANISM: Artificial Sequence
<220> FEATURE:
<223> OTHER INFORMATION: Description of Artificial Sequence: ERK -continued sensitive hammerhead nucleic acid sensor molecule
<220> FEATURE:
<221> NAME/KEY: misc_feature
<222> LOCATION: (17)
<223> OTHER INFORMATION: Wherein n is an a or u or c or g or nothing

<400> SEQUENCE: 169
gggcgacccu gaugagnuac gcuaaggagg auuuccgaaa gcggcuacgg uccgccagug      60
ucacgaaacg gugaaagccg uagguugcc                                        89

<210> SEQ ID NO 170
<211> LENGTH: 88
<212> TYPE: RNA
<213> ORGANISM: Artificial Sequence
<220> FEATURE:
<223> OTHER INFORMATION: Description of Artificial Sequence: ERK
        sensitive hammerhead nucleic acid sensor molecule
<220> FEATURE:
<221> NAME/KEY: misc_feature
<222> LOCATION: (82)
<223> OTHER INFORMATION: Wherein n is an a or u or c or g or nothing
<220> FEATURE:
<221> NAME/KEY: misc_feature
<222> LOCATION: (84)
<223> OTHER INFORMATION: Wherein n is an a or u or c or g or nothing

<400> SEQUENCE: 170
gggcgacccu gaugaguugc gcuaaggagg auuuccgaaa gcggcuacgg uccgccaguu      60
acgcgaaacg gugaaagcgu angnugcc                                         88

<210> SEQ ID NO 171
<211> LENGTH: 89
<212> TYPE: RNA
<213> ORGANISM: Artificial Sequence
<220> FEATURE:
<223> OTHER INFORMATION: Description of Artificial Sequence: ERK
        sensitive hammerhead nucleic acid sensor molecule
<220> FEATURE:
<221> NAME/KEY: misc_feature
<222> LOCATION: (18)
<223> OTHER INFORMATION: Wherein n is an a or u or c or g or nothing
<220> FEATURE:
<221> NAME/KEY: misc_feature
<222> LOCATION: (20)
<223> OTHER INFORMATION: Wherein n is an a or u or c or g or nothing
<220> FEATURE:
<221> NAME/KEY: misc_feature
<222> LOCATION: (60)..(61)
<223> OTHER INFORMATION: Wherein n is an a or u or c or g or nothing

<400> SEQUENCE: 171
gggcgacccu gaugagunun gcuaaggagg auuuccgaaa gcggcuacgg uccgccagun      60
nuacgaaacg gugaaagccg uagguugcc                                        89

<210> SEQ ID NO 172
<211> LENGTH: 89
<212> TYPE: RNA
<213> ORGANISM: Artificial Sequence
<220> FEATURE:
<223> OTHER INFORMATION: Description of Artificial Sequence: ERK
        sensitive hammerhead nucleic acid sensor molecule
<220> FEATURE:
<221> NAME/KEY: misc_feature
<222> LOCATION: (21)
<223> OTHER INFORMATION: Wherein n is an a or u or c or g or nothing

<400> SEQUENCE: 172
gggcgacccu gaugagacug ncuaaggagg auuuccgaaa gcggcuacgg uccgccaguu      60

-continued

```
ggacgaaacg gugaaagccg uagguugcc                                          89
```

<210> SEQ ID NO 173
<211> LENGTH: 88
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 173

```
gggcgacccu gaugaggugc gcuaaggagg auuuccgaaa gcggcuacgg uccgccagac        60
gucgaaacgg ugaaagccgu agguugcc                                          88
```

<210> SEQ ID NO 174
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 174

```
gggcgacccu gaugaguauu gcuaaggagg auuuccgaaa gcggcuacgg uccgccaguu        60
uagcgaaacg gugaaagccg uagguugcc                                         89
```

<210> SEQ ID NO 175
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 175

```
gggcgacccu gaugaguggc gcuaaggagg auuuccgaaa gcggcuacgg uccgccaguu        60
aaccgaaacg gugaaagccg uagguugcc                                         89
```

<210> SEQ ID NO 176
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 176

```
gggcgacccu gaugagcuca gcuaaggagg auuuccgaaa gcggcuacgg uccgccaguu        60 ugcgaaacg gugaaagccg uagguugcc                                          89
```

<210> SEQ ID NO 177
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (20)
<223> OTHER INFORMATION: Wherein n is an a or u or c or g or nothing
<220> FEATURE:
<221> NAME/KEY: misc_feature
<222> LOCATION: (60)
<223> OTHER INFORMATION: Wherein n is an a or u or c or g or nothing -continued

```
<400> SEQUENCE: 177
gggcgacccu gaugagccun gcuaaggagg auuuccgaaa gcggcuacgg uccgccagun    60
acugcgaaac ggugaaagcc guagguugcc                                    90

<210> SEQ ID NO 178
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 178
gggcgacccu gaugagucau gcuaaggagg auuuccgaaa gcggcuacgg uccgccaguu    60
uugcgaaacg gugaaagccg uagguugcc                                     89

<210> SEQ ID NO 179
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 179
gggcgacccu gaugagaacc gcuaaggagg auuuccgaaa gcggcuacgg uccgccaguu    60
augcgaaacg gugaaagccg uagguugcc                                     89

<210> SEQ ID NO 180
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (19)
<223> OTHER INFORMATION: Wherein n is an a or u or c or g or nothing

<400> SEQUENCE: 180
gggcgacccu gaugagggng gcuaaagagg auuuccgaaa gcggcuacgg uccgccaguu    60
acacgaaacg gugaaagccg uagguugcc                                     89

<210> SEQ ID NO 181
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (54)
<223> OTHER INFORMATION: Wherein n is an a or u or c or g or nothing
<220> FEATURE:
<221> NAME/KEY: misc_feature
<222> LOCATION: (83)
<223> OTHER INFORMATION: Wherein n is an a or u or c or g or nothing

<400> SEQUENCE: 181
gggcgacccu gaugagugac gcuaangagg auuuccgaaa gcggcuacgg uccnccaguu    60
uaacgaaacg gugaaagccg uanguugcc                                     89
```

```
<210> SEQ ID NO 182
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (19)..(20)
<223> OTHER INFORMATION: Wherein n is an a or u or c or g or nothing
<220> FEATURE:
<221> NAME/KEY: misc_feature
<222> LOCATION: (40)
<223> OTHER INFORMATION: Wherein n is an a or u or c or g or nothing
<220> FEATURE:
<221> NAME/KEY: misc_feature
<222> LOCATION: (60)..(61)
<223> OTHER INFORMATION: Wherein n is an a or u or c or g or nothing

<400> SEQUENCE: 182
gggcgacccu gagaguacnn gcuaaggagg auuuccgaan gcggcuacgg uccgccagun    60
naacgaaacg gugaaagccg uagguugcc                                     89

<210> SEQ ID NO 183
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 183
gggcgacccu gaugagcuca gcuaaggagg auuuccgaaa gcggcuacgg uccgccaguc    60
aguacgaaac ggugaaagcc guagguugcc                                    90

<210> SEQ ID NO 184
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (20)
<223> OTHER INFORMATION: Wherein n is an a or u or c or g or nothing
<220> FEATURE:
<221> NAME/KEY: misc_feature
<222> LOCATION: (40)
<223> OTHER INFORMATION: Wherein n is an a or u or c or g or nothing

<400> SEQUENCE: 184
gggcgacccu gagaggauan gcuaaggagg auuuccgaan gcggcuacgg uccgccagua    60
caacgaaacg gugaaagccg uagguugcc                                     89

<210> SEQ ID NO 185
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 185
gggcgacccu gaugaguagu gcuaaggagg auuuccgaaa gcggcuacgg uccgccagug    60
ugacgaaacg gugaaagccg uagguugcc                                     89
```

<210> SEQ ID NO 186
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 186
gggcgacccu gaugagucgu gcuaaggagg auuuccgaaa gcggcuacgg uccgccaguu    60
gaacgaaacg gugaaagccg uagguugcc                                     89

<210> SEQ ID NO 187
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (12)..(13)
<223> OTHER INFORMATION: Wherein n is an a or u or c or g or nothing

<400> SEQUENCE: 187
gggcgacccu gnngagaacu gcuaaggagg auuuccgaaa gcggcuacgg uccgccaguu    60
augcgaaacg gugaaagccg uanguugcc                                     89

<210> SEQ ID NO 188
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (13)
<223> OTHER INFORMATION: Wherein n is an a or u or c or g or nothing
<220> FEATURE:
<221> NAME/KEY: misc_feature
<222> LOCATION: (17)
<223> OTHER INFORMATION: Wherein n is an a or u or c or g or nothing
<220> FEATURE:
<221> NAME/KEY: misc_feature
<222> LOCATION: (20)
<223> OTHER INFORMATION: Wherein n is an a or u or c or g or nothing
<220> FEATURE:
<221> NAME/KEY: misc_feature
<222> LOCATION: (24)
<223> OTHER INFORMATION: Wherein n is an a or u or c or g or nothing

<400> SEQUENCE: 188
gggcgacccu gangagnucn gcunaggagg auuuccgaaa gcggcuacgg agccgucagu    60
auugcgaaac ggcgaaagcc guagguugnc                                    90

<210> SEQ ID NO 189
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 189
gggcgacccu gaugaguaac gcuaaggagg auuuccgaaa gcggcuacgg uccgccagua    60
uugcgaaacg gugaaagccg uagguugcc                                     89

<210> SEQ ID NO 190
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 190
gggcgacccu gaugagcuua gcuaaggagg auuuccgaaa gcggcuacgg uccgccagug    60
aaacgaaacg gugaaagccg uagguugcc                                     89

<210> SEQ ID NO 191
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (17)
<223> OTHER INFORMATION: Wherein n is an a or u or c or g or nothing
<220> FEATURE:
<221> NAME/KEY: misc_feature
<222> LOCATION: (17)
<223> OTHER INFORMATION: Wherein n is an a or u or c or g or nothing
<220> FEATURE:
<221> NAME/KEY: misc_feature
<222> LOCATION: (51)
<223> OTHER INFORMATION: Wherein n is an a or u or c or g or nothing
<220> FEATURE:
<221> NAME/KEY: misc_feature
<222> LOCATION: (72)
<223> OTHER INFORMATION: Wherein n is an a or u or c or g or nothing
<220> FEATURE:
<221> NAME/KEY: misc_feature
<222> LOCATION: (83)
<223> OTHER INFORMATION: Wherein n is an a or u or c or g or nothing

<400> SEQUENCE: 191
gggcgacccu gaugagncca gcuaaggagg auuuccgaaa gcggcuacgg nccgccaguu    60
acccgaaacg gngaaagccg uanguugcc                                     89

<210> SEQ ID NO 192
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (17)..(18)
<223> OTHER INFORMATION: Wherein n is an a or u or c or g or nothing
<220> FEATURE:
<221> NAME/KEY: misc_feature
<222> LOCATION: (51)
<223> OTHER INFORMATION: Wherein n is an a or u or c or g or nothing
<220> FEATURE:
<221> NAME/KEY: misc_feature
<222> LOCATION: (72)
<223> OTHER INFORMATION: Wherein n is an a or u or c or g or nothing

<400> SEQUENCE: 192
gggcgacccu gaugagnnca gcuaaggagg auuuccgaaa gcggcuacgg nccgccaguu    60
acccgaaacg gngaaagccg uagguugcc                                     89

<210> SEQ ID NO 193
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 193
gggcgacccu gaugagcuuc gcuaaggagg auuuccgaaa gcggcuacgg uccgccaguu      60
agucgaaacg gugaaagccg uagguugcc                                        89

<210> SEQ ID NO 194
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (18)..(20)
<223> OTHER INFORMATION: Wherein n is an a or u or c or g or nothing
<220> FEATURE:
<221> NAME/KEY: misc_feature
<222> LOCATION: (61)
<223> OTHER INFORMATION: Wherein n is an a or u or c or g or nothing
<220> FEATURE:
<221> NAME/KEY: misc_feature
<222> LOCATION: (63)
<223> OTHER INFORMATION: Wherein n is an a or u or c or g or nothing

<400> SEQUENCE: 194
gggcgacccu gaugagcnnn gcuaaggagg auuuccgaaa gcggcuacgg uccgccaguu      60
nuncgaaacg gugaaagccg uagguugccu                                       90

<210> SEQ ID NO 195
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 195
gggcgacccu gaugagaccu gcuaaggagg auuuccgaaa gcggcuacgg uccgccaguu      60
aaucgaaacg gugaaagccg uagguugcc                                        89

<210> SEQ ID NO 196
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 196
gggcgacccu gaugagcacu gcuaaggagg auuuccgaaa gcggcuacgg uccgccaguc      60
gcgcgaaacg gugaaagccg uagguugcc                                        89

<210> SEQ ID NO 197
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

```
<220> FEATURE:
<221> NAME/KEY: misc_feature
<222> LOCATION: (60)
<223> OTHER INFORMATION: Wherein n is an a or u or c or g or nothing

<400> SEQUENCE: 197
gggcgacccu gaugagaucu gcuaaggagg auuuccgaaa gcggcuacgg uccgccagun     60
acgcgaaacg gugaaagccg uagguugcc                                       89

<210> SEQ ID NO 198
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (13)
<223> OTHER INFORMATION: Wherein n is an a or u or c or g or nothing
<220> FEATURE:
<221> NAME/KEY: misc_feature
<222> LOCATION: (40)
<223> OTHER INFORMATION: Wherein n is an a or u or c or g or nothing

<400> SEQUENCE: 198
gggcgacccu gangaguuuu gcuaaggagg auuuccgaan gcggcuacgg uccgccagua     60
auccgaaacg gugaaagccg uagguugcc                                       89

<210> SEQ ID NO 199
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (12)..(13)
<223> OTHER INFORMATION: Wherein n is an a or u or c or g or nothing
<220> FEATURE:
<221> NAME/KEY: misc_feature
<222> LOCATION: (40)
<223> OTHER INFORMATION: Wherein n is an a or u or c or g or nothing

<400> SEQUENCE: 199
gggcgacccu gnngaguuua gcuaaggagg auuuccgaan gcggcuacgg uccgccaguu     60
uagcgaaacg gugaaagccg uagguugcc                                       89

<210> SEQ ID NO 200
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (12)..(13)
<223> OTHER INFORMATION: Wherein n is an a or u or c or g or nothing
<220> FEATURE:
<221> NAME/KEY: misc_feature
<222> LOCATION: (40)
<223> OTHER INFORMATION: Wherein n is an a or u or c or g or nothing

<400> SEQUENCE: 200
gggcgacccu gnngaggcgu gcuaaggagg auuuccgaan gcggcuacgg uccgccaguu     60
agacgaaacg gugaaagccg uagguugcc                                       89
```

<210> SEQ ID NO 201
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (40)
<223> OTHER INFORMATION: Wherein n is an a or u or c or g or nothing

<400> SEQUENCE: 201
gggcgacccu gaugaguacu gcuaaggagg auuuccgaan gcggcuacgg uccgccagua    60
cuacgaaacg gugaaagccg uagguugcc                                     89

<210> SEQ ID NO 202
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 202
gggcgacccu gaugagcaga gcuaaggagg auuuccgaaa gcggcuacgg uccgccaguu    60
uuacgaaacg gugaaagccg uagguugcc                                     89

<210> SEQ ID NO 203
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (39)
<223> OTHER INFORMATION: Wherein n is an a or u or c or g or nothing

<400> SEQUENCE: 203
gggcgacccu gaugagcaua gcuaaggagg auuuccgana gcggcuacgg uccgccaguu    60
gcacgaaacg gugaaagccg uagguugcc                                     89

<210> SEQ ID NO 204
<211> LENGTH: 81
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (3)
<223> OTHER INFORMATION: Wherein n is an a or u or c or g or nothing
<220> FEATURE:
<221> NAME/KEY: misc_feature
<222> LOCATION: (34)
<223> OTHER INFORMATION: Wherein n is an a or u or c or g or nothing

<400> SEQUENCE: 204
ugnagagcgu ugcuaaggag gauuuccgaa agcngcuacg uccgccagua acacgaaacg    60
gugaaagccg uagguugccu u                                             81

<210> SEQ ID NO 205

```
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 205
gggcgacccu gaugagcaac gcuaaggaga auuuccgaaa gcggcuacgg uccgccaguu    60
acccgaaacg gugaaagccg uagguugcc                                     89

<210> SEQ ID NO 206
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 206
gggcgacccu gaugagggag gcuaaggagg auuuccgaaa ucggcuacgg uccgccaguc    60
auacgaaacg gugaaagccg uagguugcc                                     89

<210> SEQ ID NO 207
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (9)
<223> OTHER INFORMATION: Wherein n is an a or u or c or g or nothing
<220> FEATURE:
<221> NAME/KEY: misc_feature
<222> LOCATION: (45)
<223> OTHER INFORMATION: Wherein n is an a or u or c or g or nothing

<400> SEQUENCE: 207
gggcgaccnu gaugagcuuc gcuaaggagg auuuccgaaa gcggnuacgg uccgccagug    60
auucgaaacg gugaaagccg uagguugcc                                     89

<210> SEQ ID NO 208
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (45)
<223> OTHER INFORMATION: Wherein n is an a or u or c or g or nothing
<220> FEATURE:
<221> NAME/KEY: misc_feature
<222> LOCATION: (73)
<223> OTHER INFORMATION: Wherein n is an a or u or c or g or nothing

<400> SEQUENCE: 208
gggcgacccu gaugagaccg gcuaaggagg auuuccgaaa gcggnuacgg uccgccaguc    60
uaucgaaacg gunaaagccg uagguugcc                                     89

<210> SEQ ID NO 209
<211> LENGTH: 89
<212> TYPE: RNA
<213> ORGANISM: Artificial Sequence
```

```
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (9)
<223> OTHER INFORMATION: Wherein n is an a or u or c or g or nothing
<220> FEATURE:
<221> NAME/KEY: misc_feature
<222> LOCATION: (45)
<223> OTHER INFORMATION: Wherein n is an a or u or c or g or nothing

<400> SEQUENCE: 209
gggcgaccnu gaugaguuau gcuaaggagg auuuccgaaa gcggnuacgg uccgccagug    60
aaucgaaacg gugaaagccg uagguugcc                                     89

<210> SEQ ID NO 210
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (9)
<223> OTHER INFORMATION: Wherein n is an a or u or c or g or nothing
<220> FEATURE:
<221> NAME/KEY: misc_feature
<222> LOCATION: (45)
<223> OTHER INFORMATION: Wherein n is an a or u or c or g or nothing

<400> SEQUENCE: 210
gggcgaccnu gaugaguaua gcuaaggagg auuuccgaaa gcggnuacgg uccgccaguc    60
agacgaaacg gugaaagccg uagguugcc                                     89

<210> SEQ ID NO 211
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (9)
<223> OTHER INFORMATION: Wherein n is an a or u or c or g or nothing
<220> FEATURE:
<221> NAME/KEY: misc_feature
<222> LOCATION: (18)
<223> OTHER INFORMATION: Wherein n is an a or u or c or g or nothing
<220> FEATURE:
<221> NAME/KEY: misc_feature
<222> LOCATION: (63)
<223> OTHER INFORMATION: Wherein n is an a or u or c or g or nothing

<400> SEQUENCE: 211
gggcgaccnu gaugagungc gcuaaggagg auuuccguaa gcggcuacgg uccgccaguu    60
auncgaaacg gugaaagccg uagguugcc                                     89

<210> SEQ ID NO 212
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 212
```

```
gggcgacccu gaugagcaac gcuaaggagg auuuccgaaa gcggcuacgg uccgccagua    60
ccacgaaacg gugaaagccg uagguugcc                                     89

<210> SEQ ID NO 213
<211> LENGTH: 89
<212> TYPE: RNA
<213> ORGANISM: Artificial Sequence
<220> FEATURE:
<223> OTHER INFORMATION: Description of Artificial Sequence: ERK
      Sensitive hammerhead nucleic acid sensor molecule
<220> FEATURE:
<221> NAME/KEY: misc_feature
<222> LOCATION: (60)
<223> OTHER INFORMATION: Wherein n is an a or u or c or g or nothing
<220> FEATURE:
<221> NAME/KEY: misc_feature
<222> LOCATION: (63)
<223> OTHER INFORMATION: Wherein n is an a or u or c or g or nothing

<400> SEQUENCE: 213
gggcgacccu gaugagucgc gcuaaggagg auuuccgaaa gcggcuacgg uccgccagun    60
aancgaaacg gugaaagccg uagguugcc                                     89

<210> SEQ ID NO 214
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (45)
<223> OTHER INFORMATION: Wherein n is an a or u or c or g or nothing

<400> SEQUENCE: 214
gggcgacccu gaugagucac gcuaaggagg auuuccgaaa gcggnuacgg uccgccaguu    60
acacgaaacg gugaaagccg uagguugcc                                     89

<210> SEQ ID NO 215
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (5)
<223> OTHER INFORMATION: Wherein n is an a or u or c or g or nothing
<220> FEATURE:
<221> NAME/KEY: misc_feature
<222> LOCATION: (27)
<223> OTHER INFORMATION: Wherein n is an a or u or c or g or nothing
<220> FEATURE:
<221> NAME/KEY: misc_feature
<222> LOCATION: (30)
<223> OTHER INFORMATION: Wherein n is an a or u or c or g or nothing
<220> FEATURE:
<221> NAME/KEY: misc_feature
<222> LOCATION: (38)
<223> OTHER INFORMATION: Wherein n is an a or u or c or g or nothing
<220> FEATURE:
<221> NAME/KEY: misc_feature
<222> LOCATION: (41)
<223> OTHER INFORMATION: Wherein n is an a or u or c or g or nothing
<220> FEATURE:
<221> NAME/KEY: misc_feature
<222> LOCATION: (45)
<223> OTHER INFORMATION: Wherein n is an a or u or c or g or nothing
<220> FEATURE:
```

```
<221> NAME/KEY: misc_feature
<222> LOCATION: (53)
<223> OTHER INFORMATION: Wherein n is an a or u or c or g or nothing
<220> FEATURE:
<221> NAME/KEY: misc_feature
<222> LOCATION: (73)
<223> OTHER INFORMATION: Wherein n is an a or u or c or g or nothing
<220> FEATURE:
<221> NAME/KEY: misc_feature
<222> LOCATION: (86)
<223> OTHER INFORMATION: wherein n is an a or u or c or g or nothing

<400> SEQUENCE: 215
gggcnaccuc ugaguagcag gcuaagnagn auuuccgnaa ncggnuacgg ucngccagua    60
ugacgaaacg gunaaagccg uaggungcc                                     89

<210> SEQ ID NO 216
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (45)..(46)
<223> OTHER INFORMATION: Wherein n is an a or u or c or g or nothing

<400> SEQUENCE: 216
gggcgacccu gaugagcugu gcuaaggagg auuuccgaaa gcggnnacgg uccgccaguu    60
ucccgaaacg gugaaagccg uagguugcc                                     89

<210> SEQ ID NO 217
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (5)
<223> OTHER INFORMATION: Wherein n is an a or u or c or g or nothing
<220> FEATURE:
<221> NAME/KEY: misc_feature
<222> LOCATION: (19)..(20)
<223> OTHER INFORMATION: Wherein n is an a or u or c or g or nothing
<220> FEATURE:
<221> NAME/KEY: misc_feature
<222> LOCATION: (27)
<223> OTHER INFORMATION: Wherein n is an a or u or c or g or nothing
<220> FEATURE:
<221> NAME/KEY: misc_feature
<222> LOCATION: (37)..(38)
<223> OTHER INFORMATION: Wherein n is an a or u or c or g or nothing
<220> FEATURE:
<221> NAME/KEY: misc_feature
<222> LOCATION: (41)
<223> OTHER INFORMATION: Wherein n is an a or u or c or g or nothing
<220> FEATURE:
<221> NAME/KEY: misc_feature
<222> LOCATION: (60)..(63)
<223> OTHER INFORMATION: Wherein n is an a or u or c or g or nothing
<220> FEATURE:
<221> NAME/KEY: misc_feature
<222> LOCATION: (66)
<223> OTHER INFORMATION: Wherein n is an a or u or c or g or nothing
<220> FEATURE:
<221> NAME/KEY: misc_feature
<222> LOCATION: (73)
<223> OTHER INFORMATION: Wherein n is an a or u or c or g or nothing

<400> SEQUENCE: 217
```
gggcnaccuu gaugagcann gcuaagnagu auuuccnnaa ncggauacgg uccgccagun    60
nnncgnaacg gunaaagccg uagguugcc                                     89

<210> SEQ ID NO 218
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 218
gggcgacccu gaugagcaua gcuaaggagg auuuccgaaa gcggcuacgg uccgccagua    60
cgacgaaacg gugaaagccg uagguugcc                                     89

<210> SEQ ID NO 219
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (9)
<223> OTHER INFORMATION: Wherein n is an a or u or c or g or nothing
<220> FEATURE:
<221> NAME/KEY: misc_feature
<222> LOCATION: (45)
<223> OTHER INFORMATION: Wherein n is an a or u or c or g or nothing

<400> SEQUENCE: 219
gggcgaccnu gaugagcucu gcuaaggagg auuuccgaaa gcggnuacgg uccgccaguu    60
caacgaaacg gugaaagccg uagguugcc                                     89

<210> SEQ ID NO 220
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 220
gggcgacccu gaugagacca gcuaaggagg auuuccgaaa gcggcuacgg uccgccagug    60
auucgaaacg gugaaagccg uagguugcc                                     89

<210> SEQ ID NO 221
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (9)
<223> OTHER INFORMATION: Wherein n is an a or u or c or g or nothing
<220> FEATURE:
<221> NAME/KEY: misc_feature
<222> LOCATION: (18)
<223> OTHER INFORMATION: Wherein n is an a or u or c or g or nothing
<220> FEATURE:
<221> NAME/KEY: misc_feature
<222> LOCATION: (45)
<223> OTHER INFORMATION: Wherein n is an a or u or c or g or nothing

```
<400> SEQUENCE: 221
gggcgaccnu gaugagcnug gcuaaggagg auuuccgaaa gcggnuacgg uccgccagug      60
uuacgaaacg gugaaagccg uagguugcc                                       89

<210> SEQ ID NO 222
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (9)
<223> OTHER INFORMATION: Wherein n is an a or u or c or g or nothing
<220> FEATURE:
<221> NAME/KEY: misc_feature
<222> LOCATION: (45)
<223> OTHER INFORMATION: Wherein n is an a or u or c or g or nothing

<400> SEQUENCE: 222
gggcgaccnu gaugagucuc gcuaaggagg auuuccgaaa gcggnuacgg uccgccagua      60
augcgaaacg gugaaagccg uagguugcc                                       89

<210> SEQ ID NO 223
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (5)
<223> OTHER INFORMATION: Wherein n is an a or u or c or g or nothing
<220> FEATURE:
<221> NAME/KEY: misc_feature
<222> LOCATION: (22)
<223> OTHER INFORMATION: Wherein n is an a or u or c or g or nothing
<220> FEATURE:
<221> NAME/KEY: misc_feature
<222> LOCATION: (41)
<223> OTHER INFORMATION: Wherein n is an a or u or c or g or nothing
<220> FEATURE:
<221> NAME/KEY: misc_feature
<222> LOCATION: (73)
<223> OTHER INFORMATION: Wherein n is an a or u or c or g or nothing

<400> SEQUENCE: 223
gggcnaccuu gaugaggugg gnuaaggagu auuuccgaaa ncggauacgg uccgccagua      60
acccgaaacg gunaaagccg uagguugcc                                       89

<210> SEQ ID NO 224
<211> LENGTH: 88
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (4)
<223> OTHER INFORMATION: Wherein n is an a or u or c or g or nothing
<220> FEATURE:
<221> NAME/KEY: misc_feature
<222> LOCATION: (37)
<223> OTHER INFORMATION: Wherein n is an a or u or c or g or nothing
<220> FEATURE:
<221> NAME/KEY: misc_feature
<222> LOCATION: (58)
```

<223> OTHER INFORMATION: Wherein n is an a or u or c or g or nothing
<220> FEATURE:
<221> NAME/KEY: misc_feature
<222> LOCATION: (60)
<223> OTHER INFORMATION: Wherein n is an a or u or c or g or nothing

<400> SEQUENCE: 224
gggngacccu gaugaguagg gcuaaggagg auuuccnaaa gcggcuacgg uccgccanan    60
gucgaaacgg ugaaagccgu agguugcc                                      88

<210> SEQ ID NO 225
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (4)
<223> OTHER INFORMATION: Wherein n is an a or u or c or g or nothing
<220> FEATURE:
<221> NAME/KEY: misc_feature
<222> LOCATION: (30)
<223> OTHER INFORMATION: Wherein n is an a or u or c or g or nothing
<220> FEATURE:
<221> NAME/KEY: misc_feature
<222> LOCATION: (41)
<223> OTHER INFORMATION: Wherein n is an a or u or c or g or nothing
<220> FEATURE:
<221> NAME/KEY: misc_feature
<222> LOCATION: (45)
<223> OTHER INFORMATION: Wherein n is an a or u or c or g or nothing
<220> FEATURE:
<221> NAME/KEY: misc_feature
<222> LOCATION: (53)
<223> OTHER INFORMATION: Wherein n is an a or u or c or g or nothing

<400> SEQUENCE: 225
gggnagacuu gaugaguagc gcuaaggagn auuccgaaa ncggnuacgg ucngccaguu     60
gagcgcaacg gugaaagccg uagguugcc                                     89

<210> SEQ ID NO 226
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 226
gggcgacccu gaugagcucu gcuaaggagg auuccgaaa gcggcuacgg uccgccaguu    60
ggucgaaacg gugaaagccg uagguugcc                                     89

<210> SEQ ID NO 227
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 227
gggcgacccu gaugagggcu gcuaaggagg auuccgaaa gcggcuacgg uccgccaguu    60
aaacgaaacg gugaaagccg uagguugcc                                     89

<210> SEQ ID NO 228

```
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (4)
<223> OTHER INFORMATION: Wherein n is an a or u or c or g or nothing
<220> FEATURE:
<221> NAME/KEY: misc_feature
<222> LOCATION: (30)
<223> OTHER INFORMATION: Wherein n is an a or u or c or g or nothing
<220> FEATURE:
<221> NAME/KEY: misc_feature
<222> LOCATION: (37)
<223> OTHER INFORMATION: Wherein n is an a or u or c or g or nothing
<220> FEATURE:
<221> NAME/KEY: misc_feature
<222> LOCATION: (46)
<223> OTHER INFORMATION: Wherein n is an a or u or c or g or nothing

<400> SEQUENCE: 228
gggngacccu gaugagccau gcuaacgagn auuucunaaa gcggcnacgg uccgccaguu      60
ucgcgaaacg gugaaagccg uagguugcc                                       89

<210> SEQ ID NO 229
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (9)
<223> OTHER INFORMATION: Wherein n is an a or u or c or g or nothing
<220> FEATURE:
<221> NAME/KEY: misc_feature
<222> LOCATION: (27)
<223> OTHER INFORMATION: Wherein n is an a or u or c or g or nothing

<400> SEQUENCE: 229
gggcgaccnu gaugagucac gcuaagnagg auuuccgaaa gcggcuacgg uccgccaguc      60
ucacgaaacg gugaaagccg uagguugcc                                       89

<210> SEQ ID NO 230
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (50)
<223> OTHER INFORMATION: Wherein n is an a or u or c or g or nothing
<220> FEATURE:
<221> NAME/KEY: misc_feature
<222> LOCATION: (53)..(54)
<223> OTHER INFORMATION: Wherein n is an a or u or c or g or nothing

<400> SEQUENCE: 230
gggcgacccu gaugagacuu gguaaggagg auuuccgaaa ncgnnuacgg uccgccaugu      60
uuagcgaaac ggugaaagcc guagguugcc                                      90

<210> SEQ ID NO 231
<211> LENGTH: 89
<212> TYPE: RNA
```

```
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (9)
<223> OTHER INFORMATION: Wherein n is an a or u or c or g or nothing
<220> FEATURE:
<221> NAME/KEY: misc_feature
<222> LOCATION: (17)
<223> OTHER INFORMATION: Wherein n is an a or u or c or g or nothing
<220> FEATURE:
<221> NAME/KEY: misc_feature
<222> LOCATION: (45)
<223> OTHER INFORMATION: Wherein n is an a or u or c or g or nothing

<400> SEQUENCE: 231
gggcgaccnu gaugagnuuu gcuaaggagg auuuccgaaa gcggnuacgg uccgccaguu       60
uaucgaaacg gugaaagccg uagguugcc                                        89

<210> SEQ ID NO 232
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (9)
<223> OTHER INFORMATION: Wherein n is an a or u or c or g or nothing
<220> FEATURE:
<221> NAME/KEY: misc_feature
<222> LOCATION: (45)..(46)
<223> OTHER INFORMATION: Wherein n is an a or u or c or g or nothing

<400> SEQUENCE: 232
gggcgaccnu gaugagcuac gcuaaggagg auuuccgaaa gcggnnacgg uccgccaguu       60
ccacgaaacg gugaaagccg uagguugcc                                        89

<210> SEQ ID NO 233
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (9)
<223> OTHER INFORMATION: Wherein n is an a or u or c or g or nothing
<220> FEATURE:
<221> NAME/KEY: misc_feature
<222> LOCATION: (17)..(18)
<223> OTHER INFORMATION: Wherein n is an a or u or c or g or nothing
<220> FEATURE:
<221> NAME/KEY: misc_feature
<222> LOCATION: (20)
<223> OTHER INFORMATION: Wherein n is an a or u or c or g or nothing
<220> FEATURE:
<221> NAME/KEY: misc_feature
<222> LOCATION: (22)
<223> OTHER INFORMATION: Wherein n is an a or u or c or g or nothing
<220> FEATURE:
<221> NAME/KEY: misc_feature
<222> LOCATION: (30)
<223> OTHER INFORMATION: Wherein n is an a or u or c or g or nothing
<220> FEATURE:
<221> NAME/KEY: misc_feature
<222> LOCATION: (46)
<223> OTHER INFORMATION: Wherein n is an a or u or c or g or nothing
<220> FEATURE:
```

```
<221> NAME/KEY: misc_feature
<222> LOCATION: (53)
<223> OTHER INFORMATION: Wherein n is an a or u or c or g or nothing
<220> FEATURE:
<221> NAME/KEY: misc_feature
<222> LOCATION: (60)
<223> OTHER INFORMATION: Wherein n is an a or u or c or g or nothing
<220> FEATURE:
<221> NAME/KEY: misc_feature
<222> LOCATION: (62)
<223> OTHER INFORMATION: Wherein n is an a or u or c or g or nothing
<220> FEATURE:
<221> NAME/KEY: misc_feature
<222> LOCATION: (66)
<223> OTHER INFORMATION: Wherein n is an a or u or c or g or nothing

<400> SEQUENCE: 233
gggcgaccnu gaugagnncn gnuaaggagn auuuccgaaa gcgganacgg ucngccagun    60
anccgnaacg gugaaagccg uagguugcc                                     89

<210> SEQ ID NO 234
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (9)
<223> OTHER INFORMATION: Wherein n is an a or u or c or g or nothing
<220> FEATURE:
<221> NAME/KEY: misc_feature
<222> LOCATION: (45)
<223> OTHER INFORMATION: Wherein n is an a or u or c or g or nothing

<400> SEQUENCE: 234
gggcgaccnu gaugaggaau gcuaaggagg auuuccgaaa gcggnuacgg uccgccagua    60
cagcgaaacg gugaaagccg uagguugcc                                     89

<210> SEQ ID NO 235
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (9)
<223> OTHER INFORMATION: Wherein n is an a or u or c or g or nothing
<220> FEATURE:
<221> NAME/KEY: misc_feature
<222> LOCATION: (45)..(46)
<223> OTHER INFORMATION: Wherein n is an a or u or c or g or nothing

<400> SEQUENCE: 235
gggcgaccnu gaugaguccu gcuaaggagg auuuccgaaa gcggnnacgg uccgccagua    60
aagcgaaacg gugaaagccg uagguugcc                                     89

<210> SEQ ID NO 236
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (45)
```

<223> OTHER INFORMATION: Wherein n is an a or u or c or g or nothing

<400> SEQUENCE: 236
gggcgacccu gaugaguucu gcuaaggagg auuuccgaaa gcggnuacgg uccgccaguu     60
uuacgaaacg gugaaagccg uagguugcc                                      89

<210> SEQ ID NO 237
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (9)
<223> OTHER INFORMATION: Wherein n is an a or u or c or g or nothing
<220> FEATURE:
<221> NAME/KEY: misc_feature
<222> LOCATION: (17)
<223> OTHER INFORMATION: Wherein n is an a or u or c or g or nothing
<220> FEATURE:
<221> NAME/KEY: misc_feature
<222> LOCATION: (20)
<223> OTHER INFORMATION: Wherein n is an a or u or c or g or nothing
<220> FEATURE:
<221> NAME/KEY: misc_feature
<222> LOCATION: (62)..(63)
<223> OTHER INFORMATION: Wherein n is an a or u or c or g or nothing

<400> SEQUENCE: 237
gggcgaccnu gaugagnaun gcuaaggagg auuuccgaaa gcggcuacgg uccgccaguu     60
anncgaaacg gugaaagccg uagguugcc                                      89

<210> SEQ ID NO 238
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 238
gggcgacccu gaugaggaau gcuaaagagg auuuccgaaa gcggcuacgg uccgccaguu     60
aagcgaaacg gugaaagccg uagguugcc                                      89

<210> SEQ ID NO 239
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 239
gggcgacccu gaugagcagu gcuaaggagg auuuccgaaa gcggcuacgg uccgccagug     60
gagcgaaacg gugaaagccg uagguugcc                                      89

<210> SEQ ID NO 240
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature

```
<222> LOCATION: (17)
<223> OTHER INFORMATION: Wherein n is an a or u or c or g or nothing
<220> FEATURE:
<221> NAME/KEY: misc_feature
<222> LOCATION: (63)
<223> OTHER INFORMATION: Wherein n is an a or u or c or g or nothing

<400> SEQUENCE: 240
gggcgacccu gaugagnuau gcuaaggagg auuuccgaaa gcggcuacgg uccgccagun    60
agncgaaacg gugaaagccg uagguugcc                                     89

<210> SEQ ID NO 241
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 241
gggcgacccu gaugagcacu gcuaaggagg auuuccgaaa gcggcuacgg uccgccagug    60
agacgaaacg gugaaagccg uagguugcc                                     89

<210> SEQ ID NO 242
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (34)
<223> OTHER INFORMATION: Wherein n is an a or u or c or g or nothing

<400> SEQUENCE: 242
gggcgacccu gaugagcuca gcuaaggagg auuuccgaaa gcggcuacgg uccgccaguu    60
ucgcgaaacg gugaaagccg uagguugcc                                     89

<210> SEQ ID NO 243
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (46)
<223> OTHER INFORMATION: Wherein n is an a or u or c or g or nothing

<400> SEQUENCE: 243
gggcgacccu gaugaggcuu gcuaaggagg auuuccgaaa gcggcnacgg uccgccaguc    60
cgucgaaacg gugaaagccg uagguugcc                                     89

<210> SEQ ID NO 244
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 244
gggcgacccu gaugagcucu gcuaaggagg auuuccgaaa gcggcuacgg uccgccaguu    60
```

```
cggcgaaacg gugaaagccg uagguugcc                                    89

<210> SEQ ID NO 245
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 245
gggcgacccu gaugaggcaa gcuaaggagg auuuccgaaa gcggcuacgg uccgccaguu   60
caacgaaacg gugaaagccg uagguugcc                                    89

<210> SEQ ID NO 246
<211> LENGTH: 82
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 246
gggcgacccu gaugagcguc gcuaaggagg auuuccgaaa gcggcuacgg uccgccagua   60
ucucgaaacg gugaaagccg ua                                           82

<210> SEQ ID NO 247
<211> LENGTH: 85
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 247
gggcgacccu gaugagcuuc gcuaaggagg auuuccgaaa gcggcuacgg uccgccaguu   60
aaacgaaacg gugaaagccg uaggu                                        85

<210> SEQ ID NO 248
<211> LENGTH: 75
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 248
gggcgacccu gaugauggc gcuaaggagg auuuccgaaa gcggcuacgg uccgccaguu    60
uaacgaaacg gugaa                                                   75

<210> SEQ ID NO 249
<211> LENGTH: 85
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 249
gggcgacccu gaugagacuc gcuaaggagg auuuccgaaa gcggcuacgg uccgccagug   60
guacgaaacg gugaaagccg uaggu                                        85

<210> SEQ ID NO 250
```

<211> LENGTH: 91
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (35)
<223> OTHER INFORMATION: Wherein n is an a or u or c or g or nothing

<400> SEQUENCE: 250
gggcgacccu gaugaguauu gcuaaggagg auuunccgaa agcggcucac ggugccgcca      60
guugagcgaa acggugaaag ccuagguugc c                                    91

<210> SEQ ID NO 251
<211> LENGTH: 88
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (18)
<223> OTHER INFORMATION: Wherein n is an a or u or c or g or nothing

<400> SEQUENCE: 251
gggcgacccu gaugagcnuc gcuaaggagg auuuccgaaa gcggcuacgg uccgccagua      60
auacgaaacg gugaaagccg uagguugc                                        88

<210> SEQ ID NO 252
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (19)..(20)
<223> OTHER INFORMATION: Wherein n is an a or u or c or g or nothing
<220> FEATURE:
<221> NAME/KEY: misc_feature
<222> LOCATION: (62)
<223> OTHER INFORMATION: Wherein n is an a or u or c or g or nothing

<400> SEQUENCE: 252
gggcgacccu gaugagcunn gcuaaggagg auuuccgaaa gcggcuacgg uccgccaguu      60
cnacgaaacg gugaaagccg uagguugcc                                       89

<210> SEQ ID NO 253
<211> LENGTH: 85
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 253
gggcgacccu gaugaguucg gcuaaggagg auuuccgaaa gcggcuacgg uccgccagug      60
aagcgaaacg gugaaagccg uaggu                                           85

<210> SEQ ID NO 254
<211> LENGTH: 89
<212> TYPE: RNA
<213> ORGANISM: Artificial Sequence

```
<220> FEATURE:
<223> OTHER INFORMATION: Description of Artificial Sequence: ERK
      sensitive hammerhead nucleic acid sensor molecule

<400> SEQUENCE: 254
gggcgacccu gaugagauga gcuaaggagg auuuccgaaa gcggcuacgg uccgccagua      60
aaccgaaacg gugaaagccg uagguugcc                                       89

<210> SEQ ID NO 255
<211> LENGTH: 77
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (40)
<223> OTHER INFORMATION: Wherein n is an a or u or c or g or nothing
<220> FEATURE:
<221> NAME/KEY: misc_feature
<222> LOCATION: (44)
<223> OTHER INFORMATION: Wherein n is an a or u or c or g or nothing

<400> SEQUENCE: 255
gggcgacccu gaugagaauc gcuaaggagg auuuccgaan gcgncuacgg uccgccaguu      60
ccccgaaacg gugaaag                                                    77

<210> SEQ ID NO 256
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (62)
<223> OTHER INFORMATION: Wherein n is an a or u or c or g or nothing

<400> SEQUENCE: 256
gggcgacccu gaugagucac gcuaaggagg auuuccgaaa gcggcuacgg uccgccaguu      60
gncgcgaaac ggugaaagcc guagguugcc                                      90

<210> SEQ ID NO 257
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 257
gggcgacccu gaugagcauc gcuaaggagg auuuccgaaa gcggcuacgg uccgccaguu      60
aagcgaaacg gugaaagccg uagguugcc                                       89

<210> SEQ ID NO 258
<211> LENGTH: 84
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 258
gggcgacccu gaugagguca gcuaaggagg auuuccgaaa gcggcuacgg uccgccaguu      60
```

```
cagcgaaacg gugaaagccg uagg                                      84
```

<210> SEQ ID NO 259
<211> LENGTH: 79
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 259

```
gggcgacccu gaugagaagc gcuaaggagg auuccgaaa gcggcuacgg uccgccaguc   60
uagcgaaacg gugaaagcc                                               79
```

<210> SEQ ID NO 260
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 260

```
gggcgacccu gaugaggcuu gcuaaggagg auuccgaaa gcggcuacgg uccgccaguu   60
gaucgaaacg gugaaagccg ugagguugcc                                   90
```

<210> SEQ ID NO 261
<211> LENGTH: 91
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 261

```
gggcgacccu gaugaggcug gcuaaggagg auuccgaaa gcggcucacg guccgccagu   60
ccuaacgaaa cggugaaagc cguagguugc c                                 91
```

<210> SEQ ID NO 262
<211> LENGTH: 88
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 262

```
gggcgacccu gaugagccuu gcuaaggagg auuccgaaa gcggcuacgg uccgccaguu   60
agucgaaacg gugaaagccg uagguugc                                     88
```

<210> SEQ ID NO 263
<211> LENGTH: 67
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (61)
<223> OTHER INFORMATION: Wherein n is an a or u or c or g or nothing

<400> SEQUENCE: 263

```
gggcgacccu gaugagucac gcuaaggagg auuccgaaa gcggcuacgg uccgccaguu   60
```

```
ncgcgaa                                                             67

<210> SEQ ID NO 264
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 264
gggcgacccu gaugagaacu gcuaaggagg auuuaccgaa agcggcuacg guccgccagu    60
ugcgcgaaac ggugaaagcc guagguugcc                                    90

<210> SEQ ID NO 265
<211> LENGTH: 84
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 265
gggcgacccu gaugagcgac gcuaaggagg auuuccgaaa gcggcuacgg uccgccaguu    60
gggcgaaacg gugaaagccg uagg                                          84

<210> SEQ ID NO 266
<211> LENGTH: 85
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 266
gggcgacccu gaugaguaac gcuaaggagg auuuccgaaa gcggcuacgg uccgccaguc    60
agacgaaacg gugaaagccg uaggu                                         85

<210> SEQ ID NO 267
<211> LENGTH: 85
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 267
gggcgacccu gaugaggacu gcuaaggagg auuuccgaaa gcggcuacgg uccgccaguu    60
acucgaaacg gugaaagccg uaggu                                         85

<210> SEQ ID NO 268
<211> LENGTH: 89
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 268
gggcgacccu gaugagccgg gcuaaggagg auuuccgaaa gcggcuacgg uccgccaguu    60
gagcgaaacg gugaaagccg uagguugcc                                     89
```

<210> SEQ ID NO 269
<211> LENGTH: 41
<212> TYPE: RNA
<213> ORGANISM: Artificial Sequence
<220> FEATURE:
<223> OTHER INFORMATION: Description of Artificial Sequence: ERK sensitive hammerhead nucleic acid sensor molecule
<220> FEATURE:
<221> NAME/KEY: misc_feature
<222> LOCATION: (19)
<223> OTHER INFORMATION: Wherein n is an a or u or c or g or nothing

<400> SEQUENCE: 269
gggcgacccu gaugagcana gcuaaggagg auuuccgaaa g            41

<210> SEQ ID NO 270
<211> LENGTH: 85
<212> TYPE: RNA
<213> ORGANISM: Artificial Sequence
<220> FEATURE:
<223> OTHER INFORMATION: Description of Artificial Sequence: ERK sensitive hammerhead nucleic acid sensor molecule

<400> SEQUENCE: 270
gggcgacccu gaugaguugc gcuaaggagg auuuccgaaa gcggcuacgg uccgccaguu     60
uagcgaaacg gugaaagccg uaggu            85

<210> SEQ ID NO 271
<211> LENGTH: 85
<212> TYPE: RNA
<213> ORGANISM: Artificial Sequence
<220> FEATURE:
<223> OTHER INFORMATION: Description of Artificial Sequence: ERK sensitive hammerhead nucleic acid sensor molecule

<400> SEQUENCE: 271
gggcgacccu gaugagcagc gcuaaggagg auuuccgaaa gcggcuaggu ccgccagucu     60
ucgaaacggu gaaagccgua gguug            85

<210> SEQ ID NO 272
<211> LENGTH: 75
<212> TYPE: RNA
<213> ORGANISM: Artificial Sequence
<220> FEATURE:
<223> OTHER INFORMATION: Description of Artificial Sequence: ERK sensitive hammerhead nucleic acid sensor molecule

<400> SEQUENCE: 272
gggcgacccu gaugaguaag gcuaaggagg auuuccgaaa gcggcuacgg uccgccagug     60
uugcgaaacg gugaa            75

<210> SEQ ID NO 273
<211> LENGTH: 89
<212> TYPE: RNA
<213> ORGANISM: Artificial Sequence
<220> FEATURE:
<223> OTHER INFORMATION: Description of Artificial Sequence: ERK sensitive hammerhead nucleic acid sensor molecule

<400> SEQUENCE: 273
gggcgacccu gaugagcacc gcuaaggagg auuuccgaaa gcggcuacgg uccgccaguu     60
acgcgaaacg gugaaagccg uagguugcc           89

<210> SEQ ID NO 274
<211> LENGTH: 82

```
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 274
gggcgacccu gaugaggcau gcuaaggagg auuuccgaaa gcggcuacgg uccgccagua    60
aggcgaaacg gugaaagccg ua                                            82

<210> SEQ ID NO 275
<211> LENGTH: 77
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 275
gggcgacccu gaugaguuua gcuaaggagg auuuccgaaa gcggcuacgg uccgccagua    60
gaccgaaacg gugaaag                                                  77

<210> SEQ ID NO 276
<211> LENGTH: 77
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 276
gggcgacccu gaugagaagc gcuaaggagg auuuccgaaa gcggcuacgg uccgccagua    60
augcgaaacg gugaaag                                                  77

<210> SEQ ID NO 277
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (46)
<223> OTHER INFORMATION: Wherein n is an a or u or c or g or nothing

<400> SEQUENCE: 277
gggugaccuc ugauaguguu gcuaaggagg gauuuccgaa agcggnuacg guccgccagu    60
agagcgaaac ggugaaagcc guagguugcc                                    90

<210> SEQ ID NO 278
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (9)
<223> OTHER INFORMATION: Wherein n is an a or u or c or g or nothing
<220> FEATURE:
<221> NAME/KEY: misc_feature
<222> LOCATION: (19)
<223> OTHER INFORMATION: Wherein n is an a or u or c or g or nothing
<220> FEATURE:
<221> NAME/KEY: misc_feature
```

```
<222> LOCATION: (46)
<223> OTHER INFORMATION: Wherein n is an a or u or c or g or nothing

<400> SEQUENCE: 278
gggcgaccnu gaugagcang cgcuaaggag gauuuccgaa agcggnuacg guccgccagu    60
gacucgaaac ggugaaagcc guagguugcc                                    90

<210> SEQ ID NO 279
<211> LENGTH: 80
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (33)
<223> OTHER INFORMATION: Wherein n is an a or u or c or g or nothing
<220> FEATURE:
<221> NAME/KEY: misc_feature
<222> LOCATION: (70)..(71)
<223> OTHER INFORMATION: Wherein n is an a or u or c or g or nothing
<220> FEATURE:
<221> NAME/KEY: misc_feature
<222> LOCATION: (76)
<223> OTHER INFORMATION: Wherein n is an a or u or c or g or nothing

<400> SEQUENCE: 279
gggcgacccu gauaguagcg cuaaguaagg aunuuccgaa agcgcgcuca cgguccgcca    60
gucucacgan ncggunaaag                                               80

<210> SEQ ID NO 280
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (4)
<223> OTHER INFORMATION: Wherein n is an a or u or c or g or nothing
<220> FEATURE:
<221> NAME/KEY: misc_feature
<222> LOCATION: (20)
<223> OTHER INFORMATION: Wherein n is an a or u or c or g or nothing
<220> FEATURE:
<221> NAME/KEY: misc_feature
<222> LOCATION: (52)
<223> OTHER INFORMATION: Wherein n is an a or u or c or g or nothing
<220> FEATURE:
<221> NAME/KEY: misc_feature
<222> LOCATION: (65)
<223> OTHER INFORMATION: Wherein n  is an a or u or c or g or nothing

<400> SEQUENCE: 280
gggngacccu gaugaguaun agcuaaggag gauuuccgaa agcggcuacg gnccgccagu    60
aaugngaaac ggugaaagcc guagguugcc                                    90

<210> SEQ ID NO 281
<211> LENGTH: 90
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (19)
<223> OTHER INFORMATION: Wherein n is an a or u or c or g or nothing
```

```
<220> FEATURE:
<221> NAME/KEY: misc_feature
<222> LOCATION: (23)
<223> OTHER INFORMATION: Wherein n is an a or u or c or g or nothing
<220> FEATURE:
<221> NAME/KEY: misc_feature
<222> LOCATION: (46)
<223> OTHER INFORMATION: Wherein n is an a or u or c or g or nothing

<400> SEQUENCE: 281
gggcgaccuu gaugaaggnc agnuaaggag gauuuccgaa agcggnuacg gucagccagu    60
ggcacgaaac ggugaaagcc guagguugcc                                    90

<210> SEQ ID NO 282
<211> LENGTH: 88
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 282
gggcgacccu gaugagcaug cuaaggagga uuuccgaaag cggcuacggu ccgccaguua    60
gucgaaacgg ugaaagccgu agguugcc                                      88

<210> SEQ ID NO 283
<211> LENGTH: 87
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (16)..(17)
<223> OTHER INFORMATION: Wherein n is an a or u or c or g or nothing
<220> FEATURE:
<221> NAME/KEY: misc_feature
<222> LOCATION: (22)
<223> OTHER INFORMATION: Wherein n is an a or u or c or g or nothing
<220> FEATURE:
<221> NAME/KEY: misc_feature
<222> LOCATION: (40)
<223> OTHER INFORMATION: Wherein n is an a or u or c or g or nothing
<220> FEATURE:
<221> NAME/KEY: misc_feature
<222> LOCATION: (56)
<223> OTHER INFORMATION: Wherein n is an a or u or c or g or nothing
<220> FEATURE:
<221> NAME/KEY: misc_feature
<222> LOCATION: (60)..(61)
<223> OTHER INFORMATION: Wherein n is an a or u or c or g or nothing
<220> FEATURE:
<221> NAME/KEY: misc_feature
<222> LOCATION: (72)
<223> OTHER INFORMATION: Wherein n is an a or u or c or g or nothing
<220> FEATURE:
<221> NAME/KEY: misc_feature
<222> LOCATION: (76)
<223> OTHER INFORMATION: Wherein n is an a or u or c or g or nothing
<220> FEATURE:
<221> NAME/KEY: misc_feature
<222> LOCATION: (81)
<223> OTHER INFORMATION: Wherein n is an a or u or c or g or nothing
<220> FEATURE:
<221> NAME/KEY: misc_feature
<222> LOCATION: (86)
<223> OTHER INFORMATION: Wherein n is an a or u or c or g or nothing

<400> SEQUENCE: 283
gggcgacccu gauganngcu gnuaggagga uuuccgaaan ugcuucuggc ccgcanuuan    60
```

```
nccgaacggg cnaaancgaa nggugnc                                          87
```

<210> SEQ ID NO 284
<211> LENGTH: 65
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule

<400> SEQUENCE: 284

```
gggcgacccu gaugaguagg cuaaggagga uuucgaaagc ggcuacgguc cgccagugug      60
ccgaa                                                                  65
```

<210> SEQ ID NO 285
<211> LENGTH: 88
<212> TYPE: RNA
<213> ORGANISM: Artificial Sequence
<220> FEATURE:
<223> OTHER INFORMATION: Description of Artificial Sequence: ERK
      sensitive hammerhead nucleic acid sensor molecule
<220> FEATURE:
<221> NAME/KEY: misc_feature
<222> LOCATION: (18)
<223> OTHER INFORMATION: Wherein n is a or u or c or g or nothing.
<220> FEATURE:
<221> NAME/KEY: misc_feature
<222> LOCATION: (25)
<223> OTHER INFORMATION: Wherein n is a or u or c or g or nothing.
<220> FEATURE:
<221> NAME/KEY: misc_feature
<222> LOCATION: (50)
<223> OTHER INFORMATION: Wherein n is a or u or c or g or nothing.
<220> FEATURE:
<221> NAME/KEY: misc_feature
<222> LOCATION: (60)
<223> OTHER INFORMATION: Wherein n is a or u or c or g or nothing.

<400> SEQUENCE: 285

```
gggcgacccu gcugagcnac gcuangagga uuuccgaaag cggcuacggn ccgccagucn      60
gacgaaacgg ugaaagccgu agguugcc                                         88
```

<210> SEQ ID NO 286
<211> LENGTH: 87
<212> TYPE: RNA
<213> ORGANISM: Artificial Sequence
<220> FEATURE:
<223> OTHER INFORMATION: Description of Artificial Sequence: Construct
      1-14

<400> SEQUENCE: 286

```
gggcgacccu gaugaggguc gcuaaggagg auuccgaaa gcggcacggu ccgccagacg       60
ucgaaacggu gaaagccgua gguugcc                                          87
```

<210> SEQ ID NO 287
<211> LENGTH: 87
<212> TYPE: RNA
<213> ORGANISM: Artificial Sequence
<220> FEATURE:
<223> OTHER INFORMATION: Description of Artificial Sequence: Construct
      1-13

<400> SEQUENCE: 287

```
gggcgacccu gaugagucuu cuaaggagga uuuccgaaag cggcacgguc cgccaguacg      60
ucgaaacggu gaaagccgua gguugcc                                          87
```

<210> SEQ ID NO 288
<211> LENGTH: 86
<212> TYPE: RNA
<213> ORGANISM: Artificial Sequence
<220> FEATURE:
<223> OTHER INFORMATION: Description of Artificial Sequence: Construct 1-2

<400> SEQUENCE: 288
gggcgacccu gaugagccuu cuaaggagga uuuccgaaag cggcacgguc cgccagacgu    60
cgaaacggug aaagccguag guugcc                                       86

<210> SEQ ID NO 289
<211> LENGTH: 87
<212> TYPE: RNA
<213> ORGANISM: Artificial Sequence
<220> FEATURE:
<223> OTHER INFORMATION: Description of Artificial Sequence: Construct 1-6

<400> SEQUENCE: 289
gggcgacccu gaugagucau gcuaaggagg auuuccgaaa gcggcacggu ccgccagacg    60
ucgaaacggu gaaagccgua gguugcc                                      87

<210> SEQ ID NO 290
<211> LENGTH: 88
<212> TYPE: RNA
<213> ORGANISM: Artificial Sequence
<220> FEATURE:
<223> OTHER INFORMATION: Description of Artificial Sequence: Construct 2-7

<400> SEQUENCE: 290
gggcgacccu gaugagccuu gcuaaggagg auuuccgaaa gcggcacggu ccgccaguca    60
gucgaaacgg ugaaagccgu agguugcc                                     88

<210> SEQ ID NO 291
<211> LENGTH: 87
<212> TYPE: RNA
<213> ORGANISM: Artificial Sequence
<220> FEATURE:
<223> OTHER INFORMATION: Description of Artificial Sequence: Construct 2-2

<400> SEQUENCE: 291
gggcgacccu gaugagccuc gcuaaggagg auuuccgaaa gcggcacggu ccgccagcua    60
gcgaaacggu gaaagccgua gguugcc                                      87

<210> SEQ ID NO 292
<211> LENGTH: 88
<212> TYPE: RNA
<213> ORGANISM: Artificial Sequence
<220> FEATURE:
<223> OTHER INFORMATION: Description of Artificial Sequence: Construct 2-3

<400> SEQUENCE: 292
gggcgacccu gaugagaacu gcuaaggagg auuuccgaaa gcggcacggu ccgccaguuu    60
aacgaaacgg ugaaagccgu agguugcc                                     88

<210> SEQ ID NO 293
<211> LENGTH: 88
<212> TYPE: RNA
<213> ORGANISM: Artificial Sequence

```
<220> FEATURE:
<223> OTHER INFORMATION: Description of Artificial Sequence: Construct
      2-13

<400> SEQUENCE: 293
gggcgacccu gaugaguaaa gcuaaggagg auuuccgaaa gcggcacggu ccgccagucu    60
ggcgaaacgg ugaaagccgu agguugcc                                      88

<210> SEQ ID NO 294
<211> LENGTH: 88
<212> TYPE: RNA
<213> ORGANISM: Artificial Sequence
<220> FEATURE:
<223> OTHER INFORMATION: Description of Artificial Sequence: Construct
      2-14

<400> SEQUENCE: 294
gggcgacccu gaugaguuuu gcuaaggagg auuuccgaaa gcggcacggu ccgccaguga    60
uccgaaacgg ugaaagccgu agguugcc                                      88

<210> SEQ ID NO 295
<211> LENGTH: 88
<212> TYPE: RNA
<213> ORGANISM: Artificial Sequence
<220> FEATURE:
<223> OTHER INFORMATION: Description of Artificial Sequence: Construct
      2-20

<400> SEQUENCE: 295
gggcgacccu gaugaggcga gcuaaggagg auuuccgaaa gcggcacggu ccgccaguuu    60
aacgaaacgg ugaaagccgu agguugcc                                      88

<210> SEQ ID NO 296
<211> LENGTH: 35
<212> TYPE: DNA
<213> ORGANISM: Artificial Sequence
<220> FEATURE:
<223> OTHER INFORMATION: Description of Combined DNA/RNA Molecule:
      Oligonucleotide substrate
<220> FEATURE:
<223> OTHER INFORMATION: Description of Artificial Sequence: 5' primer

<400> SEQUENCE: 296
tctaatacga ctcactatag gacctcggcg aaagc                              35

<210> SEQ ID NO 297
<211> LENGTH: 25
<212> TYPE: DNA
<213> ORGANISM: Artificial Sequence
<220> FEATURE:
<223> OTHER INFORMATION: Description of Artificial Sequence: 3' Primer A

<400> SEQUENCE: 297
actctcgcta acctctctag tcata                                         25

<210> SEQ ID NO 298
<211> LENGTH: 27
<212> TYPE: DNA
<213> ORGANISM: Artificial Sequence
<220> FEATURE:
<223> OTHER INFORMATION: Description of Artificial Sequence: 3' Primer B

<400> SEQUENCE: 298
agtgctctcg cacctaacct ctctagt                                       27
```

<210> SEQ ID NO 299
<211> LENGTH: 37
<212> TYPE: DNA
<213> ORGANISM: Artificial Sequence
<220> FEATURE:
<223> OTHER INFORMATION: Description of Artificial Sequence: 3' Primer C

<400> SEQUENCE: 299
agtgcgagcc tctcggctcg cacctaacct ctctagt         37

<210> SEQ ID NO 300
<211> LENGTH: 35
<212> TYPE: DNA
<213> ORGANISM: Artificial Sequence
<220> FEATURE:
<223> OTHER INFORMATION: Description of Artificial Sequence: Primer #1
      from first set

<400> SEQUENCE: 300
tctaatacga ctcactatag gacctcggcg aaagc         35

<210> SEQ ID NO 301
<211> LENGTH: 27
<212> TYPE: DNA
<213> ORGANISM: Artificial Sequence
<220> FEATURE:
<223> OTHER INFORMATION: Description of Artificial Sequence: Primer #2
      from first set

<400> SEQUENCE: 301
agtgctctcg cacctaacct ctctagt         27

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Primer 1
      from second set

<400> SEQUENCE: 302
gttgctacaa atgatatgac         20

<210> SEQ ID NO 303
<211> LENGTH: 20
<212> TYPE: DNA
<213> ORGANISM: Artificial Sequence
<220> FEATURE:
<223> OTHER INFORMATION: Description of Artificial Sequence: Primer #2
      from second set

<400> SEQUENCE: 303
atggcaattt agccatgaga         20

<210> SEQ ID NO 304
<211> LENGTH: 106
<212> TYPE: RNA
<213> ORGANISM: Artificial Sequence
<220> FEATURE:
<223> OTHER INFORMATION: Description of Artificial Sequence: Ligase RNA
      sequence

<400> SEQUENCE: 304
ggaccucggc gaaagcuaac gucucauggc uaaauugcca uguugcuaca aaugauauga         60
cuagagaggu uaggugcauc uucaugucca gucgcuugca augccc         106

-continued

<210> SEQ ID NO 305
<211> LENGTH: 23
<212> TYPE: DNA
<213> ORGANISM: Artificial Sequence
<220> FEATURE:
<223> OTHER INFORMATION: Description of Artificial Sequence: Reverse
      transcriptase primer

<400> SEQUENCE: 305
gggcattgca agcgactgga cat                                              23

<210> SEQ ID NO 306
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide substrate

<400> SEQUENCE: 306
actgaacctg accgtacaaa gatgcacu                                         28

<210> SEQ ID NO 307
<211> LENGTH: 22
<212> TYPE: DNA
<213> ORGANISM: Artificial Sequence
<220> FEATURE:
<223> OTHER INFORMATION: Description of Artificial Sequence: TaqMan
      forward primer

<400> SEQUENCE: 307
actgaacctg accgtacaaa ga                                               22

<210> SEQ ID NO 308
<211> LENGTH: 22
<212> TYPE: DNA
<213> ORGANISM: Artificial Sequence
<220> FEATURE:
<223> OTHER INFORMATION: Description of Artificial Sequence: TaqMan
      reverse primer

<400> SEQUENCE: 308
tttgtagcaa catggcaatt ta                                               22

<210> SEQ ID NO 309
<211> LENGTH: 23
<212> TYPE: DNA
<213> ORGANISM: Artificial Sequence
<220> FEATURE:
<223> OTHER INFORMATION: Description of Artificial Sequence: TaqMan
      probe primer

<400> SEQUENCE: 309
cggcgaaagc taacgtctca tgg                                              23

<210> SEQ ID NO 310
<211> LENGTH: 22
<212> TYPE: DNA
<213> ORGANISM: Artificial Sequence
<220> FEATURE:
<223> OTHER INFORMATION: Description of Artificial Sequence: Forward
      primer

<400> SEQUENCE: 310
actgaacctg accgtacaaa ga                                               22

```
<210> SEQ ID NO 311
<211> LENGTH: 22
<212> TYPE: DNA
<213> ORGANISM: Artificial Sequence
<220> FEATURE:
<223> OTHER INFORMATION: Description of Artificial Sequence: Reverse
      primer

<400> SEQUENCE: 311
tttgtagcaa catggcaatt ta                                              22

<210> SEQ ID NO 312
<211> LENGTH: 95
<212> TYPE: RNA
<213> ORGANISM: Artificial Sequence
<220> FEATURE:
<223> OTHER INFORMATION: Description of Artificial Sequence: Lysozyme
      dependent nucleic acid sensor molecule

<400> SEQUENCE: 312
ggaccucggc gaaagcuaac gucucauggc uaaauugcca uguugcuaca aaugauauga     60
cuagagaggu uaggugccuc gugaugucca gucgc                                95

<210> SEQ ID NO 313
<211> LENGTH: 18
<212> TYPE: DNA
<213> ORGANISM: Artificial Sequence
<220> FEATURE:
<223> OTHER INFORMATION: Description of Artificial Sequence: Effector
      oligo

<400> SEQUENCE: 313
gcgactggac atcacgag                                                   18

<210> SEQ ID NO 314
<211> LENGTH: 32
<212> TYPE: DNA
<213> ORGANISM: Artificial Sequence
<220> FEATURE:
<223> OTHER INFORMATION: Description of Combined DNA/RNA Molecule:
      Substrate
<220> FEATURE:
<223> OTHER INFORMATION: Description of Artificial Sequence:
      Oligonucleotide substrate

<400> SEQUENCE: 314
gtacgatgcg atgctagcga ttgttgugca cu                                   32

<210> SEQ ID NO 315
<211> LENGTH: 42
<212> TYPE: DNA
<213> ORGANISM: Artificial Sequence
<220> FEATURE:
<223> OTHER INFORMATION: Description of Artificial Sequence: Forward
      primer

<400> SEQUENCE: 315
taatacgact cactatagga cttcggcgaa agccgttcga cc                        42

<210> SEQ ID NO 316
<211> LENGTH: 47
<212> TYPE: DNA
<213> ORGANISM: Artificial Sequence
<220> FEATURE:
<223> OTHER INFORMATION: Description of Artificial Sequence: Primer
      spanning the 3' proximal portion of the L1 ligase
      domain
```

```
<400> SEQUENCE: 316
attcgagatg tccttggacc aaagccgcac ctaacctcct gtctaag              47

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: Forward
      primer

<400> SEQUENCE: 317
gcgaccttac gatcagatga c                                         21

<210> SEQ ID NO 318
<211> LENGTH: 22
<212> TYPE: DNA
<213> ORGANISM: Artificial Sequence
<220> FEATURE:
<223> OTHER INFORMATION: Description of Artificial Sequence: Reverse
      primer

<400> SEQUENCE: 318
ccgcacctaa cctcctgtct aa                                        22

<210> SEQ ID NO 319
<211> LENGTH: 26
<212> TYPE: DNA
<213> ORGANISM: Artificial Sequence
<220> FEATURE:
<223> OTHER INFORMATION: Description of Artificial Sequence: ERK ligase
      probe primer

<400> SEQUENCE: 319
aaggaggatt tccgaaagcg gctacg                                    26

<210> SEQ ID NO 320
<211> LENGTH: 26
<212> TYPE: DNA
<213> ORGANISM: Artificial Sequence
<220> FEATURE:
<223> OTHER INFORMATION: Description of Artificial Sequence: ppERK
      ligase probe primer

<400> SEQUENCE: 320
cgctagcgaa ttggttcctc gaaagg                                    26

<210> SEQ ID NO 321
<211> LENGTH: 32
<212> TYPE: DNA
<213> ORGANISM: Artificial Sequence
<220> FEATURE:
<223> OTHER INFORMATION: Description of Combined DNA/RNA Molecule:
      Substrate
<220> FEATURE:
<223> OTHER INFORMATION: Description of Artificial Sequence: Substrate 3

<400> SEQUENCE: 321
catgcgacct tacgatcaga tgacctugca cu                             32

<210> SEQ ID NO 322
<211> LENGTH: 21
<212> TYPE: DNA
<213> ORGANISM: Artificial Sequence
<220> FEATURE:
<223> OTHER INFORMATION: Description of Artificial Sequence: Substrate 3
      specific 5' PCR primer
```

```
<400> SEQUENCE: 322
catgcgacct tacgatcaga t                                            21

<210> SEQ ID NO 323
<211> LENGTH: 35
<212> TYPE: DNA
<213> ORGANISM: Artificial Sequence
<220> FEATURE:
<223> OTHER INFORMATION: Description of Artificial Sequence:
      Regeneration 5' PCR primer

<400> SEQUENCE: 323
tctaatacga ctcactatag gacttcggcg aaagc                             35

<210> SEQ ID NO 324
<211> LENGTH: 109
<212> TYPE: DNA
<213> ORGANISM: Artificial Sequence
<220> FEATURE:
<223> OTHER INFORMATION: Description of Artificial Sequence: Library
      (DNA) (random regions 3-5 nucleotides in length)
<220> FEATURE:
<221> NAME/KEY: misc_feature
<222> LOCATION: (26)..(30)
<223> OTHER INFORMATION: Wherein n is an a or t or c or g or nothing
<220> FEATURE:
<221> NAME/KEY: misc_feature
<222> LOCATION: (64)..(68)
<223> OTHER INFORMATION: Wherein n is an a or t or c or g or nothing

<400> SEQUENCE: 324
ggacttcggc gaaagccgtt cgaccnnnnn aaggaggatt tccgaaagcg gctacggtcc   60
gccnnnnnct tagacaggag gttaggtgcg taggtaaccg atagttccg              109

<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Effector
      primer

<400> SEQUENCE: 325
cggaactatc ggttacctac                                              20

<210> SEQ ID NO 326
<211> LENGTH: 135
<212> TYPE: DNA
<213> ORGANISM: Artificial Sequence
<220> FEATURE:
<223> OTHER INFORMATION: Description of Artificial Sequence: ppERK
      selection-specific oligonucleotides
<220> FEATURE:
<221> NAME/KEY: misc_feature
<222> LOCATION: (26)..(31)
<223> OTHER INFORMATION: Wherein n is an a or t or c or g or nothing
<220> FEATURE:
<221> NAME/KEY: misc_feature
<222> LOCATION: (89)..(94)
<223> OTHER INFORMATION: Wherein n is an a or t or c or g or nothing

<400> SEQUENCE: 326
ggacttcggc gaaagccgtt cgaccnnnnn ncagacgcta gcgaattggt tcctcgaaag   60
gggaaagcgt tattaagaaa ccaaaatgnn nnnncttaga caggaggtta ggtgcgtcaa  120
tgctgcaagt tactg                                                  135
```

```
<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Effector
      primer

<400> SEQUENCE: 327
cagtaacttg cagcattgac                                                    20

<210> SEQ ID NO 328
<211> LENGTH: 101
<212> TYPE: DNA
<213> ORGANISM: Artificial Sequence
<220> FEATURE:
<223> OTHER INFORMATION: Description of Artificial Sequence: bFGF
      selection specific oligonucleotide
<220> FEATURE:
<221> NAME/KEY: misc_feature
<222> LOCATION: (26)..(32)
<223> OTHER INFORMATION: Wherein n is an a or t or c or g or nothing
<220> FEATURE:
<221> NAME/KEY: misc_feature
<222> LOCATION: (54)..(60)
<223> OTHER INFORMATION: Wherein n is an a or t or c or g or nothing

<400> SEQUENCE: 328
ggacttcggc gaaagccgtt cgaccnnnnn nngcaacgct acagacaagt gcannnnnnn         60
cttagacagg aggttaggtg cccgagttgt cgaacgaga c                            101

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Effector
      primer

<400> SEQUENCE: 329
gtctcgttcg aacaactcgg                                                    20

<210> SEQ ID NO 330
<211> LENGTH: 92
<212> TYPE: DNA
<213> ORGANISM: Artificial Sequence
<220> FEATURE:
<223> OTHER INFORMATION: Description of Artificial Sequence: Thrombin
      selection specific oligonucleotide
<220> FEATURE:
<221> NAME/KEY: misc_feature
<222> LOCATION: (26)..(31)
<223> OTHER INFORMATION: Wherein n is an a or t or c or g or nothing
<220> FEATURE:
<221> NAME/KEY: misc_feature
<222> LOCATION: (47)..(51)
<223> OTHER INFORMATION: Wherein n is an a or t or c or g or nothing

<400> SEQUENCE: 330
ggacttcggc gaaagccgtt cgaccnnnnn natcgaagtt agtaggnnnn ncttagacag         60
gaggttaggt gcgtcaatcg attgcagatc cg                                      92

<210> SEQ ID NO 331
<211> LENGTH: 20
<212> TYPE: DNA
<213> ORGANISM: Artificial Sequence
<220> FEATURE:
<223> OTHER INFORMATION: Description of Artificial Sequence: Effector
```

-continued primer

<400> SEQUENCE: 331
cggatctgca atcgattgac                                                    20

<210> SEQ ID NO 332
<211> LENGTH: 77
<212> TYPE: RNA
<213> ORGANISM: Artificial Sequence
<220> FEATURE:
<223> OTHER INFORMATION: Description of Artificial Sequence: Nucleic
      acid sensor molecule with effector domain deleted

<400> SEQUENCE: 332
ggaccucggc gaaagcuaac gucucauggc uaaauugcca uguugcuaca aaugauauga       60
cuagagaggu uaggugc                                                       77

<210> SEQ ID NO 333
<211> LENGTH: 83
<212> TYPE: DNA
<213> ORGANISM: Artificial Sequence
<220> FEATURE:
<223> OTHER INFORMATION: Description of Artificial Sequence: MK.08.92.A

<400> SEQUENCE: 333
gcttgcaagc ccttagaccc tgatgagcct tgcgatgcaa aaggtgctg acgacacatc        60 gaaacggtga agccgtagg tct                                                 83

<210> SEQ ID NO 334
<211> LENGTH: 24
<212> TYPE: DNA
<213> ORGANISM: Artificial Sequence
<220> FEATURE:
<223> OTHER INFORMATION: Description of Artificial Sequence: MK.08.66.B

<400> SEQUENCE: 334
agacctacgg ctttcaccgt ttcg                                               24

<210> SEQ ID NO 335
<211> LENGTH: 57
<212> TYPE: DNA
<213> ORGANISM: Artificial Sequence
<220> FEATURE:
<223> OTHER INFORMATION: Description of Artificial Sequence: MK.08.130.B

<400> SEQUENCE: 335
atacgactca ctataggatg tccagtcgct tgcaatgccc ttttagaccc tgatgag         57

<210> SEQ ID NO 336
<211> LENGTH: 82
<212> TYPE: DNA
<213> ORGANISM: Artificial Sequence
<220> FEATURE:
<223> OTHER INFORMATION: Description of Artificial Sequence:
      LYS.LIG.TMPLT.L1-11.2

<400> SEQUENCE: 336
ctataggact tcggcgaaag ctaacgtctc atggctaaat tgccatgttg ctacaaatga       60
tatgactaga gaggttaggt gc                                                 82

<210> SEQ ID NO 337
<211> LENGTH: 92
<212> TYPE: DNA
<213> ORGANISM: Artificial Sequence

```
<220> FEATURE:
<223> OTHER INFORMATION: Description of Artificial Sequence:
      FMN.LIG.TMPLT.L1-R7C13

<400> SEQUENCE: 337
ctataggact tcggtccagt gctcgtgcac taggccgttc gaccttcagg atatgcttcg    60
gcagaaggga acttagacag gaggttaggt gc                                  92

<210> SEQ ID NO 338
<211> LENGTH: 101
<212> TYPE: DNA
<213> ORGANISM: Artificial Sequence
<220> FEATURE:
<223> OTHER INFORMATION: Description of Artificial Sequence:
      THEO.LIG.TMPLT.L1-D1

<400> SEQUENCE: 338
ctataggact tcggtccagt gctcgtgcac taggccgttc gaccatgata ccagcatcgt    60
cttgatgccc ttggcagcat cttagacagg aggttaggtg c                       101

<210> SEQ ID NO 339
<211> LENGTH: 27
<212> TYPE: DNA
<213> ORGANISM: Artificial Sequence
<220> FEATURE:
<223> OTHER INFORMATION: Description of Artificial Sequence: TK.16.32.A

<400> SEQUENCE: 339
ttctaatacg actcactata ggacttc                                        27

<210> SEQ ID NO 340
<211> LENGTH: 38
<212> TYPE: DNA
<213> ORGANISM: Artificial Sequence
<220> FEATURE:
<223> OTHER INFORMATION: Description of Artificial Sequence: TK.16.32.B

<400> SEQUENCE: 340
attcgagatg tccttggacc aaagccgcac ctaacctc                            38

<210> SEQ ID NO 341
<211> LENGTH: 48
<212> TYPE: DNA
<213> ORGANISM: Artificial Sequence
<220> FEATURE:
<223> OTHER INFORMATION: Description of Combined DNA/RNA Molecule:
      Substrate
<220> FEATURE:
<223> OTHER INFORMATION: Description of Artificial Sequence:
      TK.16.32.15NT

<400> SEQUENCE: 341
attcgagatg tccttggacc aaagcctcca tcgtgcgcac ctaacctc                 48

<210> SEQ ID NO 342
<211> LENGTH: 32
<212> TYPE: DNA
<213> ORGANISM: Artificial Sequence
<220> FEATURE:
<223> OTHER INFORMATION: Description of Combined DNA/RNA Molecule:
      Substrate
<220> FEATURE:
<223> OTHER INFORMATION: Description of Artificial Sequence:
      TK.04.82.A

<400> SEQUENCE: 342
```

```
catgcgacct tacgatcaga tgacctugca cu                          32
```

<210> SEQ ID NO 343
<211> LENGTH: 15
<212> TYPE: DNA
<213> ORGANISM: Artificial Sequence
<220> FEATURE:
<223> OTHER INFORMATION: Description of Artificial Sequence:
     MK.08.125A

<400> SEQUENCE: 343

```
tccatcgtgc gcacu                                             15
```

<210> SEQ ID NO 344
<211> LENGTH: 27
<212> TYPE: DNA
<213> ORGANISM: Artificial Sequence
<220> FEATURE:
<223> OTHER INFORMATION: Description of Artificial Sequence: TK16.32.A

<400> SEQUENCE: 344

```
ttctaatacg actcactata ggacttc                                27
```

<210> SEQ ID NO 345
<211> LENGTH: 22
<212> TYPE: DNA
<213> ORGANISM: Artificial Sequence
<220> FEATURE:
<223> OTHER INFORMATION: Description of Artificial Sequence: MK.08.125B

<400> SEQUENCE: 345

```
tccatcgtgc gcacctaacc tc                                     22
```

<210> SEQ ID NO 346
<211> LENGTH: 15
<212> TYPE: DNA
<213> ORGANISM: Artificial Sequence
<220> FEATURE:
<223> OTHER INFORMATION: Description of Artificial Sequence: MK.08.125A

<400> SEQUENCE: 346

```
tccatcgtgc gcacu                                             15
```

<210> SEQ ID NO 347
<211> LENGTH: 55
<212> TYPE: RNA
<213> ORGANISM: Artificial Sequence
<220> FEATURE:
<223> OTHER INFORMATION: Description of Combined DNA/RNA Molecule:
     Oligonucleotide substrate
<220> FEATURE:
<223> OTHER INFORMATION: Description of Artificial Sequence: 2-piece
     ligase
     template
<220> FEATURE:
<221> NAME/KEY: misc_feature
<222> LOCATION: (26)..(33)
<223> OTHER INFORMATION: Wherein n is an a or u or c or g or nothing

<400> SEQUENCE: 347

```
ggacuucggc gaaagccguu cgaccnnnnn nnncuuagac aggagguuag gugcg  55
```

<210> SEQ ID NO 348
<211> LENGTH: 15
<212> TYPE: DNA
<213> ORGANISM: Artificial Sequence
<220> FEATURE:
<223> OTHER INFORMATION: Description of Artificial Sequence:

-continued

Oligonucleotide substrate

<400> SEQUENCE: 348
tccatcgtgc gcacu                                                          15

<210> SEQ ID NO 349
<211> LENGTH: 99
<212> TYPE: RNA
<213> ORGANISM: Artificial Sequence
<220> FEATURE:
<223> OTHER INFORMATION: Description of Artificial Sequence:
      Construct 29

<400> SEQUENCE: 349
ggacuucggc gaaagccguu cgaccacgcu aaggaggauu uccgaaagcg gcuacgugcc         60
gccagugucu uagacaggag guuaggugcg cacgaugga                               99

<210> SEQ ID NO 350
<211> LENGTH: 6
<212> TYPE: RNA
<213> ORGANISM: Artificial Sequence
<220> FEATURE:
<223> OTHER INFORMATION: Description of Artificial Sequence:
      Oligonucleotide substrate

<400> SEQUENCE: 350 ugcacu                                                                    6

<210> SEQ ID NO 351
<211> LENGTH: 97
<212> TYPE: RNA
<213> ORGANISM: Artificial Sequence
<220> FEATURE:
<223> OTHER INFORMATION: Description of Artificial Sequence:
      Construct 30

<400> SEQUENCE: 351
ggacuucggc gaaagccguu cgaccagcua aggaggauuu ccgaaagcgg cuacgugccg         60
ccagcucuua gacaggaggu uaggugcgca cgaugga                                 97

<210> SEQ ID NO 352
<211> LENGTH: 138
<212> TYPE: RNA
<213> ORGANISM: Artificial Sequence
<220> FEATURE:
<223> OTHER INFORMATION: Description of Artificial Sequence: ppERK
      dependent ligase template
<220> FEATURE:
<221> NAME/KEY: misc_feature
<222> LOCATION: (27)..(30)
<223> OTHER INFORMATION: Wherein n is an a or u or c or g or nothing
<220> FEATURE:
<221> NAME/KEY: misc_feature
<222> LOCATION: (87)..(90)
<223> OTHER INFORMATION: Wherein n is an a or u or c or g or nothing

<400> SEQUENCE: 352
ggacuucggc gaaagccguu cgaccannnn cagacgcuag cgaauugguu ccucgaaagg         60
gaaagcguua uuaagaaacc aaaaugnnnn ucuuagacag gagguuaggu gccguccgac        120
ugaucucgga guuaaacg                                                     138

<210> SEQ ID NO 353
<211> LENGTH: 107
<212> TYPE: RNA
<213> ORGANISM: Artificial Sequence

```
<220> FEATURE:
<223> OTHER INFORMATION: Description of Artificial Sequence: ppERK
      sensitive hammerhead template
<220> FEATURE:
<221> NAME/KEY: misc_feature
<222> LOCATION: (17)..(21)
<223> OTHER INFORMATION: Wherein n is an a or u or c or g or nothing
<220> FEATURE:
<221> NAME/KEY: misc_feature
<222> LOCATION: (76)..(80)
<223> OTHER INFORMATION: Wherein n is an a or u or c or g or nothing

<400> SEQUENCE: 353
gggcgacccu gaugagnnnn nagacgcuag cgaauugguu ccucgaaagg ggaaagcguu     60
auuaagaaac caaaannnnn cgaaacggug aaagccguag guugccc                  107

<210> SEQ ID NO 354
<211> LENGTH: 134
<212> TYPE: DNA
<213> ORGANISM: Artificial Sequence
<220> FEATURE:
<223> OTHER INFORMATION: Description of Artificial Sequence: ppERK
      nucleic acid sensor molecule template
<220> FEATURE:
<221> NAME/KEY: misc_feature
<222> LOCATION: (25)..(31)
<223> OTHER INFORMATION: Wherein n is an a or t or c or g or nothing
<220> FEATURE:
<221> NAME/KEY: misc_feature
<222> LOCATION: (88)..(93)
<223> OTHER INFORMATION: Wherein n is an a or t or c or g or nothing

<400> SEQUENCE: 354
ggacttcggc gaaagccgtt cgaccnnnnn ncagacgcta gcgaattggt tcctcgaaag     60
ggaaagcgtt attaagaaac caaaatgnnn nnncttagac aggaggttag gtgcgtcaat    120
gctgcaagtt actg                                                     134

<210> SEQ ID NO 355
<211> LENGTH: 109
<212> TYPE: DNA
<213> ORGANISM: Artificial Sequence
<220> FEATURE:
<223> OTHER INFORMATION: Description of Artificial Sequence: ERK
      sensitive nucleic acid sensor molecule template
<220> FEATURE:
<221> NAME/KEY: misc_feature
<222> LOCATION: (26)..(30)
<223> OTHER INFORMATION: Wherein n is an a or t or c or g or nothing
<220> FEATURE:
<221> NAME/KEY: misc_feature
<222> LOCATION: (64)..(68)
<223> OTHER INFORMATION: Wherein n is an a or t or c or g or nothing

<400> SEQUENCE: 355
ggacttcggc gaaagccgtt cgaccnnnnn aaggaggatt tccgaaagcg gctacggtcc     60
gccnnnnnct tagacaggag gttaggtgcg taggtaaccg atagttccg                109

<210> SEQ ID NO 356
<211> LENGTH: 131
<212> TYPE: RNA
<213> ORGANISM: Artificial Sequence
<220> FEATURE:
<223> OTHER INFORMATION: Description of Artificial Sequence: CW45-33-A08
      ERK sensitive nucleic acid sensor molecule
<220> FEATURE:
<223> OTHER INFORMATION: Description of Combined DNA/RNA Molecule:
      Oligonucleotide substrate

<400> SEQUENCE: 356
```

```
ggacuucggc gaaagccguu cgacccucuc agacgcuagc gaauugguuc cucgaaaggg      60
aaagcguuau uaagaaacca aaaugagagg cuuagacagg agguuaggug cgucaaugcu     120
gcaaguuacu g                                                         131

<210> SEQ ID NO 357
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide substrate

<400> SEQUENCE: 357
acgtagcata gcatcgatag ctgttgugca cu                                   32

<210> SEQ ID NO 358
<211> LENGTH: 265
<212> TYPE: DNA
<213> ORGANISM: Artificial Sequence
<220> FEATURE:
<223> OTHER INFORMATION: Description of Artificial Sequence: Thymidylate
      synthase ("td") intron

<400> SEQUENCE: 358
taattgaggc ctgagtataa ggtgacttat acttgtaatc tatctaaacg gggaacctct     60
ctagtagaca atcccgtgct aaattgtagg actgcccggg ttctacataa atgcctaacg    120
actatccctt tggggagtag ggtcaagtga ctcgaaacga tagacaactt gctttaacaa    180
gttggagata tagtctgctc tgcatggtga catgcagctg gatataattc cggggtaaga    240
ttaacgacct tatctgaaca taatg                                          265

<210> SEQ ID NO 359
<211> LENGTH: 276
<212> TYPE: DNA
<213> ORGANISM: Artificial Sequence
<220> FEATURE:
<223> OTHER INFORMATION: Description of Artificial Sequence:
      Theophylline dependent td group I intron

<400> SEQUENCE: 359
taattgaggc ctgagtataa ggtgacttat acttgtaatc tatctaaacg gggaacctct     60
ctagtagaca atcccgtgct aaattgatac cagcatcgtc ttgatgccct tggcagcata    120
aatgcctaac gactatccct tggggagtag ggtcaagtg actcgaaacg atagacaact    180
tgctttaaca agttggagat atagtctgct ctgcatggtg acatgcagct ggatataatt    240
ccggggtaag attaacgacc ttatctgaac ataatg                              276

<210> SEQ ID NO 360
<211> LENGTH: 10
<212> TYPE: DNA
<213> ORGANISM: Artificial Sequence
<220> FEATURE:
<223> OTHER INFORMATION: Description of Artificial Sequence: Exon 1, the
      5'-exon

<400> SEQUENCE: 360
tttcttgggt                                                            10

<210> SEQ ID NO 361
<211> LENGTH: 10
<212> TYPE: DNA
```

<213> ORGANISM: Artificial Sequence
<220> FEATURE:
<223> OTHER INFORMATION: Description of Artificial Sequence: Exon 2, the 3'-exon

<400> SEQUENCE: 361
ctaccgttta                                                          10

<210> SEQ ID NO 362
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 362
agtgctctcg cacctaacct cctgtct                                       27

<210> SEQ ID NO 363
<211> LENGTH: 16
<212> TYPE: DNA
<213> ORGANISM: Artificial Sequence
<220> FEATURE:
<223> OTHER INFORMATION: Description of Artificial Sequence: PCR primer

<400> SEQUENCE: 363
ggacttcggc gaaagc                                                   16

<210> SEQ ID NO 364
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 364
agtgctctcg cacctaacct cctgtct                                       27

<210> SEQ ID NO 365
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 365
gctacggtcc gccagttctt                                               20

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 366
cgctttcgga aatcctcctt                                               20

<210> SEQ ID NO 367
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 367

```
gctacggtcc gccagggct                                           20

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 368
cgctttcgga aatcctcctt                                          20

<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 369
gctacggtcc gccaaaagct                                          20

<210> SEQ ID NO 370
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 370
cgctttcgga aatcctcctt                                          20

<210> SEQ ID NO 371
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 371
aaggggaaag cgttattaag                                          20

<210> SEQ ID NO 372
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 372
tcgaggaacc aattcgctag                                          20
```

We claim:

1. A nucleic acid sensor molecule comprising
   (a) a target modulation domain, wherein said target modulation domain recognizes a target molecule;
   (b) a linker domain; and
   (c) a catalytic domain wherein said catalytic domain comprises a cis-endonucleolytic ribozyme,
   wherein said nucleic acid sensor molecule comprises an optical signal generating unit.

2. The nucleic acid sensor molecule of claim 1, wherein said optical signal generating unit includes at least one signaling moiety.

3. The nucleic acid sensor molecule of claim 1, wherein said optical signal generating unit comprises at least a first signaling moiety and a second signaling moiety.

4. The nucleic acid sensor molecule of claim 3, wherein said first and second signaling moieties change proximity to each other upon recognition of a target by the target modulation domain.

5. The nucleic acid sensor molecule of claim 4, wherein said first and second signaling moieties comprise a fluorescent donor and a fluorescent quencher, and recognition of a target by the target modulation domain results in an increase in detectable fluorescence of said fluorescent donor.

6. The nucleic acid sensor molecule of claim 4, wherein said first signaling moiety and said second signaling moiety comprise fluorescent energy transfer (FRET) donor and acceptor groups, and recognition of a target by the target modulation domain results in a change in distance between said donor and acceptor groups, thereby changing optical properties of said molecule.

7. The nucleic acid sensor molecule of claim 1, wherein said optical signal generating unit consists essentially of a first signaling moiety, wherein said first signaling moiety changes conformation upon recognition of a target by the target modulation domain, thereby resulting in a detectable optical signal.

8. The nucleic acid sensor molecule of claim 1, wherein said nucleic acid sensor molecule includes at least one modified nucleic acid.

9. The nucleic acid sensor molecule of claim 1, wherein said endonucleolytic ribozyme is a hammerhead ribozyme.

10. The nucleic acid sensor molecule of claim 1, wherein said target recognition domain recognizes a small molecule.

11. The nucleic acid sensor molecule of claim 1, wherein said nucleic acid sensor molecule comprises RNA, DNA, or both RNA and DNA.

12. A composition comprising the nucleic acid sensor molecule of any one of claims 1–8, 9, 10, or 11 and a buffer.

13. A composition comprising the nucleic acid sensor molecule of any one of claims 1–8, 9, 10, or 11 and a tissue extract, a cell extract or an in vitro cell culture.

14. The composition of claim 12, further comprising an RNase inhibitor.

15. The composition of claim 14, wherein said RNase inhibitor is selected from the group consisting of Va-riboside, vanadyl, tRNA, polyU, RNaseIn and RNaseOut.

16. The composition of claim 12, wherein said composition is substantially RNase-free.

17. A composition comprising at least one nucleic acid sensor molecule according to any one of claims 1–8 or 9, affixed to a substrate.

18. The composition of claim 17, wherein said substrate is glass, gold or other metal, silicon or other semiconductor material, nitrocellulose, nylon, or plastic.

19. The composition of claim 17, wherein the nucleic acid sensor molecule is covalently attached to said substrate.

20. The composition of claim 17, wherein the nucleic acid sensor molecule is non-covalently attached to said substrate.

21. The composition of claim 17, wherein the nucleic acid sensor molecule is immobilized to the substrate via hybridization of a terminal portion of the nucleic acid sensor molecule to an oligonucleotide that is bound to the surface of the substrate.

22. The composition of claim 17, wherein said composition comprises a plurality of nucleic acid sensor molecules immobilized to the substrate via hybridization of a terminal portion of the nucleic acid sensor molecule to an array of oligonucleotides bound to the substrate at spatially discrete regions.

23. The composition of claim 17, wherein at least two members of said plurality each recognize different target molecules.

24. The composition of claim 17, wherein said substrate comprises at least 50 nucleic acid sensor molecules.

25. The composition of claim 17, wherein said substrate comprises at least 250 nucleic acid sensor molecules.

26. The composition of claim 17, wherein said substrate comprises at least 500 nucleic acid sensor molecules.

27. The composition of claim 17, wherein said substrate comprises at least 5000 nucleic acid sensor molecules.

28. A system for detecting a target molecule comprising a composition according to claim 17, and a detector in optical communication with said composition, wherein said detector detects changes in the optical properties of said composition.

29. The system of claim 28, further comprising a light source in optical communication with said composition.

30. The system of claim 29, further comprising a processor for processing optical signals detected by the detector.

31. The system of claim 28, wherein said system comprises a plurality of nucleic acid sensor molecules, wherein at least two of said biosensor molecules each recognize different target molecules.

32. A method of identifying or detecting a target molecule in a sample, the method comprising:
    contacting a sample suspected of containing a target molecule with a nucleic acid sensor molecule according to any one of claims 1–8, 9, 10, or 11, wherein a change in the signal generated by the optical signal generating unit indicates the presence of said target in said sample.

33. The method of claim 32 further comprising quantifying the change signal generated by the optical signal generating unit to quantify the amount of target molecule in the sample.

34. The method of claim 32 wherein the sample is selected from the group consisting of: environmental samples, biohazard materials, organic samples, drugs and toxins, flavors and fragrances, and biological samples.

35. The method of claim 32 wherein the sample is a biological sample, including cells, cell extracts or lysates, tissues or tissue extracts, bodily fluids, serum, blood and blood products.

36. The method of claim 32 wherein the target is selected from the group consisting of proteins, post-translationally modified forms of proteins, peptides, nucleic acids, oligosaccharides, nucleotides, metabolites, drugs, toxins, biohazards, ions, carbohydrates, polysaccharides, hormones, receptors, antigens, antibodies, viruses, metabolites, cofactors, drugs, dyes, nutrients, and growth factors.

37. The method of claim 32 wherein the target is selected from the group consisting of proteins and post-translationally modified forms of proteins.

38. The method of claim 37, wherein said target is a post-translationally modified protein, and wherein the post-translation modifications are selected from the group consisting of: phosphorylation, prenylation, glycosylation, methionine removal, N-acetylation, acylation, acylation of cysteines, myristoylation, alkylation, ubiquitinylation, prolyl-4-hydroxylation, carboxylation of glutaminyl residues, advanced glycosylation, deamination of glutamine and asparagine, addition of glycophosphatidylinositol, disulfide bond formation, hydroxylation, and lipidation.

39. The method of claim 32 wherein the target is a protein kinase.

40. The method of claim 32 wherein said target is a phosphorylated protein kinase.

41. A diagnostic system for identifying or detecting a target molecule, the diagnostic system comprising
    a nucleic acid sensor molecule according to any one of claims 1–8, 9, 10, or 11; and
    a detector in communication with said nucleic acid sensor molecule, wherein said detector detects changes in the signal generated by the optical signal generating unit of said nucleic acid sensor.

42. The diagnostic system of claim 41, further comprising a processor for processing signals detected by the detector.

43. A method of identifying or detecting a protein kinase in a sample, the method comprising:
    contacting a sample suspected of containing a protein kinase with a nucleic acid sensor molecule according to claim 1, wherein said nucleic acid sensor molecule has a target recognition domain that recognizes a protein kinase,
    wherein a change in the signal generated by the optical signal generating unit indicates the presence of protein kinase in said sample.

44. The method of claim 43, further comprising quantifying the amount of signal generated by the optical signal generating unit to quantify the amount of protein kinase in the sample.

45. The composition of claim 13, further comprising an RNase inhibitor.

46. The composition of claim 45, wherein said RNase inhibitor is selected from the group consisting of Va-riboside, vanadyl, tRNA, polyU, RNaseIn and RNaseOut.

47. The composition of claim 13, wherein said composition is substantially RNase-free.

48. The method of claim 33 wherein the sample is selected from the group consisting of: environmental samples, biohazard materials, organic samples, drugs and toxins, flavors and fragrances, and biological samples.

49. The method of claim 33 wherein the sample is a biological sample, including cells, cell extracts or lysates, tissues or tissue extracts, bodily fluids, serum, blood and blood products.

50. The method of claim 33 wherein the target is selected from the group consisting of proteins, post-translationally modified forms of proteins, peptides, nucleic acids, oligosaccharides, nucleotides, metabolites, drugs, toxins, biohazards, ions, carbohydrates, polysaccharides, hormones, receptors, antigens, antibodies, viruses, metabolites, cofactors, drugs, dyes, nutrients, and growth factors.

51. The method of claim 33 wherein the target is selected from the group consisting of proteins and post-translationally modified forms of proteins.

52. The method of claim 51, wherein said target is a post-translationally modified protein, and wherein the post-translation modifications are selected from the group consisting of: phosphorylation, prenylation, glycosylation, methionine removal, N-acetylation, acylation, acylation of cysteines, myristoylation, alkylation, ubiquitinylation, prolyl-4-hydroxylation, carboxylation of glutaminyl residues, advanced glycosylation, deamination of glutamine and asparagine, addition of glycophosphatidylinositol, disulfide bond formation, hydroxylation, and lipidation.

53. The method of claim 33 wherein the target is a protein kinase.

54. The method of claim 33, wherein said target is a phosphorylated protein kinase.

* * * * *